United States Patent
Aicher et al.

(10) Patent No.: US 9,809,561 B2
(45) Date of Patent: *Nov. 7, 2017

(54) TETRAHYDRONAPHTHYRIDINE, BENZOXAZINE, AZA-BENZOXAZINE AND RELATED BICYCLIC COMPOUNDS FOR INHIBITION OF RORGAMMA ACTIVITY AND THE TREATMENT OF DISEASE

(71) Applicants: Merck Sharp & Dohme Corp., Rahway, NJ (US); Lycera Corporation, Ann Arbor, MI (US)

(72) Inventors: Thomas D. Aicher, Ann Arbor, MI (US); Chad A. VanHuis, Hartland, MI (US); William D. Thomas, San Jose, CA (US); John K. MacLean, Brookline, MA (US); Brian M. Andresen, Boston, MA (US); Kenneth J. Barr, Boston, MA (US); Corey E. Bienstock, Natick, MA (US); Neville J. Anthony, Northborough, MA (US); Matthew Daniels, Somerville, MA (US); Kun Liu, Boston, MA (US); Yuan Liu, Billerica, MA (US); Catherine M. White, Boston, MA (US); Blair T. Lapointe, Boston, MA (US); Nunzio Sciammetta, Boston, MA (US); Vladimir Simov, Boston, MA (US)

(73) Assignees: MERCK SHARP & DOHME CORP., Rahway, NJ (US); LYCERA CORPORATION, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/103,414

(22) PCT Filed: Dec. 19, 2014

(86) PCT No.: PCT/US2014/071671
§ 371 (c)(1),
(2) Date: Jun. 10, 2016

(87) PCT Pub. No.: WO2015/095795
PCT Pub. Date: Jun. 25, 2015

(65) Prior Publication Data
US 2016/0304476 A1    Oct. 20, 2016

Related U.S. Application Data

(60) Provisional application No. 61/919,120, filed on Dec. 20, 2013.

(51) Int. Cl.
*C07D 265/36* (2006.01)
*C07D 413/14* (2006.01)
(Continued)

(52) U.S. Cl.
CPC ........ *C07D 265/36* (2013.01); *A61K 31/4375* (2013.01); *A61K 31/47* (2013.01);
(Continued)

(58) Field of Classification Search
CPC ................................................... C07D 265/36
(Continued)

(56) References Cited

U.S. PATENT DOCUMENTS

| | | |
|---|---|---|
| 5,985,903 A | 11/1999 | Assmann et al. |
| 6,020,354 A | 2/2000 | Assmann et al. |
| 6,037,367 A | 3/2000 | Christensen, IV et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |

(Continued)

FOREIGN PATENT DOCUMENTS

| | | |
|---|---|---|
| EP | 0882718 A1 | 12/1998 |
| EP | 1820515 A1 | 8/2007 |

(Continued)

OTHER PUBLICATIONS

International Search Report and Written Opinion for PCT/US2014/071671 dated Apr. 28, 2015 (10 pages).

(Continued)

*Primary Examiner* — Kahsay Habte
(74) *Attorney, Agent, or Firm* — Goodwin Procter LLP

(57) ABSTRACT

The invention provides certain bicylic heterocyclic compounds of the Formula (I) or pharmaceutically acceptable salts thereof, wherein $X^1$, $X^2$, $R^1$, $R^2$, $R^3$, R4, and Cy are as defined herein. The invention also provides pharmaceutical compositions comprising such compounds of the Formula (I) or pharmaceutically acceptable salts thereof, and methods of using the compounds of the Formula (I) or pharmaceutically acceptable salts thereof or pharmaceutical compositions comprising the same for treating diseases or conditions mediated by RORgammaT.

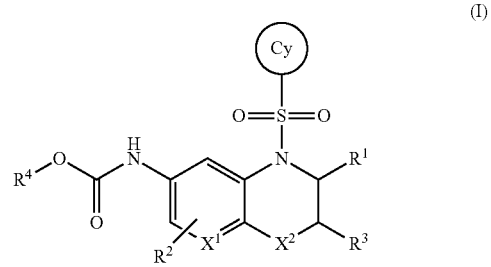

(I)

16 Claims, No Drawings

(51) Int. Cl.
| C07D 215/58 | (2006.01) |
| C07D 401/06 | (2006.01) |
| C07D 401/12 | (2006.01) |
| C07D 413/04 | (2006.01) |
| C07D 471/04 | (2006.01) |
| A61K 31/4375 | (2006.01) |
| A61K 31/47 | (2006.01) |
| A61K 31/4709 | (2006.01) |
| A61K 31/538 | (2006.01) |
| A61K 45/06 | (2006.01) |
| C07D 413/06 | (2006.01) |
| C07D 413/12 | (2006.01) |
| C07D 417/06 | (2006.01) |
| C07D 487/04 | (2006.01) |

(52) U.S. Cl.
CPC ........ *A61K 31/4709* (2013.01); *A61K 31/538* (2013.01); *A61K 45/06* (2013.01); *C07D 215/58* (2013.01); *C07D 401/06* (2013.01); *C07D 401/12* (2013.01); *C07D 413/04* (2013.01); *C07D 413/06* (2013.01); *C07D 413/12* (2013.01); *C07D 413/14* (2013.01); *C07D 417/06* (2013.01); *C07D 471/04* (2013.01); *C07D 487/04* (2013.01)

(58) Field of Classification Search
USPC ........................................ 544/105; 514/230.5
See application file for complete search history.

(56) References Cited

U.S. PATENT DOCUMENTS

| 6,828,344 | B1 | 12/2004 | Seehra et al. |
| 7,084,176 | B2 | 8/2006 | Morie et al. |
| 7,115,750 | B1 | 10/2006 | Kato et al. |
| 7,138,401 | B2 | 11/2006 | Kasibhatla et al. |
| 7,329,675 | B2 | 2/2008 | Cox et al. |
| 7,420,059 | B2 | 9/2008 | O'Connor et al. |
| 7,482,342 | B2 | 1/2009 | D'Orchymont et al. |
| 7,569,571 | B2 | 8/2009 | Dong et al. |
| 7,696,200 | B2 | 4/2010 | Ackermann et al. |
| 7,713,996 | B2 | 5/2010 | Ackermann et al. |
| 7,741,495 | B2 | 6/2010 | Liou et al. |
| 7,799,933 | B2 | 9/2010 | Ceccarelli et al. |
| 9,266,827 | B2 | 2/2016 | Aicher et al. |
| 9,512,111 | B2 | 12/2016 | Glick et al. |
| 2006/0004000 | A1 | 1/2006 | D'Orchymont et al. |
| 2006/0100230 | A1 | 5/2006 | Bischoff et al. |
| 2007/0010537 | A1 | 1/2007 | Hamamura et al. |
| 2007/0010670 | A1 | 1/2007 | Hirata et al. |
| 2007/0049556 | A1 | 3/2007 | Zhang et al. |
| 2007/0060567 | A1 | 3/2007 | Ackermann et al. |
| 2007/0154487 | A1 | 7/2007 | Littman et al. |
| 2007/0191603 | A1 | 8/2007 | Ackermann et al. |
| 2007/0197782 | A1 | 8/2007 | Clough et al. |
| 2007/0281922 | A1 | 12/2007 | Liu et al. |
| 2008/0027100 | A1 | 1/2008 | McCormick et al. |
| 2008/0058386 | A1 | 3/2008 | Liou et al. |
| 2008/0153805 | A1 | 6/2008 | Ceccarelli et al. |
| 2008/0305169 | A1 | 12/2008 | Miki et al. |
| 2009/0005410 | A1 | 1/2009 | Charvat et al. |
| 2009/0075973 | A1 | 3/2009 | Newcom et al. |
| 2009/0247502 | A1 | 10/2009 | Newcom et al. |
| 2009/0275586 | A1 | 11/2009 | Govek et al. |
| 2010/0022515 | A1 | 1/2010 | Alper et al. |
| 2010/0130484 | A1 | 5/2010 | Ackermann et al. |
| 2010/0234340 | A1 | 9/2010 | Schunk et al. |
| 2011/0053915 | A1 | 3/2011 | Ivaschenko et al. |
| 2011/0112070 | A1 | 5/2011 | Baldwin et al. |
| 2011/0118246 | A1 | 5/2011 | Baldwin et al. |
| 2011/0130384 | A1 | 6/2011 | Setoh et al. |
| 2011/0178063 | A1 | 7/2011 | Baldwin et al. |
| 2014/0088094 | A1 | 3/2014 | Glick et al. |
| 2015/0111877 | A1 | 4/2015 | Aicher et al. |
| 2015/0126493 | A1 | 5/2015 | Aicher et al. |
| 2016/0304505 | A1 | 10/2016 | Aicher et al. |
| 2016/0311787 | A1 | 10/2016 | Aicher et al. |

FOREIGN PATENT DOCUMENTS

| EP | 2181710 A1 | 5/2010 |
| JP | 6-250441 A | 9/1994 |
| JP | 2004307487 A | 11/2004 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/12600 A1 | 2/2001 |
| WO | WO-02/100819 A1 | 12/2002 |
| WO | WO-03/014075 A2 | 2/2003 |
| WO | WO-2004/056830 A1 | 7/2004 |
| WO | WO-2005/028434 A2 | 3/2005 |
| WO | WO-2005/037834 A1 | 4/2005 |
| WO | WO-2006/007486 A2 | 1/2006 |
| WO | WO-2006/057460 A1 | 6/2006 |
| WO | WO-2007/024944 A2 | 3/2007 |
| WO | WO-2007/031429 A1 | 3/2007 |
| WO | WO-2007/093507 A1 | 8/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/057101 A2 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/139775 A1 | 10/2012 |
| WO | WO-2013/169704 A2 | 11/2013 |

OTHER PUBLICATIONS

Annunziato et al., "Type 17 T helper cells-origins, features and possible roles in rheumatic disease," 5 Nat. Rev. Rheumatol. 325-31 (2009).

Boaventura et al., "Human mucosal leishmaniasis: Neutrophils infiltrate areas of tissue damage that express high levels of Th17-related cytokines," 40 Eur. J. Immunol. 2830-36 (2010).

Buonocore et al., "Innate lymphoid cells drive interleukin-23-dependent innate intestinal pathology," 464 Nature 1371-75 (2010).

Eberl et al., "An essential function for the nuclear receptor RORγt in the generation of fetal lymphoid tissue inducer cells," 5(1) Nat. Immunol. 64-73 (2004).

(56) References Cited

OTHER PUBLICATIONS

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).
Gennaro (ed.), Remington: The Science and Practice of Pharmacy, 20th edition (2000).
He et al., "RORγt, a Novel Isoform of an Orphan Receptor, Negatively Regulates Fas Ligand Expression and IL-2 Production in T Cells," 9 Immunity 797-806 (1998).
Hirose et al., "RORγ: the third member of ROR/RZR orphan receptor subfamily that is highly expressed in skeletal muscle," 205 Biochem. Biophys. Res. Comm. 1976-83 (1994).
Hueber et al., "Cutting Edge: Mast Cells Express IL-17A in Rheumatoid Arthritis Synovium," 184 J. Immunol. 3336-40 (2010).
Ivanov et al., "The Orphan Nuclear Receptor RORγt Directs the Differentiation Program of Proinflammatory IL-17+ T Helper Cells," 126 Cell 1121-33 (2006).
Jia et al., "The T helper type 17/regulatory T cell imbalance in patients with acute Kawasaki disease," 162 Clin. Exp. Immunol. 131-37 (2010).
Jin et al., "Structural Basis for Hydroxycholesterols as Natural Ligands of Orphans Nuclear Receptor RORγ," 24(5) Mol. Endocrinol. 923-29 (2010).
Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor RORγ," 315 Biochem. Biophys. Res. Comm. 919-27 (2004).
Louten et al., "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδT Cells, Amplifying Th17 Responses and Autoimmunity," 31 Immunity 331-41 (2009).
Wang et al., "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," 285(7) J. Bio. Chem. 5013-25 (2010).
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
André et al., "Disruption of retinoid-related orphan receptor β changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδT Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.

Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
Giguére et al., "Isoform-specific amino-terminal domains dictate DNA-binding properties of RORα, a novel family of orphan hormone nuclear receptors," 8 Genes & Develop. 538-53 (1994).
Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, et al., "Pharmacologic Inhibition of RORγt RegulatesTh17 Signature Gene Expression and Suppresses Cutaneous Inflammation in Vivo", The Journal of Immunology, (2014) pp. 1-12.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Lefthand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-γ-azabicyclo[2.2.1]heptanes: Epibatidine Analogues," 45 J. Med. Chem. 4755-61 (2002).

(56) References Cited

OTHER PUBLICATIONS

Chang et al., "7-Aroyl-aminoindoline-1-sulfonamides as a Novel Class of Potent Antitubulin Agents," 49 J. Med. Chem. 6656-59 (2006).

Colbon et al., "Double Arylation of Allyl Alcohol via a One-Pot Heck Arylation—Isomerization—Acylation Cascade," 13 Org. Lett. 5456-59 (2011).

De et al., Methods in Molecular Biology 1184, second edition, Human Press (2014).

Gould, "Salt selection for basic drugs," 33 Int'l J. Pharmaceutics 201-217 (1986).

Grasa et al., "Amination Reactions of Aryl Halides with Nitrogen-Containing Reagents Mediated by Palladium/Imidazolium Salt Systems," 66 J. Org. Chem. 7729-37 (2001).

Greene & Wuts, Protective Groups in Organic Synthesis, 2d Edition (1991).

Guimond et al., "Rhodium(III)-Catalyzed Isoquinolone Synthesis: The N-O Bond as a Handle for C-N Bond Formation and Catalyst Turnover," 132(20) J. Am. Chem. Soc. 6908-09 (2010).

Hanessian et al., "A versatile protocol for the stereocontrolled elaboration of vicinal secondary and tertiary centers of relevance to natural product synthesis," 52(6) J. Org. Chem. 1170-72 (1987).

Hauser et al., "Relative Ease of Cyclization of 2-, 3-, and 4-Aminopyridine Derivatives. Synthesis of Naphthyridines," 15 J. Org. Chem. 1224-32 (1950).

International Search Report and Written Opinion for PCT/US2011/059788 dated May 23, 2012 (23 pages).

International Search Report and Written Opinion for PCT/US2013/039422 dated Oct. 11, 2013 (9 pages).

International Search Report and Written Opinion for PCT/US2013/039839 dated Oct. 18, 2013 (8 pages).

International Search Report and Written Opinion for PCT/US2013/040085 dated Oct. 23, 2013 (9 pages).

Ishikura et al., "An Efficient Synthesis of 3-Heteroarylpyridines via Diethyl-(3-pyridyl)-borane," Synthesis 936-38 (1984).

Jayashree et al., "Design and synthesis of 2-quinolones as antioxidants and antimicrobials: a rational approach," 19 Med. Chem. Res. 193-209 (2010).

Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).

Li et al., "Chemical Libraries via Sequential C-H Functionalization of Phenols," 10 J. Comb. Chem. 170-74 (2008).

Li et al., "Synthesis and Resolution of a Novel Chiral Diamine Ligand and Application to Asymmetric Lithiation-Substitution," 2 Org. Lett. 875-78 (2000).

Liu et al., "1-Sulfonylindazoles as potent and selective 5-HT6 ligands," 19 Bioorg. Med. Chem. Lett. 2413-15 (2009).

Murase et al., "A New Concise Synthesis of Arcyriacyanin A and Its Unique Inhibitory Activity against a Panel of Human Cancer Cell Line," 48(1) Chem. Pharm. Bull. 81-84 (2000).

Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).

Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).

Santilli et al., "Synthesis of 5,6,7,8-Tetrahydro-5-oxopyrido[2,3-d]pyrimidine-6-carbonitriles and—6-carboxylic Acid Esters," 12 J. Het. Chem. 311-16 (1975).

Skraup, "Eine Synthese des Chinolins," 13 Berichte 2086-87 (1880).

Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).

STN Columbus, pp. 1-40 (2011).

Takano et al., "A new synthesis of a steroid side chain via stereocontrolled protonation: synthesis of (-)-desmosterol," 14 J. Chem. Soc., Chem. Commun. 760-61 (1983).

van Heerden et al., "Dibutylboron triflate promoted conjugate addition of benzylic and allylic organocopper reagents to chiral $\alpha,\beta$-unsaturated N-acyl imidazolidinones" 38(10) Tet. Lett. 182-124 (1997).

Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).

Yeh et al., "Practical Cu-catalyzed amination of functionalized heteroaryl halides," 47(34) Tetrahedron Lett. 6011-16 (2006).

Zhu et al., "The Direct Formulation of Functionalized Alkyl(aryl)zinc halides by Oxidative Addition of Highly Reactive Zinc with Organic Halides and Their Reactions with Acid Chlorides, $\alpha,\beta$-Unsaturated Ketones, and Allylic, Aryl, and Vinyl Halides," 56 J. Org. Chem. 1445-53 (1991).

International Search Report and Written Opinion for PCT/US2014/071663 dated Apr. 17, 2015 (6 pages).

International Search Report and Written Opinion for PCT/US2014/071656 dated Mar. 12, 2015 (8 pages).

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: SRC1_2 peptide
<220> FEATURE:
<221> NAME/KEY: MISC_FEATURE
<222> LOCATION: (2)..(3)
<223> OTHER INFORMATION: Xaa can be any naturally occurring amino acid
```

```
<400> SEQUENCE: 1

Leu Xaa Xaa Leu Leu
1               5

<210> SEQ ID NO 2
<211> LENGTH: 24
<212> TYPE: PRT
<213> ORGANISM: Artificial Sequence
<220> FEATURE:
<223> OTHER INFORMATION: SRC1_2 peptide

<400> SEQUENCE: 2

Ser Pro Ser Ser His Ser Ser Leu Thr Glu Arg His Lys Ile Leu His
1               5                   10                  15

Arg Leu Leu Gln Glu Gly Ser Pro
            20
```

TETRAHYDRONAPHTHYRIDINE, BENZOXAZINE, AZA-BENZOXAZINE AND RELATED BICYCLIC COMPOUNDS FOR INHIBITION OF RORGAMMA ACTIVITY AND THE TREATMENT OF DISEASE

CROSS-REFERENCE TO RELATED APPLICATIONS

This application is the national stage of International (PCT) Patent Application Serial No. PCT/US2014/071671, filed Dec. 19, 2014 which claims the benefit of and priority to U.S. Provisional Patent Application Ser. No. 61/919,120, filed Dec. 20, 2013, the contents of each of which are hereby incorporated by reference in their entirety.

FIELD OF THE INVENTION

The present invention relates to certain bicyclic heterocyclic compounds of the Formula (I) (also referred to herein as the "compounds of the Formula (I)" or "compounds of Formula (I)") which are antagonists of a Thymocyte/T cell specific variant of Retinoic Acid Receptor-related Orphan Receptor (ROR), RORgammaT. The present invention also provides compositions comprising such compounds, and methods of using such compounds for treating conditions or disorders associated with inappropriate RORgammaT activity, in particular in the treatment and prevention of disease states mediated by RORgammaT. Such disease states may include immune and inflammatory disorders such as rheumatoid arthritis, psoriasis, multiple sclerosis, inflammatory bowel disease, and asthma.

BACKGROUND OF THE INVENTION

Upon activation by antigen-presenting cells naïve T helper cells undergo clonal expansion and will ultimately differentiate into cytokine secreting effector T cells, such as Th1 and Th2 subtypes. A third and distinct effector subset has been identified, which plays a key role in providing immunity to bacteria and fungi at mucosal surfaces (Kastelein et al., Annu. Rev. Immunol. 25: 221-242, 2007). This effector T helper cell subset can be distinguished based on its ability to produce large quantities of IL-17/F, IL-21 and IL-22, and is named Th17 (Miossec et al., New Eng. J. Med. 361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., Immunity 9: 797-806, 1998). RORgammaT belongs to the nuclear hormone receptor superfamily (Hirose et al., Biochem. Biophys. Res. Comm. 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., Science 288: 2369-2372, 2000; Eberl et al., Nat Immunol. 5: 64-73, 2004).

Studies using heterozygous knock-in mice replacing the RORgammaT open reading frame with GFP (green fluorescent protein) revealed a constitutive expression of GFP in approximately 10% of the CD4+ T cells in the small intestinal lamina propria (LP), co-expressing the Th17 cytokines IL-17/F and IL-22 (Ivanov et al., Cell 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., Cell 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., Immunity 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., Nature 464: 1371-1375, 2010). In addition, RORgammaT was shown to play a crucial role in other non-Th17 cells, such as mast cells (Hueber et al., J. Immunol. 184: 3336-3340, 2010). Finally, RORgammaT expression and secretion of Th17-type of cytokines was reported for Lymphoid Tissue Inducer cells, NK T-cells, NK cells (Eberl et al., Nat. Immunol. 5: 64-73, 2004) and gamma-delta T-cells (Sutton et al., Immunity 31: 331-341, 2009; Louten et al., J. Allergy Clin. Immunol. 123: 1004-1011, 2009), suggesting an important function for RORgammaT in these subtypes of cells.

Based on the role of IL-17 producing cells (either Th17 or non-Th17 cells) RORgammaT has been identified as a key mediator in the pathogenesis of several diseases (Louten et al., J. Allergy Clin. Immunol. 123: 1004-1011, 2009; Annunziato et al., Nat. Rev. Rheumatol. 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., Cell 126:1121-33, 2006; Buonocore et al., Nature 464: 1371-1375, 2010).

With RORgammaT being a critical mediator in Th17-cells and non-Th17 cells, antagonism of the transcriptional activity of RORgammaT is expected to have a beneficial effect on autoimmune diseases, such as but not limited to rheumatoid arthritis, psoriasis, multiple sclerosis, inflammatory bowel disease (e.g., Crohn's disease, ulcerative colitis), and asthma (Annunziato et al., Nat. Rev. Rheumatol. 5: 325-331, 2009; Louten et al., J. Allergy Clin. Immunol. 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., Clin. Exp. Immunol. 162: 131-137, 2010) and Hashimoto's thyroiditis (Figueroa-Vega et al., J. Clin. Endocrinol. Metab. 95: 953-62, 2010). Another example includes infectious diseases, such as but not limited to mucosal leishmaniasis (Boaventura et al., Eur. J. Immunol. 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., ACS Chem. Biol. 5:1029-1034, 2010). In addition, antagonists have been reported such as 7-oxygenated sterols (Wang et al., *J. Biol. Chem.* 285: 5013-5025, 2010) and the compounds described in EP 2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT and thereby antagonize RORgammaT-mediated transcriptional activity; pharmaceutical compositions comprising such compounds and pharmaceutically acceptable excipients; and use of such compounds or such pharmaceutical compositions for the treatment of RORgammaT-mediated diseases or conditions, in particular autoimmune diseases and inflammatory diseases.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein refers to an amount of the compound of Formula (I) and/or an additional therapeutic agent, or a composition thereof that is effective in producing the desired therapeutic, ameliorative, inhibitory, or preventative effect when administered to a patient suffering from a disease or condition mediated by RORgammaT. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to an inflammatory disease or disorder, refers to reducing the likelihood of an autoimmune or inflammatory disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl, and neohexyl. In one embodiment, an alkyl group is linear. In another embodiment, an alkyl group is branched.

The term "fluoroalkyl," as used herein, refers to an alkyl group as defined above, wherein one or more of the alkyl group's hydrogen atoms have been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 fluorine atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$—, and —$CH_2CH(CH_3)CH_2$—. In one embodiment, an alkylene group has from 1 to about 6 carbon atoms ($C_1$-$C_6$ alkylene). In another embodiment, an alkylene group has from 1 to 3 carbon atoms ($C_1$-$C_3$ alkylene). In another embodiment, an alkylene group is branched. In another embodiment, an alkylene group is linear. In one embodiment, an alkylene group is —$CH_2$—. The term "$C_1$-$C_3$ alkylene" refers to an alkylene group having from 1 to 3 carbon atoms. Unless otherwise indicated, an alkylene group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to 4 carbon atoms. Non-limiting examples of alkenyl groups include ethenyl, propenyl, n-butenyl, 3-methylbut-2-enyl, n-pentenyl, octenyl, and decenyl. The term "$C_2$-$C_6$ alkenyl" refers to an alkenyl group having from 2 to 6 carbon atoms. The term "$C_2$-$C_4$ alkenyl" refers to an alkenyl group having from 2 to 4 carbon atoms. Unless otherwise indicated, an alkenyl group is unsubstituted.

The term "alkoxy," as used herein, refers to an —O-alkyl group, wherein an alkyl group is as defined above. Non-limiting examples of alkoxy groups include methoxy, ethoxy, n-propoxy, isopropoxy, n-butoxy, and tert-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "carbocycle," as used herein, refers to a fully saturated, partially unsaturated, or an aromatic monocyclic or multicyclic ring system comprising from about 6 to 14 carbon atoms. In one embodiment, an aryl group contains from 3 to 10 carbon atoms ($C_3$-$C_{10}$ carbocycle). Non-limiting examples of carbocyclic groups include cycloalkyl and aryl groups, as defined herein. In specific embodiments, the carbocyclic groups are selected from cyclopropyl, cyclobutyl, cyclopentyl, cyclohexyl, phenyl, indanyl, naphthyl, and tetrahydronaphthyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

"Heterocyclyl" refers to a 4-, 5-, 6-, or 7-membered monocyclic ring or 8-, 9-, or 10-membered bicyclic ring, or 13- or 14-membered tricyclic ring, saturated, unsaturated or aromatic, containing 1, 2, 3, or 4 heteroatoms selected from O, N, or S, and the heterocyclyl may optionally be substituted with one to four substituents. The nitrogen or sulfur atom of the heterocyclyl can be optionally oxidized to the corresponding N-oxide, S-oxide, or S,S-dioxide. A heterocyclyl group can be joined to the rest of the molecule via a ring carbon or ring nitrogen atom. Representative heterocyclyls are as follows: azetidinyl, pyrrolidinyl, pyrrolyl, tetrahydrofuran, imidazolyl, imidazolinyl, 1,3-oxazolidinyl, 1,2-oxazolidinyl, isoxazolyl, 1,2,4-oxadiazolyl, 1,3,4-oxadiazolyl, tetrahydropyranyl, piperidinyl, piperazinyl, morpholinyl, pyrimidinyl, pyrrolopyrazine, pyrrolopyridine, and indolyl.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation from a reaction mixture to a useful degree of purity, and formulation into an efficacious therapeutic agent.

When any substituent or variable occurs more than one time in any constituent or in the compound of Formula (I), its definition on each occurrence is independent of its definition at every other occurrence, unless otherwise indicated.

When an integer defining the presence of a certain number of atoms in a group is equal to zero, it means that the atoms adjacent thereto are connected directly by a bond; for example, in the structure

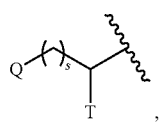

wherein s is an integer equal to zero, 1 or 2, the structure is

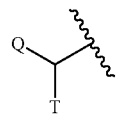

when s is zero; or it means that the indicated atom is absent; for example, —S(O)$_0$— means —S—.

The term "in purified form," as used herein, refers to the physical state of a compound after the compound has been isolated through a synthetic process (e.g., from a reaction mixture), from a natural source, or a combination thereof. The term "in purified form" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

It should also be noted that any carbon as well as heteroatom with unsatisfied valences in the text, schemes, examples, and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves various degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures, and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures, or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers, and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers, and the like) of the present compounds (including stereoisomers of salts and solvates of the present compounds as well as stereoisomers of salts, solvates, and esters of prodrugs of the present compounds), such as those that may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) can form salts which are also within the scope of this invention. Reference to a compound of Formula (I) herein is understood to include reference to salts thereof, unless otherwise indicated. The term "salt(s)," as employed herein, denotes acidic salts formed with inorganic and/or organic acids, as well as basic salts formed with inorganic and/or organic bases. In addition, when a compound of Formula (I) contains both a basic moiety, such as but not limited to a pyridine or imidazole, and an acidic moiety, such as but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids that are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine, and the like. Basic nitrogen-containing groups may be quaternized with agents such as lower alkyl halides (e.g., methyl, ethyl, and butyl chlorides, bromides, and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds, such as any solvates, hydrates, stereoisomers, and tautomers thereof.

As used herein, the term "composition" is intended to encompass a product comprising the specified ingredients in the specified amounts, as well as any product that results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formula (I) can be prepared without undue experimentation by conventional techniques well known to those skilled in the art or by processes analogous to those described in the examples herein using appropriate isotopically-enriched reagents and/or intermediates.

Compounds of the Invention

The present invention provides a compound of Formula (I) or a pharmaceutically acceptable salt thereof, wherein $X^1$, $X^2$, $R^1$, $R^2$, $R^3$, $R^4$, and Cy are as defined below. Described below are embodiments of the compound of Formula (I). The compound of the Formula (IA), shown below, is an embodiment of the compound of Formula (I).

In embodiment no. 1, the invention provides a compound of Formula (I),

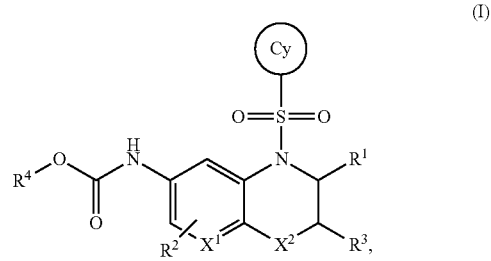

or a pharmaceutically acceptable salt thereof, wherein:
$X^1$ is $C(R^2)$ or N;
$X^2$ is O, S, S(O), $S(O)_2$, $CH_2$, or C(O);
$R^1$ is H, $C_1$-$C_3$ alkyl, or $C_1$-$C_3$ alkyl substituted by hydroxy;
$R^2$ is H, halo, or $C_1$-$C_3$ alkyl;
$R^3$ is selected from the group consisting of:
- (a.) H;
- (b.) $C_1$-$C_6$ alkyl;
- (c.) —$(C(R^a)_2)_{n1}OH$;
- (d.) —$(C(R^a)_2)_{n1}N(R^b)_2$;
- (e.) —$(C(R^a)_2)_{n1}N(H)C(O)N(R^b)_2$;
- (f.) —$(C(R^a)_2)_{n1}N(H)C(O)R^d$;
- (g.) —$(C(R^a)_2)_{n1}N(H)S(O)_2N(R^b)_2$;
- (h.) —$(C(R^a)_2)_{n1}N(H)S(O)_2R^d$;
- (i.) —$(C(R^a)_2)_{n1}CO_2R^c$;
- (j.) —$(C(R^a)_2)_{n2}C(O)N(R^b)_2$;
- (k.) —$(C(R^a)_2)_{n1}S(O)_2N(R^b)_2$;
- (l.) —$(C(R^a)_2)_{n2}N(H)C(O)OR^d$;
- (m.) —$(C(R^a)_2)_{n2}C(O)N(H)S(O)_2R^d$;
- (n.) —$(C(R^a)_2)_{n1}N(H)S(O)_2OR^d$;
- (o.) —$(C(R^a)_2)_{n1}S(O)_{n3}R^d$;
- (p.) —$(C(R^a)_2)_{n2}C(O)N(H)OR^d$;
- (q.) —$(C(R^a)_2)_{n1}CN$;
- (r.) —$C^H$ or —$(C(R^a)_2)_{n1}$—$C^H$;
- (s.) —$C(R^a)_2O$—$C^C$;
- (t.) —$C(O)CF_3$;
- (u.) —OH, with the proviso that $R^3$ is —OH only when $X^2$ is $CH_2$; and
- (v.) —$N(R^b)_2$, with the proviso that $R^3$ is —$N(R^b)_2$ only when $X^2$ is $CH_2$;
  - each $R^a$ is independently H, $C_1$-$C_3$ alkyl, $C_1$-$C_3$ fluoroalkyl, or $C_3$-$C_6$ cycloalkyl, or alternatively two $R^a$ when bonded to a common carbon atom may together with the common carbon atom form a cyclopropyl ring;
  - each $R^b$ is independently:
    - (i.) H;
    - (ii.) $C_1$-$C_6$ alkyl, wherein said $C_1$-$C_6$ alkyl is unsubstituted or independently substituted by 1 to 3 fluoro, or hydroxyl;
    - (iii.) —$(CH_2)_{n3}CO_2R^e$; or
    - (iv.) —$C^C$ or —$CH_2$—$C^C$; or
    - alternatively, two $R^b$ together with the N atom to which they are attached form a 5- to 9-membered heterocyclyl, wherein said heterocyclyl is a saturated, partially saturated, or aromatic ring system containing 0, 1, or 2 additional heteroatoms independently selected from the group consisting of N, O, S, and $S(O)_2$; wherein said heterocyclyl is unsubstituted or substituted by 1 to 4 moieties independently selected from the group consisting of $C_1$-$C_6$ alkyl, $C_1$-$C_3$ alkoxy, fluoro, hydroxyl, oxo, cyano, amino, $C_1$-$C_3$ alkylamino, and $C_1$-$C_3$ dialkylamino;
  - $R^c$ is
    - (i.) H;
    - (ii.) $C_1$-$C_6$ alkyl, wherein said $C_1$-$C_6$ alkyl is unsubstituted or independently substituted by 1 to 3 fluoro or hydroxy; or
    - (iii.) —$C^C$ or $CH_2$—$C^C$;
  - $R^d$ is
    - (i.) $C_1$-$C_6$ alkyl, wherein said $C_1$-$C_6$ alkyl is unsubstituted or independently substituted by 1 to 3 fluoro or hydroxy;
    - (ii). —$C(O)N(R^f)_2$; or
    - (iii.) —$C^C$ or $CH_2$—$C^C$;
  - $R^e$ is H or $C_1$-$C_3$ alkyl;
  - $R^f$ is H or $C_1$-$C_3$ alkyl;

ring $C^H$ is
- (i.) $C_3$-$C_6$ cycloalkyl;
- (ii.) phenyl; or
- (iii.) a 4- to 9-membered mono- or bicyclic heterocyclyl, wherein said heterocyclyl is a saturated, partially saturated, or aromatic ring system containing 1 to 4 heteroatoms independently selected from the group consisting of N, O, S, and $S(O)_2$;
  - wherein ring $C^H$ is unsubstituted or independently substituted by 1 to 4 $C_1$-$C_6$ alkyl, $C_1$-$C_3$ alkoxy, halo, hydroxyl, oxo, cyano, amino, $C_1$-$C_3$ alkylamino, or $C_1$-$C_3$ dialkylamino;

ring $C^C$ is
- (i.) $C_3$-$C_6$ cycloalkyl;
- (ii.) phenyl; or
- (iii.) a heterocyclyl of the formula

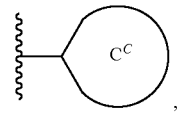

, wherein said heterocyclyl is a 5- to 9-membered heterocyclyl, wherein said heterocyclyl is a saturated, partially saturated, or aromatic ring system that contains 1, 2, or 3 heteroatoms independently selected from the group consisting of N, O, S, and $S(O)_2$;
  - wherein ring $C^C$ is unsubstituted or independently substituted by 1 to 4 $C_1$-$C_6$ alkyl, $C_1$-$C_3$ alkoxy, halo, hydroxyl, oxo, cyano, amino, $C_1$-$C_3$ alkylamino, or $C_1$-$C_3$ dialkylamino;

the subscript n1 is 1, 2, or 3;
the subscript n2 is 0, 1, 2, or 3;
the subscript n3 is 1 or 2;
$R^4$ is
- (a.) $C_1$-$C_8$ alkyl, wherein said $C_1$-$C_8$ alkyl of $R^4$ is unsubstituted or independently substituted by 1 to 6 halo, $C_1$-$C_3$ alkoxy, hydroxy, cyano, trimethylsilyl, or methylsulfonyl;
- (b.) $C_2$-$C_8$ alkenyl, wherein said $C_2$-$C_8$ alkenyl of $R^4$ is unsubstituted or independently substituted by 1 to 6 fluoro or cyano; or
- (c.) a group of the formula -M-$R^{CH}$;
  M is
  - (i.) a bond; or
  - (ii.) $C_1$-$C_6$ alkylene, wherein said $C_1$-$C_6$ alkylene of M is unsubstituted or substituted by 1 to 6 fluoro;
  $R^{CH}$ is a ring selected from the group consisting of
  - (i.) $C_3$-$C_9$ mono- or bicycloalkyl;
  - (ii.) phenyl; and
  - (iii.) a 3- to 6-membered heterocyclyl, wherein said heterocyclyl of $R^{CH}$ is a saturated, partially saturated or aromatic ring system containing 1 to 2 heteroatoms independently selected from the group consisting of N, O, and S;
    - wherein $R^{CH}$ is unsubstituted or independently substituted by 1 to 4 halo, $C_1$-$C_3$ alkyl, $C_1$-$C_3$ trifluoroalkyl, cyano, $C_1$-$C_4$ alkylcarbonylamino, or oxo;

Cy is
- (a.) phenyl;
- (b.) $C_3$-$C_6$ cycloalkyl;
- (c.) a 5- to 9-membered mono- or bicyclic heterocyclyl, wherein said heterocyclyl of Cy is a saturated, partially saturated, or aromatic ring system containing 1 to 3 heteroatoms independently selected from the group consisting of N, O, S and S(O)$_2$; or wherein Cy is unsubstituted or independently substituted by 1 to 4 R$^k$ moieties selected from the group consisting of:
- (i.) C$_1$-C$_6$ alkyl, wherein said C$_1$-C$_6$ alkyl is unsubstituted or independently substituted by 1 to 3 hydroxy or fluoro;
- (ii.) C$_1$-C$_6$ alkoxy, wherein said C$_1$-C$_6$ alkoxy is unsubstituted or independently substituted by 1 to 3 fluoro, hydroxy, amino, (C$_1$-C$_3$ alkyl)amino, di(C$_1$-C$_3$ alkyl)amino, methoxy, or phenyl;
- (iii.) —N(R$^{e1}$)$_2$;
- (iv.) —O(CH$_2$)$_{n4}$C(O)N(R$^{e1}$)$_2$;
- (v.) —O(CH$_2$)$_{n5}$CO$_2$R$^{e1}$;
- (vi.) hydroxyl;
- (vii.) oxo;
- (viii.) halo;
- (ix.) C$_1$-C$_3$ alkylsulfonyl;
- (x.) cyano;
- (xi.) oxetanyl; and
- (xii.) cyclopropyl;

or alternatively, two R$^k$ moieties, when substituted on adjacent ring atoms of Cy, form a second ring, wherein said second ring is a 5- to 7-membered saturated, partially saturated, or aromatic ring system that contains 0, 1, or 2 heteroatoms independently selected from the group consisting of N, O, and S; wherein said second ring is unsubstituted or substituted by 1 to 3 R$^k$ moieties independently selected from (i)-(xi);
each R$^{e1}$ is independently H or C$_1$-C$_3$ alkyl;
the subscript n4 is 1, 2, or 3;
the subscript n5 is 1, 2, or 3;

In embodiment no. 2, the invention provides a compound of Formula (I), wherein
- (a.) X$^1$ is C(R$^2$) and X$^2$ is O;
- (b.) X$^1$ is N and X$^2$ is O; or
- (c.) X$^1$ is N and X$^2$ is CH$_2$; and the remaining variables are as described in embodiment no. 1.

In embodiment no. 3, the invention provides a compound of Formula (I), wherein
X$^1$ is C(R$^2$) and X$^2$ is O. and
the remaining variables are as described in embodiment no. 1.

In embodiment no. 4, the invention provides a compound of Formula (I), wherein R$^3$ is other than —C(R$^a$)$_2$N(H)C(O)R$^d$, —C(R$^a$)$_2$N(H)S(O)$_2$R$^d$, or —(C(R$^a$)$_2$)$_2$CO$_2$R$^c$, and the remaining variables are as described in embodiment no. 1.

In embodiment no. 5, the invention provides a compound of Formula (I), wherein R$^3$ is a group of the formula —(C(R$^a$)$_2$)$_{n1}$N(H)S(O)$_2$N(R$^b$)$_2$ and the remaining variables are as described in embodiment no. 1.

In embodiment no. 6, the invention provides a compound of Formula (I), wherein R$^3$ is as described in embodiment no. 5, the subscript n1 is 1, and the remaining variables are as described in embodiment no. 1.

In embodiment no. 7, the invention provides a compound of Formula (I), wherein R$^3$ is as described in embodiment no. 5, the subscript n1 is 1, and each R$^b$ is independently:
- (i.) H;
- (ii.) C$_1$-C$_4$ alkyl, wherein said C$_1$-C$_4$ alkyl is unsubstituted or substituted by 1 to 3 fluoro;
- (iii.) —C$^c$;

alternatively, two R$^b$ together with the N atom to which they are attached form a 5- to 6-membered heterocyclyl, wherein said heterocyclyl is selected from the group consisting of pyrrolidinyl, piperidinyl, and morpholinyl; wherein said heterocyclyl is unsubstituted or substituted by 1 to 2 moieties independently selected from the group consisting of C$_1$-C$_6$ alkyl, C$_1$-C$_3$ alkoxy, fluoro, hydroxyl, oxo, cyano, amino, C$_1$-C$_3$ alkylamino, and C$_1$-C$_3$ dialkylamino; and ring C$^C$ is C$_3$-C$_6$ cycloalkyl;
wherein ring C$^C$ is unsubstituted or independently substituted by 1 to 2 C$_1$-C$_6$ alkyl, C$_1$-C$_3$ alkoxy, halo, hydroxyl, oxo, cyano, amino, C$_1$-C$_3$ alkylamino, or C$_1$-C$_3$ dialkylamino;

and the remaining variables are as described in embodiment no. 1.

In embodiment no. 8, the invention provides a compound of Formula (I), wherein Cy is a group of the formula

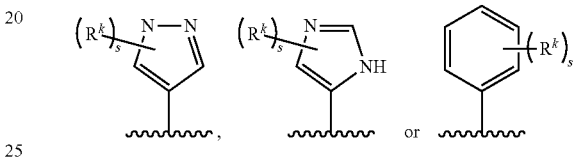

wherein the subscript s is 0, 1, 2, or 3; and the remaining variables are as described in embodiment no. 1.

In embodiment no. 9, the invention provides a compound of Formula (I), wherein Cy is a group of the formula

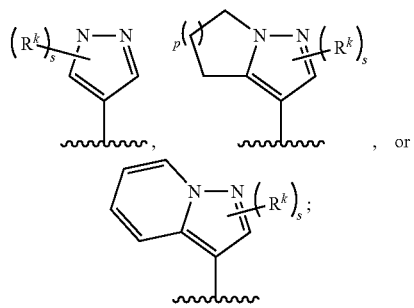

wherein
the subscript p is 1 or 2;
the subscript s is 0, 1, or 2; and the remaining variables are as described in embodiment no. 1.

In embodiment no. 10, the invention provides a compound of Formula (I), wherein Cy is

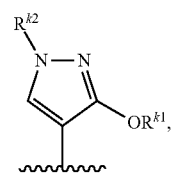

wherein
R$^{k1}$ is C$_1$-C$_6$ alkyl or CH$_2$CH$_2$OH;
R$^{k2}$ is C$_1$-C$_3$ alkyl or CHF$_2$; and the remaining variables are as described in embodiment no. 1.

In embodiment no. 11, the invention provides a compound of Formula (I), wherein Cy is

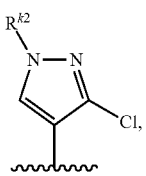

wherein $R^{k2}$ is $C_1$-$C_3$ alkyl or $CHF_2$; and the remaining variables are as described in embodiment no. 1.

In embodiment no. 12, the invention provides a compound of Formula (I), wherein Cy is a group of the formula:

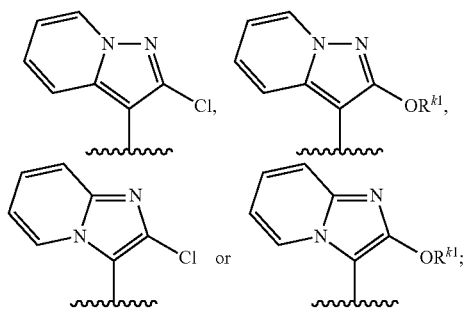

wherein
$R^{k1}$ is $C_1$-$C_6$ alkyl or $CH_2CH_2OH$; and the remaining variables are as described in embodiment no. 1.

In embodiment no. 13, the invention provides a compound of Formula (I), wherein

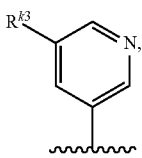

wherein $R^{k3}$ is $C_1$-$C_3$ alkyl or $C_1$-$C_3$ fluoroalkyl; and the remaining variables are as described in embodiment no. 1.

In embodiment no. 14, the invention provides a compound of Formula (I), wherein $R^4$ is a group of the formula

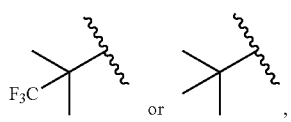

and the remaining variables are as described in embodiment no. 1.

In embodiment no. 15, the invention provides a compound of Formula (I), wherein $R^1$ is H or methyl, and the remaining variables are as described in embodiment no. 1.

In embodiment no. 16, the invention provides a compound of Formula (I), wherein:
$X^1$ and $X^2$ are as described in embodiment no. 2;
$R^1$ is as described in embodiment no. 15;
$R^2$ is H;
$R^3$ is as described in embodiment no. 4;
$R^4$ is as described in embodiment no. 14; and
Cy is as described in any one of embodiments nos. 8-13.

In embodiment no. 17, the invention provides a compound of Formula (I), wherein:
$X^1$ and $X^2$ are as described in embodiment no. 2;
$R^1$ is as described in embodiment no. 15;
$R^2$ is H;
$R^3$ is as described in embodiment no. 6;
$R^4$ is as described in embodiment no. 14; and
Cy is as described in any one of embodiments nos. 8-13.

In embodiment no. 18, the invention provides a compound of Formula (I), wherein $R^b$ is as described in embodiment no. 7; and $R^1$, $R^2$, $R^3$, $R^4$, and Cy are as described in embodiment no. 17.

In embodiment no. 19, the invention provides a compound of Formula (I), wherein $X^1$ and $X^2$ are as described in embodiment no. 3, and $R^1$, $R^2$, $R^3$, $R^4$, and Cy are as described in embodiment no. 16.

In embodiment no. 20, the invention provides a compound of Formula (I), wherein $X^1$ and $X^2$ are as described in embodiment no. 3, and $R^1$, $R^2$, $R^3$, $R^4$, and Cy are as described in embodiment no. 17.

In embodiment no. 21, the invention provides a compound of Formula (I), wherein $X^1$ and $X^2$ are as described in embodiment no. 3,
$R^3$ is as described in embodiment no. 7; and
$R^1$, $R^2$, $R^4$, and Cy are as described in embodiment no. 17.

In embodiment no. 22, the invention provides a compound of Formula (I), wherein Cy is as described in embodiment no. 8;
$X^1$ and $X^2$ are as described in embodiment no. 3; and
$R^1$, $R^2$, $R^3$, and $R^4$ are as described in embodiment no. 17.

In embodiment no. 23, the invention provides a compound as set forth in any one of embodiment nos. 1-15, wherein $R^2$ is H.

In embodiment no. 24, the invention provides a compound as set forth in any one of embodiment nos. 1-23, wherein the compound of Formula (I) has the Formula (IA):

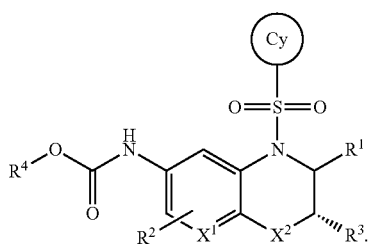

(IA)

In embodiment no. 25, the invention provides a compound of the Formula (I) wherein;
$X^1$ is C(H);
$X^2$ is $CH_2$;
$R^1$ is H;
$R^2$ is H;
$R^3$ is:
  (a.) H;
  (b.) —$CH_2N(H)C(O)CH_3$; and
  (c.) —$(CH_2)_3CO_2H$;
$R^4$ is as described in embodiment no. 14;
Cy is phenyl, pyrazolyl, or pyridyl, wherein Cy is unsubstituted or substituted by 1 or 2 $R^k$ moieties selected from the group consisting of $C_1$-$C_3$ alkyl, $C_1$-$C_3$ alkoxy, trifluoromethyl, halo, and —$CH_2CH_2OH$.

In embodiment no. 26, the invention provides a compound of the Formula (I) wherein;
$X^1$ is N;
$X^2$ is $CH_2$;
$R^1$ is H or methyl;
$R^2$ is H;
$R^3$ is:
(a.) H;
(b.) —N(H)C(O)O—($C_1$-$C_6$ alkyl);
(c.) —$CH_2OH$;
(d.) —$CH_2S(O)_2CH_2CH_3$; or
(e.) a group of the formula

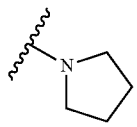 [SMILES: *N1CCCC1]

which is unsubstituted or substituted by oxo or hydroxyl;
$R^4$ is:
(a.) $C_1$-$C_8$ alkyl, wherein said $C_1$-$C_8$ alkyl of R4 is unsubstituted or substituted by 1 to 3 fluoro; or
(b.) —$CH_2$-phenyl; and
Cy is phenyl or pyrazolyl, wherein Cy is unsubstituted or substituted by 1 or 2 $R^k$ moieties selected from the group consisting of $C_1$-$C_3$ alkyl, $C_1$-$C_3$ fluoroalkyl, cyano, and halo.

In embodiment no. 27, the invention provides a compound of the Formula (I) wherein;
$X^1$ is C(H);
$X^2$ is O;
$R^1$ is H;
$R^2$ is H;
$R^3$ is:
(a.) —$CH_2N(H)S(O)_2N(R^b)_2$; or
(b.) a group of the formula

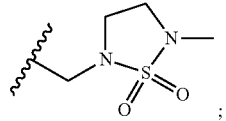 [SMILES: *CN1CCN(C)S1(=O)=O]

$R^b$ is as set forth in embodiment no. 1;
$R^4$ is as described in embodiment no. 14;
Cy is phenyl or pyrazolyl, wherein Cy is unsubstituted or substituted by 1 or 2 $R^k$ moieties selected from the group consisting of $C_1$-$C_3$ alkyl, $C_1$-$C_3$ alkoxy, trifluoromethyl, halo, and —$CH_2CH_2OH$.

In embodiment no. 28, the invention provides a compound of the Formula (I) wherein;
$X^1$ is C(H);
$X^2$ is O;
$R^1$ is methyl;
$R^2$ is H;
$R^3$ is:
(a.) H;
(b.) —C(H)($R^a$)N(H)C(O)O$R^d$; or
(c.) —$CH_2N(H)S(O)_2N(R^b)_2$;
$R^b$ and $R^d$ are as described in embodiment no. 1;

$R^4$ is as described in embodiment no. 14; and
Cy is phenyl or pyrazolyl, wherein Cy is unsubstituted or substituted by 1 or 2 $R^k$ moieties selected from the group consisting of $C_1$-$C_3$ alkyl, $C_1$-$C_3$ alkoxy, trifluoromethyl, halo, and —$CH_2CH_2OH$.

In embodiment no. 29, the invention provides a compound of the Formula (I) wherein;
$X^1$ is C(H);
$X^2$ is O;
$R^1$ is H;
$R^2$ is H;
$R^3$ is:
(a.) —$CH_2N(H)C(O)N(R^b)_2$; or
(b.) —$CH_2N(H)C(O)OR^d$;
$R^b$ and $R^d$ are as described in embodiment no. 1;
$R^4$ is as described in embodiment no. 14; and
Cy is phenyl, pyrazolyl, or pyridyl, wherein Cy is unsubstituted or substituted by 1 or 2 $R^k$ moieties selected from the group consisting of $C_1$-$C_3$ alkyl, $C_1$-$C_3$ alkoxy, trifluoromethyl, halo, and —$CH_2CH_2OH$.

In embodiment no. 30, the compound is selected from any one of the compounds described in Examples 1-121 (or a pharmaceutically acceptable salt thereof).

In embodiment no. 31, the compound is selected from any one of the following compounds (or a pharmaceutically acceptable salt thereof):
(R)-tert-butyl (2-(hydroxymethyl)-4-((3-(trifluoromethyl)phenyl)sulfonyl)-3,4-dihydro-2H-benzo[b][1,4]oxazin-6-yl)carbamate;
(R)-tert-butyl (4-((5-bromo-2-chloropyridin-3-yl)sulfonyl)-2-(hydroxymethyl)-3,4-dihydro-2H-benzo[b][1,4]oxazin-6-yl)carbamate;
(R)-4-((6-(((tert-butoxycarbonyl)amino)-2-(hydroxymethyl)-2H-benzo[b][1,4]oxazin-4(3H)-yl)sulfonyl)-1-(difluoromethyl)-3-methyl-1H-pyrazol-2-e;
[(R)-4-((3-chloro-benzenesulfonyl)-2-hydroxymethyl-3,4-dihydro-2H-benzo[1,4]oxazin-6-yl]-carbamic acid tert-butyl ester;
(R)-tert-butyl (4-((5-bromopyridin-3-yl)sulfonyl)-2-(hydroxymethyl)-3,4-dihydro-2H-benzo[b][1,4]oxazin-6-yl)carbamate;
(R)-tert-butyl (2-(hydroxymethyl)-4-((1-methyl-1H-pyrazol-4-yl)sulfonyl)-3,4-dihydro-2H-benzo[b][1,4]oxazin-6-yl)carbamate;
(R)-tert-butyl (2-(hydroxymethyl)-4-((3-(methylsulfonyl)phenyl)sulfonyl)-3,4-dihydro-2H-benzo[b][1,4]oxazin-6-yl)carbamate;
(R)-tert-butyl (4-((2-chloro-5-methylpyridin-3-yl)sulfonyl)-2-(hydroxymethyl)-3,4-dihydro-2H-benzo[b][1,4]oxazin-6-yl)carbamate;
(R)-tert-butyl (4-((3-cyanophenyl)sulfonyl)-2-(hydroxymethyl)-3,4-dihydro-2H-benzo[b][1,4]oxazin-6-yl)carbamate;
(R)-tert-butyl (2-(hydroxymethyl)-4-((5-methyl-2-oxo-1,2-dihydropyridin-3-yl)sulfonyl)-3,4-dihydro-2H-benzo[b][1,4]oxazin-6-yl)carbamate;
(R)-tert-butyl (4-((4-fluorophenyl)sulfonyl)-2-(2-hydroxypropan-2-yl)-3,4-dihydro-2H-benzo[b][1,4]oxazin-6-yl)carbamate;
(S)-tert-butyl (4-((4-fluorophenyl)sulfonyl)-2-(2-hydroxypropan-2-yl)-3,4-dihydro-2H-benzo[b][1,4]oxazin-6-yl)carbamate;
(R and S)-1,1,1-trifluoro-2-methylpropan-2-yl 4-(3,4-difluorophenylsulfonyl)-2-(2,2,2-trifluoroacetyl)-3,4-dihydro-2H-benzo[b][1,4]oxazin-6-ylcarbamate;

(R and S)-1,1,1-trifluoro-2-methylpropan-2-yl (4-((3-chloro-1-ethyl-1H-pyrazol-4-yl)sulfonyl)-2-(2,2,2-trifluoroacetyl)-3,4-dihydro-2H-benzo[b][1,4]oxazin-6-yl)carbamate;

(S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(((benzyloxy)carbonyl)aminomethyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-(tetrahydro-2H-pyran-4-yl)ureido)methyl)-3,4-dihydro-2H-benzo[b][1,4]oxazin-6-yl)carbamate;

(S)-tert-butyl (2-(((benzyloxy)carbonyl)aminomethyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (2-(((benzyloxy)carbonyl)aminomethyl)-4-((4-fluorophenyl)sulfonyl)-3,4-dihydro-2H-benzo[b][1,4]oxazin-6-yl)carbamate;

(S)-tert-butyl (2-(((methoxy)carbonyl)aminomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-cyclopropylureido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-cyclobutylureido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-(tert-butyl)ureido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-isopropylureido)methyl)-3,4-dihydro-2H-benzo[b][1,4]oxazin-6-yl)carbamate;

(S)-1,1,1-trifluoro-2-methylpropan-2-yl(4-((4-fluorophenyl)sulfonyl)-2-((3-(thiophen-3-yl)ureido)methyl)-3,4-dihydro-2H-benzo[b][1,4]oxazin-6-yl)carbamate;

(S)-1,1,1-trifluoro-2-methylpropan-2-yl (2-((3-ethylureido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-cyclohexylureido)methyl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (4-((3-chloro-4-fluorophenyl)sulfonyl)-2-((5-methyl-1,1-dioxido-1,2,5-thiadiazolidin-2-yl)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((morpholine-4-sulfonamido)methyl)-3,4-dihydro-2H-benzo[b][1,4]oxazin-6-yl)carbamate;

(S)-1,1,1-trifluoro-2-methylpropan-2-yl (2-(((N,N-diethylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(((N,N-dimethylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl(4-((4-fluorophenyl)sulfonyl)-2-((piperidine-1-sulfonamido)methyl)-3,4-dihydro-2H-benzo[b][1,4]oxazin-6-yl)carbamate;

(S)-1,1,1-trifluoro-2-methylpropan-2-yl(4-((4-fluorophenyl)sulfonyl)-2-((pyrrolidine-1-sulfonamido)methyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((2-methylpiperidine-1-sulfonamido)methyl)-3,4-dihydro-2H-benzo[b][1,4]oxazin-6-yl)carbamate;

1,1,1-trifluoro-2-methylpropan-2-yl((2S)-2-((2,6-dimethylmorpholine-4-sulfonamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((4-methylpiperidine-1-sulfonamido)methyl)-3,4-dihydro-2H-benzo[b][1,4]oxazin-6-yl)carbamate;

1,1,1-trifluoro-2-methylpropan-2-yl((2S)-4-((4-fluorophenyl)sulfonyl)-2-((2-methylmorpholine-4-sulfonamido)methyl)-3,4-dihydro-2H-benzo[b][1,4]oxazin-6-yl)carbamate;

(S)-1,1,1-trifluoro-2-methylpropan-2-yl (2-(((N-cyclopropyl-N-methylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl(2-(((N-cyclopentyl-N-methylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(((N-methyl-N-(2,2,2-trifluoroethyl)sulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((piperidine-1-sulfonamido)methyl)-3,4-dihydro-2H-benzo[b][1,4]oxazin-6-yl)carbamate;

1,1,1-trifluoro-2-methylpropan-2-yl((2S)-4-((3-chloro-4-fluorophenyl)sulfonyl)-2-(2-methylpiperidine-1-sulfonamido)methyl)-3,4-dihydro-2H-benzo[b][1,4]oxazin-6-yl)carbamate;

1,1,1-trifluoro-2-methylpropan-2-yl((2S)-4-((3-chloro-4-fluorophenyl)sulfonyl)-2-((2-methylmorpholine-4-sulfonamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-methyl-N-(2,2,2-trifluoroethyl)sulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-isobutyl-N-methylsulfamoyl)amino)methyl)-3,4-dihydro-2H-benzo[b][1,4]oxazin-6-yl)carbamate;

1,1,1-trifluoro-2-methylpropan-2-yl((2S)-4-((3-chloro-4-fluorophenyl)sulfonyl)-2-((3-methylpyrrolidine-1-sulfonamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-ethylsulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-isopropylsulfamoyl)amino)methyl)-3,4-dihydro-2H-benzo[b][1,4]oxazin-6-yl)carbamate;

(S)-1,1,1-trifluoro-2-methylpropan-2-yl (2-(((N-ethylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl(4-((4-fluorophenyl)sulfonyl)-2-(((N-isopropylsulfamoyl)amino)methyl)-3,4-dihydro-2H-benzo[b][1,4]oxazin-6-yl)carbamate;

(S)-1,1,1-trifluoro-2-methylpropan-2-yl (2-(((N-(tert-butyl)sulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((3,4-difluorophenyl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((3-ethoxy-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((1-ethyl-3-methyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((3-(2,2-difluoroethoxy)-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((1-(2,2-difluoroethyl)-3-ethoxy-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((1-(difluoromethyl)-3-methyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((2-methoxy-5,6-dihydro-4H-pyrrolo[1,2-b]pyrazol-3-yl)sulfonyl)-2-(((N-methylsulfamoyl)amino)methyl)-3,4-dihydro-2H-benzo[b][1,4]oxazin-6-yl)carbamate;

(R)-tert-butyl (2-((pyridin-2-ylthio)methyl)-4-((3-(trifluoromethyl)phenyl)sulfonyl)-3,4-dihydro-2H-benzo[b][1,4]oxazin-6-yl)carbamate;

(R)-tert-butyl (2-((cyclopentylthio)methyl)-4-((3-(trifluoromethyl)phenyl)sulfonyl)-3,4-dihydro-2H-benzo[b][1,4]oxazin-6-yl)carbamate;

(R)-tert-butyl (2-((benzylthio)methyl)-4-((3-(trifluoromethyl)phenyl)sulfonyl)-3,4-dihydro-2H-benzo[b][1,4]oxazin-6-yl)carbamate;

(R)-tert-butyl (2-((tert-butylthio)methyl)-4-((3-(trifluoromethyl)phenyl)sulfonyl)-3,4-dihydro-2H-benzo[b][1,4]oxazin-6-yl)carbamate;

(R)-tert-butyl (2-(((4,5-dimethyl-1H-imidazol-2-yl)thio)methyl)-4-((3-(trifluoromethyl)phenyl)sulfonyl)-3,4-dihydro-2H-benzo[b][1,4]oxazin-6-yl)carbamate;

(R)-tert-butyl (2-((phenylthio)methyl)-4-((3-(trifluoromethyl)phenyl)sulfonyl)-3,4-dihydro-2H-benzo[b][1,4]oxazin-6-yl)carbamate;

(R)-tert-butyl (2-((methylthio)methyl)-4-((3-(trifluoromethyl)phenyl)sulfonyl)-3,4-dihydro-2H-benzo[b][1,4]oxazin-6-yl)carbamate;

(R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((tert-butylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-(((4,5-dimethyl-1H-imidazol-2-yl)sulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((phenylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((cyclopentylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((benzylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((methylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((N-cyclopropylsulfamoyl)methyl)-4-((3-(trifluoromethyl)phenyl)sulfonyl)-3,4-dihydro-2H-benzo[b][1,4]oxazin-6-yl)carbamate;

(R)-tert-butyl (2-((N-(2,2,2-trifluoroethyl)sulfamoyl)methyl)-4-((3-(trifluoromethyl)phenyl)sulfonyl)-3,4-dihydro-2H-benzo[b][1,4]oxazin-6-yl)carbamate;

(R)-tert-butyl (2-((morpholinosulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((N-ethylsulfamoyl)methyl)-4-((3-(trifluoromethyl)phenyl)sulfonyl)-3,4-dihydro-2H-benzo[b][1,4]oxazin-6-yl)carbamate;

(R)-tert-butyl (2-((N,N-dimethylsulfamoyl)methyl)-4-((3-(trifluoromethyl)phenyl)sulfonyl)-3,4-dihydro-2H-benzo[b][1,4]oxazin-6-yl)carbamate;

1,1,1-trifluoro-2-methylpropan-2-yl (S)-(4-((3-ethoxy-1-ethyl-1H-pyrazol-4-yl)sulfonyl)-2-methyl-3,4-dihydro-2H-benzo[b][1,4]oxazin-6-yl)carbamate;

[(2S,3S and 2R,3R)-4-(3-cyano-benzenesulfonyl)-2-hydroxymethyl-3-methyl-3,4-dihydro-2H-benzo[1,4]oxazin-6-yl]-carbamic acid 2,2-dimethyl-propyl ester;

(S)-1,1,1-trifluoro-2-methylpropan-2-yl (4-((4-fluorophenyl)sulfonyl)-3-methyl-3,4-dihydro-2H-benzo[b][1,4]oxazin-6-yl)carbamate;

(R)-1,1,1-trifluoro-2-methylpropan-2-yl(4-((4-fluorophenyl)sulfonyl)-3-methyl-3,4-dihydro-2H-benzo[b][1,4]oxazin-6-yl)carbamate;

(R)-1,1,1-trifluoro-2-methylpropan-2-yl(4-((4-fluorophenyl)sulfonyl)-3-(hydroxymethyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-3-(hydroxymethyl)-3,4-dihydro-2H-benzo[b][1,4]oxazin-6-yl)carbamate;

[(S)-4-(3-cyano-benzenesulfonyl)-2-(2,4-dioxo-oxazolidin-3-ylmethyl)-3,4-dihydro-2H-benzo[1,4]oxazin-6-yl]-carbamic acid tert-butyl ester;

(1S,2R,4R)-bicyclo[2.2.1]heptan-2-yl ((S)-4-((3-cyanophenyl)sulfonyl)-2-((2,4-dioxooxazolidin-3-yl)methyl)-3,4-dihydro-2H-benzo[b][1,4]oxazin-6-yl)carbamate;

(S)-neopentyl (4-((3-cyanophenyl)sulfonyl)-2-((2,4-dioxooxazolidin-3-yl)methyl)-3,4-dihydro-2H-benzo[b][1,4]oxazin-6-yl)carbamate;

(1S,4R)-bicyclo[2.2.1]heptan-2-yl((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

(S)-tert-butyl (2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

(S)-neopentyl (2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

(tetrahydro-2H-pyran-2-yl)methyl ((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

(2S)-bicyclo[2.2.1]heptan-2-yl((S)-4-((3-cyanophenyl)sulfonyl)-2-((2,4-dioxooxazolidin-3-yl)methyl)-3,4-dihydro-2H-benzo[b][1,4]oxazin-6-yl)carbamate;

(2S)-bicyclo[2.2.1]heptan-2-yl((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

[(S)-4-(3-cyano-benzenesulfonyl)-2-dimethylaminomethyl-3,4-dihydro-2H-benzo[1,4]oxazin-6-yl]-carbamic acid tert-butyl ester;

[(S)-4-(3-cyano-benzenesulfonyl)-2-dimethylaminomethyl-3,4-dihydro-2H-benzo[1,4]oxazin-6-yl]-carbamic acid 2,2-dimethyl-propyl ester;

(1S,4R)-bicyclo[2.2.1]heptan-2-yl((S)-4-((3-cyanophenyl)sulfonyl)-2-((dimethylamino)methyl)-3,4-dihydro-2H-benzo[b][1,4]oxazin-6-yl)carbamate;

(1S,2R,4R)-bicyclo[2.2.1]heptan-2-yl((S)-4-((3-cyanophenyl)sulfonyl)-2-((dimethylamino)methyl)-3,4-dihydro-2H-benzo[b][1,4]oxazin-6-yl)carbamate;

(S)-neopentyl (2-((dimethylamino)methyl)-4-((1-methyl-1H-pyrazol-4-yl)sulfonyl)-3,4-dihydro-2H-benzo[b][1,4]oxazin-6-yl)carbamate;

bicyclo[2.2.1]heptan-2-yl ((S)-2-((dimethylamino)methyl)-4-((1-methyl-1H-pyrazol-4-yl)sulfonyl)-3,4-dihydro-2H-benzo[b][1,4]oxazin-6-yl)carbamate;

(2S)-bicyclo[2.2.1]heptan-2-yl ((S)-2-((dimethylamino)methyl)-4-((1-methyl-1H-pyrazol-4-yl)sulfonyl)-3,4-dihydro-2H-benzo[b][1,4]oxazin-6-yl)carbamate;

(S)-tetrahydro-2H-pyran-4-yl(4-((3-cyanophenyl)sulfonyl)-2-((dimethylamino)methyl)-3,4-dihydro-2H-benzo[b][1,4]oxazin-6-yl)carbamate;

(S)-methyl 2-(6-(((tert-butoxycarbonyl)amino)-4-((3-(trifluoromethyl)phenyl)sulfonyl)-3,4-dihydro-2H-benzo[b][1,4]oxazin-2-yl)acetate;

(S)-methyl 2-(6-(((tert-butoxycarbonyl)amino)-4-((3-chloro-4-fluorophenyl)sulfonyl)-3,4-dihydro-2H-benzo[b][1,4]oxazin-2-yl)acetate;

(S)-methyl 2-(6-(((tert-butoxycarbonyl)amino)-4-((4-fluoro-3-(trifluoromethyl)phenyl)sulfonyl)-3,4-dihydro-2H-benzo[b][1,4]oxazin-2-yl)acetate;

(S)-methyl 2-(6-(((tert-butoxycarbonyl)amino)-4-((4-fluoro-3-methoxyphenyl)sulfonyl)-3,4-dihydro-2H-benzo[b][1,4]oxazin-2-yl)acetate;

(R)-methyl 2-(6-(((tert-butoxycarbonyl)amino)-4-((3-(trifluoromethyl)phenyl)sulfonyl)-3,4-dihydro-2H-benzo[b][1,4]oxazin-2-yl)acetate;

(S)-methyl 2-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)acetate;

[(S)-6-tert-butoxycarbonylamino-4-(1-difluoromethyl-3-methyl-1H-pyrazole-4-sulfonyl)-3,4-dihydro-2H-benzo[1,4]oxazin-2-yl]-acetic acid;

(S)-2-(6-(((tert-butoxycarbonyl)amino)-4-((4-fluoro-3-methoxyphenyl)sulfonyl)-3,4-dihydro-2H-benzo[b][1,4]oxazin-2-yl)acetic acid;

(S)-2-(6-(((tert-butoxycarbonyl)amino)-4-((4-fluoro-3-(trifluoromethyl)phenyl)sulfonyl)-3,4-dihydro-2H-benzo[b][1,4]oxazin-2-yl)acetic acid;

(S)-2-(6-(((tert-butoxycarbonyl)amino)-4-((3-chloro-4-fluorophenyl)sulfonyl)-3,4-dihydro-2H-benzo[b][1,4]oxazin-2-yl)acetic acid;

(S)-2-(6-(((tert-butoxycarbonyl)amino)-4-((3-(trifluoromethyl)phenyl)sulfonyl)-3,4-dihydro-2H-benzo[b][1,4]oxazin-2-yl)acetic acid;

(S)-2-(6-(((tert-butoxycarbonyl)amino)-4-((4-fluorophenyl)sulfonyl)-3,4-dihydro-2H-benzo[b][1,4]oxazin-2-yl)acetic acid;

(S)-2-(4-((4-fluorophenyl)sulfonyl)-6-(((neopentyloxy)carbonyl)amino)-3,4-dihydro-2H-benzo[b][1,4]oxazin-2-yl)acetic acid;

(S)-2-(6-(((tert-butoxycarbonyl)amino)-4-((3-chlorophenyl)sulfonyl)-3,4-dihydro-2H-benzo[b][1,4]oxazin-2-yl)acetic acid;

(S)-2-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)acetic acid;

(R)-6-(((tert-butoxycarbonyl)amino)-4-((3-chloro-4-fluorophenyl)sulfonyl)-3,4-dihydro-2H-benzo[b][1,4]oxazine-2-carboxylic acid;

(R)-6-(((tert-butoxycarbonyl)amino)-4-((4-fluorophenyl)sulfonyl)-3,4-dihydro-2H-benzo[b][1,4]oxazine-2-carboxylic acid;

(R)-6-(((tert-butoxycarbonyl)amino)-4-((4-fluoro-3-methoxyphenyl)sulfonyl)-3,4-dihydro-2H-benzo[b][1,4]oxazine-2-carboxylic acid;

(R)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazine-2-carboxylic acid;

(R)-6-(((tert-butoxycarbonyl)amino)-4-((1-(difluoromethyl)-3-methyl-1H-pyrazol-4-yl)sulfonyl)-3,4-dihydro-2H-benzo[b][1,4]oxazine-2-carboxylic acid;

(R)-6-(((tert-butoxycarbonyl)amino)-4-((4-fluoro-3-(trifluoromethyl)phenyl)sulfonyl)-3,4-dihydro-2H-benzo[b][1,4]oxazine-2-carboxylic acid;

[(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid tert-butyl ester;

[(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid 1,2,2-trimethyl-propyl ester;

(S)-tert-butyl (2-(2-amino-2-oxoethyl)-4-((4-fluorophenyl)sulfonyl)-3,4-dihydro-2H-benzo[b][1,4]oxazin-6-yl)carbamate;

(S)-tert-butyl (2-(2-amino-2-oxoethyl)-4-((3-(trifluoromethyl)phenyl)sulfonyl)-3,4-dihydro-2H-benzo[b][1,4]oxazin-6-yl)carbamate;

(S)-tert-butyl (4-((4-fluorophenyl)sulfonyl)-2-(2-(methylamino)-2-oxoethyl)-3,4-dihydro-2H-benzo[b][1,4]oxazin-6-yl)carbamate;

(S)-tert-butyl (2-(2-(methylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(dimethylamino)-2-oxoethyl)-4-((3-(trifluoromethyl)phenyl)sulfonyl)-3,4-dihydro-2H-benzo[b][1,4]oxazin-6-yl)carbamate;

tert-butyl (2-(2-(dimethylamino)-2-oxoethyl)-4-((4-fluorophenyl)sulfonyl)-3,4-dihydro-2H-benzo[b][1,4]oxazin-6-yl)carbamate;

(R)-tert-butyl (4-((3-chloro-4-fluorophenyl)sulfonyl)-2-(2-(methylamino)-2-oxoethyl)-3,4-dihydro-2H-benzo[b][1,4]oxazin-6-yl)carbamate;

(S)-tert-butyl (4-((3-chloro-4-fluorophenyl)sulfonyl)-2-(2-(methylamino)-2-oxoethyl)-3,4-dihydro-2H-benzo[b][1,4]oxazin-6-yl)carbamate;

1,1,1-trifluoro-2-methylpropan-2-yl (4-((3-chloro-4-fluorophenyl)sulfonyl)-2-(2-(methylamino)-2-oxoethyl)-3,4-dihydro-2H-benzo[b][1,4]oxazin-6-yl)carbamate;

(R)-tert-butyl (2-(2-(oxazolidin-3-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-((cyclobutylmethyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(3,3,3-trifluoropropyl)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(isobutylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-methyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-isopropyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-((pyrazolo[1,5-a]pyridin-3-ylmethyl)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-ethyl-1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(1-methylpyrrolo[3,4-c]pyrazol-5(1H,4H,6H)-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-methyl-1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-ethyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-ethyl-5-methyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1,5-dimethyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate (S)-tert-butyl (2-(2-(((1-benzyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-3-(2-(6-((tert-butoxycarbonyl)amino)-4-((3-(trifluoromethyl)phenyl)sulfonyl)-3,4-dihydro-2H-benzo[b][1,4]oxazin-2-yl)acetamido)propanoic acid (S)-methyl 3-(2-(6-((tert-butoxycarbonyl)amino)-4-((3-(trifluoromethyl)phenyl)sulfonyl)-3,4-dihydro-2H-benzo[b][1,4]oxazin-2-yl)acetamido)propanoate;

(S)-tert-butyl (2-(2-oxo-2-((4-(trifluoromethyl)benzyl)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(benzylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-((cyclopropylmethyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(propylamino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(ethylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(oxazolidin-3-yl)-2-oxoethyl)-4-((3-(trifluoromethyl)phenyl)sulfonyl)-3,4-dihydro-2H-benzo[b][1,4]oxazin-6-yl)carbamate;

(S)-neopentyl (2-(2-(methylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((2H-tetrazol-5-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-((2-hydroxyethyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(tert-butylamino)-2-oxoethyl)-4-((3-(trifluoromethyl)phenyl)sulfonyl)-3,4-dihydro-2H-benzo[b][1,4]oxazin-6-yl)carbamate;

tert-butyl ((2S)-2-(2-(2-methylazetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(3-cyanoazetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(3-methoxyazetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(azetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(azetidin-1-yl)-2-oxoethyl)-4-((4-fluorophenyl)sulfonyl)-3,4-dihydro-2H-benzo[b][1,4]oxazin-6-yl)carbamate;

(S)-tert-butyl (2-(2-(3-methylazetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-neopentyl (2-(2-(azetidin-1-yl)-2-oxoethyl)-4-((1-(difluoromethyl)-3-methyl-1H-pyrazol-4-yl)sulfonyl)-3,4-dihydro-2H-benzo[b][1,4]oxazin-6-yl)carbamate;

(R)-tert-butyl (2-carbamoyl-4-((4-fluoro-3-(trifluoromethyl)phenyl)sulfonyl)-3,4-dihydro-2H-benzo[b][1,4]oxazin-6-yl)carbamate;

(R)-1,1,1-trifluoro-2-methylpropan-2-yl(2-carbamoyl-4-((4-fluoro-3-(trifluoromethyl)phenyl)sulfonyl)-3,4-dihydro-2H-benzo[b][1,4]oxazin-6-yl)carbamate;

(R)-tert-butyl (2-carbamoyl-4-((4-fluoro-3-methoxyphenyl)sulfonyl)-3,4-dihydro-2H-benzo[b][1,4]oxazin-6-yl)carbamate;

(R)-methyl 3-(6-((tert-butoxycarbonyl)amino)-4-((3-chloro-4-fluorophenyl)sulfonyl)-3,4-dihydro-2H-benzo[b][1,4]oxazine-2-carboxamido)propanoate;

(R)-tert-butyl (2-carbamoyl-4-((1-(difluoromethyl)-3-methyl-1H-pyrazol-4-yl)sulfonyl)-3,4-dihydro-2H-benzo[b][1,4]oxazin-6-yl)carbamate;

(R)-tert-butyl (4-((1-(difluoromethyl)-3-methyl-1H-pyrazol-4-yl)sulfonyl)-2-(dimethylcarbamoyl)-3,4-dihydro-2H-benzo[b][1,4]oxazin-6-yl)carbamate;

(R)-3-(6-((tert-butoxycarbonyl)amino)-4-((3-chloro-4-fluorophenyl)sulfonyl)-3,4-dihydro-2H-benzo[b][1,4]oxazine-2-carboxamido)propanoic acid;

tert-butyl (2-(2-cyanopropan-2-yl)-4-((4-fluorophenyl)sulfonyl)-3,4-dihydro-2H-benzo[b][1,4]oxazin-6-yl)carbamate;

(R and S) 2-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R and S)-1,1,1-trifluoro-2-methylpropan-2-yl(4-((4-fluorophenyl)sulfonyl)-2-(2-(4-methyl-5-oxo-4,5-dihydro-1H-1,2,4-triazol-3-yl)propan-2-yl)-3,4-dihydro-2H-benzo[b][1,4]oxazin-6-yl)carbamate;

(S)-tert-butyl (2-(2-oxo-2-(trifluoromethylsulfonamido)ethyl)-4-((3-(trifluoromethyl)phenyl)sulfonyl)-3,4-dihydro-2H-benzo[b][1,4]oxazin-6-yl)carbamate;

(S)-neopentyl (2-(2-(cyclopropanesulfonamido)-2-oxoethyl)-4-((3-(trifluoromethyl)phenyl)sulfonyl)-3,4-dihydro-2H-benzo[b][1,4]oxazin-6-yl)carbamate;

(S)-neopentyl (4-((1-(difluoromethyl)-3-methyl-1H-pyrazol-4-yl)sulfonyl)-2-(2-oxo-2-(trifluoromethylsulfonamido)ethyl)-3,4-dihydro-2H-benzo[b][1,4]oxazin-6-yl)carbamate;

(S)-tert-butyl (2-(2-oxo-2-(thiazole-2-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(pyridine-4-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(1,1-dimethylethylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(5-(trifluoromethyl)pyridine-2-sulfonamido)ethyl)-4-((3-(trifluoromethyl)phenyl)sulfonyl)-3,4-dihydro-2H-benzo[b][1,4]oxazin-6-yl)carbamate;

(S)-neopentyl (4-((4-fluorophenyl)sulfonyl)-2-(2-oxo-2-(trifluoromethylsulfonamido)ethyl)-3,4-dihydro-2H-benzo[b][1,4]oxazin-6-yl)carbamate;

(S)-tert-butyl (2-(2-oxo-2-(pyridine-2-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(pyridine-3-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(4-(trifluoromethyl)pyridine-2-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(1H-pyrazole-4-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(4-methylpyridine-2-sulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(2-fluoro-5-methylphenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(2-fluorophenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(2-(trifluoromethyl)phenylsulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(3-(trifluoromethyl)phenylsulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(3-fluorophenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(cyclopropanesulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(4-methylphenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(1-methylethylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(ethylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(methylsulfonamido)-2-oxoethyl)-4-((3-(trifluoromethyl)phenyl)sulfonyl)-3,4-dihydro-2H-benzo[b][1,4]oxazin-6-yl)carbamate;

(S)-neopentyl (2-(2-(cyclopropanesulfonamido)-2-oxoethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-(2-(cyclopentanesulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(2-methylphenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(4-fluorophenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(2,5-dimethylphenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(4-propylphenylsulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(6-methylpyridine-2-sulfonamido)-2-oxoethyl)-4-((3-(trifluoromethyl)phenyl)sulfonyl)-3,4-dihydro-2H-benzo[b][1,4]oxazin-6-yl)carbamate;

(S)-neopentyl (2-(2-(cyclopropanesulfonamido)-2-oxoethyl)-4-((4-fluorophenyl)sulfonyl)-3,4-dihydro-2H-benzo[b][1,4]oxazin-6-yl)carbamate;

(S)-(2-(2-(methoxyamino)-2-oxoethyl)-4-((3-(trifluoromethyl)phenyl)sulfonyl)-3,4-dihydro-2H-benzo[b][1,4]oxazin-6-yl)carbamic acid;

(S)-tert-butyl (2-(2-oxo-2-((2-(trifluoromethyl)phenoxy)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-((pyridin-3-ylmethoxy)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(((4-(trifluoromethyl)benzyl)oxy)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(((3-(trifluoromethyl)benzyl)oxy)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-((4-fluorophenoxy)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((cyclopentyloxy)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(ethoxyamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-((benzyloxy)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((4-methylbenzyl)oxy)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(isopropoxyamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(propoxyamino)ethyl)-4-((3-(trifluoromethyl)phenyl)sulfonyl)-3,4-dihydro-2H-benzo[b][1,4]oxazin-6-yl)carbamate;

(R)-tert-butyl (4-((4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate;

(R)-1,1,1-trifluoro-2-methylpropan-2-yl (4-((4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate;

(R)-tert-butyl (4-((1-(difluoromethyl)-3-methyl-1H-pyrazol-4-yl)sulfonyl)-2-(5-oxo-4,5-dihydro-1,3,4-oxadiazol-2-yl)-3,4-dihydro-2H-benzo[b][1,4]oxazin-6-yl)carbamate;

(R)-1,1,1-trifluoro-2-methylpropan-2-yl (4-((1-(difluoromethyl)-3-methyl-1H-pyrazol-4-yl)sulfonyl)-2-(5-oxo-4,5-dihydro-1,3,4-oxadiazol-2-yl)-3,4-dihydro-2H-benzo[b][1,4]oxazin-6-yl)carbamate;

(R)-tert-butyl (4-((3-chloro-4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate;

(R)-tert-butyl (4-((4-fluoro-3-(trifluoromethyl)phenyl)sulfonyl)-2-(5-oxo-4,5-dihydro-1,3,4-oxadiazol-2-yl)-3,4-dihydro-2H-benzo[b][1,4]oxazin-6-yl)carbamate;

(S)-tert-butyl (4-((4-fluorophenyl)sulfonyl)-2-((4-methyl-5-oxo-4,5-dihydro-1,3,4-oxadiazol-2-yl)methyl)-3,4-dihydro-2H-benzo[b][1,4]oxazin-6-yl)carbamate;

(S)-tert-butyl (4-((1-(difluoromethyl)-3-methyl-1H-pyrazol-4-yl)sulfonyl)-2-((4-methyl-5-oxo-4,5-dihydro-1,3,4-oxadiazol-2-yl)methyl)-3,4-dihydro-2H-benzo[b][1,4]oxazin-6-yl)carbamate;

(S)-tert-butyl (2-((4-methyl-5-oxo-4,5-dihydro-1,3,4-oxadiazol-2-yl)methyl)-4-((3-(trifluoromethyl)phenyl)sulfonyl)-3,4-dihydro-2H-benzo[b][1,4]oxazin-6-yl)carbamate;

(R)-tert-butyl (4-((4-fluorophenyl)sulfonyl)-2-(4-methyl-5-oxo-4,5-dihydro-1H-1,2,4-triazol-3-yl)-3,4-dihydro-2H-benzo[b][1,4]oxazin-6-yl)carbamate;

tert-butyl (2-(cyanomethyl)-4-((3-(trifluoromethyl)phenyl)sulfonyl)-3,4-dihydro-2H-benzo[b][1,4]oxazin-6-yl)carbamate;

tert-butyl (2-(2-hydroxypropyl)-4-((3-(trifluoromethyl)phenyl)sulfonyl)-3,4-dihydro-2H-benzo[b][1,4]oxazin-6-yl)carbamate;

(S)-tert-butyl (2-(2-amino-2-methylpropyl)-4-((3-(trifluoromethyl)phenyl) sulfonyl)-3,4-dihydro-2H-benzo[b][1,4]oxazin-6-yl)carbamate;

(S)-tert-butyl (2-(2-acetamido-2-methylpropyl)-4-((3-(trifluoromethyl)phenyl)sulfonyl)-3,4-dihydro-2H-benzo[b][1,4]oxazin-6-yl)carbamate;

(S)-tert-butyl (2-(2-propionamidoethyl)-4-((3-(trifluoromethyl)phenyl)sulfonyl)-3,4-dihydro-2H-benzo[b][1,4]oxazin-6-yl)carbamate;

tert-butyl ((2S)-2-(2-(2-hydroxypropanamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(oxetane-3-carboxamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-isobutyramidoethyl)-4-((3-(trifluoromethyl)phenyl)sulfonyl)-3,4-dihydro-2H-benzo[b][1,4]oxazin-6-yl)carbamate;

(S)-tert-butyl (2-(2-acetamidoethyl)-4-((3-(trifluoromethyl)phenyl)sulfonyl)-3,4-dihydro-2H-benzo[b][1,4]oxazin-6-yl)carbamate;

(S)-tert-butyl (2-(2-(cyclopropanecarboxamido)ethyl)-4-((3-(trifluoromethyl)phenyl)sulfonyl)-3,4-dihydro-2H-benzo[b][1,4]oxazin-6-yl)carbamate;

(S)-tert-butyl (4-((4-fluorophenyl)sulfonyl)-2-(2-propionamidoethyl)-3,4-dihydro-2H-benzo[b][1,4]oxazin-6-yl)carbamate;

(S)-tert-butyl (2-(2-acetamidoethyl)-4-((4-fluorophenyl)sulfonyl)-3,4-dihydro-2H-benzo[b][1,4]oxazin-6-yl)carbamate;

tert-butyl ((2S)-4-((4-fluorophenyl)sulfonyl)-2-(2-(2-hydroxypropanamido)ethyl)-3,4-dihydro-2H-benzo[b][1,4]oxazin-6-yl)carbamate;

(S)-tert-butyl (2-(2-(cyclopropanecarboxamido)ethyl)-4-((4-fluorophenyl)sulfonyl)-3,4-dihydro-2H-benzo[b][1,4]oxazin-6-yl)carbamate;

(S)-neopentyl (4-((4-fluorophenyl)sulfonyl)-2-(2-propionamidoethyl)-3,4-dihydro-2H-benzo[b][1,4]oxazin-6-yl)carbamate;

(S)-neopentyl (2-(2-acetamidoethyl)-4-((4-fluorophenyl)sulfonyl)-3,4-dihydro-2H-benzo[b][1,4]oxazin-6-yl)carbamate;

(S)-neopentyl (2-(2-(cyclopropanecarboxamido)ethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-amino-2-methylpropyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-amino-2-methylpropyl)-4-((3-(trifluoromethyl)phenyl)sulfonyl)-3,4-dihydro-2H-benzo[b][1,4]oxazin-6-yl)carbamate;

(R)-1,1,1-trifluoro-2-methylpropan-2-yl(2-(2-(2-oxopyrrolidin-1-yl)ethyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-(2-oxopyrrolidin-1-yl)ethyl)-4-((3-(trifluoromethyl)phenyl)sulfonyl)-3,4-dihydro-2H-benzo[b][1,4]oxazin-6-yl)carbamate;

(S)-tert-butyl (2-(2-acetamido-2-methylpropyl)-4-((3-chloro-4-fluorophenyl) sulfonyl)-3,4-dihydro-2H-benzo[b][1,4]oxazin-6-yl)carbamate;

(S)-tert-butyl (2-(2-acetamido-2-methylpropyl)-4-((3,4-difluorophenyl)sulfonyl)-3,4-dihydro-2H-benzo[b][1,4]oxazin-6-yl)carbamate;

(S)-tert-butyl (2-(2-acetamido-2-methylpropyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-(2-acetamido-2-methylpropyl)-4-((1-(difluoromethyl)-5-methyl-1H-pyrazol-4-yl)sulfonyl)-3,4-dihydro-2H-benzo[b][1,4]oxazin-6-yl)carbamate;

(S)-tert-butyl (2-(2-acetamido-2-methylpropyl)-4-((4-fluorophenyl)sulfonyl)-3,4-dihydro-2H-benzo[b][1,4]oxazin-6-yl)carbamate;

(R)-tert-butyl (2-(2-acetamido-2-methylpropyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((1-(difluoromethyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(2-methyl-2-(methylsulfonamido)propyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3,4-difluorophenyl)sulfonyl)-3,4-dihydro-2H-benzo[b][1,4]oxazin-6-yl)carbamate;

(S)-1,1,1-trifluoro-2-methylpropan-2-yl(4-((3-chloro-4-fluorophenyl)sulfonyl)-2-(2-methyl-2-(methylsulfonamido)propyl)-3,4-dihydro-2H-benzo[b][1,4]oxazin-6-yl) carbamate;

(S)-1,1,1-trifluoro-2-methylpropan-2-yl (4-((3,4-difluorophenyl)sulfonyl)-2-(2-methyl-2-(methylsulfonamido)propyl)-3,4-dihydro-2H-benzo[b][1,4]oxazin-6-yl)carbamate;

(S)-1,1,1-trifluoro-2-methylpropan-2-yl (2-(2-(cyclopropanesulfonamido)-2-methylpropyl)-4-((3,4-difluorophenyl)sulfonyl)-3,4-dihydro-2H-benzo[b][1,4]oxazin-6-yl)carbamate;

(S)-1,1,1-trifluoro-2-methylpropan-2-yl (2-(2-methyl-2-(methylsulfonamido)propyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-(cyclopropanesulfonamido)-2-methylpropyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(2-methyl-2-(methylsulfonamido)propyl)-3,4-dihydro-2H-benzo[b][1,4]oxazin-6-yl)carbamate;

(S)-1,1,1-trifluoro-2-methylpropan-2-yl (2-(2-(cyclopropanesulfonamido)-2-methylpropyl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl(2-(2-(cyclopropanesulfonamido)-2-methylpropyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-methyl-2-(trifluoromethylsulfonamido)propyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-(2-(dimethylamino)-2-oxoacetamido)-2-methylpropyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((4-fluoro-3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl(2-(2-acetamido-2-methylpropyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-methoxy-1,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((1-(difluoromethyl)-3-ethoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-(difluoromethoxy)-1-ethyl-1H-pyrazol-4-yl)sulfonyl)-3,4-dihydro-2H-benzo[b][1,4]oxazin-6-yl)carbamate;

tert-butyl (2-(2-hydroxyethyl)-4-((3-(trifluoromethyl)phenyl)sulfonyl)-3,4-dihydro-2H-benzo[b][1,4]oxazin-6-yl)carbamate;

tert-butyl (2-((1H-imidazol-2-yl)methyl)-4-((3-(trifluoromethyl)phenyl)sulfonyl)-3,4-dihydro-2H-benzo[b][1,4]oxazin-6-yl)carbamate;

tert-butyl (2-((1-methyl-1H-imidazol-2-yl)methyl)-4-((3-(trifluoromethyl)phenyl)sulfonyl)-3,4-dihydro-2H-benzo[b][1,4]oxazin-6-yl)carbamate;

(S)-tert-butyl (4-((4-fluorophenyl)sulfonyl)-2-((2-oxopyrrolidin-1-yl)methyl)-3,4-dihydro-2H-benzo[b][1,4]oxazin-6-yl)carbamate;

(S)-tert-butyl (2-((1H-pyrazol-1-yl)methyl)-4-((3-(trifluoromethyl)phenyl)sulfonyl)-3,4-dihydro-2H-benzo[b][1,4]oxazin-6-yl)carbamate;

(S)-tert-butyl (2-((2H-1,2,3-triazol-2-yl)methyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-((4H-1,2,4-triazol-4-yl)methyl)-4-((3-(trifluoromethyl)phenyl)sulfonyl)-3,4-dihydro-2H-benzo[b][1,4]oxazin-6-yl)carbamate;

(S)-tert-butyl (2-((1H-1,2,4-triazol-1-yl)methyl)-4-((3-(trifluoromethyl)phenyl)sulfonyl)-3,4-dihydro-2H-benzo[b][1,4]oxazin-6-yl)carbamate;

(S)-tert-butyl (2-((1H-1,2,3-triazol-1-yl)methyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-((1H-1,2,3-triazol-1-yl)methyl)-4-((3-(trifluoromethyl)phenyl)sulfonyl)-3,4-dihydro-2H-benzo[b][1,4]oxazin-6-yl)carbamate;

(S)-tert-butyl (2-((2H-1,2,3-triazol-2-yl)methyl)-4-((3-(trifluoromethyl)phenyl)sulfonyl)-3,4-dihydro-2H-benzo[b][1,4]oxazin-6-yl)carbamate;

(R)-tert-butyl (2-((pyridin-2-yloxy)methyl)-4-((3-(trifluoromethyl)phenyl)sulfonyl)-3,4-dihydro-2H-benzo[b][1,4]oxazin-6-yl)carbamate;

(S)-tert-butyl (2-((2-oxopyridin-1(2H)-yl)methyl)-4-((3-(trifluoromethyl)phenyl)sulfonyl)-3,4-dihydro-2H-benzo[b][1,4]oxazin-6-yl)carbamate;

(S)-tert-butyl (2-((5-oxo-2,5-dihydro-1,2,4-oxadiazol-3-yl)methyl)-4-((3-(trifluoromethyl)phenyl)sulfonyl)-3,4-dihydro-2H-benzo[b][1,4]oxazin-6-yl)carbamate;

tert-butyl (2-(2-hydroxy-2-methylpropyl)-4-((3-(trifluoromethyl)phenyl)sulfonyl)-3,4-dihydro-2H-benzo[b][1,4]oxazin-6-yl)carbamate;

(S)-tert-butyl (2-((3-hydroxyazetidin-1-yl)methyl)-4-((3-(trifluoromethyl)phenyl)sulfonyl)-3,4-dihydro-2H-benzo[b][1,4]oxazin-6-yl)carbamate;

(S)-tert-butyl (2-(((3-methyloxetan-3-yl)amino)methyl)-4-((3-(trifluoromethyl)phenyl)sulfonyl)-3,4-dihydro-2H-benzo[b][1,4]oxazin-6-yl)carbamate;

tert-butyl ((2S)-4-((3-(trifluoromethyl)phenyl)sulfonyl)-2-(((1,1,1-trifluoropropan-2-yl)amino)methyl)-3,4-dihydro-2H-benzo[b][1,4]oxazin-6-yl)carbamate;

1,1,1-trifluoro-2-methylpropan-2-yl((2S)-4-((4-fluorophenyl)sulfonyl)-2-(2-methylazetidin-1-yl)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(3-hydroxyazetidin-1-yl)methyl)-3,4-dihydro-2H-benzo[b][1,4]oxazin-6-yl)carbamate;

(S)-1,1,1-trifluoro-2-methylpropan-2-yl(2-(azetidin-1-ylmethyl)-4-((4-fluorophenyl)sulfonyl)-3,4-dihydro-2H-benzo[b][1,4]oxazin-6-yl)carbamate;

(S)-tert-butyl (3-methyl-2-oxo-2,3-dihydro-1H-pyrido[2,3-b][1,4]oxazin-7-yl)carbamate;

[(R)-1-((3-chloro-benzenesulfonyl)-3-hydroxymethyl-2,3-dihydro-1H-pyrido[2,3-b][1,4]oxazin-7-yl]-carbamic acid tert-butyl ester;

[(S)-1-(3-chloro-benzenesulfonyl)-3-(2,4-dioxo-oxazolidin-3-ylmethyl)-2,3-dihydro-1H-pyrido[2,3-b][1,4]oxazin-7-yl]-carbamic acid tert-butyl ester;

4-[(S)-6-amino-4-((3-chloro-benzenesulfonyl)-3,4-dihydro-2H-benzo[1,4]oxazin-2-ylmethyl]-1-methyl-piperazin-2-one;

(S)-tert-butyl (5-((4-fluorophenyl)sulfonyl)-6-methyl-5,6,7,8-tetrahydro-1,5-naphthyridin-3-yl)carbamate;

(S)-benzyl tert-butyl (1-((4-fluorophenyl)sulfonyl)-1,2,3,4-tetrahydro-1,5-naphthyridine-3,7-diyl)dicarbamate;

benzyl tert-butyl (1-((3-(trifluoromethyl)phenyl)sulfonyl)-1,2,3,4-tetrahydro-1,5-naphthyridine-3,7-diyl)dicarbamate;

benzyl tert-butyl (1-((3-cyanophenyl)sulfonyl)-1,2,3,4-tetrahydro-1,5-naphthyridine-3,7-diyl)dicarbamate;

benzyl tert-butyl (1-((1-(difluoromethyl)-3-methyl-1H-pyrazol-4-yl)sulfonyl)-1,2,3,4-tetrahydro-1,5-naphthyridine-3,7-diyl)dicarbamate;

(S)-benzyl (5-((4-fluorophenyl)sulfonyl)-7-(2-oxopyrrolidin-1-yl)-5,6,7,8-tetrahydro-1,5-naphthyridin-3-yl)carbamate;

(S)-neopentyl (5-((4-fluorophenyl)sulfonyl)-7-(2-oxopyrrolidin-1-yl)-5,6,7,8-tetrahydro-1,5-naphthyridin-3-yl)carbamate;

(R)-neopentyl (5-((4-fluorophenyl)sulfonyl)-7-(2-oxopyrrolidin-1-yl)-5,6,7,8-tetrahydro-1,5-naphthyridin-3-yl)carbamate;

tert-butyl (5-((4-fluorophenyl)sulfonyl)-7-hydroxy-5,6,7,8-tetrahydro-1,5-naphthyridin-3-yl)carbamate;

(R)-neopentyl (5-((1-(difluoromethyl)-3-methyl-1H-pyrazol-4-yl)sulfonyl)-7-(hydroxymethyl)-5,6,7,8-tetrahydro-1,5-naphthyridin-3-yl)carbamate;

(S)-neopentyl (5-((1-(difluoromethyl)-3-methyl-1H-pyrazol-4-yl)sulfonyl)-7-(hydroxymethyl)-5,6,7,8-tetrahydro-1,5-naphthyridin-3-yl)carbamate;

tert-butyl (7-(hydroxymethyl)-5-(m-tolylsulfonyl)-5,6,7,8-tetrahydro-1,5-naphthyridin-3-yl)carbamate;

tert-butyl (5-((3,4-difluorophenyl)sulfonyl)-7-(hydroxymethyl)-5,6,7,8-tetrahydro-1,5-naphthyridin-3-yl)carbamate;

(R or S)-neopentyl (5-((4-fluorophenyl)sulfonyl)-7-(hydroxymethyl)-5,6,7,8-tetrahydro-1,5-naphthyridin-3-yl)carbamate;

(S or R)-neopentyl (5-((4-fluorophenyl)sulfonyl)-7-(hydroxymethyl)-5,6,7,8-tetrahydro-1,5-naphthyridin-3-yl)carbamate;

neopentyl ((S)-5-((1-(difluoromethyl)-3-methyl-1H-pyrazol-4-yl)sulfonyl)-7-(((R)-3-hydroxypyrrolidin-1-yl)methyl)-5,6,7,8-tetrahydro-1,5-naphthyridin-3-yl)carbamate;

1,1,1-trifluoro-2-methylpropan-2-yl (4-((4-fluorophenyl)sulfonyl)-2-(2,2,2-trifluoroacetyl)-3,4-dihydro-2H-benzo[b][1,4]oxazin-6-yl)carbamate;

2,2,2-trifluoro-1,1-dimethylethyl [(2S)-4-{[1-(difluoromethyl)-3-(2-hydroxyethoxy)-1H-pyrazol-4-yl]sulfonyl}-2-{[(methylsulfamoyl)amino]methyl}-3,4-dihydro-2H-1,4-benzoxazin-6-yl]carbamate;

2,2,2-trifluoro-1,1-dimethylethyl [(2S)-2-[2-(acetylamino)-2-methylpropyl]-4-{[1-ethyl-3-(2-hydroxyethoxy)-1H-pyrazol-4-yl]sulfonyl}-3,4-dihydro-2H-1,4-benzoxazin-6-yl]carbamate;

1,1,1-trifluoro-2-methylpropan-2-yl ((R)-4-((3,4-difluorophenyl)sulfonyl)-2-((S)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((S)-4-((3,4-difluorophenyl)sulfonyl)-2-((R)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((R)-4-((3,4-difluorophenyl)sulfonyl)-2-((R)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((S)-4-((3,4-difluorophenyl)sulfonyl)-2-((S)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((R)-4-((3-chloro-1-ethyl-1H-pyrazol-4-yl)sulfonyl)-2-((S)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((R)-4-((3-chloro-1-ethyl-1H-pyrazol-4-yl)sulfonyl)-2-((R)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((S)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((R)-4-((3-chloro-1-ethyl-1H-pyrazol-4-yl)sulfonyl)-2-((R)-2,2,2-trifluoro-1-hydroxyethyl)-3,4-dihydro-2H-benzo[b][1,4]oxazin-6-yl)carbamate;

1,1,1-trifluoro-2-methylpropan-2-yl (4-((4-fluorophenyl)sulfonyl)-2-(2,2,2-trifluoro-1-hydroxyethyl)-3,4-dihydro-2H-benzo[b][1,4]oxazin-6-yl)carbamate;

1,1,1-trifluoro-2-methylpropan-2-yl ((S)-2-((R)-1-amino-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S)-2-((S)-1-amino-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((R)-1-amino-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((S)-1-amino-2,2,2-trifluoroethyl)-4-((4-fluorophenyl)sulfonyl)-3,4-dihydro-2H-benzo[b][1,4]oxazin-6-yl)carbamate;

(S)-tert-butyl (2-(2-(ethylsulfonyl)ethyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-(ethylsulfonyl)ethyl)-4-((3-(trifluoromethyl)phenyl)sulfonyl)-3,4-dihydro-2H-benzo[b][1,4]oxazin-6-yl)carbamate;

1,1,1-trifluoro-2-methylpropan-2-yl ((2S,3R)-4-((1-(difluoromethyl)-3-methyl-1H-pyrazol-4-yl)sulfonyl)-3-methyl-2-(((N-methylsulfamoyl)amino)methyl)-3,4-dihydro-2H-benzo[b][1,4]oxazin-6-yl)carbamate;

1,1,1-trifluoro-2-methylpropan-2-yl N-[(2S,3R)-2-[(1S)-1-[[(benzyloxy)carbonyl]amino]ethyl]-4-[(3,4-difluorobenzene)sulfonyl]-3-methyl-3,4-dihydro-2H-1,4-benzoxazin-6-yl]carbamate;

1,1,1-trifluoro-2-methylpropan-2-yl (3-(acetamidomethyl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl(2-((1-carbamoylcyclopropyl)methyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl(2-((1-carbamoylcyclopropyl)methyl)-4-((3-chloro-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-2-((R)-3-amino-2-cyclopropyl-3-oxopropyl)-4-((3-chloro-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-2-((S)-3-amino-2-cyclopropyl-3-oxopropyl)-4-((3-chloro-1-ethyl-1H-pyrazol-4-yl)sulfonyl)-3,4-dihydro-2H-benzo[b][1,4]oxazin-6-yl)carbamate;

(R)-1,1,1-trifluoro-2-methylpropan-2-yl(2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl(2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate;

(R)-1,1,1-trifluoro-2-methylpropan-2-yl (2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate;

2,2,2-trifluoro-1,1-dimethylethyl {(2S)-2-(3-amino-2,2-dimethyl-3-oxopropyl)-4-[(4-fluoro-3-methoxyphenyl)sulfonyl]-3,4-dihydro-2H-1,4-benzoxazin-6-yl}carbamate;

1,1,1-trifluoro-2-methylpropan-2-yl((S)-2-((S)-3-amino-2-cyclopropyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl((S)-2-((S)-3-amino-2-cyclopropyl-3-oxopropyl)-4-((3-ethoxy-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl((S)-2-((R)-3-amino-2-cyclopropyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-2-((R)-3-amino-2-cyclopropyl-3-oxopropyl)-4-((3-ethoxy-1-ethyl-1H-pyrazol-4-yl)sulfonyl)-3,4-dihydro-2H-benzo[b][1,4]oxazin-6-yl)carbamate;

2,2,2-trifluoro-1,1-dimethylethyl [(2S)-2-(3-amino-2,2-dimethyl-3-oxopropyl)-4-{[5-(trifluoromethyl)pyridin-3-yl]sulfonyl}-3,4-dihydro-2H-1,4-benzoxazin-6-yl]carbamate;

2,2,2-trifluoro-1,1-dimethylethyl {2-(3-amino-2,2-dimethyl-3-oxopropyl)-4-[(3-ethoxy-1-ethyl-1H-pyrazol-4-yl)sulfonyl]-3,4-dihydro-2H-1,4-benzoxazin-6-yl}carbamate;

2,2,2-trifluoro-1,1-dimethylethyl [2-(3-amino-2,2-dimethyl-3-oxopropyl)-4-{[1-ethyl-3-(2-hydroxyethoxy)-1H-pyrazol-4-yl]sulfonyl}-3,4-dihydro-2H-1,4-benzoxazin-6-yl]carbamate;

(S)-methyl 2-((4-((2-(3-amino-2,2-dimethyl-3-oxopropyl)-6-(((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

(S)-1,1,1-trifluoro-2-methylpropan-2-yl(2-(2-cyanoethyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl(4-((3-chloro-1-ethyl-1H-pyrazol-4-yl)sulfonyl)-2-((1-cyanocyclopropyl)methyl)-3,4-dihydro-2H-benzo[b][1,4]oxazin-6-yl)carbamate;

(R)-1,1,1-trifluoro-2-methylpropan-2-yl (4-((3-chloro-1-ethyl-1H-pyrazol-4-yl)sulfonyl)-2-((1-cyanocyclopropyl)methyl)-3,4-dihydro-2H-benzo[b][1,4]oxazin-6-yl)carbamate;

(S)-1,1,1-trifluoro-2-methylpropan-2-yl(4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate;

(R)-1,1,1-trifluoro-2-methylpropan-2-yl (4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate;

(R)-1,1,1-trifluoro-2-methylpropan-2-yl(2-(2-cyano-2-methylpropyl)-4-((4-fluoro-3-(trifluoromethyl)phenyl)sulfonyl)-3,4-dihydro-2H-benzo[b][1,4]oxazin-6-yl)carbamate;

(R)-1,1,1-trifluoro-2-methylpropan-2-yl(2-(2-cyano-2-methylpropyl)-4-((4-fluoro-3-methoxyphenyl)sulfonyl)-3,4-dihydro-2H-benzo[b][1,4]oxazin-6-yl)carbamate;

(R)-1,1,1-trifluoro-2-methylpropan-2-yl (2-(2-cyano-2-methylpropyl)-4-((4-fluoro-3-methylphenyl)sulfonyl)-3,4-dihydro-2H-benzo[b][1,4]oxazin-6-yl)carbamate;

(S)-1,1,1-trifluoro-2-methylpropan-2-yl (2-(2-cyano-2-methylpropyl)-4-((4-fluoro-3-methoxyphenyl)sulfonyl)-3,4-dihydro-2H-benzo[b][1,4]oxazin-6-yl)carbamate;

(S)-1,1,1-trifluoro-2-methylpropan-2-yl(2-(2-cyano-2-methylpropyl)-4-((4-fluoro-3-methylphenyl)sulfonyl)-3,4-dihydro-2H-benzo[b][1,4]oxazin-6-yl)carbamate;

(R)-1,1,1-trifluoro-2-methylpropan-2-yl(2-(2-cyano-2-methylpropyl)-4-((3-ethoxy-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(2-cyano-2-methylpropyl)-4-((3-ethoxy-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(3-(cyclopropanesulfonamido)-3-oxopropyl)-4-((4-fluoro-3-(trifluoromethyl)phenyl)sulfonyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((S)-3-(cyclopropanesulfonamido)-2-methyl-3-oxopropyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((R)-3-(cyclopropanesulfonamido)-2-methyl-3-oxopropyl)-3,4-dihydro-2H-benzo[b][1,4]oxazin-6-yl)carbamate;

2,2,2-trifluoro-1,1-dimethylethyl [(2S)-2-{3-[(tert-butylsulfonyl)amino]-3-oxopropyl}-4-{[4-fluoro-3-(trifluoromethyl)phenyl]sulfonyl}-3,4-dihydro-2H-1,4-benzoxazin-6-yl]carbamate;

2,2,2-trifluoro-1,1-dimethylethyl [(2S)-4-{[4-fluoro-3-(trifluoromethyl)phenyl]sulfonyl}-2-(3-{[(4-methylphenyl)sulfonyl]amino}-3-oxopropyl)-3,4-dihydro-2H-1,4-benzoxazin-6-yl]carbamate;

2,2,2-trifluoro-1,1-dimethylethyl [(2S)-4-{[4-fluoro-3-(trifluoromethyl)phenyl]sulfonyl}-2-(3-oxo-3-{[(trifluoromethyl)sulfonyl]amino}propyl)-3,4-dihydro-2H-1,4-benzoxazin-6-yl]carbamate;

1,1,1-trifluoro-2-methylpropan-2-yl ((S)-2-((R and S)-3-(cyclopropanesulfonamido)-2-methyl-3-oxopropyl)-4-((3-(trifluoromethyl)phenyl)sulfonyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((R)-3-(1,1-dimethylethylsulfonamido)-2-methyl-3-oxopropyl)-3,4-dihydro-2H-benzo[b][1,4]oxazin-6-yl)carbamate;

1,1,1-trifluoro-2-methylpropan-2-yl((S)-2-((R)-3-(cyclopropanesulfonamido)-2-methyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl((S)-2-((R)-3-(1,1-dimethylethylsulfonamido)-2-methyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl((S)-2-((S)-3-(cyclopropanesulfonamido)-2-methyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-2-((S)-3-(1,1-dimethylethylsulfonamido)-2-methyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((S)-3-(1,1-dimethylethylsulfonamido)-2-methyl-3-oxopropyl)-3,4-dihydro-2H-benzo[b][1,4]oxazin-6-yl)carbamate;

(S)-1,1,1-trifluoro-2-methylpropan-2-yl (4-((4-fluoro-3-(trifluoromethyl)phenyl)sulfonyl)-2-(oxetan-3-ylmethyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(2-(5-oxo-4,5-dihydro-1H-1,2,4-triazol-3-yl)ethyl)-3,4-dihydro-2H-benzo[b][1,4]oxazin-6-yl)carbamate;

(S)-1,1,1-trifluoro-2-methylpropan-2-yl(4-((3-chloro-1-ethyl-1H-pyrazol-4-yl)sulfonyl)-2-(2-(4-methyl-5-oxo-4,5-dihydro-1H-1,2,4-triazol-3-yl)ethyl)-3,4-dihydro-2H-benzo[b][1,4]oxazin-6-yl)carbamate;

(S)-1,1,1-trifluoro-2-methylpropan-2-yl (2-(2-(5-oxo-4,5-dihydro-1,2,4-oxadiazol-3-yl)ethyl)-4-((3-(trifluoromethyl)phenyl)sulfonyl)-3,4-dihydro-2H-benzo[b][1,4]oxazin-6-yl)carbamate;

(R)-1,1,1-trifluoro-2-methylpropan-2-yl(4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(S)-1,1,1-trifluoro-2-methylpropan-2-yl(4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

2,2,2-trifluoro-1,1-dimethylethyl [(2S)-2-[2-(5-oxo-4,5-dihydro-1,2,4-oxadiazol-3-yl)ethyl]-4-{[3-(trifluoromethyl)phenyl]sulfonyl}-3,4-dihydro-2H-1,4-benzoxazin-6-yl]carbamate;

2,2,2-trifluoro-1,1-dimethylethyl {(2S)-4-[(3-cyclopropylphenyl)sulfonyl]-2-[2-(5-oxo-4,5-dihydro-1,2,4-oxadiazol-3-yl)ethyl]-3,4-dihydro-2H-1,4-benzoxazin-6-yl}carbamate;

tert-butyl {(2S)-4-[(3-cyclopropylphenyl)sulfonyl]-2-[2-(5-oxo-4,5-dihydro-1,2,4-oxadiazol-3-yl)ethyl]-3,4-dihydro-2H-1,4-benzoxazin-6-yl}carbamate;

(S)-1,1,1-trifluoro-2-methylpropan-2-yl (4-((3-chloro-1-ethyl-1H-pyrazol-4-yl)sulfonyl)-2-(2-(5-oxo-4,5-dihydro-1,2,4-oxadiazol-3-yl)ethyl)-3,4-dihydro-2H-benzo[b][1,4]oxazin-6-yl)carbamate;

(S)-tert-butyl (4-((3-chloro-1-ethyl-1H-pyrazol-4-yl)sulfonyl)-2-(2-(5-oxo-4,5-dihydro-1,2,4-oxadiazol-3-yl)ethyl)-3,4-dihydro-2H-benzo[b][1,4]oxazin-6-yl)carbamate;

(R)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(R)-1,1,1-trifluoro-2-methylpropan-2-yl (4-((4-fluoro-3-methoxyphenyl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(S)-1,1,1-trifluoro-2-methylpropan-2-yl(4-((4-fluoro-3-methoxyphenyl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(S)-1,1,1-trifluoro-2-methylpropan-2-yl(4-((3-chloro-1-ethyl-1H-pyrazol-4-yl)sulfonyl)-2-(2-(5-oxo-4,5-dihydro-1,3,4-oxadiazol-2-yl)ethyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,3,4-oxadiazol-2-yl)propyl)-3,4-dihydro-2H-benzo[b][1,4]oxazin-6-yl)carbamate;

2,2,2-trifluoro-1,1-dimethylethyl {(2S)-4-[(3-cyclopropylphenyl)sulfonyl]-2-[2-(5-oxo-4,5-dihydro-1,3,4-oxadiazol-2-yl)ethyl]-3,4-dihydro-2H-1,4-benzoxazin-6-yl}carbamate;

2,2,2-trifluoro-1,1-dimethylethyl {(2S)-4-[(4-fluoro-3-methoxyphenyl)sulfonyl]-2-[2-methyl-2-(5-oxo-4,5-dihydro-1,3,4-oxadiazol-2-yl)propyl]-3,4-dihydro-2H-1,4-benzoxazin-6-yl}carbamate;

(S)-1,1,1-trifluoro-2-methylpropan-2-yl(2-(2-(1H-tetrazol-5-yl)ethyl)-4-((3-(trifluoromethyl)phenyl)sulfonyl)-3,4-dihydro-2H-benzo[b][1,4]oxazin-6-yl)carbamate;

2,2,2-trifluoro-1,1-dimethylethyl {(2S)-4-[(3-cyclopropylphenyl)sulfonyl]-2-[2-(1H-tetrazol-5-yl)ethyl]-3,4-dihydro-2H-1,4-benzoxazin-6-yl}carbamate;

2,2,2-trifluoro-1,1-dimethylethyl [(2S)-2-[2-(1H-tetrazol-5-yl)ethyl]-4-{[2-(trifluoromethyl)pyridin-4-yl]sulfonyl}-3,4-dihydro-2H-1,4-benzoxazin-6-yl]carbamate;

(S)-1,1,1-trifluoro-2-methylpropan-2-yl(2-(2-(1H-tetrazol-5-yl)ethyl)-4-((3-chloro-1-ethyl-1H-pyrazol-4-yl)sulfonyl)-3,4-dihydro-2H-benzo[b][1,4]oxazin-6-yl)carbamate;

(R)-1,1,1-trifluoro-2-methylpropan-2-yl(2(4 hydroxymethyl)-5-methyl-4-((3-(trifluoromethyl)phenyl)sulfonyl)-3,4-dihydro-2H-benzo[b][1,4]oxazin-6-yl)carbamate;

(R)-1,1,1-trifluoro-2-methylpropan-2-yl(5-((3-chloro-1-ethyl-1H-pyrazol-4-yl)sulfonyl)-7-((ethylsulfonyl)methyl)-5,6,7,8-tetrahydro-1,5-naphthyridin-3-yl)carbamate;

(S)-1,1,1-trifluoro-2-methylpropan-2-yl(5-((3-chloro-1-ethyl-1H-pyrazol-4-yl)sulfonyl)-7-((ethylsulfonyl)methyl)-5,6,7,8-tetrahydro-1,5-naphthyridin-3-yl)carbamate;

(S)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoic acid;

(R)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoic acid;

1,1,1-trifluoro-2-methylpropan-2-yl (1-((4-fluorophenyl)sulfonyl)-1,2,3,4-tetrahydroquinolin-7-yl)carbamate;

2,2,2-trifluoro-1,1-dimethylethyl {1-[(3-chloro-1-ethyl-1H-pyrazol-4-yl)sulfonyl]-1,2,3,4-tetrahydroquinolin-7-yl}carbamate;

2,2,2-trifluoro-1,1-dimethylethyl (1-{[1-ethyl-3-(2-hydroxyethoxy)-1H-pyrazol-4-yl]sulfonyl}-1,2,3,4-tetrahydroquinolin-7-yl)carbamate;

2,2,2-trifluoro-1,1-dimethylethyl {1-[(3-ethoxy-1-ethyl-1H-pyrazol-4-yl)sulfonyl]-1,2,3,4-tetrahydroquinolin-7-yl}carbamate;

2,2,2-trifluoro-1,1-dimethylethyl (1-{[2-(trifluoromethyl)pyridin-4-yl]sulfonyl}-1,2,3,4-tetrahydroquinolin-7-yl)carbamate;

(R)-1,1,1-trifluoro-2-methylpropan-2-yl (3-(acetamidomethyl)-1-((4-fluoro-3-methoxyphenyl)sulfonyl)-1,2,3,4-tetrahydroquinolin-7-yl)carbamate;

(S)-1,1,1-trifluoro-2-methylpropan-2-yl (3-(acetamidomethyl)-1-((4-fluoro-3-methoxyphenyl)sulfonyl)-1,2,3,4-tetrahydroquinolin-7-yl)carbamate;

(R)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydroquinolin-3-yl)propanoic acid;

(S)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydroquinolin-3-yl)propanoic acid;

(R)-3-(7-((((1,1,1-trifluoro-2-methylpropan-2-yl)oxy)carbonyl)amino)-1-((5-(trifluoromethyl)pyridin-3-yl)sulfonyl)-1,2,3,4-tetrahydroquinolin-3-yl)propanoic acid;

(R)-3-(1-((4-fluoro-3-methoxyphenyl)sulfonyl)-7-((((1,1,1-trifluoro-2-methylpropan-2-yl)oxy)carbonyl)amino)-1,2,3,4-tetrahydroquinolin-3-yl)propanoic acid;

(S)-3-(7-((((1,1,1-trifluoro-2-methylpropan-2-yl)oxy)carbonyl)amino)-1-((5-(trifluoromethyl)pyridin-3-yl)sulfonyl)-1,2,3,4-tetrahydroquinolin-3-yl)propanoic acid;

(S)-3-(1-((4-fluoro-3-methoxyphenyl)sulfonyl)-7-((((1,1,1-trifluoro-2-methylpropan-2-yl)oxy)carbonyl)amino)-1,2,3,4-tetrahydroquinolin-3-yl)propanoic acid;

1,1,1-trifluoro-2-methylpropan-2-yl (5-((3-chloro-1-ethyl-1H-pyrazol-4-yl)sulfonyl)-8-oxo-5,6,7,8-tetrahydro-1,5-naphthyridin-3-yl)carbamate; and 1,1,1-trifluoro-2-methylpropan-2-yl (1-((4-fluoro-3-(trifluoromethyl)phenyl)sulfonyl)-4-oxo-1,2,3,4-tetrahydroquinolin-7-yl)carbamate.

The invention also provides a compound of Formula (I) or a pharmaceutically acceptable salt thereof in purified form.

Uses of the Compounds

Compounds of Formula (I) alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound of Formula (I) that is effective for treating the disease or condition mediated by RORgammaT in the subject.

The compounds according to the invention can be used in therapy.

A further aspect of the invention resides in the use of compounds of Formula (I) for the treatment of RORgammaT-mediated diseases or RORgammaT-mediated conditions.

Another aspect of the invention resides in the use of a compound of Formula (I) in the manufacture of a medicament for the treatment of a disease or condition mediated by RORgammaT.

Another aspect of the invention resides in the use of compounds of Formula (I) for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease (e.g., Crohn's disease, ulcerative colitis), ankylosing spondylitis, and multiple sclerosis.

In another aspect, compounds of Formula (I) can be used for treatment of inflammatory diseases in which Th17 cells and/or non-Th17 cells, which express Th17 hallmark cytokines, play a prominent role, such as but not limited to respiratory diseases, osteoarthritis, and asthma. Also, compounds of Formula (I) can be used for treatment of infectious diseases in which Th17 cells and/or non-Th17 cells, which express Th17 hallmark cytokines, play a prominent role, such as but not limited to mucosal leishmaniasis.

In another aspect, compounds of Formula (I) can be used in the treatment of cancer. Those skilled in the art will recognize the term "cancer" to be a name for diseases in which the body's cells become abnormal and divide without control. The term cancer includes, but is not limited to, colorectal, lung, and pancreatic cancer.

Compounds of Formula (I) can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect, the disease or condition is an autoimmune disease or inflammatory disease. The disease or condition includes, but is not limited to, multiple sclerosis, inflammatory bowel disease (e.g., Crohn's disease, ulcerative colitis), psoriasis, rheumatoid arthritis, asthma, osteoarthritis, Kawasaki disease, Hashimoto's thyroiditis, and mucosal leishmaniasis.

In another aspect, the compounds of Formula (I) can be used in therapies to treat or prevent multiple sclerosis, inflammatory bowel disease (e.g., Crohn's disease, ulcerative colitis), psoriasis, rheumatoid arthritis, asthma, osteoarthritis, Kawasaki disease, Hashimoto's thyroiditis, and mucosal leishmaniasis.

In another aspect, the compounds of Formula (I) can be used to treat or prevent psoriasis.

In yet another aspect, the compounds of Formula (I) can be used to treat inflammatory bowel disease (e.g., Crohn's disease, ulcerative colitis).

In another aspect, the compound of Formula (I) can be used to treat colorectal cancer.

In another aspect, the compound of Formula (I) can be used to treat lung cancer.

In another aspect, the compound of Formula (I) can be used to treat pancreatic cancer.

Route of Administration/Dosage

The compounds of this invention can be administered for the treatment or prevention of afflictions, diseases, and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal, and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health, and weight of the recipient; the extent of disease; kind of concurrent treatment, if any; frequency of treatment; and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases, and illnesses described above, e.g., autoimmune and inflammatory diseases and disorders.

Compositions include those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g., injection liquids in predetermined amounts, for example in sealed vials and ampoules, and may also be stored in a freeze dried (lyophilized) condition requiring only the addition of sterile liquid carrier, e.g., water, prior to use.

Mixed with such pharmaceutically acceptable auxiliaries, e.g., as described in the standard reference, Gennaro, A. R. et al., Remington: The Science and Practice of Pharmacy (20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g., as an injection preparation, in the form of a solution, suspension, emulsion, or as a spray, e.g., a nasal spray.

For making solid dosage units, the use of conventional additives such as fillers, colorants, polymeric binders, and the like is contemplated. In general any pharmaceutically acceptable additive that does not interfere with the function of the active compounds can be used. Suitable carriers with which the active agent of the invention can be administered as solid compositions include lactose, starch, cellulose derivatives, and the like, or mixtures thereof, used in suitable amounts. For parenteral administration, aqueous suspensions, isotonic saline solutions, and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formula (I) or a pharmaceutically acceptable salt thereof and one or more pharmaceutically acceptable excipients. The term "excipient" and "carrier" may be used interchangeably. The term "composition," as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I), additional active ingredient(s), and pharmaceutically acceptable excipients.

The pharmaceutical compositions of the present invention comprise a compound represented by Formula (I) (or pharmaceutically acceptable salts thereof) as an active ingredient, a pharmaceutically acceptable carrier, and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy in light of the present disclosure.

The active ingredient can be administered orally in solid dosage forms, such as capsules, tablets, troches, dragées, granules, and powders, or in liquid dosage forms, such as elixirs, syrups, emulsions, dispersions, and suspensions. The active ingredient can also be administered parenterally, in sterile liquid dosage forms, such as dispersions, suspensions, or solutions. Other dosages forms that can also be used to administer the active ingredient as an ointment, cream, drops, transdermal patch, or powder for topical administration, as an ophthalmic solution or suspension formation, i.e., eye drops, for ocular administration, as an aerosol spray or powder composition for inhalation or intranasal administration, or as a cream, ointment, spray, or suppository for rectal or vaginal administration.

Gelatin capsules can contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours, for example. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, A. Osol, a standard reference text in this field.

For administration by inhalation, the compounds of Formula (I) may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula (I) in suitable propellants, such as fluorocarbons or hydrocarbons.

For ocular administration, an ophthalmic preparation may be formulated with an appropriate weight percent solution or suspension of the compounds of Formula (I) in an appropriate ophthalmic vehicle, such that the compound is maintained in contact with the ocular surface for a sufficient time period to allow the compound to penetrate the corneal and internal regions of the eye.

Useful pharmaceutical dosage forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil, or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contains 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term "coadministration" is understood to include the administration of the two agents concomitantly or sequentially, or alternatively as a fixed dose combination of the two active components.

The present invention also relates to a pharmaceutical composition comprising compounds of Formula (I) or pharmaceutically acceptable salts thereof in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of Formula (I), and pharmaceutically acceptable salts and physiologically functional derivatives (e.g., prodrugs) thereof, may be employed alone or in combination with other therapeutic agents for the treatment of diseases and conditions associated with inappropriate IL-17 pathway activity. Combination therapies according to the present invention thus comprise the administration of at least one compound of Formula (I) or a pharmaceutically acceptable salt thereof, or a physiologically functional derivative thereof, and the use of at least one other pharmaceutically active agent. The compound(s) of Formula (I) and the other pharmaceutically active agent(s) may be administered together or separately and, when administered separately, this may occur simultaneously or sequentially in any order. The amounts of the compound(s) of Formula (I) and the other pharmaceutically active agent(s) and the relative timings of administration will be selected in order to achieve the desired combined therapeutic effect.

For the treatment of the inflammatory and autoimmune diseases, rheumatoid arthritis, psoriasis, inflammatory bowel disease, ankylosing spondylitis, SLE (systemic lupus erythematosus), uveitis, atopic dermatitis, COPD, asthma, and allergic rhinitis, a compound of Formula (I) may be combined with one or more other active agents such as: (1) TNF-a inhibitors; (2) non-selective COX-1/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK1 and/or JAK2 and/or JAK3 and/or TYK2), p38 MAPK and IKK2; (15) B-cell targeting biologics such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. The compound of Formula (I) may also be combined with anti-IL17 antibodies to obtain additive/synergistic responses for the treatment of inflammatory and autoimmune diseases.

For the treatment of cancer, the compounds of Formula (I) can be combined with other therapeutic, chemotherapeutic, and anti-cancer agents. Combinations of the compounds of Formula (I) with other therapeutic, chemotherapeutic, and anti-cancer agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. In light of the present disclosure, a person of ordinary skill in the art would be able to discern which combinations of the compounds of Formula (I) with the other therapeutic, chemotherapeutic, and anti-cancer agents would be useful based on the particular characteristics of the drugs and the cancer involved. The compounds of Formula (I) may also be useful when co-administered with radiation therapy. The compounds of Formula (I) can be present in the same dosage unit as the other therapeutic, chemotherapeutic, and anti-cancer agents. The compounds of Formula (I) and the other therapeutic, chemotherapeutic, and anti-cancer agents can also be present in separate dosage units.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the other therapeutic ingredients may be used in optically pure form.

The combinations referred to above may conveniently be presented for use in the form of a pharmaceutical composition and thus, pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formula (I).

The invention further includes a compound of Formula (I) in combination with one or more other drug(s).

Methods of Preparing the Compounds of Formula (I)

The compounds of this invention may be made by a variety of methods, including standard chemistry in light of the present disclosure. Illustrative general synthetic methods are set out below and then specific compounds of the Formula (I) are prepared in the Examples.

Compounds of Formula (I) may be prepared in light of the present disclosure via techniques known in the art of organic synthesis, examples of which are set forth in the following synthesis schemes. It would be well understood by those skilled in the art in light of the present disclosure that in all of the schemes described below, protecting groups for sensitive or reactive groups should be employed where necessary in accordance with general principles of chemistry. Protecting groups can be manipulated according to standard methods of organic synthesis (T. W. Green and P. G. M. Wuts (1991) Protecting Groups in Organic Synthesis, John Wiley & Sons). These groups can be removed at a convenient stage of the compound synthesis using methods that are readily apparent to those skilled in the art. In certain other embodiments, a functional group presented in these schemes below can be converted to another functional group using standard functional group manipulation procedures known in the art. See, for example, "Comprehensive Organic Synthesis" (B. M. Trost & I. Fleming, eds., 1991-1992).

The selection of protecting groups as well as the reaction conditions and order of reaction steps shall be consistent with the preparation of compounds of Formula (I). Those skilled in the art will recognize in light of the present disclosure whether a stereocenter exists in compounds of Formula (I). When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations:

Me=methyl; Et=ethyl; Pr=propyl; i-Pr=isopropyl, Bu=butyl; tert-Bu=tert-butyl; Ph=phenyl, and Ac=acetyl
µL=microliters
AcOH or HOAc=acetic acid
APCI=atmospheric-pressure chemical ionization
aq=aqueous
Bn=benzyl
Boc or BOC=tert-butoxycarbonyl
Bz=benzoyl
Cbz=benzyloxycarbonyl
DAST=diethylaminosulfur trifluoride
DBU=1,8-diazabicyclo[5.4.0]undec-7-ene DCM=dichloromethane
DDQ=2,3-Dichloro-5,6-dicyano-1,4-benzoquinone
DEA=diethylamine
DMAP=4-Dimethylaminopyridine
DIBAL=diisobutylaluminum hydride
DIAD=diisopropyl azodicarboxylate
DIEA or Hünig's Base=N,N-diisopropylethylamine
DMF=dimethylformamide
DMSO=dimethyl sulfoxide
EA=ethyl acetate
EDC=1-ethyl-3-(3-dimethylaminopropyl)carbodiimide
EDTA=ethylenediamine tetraacetic acid
ESI=electrospray ionization
EtOAc=ethyl acetate
g=grams
h=hour
HMDS=1,1,1,3,3,3-hexamethyldisilazane
Hex=hexanes
HPLC=high-performance liquid chromatography
LDA=lithium diisopropylamide
LCMS=liquid chromatography mass spectrometry
LRMS=low resolution mass spectroscopy
min=minute
mg=milligrams
mL=milliliters
mmol=millimoles
MeOH=methanol
MPLC=medium pressure liquid chromatography
MTBE=methyl tert-butyl ether
MS=mass spectrometry
NBS=N-bromosuccinimide
NMO=4-methylmorpholine N-oxide
NMR=nuclear magnetic resonance spectroscopy
PE=petroleum ether
rac=racemic mixture
rt=room temperature (ambient, about 25° C.)
sat=saturated
SFC=supercritical fluid chromatography
TBSCl=t-butyldimethylsilyl chloride
TBS=t-butyldimethyl silyl
TEA=triethylamine (Et$_3$N)
TFA=trifluoroacetic acid
THF=tetrahydrofuran
TLC=thin layer chromatography
TMS=trimethylsilyl
TPAP=tetrapropylammonium perruthenate
TsOH=p-toluenesulfonic acid General Methods Methods for preparing compounds described herein are illustrated in the following synthetic schemes. The schemes are given for the purpose of illustrating the invention, but not for limiting the scope or spirit of the invention. Starting materials shown in the schemes can be obtained from commercial sources or be prepared based on procedures described in the literature.

The synthetic route illustrated in Scheme 1 is a general method for preparing various carbamates. Reaction of a starting amine A with a carbamoylating agent of structure B where X is a leaving group which includes halides, electron deficient phenols, imidazole, triazoles, or other moieties well-known to those trained in the art affords the target carbamate C.

The reaction procedures in Scheme 1 are contemplated to be amenable to preparing a wide variety of carbamoyl-substituted tetrahydroquinolines, carbamoyl-substituted benzoxazines, carbamoyl substituted tetrahydronaphthyridines, carbamoyl-substituted tetrahydropyridooxazines compounds having different substituents at the $R^1$, $R^2$, $R^{a1}$, $R^b$, $R^4$, and Cy positions. A wide variety of alcohol starting materials necessary to prepare the carbamoylating reagent B are commercially available or readily prepared via known methods. Furthermore, if a functional group that is part of the $R^1$, $R^2$, $R^{a1}$, $R^b$, $R^4$, or Cy group would not be amenable to a reaction condition described in Scheme 1, it is contemplated that the functional group can first be protected using standard protecting group chemistry and strategies, and then the protecting group is removed after completing the desired synthetic transformation.

SCHEME 1

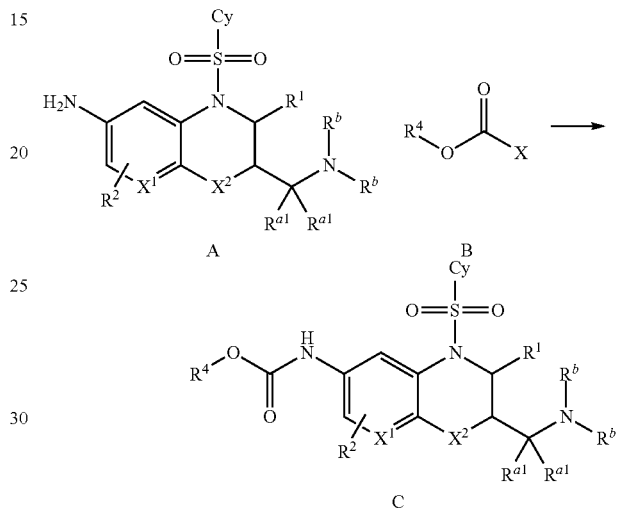

Scheme 2 illustrates a different general method for preparing carbamates. Treatment of the amine A with phosgene, triphosgene, or other reagents known to convert aromatic or heteroaromatic amines to isocyanates, affords the isocyanate B which when treated with an alcohol C either without or with a catalyst (a base which includes but is not limited to triethyl amine, DBU, Hunig's base, or a metal catalyst such as a dibutyl tin dilaurate and numerous others known to those trained in the art) affords the carbamate D.

SCHEME 2

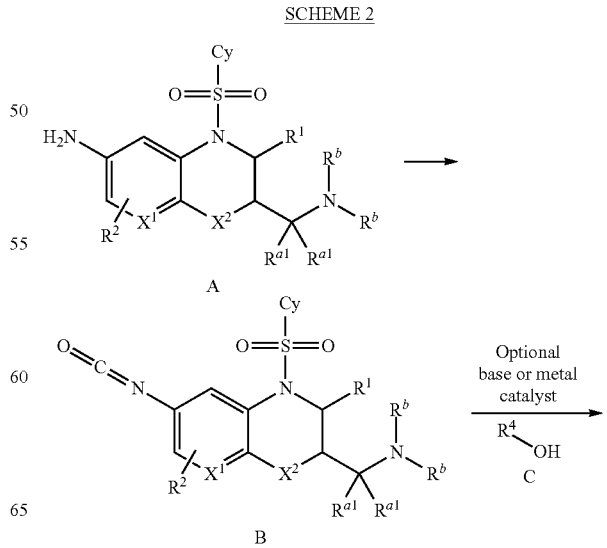

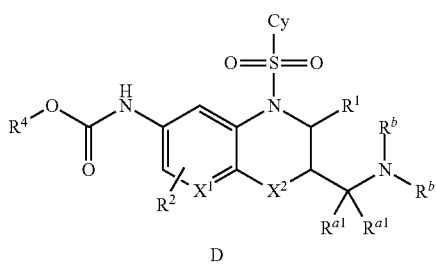

Scheme 3 illustrates a different general method for preparing carbamates. Treatment of the carboxylic acid A with conditions suitable to prepare an acyl azide (diphenyl phosphoryl azide, or isobutyl chloroformate and sodium azide, or other similar conditions known to those trained in the art) afford the acyl azide, which upon heating rearranges to form the isocyanate B. Treatment of the isocyanate with an alcohol C affords the carbamate D.

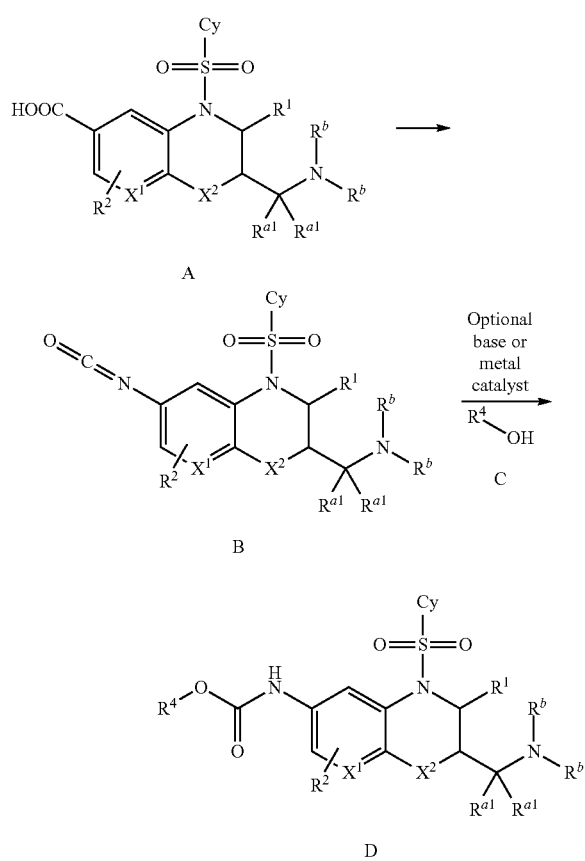

Scheme 4 illustrates another general method for preparing carbamates of the invention. Treatment of a halide or triflate (X=OTf) A under Pd-mediated coupling conditions with an unsubstituted carbamate C affords the carbamate D. The unsubstituted carbamate C can be prepared from alcohols B via treatment with either potassium isocyanate and acid or with sulfurisocyanatidic chloride.

SCHEME 4

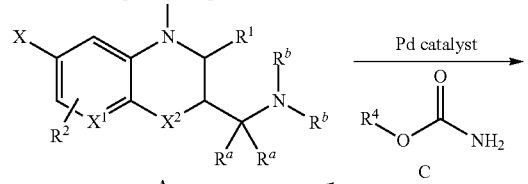

Scheme 5 illustrates a general method for preparing alcohols and carbamoylating reagents suitable for the Scheme 1 and other general schemes below. Treatment of a ketone or aldehyde A with a Grignard reagent, $R^{fs}$ Li, a $R^{fs}$ metal, or a trialkylsilyl reagent (i.e., trimethyl silyl trifluoromethane) affords the alcohol B, which can be reacted with p-nitrochloroformate, carbonyldiimide, or phosgene to afford the carbamoylating reagents.

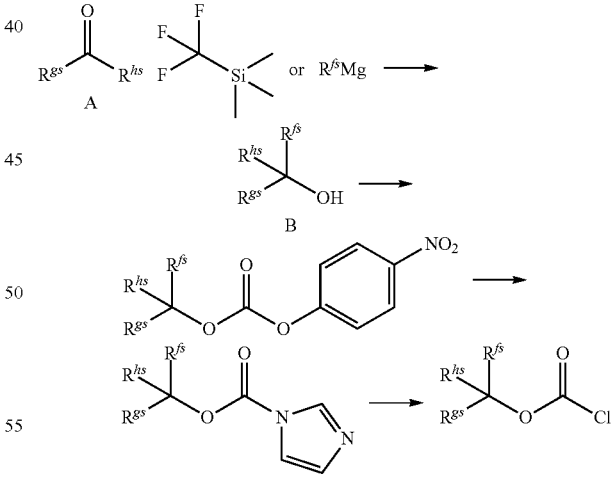

The synthetic route in Scheme 6 is a general method for preparing various carbamoyl-substituted benzoxazines and aza-benzoxazines compounds having a variety of protected aminomethyl side-chains, such as carbamates, ureas, sulfamides etc. Reaction of nitro-aryl aniline A with an epoxide provides benzoxazine B. The nitro group in benzoxazine B can be reduced in the presence of $Boc_2O$ to a Boc carbamate group to provide Boc benzoxazine C. Mitsunobu reaction of benzoxazine C, followed by hydrolysis of the phthalamide provides aminomethyl benzoxazine E. Functionalization of the aminomethyl group and sulfonylation of the benzoxazine leads to Boc-carbamate G. Removal of the Boc carbamate group under acidic conditions and subsequent installation of the desired benzoxazine carbamate affords H.

Scheme 7 shows the synthesis of 3-substituted benzoxazines and aza-benzoxazines (or pyrido oxazines). Condensation of amino phenol A with chloro ketone B leads to imine C, which upon exhaustive reduction with NaBH$_4$ affords methyl alcohol D. Bis-sulfonylation, followed by S$_N$2 displacement of the activated methyl alcohol moiety with NaN$_3$ gives azide F. Lastly, reduction of the azide, functionalization of the corresponding aminomethyl side-chain group, and replacing of the Boc-carbamate with a suitable carbamate yields 3-substituted benzoxazine carbamate H.

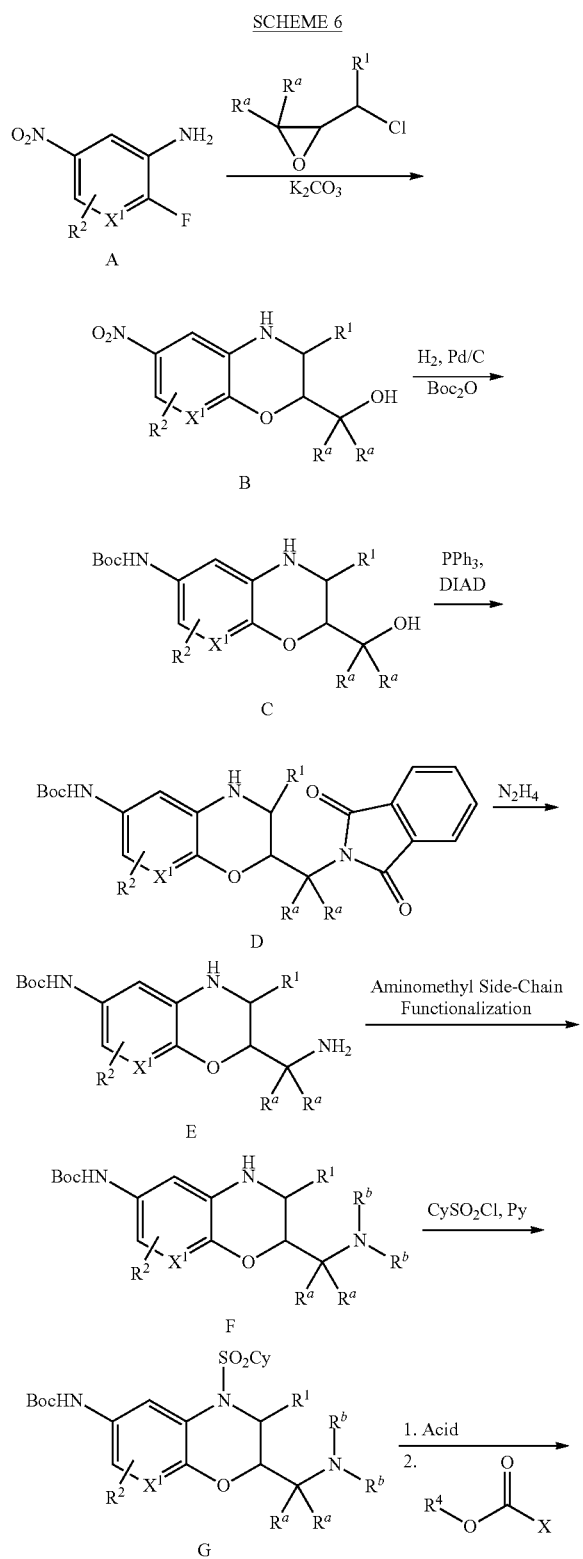

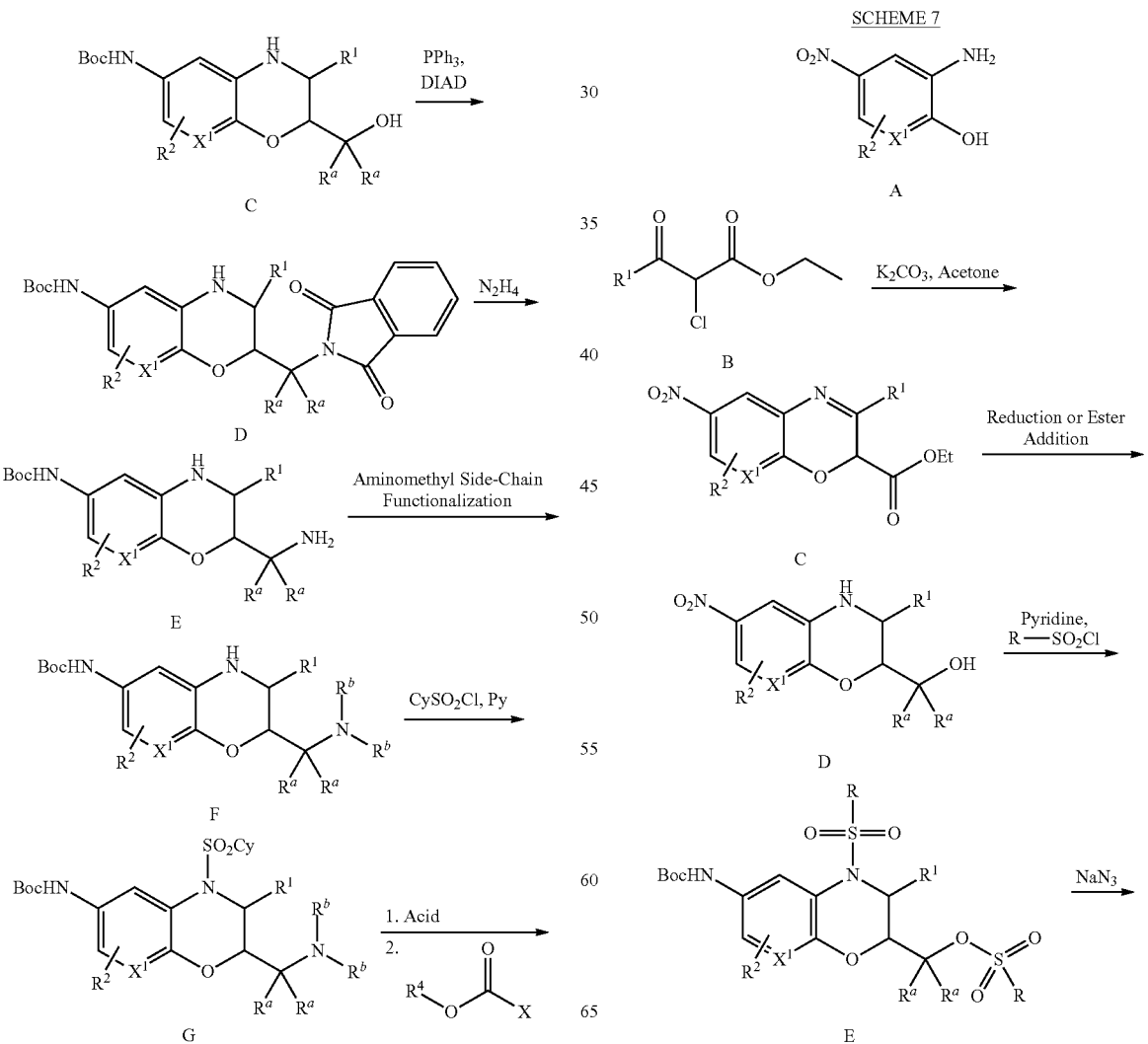

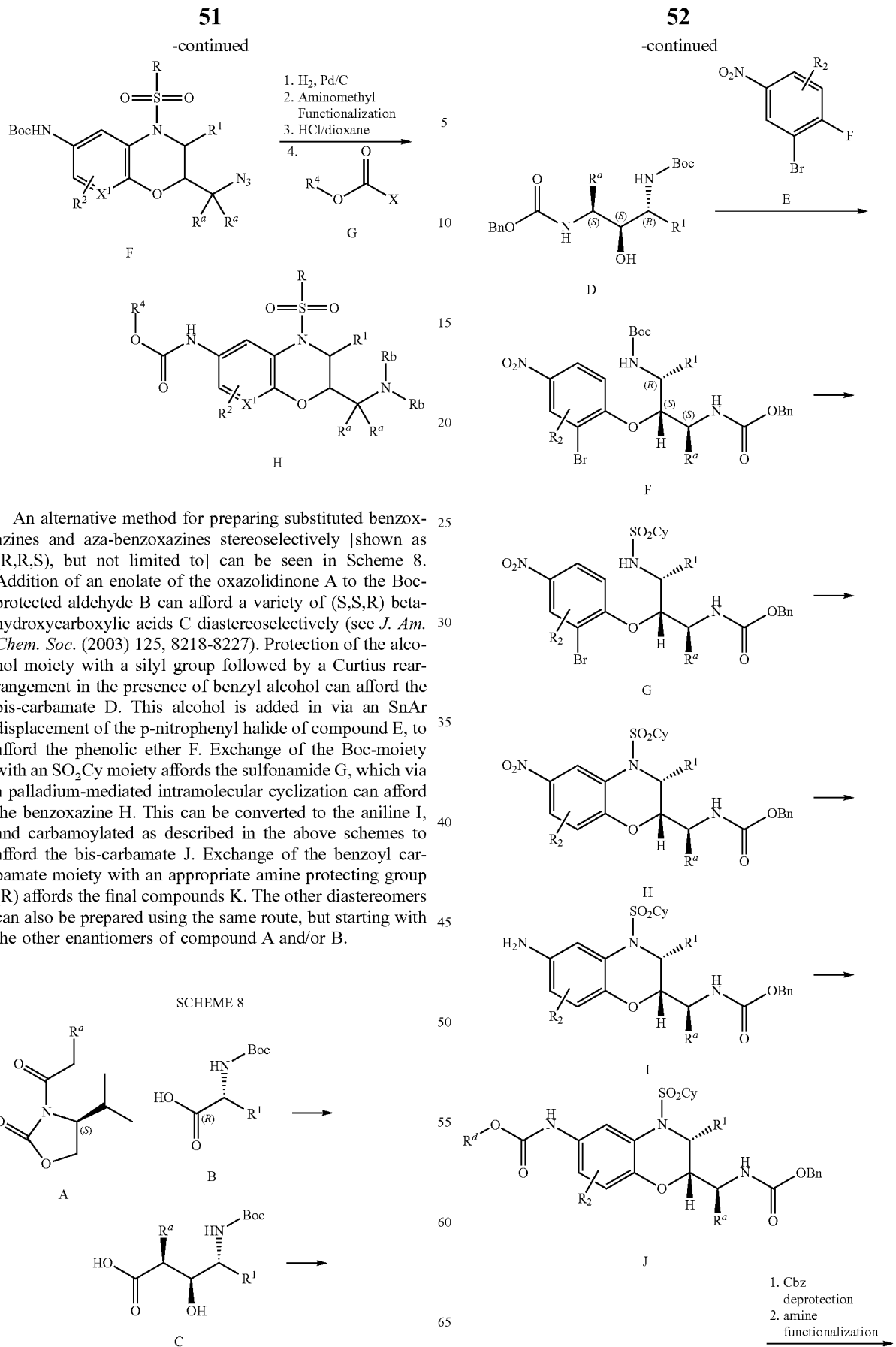

An alternative method for preparing substituted benzoxazines and aza-benzoxazines stereoselectively [shown as (R,R,S), but not limited to] can be seen in Scheme 8. Addition of an enolate of the oxazolidinone A to the Boc-protected aldehyde B can afford a variety of (S,S,R) beta-hydroxycarboxylic acids C diastereoselectively (see *J. Am. Chem. Soc.* (2003) 125, 8218-8227). Protection of the alcohol moiety with a silyl group followed by a Curtius rearrangement in the presence of benzyl alcohol can afford the bis-carbamate D. This alcohol is added in via an SnAr displacement of the p-nitrophenyl halide of compound E, to afford the phenolic ether F. Exchange of the Boc-moiety with an SO$_2$Cy moiety affords the sulfonamide G, which via a palladium-mediated intramolecular cyclization can afford the benzoxazine H. This can be converted to the aniline I, and carbamoylated as described in the above schemes to afford the bis-carbamate J. Exchange of the benzoyl carbamate moiety with an appropriate amine protecting group (R) affords the final compounds K. The other diastereomers can also be prepared using the same route, but starting with the other enantiomers of compound A and/or B.

SCHEME 8

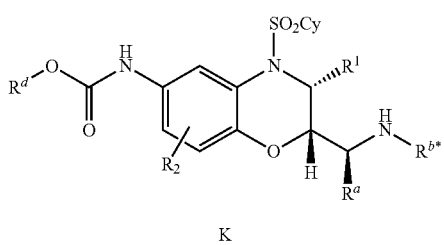

K

The synthetic route illustrated in Scheme 9 is a general method for preparing various carbamoyl-substituted tetrahydroquinoline and tetrahydronaphthyridine compounds. Nitration of A by reacting it with a mixture of nitric acid and sulfuric acid provides 7-nitro-tetrahydroquinoline or tetrahydronaphthyridine B. A sulfonamide group can be installed by reacting B with a mild base or sodium hydride and a sulfonyl chloride (Cy-SO$_2$Cl) to provide sulfonamide C. The nitro group in compound C can be reduced to an amino group providing aniline D, which can be reacted with a carbamoylating reagent from general Scheme 5 to provide the final carbamate E.

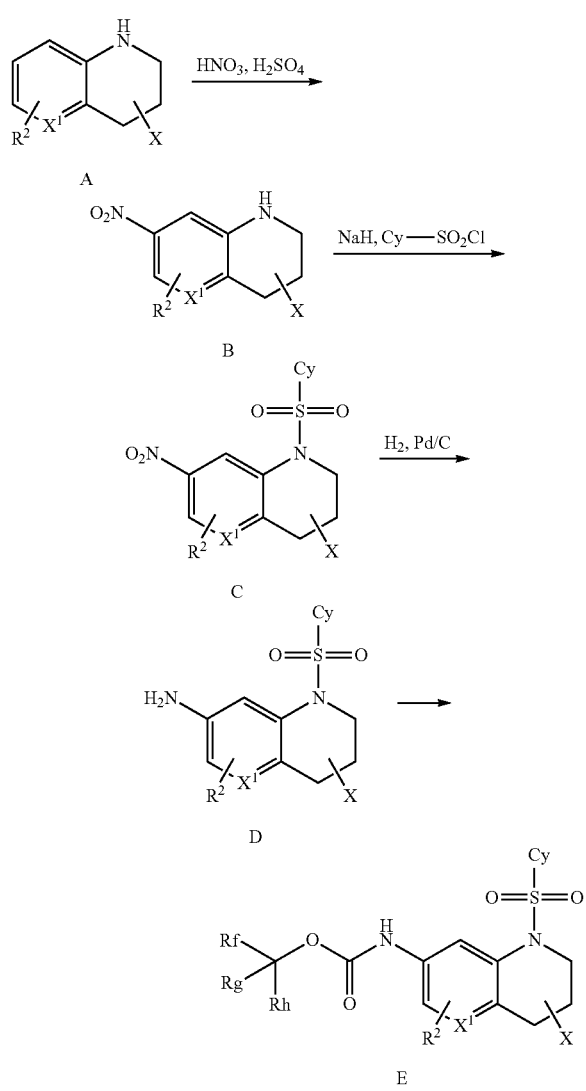

Scheme 10 illustrates a general method for preparing dihydroquinolines. Condensation of phenylene diamine A with ethyl acetoacetate under reflux (e.g., using Conrad-Limpach conditions) provides 7-amino-4-methylquinolin-2 (1H)-one B. See, for example, *Med. Chem Res*. (2010) vol. 19, pages 193-209 for additional description of synthetic procedures known to those trained in the art. The amino group on quinolinone B can be reacted with a carbamoylating reagent from Scheme 5 to afford carbamate C. Reaction of carbamate C with mild base and a sulfonyl chloride (Cy-SO$_2$Cl) provides dihydroquinoline D.

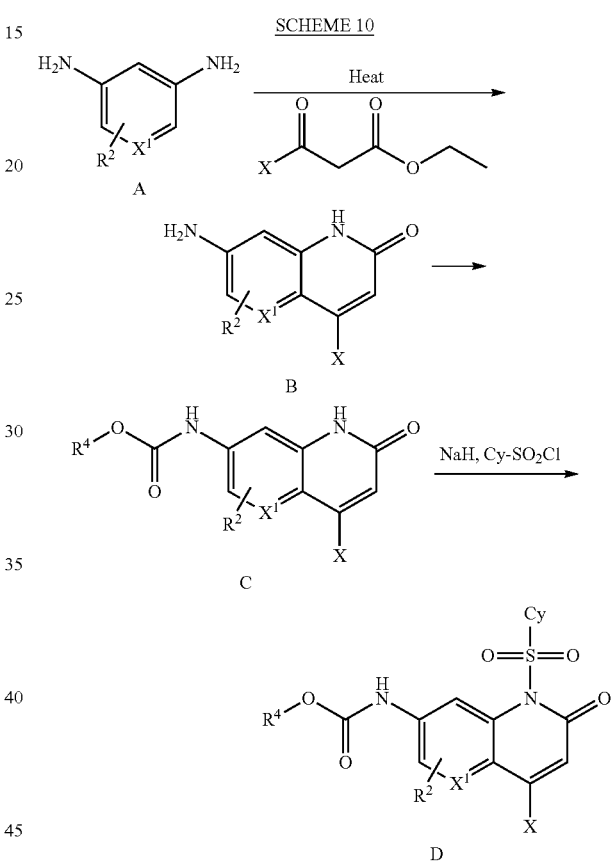

Scheme 11 illustrates a general method for preparing fluoro-substituted, hydroxyl-substituted, and alkoxy-substituted tetrahydroquinoline and tetrahydronaphthyridine compounds. Oxidation of A using potassium permanganate provides ketone B. Ketone B can be reduced to alcohol C, reacted with a fluorinating agent (such as DAST) to provide difluorotetrahydroquinoline or tetrahydronaphthyridine D, or further oxidized to enone E. The oxidative conversion of ketone B to E can be carried using, for example, manganese dioxide, DDQ or selenium dioxide. Reaction of E with a fluorinating agent (such as DAST) provides fluoro-dihydroquinoline or tetrahydronaphthyridine F. Finally, as depicted below alkoxy-substituted tetrahydroquinoline or tetrahydronaphthyridine G can be prepared by reaction of alcohol C with methanesulfonyl chloride to provide an intermediate mesylate that is reacted with an alkoxide, such as sodium methoxide, to provide G.

SCHEME 11

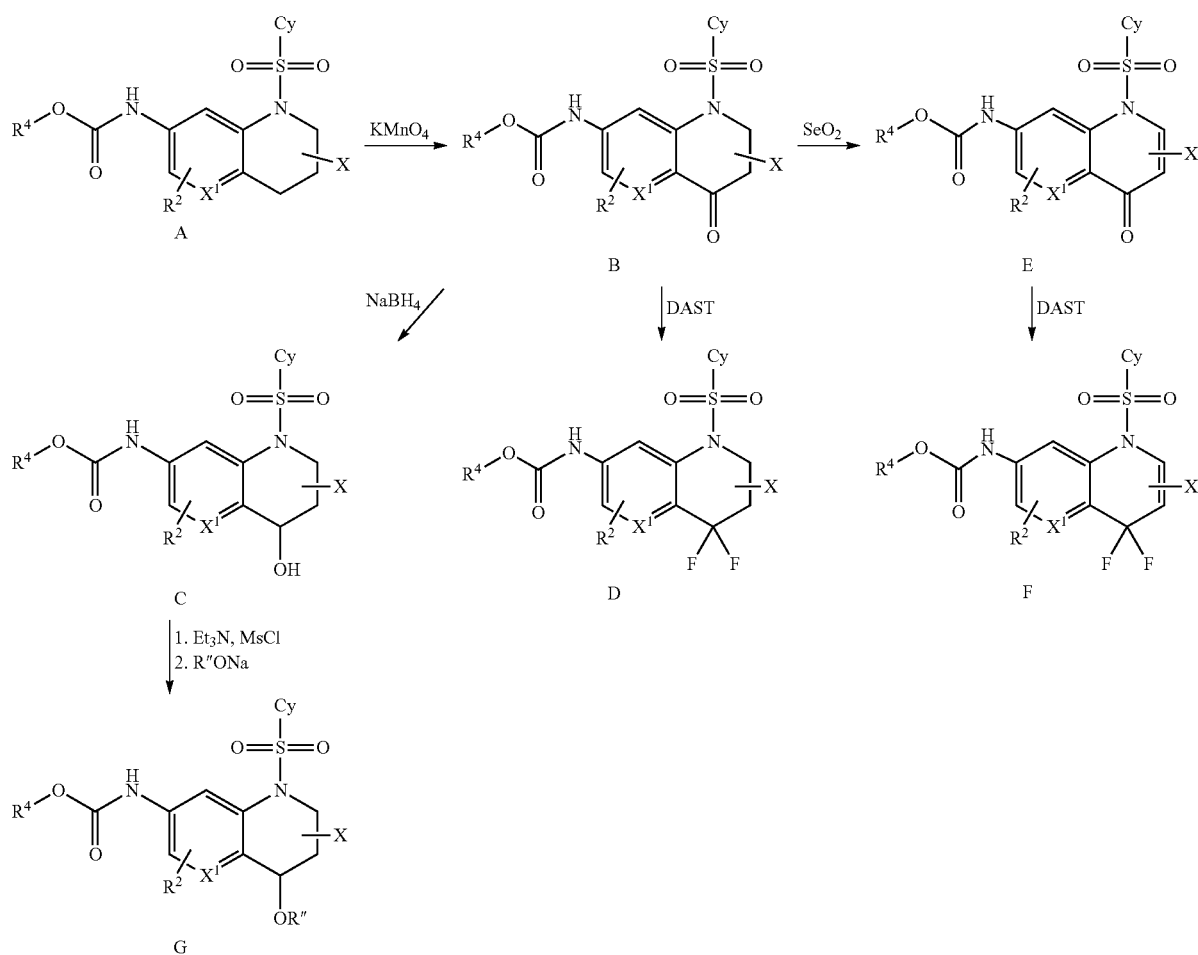

Scheme 12 illustrates a general method for preparing tetrahydroquinolines and tetrahydronaphthyridines having an alkyl substituent attached to the 4-position of the bicyclic core. Amide coupling of halo-aniline A with an acid chloride or with an carboxylic acid with a coupling reagent provides amide B. Synthetic intermediate B is subjected to Heck Coupling conditions to provide C, which can be reduced to lactam D. Synthetic intermediate D can be converted to the carbamate E, and subsequent reaction with the desired sulfonyl chloride, followed by reduction of the lactam moiety, provides the desired tetrahydroquinoline or tetrahydronaphthyridine G.

SCHEME 12

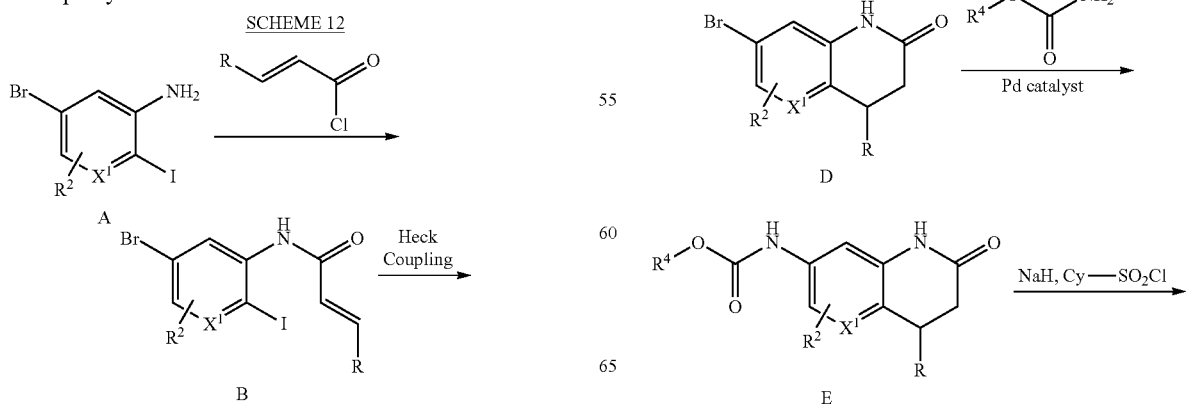

-continued

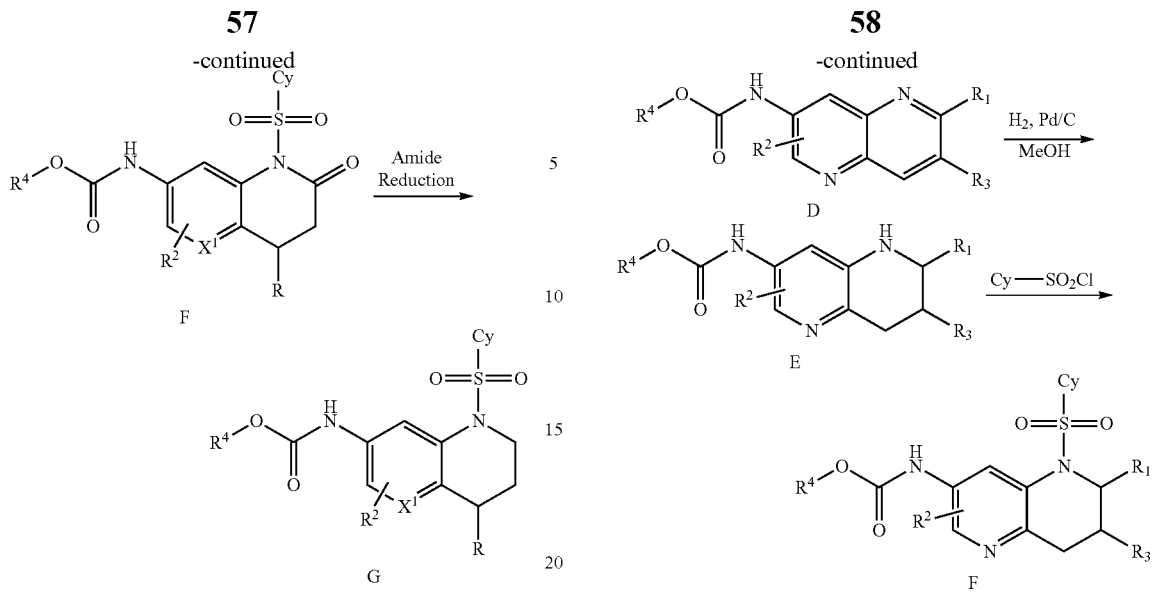

The reaction procedures in Scheme 13 are contemplated to be amenable to preparing a wide variety of carbamoyl-substituted tetrahydro-1,5-naphthyridine compounds having different substituents at the $R^1$ and $R^3$ positions. For example, numerous substituted 5-bromo-3-aminopyridines are known in the literature and/or are commercially available, such as 5-bromo-6-methyl-pyridin-3-amine, 5-bromo-4-methyl-pyridin-3-amine, 5-amino-3-bromo-2-methoxylpyridine, and 5-bromo-4,6-dimethyl-pyridin-3-amine. Furthermore, if a functional group that is part of $R^1$ or $R^3$ would not be amenable to a reaction condition described in Scheme 15, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, 2$^{nd}$ ed.; Wiley: New York, 1991, for further description of protecting chemistry and strategies known to those trained in the art. In certain other embodiments, a functional group in substituent $R^1$ and $R^3$ in tetrahydro-1,5-naphthyridine F can be converted to another functional group using standard functional group manipulation procedures known in the art. See, for example, "Comprehensive Organic Synthesis" (B. M. Trost & I. Fleming, eds., 1991-1992).

Scheme 14 illustrates an alternative general method for preparing substituted 5,6,7,8-tetrahydro-1,5-naphthyridine compounds. Reduction of halo-nitro-pyridine A with dissolving metals provides halo-amino-pyridine B. Exemplary dissolving metal reduction conditions include the use of, for example, (1) SnCl$_2$ in HCl as described by Adams et al. in WO 2008/150827, or (2) Fe in HCl or NH$_4$Cl as described by Carroll et al. in *J. Med. Chem.* 2002, 45, 4755-4761 and Oalmann et al. in WO 2010/071853. Reaction of halo-amino-pyridine B with a sulphonyl chloride or sulfamoyl chloride provides halo-pyridinyl sulfonamide C. Reaction of halo-pyridinyl sulfonamide C with a vinyl boronic acid or vinyl stannane provides alkene D, which can be allylated using, for example, an allyl halide under basic conditions or an allyl alcohol under Mitsunobu conditions to provide di-alkene E. Di-alkene E can be subjected to ring closing metathesis conditions to provide dihydro-1,5-naphthyridine F. For exemplary ring closing metathesis conditions, see, for example, Mitsuhiro et al. in *J. Org. Chem.* 2006, 71, 4255-4261. Reduction of dihydro-1,5-naphthyridine F provides saturated tetrahydro-1,5-naphthyridine G. The methyl ester on tetrahydro-1,5-naphthyridine G can be converted to a carboxylic acid under hydrolytic conditions, and the resulting carboxylic acid is subjected to reaction conditions that facilitate Curtius rearrangement (see, for example, Ninomiya in *Tetrahedron* 1974, 30, 2151-2157) to provide intermediate or final tetrahydronaphthyridinyl carbamate H. The carbamate functional group of an intermediate tetrahydronaphthyridinyl carbamate H can be converted to an amino group using standard carbamate protecting group removal procedures, and the resulting amino-tetrahydronaphthyridine can be reacted with carbamoylating reagents to provide carbamoyl-tetrahydro-1,5-naphthyridine I.

SCHEME 13

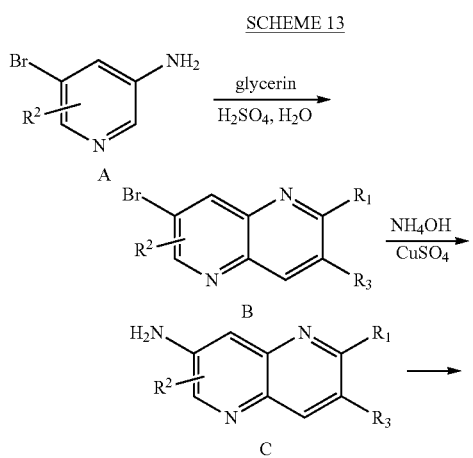

SCHEME 14

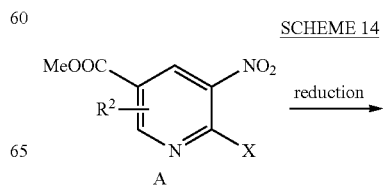

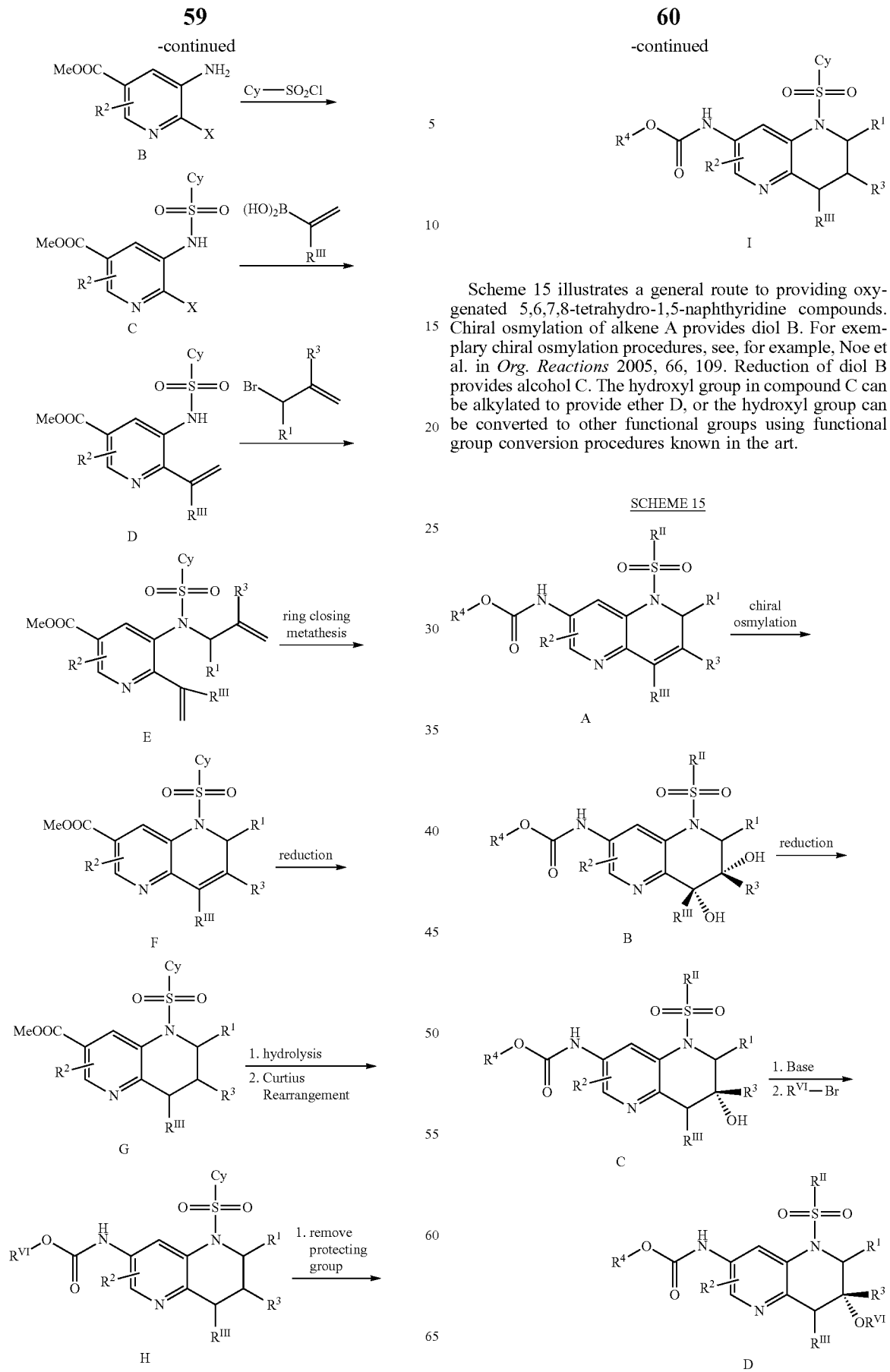

Scheme 15 illustrates a general route to providing oxygenated 5,6,7,8-tetrahydro-1,5-naphthyridine compounds. Chiral osmylation of alkene A provides diol B. For exemplary chiral osmylation procedures, see, for example, Noe et al. in *Org. Reactions* 2005, 66, 109. Reduction of diol B provides alcohol C. The hydroxyl group in compound C can be alkylated to provide ether D, or the hydroxyl group can be converted to other functional groups using functional group conversion procedures known in the art.

Scheme 16 illustrates another general procedure for preparing 5,6,7,8-tetrahydro-1,5-naphthyridine compounds. Treatment of halo-nitro-pyridine A with a Negishi reagent under Pd-mediated conditions provides diester B. For additional description of related procedures, see, for example, Zhu et al. in *J. Org. Chem.* 1991, 56, 1445-1453. Dissolving metal reduction of diester B with in situ cyclization affords dihydro-1,5-naphthyridin-2(1H)-one C. Reaction of dihydro-1,5-naphthyridin-2(1H)-one C with a protecting group installation reagent (e.g., benzylbromide (Bn-Br)) provides protected amide D, which after hydrolysis and in situ formation of the azide and Curtius rearrangement provides carbamate E. A substituent can be installed alpha to the amide group by reaction of carbamate E with base and an electrophile (e.g., R³-halide) to provide substituted-dihydro-1,5-naphthyridin-2(1H)-one F. Reduction of substituted-dihydro-1,5-naphthyridin-2(1H)-one F can be performed by reaction with a hydride (e.g., a borane or lithium aluminum hydride) to provide tetrahydro-1,5-naphthyridine G. Next, protecting groups (e.g., the benzyl and carbamate protecting group) are removed and the resulting amine is reacted with carbamoylating reagents from Scheme 5 to provide carbamoyl-tetrahydro-1,5-naphthyridine I and reacted with a sulphonyl chloride to provide the final tetrahydro-1,5-naphthyridine J.

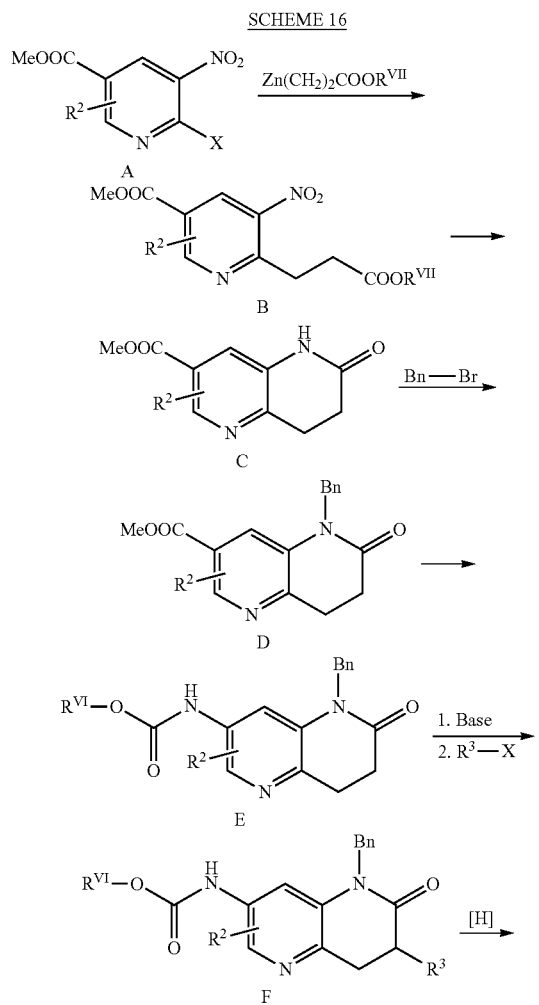

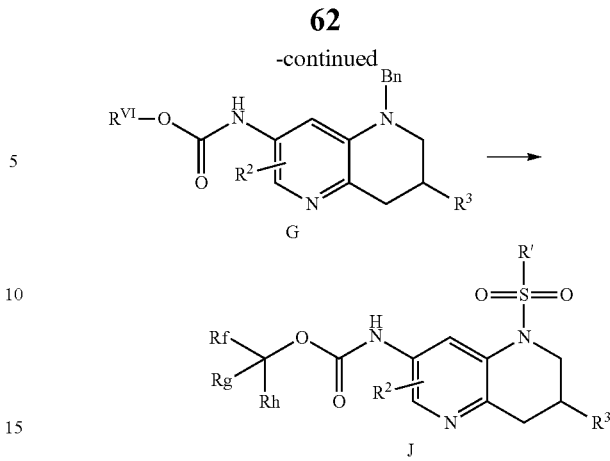

Scheme 17 illustrates another procedure for preparing substituted tetrahydro-1,5-naphthyridines. Reacting halo-nitro-pyridine A with a Negishi reagent (formed from a 2-((tert-butoxycarbonyl)amino)-3-iodopropanoate) provides amino acid B. Then, amino acid B is subjected to dissolving metal reduction conditions with in situ cyclization to provide dihydro-1,5-naphthyridin-2(1H)-one C. Subjecting dihydro-1,5-naphthyridin-2(1H)-one C to hydrolysis conditions provides a carboxylic acid (not shown), that after in situ formation of an acyl azide followed by a Curtius rearrangement provides bis-carbamate D. Selective reduction of the amide group in bis-carbamate D using borane or lithium aluminum hydride provides tetrahydro-1,5-naphthyridine E. Reaction of tetrahydro-1,5-naphthyridine E with a sulphonyl chloride or sulfamoyl chloride provides sulfonamide F. Next, the benzylcarbamate protecting group is removed from sulfonamide F to provide an amino-tetrahydro-1,5-naphthyridine (not shown) that can be subjected to carbamoylating reagents from Scheme 5 to provide carbamoyl-tetrahydro-1,5-naphthyridine G. The remaining Boc protecting group on carbamate-tetrahydro-1,5-naphthyridine G can be removed by treatment with acid to provide amino-tetrahydro-1,5-naphthyridine H. It would be understood by those trained in the art that the amino group on amino-tetrahydro-1,5-naphthyridine H can be converted to other functional groups (e.g., by reaction with an alkylating agent(s), aldehyde (reductive alkylations), acyl halide, sulphonyl chloride, isocyanate, and the like) to afford the compound I.

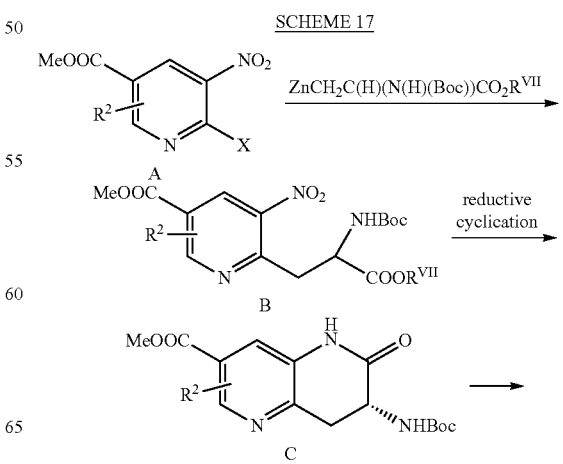

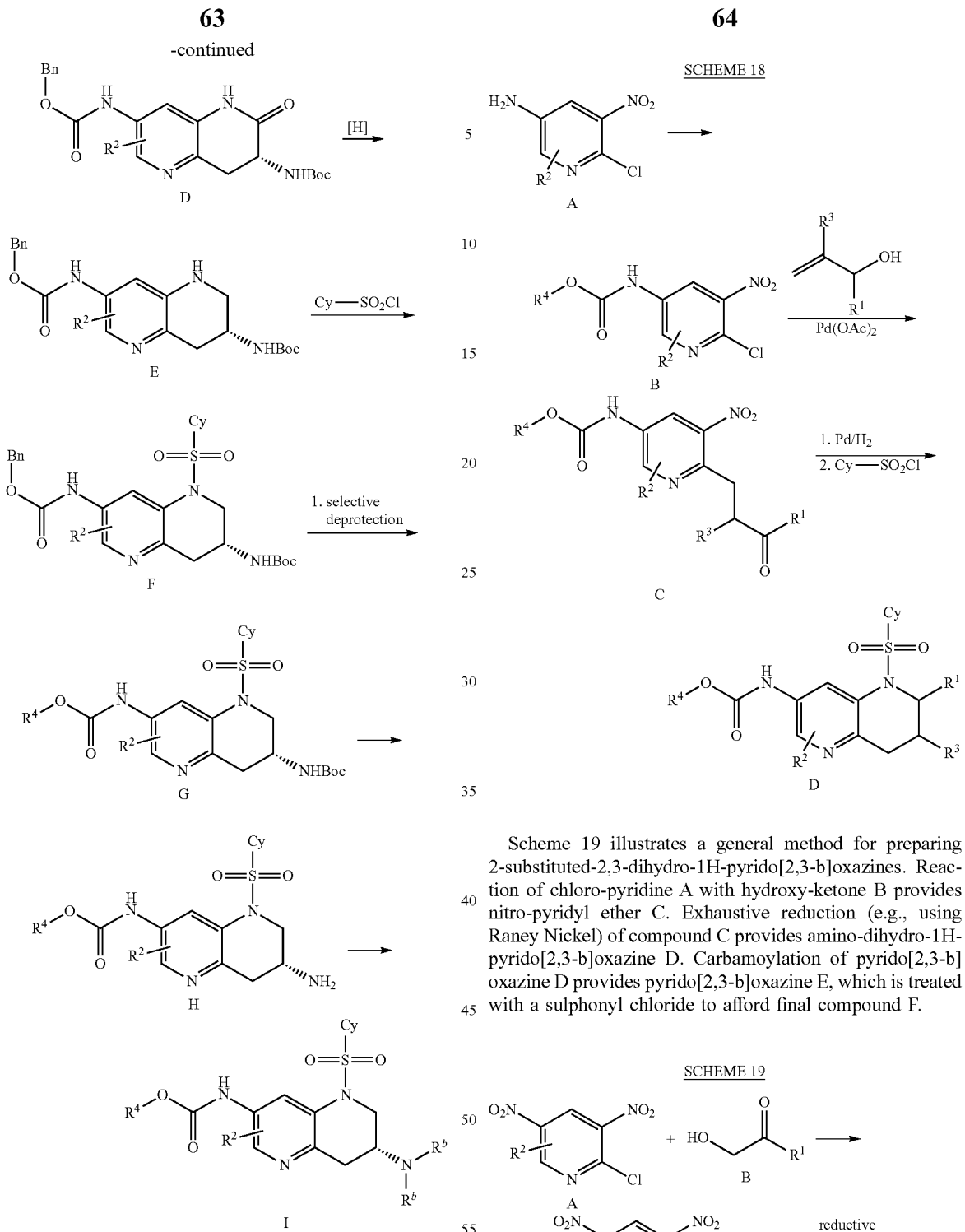

Scheme 18 illustrates another general method for preparing substituted tetrahydro-1,5-naphthyridines. Carbamoylation of amino-pyridine A provides pyridine B, which is treated with an allylic alcohol under Heck conditions to provide compound C. For an exemplary description of such Heck reaction conditions, see, for example, Colbon et al. in *J. Org. Letters* 2011, 13, 5456-5459. Subjecting Compound C to reductive cyclization conditions followed by treatment with a sulphonyl chloride provides sulfonamide-tetrahydro-1,5-naphthyridine D.

Scheme 19 illustrates a general method for preparing 2-substituted-2,3-dihydro-1H-pyrido[2,3-b]oxazines. Reaction of chloro-pyridine A with hydroxy-ketone B provides nitro-pyridyl ether C. Exhaustive reduction (e.g., using Raney Nickel) of compound C provides amino-dihydro-1H-pyrido[2,3-b]oxazine D. Carbamoylation of pyrido[2,3-b]oxazine D provides pyrido[2,3-b]oxazine E, which is treated with a sulphonyl chloride to afford final compound F.

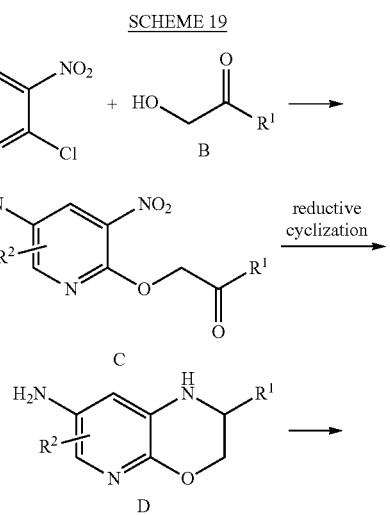

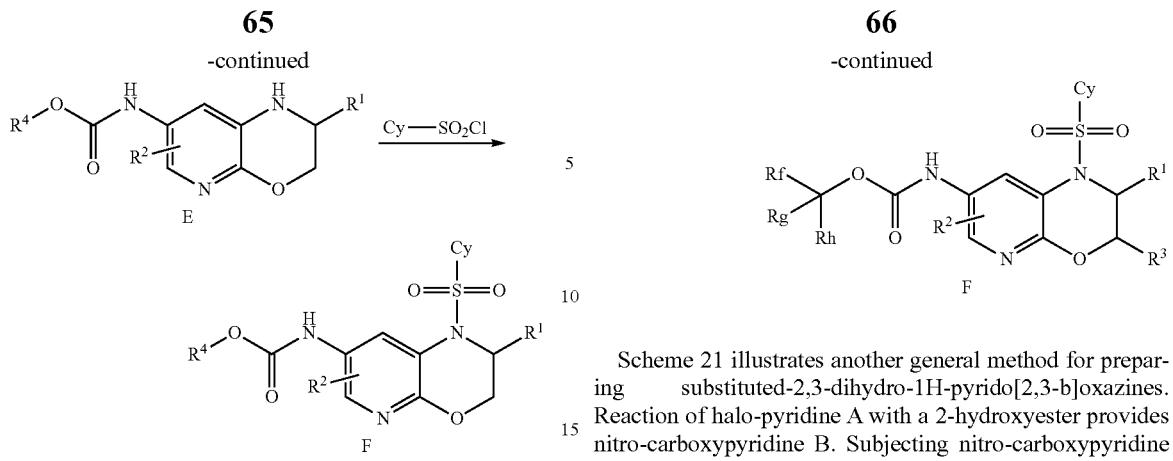

Scheme 20 illustrates a general method for preparing substituted-2,3-dihydro-1H-pyrido[2,3-b]oxazines. Reacting chloro-pyridine A with protected hydroxyketone (or a protected hydroxyaldehyde) B provides an aryl-alkyl ether intermediate (not shown) that upon acid hydrolysis provides dinitropyridyl-ketone (or dinitropyridyl-aldehyde) C. Exhaustive reduction (e.g., using Raney Nickel) of compound C provides amino-dihydro-1H-pyrido[2,3-b]oxazine D. Carbamoylation of the amino group in compound D affords dihydro-1H-pyrido[2,3-b]oxazine E, which is treated with a sulphonyl chloride or a sulfamoyl chloride to afford the final compound F.

In embodiments where it is desirable to prepare pyridooxazines F in chiral form, a protected chiral hydroxyketone B can be used as starting material.

Scheme 21 illustrates another general method for preparing substituted-2,3-dihydro-1H-pyrido[2,3-b]oxazines. Reaction of halo-pyridine A with a 2-hydroxyester provides nitro-carboxypyridine B. Subjecting nitro-carboxypyridine B to dissolving metal reduction conditions with in situ cyclization affords 1H-pyrido[2,3-b][1,4]oxazin-2(3H)-one C. Subjecting 1H-pyrido[2,3-b][1,4]oxazin-2(3H)-one C to hydrolysis conditions provides a carboxylic acid (not shown), that after in situ formation of an acyl azide followed by a Curtius rearrangement provides carbamate D. Selective reduction of the amide group in carbamate D using borane or lithium aluminum hydride provides dihydro-1H-pyrido[2,3-b]oxazine E. Reaction of dihydro-1H-pyrido[2,3-b]oxazine E with a sulphonyl chloride provides sulfonamide F. Next, the carbamate protecting group is removed from sulfonamide F to provide amino-dihydro-1H-pyrido[2,3-b]oxazine G that can be carbamoylated as described in Scheme 5 to provide dihydro-1H-pyrido[2,3-b]oxazine H.

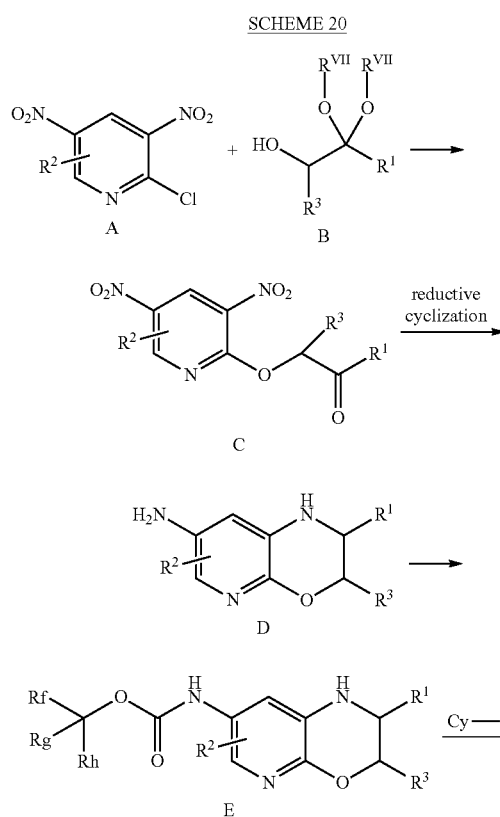

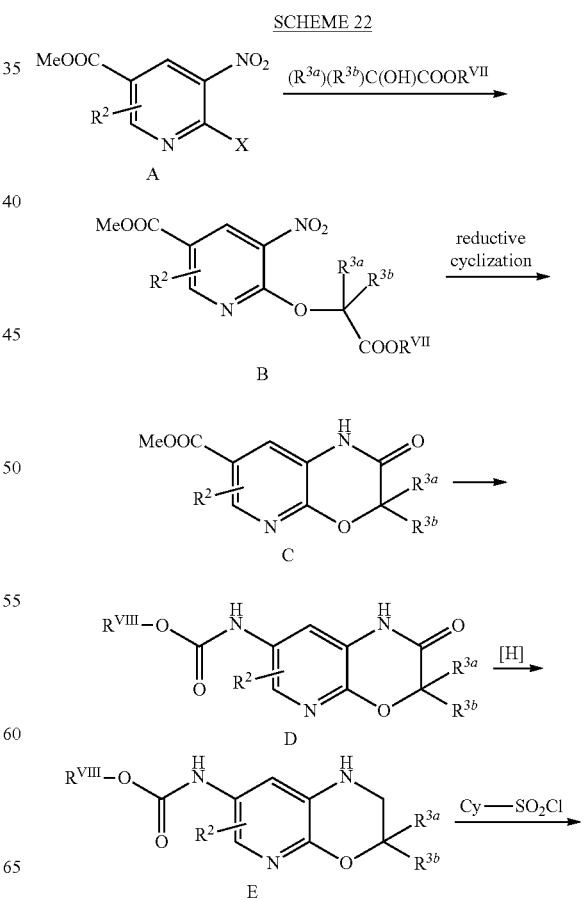

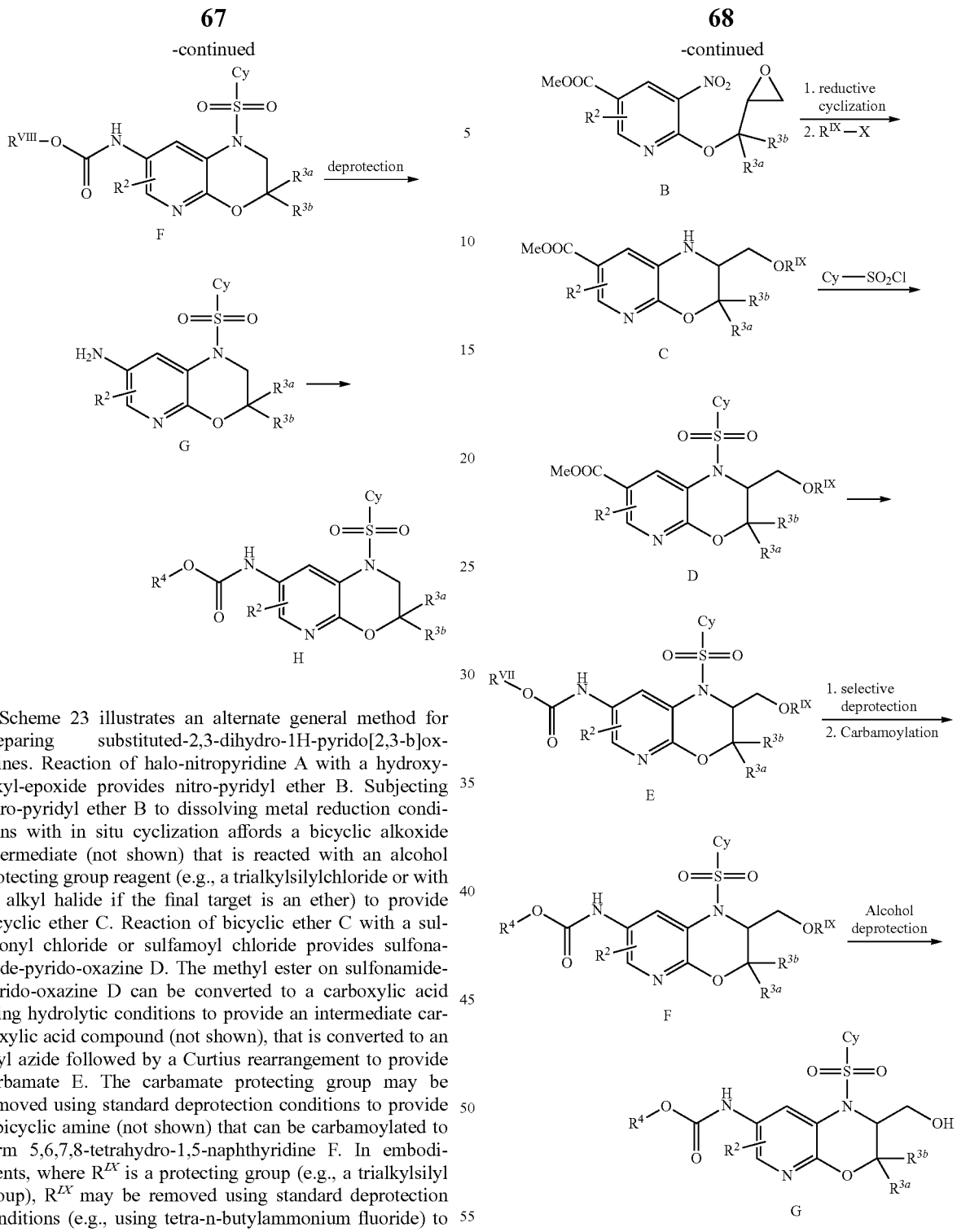

Scheme 23 illustrates an alternate general method for preparing substituted-2,3-dihydro-1H-pyrido[2,3-b]oxazines. Reaction of halo-nitropyridine A with a hydroxyalkyl-epoxide provides nitro-pyridyl ether B. Subjecting nitro-pyridyl ether B to dissolving metal reduction conditions with in situ cyclization affords a bicyclic alkoxide intermediate (not shown) that is reacted with an alcohol protecting group reagent (e.g., a trialkylsilylchloride or with an alkyl halide if the final target is an ether) to provide bicyclic ether C. Reaction of bicyclic ether C with a sulphonyl chloride or sulfamoyl chloride provides sulfonamide-pyrido-oxazine D. The methyl ester on sulfonamide-pyrido-oxazine D can be converted to a carboxylic acid using hydrolytic conditions to provide an intermediate carboxylic acid compound (not shown), that is converted to an acyl azide followed by a Curtius rearrangement to provide carbamate E. The carbamate protecting group may be removed using standard deprotection conditions to provide a bicyclic amine (not shown) that can be carbamoylated to form 5,6,7,8-tetrahydro-1,5-naphthyridine F. In embodiments, where $R^{IX}$ is a protecting group (e.g., a trialkylsilyl group), $R^{IX}$ may be removed using standard deprotection conditions (e.g., using tetra-n-butylammonium fluoride) to provide alcohol G.

SCHEME 23

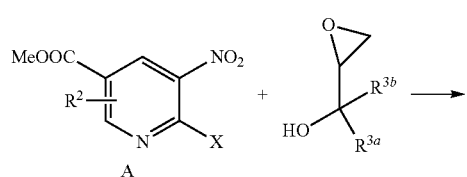

Scheme 24 shows the general synthetic route to tetrahydroquinoline carboxylic acids and acid derivatives as analogues of the benzoxazine core. Halogenation of readily available quinoline B and subsequent Heck reaction affords alpha, beta-unsubstituted ester C. Partial reduction of the quinoline moiety, in addition to reduction of the nitro and double bond groups in the presence of Boc$_2$O, affords Boc-carbamate D. Compound D can subsequently be elaborated to the desired tetrahydroquinoline carboxylic acid derivative H using similar chemistry as described above.

SCHEME 24

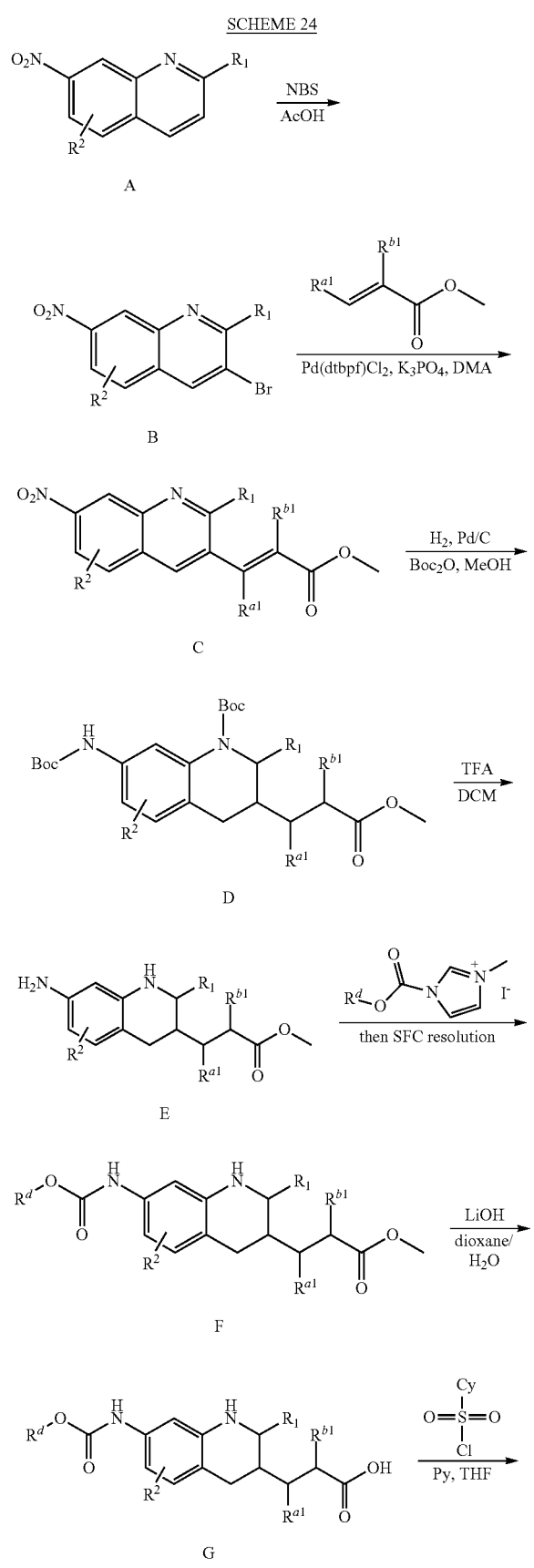

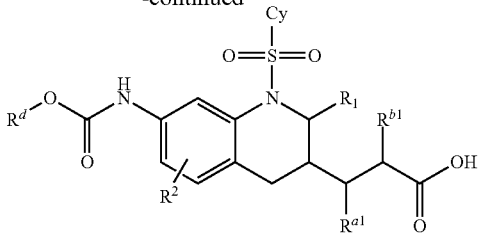

EXAMPLES

The invention now being generally described will be more readily understood by reference to the following examples, which are included for purposes of illustration of certain aspects and embodiments of the present invention, and are not intended to limit the invention. Starting materials useful for preparing the compounds of Formula (I) can be obtained from commercial sources or are readily prepared from commercially available materials using transformations which are known to those of skill in the art of organic chemistry.

Example 1—Synthesis of (R)-tert-butyl (2-(hydroxymethyl)-4-((3-(trifluoromethyl)phenyl)sulfonyl)-3,4-dihydro-2H-benzo[b][1,4]oxazin-6-yl)carbamate (1)

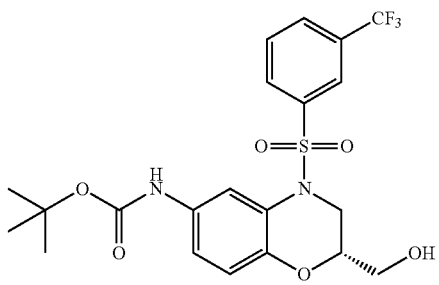 [SMILES: CC(C)(C)OC(=O)Nc1ccc2c(c1)N(S(=O)(=O)c1cccc(C(F)(F)F)c1)C[C@H](CO)O2]

The title compound was prepared according to the procedures described below.

Part I—Synthesis of 2-[[(2S)-3-chloro-2-hydroxypropyl]amino]-4-nitrophenol

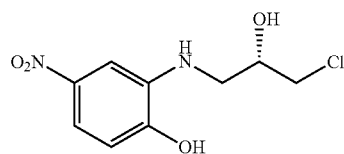 [SMILES: O=[N+]([O-])c1ccc(O)c(NC[C@H](O)CCl)c1]

A solution of 2-amino-4-nitrophenol (250.0 g, 1.62 mol) and (2S)-2-(chloromethyl)oxirane (330.0 g, 3.57 mol) in ethanol:water (2500 mL:25 mL) was stirred for twelve hours at 60° C. in an oil bath. The resulting mixture was cooled and concentrated to afford 2-[[(2S)-3-chloro-2-hydroxypropyl]amino]-4-nitrophenol as a brown oil.

Part II—Synthesis of [(2R)-6-nitro-3,4-dihydro-2H-1,4-benzoxazin-2-yl]methanol

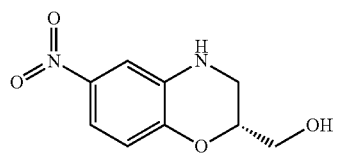 [SMILES: O=[N+]([O-])c1ccc2c(c1)NC[C@H](CO)O2]

A solution of 2-[[(2S)-3-chloro-2-hydroxypropyl]amino]-4-nitrophenol (400 g, 1.62 mol) in ethanol (2.5 L) and potassium carbonate (134.5 g, 973 mmol) was stirred for twelve hours at 90° C. in an oil bath. The mixture was filtered and the filtrate was concentrated. The residue was diluted with water (1.5 L) and extracted three times with ethyl acetate (1 L). The combined organic layers were washed with brine, dried ($Na_2SO_4$), and concentrated. The residue was purified via MPLC over silica gel eluting with ethyl acetate/petroleum ether (1:1) to afford [(2R)-6-nitro-3,4-dihydro-2H-1,4-benzoxazin-2-yl]methanol as a red solid.

Part III—Synthesis of ((R)-2-hydroxymethyl-3,4-dihydro-2H-benzo[1,4]oxazin-6-yl)-carbamic acid tert-butyl ester

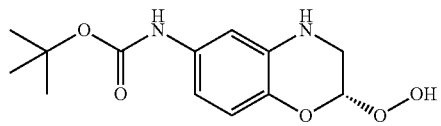 [SMILES: CC(C)(C)OC(=O)Nc1ccc2c(c1)NC[C@H](OO)O2]

The atmosphere above a solution of [(2R)-6-nitro-3,4-dihydro-2H-1,4-benzoxazin-2-yl]methanol (137 g, 652 mmol), palladium on carbon (13.7 g) and di-tert-butyl dicarbonate (157 g, 717 mmol) in methanol (1400 mL) was exchanged with hydrogen. The resulting solution was stirred for twelve hours at room temperature. The mixture was filtered, and the filtrate was concentrated. The crude product was purified by re-crystallization from ether to afford ((R)-2-hydroxymethyl-3,4-dihydro-2H-benzo[1,4]oxazin-6-yl)-carbamic acid tert-butyl ester as an off-white solid. LRMS (ESI) calculated for $C_{14}H_{20}N_2O_4$ 280: Found: 225 (M-$C_4H_8$+H)$^+$; 281 (M+H)$^+$. $^1$H NMR (300 MHz, CDCl$_3$): δ 6.92 (s, 1H), 6.71 (d, J=8.7 Hz, 1H), 6.41 (dd, J=8.7, 2.4 Hz, 1H), 6.26 (s, 1H), 4.20-4.21 (m, 1H), 3.76-3.86 (m, 2H), 3.26-3.35 (m, 2H), 1.53 (s, 9H).

Part IV—Synthesis of (R)-tert-butyl (2-(hydroxymethyl)-4-((3-(trifluoromethyl)phenyl)sulfonyl)-3,4-dihydro-2H-benzo[b][1,4]oxazin-6-yl)carbamate

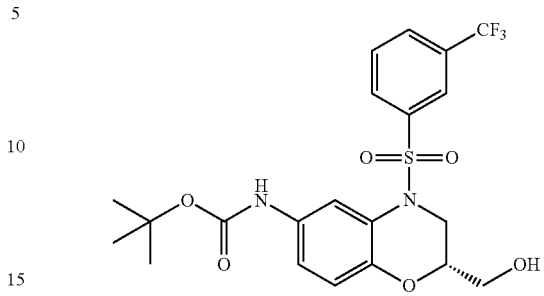

To a stirred solution of (R)-tert-butyl (2-(hydroxymethyl)-3,4-dihydro-2H-benzo[b][1,4]oxazin-6-yl)carbamate (2.0 g, 7.1 mmol) in pyridine (14 mL) and anhydrous THF (7 mL) was added dropwise 3-(trifluoromethyl) benzene-1-sulfonyl chloride (2.6 g, 10.6 mmol) at room temperature. After an hour, the resulting mixture was concentrated and the residue was partitioned between ethyl acetate (30 mL) and water (30 mL). The aqueous layer was extracted three times with ethyl acetate. The combined organic layers were dried (MgSO$_4$) and concentrated. The residue was purified by column chromatography on silica gel eluting with petroleum ether: ethyl acetate (5:1) to give (R)-tert-butyl (2-(hydroxymethyl)-4-((3-(trifluoromethyl)phenyl)sulfonyl)-3,4-dihydro-2H-benzo[b][1,4]oxazin-6-yl)carbamate as a white solid. $^1$H NMR (400 MHz, CDCl$_3$) δ 1.52 (s, 10H) 1.88 (t, J=6.4 Hz, 1H) 3.39-3.46 (m, 1H) 3.57 (dd, J=9.2, 2.4 Hz, 1H) 3.65-3.81 (m, 2H) 4.29 (dd, J=14.0, 2.0 Hz, 1H) 6.44 (br s, 1H) 6.78 (d, J=9.2 Hz, 1H) 7.17 (d, J=7.6 Hz, 1H) 7.59-7.68 (m, 1H) 7.76 (d, J=2.0 Hz, 1H) 7.84 (d, J=8.0 Hz, 1H) 7.90 (d, J=8.0 Hz, 1H) 8.05 (s, 1H). LRMS (ESI) calculated for $C_{21}H_{24}F_3N_2O_6S$ (M+H)$^+$: 489, Found: 489.

Example 2—Preparation of additional (R)-tert-butyl (2-(hydroxymethyl)-4-(optionally substituted aryl or heteroaryl-sulfonyl)-3,4-dihydro-2H-benzo[b][1,4]oxazin-6-yl)carbamates The compounds in Table 1 below were prepared based on the experimental procedures described in Example 1 and elsewhere in the detailed description, and can be achieved by one of skill in the art in light of the present disclosure. Starting materials can be obtained from commercial sources or readily prepared from commercially available materials.

TABLE 1

| Ex. No. | Structure | Name | Observed m/z |
|---|---|---|---|
| 2A | (structure) | (R)-tert-butyl (4-((5-bromo-2-chloropyridin-3-yl)sulfonyl)-2-(hydroxymethyl)-3,4-dihydro-2H-benzo[b][1,4]oxazin-6-yl)carbamate | 556 (M + Na)$^+$ |

TABLE 1-continued

| Ex. No. | Structure | Name | Observed m/z |
|---|---|---|---|
| 2B | 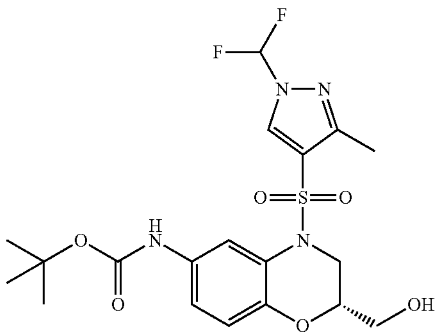 [SMILES: Cc1nn(C(F)F)cc1S(=O)(=O)N1C[C@H](CO)Oc2ccc(NC(=O)OC(C)(C)C)cc21] | (R)-4-((6-((tert-butoxycarbonyl)amino)-2-(hydroxymethyl)-2H-benzo[b][1,4]oxazin-4(3H)-yl)sulfonyl)-1-(difluoromethyl)-3-methyl-1H-pyrazol-2-e | 419.2 (M-tBu + H)+ |
| 2C | 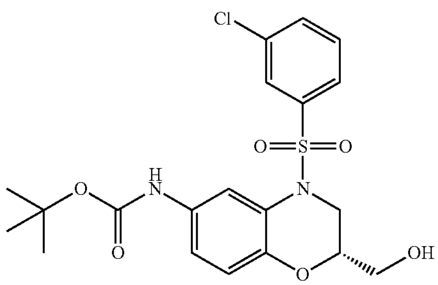 [SMILES: CC(C)(C)OC(=O)Nc1ccc2c(c1)N(S(=O)(=O)c1cccc(Cl)c1)C[C@H](CO)O2] | [(R)-4-(3-chloro-benzenesulfonyl)-2-hydroxymethyl-3,4-dihydro-2H-benzo[1,4]oxazin-6-yl]-carbamic acid tert-butyl ester | 399.0 (M-tBu + H)+ |
| 2D | 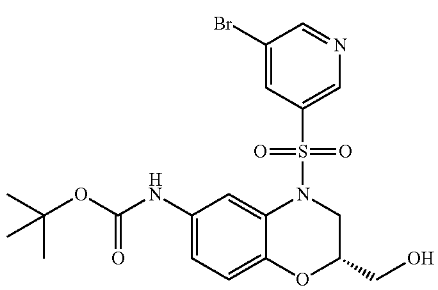 [SMILES: CC(C)(C)OC(=O)Nc1ccc2c(c1)N(S(=O)(=O)c1cncc(Br)c1)C[C@H](CO)O2] | (R)-tert-butyl (4-((5-bromopyridin-3-yl)sulfonyl)-2-(hydroxymethyl)-3,4-dihydro-2H-benzo[b][1,4]oxazin-6-yl)carbamate | 500 (M + H)+ |
| 2E | 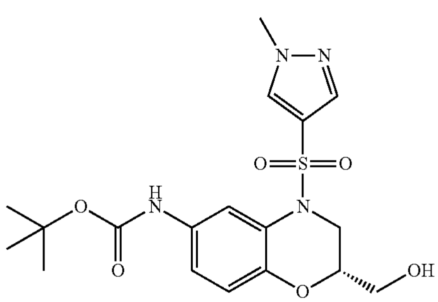 [SMILES: Cn1cc(S(=O)(=O)N2C[C@H](CO)Oc3ccc(NC(=O)OC(C)(C)C)cc32)cn1] | (R)-tert-butyl (2-(hydroxymethyl)-4-((1-methyl-1H-pyrazol-4-yl)sulfonyl)-3,4-dihydro-2H-benzo[b][1,4]oxazin-6-yl)carbamate | 369 (M-tBu + H)+ |
| 2F | 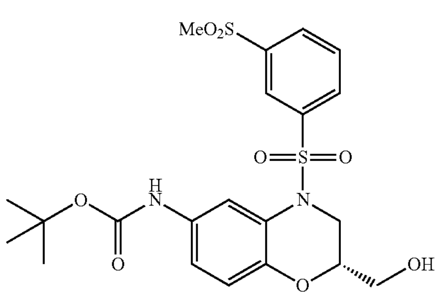 [SMILES: CC(C)(C)OC(=O)Nc1ccc2c(c1)N(S(=O)(=O)c1cccc(S(C)(=O)=O)c1)C[C@H](CO)O2] | (R)-tert-butyl (2-(hydroxymethyl)-4-((3-(methylsulfonyl)phenyl)sulfonyl)-3,4-dihydro-2H-benzo[b][1,4]oxazin-6-yl)carbamate | 443.0 (M-tBu + H)+ |

| Ex. No. | Structure | Name | Observed m/z |
|---|---|---|---|
| 2G | 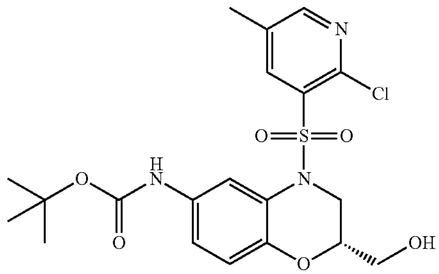 [SMILES: Cc1cnc(Cl)c(S(=O)(=O)N2C[C@H](CO)Oc3ccc(NC(=O)OC(C)(C)C)cc32)c1] | (R)-tert-butyl (4-((2-chloro-5-methylpyridin-3-yl)sulfonyl)-2-(hydroxymethyl)-3,4-dihydro-2H-benzo[b][1,4]oxazin-6-yl)carbamate | 470 (M + H)⁺ |
| 2H | 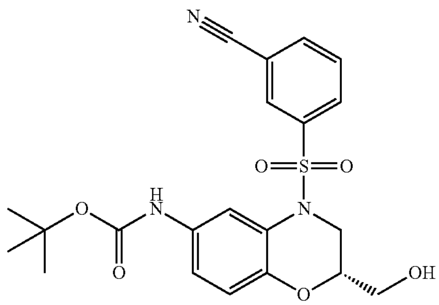 [SMILES: CC(C)(C)OC(=O)Nc1ccc2c(c1)N(S(=O)(=O)c1cccc(C#N)c1)C[C@H](CO)O2] | (R)-tert-butyl (4-((3-cyanophenyl)sulfonyl)-2-(hydroxymethyl)-3,4-dihydro-2H-benzo[b][1,4]oxazin-6-yl)carbamate | 390.0 (M-tBu + H)⁺ |

Example 3—Synthesis of (R)-tert-butyl (2-(hydroxymethyl)-4-((5-methyl-2-oxo-1,2-dihydropyridin-3-yl)sulfonyl)-3,4-dihydro-2H-benzo[b][1,4]oxazin-6-yl)carbamate (3)

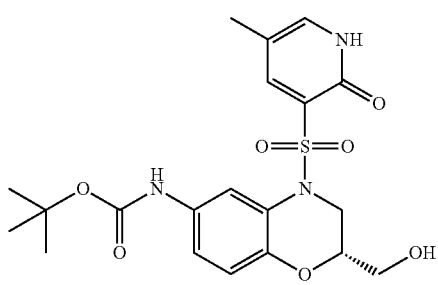 [SMILES: Cc1c[nH]c(=O)c(S(=O)(=O)N2C[C@H](CO)Oc3ccc(NC(=O)OC(C)(C)C)cc32)c1]

A solution of (R)-tert-butyl (4-((2-chloro-5-methylpyridin-3-yl)sulfonyl)-2-(hydroxymethyl)-3,4-dihydro-2H-benzo[b][1,4]oxazin-6-yl)carbamate (102 mg, 0.217 mmol), and chloro[2-(di-tert-butylphosphino)-2',4',6'-triisopropyl-1,1'-biphenyl][2-(2-aminoethyl)phenyl)]palladium(II) (22.36 mg, 0.033 mmol) in p-dioxane (1085 μL) and water (1085 μl) was purged thoroughly with argon. Potassium hydroxide (48.7 mg, 0.868 mmol) was then added and the reaction was sealed and heated at 80° C. for two hours. The mixture was cooled, diluted with ethyl acetate, washed twice with aqueous sodium hydrogen carbonate and then with brine. The aqueous layers were back extracted once with ethyl acetate. The combined organic layers were dried (Na₂SO₄) and concentrated. The residue was purified by MPLC eluting with a gradient of 1-10% methanol in dichloromethane to afford (R)-tert-butyl (2-(hydroxymethyl)-4-((5-methyl-2-oxo-1,2-dihydropyridin-3-yl)sulfonyl)-3,4-dihydro-2H-benzo[b][1,4]oxazin-6-yl)carbamate as a yellow solid. ¹H NMR (600 MHz, DMSO-d6) δ 12.17 (s, 1H), 9.11 (s, 1H), 8.19 (d, J=2.2 Hz, 1H), 7.74 (s, 1H), 7.52 (s, 1H), 6.76 (dd, J=1.9, 8.8 Hz, 1H), 6.69 (d, J=8.8 Hz, 1H), 5.01 (t, J=5.6 Hz, 1H), 4.38 (dd, J=1.8, 13.5 Hz, 1H), 4.08-4.02 (m, 1H), 3.64-3.56 (m, 1H), 3.57-3.51 (m, 1H), 3.44 (dd, J=9.1, 13.3 Hz, 1H), 2.09 (s, 3H), 1.42 (s, 9H). LRMS (ESI) calculated for C₂₀H₂₅N₃O₇S (M+H)⁺: 452, Found: 452.

Example 4—Synthesis of (R)-tert-butyl (4-((4-fluorophenyl)sulfonyl)-2-(2-hydroxypropan-2-yl)-3,4-dihydro-2H-benzo[b][1,4]oxazin-6-yl)carbamate and (S)-tert-butyl (4-((4-fluorophenyl)sulfonyl)-2-(2-hydroxypropan-2-yl)-3,4-dihydro-2H-benzo[b][1,4]oxazin-6-yl)carbamate (Example Nos. 4A and 4B)

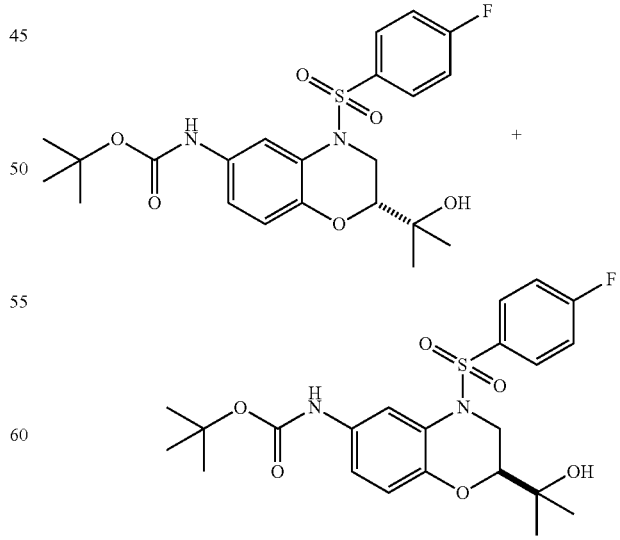

The title compound was prepared according to the procedures described below.

Part I—Synthesis of ethyl 4-((4-fluorophenyl)sulfonyl)-6-nitro-3,4-dihydro-2H-benzo[b][1,4]oxazine-2-carboxylate

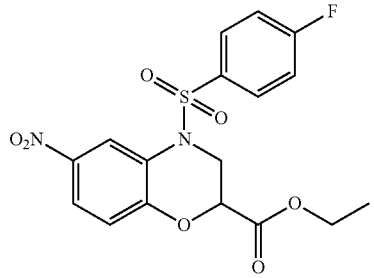 [SMILES: CCOC(=O)C1CN(S(=O)(=O)c2ccc(F)cc2)c2cc([N+](=O)[O-])ccc2O1]

A mixture of ethyl 6-nitro-3,4-dihydro-2H-benzo[b][1,4]oxazine-2-carboxylate (4.5 g, 17.9 mmol), 4-fluorobenzene-1-sulfonyl chloride (4.52 g, 23.3 mmol) and pyridine (7.07 g, 89.5 mmol) in THF (100 mL) was stirred at 60° C. for fifteen hours. The reaction mixture was concentrated, and the residue was partitioned between dichloromethane (100 mL) and water (100 mL). The aqueous layer was extracted twice with dichloromethane, and the combined organic layers were washed with brine, dried (Na$_2$SO$_4$), and concentrated. The residue was purified by column chromatography on silica gel eluting with petroleum ether:ethyl acetate (5:1) to afford ethyl 4-((4-fluorophenyl)sulfonyl)-6-nitro-3,4-dihydro-2H-benzo[b][1,4]oxazine-2-carboxylate as a yellow solid. LRMS (ESI) calculated for C$_{17}$H$_{16}$FN$_2$O$_7$S (M+H)$^+$: 411, Found: 411.

Part II—Synthesis of ethyl 6-((tert-butoxycarbonyl)amino)-4-((4-fluorophenyl)sulfonyl)-3,4-dihydro-2H-benzo[b][1,4]oxazine-2-carboxylate

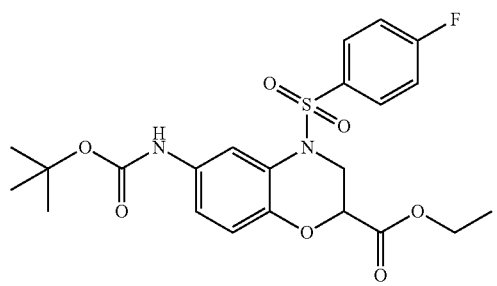 [SMILES: CCOC(=O)C1CN(S(=O)(=O)c2ccc(F)cc2)c2cc(NC(=O)OC(C)(C)C)ccc2O1]

To a solution of ethyl 4-((4-fluorophenyl)sulfonyl)-6-nitro-3,4-dihydro-2H-benzo[b][1,4]oxazine-2-carboxylate (5.0 g, 12.2 mmol) and di-tert-butyl dicarbonate (2.92 g, 13.4 mmol) in ethanol (100 mL) was added Pd/C (1.0 g, 10% wt) under argon. The suspension was degassed under vacuo and purged with hydrogen three times. The mixture was stirred under the pressure of 40 psi hydrogen at 30° C. for four hours. The suspension was filtered through a pad of CELITE and the filter cake was washed with ethanol (20 mL). The combined filtrates were concentrated to dryness to give ethyl 6-((tert-butoxycarbonyl)amino)-4-((4-fluorophenyl)sulfonyl)-3,4-dihydro-2H-benzo[b][1,4]oxazine-2-carboxylate as a yellow solid. LRMS (ESI) calculated for C$_{22}$H$_{26}$FN$_2$O$_7$S (M+H)$^+$: 481, Found: 481.

Part III—Synthesis of (R)-tert-butyl (4-((4-fluorophenyl)sulfonyl)-2-(2-hydroxypropan-2-yl)-3,4-dihydro-2H-benzo[b][1,4]oxazin-6-yl)carbamate and (S)-tert-butyl (4-((4-fluorophenyl) sulfonyl)-2-(2-hydroxypropan-2-yl)-3,4-dihydro-2H-benzo[b][1,4]oxazin-6-yl)carbamate

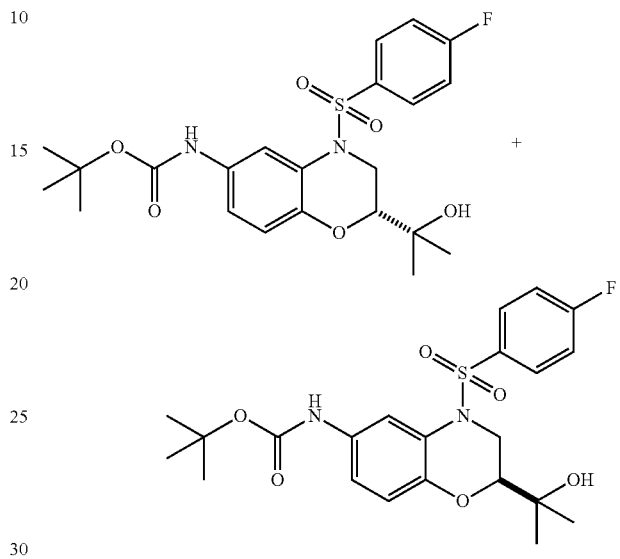

To a stirred solution of ethyl 6-((tert-butoxycarbonyl)amino)-4-((4-fluorophenyl)sulfonyl)-3,4-dihydro-2H-benzo[b][1,4]oxazine-2-carboxylate (5.5 g, 11.5 mmol) in anhydrous THF (70 mL) was added a 3M solution of methyl magnesium bromide (38.3 mL, 115 mmol) in ethyl ether at −78° C., and the resultant mixture was warmed to 25° C. and stirred for an additional hour. The reaction mixture was poured into saturated ammonium chloride (500 mL), and extracted twice with dichloromethane (500 mL each). The combined organic layers were dried (Na$_2$SO$_4$), and concentrated. The residue was purified by column chromatography on silica gel eluting with petroleum ether:ethyl acetate (3:1) to afford a racemic mixture of the title compounds as a white solid, which was chirally separated by SFC (Instrument: Thar SFC 350; Column: AD 300 mm*50 mm, 10 um; Mobile phase: A: Supercritical CO$_2$, B: MeOH (0.1% NH$_3$.H$_2$O), A:B=65:35 at 240 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the two isomers.

Isomer 1: (R)-tert-butyl (4-((4-fluorophenyl)sulfonyl)-2-(2-hydroxypropan-2-yl)-3,4-dihydro-2H-benzo[b][1,4]oxazin-6-yl)carbamate $^1$H NMR (400 MHz, CDCl$_3$) δ 7.62-7.75 (m, 3H), 7.32 (br. s., 1H), 7.15 (t, J=8.4 Hz, 2H), 6.81 (d, J=9.2 Hz, 1H), 6.44 (br. s., 1H), 4.38 (dd, J=2.0, 14.4 Hz, 1H), 3.19 (dd, J=10.4, 14.4 Hz, 1H), 3.03 (dd, J=1.6, 10.4 Hz, 1H), 1.53 (s, 9H), 1.20 (d, J=12.4 Hz, 6H). LRMS (ESI) calculated for C$_{22}$H$_{28}$FN$_2$O$_6$S (M+H)$^+$: 467, Found: 467.

Isomer 2: (S)-tert-butyl (4-((4-fluorophenyl)sulfonyl)-2-(2-hydroxypropan-2-yl)-3,4-dihydro-2H-benzo[b][1,4]oxazin-6-yl)carbamate. $^1$H NMR (400 MHz, CDCl$_3$) δ 7.65-7.74 (m, 3H), 7.33 (br. s, 1H), 7.15 (t, J=8.4 Hz, 2H), 6.81 (d, J=8.4 Hz, 1H), 6.44 (br. s, 1H), 4.38 (dd, J=2.0, 14.0 Hz, 1H), 3.19 (dd, J=10.4, 14.0 Hz, 1H), 3.03 (dd, J=1.6, 10.4 Hz, 1H), 1.53 (s, 9H), 1.20 (d, J=12.4 Hz, 6H). LRMS (ESI) calculated for C$_{22}$H$_{28}$FN$_2$O$_6$S (M+H)$^+$: 467, Found: 467.

Example 5—Preparation of (R and S)-1,1,1-trifluoro-2-methylpropan-2-yl 4-(3,4-difluorophenylsulfonyl)-2-(2,2,2-trifluoroacetyl)-3,4-dihydro-2H-benzo[b][1,4]oxazin-6-ylcarbamate (5)

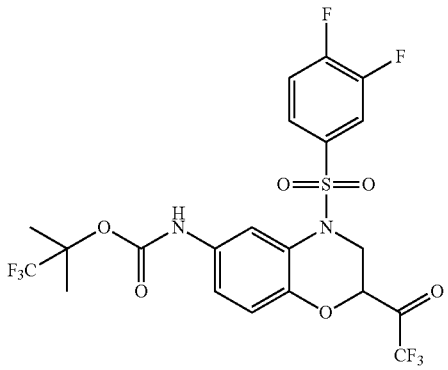 [SMILES: CC(C)(OC(=O)Nc1ccc2c(c1)N(S(=O)(=O)c1ccc(F)c(F)c1)CC(C(=O)C(F)(F)F)O2)C(F)(F)F]

Step 1-Preparation of 1-(4-benzyl-6-nitro-3,4-dihydro-2H-benzo[b][1,4]oxazin-2-yl)-2,2,2-trifluoroethanone

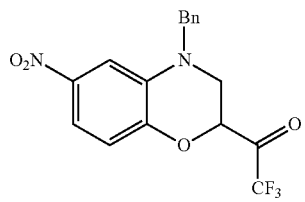 [SMILES: O=C(C1CN(Cc2ccccc2)c2cc([N+](=O)[O-])ccc2O1)C(F)(F)F]

To a solution of (R)-4-benzyl-6-nitro-3,4-dihydro-2H-benzo[b][1,4]oxazine-2-carboxylic acid (7.5 g, 23.85 mmol) in dichloromethane (150 mL) and 2 drops of DMF at 0° C. was added oxalyl chloride (12 mL). The mixture was allowed to warm to room temperature and was stirred for an additional two hours. The mixture was concentrated. To a solution of the resulting residue in dichloromethane (150 mL) at 0° C. was added trifluoroacetic anhydride (19.5 mL, 143.1 mmol) followed by slow addition of pyridine (15 mL). The mixture was allowed to warm to room temperature and stirred for 24 hours. The mixture was cooled in an ice bath, ice water was added into the mixture slowly, and the mixture was stirred at room temperature for an additional hour. The mixture was extracted twice with dichloromethane. The combined organic phases were washed with 1 N HCl, brine, dried (Na$_2$SO$_4$) and concentrated. The residue was purified by column chromatography on silica gel eluting with petroleum ether:ethyl acetate (20:1 to 10:1) to give the title compound as a red oil. LCMS (ESI): calculated for C$_{17}$H$_{13}$F$_3$N$_2$O$_4$ (M+H)$^+$: 367, found: (M+H$_2$O+H)$^+$ 385.

Step 2—Preparation of 1-(6-amino-3,4-dihydro-2H-benzo[b][1,4]oxazin-2-yl)-2,2,2-trifluoroethanone

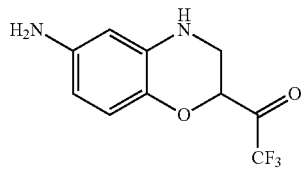

To a solution of 1-(4-benzyl-6-nitro-3,4-dihydro-2H-benzo[b][1,4]oxazin-2-yl)-2,2,2-trifluoroethanone (1.0 g, 2.73 mmol) in ethyl acetate (30 mL) purged with nitrogen was added Pd/C (1 g). The atmosphere above the solution was exchanged with a balloon of hydrogen and was stirred at room temperature for 16 hours. The mixture was filtered through a pad of CELITE and the filtrate was concentrated to afford the title compound as a dark-white solid which was used without any further purification. LCMS (ESI): calculated for C$_{10}$H$_9$F$_3$N$_2$O$_2$ (M+H)$^+$: 247, found: 247.

Step 3-Preparation of 1,1,1-trifluoro-2-methylpropan-2-yl 2-(2,2,2-trifluoroacetyl)-3,4-dihydro-2H-benzo[b][1,4]oxazin-6-ylcarbamate

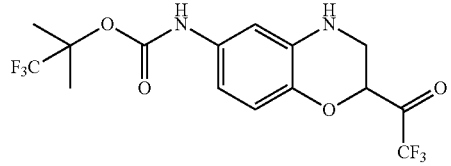 [SMILES: CC(C)(OC(=O)Nc1ccc2c(c1)NCC(C(=O)C(F)(F)F)O2)C(F)(F)F]

To a solution of 1-(6-amino-3,4-dihydro-2H-benzo[b][1,4]oxazin-2-yl)-2,2,2-trifluoroethanone (2.8 g, 23.6 mmol) and 1,1,1-trifluoro-2-methylpropan-2-yl 1H-imidazole-1-carboxylate (2.78 g, 25.9 mmol) in DMSO (28 mL) was added concentrated HCl (1.2 mL, 13.44 mmol) and the mixture was stirred at 70° C. for 5 hours. The mixture was diluted with saturated NaHCO$_3$ and extracted three times with ethyl acetate. The combined organic layers were washed with brine, dried (Na$_2$SO$_4$), and concentrated. The residue was purified via MPLC to afford an off-white solid (dichloromethane: ethyl acetate=20:1-10:1). LCMS (ESI): calculated for C$_{15}$H$_{14}$F$_6$N$_2$O$_4$ (M+H)$^+$: 401, found (M+H$_2$O+H)$^+$: 419.

Step 4—Preparation of (R and S)-1,1,1-trifluoro-2-methylpropan-2-yl 4-(3,4-difluorophenylsulfonyl)-2-(2,2,2-trifluoroacetyl)-3,4-dihydro-2H-benzo[b][1,4]oxazin-6-ylcarbamate

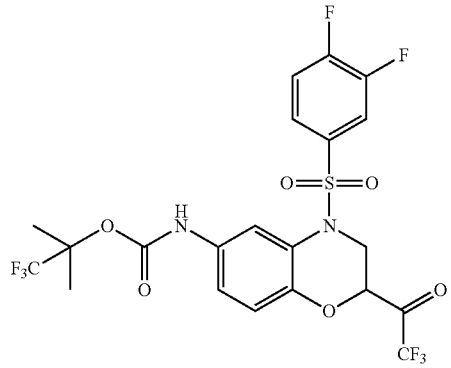 [SMILES: CC(C)(OC(=O)Nc1ccc2c(c1)N(S(=O)(=O)c1ccc(F)c(F)c1)CC(C(=O)C(F)(F)F)O2)C(F)(F)F]

To a room temperature solution of 1,1,1-trifluoro-2-methylpropan-2-yl 2-(2,2,2-trifluoroacetyl)-3,4-dihydro-2H-benzo[b][1,4]oxazin-6-ylcarbamate (400 mg, 1.0 mmol) in THF (6 mL) and pyridine (2 mL) was added 3,4-difluorobenzene-1-sulfonyl chloride (425 mg, 2.0 mmol) and the mixture was stirred overnight. The mixture was diluted with 1 N of HCl (final mixture had a pH=3) and was extracted twice with ethyl acetate. The combined organic phase was washed with brine, dried (Na$_2$SO$_4$) and concentrated. The residue was purified by column chromatography on silica gel eluting with a gradient of petroleum ether:ethyl acetate of 10:1 to 3:1 to afford the title compound as a yellow oil. LCMS (ESI): calculated for C$_{21}$H$_{16}$F$_8$N$_2$O$_6$S (M+H)$^+$: 577, found (M+H$_2$O+Na)$^+$: 617; $^1$H-NMR (400 MHz, CD$_3$OD) δ 7.92 (br s, 1H), 7.61-7.65 (m, 1H), 7.42-7.50 (m, 2H), 7.09-7.10 (m, 1H), 6.75-6.81 (m, 1H), 4.44-4.55 (m, 1H), 3.45-3.47 (m, 1H), 3.24-3.25 (m, 2H), 1.73 (s, 6H).

Example 6—Preparation of additional 1,1,1-trifluoro-2-methylpropan-2-yl benzoxazines The compound in Table 2 below is prepared based on the experimental procedures described in Example 5, and can be achieved by one of skill in the art in light of the present disclosure.

TABLE 2

| Ex. No. | Structure | Name | Observed m/z |
|---|---|---|---|
| 6A | 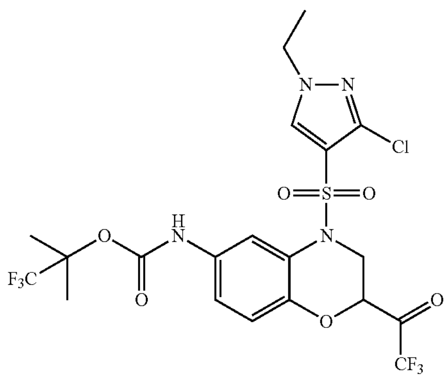 | (R and S)-1,1,1-trifluoro-2-methylpropan-2-yl (4-((3-chloro-1-ethyl-1H-pyrazol-4-yl)sulfonyl)-2-(2,2,2-trifluoroacetyl)-3,4-dihydro-2H-benzo[b][1,4]oxazin-6-yl)carbamate | 633 (M + H$_2$O + Na)$^+$ |
| 6B | 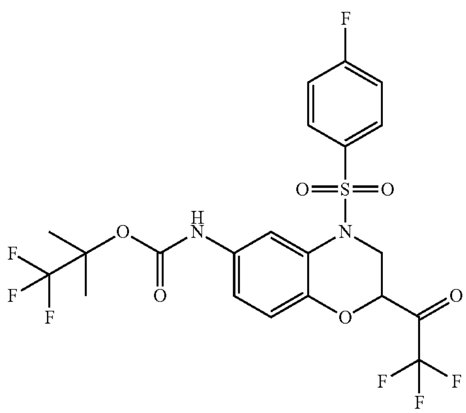 [SMILES: CC(C)(OC(=O)Nc1ccc2c(c1)N(S(=O)(=O)c1ccc(F)cc1)CC(C(=O)C(F)(F)F)O2)C(F)(F)F] | (R and S)-1,1,1-trifluoro-2-methylpropan-2-yl (4-((4-fluorophenyl)sulfonyl)-2-(2,2,2-trifluoroacetyl)-3,4-dihydro-2H-benzo[b][1,4]oxazin-6-yl)carbamate | 559 (M + H)+ |

Example 7—Synthesis of (S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl)carbamate (7)

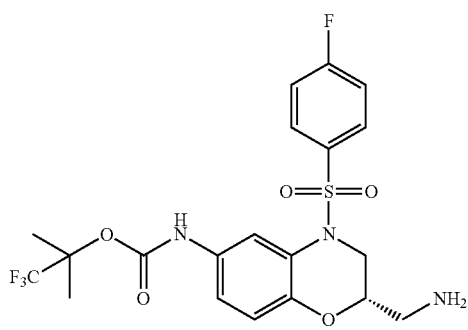 [SMILES: CC(C)(OC(=O)Nc1ccc2c(c1)N(S(=O)(=O)c1ccc(F)cc1)C[C@H](CN)O2)C(F)(F)F]

The title compound was prepared according to the procedures described below.

Part I—Synthesis of (S)-tert-butyl (2-(((benzyloxy)carbonyl)aminomethyl)-3,4-dihydro-2H-benzo[b][1,4]oxazin-6-yl)carbamate

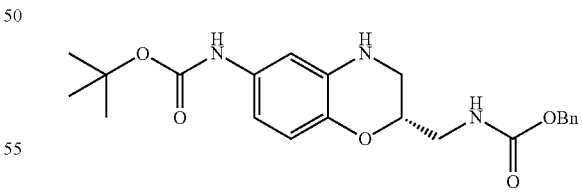

To (S)-tert-butyl (2-(aminomethyl)-3,4-dihydro-2H-benzo[b][1,4]oxazin-6-yl)carbamate (2.5 g, 8.95 mmol), N,N'-diisopropylethylamine (3.91 mL, 22.4 mmol), and dichloromethane (44.7 mL) was added dropwise benzyl chloroformate (1.28 mL, 8.95 mmol) over five minutes at 0° C. The reaction was warmed to room temperature and stirred for four hours. The mixture was diluted in saturated sodium bicarbonate and extracted with isopropanol/chloroform (1:3 v/v). The combined organic layers were washed with brine, Part II—Synthesis of (S)-tert-butyl (2-(((benzyloxy)carbonyl)aminomethyl)-4-((4-fluorophenyl)sulfonyl)-3,4-dihydro-2H-benzo[b][1,4]oxazin-6-yl)carbamate

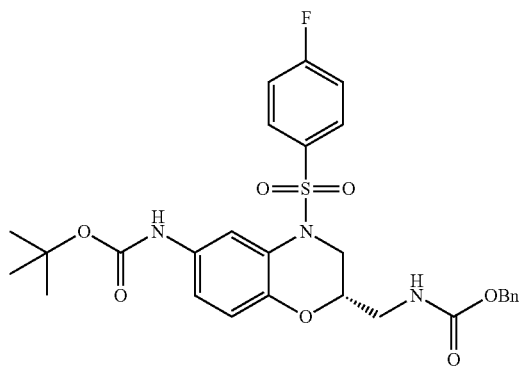 [SMILES: CC(C)(C)OC(=O)Nc1ccc2c(c1)N(S(=O)(=O)c1ccc(F)cc1)C[C@H](CNC(=O)OCc1ccccc1)O2]

A mixture of (S)-tert-butyl (2-(((benzyloxy)carbonyl)aminomethyl)-3,4-dihydro-2H-benzo[b][1,4]oxazin-6-yl)carbamate (7.4 g, 17.90 mmol), pyridine (89 mL), and 4-fluorobenzene-1-sulfonyl chloride (6.97 g, 35.8 mmol) was heated at 60° C. for two hours. The mixture was partitioned between isopropanol chloroform and saturated sodium bicarbonate. The organic layer was washed with brine, dried (MgSO$_4$) and concentrated to afford (S)-tert-butyl (2-(((benzyloxy)carbonyl)aminomethyl)-4-((4-fluorophenyl)sulfonyl)-3,4-dihydro-2H-benzo[b][1,4]oxazin-6-yl)carbamate.

Part III—Synthesis of (S)-benzyl ((6-amino-4-((4-fluorophenyl)sulfonyl)-3,4-dihydro-2H-benzo[b][1,4]oxazin-2-yl)methyl)carbamate

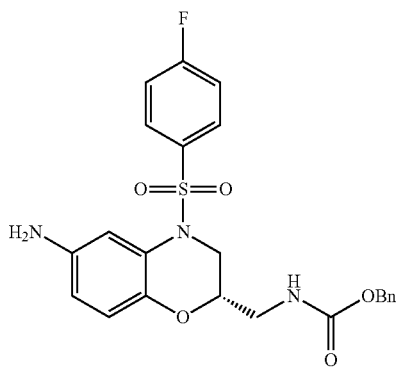 [SMILES: Nc1ccc2c(c1)N(S(=O)(=O)c1ccc(F)cc1)C[C@H](CNC(=O)OCc1ccccc1)O2]

A mixture of (S)-tert-butyl (2-(((benzyloxy)carbonyl)aminomethyl)-4-((4-fluorophenyl)sulfonyl)-3,4-dihydro-2H-benzo[b][1,4]oxazin-6-yl)carbamate (10 g, 17.49 mmol) and 4M HCl in p-dioxane (109 mL, 437 mmol) was stirred at room temperature for 30 minutes and concentrated to afford (S)-benzyl ((6-amino-4-((4-fluorophenyl)sulfonyl)-3,4-dihydro-2H-benzo[b][1,4]oxazin-2-yl)methyl)carbamate.

Part IV—Synthesis of (S)-1,1,1-trifluoro-2-methylpropan-2-yl (2-(((benzyloxy)carbonyl)aminomethyl)-4-((4-fluorophenyl)sulfonyl)-3,4-dihydro-2H-benzo[b][1,4]oxazin-6-yl)carbamate

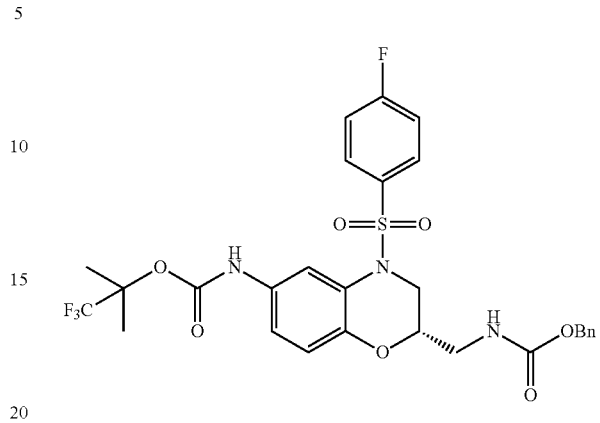

To a solution of (S)-benzyl ((6-amino-4-((4-fluorophenyl)sulfonyl)-3,4-dihydro-2H-benzo[b][1,4]oxazin-2-yl)methyl)carbamate (4.00 g, 7.87 mmol), dichloromethane (39.4 mL), and triethyl amine (6.59 mL, 47.2 mmol) was added 4-nitrophenyl (1,1,1-trifluoro-2-methylpropan-2-yl) carbonate (5.77 g, 19.69 mmol) and 4-N,N-dimethylaminopyridine (0.192 g, 1.575 mmol). The mixture was stirred at room temperature overnight and poured into saturated sodium bicarbonate. The mixture was extracted with isopropanol/chloroform. The combined organic layers were washed with 1N NaOH, dried (MgSO$_4$) and concentrated. The residue was purified via chromatography eluting with a gradient of (0-100% ethyl acetate/hexanes) to afford (S)-1,1,1-trifluoro-2-methylpropan-2-yl(2-(((benzyloxy)carbonyl)aminomethyl)-4-((4-fluorophenyl)sulfonyl)-3,4-dihydro-2H-benzo[b][1,4]oxazin-6-yl)carbamate.

Part V—Synthesis of (S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl)carbamate

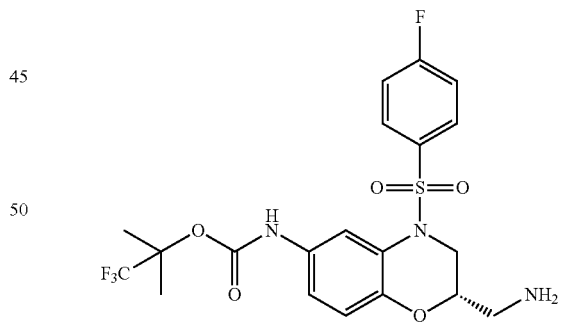

A solution of (S)-1,1,1-trifluoro-2-methylpropan-2-yl (2-(((benzyloxy)carbonyl)aminomethyl)-4-((4-fluorophenyl)sulfonyl)-3,4-dihydro-2H-benzo[b][1,4]oxazin-6-yl)carbamate (750 mg, 1.20 mmol) and methanol (12 mL) was purged with nitrogen. Palladium 10% on carbon (76 mg, 0.072 mmol) was added. The atmosphere was exchanged with hydrogen at one atmosphere and stirred for four hours. The mixture was filtered through CELITE. The filtrate was concentrated to afford (S)-1,1,1-trifluoro-2-methylpropan-2-yl(2-(aminomethyl)-4-((4-fluorophenyl)sulfonyl)-3,4-dihydro-2H-benzo[b][1,4]oxazin-6-yl)carbamate as a white solid. $^1$H NMR: (300 MHz, CDCl$_3$): δ 9.81 (1H, s), 8.00 (2H, s), 7.92 (1H, s), 7.84 (2H, m), 7.46 (2H, m), 7.22 (1H, d, J=9.7 Hz), 6.80 (1H, d, J=8.24 Hz), 4.41 (1H, dd, J=11.79 Hz, 2.66 Hz), 3.72 (1H, m), 3.34 (1H, m), 3.20 (1H, m), 2.96 (1H, m), 1.70 (6H, s). LRMS (ESI) calculated for $C_{20}H_{21}F_4N_3O_5S$ (M+H)$^+$: 492, Found 492.1.

Example 8—Synthesis of (S)-1,1,1-trifluoro-2-methylpropan-2-yl (2-(((benzyloxy)carbonyl)aminomethyl)-4-((3-chloro-4-fluorophenyl)sulfonyl)-3,4-dihydro-2H-benzo[b][1,4]oxazin-6-yl)carbamate (8)

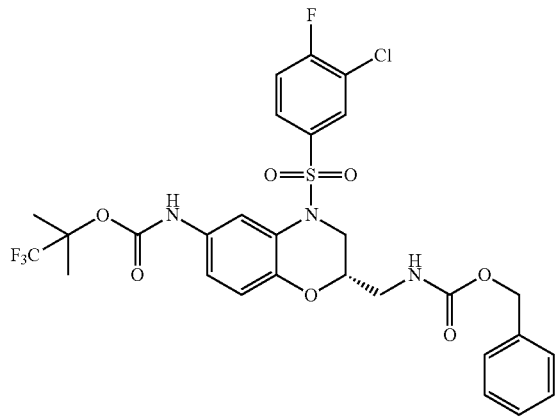 [SMILES: CC(C)(OC(=O)Nc1ccc2c(c1)N(S(=O)(=O)c1ccc(F)c(Cl)c1)C[C@H](CNC(=O)OCc1ccccc1)O2)C(F)(F)F]

To a mixture of (S)-benzyl ((6-amino-4-((3-chloro-4-fluorophenyl)sulfonyl)-3,4-dihydro-2H-benzo[b][1,4]oxazin-2-yl)methyl)carbamate hydrochloride (4.80 g, 8.85 mmol), dichloromethane (88 mL), and triethyl amine (7.40 mL, 53.1 mmol) was added 4-nitrophenyl (1,1,1-trifluoro-2-methylpropan-2-yl) carbonate (5.71 g, 19.47 mmol). The mixture was stirred for one day at room temperature. The mixture was partitioned between isopropanol/chloroform (1:3, v/v) and saturated sodium bicarbonate. The organic layer was washed with 1N NaOH, dried (MgSO$_4$) and concentrated. The residue was purified by MPLC eluting with a gradient of 0-100% ethyl acetate/hexanes to afford (S)-1,1,1-trifluoro-2-methylpropan-2-yl (2-(((benzyloxy)carbonyl)aminomethyl)-4-((3-chloro-4-fluorophenyl)sulfonyl)-3,4-dihydro-2H-benzo[b][1,4]oxazin-6-yl)carbamate as a white solid. LRMS (ESI) calculated for $C_{28}H_{26}ClF_4N_3O_7SNa$ (M+Na)$^+$: 682, Found: 682.2. $^1$H NMR: (300 MHz, CDCl$_3$) δ 9.77 (1H, s), 7.98 (1H, m), 7.90 (1H, s), 7.70 (1H, m), 7.61 (1H, t, J=10.13 Hz), 7.53 (1H, t, J=6.51 Hz), 7.35 (3H, m), 7.31 (1H, m), 7.12 (1H, d, J=9.41 Hz), 6.77 (1H, d, J=7.95 Hz), 5.04 (2H, m), 4.31 (1H, m), 3.53 (1H, m), 3.26 (3H, m), 3.19 (1H, m), 1.70 (6H, m).

Example 9—Synthesis of (S)-1,1,1-trifluoro-2-methylpropan-2-yl (4-((4-fluorophenyl)sulfonyl)-2-((3-(tetrahydro-2H-pyran-4-yl)ureido)methyl)-3,4-dihydro-2H-benzo[b][1,4]oxazin-6-yl)carbamate (9)

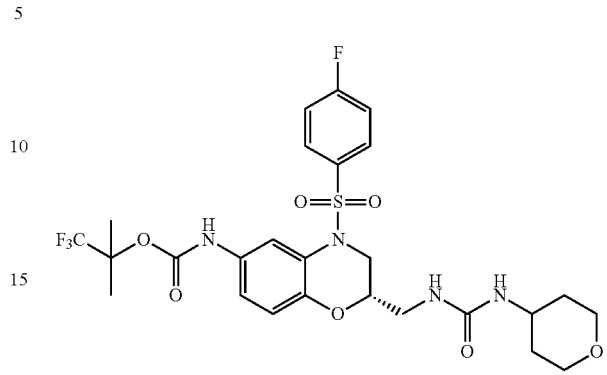

A solution of (S)-1,1,1-trifluoro-2-methylpropan-2-yl(2-(aminomethyl)-4-((4-fluorophenyl)sulfonyl)-3,4-dihydro-2H-benzo[b][1,4]oxazin-6-yl)carbamate (30 mg, 0.061 mmol), 4-isocyanatotetrahydro-2H-pyran (31.0 mg, 0.244 mmol), triethyl amine (34.0 μL, 0.244 mmol), and dichloromethane (610 μL) was stirred overnight. The mixture was partitioned between saturated sodium bicarbonate and dichloromethane. The organic layer was dried (MgSO$_4$) and concentrated. The residue was dissolved in DMSO (1.5 mL), filtered, and purified by reverse phase chromatography to afford (S)-1,1,1-trifluoro-2-methylpropan-2-yl (4-((4-fluorophenyl)sulfonyl)-2-((3-(tetrahydro-2H-pyran-4-yl)ureido)methyl)-3,4-dihydro-2H-benzo[b][1,4]oxazin-6-yl)carbamate. LRMS (ESI) calculated for $C_{26}H_{31}F_4N_4O_7S$ (M+H): $^+$: 619, Found: 619. $^1$H NMR: (300 MHz, CDCl3) δ 9.76 (1H, s), 7.90 (1H, s), 7.73 (2H, m), 7.38 (2H, t, J=8.58 Hz), 7.18 (1H, d, J=10.13 Hz), 6.76 (1H, d, J=9.36 Hz), 6.03 (1H, d, J=6.96 Hz), 5.97 (1H, m), 4.26 (1H, m), 3.78 (3H, m), 3.33 (5H, m), 3.14 (2H, m), 1.69 (7H, m), 1.30 (2H, m).

Example 10—Additional Ureas and Carbamates of Aminobenzoxazines

The urea and bis-carbamate compounds in Table 3 below were prepared based on the experimental procedures described in Examples 7, 8, and 9 and elsewhere in the detailed description, and can be achieved by one of skill in the art in light of the present disclosure.

TABLE 3

| Ex. No. | Structure | Name | Observed m/z |
|---|---|---|---|
| 10A | 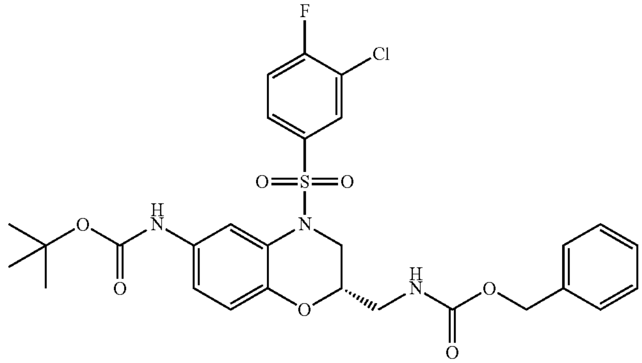 [SMILES: CC(C)(C)OC(=O)Nc1ccc2c(c1)N(S(=O)(=O)c1ccc(F)c(Cl)c1)C[C@H](CNC(=O)OCc1ccccc1)O2] | (S)-tert-butyl (2-(((benzyloxy)carbonyl)aminomethyl)-4-((3-chloro-4-fluorophenyl)sulfonyl)-3,4-dihydro-2H-benzo[b][1,4]oxazin-6-yl)carbamate | 628.2 (M + Na)$^+$ |

TABLE 3-continued

| Ex. No. | Structure | Name | Observed m/z |
|---|---|---|---|
| 10B | 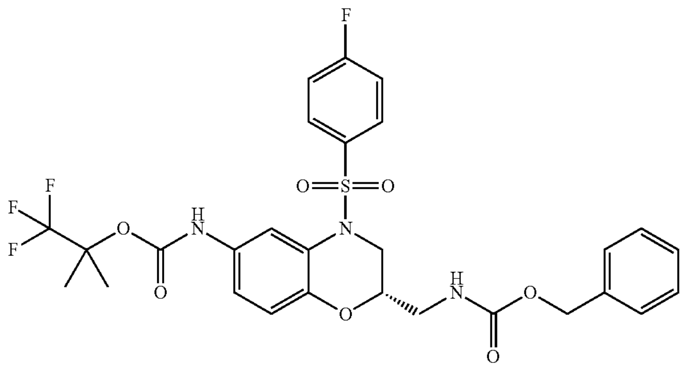 [SMILES: CC(C)(OC(=O)Nc1ccc2c(c1)N(S(=O)(=O)c1ccc(F)cc1)C[C@H](CNC(=O)OCc1ccccc1)O2)C(F)(F)F] | (S)-1,1,1-trifluoro-2-methylpropan-2-yl (2-(((benzyloxy)carbonyl)aminomethyl)-4-((4-fluorophenyl)sulfonyl)-3,4-dihydro-2H-benzo[b][1,4]oxazin-6-yl)carbamate | 626.3 (M + H)+ |
| 10C | 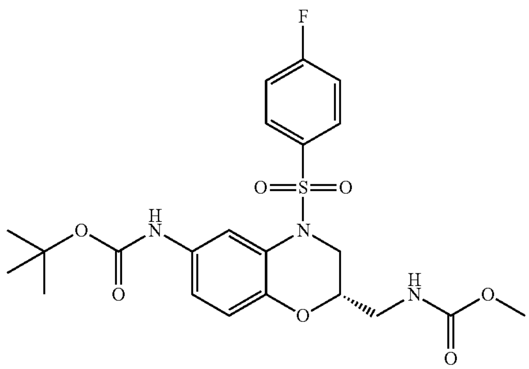 [SMILES: COC(=O)NC[C@H]1CN(S(=O)(=O)c2ccc(F)cc2)c2cc(NC(=O)OC(C)(C)C)ccc2O1] | (S)-tert-butyl (2-(((methoxy)carbonyl)aminomethyl)-4-((4-fluorophenyl)sulfonyl)-3,4-dihydro-2H-benzo[b][1,4]oxazin-6-yl)carbamate | 440.1 (M-tBu + H)+ |
| 10D | 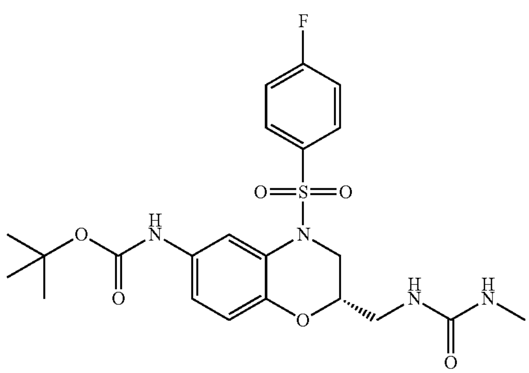 [SMILES: CNC(=O)NC[C@H]1CN(S(=O)(=O)c2ccc(F)cc2)c2cc(NC(=O)OC(C)(C)C)ccc2O1] | (S)-tert-butyl (4-((4-fluorophenyl)sulfonyl)-2-((3-methylureido)methyl)-3,4-dihydro-2H-benzo[b][1,4]oxazin-6-yl)carbamate | 439.0 (M-tBu + H)+ |
| 10E | 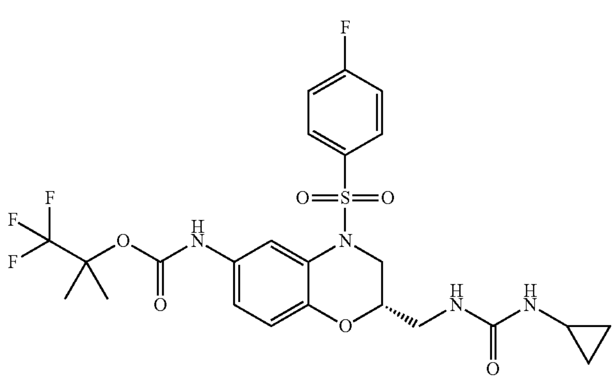 [SMILES: CC(C)(OC(=O)Nc1ccc2c(c1)N(S(=O)(=O)c1ccc(F)cc1)C[C@H](CNC(=O)NC1CC1)O2)C(F)(F)F] | (S)-1,1,1-trifluoro-2-methylpropan-2-yl (2-((3-cyclopropylureido)methyl)-4-((4-fluorophenyl)sulfonyl)-3,4-dihydro-2H-benzo[b][1,4]oxazin-6-yl)carbamate | 575.2 (M + H)+ |

TABLE 3-continued

| Ex. No. | Structure | Name | Observed m/z |
|---|---|---|---|
| 10F | 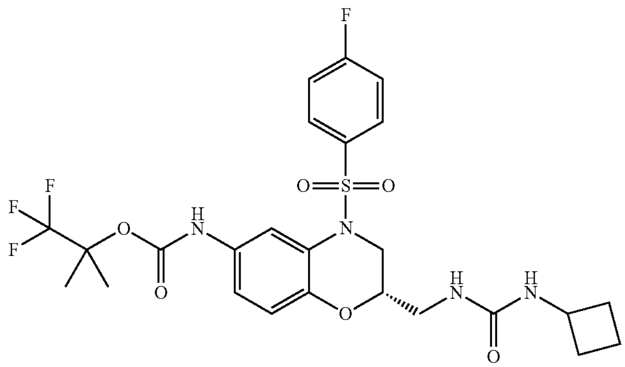 [SMILES: CC(C)(OC(=O)Nc1ccc2c(c1)N(S(=O)(=O)c1ccc(F)cc1)C[C@H](CNC(=O)NC1CCC1)O2)C(F)(F)F] | (S)-1,1,1-trifluoro-2-methylpropan-2-yl (2-((3-cyclobutylureido)methyl)-4-((4-fluorophenyl)sulfonyl)-3,4-dihydro-2H-benzo[b][1,4]oxazin-6-yl)carbamate | 589.1 (M + H)+ |
| 10G | 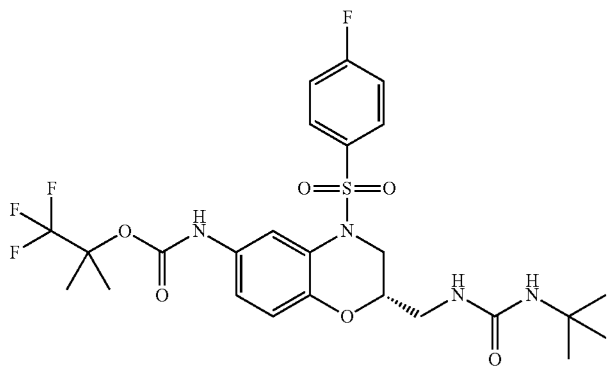 [SMILES: CC(C)(C)NC(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-((3-(tert-butyl)ureido)methyl)-4-((4-fluorophenyl)sulfonyl)-3,4-dihydro-2H-benzo[b][1,4]oxazin-6-yl)carbamate | 591.1 (M + H)+ |
| 10H | 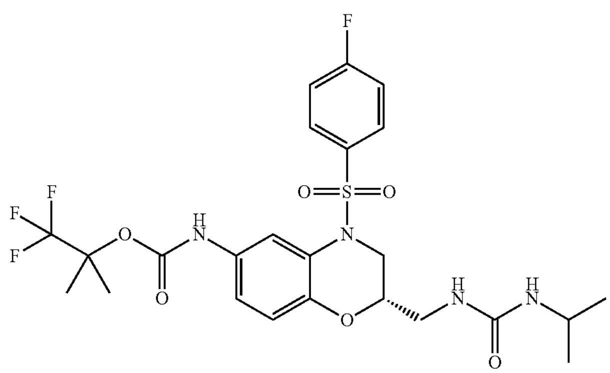 [SMILES: CC(C)NC(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (4-((4-fluorophenyl)sulfonyl)-2-((3-isopropylureido)methyl)-3,4-dihydro-2H-benzo[b][1,4]oxazin-6-yl)carbamate | 577.1 (M + H)+ |
| 10i | 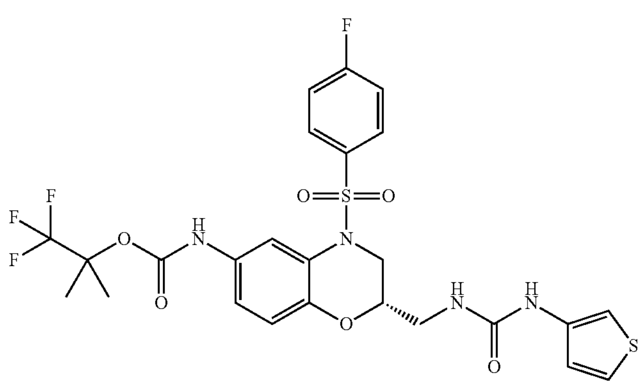 [SMILES: CC(C)(OC(=O)Nc1ccc2c(c1)N(S(=O)(=O)c1ccc(F)cc1)C[C@H](CNC(=O)Nc1ccsc1)O2)C(F)(F)F] | (S)-1,1,1-trifluoro-2-methylpropan-2-yl (4-((4-fluorophenyl)sulfonyl)-2-((3-(thiophen-3-yl)ureido)methyl)-3,4-dihydro-2H-benzo[b][1,4]oxazin-6-yl)carbamate | 617.1 (M + H)+ |

TABLE 3-continued

| Ex. No. | Structure | Name | Observed m/z |
|---|---|---|---|
| 10J | 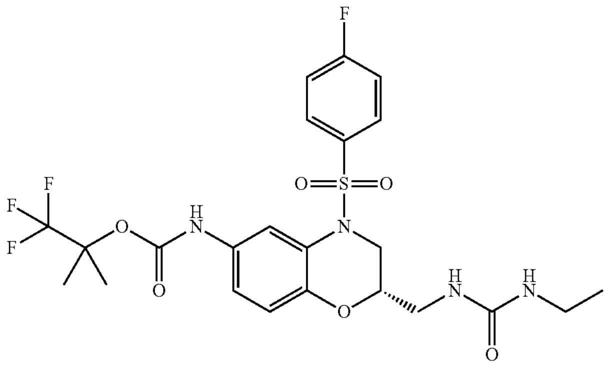 [SMILES: CCNC(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-((3-ethylureido)methyl)-4-((4-fluorophenyl)sulfonyl)-3,4-dihydro-2H-benzo[b][1,4]oxazin-6-yl)carbamate | 563.1 (M + H)+ |
| 10K | 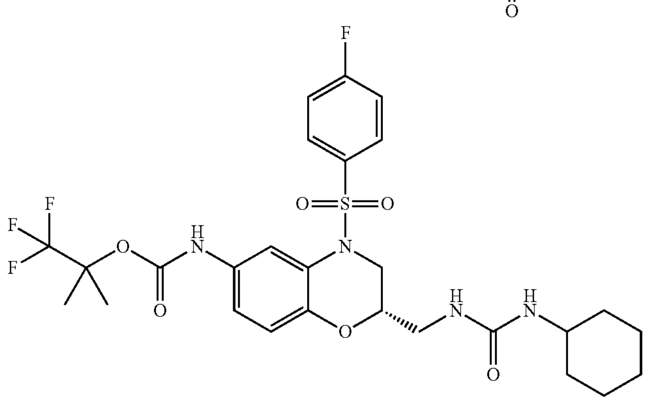 | (S)-1,1,1-trifluoro-2-methylpropan-2-yl (2-((3-cyclohexylureido)methyl)-4-((4-fluorophenyl)sulfonyl)-3,4-dihydro-2H-benzo[b][1,4]oxazin-6-yl)carbamate | 617.0 (M + H)+ |

Example 11—Synthesis of (R)-1,1,1-trifluoro-2-methylpropan-2-yl(4-((3-chloro-4-fluorophenyl)sulfonyl)-2-((5-methyl-1,1-dioxido-1,2,5-thiadiazolidin-2-yl)methyl)-3,4-dihydro-2H-benzo[b][1,4]oxazin-6-yl)carbamate (11)

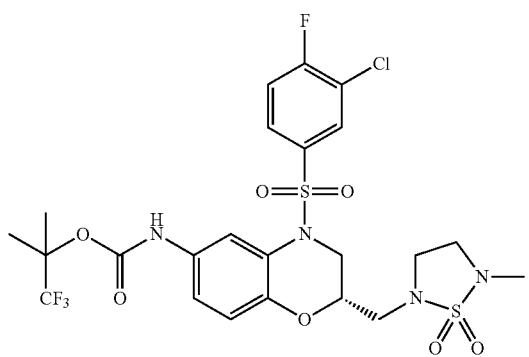 [SMILES: CN1CCN(C[C@H]2CN(S(=O)(=O)c3ccc(F)c(Cl)c3)c3cc(NC(=O)OC(C)(C)C(F)(F)F)ccc3O2)S1(=O)=O]

Part 1—Synthesis of (R)-tert-butyl (2-((5-methyl-1,1-dioxido-1,2,5-thiadiazolidin-2-yl)methyl)-3,4-dihydro-2H-benzo[b][1,4]oxazin-6-yl)carbamate

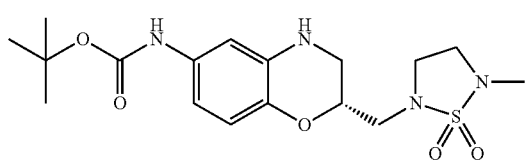 [SMILES: CN1CCN(C[C@H]2CNc3cc(NC(=O)OC(C)(C)C)ccc3O2)S1(=O)=O]

To a solution of (R)-tert-butyl (2-(hydroxymethyl)-3,4-dihydro-2H-benzo[b][1,4]oxazin-6-yl)carbamate (200 mg, 0.713 mmol), triphenylphosphine (187 mg, 0.713 mmol), 2-methyl-1,2,5-thiadiazolidine 1,1-dioxide (97 mg, 0.713 mmol), and toluene (3567 µL) was added diisopropyldiazodicarboxylate (146 µL, 0.749 mmol). The reaction was stirred at 50° C. for two hours. The mixture was partitioned between ethyl acetate and saturated NaHCO$_3$. The organic layer was washed with brine, dried (MgSO$_4$), and concentrated. The residue was purified by MPLC eluting with a gradient of 0-100% ethyl acetate in hexanes to afford the title compound: LCMS (ESI) calculated for $C_{17}H_{27}N_4O_5S$ (M+H)+: 399, Found: 399.

Part 2—Synthesis of (R)-tert-butyl (4-((3-chloro-4-fluorophenyl)sulfonyl)-2-((5-methyl-1,1-dioxido-1,2,5-thiadiazolidin-2-yl)methyl)-3,4-dihydro-2H-benzo[b][1,4]oxazin-6-yl)carbamate

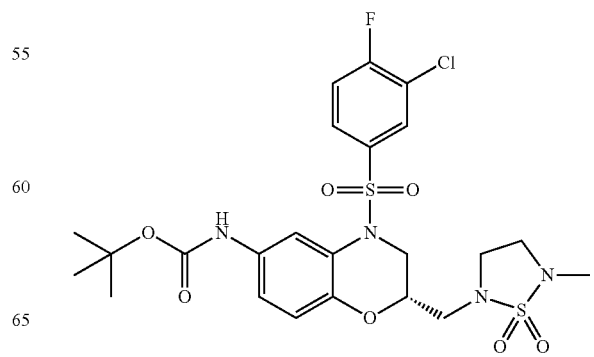

A solution of (R)-tert-butyl (2-((5-methyl-1,1-dioxido-1,2,5-thiadiazolidin-2-yl)methyl)-3,4-dihydro-2H-benzo[b][1,4]oxazin-6-yl)carbamate (148.5 mg, 0.373 mmol), 3-chloro-4-fluorobenzene-1-sulfonyl chloride (171 mg, 0.745 mmol), and pyridine (1863 µL) was heated at 50° C. overnight. The mixture was cooled, and partitioned between ethyl acetate and saturated NaHCO₃. The organic layer was washed with brine, dried (MgSO₄), and concentrated. The residue was purified via MPLC eluting with a gradient of 0-100% ethyl acetate in hexanes to afford the title compound: LCMS (ESI) calculated for $C_{19}H_{20}ClFN_4O_7S_2$ (M-tBu+H)⁺: 535, Found: 535.

Part 3—Synthesis of (R)-2-((6-amino-4-((3-chloro-4-fluorophenyl)sulfonyl)-3,4-dihydro-2H-benzo[b][1,4]oxazin-2-yl)methyl)-5-methyl-1,2,5-thiadiazolidine 1,1-dioxide

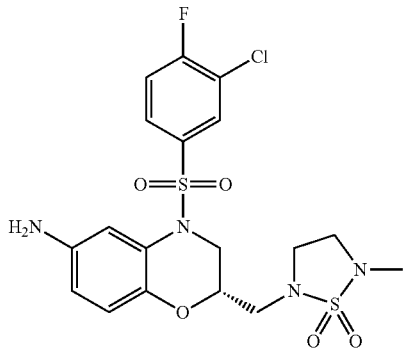 [SMILES: CN1CCN(C[C@H]2CN(S(=O)(=O)c3ccc(F)c(Cl)c3)c3cc(N)ccc3O2)S1(=O)=O]

A solution of (R)-tert-butyl (4-((3-chloro-4-fluorophenyl)sulfonyl)-2-(5-methyl-1,1-dioxido-1,2,5-thiadiazolidin-2-yl)methyl)-3,4-dihydro-2H-benzo[b][1,4]oxazin-6-yl)carbamate (208 mg, 0.352 mmol), HCl (1760 µL, 7.04 mmol), and THF (1760 µL) was heated at 50° C. for three days. The mixture was cooled and concentrated to afford the title compound: LCMS (ESI) calculated for $C_{18}H_{21}ClFN_4O_5S_2$ (M+H)⁺: 491, Found: 491.

Part 4—Synthesis of (R)-1,1,1-trifluoro-2-methylpropan-2-yl (4-((3-chloro-4-fluorophenyl)sulfonyl)-2-((5-methyl-1,1-dioxido-1,2,5-thiadiazolidin-2-yl)methyl)-3,4-dihydro-2H-benzo[b][1,4]oxazin-6-yl)carbamate

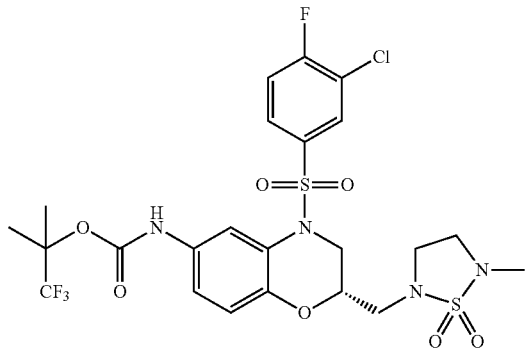 [SMILES: CN1CCN(C[C@H]2CN(S(=O)(=O)c3ccc(F)c(Cl)c3)c3cc(NC(=O)OC(C)(C)C(F)(F)F)ccc3O2)S1(=O)=O]

A solution of (R)-2-((6-amino-4-((3-chloro-4-fluorophenyl)sulfonyl)-3,4-dihydro-2H-benzo[b][1,4]oxazin-2-yl)methyl)-5-methyl-1,2,5-thiadiazolidine 1,1-dioxide (173 mg, 0.352 mmol), 1,1,1-trifluoro-2-methylpropan-2-yl 1H-imidazole-1-carboxylate (133 mg, 0.599 mmol), and DMF (1762 µL) was heated at 100° C. for two hours. The reaction was partitioned between ethyl acetate and saturated NaHCO₃. The organic layer was washed with brine, dried (MgSO₄), and concentrated. The residue was purified via MPLC eluting with a gradient of 0-100% ethyl acetate in hexanes to afford the title compound: LCMS (ESI) calculated for $C_{23}H_{26}ClF_4N_4O_7S_2$ (M+H)⁺: 645, Found: 645. ¹H NMR: (300 MHz, CDCl₃): δ 9.78 (1H, s), 8.07 (1H, d, J=7.19 Hz), 7.92 (1H, s), 7.75 (1H, m), 7.64 (1H, t, J=10.79 Hz), 7.14 (1H, d, J=7.2 Hz), 6.80 (1H, d, J=10.79 Hz), 4.39 (1H, d, J=14.32 Hz), 3.71 (1H, m), 3.63 (1H, t, J=7.16 Hz), 3.20 (2H, m), 2.60 (3H, s), 1.73 (1H, m), 1.70 (6H, s), 1.52 (1H, m), 1.31 (2H, m).

Example 12—Synthesis of (S)-1,1,1-trifluoro-2-methylpropan-2-yl (4-((4-fluorophenyl)sulfonyl)-2-(((N-methylsulfamoyl)amino)methyl)-3,4-dihydro-2H-benzo[b][1,4]oxazin-6-yl)carbamate (12)

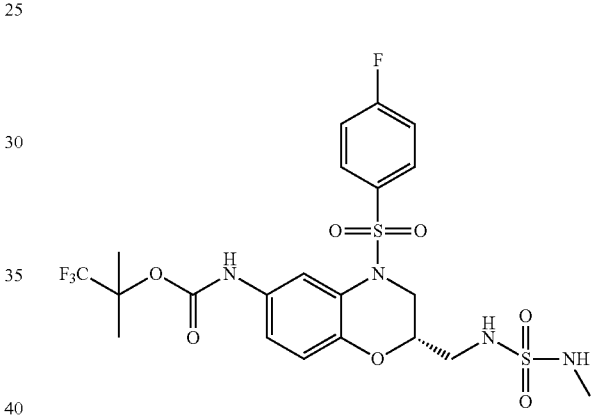

To a stirred mixture of (S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl)carbamate (50 mg, 0.102 mmol), methylsulfamoyl chloride (13.18 mg, 0.102 mmol), and dichloromethane (1017 µL was added N,N'-diisopropylethylamine (26.7 µL, 0.153 mmol) at room temperature. After twenty hours, the mixture was partitioned between ethyl acetate and saturated sodium bicarbonate. The organic layer was dried (MgSO₄) and concentrated. The residue was dissolved in DMSO (1.5 mL), filtered and purified by reverse phase chromatography to afford the title compound. LRMS (ESI) calculated for $C_{21}H_{25}F_4N_4O_7S_2$ (M+H)+: 585, Found: 585. ¹H NMR (300 MHz, CDCl₃) δ 9.77 (1H, s), 7.90 (1H, s), 7.77 (2H, m), 7.41 (2H, t, J=7.99 Hz), 7.19 (2H, m), 6.79 (1H, m), 6.76 (1H, d, J=8.71 Hz), 4.38 (1H, m), 3.52 (1H, m), 3.22 (1H, m), 3.00 (2H, m), 2.41 (3H, m), 1.69 (6H, m).

Example 13—Additional Sulfamides of Aminobenzoxazines

The compounds in Table 4 below were prepared based on the experimental procedures described in Examples 11 and 12 and elsewhere in the detailed description utilizing the appropriate sulfamoyl halide, and can be achieved by one of skill in the art in light of the present disclosure.

TABLE 4

| Ex. No. | Structure | Name | Observed m/z |
|---|---|---|---|
| 13A | 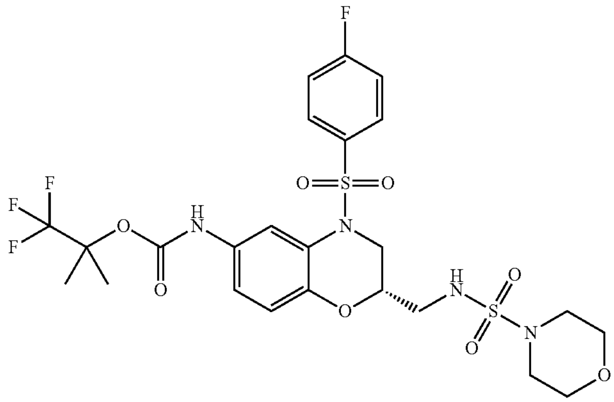 [SMILES: CC(C)(OC(=O)Nc1ccc2c(c1)N(S(=O)(=O)c1ccc(F)cc1)C[C@H](CNS(=O)(=O)N1CCOCC1)O2)C(F)(F)F] | (S)-1,1,1-trifluoro-2-methylpropan-2-yl (4-((4-fluorophenyl)sulfonyl)-2-((morpholine-4-sulfonamido)methyl)-3,4-dihydro-2H-benzo[b][1,4]oxazin-6-yl)carbamate | 641.3 (M + H)+ |
| 13B | 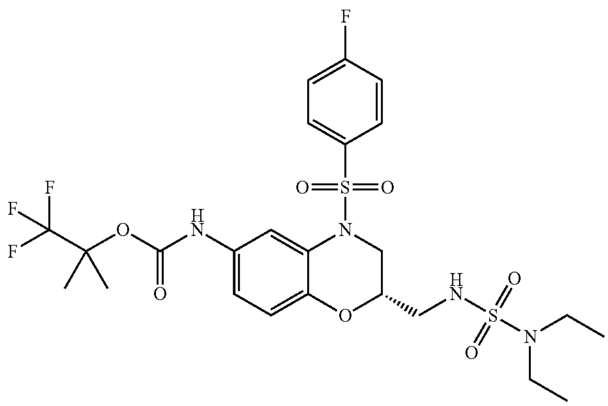 [SMILES: CCN(CC)S(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-(((N,N-diethylsulfamoyl)amino)methyl)-4-((4-fluorophenyl)sulfonyl)-3,4-dihydro-2H-benzo[b][1,4]oxazin-6-yl)carbamate | 627.2 (M + H)+ |
| 13C | 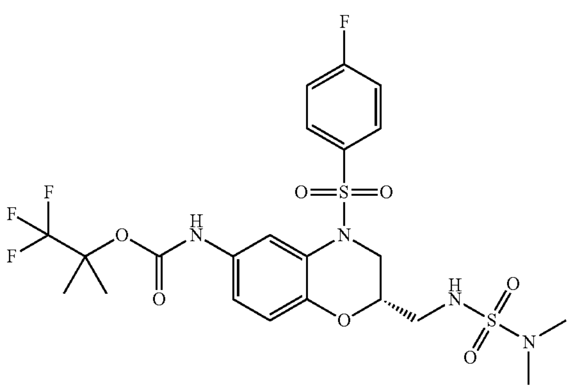 [SMILES: CN(C)S(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-(((N,N-dimethylsulfamoyl)amino)methyl)-4-((4-fluorophenyl)sulfonyl)-3,4-dihydro-2H-benzo[b][1,4]oxazin-6-yl)carbamate | 599.1 (M + H)+ |
| 13D | 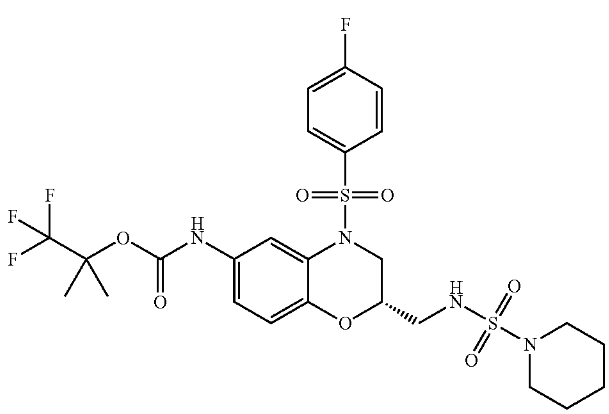 [SMILES: CC(C)(OC(=O)Nc1ccc2c(c1)N(S(=O)(=O)c1ccc(F)cc1)C[C@H](CNS(=O)(=O)N1CCCCC1)O2)C(F)(F)F] | (S)-1,1,1-trifluoro-2-methylpropan-2-yl (4-((4-fluorophenyl)sulfonyl)-2-((piperidine-1-sulfonamido)methyl)-3,4-dihydro-2H-benzo[b][1,4]oxazin-6-yl)carbamate | 639 (M + H)+ |

TABLE 4-continued

| Ex. No. | Structure | Name | Observed m/z |
|---|---|---|---|
| 13E | 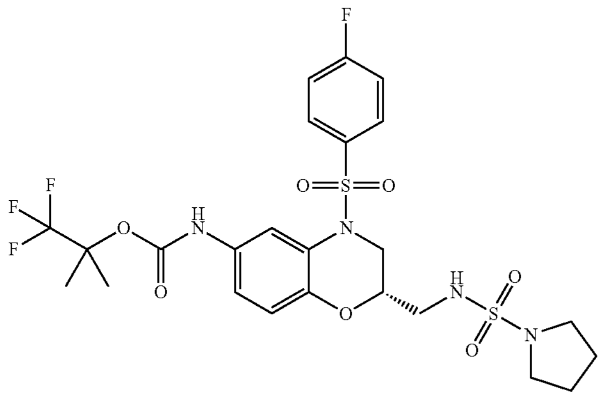 [SMILES: CC(C)(OC(=O)Nc1ccc2c(c1)N(S(=O)(=O)c1ccc(F)cc1)C[C@H](CNS(=O)(=O)N1CCCC1)O2)C(F)(F)F] | (S)-1,1,1-trifluoro-2-methylpropan-2-yl (4-((4-fluorophenyl)sulfonyl)-2-((pyrrolidine-1-sulfonamido)methyl)-3,4-dihydro-2H-benzo[b][1,4]oxazin-6-yl)carbamate | 625 (M + H)+ |
| 13F | 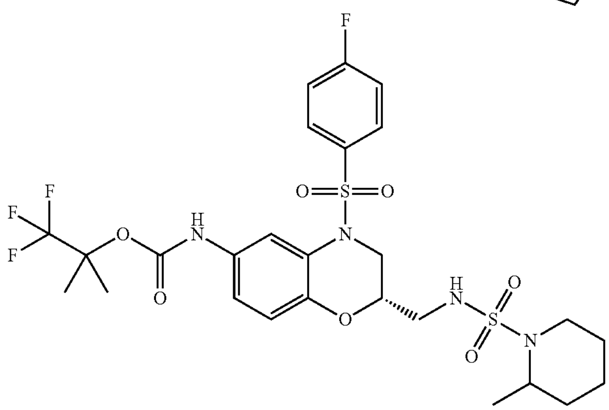 | 1,1,1-trifluoro-2-methylpropan-2-yl ((2S)-4-((4-fluorophenyl)sulfonyl)-2-((2-methylpiperidine-1-sulfonamido)methyl)-3,4-dihydro-2H-benzo[b][1,4]oxazin-6-yl)carbamate | 653 (M + H)+ |
| 13G | 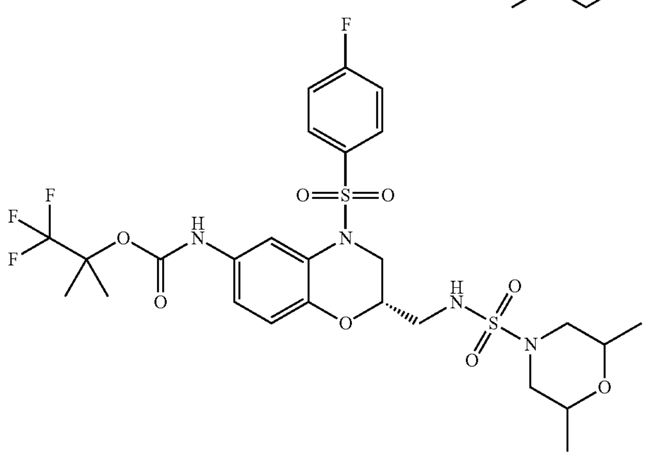 | 1,1,1-trifluoro-2-methylpropan-2-yl ((2S)-2-((2,6-dimethylmorpholine-4-sulfonamido)methyl)-4-((4-fluorophenyl)sulfonyl)-3,4-dihydro-2H-benzo[b][1,4]oxazin-6-yl)carbamate | 669 (M + H)+ |
| 13H | 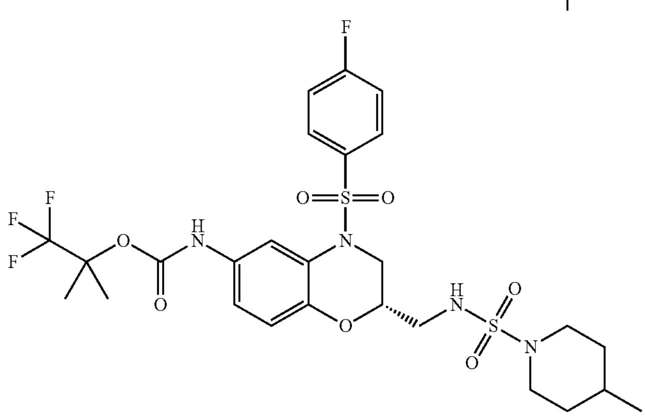 | (S)-1,1,1-trifluoro-2-methylpropan-2-yl (4-((4-fluorophenyl)sulfonyl)-2-((4-methylpiperidine-1-sulfonamido)methyl)-3,4-dihydro-2H-benzo[b][1,4]oxazin-6-yl)carbamate | 653 (M + H)+ |

TABLE 4-continued

| Ex. No. | Structure | Name | Observed m/z |
|---|---|---|---|
| 13i | 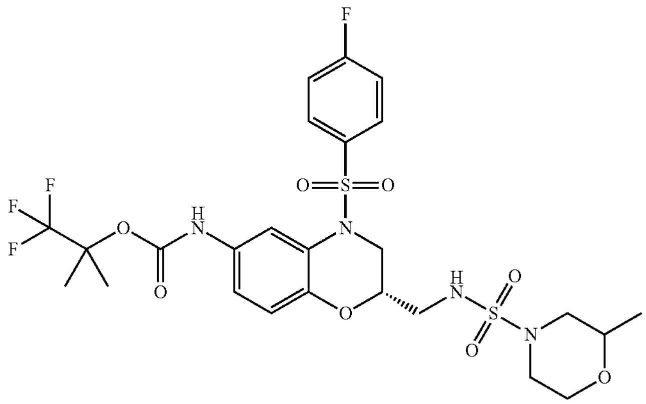 [SMILES: CC1CN(S(=O)(=O)NC[C@H]2CN(S(=O)(=O)c3ccc(F)cc3)c3cc(NC(=O)OC(C)(C)C(F)(F)F)ccc3O2)CCO1] | 1,1,1-trifluoro-2-methylpropan-2-yl ((2S)-4-((4-fluorophenyl)sulfonyl)-2-((2-methylmorpholine-4-sulfonamido)methyl)-3,4-dihydro-2H-benzo[b][1,4]oxazin-6-yl)carbamate | 655 (M + H)+ |
| 13J | 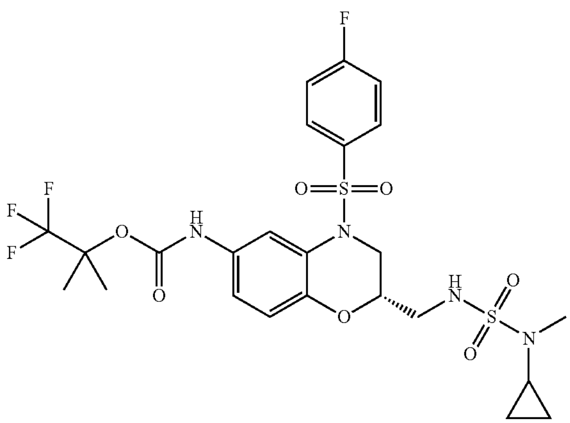 [SMILES: CN(C1CC1)S(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-(((N-cyclopropyl-N-methylsulfamoyl)amino)methyl)-4-((4-fluorophenyl)sulfonyl)-3,4-dihydro-2H-benzo[b][1,4]oxazin-6-yl)carbamate | 625 (M + H)+ |
| 13K | 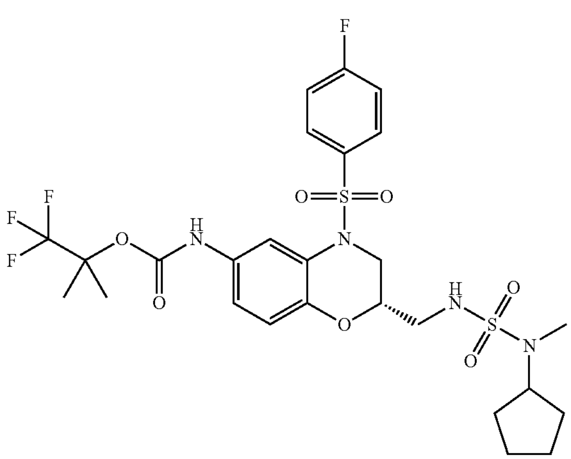 [SMILES: CN(C1CCCC1)S(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-(((N-cyclopentyl-N-methylsulfamoyl)amino)methyl)-4-((4-fluorophenyl)sulfonyl)-3,4-dihydro-2H-benzo[b][1,4]oxazin-6-yl)carbamate | 653 (M + H)+ |

TABLE 4-continued

| Ex. No. | Structure | Name | Observed m/z |
|---|---|---|---|
| 13L | 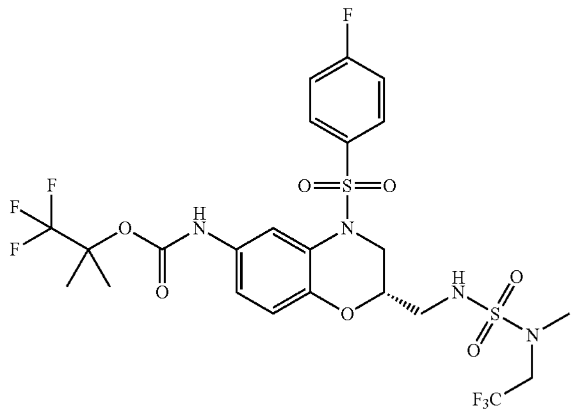 [SMILES: CN(CC(F)(F)F)S(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (4-((4-fluorophenyl)sulfonyl)-2-(((N-methyl-N-(2,2,2-trifluoroethyl)sulfamoyl)amino)methyl)-3,4-dihydro-2H-benzo[b][1,4]oxazin-6-yl)carbamate | 667 (M + H)+ |
| 13M | 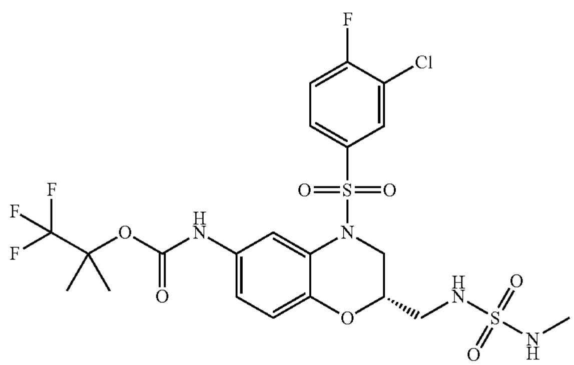 [SMILES: CNS(=O)(=O)NC[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (4-((3-chloro-4-fluorophenyl)sulfonyl)-2-(((N-methylsulfamoyl)amino)methyl)-3,4-dihydro-2H-benzo[b][1,4]oxazin-6-yl)carbamate | 619.5 (M + H)+ |
| 13N | 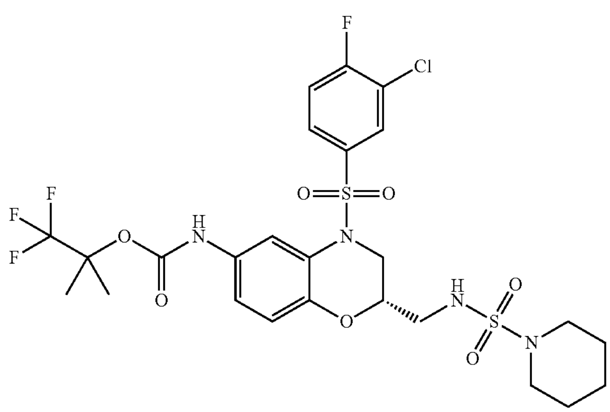 [SMILES: CC(C)(OC(=O)Nc1ccc2c(c1)N(S(=O)(=O)c1ccc(F)c(Cl)c1)C[C@H](CNS(=O)(=O)N1CCCCC1)O2)C(F)(F)F] | (S)-1,1,1-trifluoro-2-methylpropan-2-yl (4-((3-chloro-4-fluorophenyl)sulfonyl)-2-((piperidine-1-sulfonamido)methyl)-3,4-dihydro-2H-benzo[b][1,4]oxazin-6-yl)carbamate | 673 (M + H)+ |
| 13o | 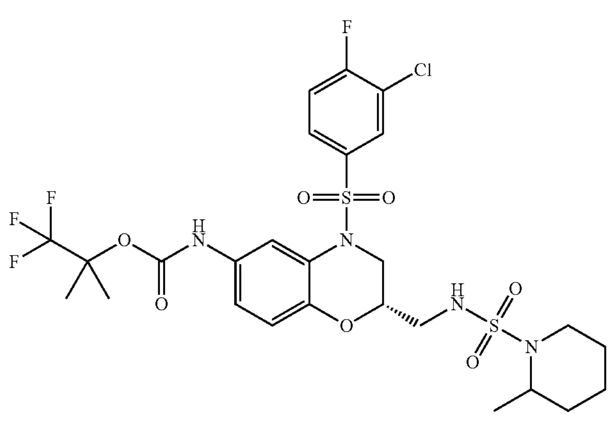 [SMILES: CC1CCCCN1S(=O)(=O)NC[C@H]1CN(S(=O)(=O)c2ccc(F)c(Cl)c2)c2cc(NC(=O)OC(C)(C)C(F)(F)F)ccc2O1] | 1,1,1-trifluoro-2-methylpropan-2-yl ((2S)-4-((3-chloro-4-fluorophenyl)sulfonyl)-2-((2-methylpiperidine-1-sulfonamido)methyl)-3,4-dihydro-2H-benzo[b][1,4]oxazin-6-yl)carbamate | 687 (M + H)+ |

TABLE 4-continued

| Ex. No. | Structure | Name | Observed m/z |
|---|---|---|---|
| 13P | 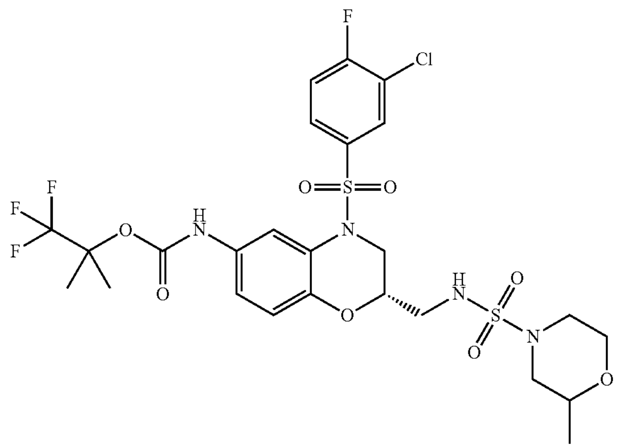 [SMILES: CC1CN(S(=O)(=O)NC[C@H]2CN(S(=O)(=O)c3ccc(F)c(Cl)c3)c3cc(NC(=O)OC(C)(C)C(F)(F)F)ccc3O2)CCO1] | 1,1,1-trifluoro-2-methylpropan-2-yl ((2S)-4-((3-chloro-4-fluorophenyl)sulfonyl)-2-((2-methylmorpholine-4-sulfonamido)methyl)-3,4-dihydro-2H-benzo[b][1,4]oxazin-6-yl)carbamate | 689 (M + H)+ |
| 13Q | 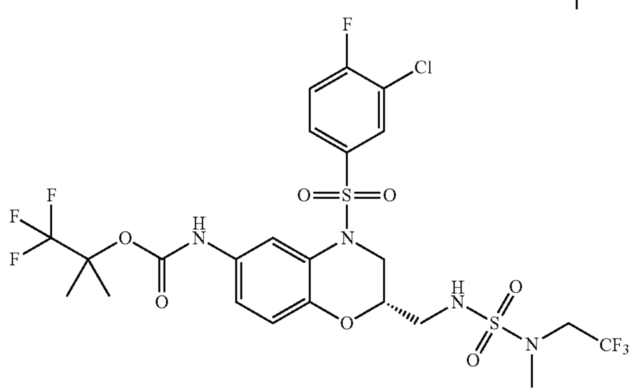 | (S)-1,1,1-trifluoro-2-methylpropan-2-yl (4-((3-chloro-4-fluorophenyl)sulfonyl)-2-(((N-methyl-N-(2,2,2-trifluoroethyl)sulfamoyl)amino)methyl)-3,4-dihydro-2H-benzo[b][1,4]oxazin-6-yl)carbamate | 701 (M + H)+ |
| 13R | 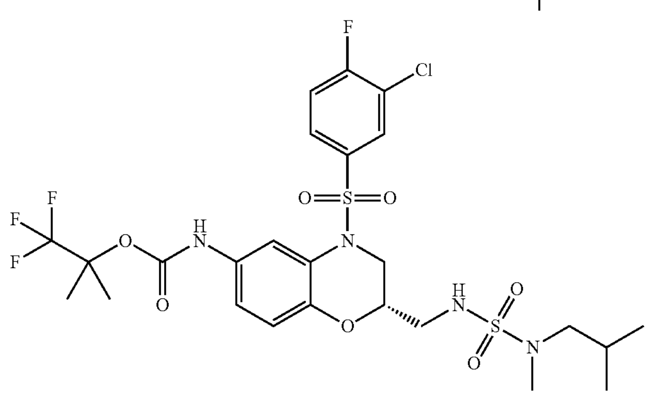 | (S)-1,1,1-trifluoro-2-methylpropan-2-yl (4-((3-chloro-4-fluorophenyl)sulfonyl)-2-(((N-isobutyl-N-methylsulfamoyl)amino)methyl)-3,4-dihydro-2H-benzo[b][1,4]oxazin-6-yl)carbamate | 675 (M + H)+ |
| 13S | 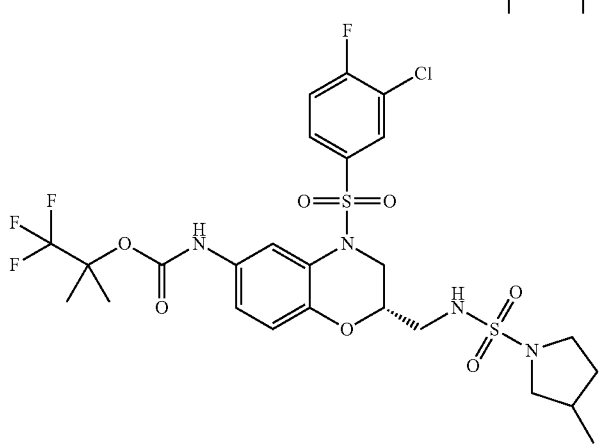 | 1,1,1-trifluoro-2-methylpropan-2-yl ((2S)-4-((3-chloro-4-fluorophenyl)sulfonyl)-2-((3-methylpyrrolidine-1-sulfonamido)methyl)-3,4-dihydro-2H-benzo[b][1,4]oxazin-6-yl)carbamate | 688 (M + H)+ |

TABLE 4-continued

| Ex. No. | Structure | Name | Observed m/z |
|---|---|---|---|
| 13T | 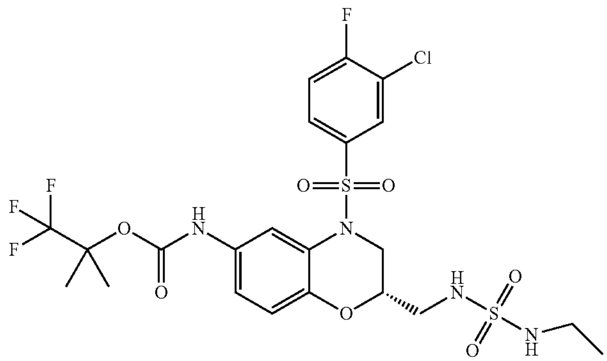 [SMILES: CCNS(=O)(=O)NC[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (4-((3-chloro-4-fluorophenyl)sulfonyl)-2-(((N-ethylsulfamoyl)amino)methyl)-3,4-dihydro-2H-benzo[b][1,4]oxazin-6-yl)carbamate | 633.0 (M + H)+ |
| 13U | 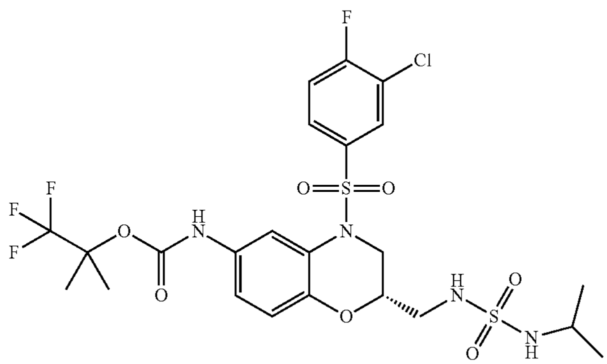 [SMILES: CC(C)NS(=O)(=O)NC[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (4-((3-chloro-4-fluorophenyl)sulfonyl)-2-(((N-isopropylsulfamoyl)amino)methyl)-3,4-dihydro-2H-benzo[b][1,4]oxazin-6-yl)carbamate | 647.0 (M + H)+ |
| 13V | 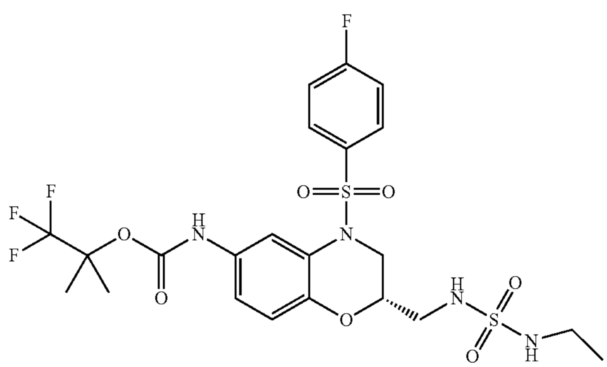 [SMILES: CCNS(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-(((N-ethylsulfamoyl)amino)methyl)-4-((4-fluorophenyl)sulfonyl)-3,4-dihydro-2H-benzo[b][1,4]oxazin-6-yl)carbamate | 599.1 (M + H)+ |
| 13W | 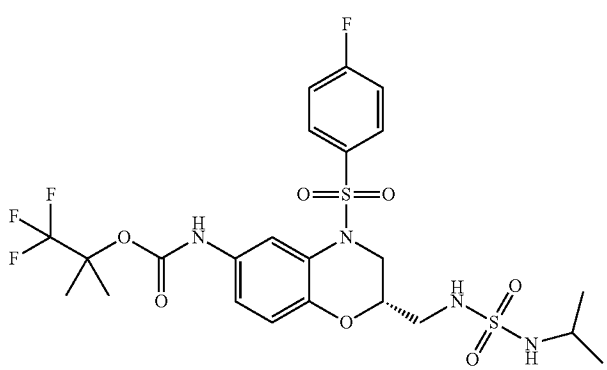 | (S)-1,1,1-trifluoro-2-methylpropan-2-yl (4-((4-fluorophenyl)sulfonyl)-2-(((N-isopropylsulfamoyl)amino)methyl)-3,4-dihydro-2H-benzo[b][1,4]oxazin-6-yl)carbamate | 613.1 (M + H)+ |

TABLE 4-continued

| Ex. No. | Structure | Name | Observed m/z |
|---|---|---|---|
| 13X | 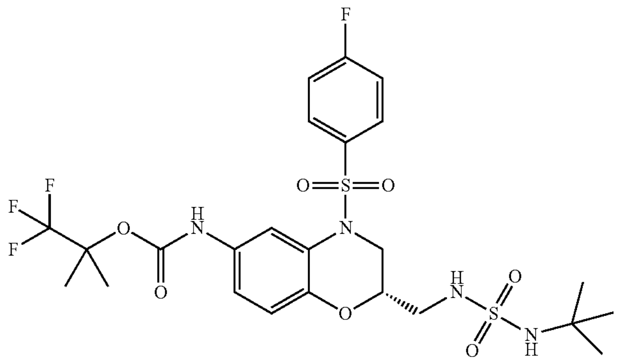 [SMILES: CC(C)(C)NS(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-(((N-(tert-butyl)sulfamoyl)amino)methyl)-4-((4-fluorophenyl)sulfonyl)-3,4-dihydro-2H-benzo[b][1,4]oxazin-6-yl)carbamate | 627.1 (M + H)+ |
| 13Y | 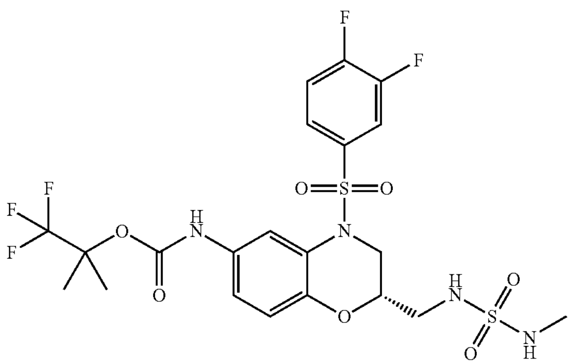 | (S)-1,1,1-trifluoro-2-methylpropan-2-yl (4-((3,4-difluorophenyl)sulfonyl)-2-(((N-methylsulfamoyl)amino)methyl)-3,4-dihydro-2H-benzo[b][1,4]oxazin-6-yl)carbamate | 603.1 (M + H)+ |
| 13Z | 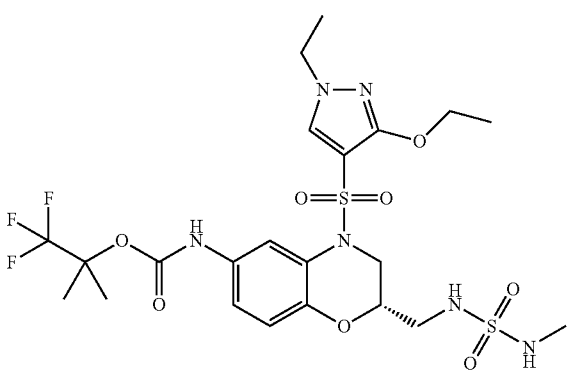 [SMILES: CCOc1nn(CC)cc1S(=O)(=O)N1C[C@H](CNS(=O)(=O)NC)Oc2ccc(NC(=O)OC(C)(C)C(F)(F)F)cc21] | (S)-1,1,1-trifluoro-2-methylpropan-2-yl (4-((3-ethoxy-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate | 629.1 (M + H)+ |
| 13AA | 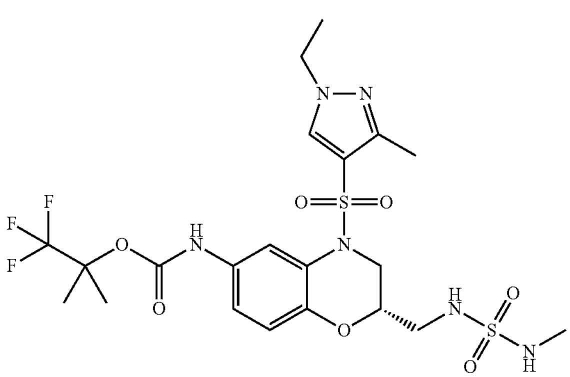 [SMILES: CCn1cc(S(=O)(=O)N2C[C@H](CNS(=O)(=O)NC)Oc3ccc(NC(=O)OC(C)(C)C(F)(F)F)cc32)c(C)n1] | (S)-1,1,1-trifluoro-2-methylpropan-2-yl (4-((1-ethyl-3-methyl-1H-pyrazol-4-yl)sulfonyl)-2-(((N-methylsulfamoyl)amino)methyl)-3,4-dihydro-2H-benzo[b][1,4]oxazin-6-yl)carbamate | 599.1 (M + H)+ |

TABLE 4-continued

| Ex. No. | Structure | Name | Observed m/z |
|---|---|---|---|
| 13AB | 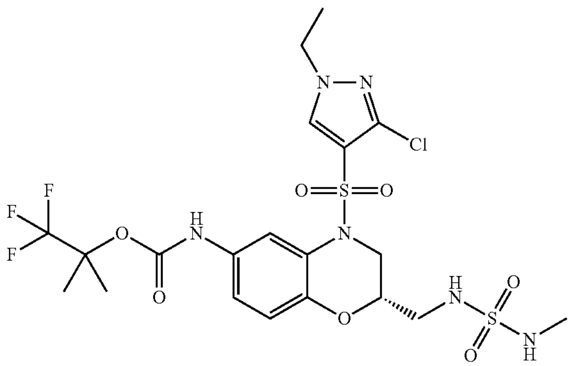 [SMILES: CCn1cc(S(=O)(=O)N2C[C@H](CNS(=O)(=O)NC)Oc3ccc(NC(=O)OC(C)(C)C(F)(F)F)cc32)c(Cl)n1] | (S)-1,1,1-trifluoro-2-methylpropan-2-yl (4-((3-chloro-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate | 619.1 (M + H)+ |
| 13AC | 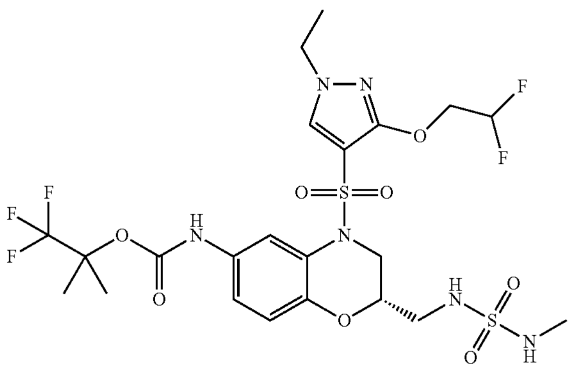 [SMILES: CCn1cc(S(=O)(=O)N2C[C@H](CNS(=O)(=O)NC)Oc3ccc(NC(=O)OC(C)(C)C(F)(F)F)cc32)c(OCC(F)F)n1] | (S)-1,1,1-trifluoro-2-methylpropan-2-yl (4-((3-(2,2-difluoroethoxy)-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate | 665.1 (M + H)+ |
| 13AD | 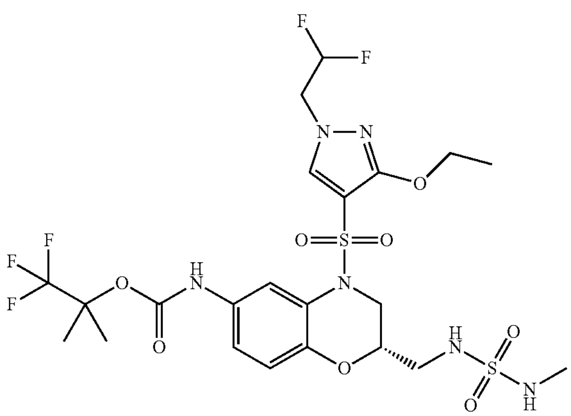 [SMILES: CCOc1nn(CC(F)F)cc1S(=O)(=O)N1C[C@H](CNS(=O)(=O)NC)Oc2ccc(NC(=O)OC(C)(C)C(F)(F)F)cc21] | (S)-1,1,1-trifluoro-2-methylpropan-2-yl (4-((1-(2,2-difluoroethyl)-3-ethoxy-1H-pyrazol-4-yl)sulfonyl)-2-(((N-methylsulfamoyl)amino)methyl)-3,4-dihydro-2H-benzo[b][1,4]oxazin-6-yl)carbamate | 665.1 (M + H)+ |
| 13AE | 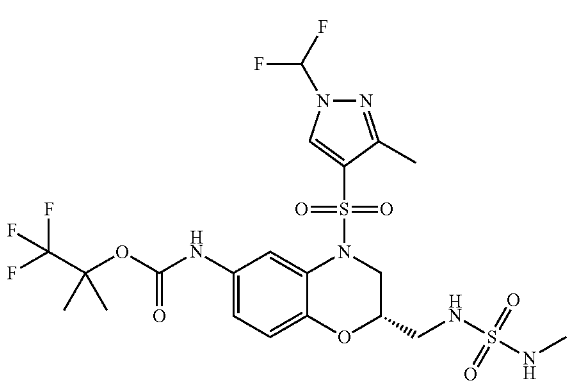 [SMILES: CNS(=O)(=O)NC[C@H]1CN(S(=O)(=O)c2cn(C(F)F)nc2C)c2cc(NC(=O)OC(C)(C)C(F)(F)F)ccc2O1] | (S)-1,1,1-trifluoro-2-methylpropan-2-yl (4-((1-(difluoromethyl)-3-methyl-1H-pyrazol-4-yl)sulfonyl)-2-(((N-methylsulfamoyl)amino)methyl)-3,4-dihydro-2H-benzo[b][1,4]oxazin-6-yl)carbamate | 621.1 (M + H)+ |

TABLE 4-continued

| Ex. No. | Structure | Name | Observed m/z |
|---|---|---|---|
| 13AF | 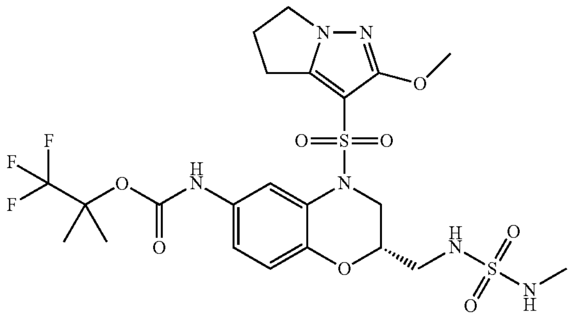 [SMILES: CNS(=O)(=O)NC[C@H]1CN(S(=O)(=O)c2c(OC)nn3c2CCC3)c2cc(NC(=O)OC(C)(C)C(F)(F)F)ccc2O1] | (S)-1,1,1-trifluoro-2-methylpropan-2-yl (4-((2-methoxy-5,6-dihydro-4H-pyrrolo[1,2-b]pyrazol-3-yl)sulfonyl)-2-(((N-methylsulfamoyl)amino)methyl)-3,4-dihydro-2H-benzo[b][1,4]oxazin-6-yl)carbamate | 627.1 (M + H)+ |
| 13AG | 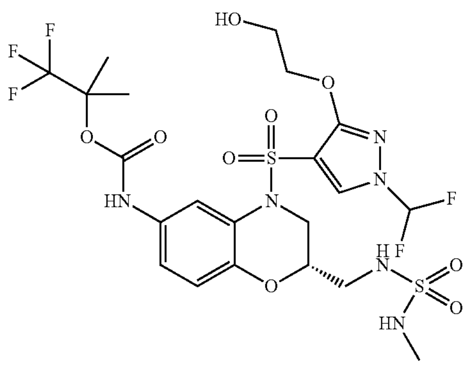 [SMILES: CNS(=O)(=O)NC[C@H]1CN(S(=O)(=O)c2cn(C(F)F)nc2OCCO)c2cc(NC(=O)OC(C)(C)C(F)(F)F)ccc2O1] | 2,2,2-trifluoro-1,1-dimethylethyl [(2S)-4-{[1-(difluoromethyl)-3-(2-hydroxyethoxy)-1H-pyrazol-4-yl]sulfonyl}-2-{[(methylsulfamoyl)amino]methyl}-3,4-dihydro-2H-1,4-benzoxazin-6-yl]carbamate | 667 (M + H)+ |

Example 14—Synthesis of (R)-tert-butyl (2-((pyridin-2-ylthio)methyl)-4-((3-(trifluoromethyl)phenyl)sulfonyl)-3,4-dihydro-2H-benzo[b][1,4]oxazin-6-yl) carbamate (14)

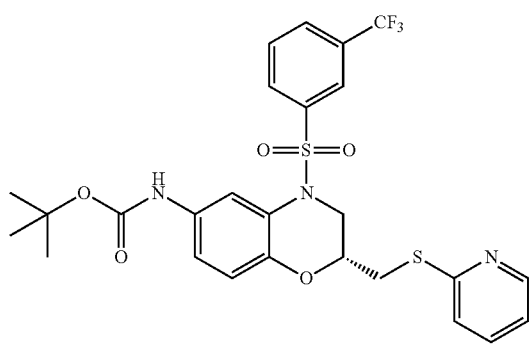 [SMILES: CC(C)(C)OC(=O)Nc1ccc2c(c1)N(S(=O)(=O)c1cccc(C(F)(F)F)c1)C[C@H](CSc1ccccn1)O2]

To (R)-(6-(((tert-butoxycarbonyl)amino)-4-((3-(trifluoromethyl)phenyl)sulfonyl)-3,4-dihydro-2H-benzo[b][1,4]oxazin-2-yl)methyl methanesulfonate (150 mg, 0.265 mmol) and cesium carbonate (431 mg, 1.32 mmol) in DMF (1 mL) at room temperature was added pyridine-2-thiol (147 mg, 1.32 mmol) and the mixture was stirred at room temperature for 16 hours. The reaction mixture was diluted with ethyl acetate, washed with saturated aqueous NaHCO$_3$, water, brine, dried (Na$_2$SO$_4$) and concentrated. The residue was purified by silica gel chromatography eluting with a gradient of ethyl acetate/hexane (0~25%) to give (R)-tert-butyl (2-((pyridin-2-ylthio)methyl)-4-((3-(trifluoromethyl)phenyl)sulfonyl)-3,4-dihydro-2H-benzo[b][1,4]oxazin-6-yl) carbamate as white solid. LRMS (ESI) calculated for C$_{26}$H$_{26}$F$_3$N$_3$O$_5$S$_2$ (M+H)+: 582, Found 582. $^1$H NMR (600 MHz, DMSO-d6) δ 9.27 (s, 1H), 8.41 (dd, J=39.2, 4.0 Hz, 1H), 8.05-7.72 (m, 4H), 7.65-7.56 (m, 2H), 7.37-7.19 (m, 1H), 7.19-6.97 (m, 2H), 6.71 (d, J=8.9 Hz, 1H), 4.40 (dd, J=14.2, 2.2 Hz, 1H), 3.60 (s, 1H), 3.45-3.38 (m, 2H), 3.15-3.20 (m, 1H) 1.43 (s, 9H).

Example 15—Preparation of Additional (R)-tert-butyl (2-((thioalkyl or thioaryl or thioheteroaryl)methyl)-4-((3-(trifluoromethyl)phenyl)sulfonyl)-3,4-dihydro-2H-benzo[b][1,4]oxazin-6-yl)carbamates The compounds in Table 5 below were prepared based on the experimental procedures described in Example 14 and elsewhere in the detailed description using the appropriate thiol in place of pyridine-2-thiol, and can be achieved by one of skill in the art in light of the present disclosure.

TABLE 5

| Ex. No. | Structure | Name | Observed m/z |
|---|---|---|---|
| 15A | 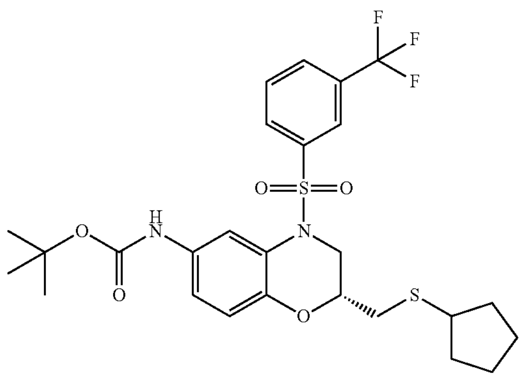 [SMILES: CC(C)(C)OC(=O)Nc1ccc2c(c1)N(S(=O)(=O)c1cccc(C(F)(F)F)c1)C[C@H](CSC1CCCC1)O2] | (R)-tert-butyl (2-((cyclopentylthio)methyl)-4-((3-(trifluoromethyl)phenyl)sulfonyl)-3,4-dihydro-2H-benzo[b][1,4]oxazin-6-yl)carbamate | 595.0 (M + Na)⁺ |
| 15B | 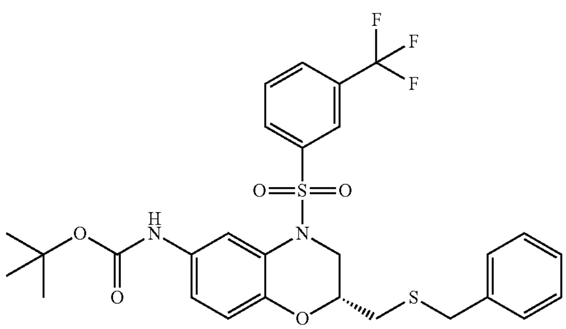 [SMILES: CC(C)(C)OC(=O)Nc1ccc2c(c1)N(S(=O)(=O)c1cccc(C(F)(F)F)c1)C[C@H](CSCc1ccccc1)O2] | (R)-tert-butyl (2-((benzylthio)methyl)-4-((3-(trifluoromethyl)phenyl)sulfonyl)-3,4-dihydro-2H-benzo[b][1,4]oxazin-6-yl)carbamate | 617.0 (M + Na)⁺ |
| 15C | 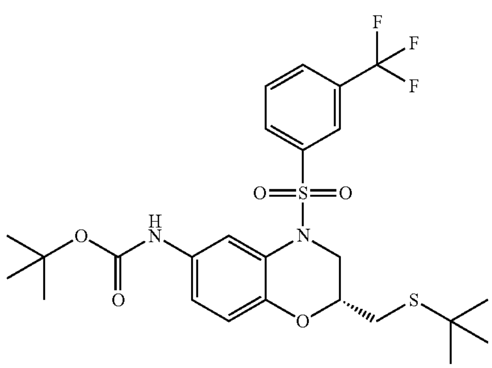 [SMILES: CC(C)(C)OC(=O)Nc1ccc2c(c1)N(S(=O)(=O)c1cccc(C(F)(F)F)c1)C[C@H](CSC(C)(C)C)O2] | (R)-tert-butyl (2-((tert-butylthio)methyl)-4-((3-(trifluoromethyl)phenyl)sulfonyl)-3,4-dihydro-2H-benzo[b][1,4]oxazin-6-yl)carbamate | 583.0 (M + Na)⁺ |
| 15D | 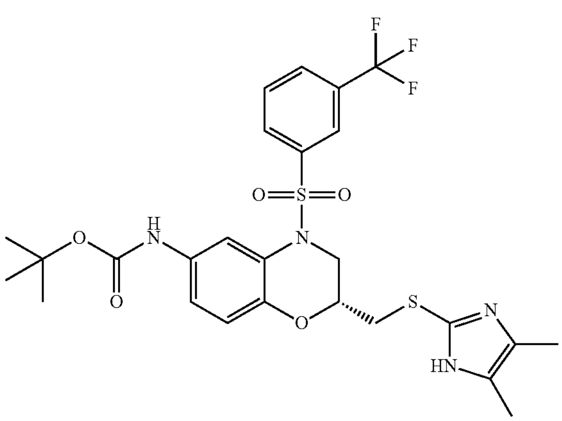 [SMILES: Cc1nc(SC[C@H]2CN(S(=O)(=O)c3cccc(C(F)(F)F)c3)c3cc(NC(=O)OC(C)(C)C)ccc3O2)[nH]c1C] | (R)-tert-butyl (2-(((4,5-dimethyl-1H-imidazol-2-yl)thio)methyl)-4-((3-(trifluoromethyl)phenyl)sulfonyl)-3,4-dihydro-2H-benzo[b][1,4]oxazin-6-yl)carbamate | 599.1 (M + H)⁺ |

TABLE 5-continued

| Ex. No. | Structure | Name | Observed m/z |
|---|---|---|---|
| 15E | 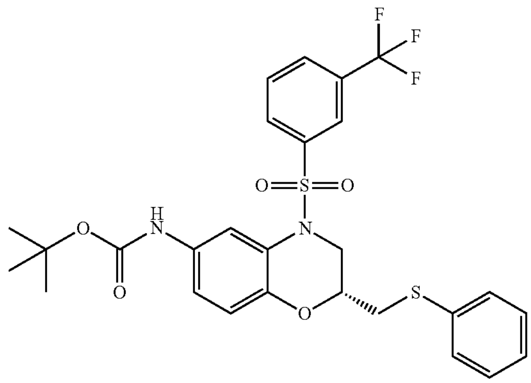 [SMILES: CC(C)(C)OC(=O)Nc1ccc2c(c1)N(S(=O)(=O)c1cccc(C(F)(F)F)c1)C[C@H](CSc1ccccc1)O2] | (R)-tert-butyl (2-((phenylthio)methyl)-4-((3-(trifluoromethyl)phenyl)sulfonyl)-3,4-dihydro-2H-benzo[b][1,4]oxazin-6-yl)carbamate | 525.0 (M-tBu + H)⁺ |
| 15F | 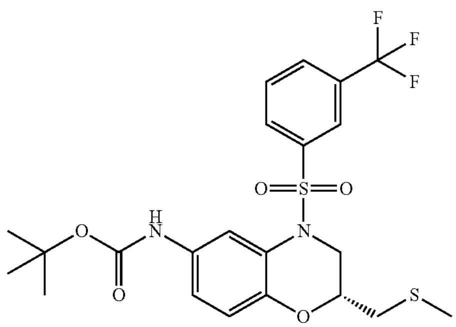 [SMILES: CSC[C@H]1CN(S(=O)(=O)c2cccc(C(F)(F)F)c2)c2cc(NC(=O)OC(C)(C)C)ccc2O1] | (R)-tert-butyl (2-((methylthio)methyl)-4-((3-(trifluoromethyl)phenyl)sulfonyl)-3,4-dihydro-2H-benzo[b][1,4]oxazin-6-yl)carbamate | 540.8 (M + Na)⁺ |

Example 16—Synthesis of (R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate (16)

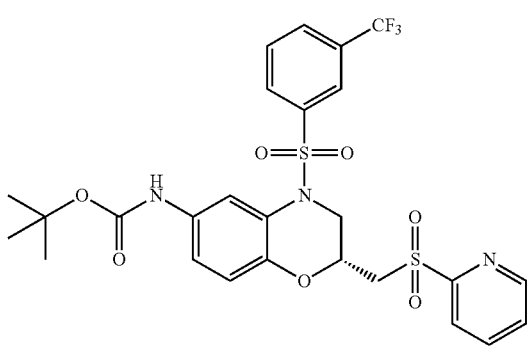 [SMILES: CC(C)(C)OC(=O)Nc1ccc2c(c1)N(S(=O)(=O)c1cccc(C(F)(F)F)c1)C[C@H](CS(=O)(=O)c1ccccn1)O2]

To a solution of (R)-tert-butyl (2-((pyridin-2-ylthio)methyl)-4-((3-(trifluoromethyl)phenyl)sulfonyl)-3,4-dihydro-2H-benzo[b][1,4]oxazin-6-yl)carbamate (100 mg, 0.172 mmol) in dichloromethane (5 mL) was added meta-chloroperbenzoic acid (148 mg, 0.860 mmol) and the mixture was stirred at room temperature for three hours. The mixture was concentrated and purified by silica gel chromatography using a gradient of ethyl acetate/hexane (0~50%), to give (R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate as a white solid. $^1$H NMR (600 MHz, DMSO-d6) δ 9.24 (s, 1H), 8.69 (d, J=4.7 Hz, 1H), 8.19-7.68 (m, 7H), 6.89 (d, J=8.9 Hz, 1H), 5.99 (d, J=8.9 Hz, 1H), 4.40 (dd, J=14.1, 2.3 Hz, 1H), 4.01-3.79 (m, 3H), 3.50 (dd, J=14.2, 9.0 Hz, 1H), 1.42 (s, 9H).

Example 17—Preparation of additional (2-((alkyl or aryl or heteroaryl sulfonyl)methyl)-benzoxazines The compounds in Table 6 below were prepared based on the experimental procedures described in Example 16 and elsewhere in the detailed description, and can be achieved by one of skill in the art in light of the present disclosure.

TABLE 6

| Ex. No. | Structure | Name | Observed m/z |
|---|---|---|---|
| 17A | 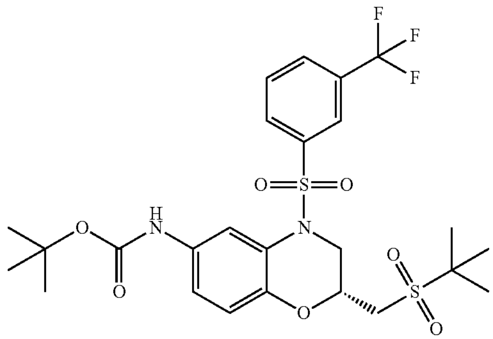 [SMILES: CC(C)(C)OC(=O)Nc1ccc2c(c1)N(S(=O)(=O)c1cccc(C(F)(F)F)c1)C[C@H](CS(=O)(=O)C(C)(C)C)O2] | (R)-tert-butyl (2-((tert-butylsulfonyl)methyl)-4-((3-(trifluoromethyl)phenyl)sulfonyl)-3,4-dihydro-2H-benzo[b][1,4]oxazin-6-yl)carbamate | 615.0 (M + Na)⁺ |
| 17B | 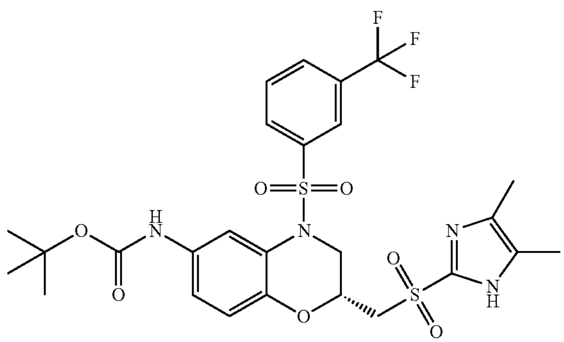 [SMILES: Cc1nc(S(=O)(=O)C[C@H]2CN(S(=O)(=O)c3cccc(C(F)(F)F)c3)c3cc(NC(=O)OC(C)(C)C)ccc3O2)[nH]c1C] | (R)-tert-butyl (2-(((4,5-dimethyl-1H-imidazol-2-yl)sulfonyl)methyl)-4-((3-(trifluoromethyl)phenyl)sulfonyl)-3,4-dihydro-2H-benzo[b][1,4]oxazin-6-yl)carbamate | 631.0 (M + H)⁺ |
| 17C | 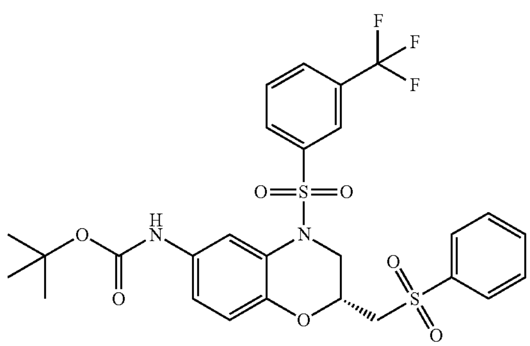 [SMILES: CC(C)(C)OC(=O)Nc1ccc2c(c1)N(S(=O)(=O)c1cccc(C(F)(F)F)c1)C[C@H](CS(=O)(=O)c1ccccc1)O2] | (R)-tert-butyl (2-((phenylsulfonyl)methyl)-4-((3-(trifluoromethyl)phenyl)sulfonyl)-3,4-dihydro-2H-benzo[b][1,4]oxazin-6-yl)carbamate | 635.0 (M + Na)⁺ |
| 17D | 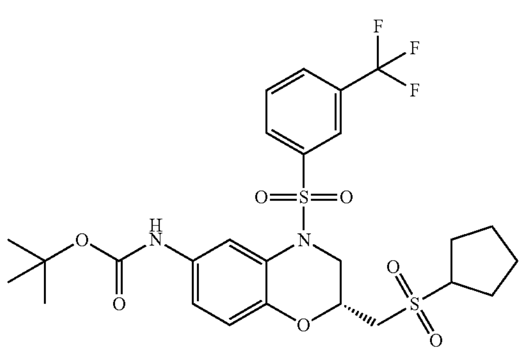 [SMILES: CC(C)(C)OC(=O)Nc1ccc2c(c1)N(S(=O)(=O)c1cccc(C(F)(F)F)c1)C[C@H](CS(=O)(=O)C1CCCC1)O2] | (R)-tert-butyl (2-((cyclopentylsulfonyl)methyl)-4-((3-(trifluoromethyl)phenyl)sulfonyl)-3,4-dihydro-2H-benzo[b][1,4]oxazin-6-yl)carbamate | 549.2 (M-tBu + H)⁺ |

| Ex. No. | Structure | Name | Observed m/z |
|---|---|---|---|
| 17E | 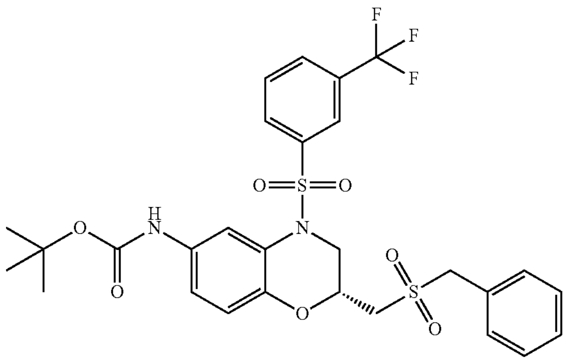 [SMILES: CC(C)(C)OC(=O)Nc1ccc2c(c1)N(S(=O)(=O)c1cccc(C(F)(F)F)c1)C[C@H](CS(=O)(=O)Cc1ccccc1)O2] | (R)-tert-butyl (2-((benzylsulfonyl)methyl)-4-((3-(trifluoromethyl)phenyl)sulfonyl)-3,4-dihydro-2H-benzo[b][1,4]oxazin-6-yl)carbamate | 644.2 (M + NH$_4$)$^+$ |
| 17F | 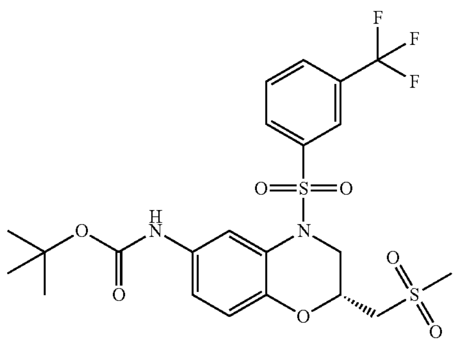 [SMILES: CC(C)(C)OC(=O)Nc1ccc2c(c1)N(S(=O)(=O)c1cccc(C(F)(F)F)c1)C[C@H](CS(C)(=O)=O)O2] | (R)-tert-butyl (2-((methylsulfonyl)methyl)-4-((3-(trifluoromethyl)phenyl)sulfonyl)-3,4-dihydro-2H-benzo[b][1,4]oxazin-6-yl)carbamate | 572.8 (M + Na)$^+$ |

Example 18—Synthesis of (R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate (18)

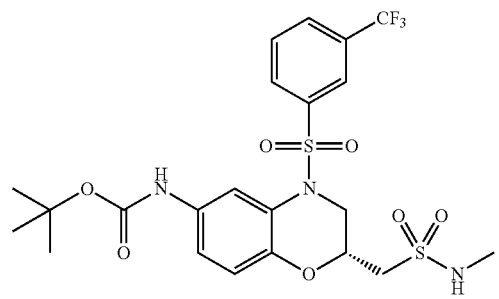 [SMILES: CNS(=O)(=O)C[C@H]1CN(S(=O)(=O)c2cccc(C(F)(F)F)c2)c2cc(NC(=O)OC(C)(C)C)ccc2O1]

The title compound was prepared according to the procedures described below.

Part I—Synthesis of (R)-tert-butyl (2-((benzylthio)methyl)-4-((3-(trifluoromethyl)phenyl)sulfonyl)-3,4-dihydro-2H-benzo[b][1,4]oxazin-6-yl)carbamate To a suspension of sodium hydride (78 mg, 1.942 mmol) in DMF (1 mL) at room temperature was added phenylmethanethiol (0.233 mL, 1.942 mmol) and the mixture was stirred at room temperature for ten minutes. Then a solution of (R)-(6-((tert-butoxycarbonyl)amino)-4-((3-(trifluoromethyl)phenyl)sulfonyl)-3,4-dihydro-2H-benzo[b][1,4]oxazin-2-yl)methyl methanesulfonate (550 mg, 0.971 mmol) in DMF (4 mL) was added and the stirring continued at room temperature overnight. The reaction mixture was diluted with ethyl acetate, washed with bleach, water and brine subsequently, then dried (Na$_2$SO$_4$) and concentrated. The residue was purified on silica chromatograph (40 g) and eluted with a gradient of ethyl acetate/hexane (0~25%) to give (R)-tert-butyl (2-((benzylthio)methyl)-4-((3-(trifluoromethyl)phenyl)sulfonyl)-3,4-dihydro-2H-benzo[b][1,4]oxazin-6-yl)carbamate as light yellow solid. LRMS (ESI) calculated for C$_{28}$H$_{29}$F$_3$N$_2$O$_5$S$_2$ (M+H)$^+$: 595, Found: 539 (M-tBu+H)$^+$ and 617 (M+Na)$^+$.

Part II—Synthesis of (R)-tert-butyl (2-((chlorosulfonyl)methyl)-4-((3-(trifluoromethyl)phenyl)sulfonyl)-3,4-dihydro-2H-benzo[b][1,4]oxazin-6-yl)carbamate

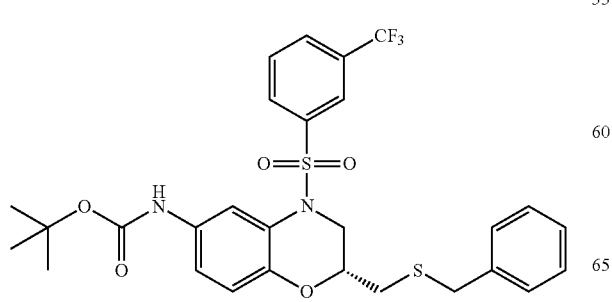

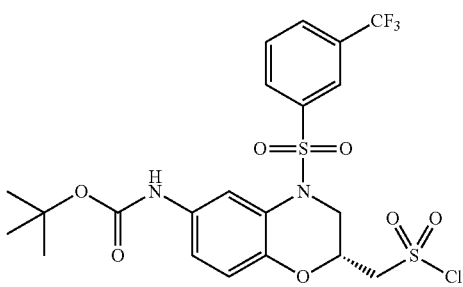 [SMILES: CC(C)(C)OC(=O)Nc1ccc2c(c1)N(S(=O)(=O)c1cccc(C(F)(F)F)c1)C[C@H](CS(=O)(=O)Cl)O2]

To a solution of (R)-tert-butyl (2-((benzylthio)methyl)-4-((3-(trifluoromethyl)phenyl)sulfonyl)-3,4-dihydro-2H-benzo[b][1,4]oxazin-6-yl)carbamate (50 mg, 0.084 mmol) in acetic acid (1 mL)/water (0.33 mL) at room temperature was added N-chlorosuccinimide (33.7 mg, 0.252 mg) and the mixture was stirred at room temperature for 2.5 hours. The mixture was diluted with ethyl acetate, washed with saturated aqueous sodium thiosulfate, water and brine, then dried (Na$_2$SO$_4$) and concentrated to give the crude product (R)-tert-butyl (2-((chlorosulfonyl)methyl)-4-((3-(trifluoromethyl)phenyl)sulfonyl)-3,4-dihydro-2H-benzo[b][1,4]oxazin-6-yl)carbamate. LRMS (ESI) calculated for C$_{21}$H$_{22}$ClF$_3$N$_2$O$_7$S$_2$ (M+H)$^+$: 571, Found: 515 (M-tBu+H)$^+$ and 593 (M+Na)$^+$.

Part III—Synthesis of (R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate

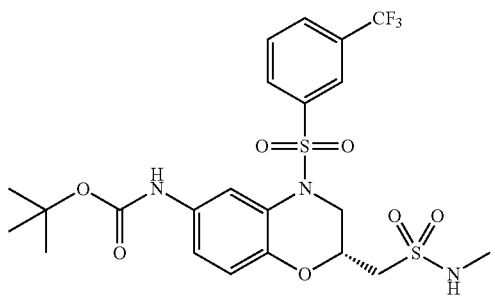 [SMILES: CNS(=O)(=O)C[C@H]1CN(S(=O)(=O)c2cccc(C(F)(F)F)c2)c2cc(NC(=O)OC(C)(C)C)ccc2O1]

To a solution of (R)-tert-butyl (2-((chlorosulfonyl)methyl)-4-((3-(trifluoromethyl)phenyl)sulfonyl)-3,4-dihydro-2H-benzo[b][1,4]oxazin-6-yl)carbamatemate (50 mg, 0.084 mmol) in dichloromethane (50 mg, 0.088 mmol) at room temperature was added methylamine hydrochloride (0.219 mL, 0.438 mmol) followed by triethyl amine (0.037 mL, 0.263 mmol) and the mixture was stirred at room temperature for an hour. The solvent was concentrated and the residue was purified via MPLC eluting with an ethyl acetate/hexanes gradient (0-50%) to afford (R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate. LRMS (ESI) calculated for C$_{22}$H$_{26}$F$_3$N$_3$O$_7$S$_2$ (M+H)$^+$: 566, Found: 510 (M-tBu)$^+$ and 588 (M+Na)$^+$. $^1$H NMR (600 MHz, DMSO-d6) δ 9.28 (s, 1H), 8.04 (dd, J=33.5, 7.6 Hz, 4H), 7.82 (t, J=8.0 Hz, 1H), 7.03 (dd, J=13.1, 7.3 Hz, 2H), 6.74 (d, J=8.9 Hz, 1H), 4.49 (d, J=14.0 Hz, 1H), 3.84 (s, 1H), 3.51-3.37 (m, 2H), 3.29 (dd, J=14.7, 7.1 Hz, 1H), 2.50 (s, 3H), 1.44 (s, 9H).

Example 19—Preparation of Additional Reverse 2-alkyl Sulfonamide Benzoxazines

The compounds in Table 7 below were prepared based on the experimental procedures described in Example 18 and elsewhere in the detailed description, and can be achieved by one of skill in the art in light of the present disclosure.

TABLE 7

| Ex. No. | Structure | Name | Observed m/z |
| --- | --- | --- | --- |
| 19A | 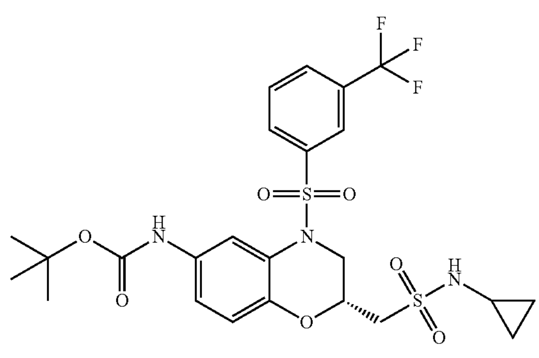 [SMILES: CC(C)(C)OC(=O)Nc1ccc2c(c1)N(S(=O)(=O)c1cccc(C(F)(F)F)c1)C[C@H](CS(=O)(=O)NC1CC1)O2] | (R)-tert-butyl (2-((N-cyclopropylsulfamoyl)methyl)-4-((3-(trifluoromethyl)phenyl)sulfonyl)-3,4-dihydro-2H-benzo[b][1,4]oxazin-6-yl)carbamate | 535.9 (M-tBu + H)$^+$ |
| 19B | 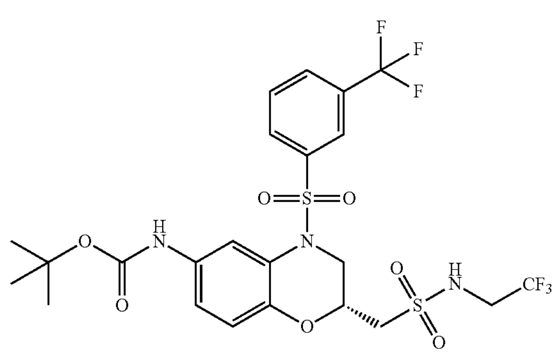 [SMILES: CC(C)(C)OC(=O)Nc1ccc2c(c1)N(S(=O)(=O)c1cccc(C(F)(F)F)c1)C[C@H](CS(=O)(=O)NCC(F)(F)F)O2] | (R)-tert-butyl (2-((N-(2,2,2-trifluoroethyl)sulfamoyl)methyl)-4-((3-(trifluoromethyl)phenyl)sulfonyl)-3,4-dihydro-2H-benzo[b][1,4]oxazin-6-yl)carbamate | 655.9 (M + Na)$^+$ |

TABLE 7-continued

| Ex. No. | Structure | Name | Observed m/z |
|---|---|---|---|
| 19C | 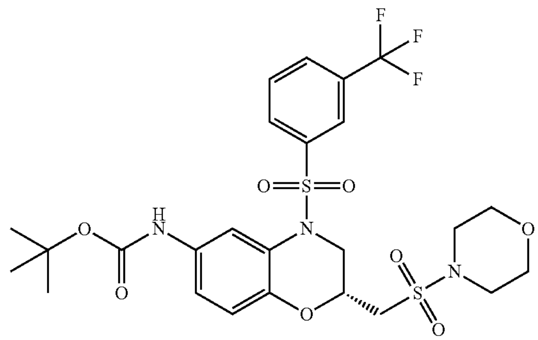 [SMILES: CC(C)(C)OC(=O)Nc1ccc2c(c1)N(S(=O)(=O)c1cccc(C(F)(F)F)c1)C[C@H](CS(=O)(=O)N1CCOCC1)O2] | (R)-tert-butyl (2-((morpholinosulfonyl)methyl)-4-((3-(trifluoromethyl)phenyl)sulfonyl)-3,4-dihydro-2H-benzo[b][1,4]oxazin-6-yl)carbamate | 566.0 (M-tBu + H)+ |
| 19D | 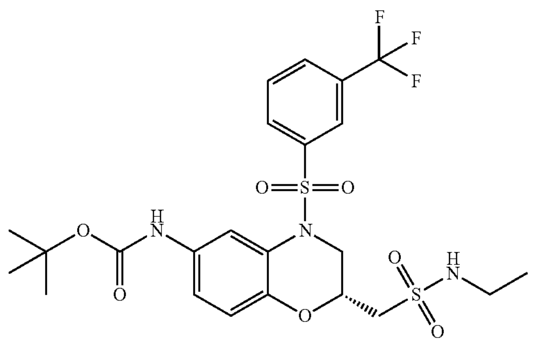 [SMILES: CCNS(=O)(=O)C[C@H]1CN(S(=O)(=O)c2cccc(C(F)(F)F)c2)c2cc(NC(=O)OC(C)(C)C)ccc2O1] | (R)-tert-butyl (2-((N-ethylsulfamoyl)methyl)-4-((3-(trifluoromethyl)phenyl)sulfonyl)-3,4-dihydro-2H-benzo[b][1,4]oxazin-6-yl)carbamate | 602.0 (M + Na)+ |
| 19E | 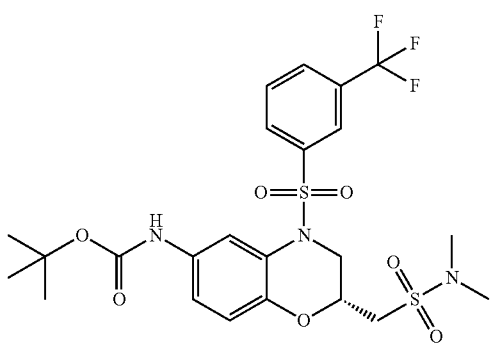 [SMILES: CN(C)S(=O)(=O)C[C@H]1CN(S(=O)(=O)c2cccc(C(F)(F)F)c2)c2cc(NC(=O)OC(C)(C)C)ccc2O1] | (R)-tert-butyl (2-((N,N-dimethylsulfamoyl)methyl)-4-((3-(trifluoromethyl)phenyl)sulfonyl)-3,4-dihydro-2H-benzo[b][1,4]oxazin-6-yl)carbamate | 523.9 (M-tBu + H)+ |

Example 20—Synthesis of 1,1,1-trifluoro-2-methyl-propan-2-yl(S)-(4-((3-ethoxy-1-ethyl-1H-pyrazol-4-yl)sulfonyl)-2-methyl-3,4-dihydro-2H-benzo[b][1,4]oxazin-6-yl)carbamate (20)

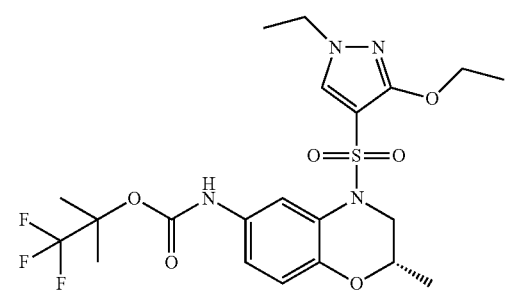 [SMILES: CCOc1nn(CC)cc1S(=O)(=O)N1C[C@H](C)Oc2ccc(NC(=O)OC(C)(C)C(F)(F)F)cc21]

Part 1—Synthesis of 1-ethyl-1,2-dihydro-3H-pyrazol-3-one

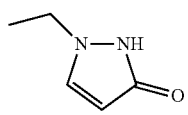

To methyl 2-chloroprop-2-enoate (5 mL, 49.8 mmol) in anhydrous tetrahydrofuran (75 mL) was added ethylhydrazine oxalate (11.2 g, 74.7 mmol) followed by triethylamine (13.9 mL, 99.6 mmol). The reaction was stirred at ambient temperature overnight. The solids were filtered off, then the filtrates were concentrated. The residue was purified by column chromatography eluting with a gradient of methanol in dichloromethane. The pure fractions were combined and concentrated in vacuo to yield the title compound.

Part 2—Synthesis of 3-ethoxy-1-ethyl-1H-pyrazole

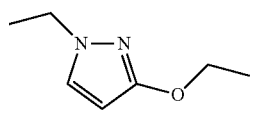

To a solution of 1-ethyl-1,2-dihydro-3H-pyrazol-3-one (1.55 g, 13.8 mmol) in N,N-dimethylformamide (15 mL) was added potassium carbonate (3.8 g, 27.6 mmol) followed by ethyl bromide (2.1 mL, 27.6 mmol). The reaction was stirred at ambient temperature for 3 hours. The solution was diluted with ethyl acetate, washed with water, brine, dried with sodium sulfate, filtered and concentrated in vacuo to yield the title compound.

Part 3—Synthesis of 3-Ethoxy-1-ethyl-1H-pyrazole-4-sulfonyl chloride

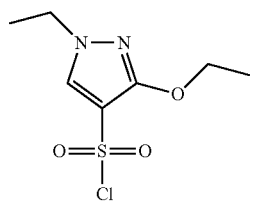

To 3-ethoxy-1-ethyl-1H-pyrazole (3.14 g, 22.4 mmol) in chloroform (25 mL) at 0° C. was added chlorosulfonic acid (15 mL, 224 mmol) dropwise. The resulting solution was stirred for 3 hours at 70° C. The solution was cooled in an ice bath and then quenched by pouring into ice water. The resulting suspension was extracted with dichloromethane and the combined organic layers were dried over anhydrous sodium sulfate and concentrated under vacuum to yield the title compound as an oil.

Part 4—Synthesis of Methyl (S)-2-(4-bromo-2-nitrophenoxy)propanoate

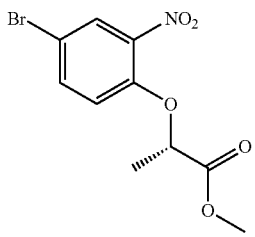 [SMILES: COC(=O)[C@H](C)Oc1ccc(Br)cc1[N+](=O)[O-]]

To a solution of 5-bromo-2-fluoronitrobenzene (5.4 g, 24.5 mmol) in tetrahydrofuran (50 mL) at 0° C. was added (S)-lactic acid methyl ester (3.1 g, 29.4 mmol) followed by 1,8-diazabicyclo[5.4.0]undec-7-ene (4.4 mL, 26.9 mmol). The cooling bath was removed and reaction was stirred at ambient temperature overnight. The solution was partitioned between ethyl acetate and water, washed with water, brine, dried with sodium sulfate, filtered and concentrated in the presence of silica. The residue was purified by column chromatography eluting with a gradient of 0-60% ethyl acetate in hexanes. The pure fractions were combined and concentrated in vacuo to yield the title compound.

Part 5—Synthesis of (S)-6-Bromo-2-methyl-2H-benzo[b][1,4]oxazin-3(4H)-one

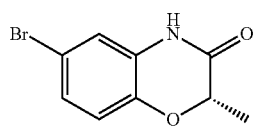

To methyl (S)-2-(4-bromo-2-nitrophenoxy)propanoate (2.4 g, 7.9 mmol) in acetic acid (30 mL) was added powdered iron (2.2 g, 39.5 mmol) and the reaction was heated to 70° C. for 2 hours. The warm suspension was filtered through CELITE, and washed with ethyl acetate. The filtrates were partitioned between ethyl acetate and water, washed with water, brine, dried with sodium sulfate, filtered and concentrated in vacuo to yield the title compound.

Part 6—Synthesis of (S)-6-Bromo-2-methyl-3,4-dihydro-2H-benzo[b][1,4]oxazine

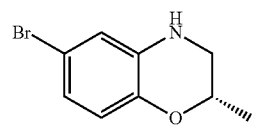

To a solution of (S)-6-bromo-2-methyl-2H-benzo[b][1,4]oxazin-3(4H)-one (1.55 g, 6.4 mmol) in anhydrous tetrahydrofuran (20 mL) under a nitrogen atmosphere at ambient temperature was carefully added borane-methyl sulfide complex (2.56 mL, 25.6 mmol). The reaction was then refluxed for 90 minutes, cooled in an ice bath and quenched with methanol (20 mL). The suspension was next heated to reflux for 20 minutes, then concentrated in vacuo. The residue was partitioned between ethyl acetate and water, washed with brine, dried with sodium sulfate, filtered and concentrated in vacuo to yield the title compound.

Part 7—Synthesis of (S)-6-Bromo-4-((3-ethoxy-1-ethyl-1H-pyrazol-4-yl)sulfonyl)-2-methyl-3,4-dihydro-2H-benzo[b][1,4]oxazine

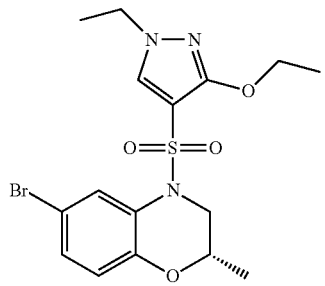 [SMILES: CCOc1nn(CC)cc1S(=O)(=O)N1C[C@H](C)Oc2ccc(Br)cc21]

A mixture of (S)-6-bromo-2-methyl-3,4-dihydro-2H-benzo[b][1,4]oxazine (0.5 g, 2.2 mmol), 3-ethoxy-1-ethyl-1H-pyrazole-4-sulfonyl chloride (0.63 g, 2.6 mmol) and pyridine (8 mL) was stirred at 70° C. overnight. The solution was cooled, diluted with ethyl acetate, washed with 10% citric acid, brine, dried (Na$_2$SO$_4$). To the suspension was added activated charcoal and the suspension was slurried. The mixture was filtered through CELITE and concentrated.

Part 8—Synthesis of 1,1,1-Trifluoro-2-methylpropan-2-yl (S)-(4-((3-ethoxy-1-ethyl-1H-pyrazol-4-yl)sulfonyl)-2-methyl-3,4-dihydro-2H-benzo[b][1,4]oxazin-6-yl)carbamate

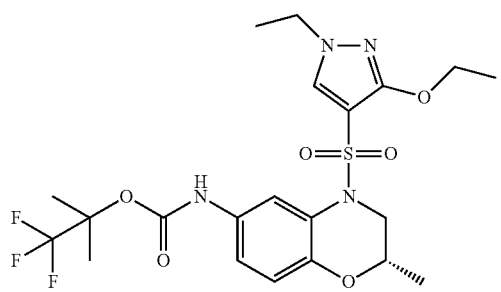 [SMILES: CCOc1nn(CC)cc1S(=O)(=O)N1C[C@H](C)Oc2ccc(NC(=O)OC(C)(C)C(F)(F)F)cc21]

In toluene (4 mL) and water (1 mL) was combined (S)-6-bromo-4-((3-ethoxy-1-ethyl-1H-pyrazol-4-yl)sulfonyl)-2-methyl-3,4-dihydro-2H-benzo[b][1,4]oxazine (0.2 g, 0.47 mmol), 2-dicyclohexylphosphino-2',4',6'-triisopropyl-biphenyl (22 mg, 0.046 mmol), tert-butyl carbamate (0.11 g, 0.93 mmol) and tripotassium phosphate (0.3 g, 1.4 mmol) followed by the addition of tris(dibenzylideneacetone)dipalladium(0) (21 mg, 0.046 mmol) and heated at 100° C. overnight. The cooled solution was partitioned between ethyl acetate and water, washed with brine, dried (Na$_2$SO$_4$), and concentrated. The mixture was purified by column chromatography eluting with a gradient of ethyl acetate in hexanes. To the intermediate was added was added 4M hydrogen chloride in dioxane (3 mL) and the result was stirred at ambient temperature for 1 hour. The resulting suspension was concentrated. The residue was redissolved in N,N-dimethylformamide (2 mL) and combined with (2,2,2-trifluoro-1,1-dimethyl-ethyl) imidazole-1-carboxylate (0.097 g, 0.44 mmol). The mixture was heated to 100° C. in the microwave for 2 hours. The cooled solution was partitioned between ethyl acetate and water, washed with brine, dried (Na$_2$SO$_4$), and concentrated. The residue was purified by column chromatography eluting with a gradient of 70-100% ethyl acetate in hexanes to afford the title compound. LCMS (ESI) calculated for C$_{21}$H$_{28}$F$_3$N$_4$O$_6$S (M+H)$^+$: 521, Found: 521.

Example 21—Synthesis of [(2S,3S and 2R,3R)-4-(3-cyano-benzenesulfonyl)-2-hydroxymethyl-3-methyl-3,4-dihydro-2H-benzo[1,4]oxazin-6-yl]-carbamic acid 2,2-dimethyl-propyl ester (21)

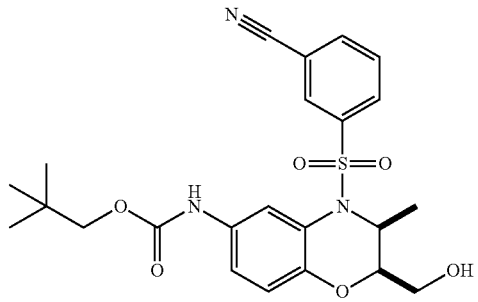 [SMILES: C[C@H]1[C@@H](CO)Oc2ccc(NC(=O)OCC(C)(C)C)cc2N1S(=O)(=O)c1cccc(C#N)c1]

The title compound was prepared according to the procedures described below.

Part I—Synthesis of N-(but-3-en-2-yl)-3-cyano-N-(2-fluoro-5-nitrophenyl)-benzenesulfonamide

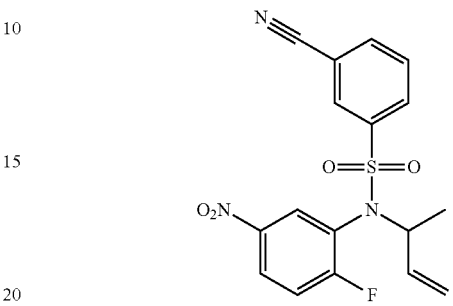

To a mixture of 3-cyano-N-(2-fluoro-5-nitro-phenyl)-benzenesulfonamide (2.8 g, 8.7 mmol), 3-buten-2-ol (0.626 g, 8.8 mmol) and triphenylphosphine was added diisopropyl-diazodicarboxylate (2.28 g, 9.6 mmol) in THF (50 mL) dropwise at 0° C. After this addition, the mixture was warmed to room temperature and stirred overnight. The solvent was removed and the resulting residue purified by silica gel chromatography (dichloromethane) to provide N-(but-3-en-2-yl)-3-cyano-N-(2-fluoro-5-nitrophenyl) benzenesulfonamide. LRMS (ESI) calculated for C$_{17}$H$_{16}$FN$_3$O$_4$S (M+H)$^+$: 376, Found: 376.2.

Part II—Synthesis of 3-cyano-N-(2,3-dihydroxy-1-methyl-propyl)-N-(2-fluoro-5-nitro-phenyl)-benzenesulfonamide

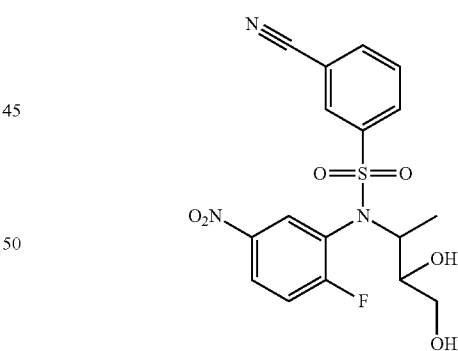

To a mixture of 3-cyano-N-(2-fluoro-5-nitro-phenyl)-N-(1-methyl-allyl)-benzenesulfonamide (2.6 g, 6.9 mmol), N-methylmorpholine N-oxide (0.97 g, 8.3 mmol) in acetone (20 mL) and water (40 mL) was added osmium tetroxide (0.3 g). The mixture was stirred overnight at room temperature and diluted with water (50 mL). White precipitate was filtered, washed with water and hexanes to provide a mixture of diastereomers of 3-cyano-N-(2,3-dihydroxy-1-methyl-propyl)-N-(2-fluoro-5-nitro-phenyl)-benzenesulfonamide. LRMS (ESI) calculated for C$_{17}$H$_{17}$FN$_3$O$_6$S (M+H)$^+$: 410, Found 410.3.

Part III—Synthesis of 3-((2S,3S and 2R,3R)-2-hydroxymethyl-3-methyl-6-nitro-2,3-dihydro-benzo[1,4]oxazine-4-sulfonyl)-benzonitrile

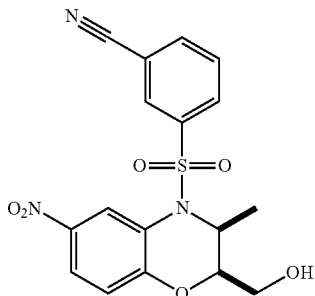

A mixture of 3-((2S,3S and 2R,3R)-2-hydroxymethyl-3-methyl-6-nitro-2,3-dihydro-benzo[1,4]oxazine-4-sulfonyl)-benzonitrile (2.5 g, 6.4 mmol), sodium hydride (0.56 g, 22.4 mmol) in THF (100 mL) was heated to reflux for three days. The mixture was cooled to 0° C. and quenched with 2N HCl, diluted with ethyl acetate, washed with water, saturated sodium bicarbonate, and concentrated. The residue was purified by silica gel chromatography (hexanes/ethyl acetate, 1.5/1) to provide 3-((2S,3S and 2R,3R)-2-hydroxymethyl-3-methyl-6-nitro-2,3-dihydro-benzo[1,4]oxazine-4-sulfonyl)-benzonitrile. LRMS (ESI) calculated for $C_{17}H_{16}N_3O_4S$ (M+H)$^+$: 390, Found: 390.1.

Part IV—Synthesis of 3-((2S,3S and 2R,3R)-6-amino-2-hydroxymethyl-3-methyl-2,3-dihydro-benzo[1,4]oxazine-4-sulfonyl)-benzonitrile

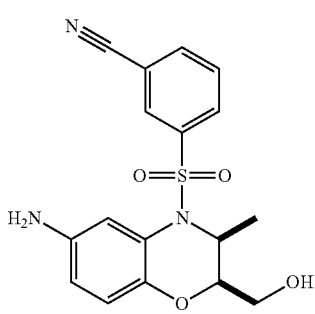 [SMILES: C[C@H]1[C@@H](CO)Oc2ccc([N+](=O)[O-])cc2N1S(=O)(=O)c1cccc(C#N)c1]

A mixture of 3-((2S,3S and 2R,3R)-2-hydroxymethyl-3-methyl-6-nitro-2,3-dihydro-benzo[1,4]oxazine-4-sulfonyl)-benzonitrile (2.5 g, 6.11 mmol), iron (1.0 g) in dioxane (50 mL) and 6N HCl (20 mL) was heated to reflux for three hours. After the mixture was cooled, saturated sodium bicarbonate and ethyl acetate (200 mL) were added. The layers were partitioned and the organic layer was washed with brine and separated, dried (Na$_2$SO$_4$) and concentrated. The residue was chromatographed on silica gel to give desired product. LRMS (ESI) calculated for $C_{17}H_{18}N_3O_2S$ (M+H)$^+$: 360, Found: 360.3.

Part V—Synthesis of [(2S,3S and 2R,3R)-4-(3-cyano-benzenesulfonyl)-2-hydroxymethyl-3-methyl-3,4-dihydro-2H-benzo[1,4]oxazin-6-yl]-carbamic acid 2,2-dimethyl-propyl ester

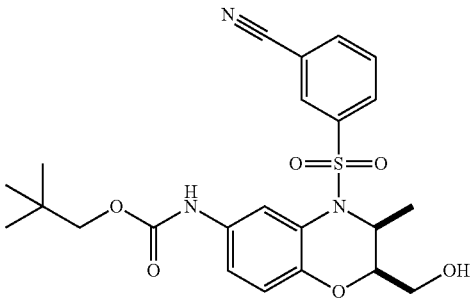 [SMILES: C[C@H]1[C@@H](CO)Oc2ccc(NC(=O)OCC(C)(C)C)cc2N1S(=O)(=O)c1cccc(C#N)c1]

3-((2S,3S and 2R,3R)-6-Amino-2-hydroxymethyl-3-methyl-2,3-dihydro-benzo[1,4]oxazine-4-sulfonyl)-benzonitrile (89.8 mg, 0.25 mmol) was treated with neopentyl chloroformate by the procedures described above to give the title compound. LRMS (ESI) calculated for $C_{23}H_{28}N_3O_6S$ (M+H)$^+$: 474, Found: 474.

Example 22—Synthesis of (S and R)-1,1,1-trifluoro-2-methylpropan-2-yl 4-(4-fluorophenylsulfonyl)-3-methyl-3,4-dihydro-2H-benzo[b][1,4]oxazin-6-ylcarbamate (Example Nos. 22A and 22B)

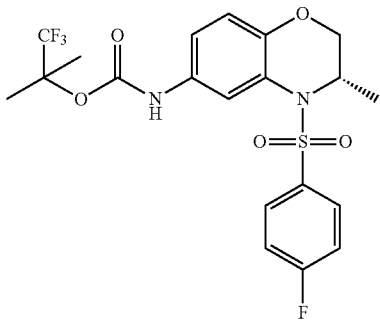

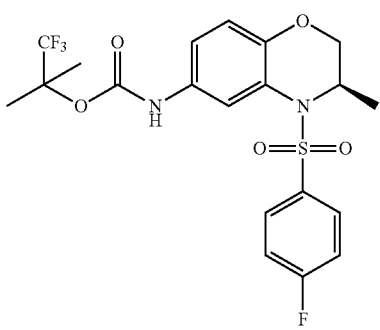

Step 1—Preparation of 3-methyl-6-nitro-2H-benzo[b][1,4]oxazine

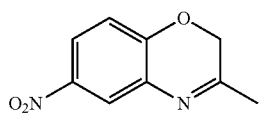

A mixture of 1-chloropropan-2-one (3.4 g, 30 mmol) and K$_2$CO$_3$ (8.3 g, 60 mmol) in acetone (100 mL) was stirred for 10 minutes at room temperature. Then 2-amino-4-nitrophenol (5 g, 30 mmol) was added and the reaction mixture was stirred for 12 hours at 80° C. The reaction mixture was cooled to 20° C., filtered, concentrated in vacuo and purified by crystallization with MeOH/petroleum ether (10:1) to afford the title compound as a yellow solid. LCMS (ESI): calculated for C$_9$H$_8$N$_2$O$_3$ [M+H]$^+$: 193, found: 193.

Step 2—Preparation of 3-methyl-6-nitro-3,4-dihydro-2H-benzo[b][1,4]oxazine

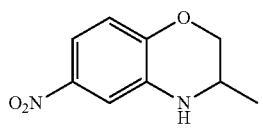

To a solution of 3-methyl-6-nitro-2H-benzo[b][1,4]oxazine (300 mg, 1.568 mmol) in ethanol (10 mL) was added NaBH$_4$ (71 mg, 1.87 mmol). The mixture was stirred at room temperature for an hour. The reaction was quenched with water and extracted three times with EtOAc (50 mL each). The combined organic layers were washed with brine, dried (Na$_2$SO$_4$), filtered and concentrated to afford the title compound as a yellow solid. LCMS (ESI): calculated for C$_9$H$_{10}$N$_2$O$_3$(M+H)$^+$: 195, found: 195.

Step 3—Preparation of 4-((4-fluorophenyl)sulfonyl)-3-methyl-6-nitro-3,4-dihydro-2H-benzo[b][1,4]oxazine

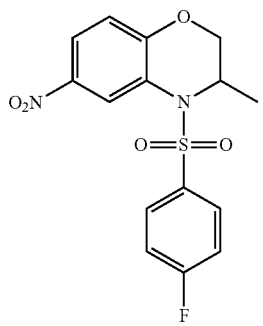

To a solution of 3-methyl-6-nitro-3,4-dihydro-2H-benzo[b][1,4]oxazine (300 mg, 1.55 mmol) in pyridine (4 mL) was added 4-fluorobenzene-1-sulfonyl chloride (1.5 g, 7.73 mmol). The reaction was stirred at 100° C. for 12 hours and diluted with water (10 mL). The mixture was extracted three times with ethyl acetate (50 mL each). The combined organic layers were dried (Na$_2$SO$_4$) and concentrated. The residue was crystallized with 1% methanol in ethyl acetate to give the title compound. LCMS (ESI): calculated for C$_{15}$H$_{13}$FN$_2$O$_5$S (M+H)$^+$: 353, found: 353.

Step 4—Preparation of 4-((4-fluorophenyl)sulfonyl)-3-methyl-3,4-dihydro-2H-benzo[b][1,4]oxazin-6-amine

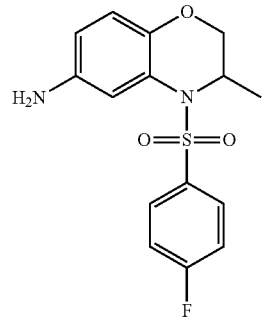 [SMILES: CC1COc2ccc([N+](=O)[O-])cc2N1S(=O)(=O)c1ccc(F)cc1]

The atmosphere above a solution of 4-((4-fluorophenyl)sulfonyl)-3-methyl-6-nitro-3,4-dihydro-2H-benzo[b][1,4]oxazine (250 mg, 0.71 mmol) in ethyl acetate (50 mL) was purged with nitrogen and 10% Pd/C (0.3 g) was added. The atmosphere was then replaced with hydrogen and stirred at 25° C. for 12 hours. The mixture was filtered through a CELITE pad, the pad was washed with ethyl acetate, and the combined filtrates were concentrated to afford the title compound as a yellow solid. LCMS (ESI): calculated for C$_{15}$H$_{15}$FN$_2$O$_3$S (M+H)$^+$: 323, found: 323.

Step 5—Preparation of (S and R)-1,1,1-trifluoro-2-methylpropan-2-yl (4-((4-fluorophenyl)sulfonyl)-3-methyl-3,4-dihydro-2H-benzo[b][1,4]oxazin-6-yl)carbamate

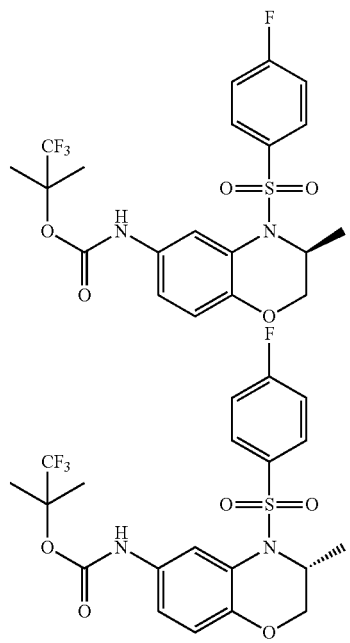

A mixture of 4-nitrophenyl (1,1,1-trifluoro-2-methylpropan-2-yl) carbonate (136 mg, 0.46 mmol) and 4-((4-fluorophenyl)sulfonyl)-3-methyl-3,4-dihydro-2H-benzo[b][1,4]

oxazin-6-amine (100 mg, 0.31 mmol) in N,N-diisopropylethylamine (1.5 mL) was heated at 100° C. for 16 hours. The reaction mixture was cooled and diluted with 1 M HCl (20 mL). The mixture was extracted three times with EtOAc (50 mL each). The combined organic layers were washed with brine, dried ($Na_2SO_4$), and concentrated. The residue was purified by prep-TLC eluting with petroleum ether:ethyl acetate (3:1) to afford the title compound as a yellow solid, which was further separated by SFC (Column: Chiralpak AD-3 150×4.6 mm I.D., 3 um Mobile phase: methanol (0.05% DEA) in $CO_2$ from 5% to 40% Flow rate: 2.5 mL/min Wavelength: 220 nm) to give two isomers. LCMS (ESI): calculated for $C_{20}H_{20}F_4N_2O_5S$ (M+H)$^+$: 477, found: 477.

Example 23—Synthesis of (R and S)-1,1,1-trifluoro-2-methylpropan-2-yl (4-((4-fluorophenyl)sulfonyl)-3-(hydroxymethyl)-3,4-dihydro-2H-benzo[b][1,4]oxazin-6-yl)carbamate (Example Nos. 23A and 23B)

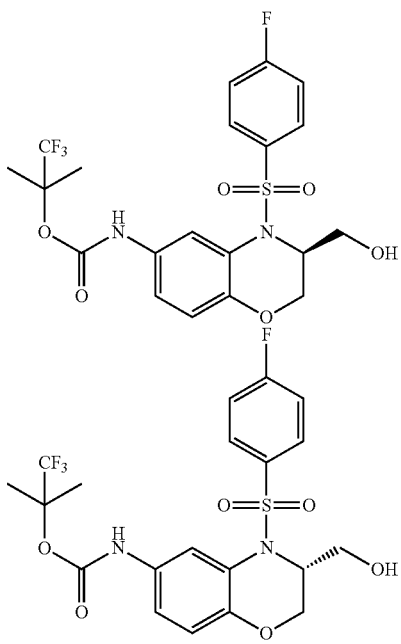

Step 1—Preparation of N-(2-(allyloxy)-5-nitrophenyl)-4-fluorobenzenesulfonamide

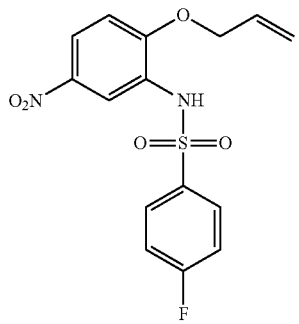 [SMILES: C=CCOc1ccc([N+](=O)[O-])cc1NS(=O)(=O)c1ccc(F)cc1]

To a solution of NaH (417 mg, 9.55 mmol) in THF (5 mL) was added prop-2-en-1-ol (554 mg, 9.55 mmol) in THF (5 mL), and the reaction mixture was stirred at 0° C. for 20 minutes. Then 4-fluoro-N-(2-fluoro-5-nitrophenyl)benzenesulfonamide (1.0 g, 3.18 mmol) in THF (10 mL) was added to the reaction mixture and the resulting mixture was stirred at 0° C. for 3 hours. The reaction was quenched with 1 N HCl (10 mL). The mixture was partitioned between and ethyl acetate and water. The organic layer was washed with brine, dried ($Na_2SO_4$) and concentrated. The residue was purified by silica gel column chromatography eluting with petroleum ether:ethyl acetate (4:1) to afford the title compound.

Step 2—Preparation of 4-fluoro-N-(5-nitro-2-(oxiran-2-ylmethoxy)phenyl) benzenesulfonamide

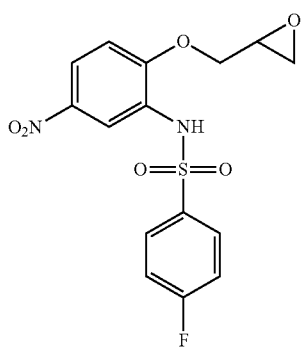 [SMILES: O=[N+]([O-])c1ccc(OCC2CO2)c(NS(=O)(=O)c2ccc(F)cc2)c1]

A mixture of N-(2-(allyloxy)-5-nitrophenyl)-4-fluorobenzenesulfonamide (600 mg, 1.7 mmol) and m-CPBA (441 mg, 2.55 mmol) in dichloroethane (15 mL) was stirred at 90° C. overnight. The mixture was cooled and concentrated. The residue was partitioned between water and ethyl acetate. The organic layer was washed with brine, dried ($Na_2SO_4$) and concentrated. The residue was purified by silica gel column chromatography eluting with petroleum ether:ethyl acetate (2:1) to afford the title compound.

Step 3—Preparation of (4-((4-fluorophenyl)sulfonyl)-6-nitro-3,4-dihydro-2H-benzo[b][1,4]oxazin-3-yl)methanol

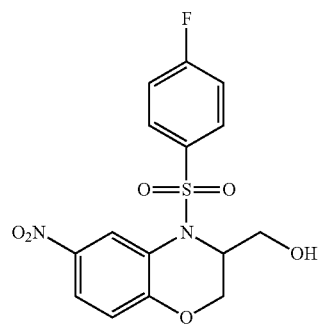 [SMILES: O=[N+]([O-])c1ccc2c(c1)N(S(=O)(=O)c1ccc(F)cc1)C(CO)CO2]

Potassium carbonate (150 mg, 1.08 mmol) was added to 4-fluoro-N-(5-nitro-2-(oxiran-2-ylmethoxy) phenyl)benzenesulfonamide (100 mg, 0.27 mmol) in acetonitrile (2 mL). The reaction mixture was heated at 120° C. by microwave irradiation for 40 minutes. The reaction mixture was diluted with water, and extracted three times with ethyl acetate. The combined organic layers were washed with brine, dried (Na₂SO₄) and concentrated. The residue was purified by prep-TLC eluting with petroleum ether:ethyl acetate (1:1) to afford the title compound.

Step 4—Preparation of (4-((4-fluorophenyl)sulfonyl)-6-nitro-3,4-dihydro-2H-benzo[b][1,4]oxazin-3-yl)methyl acetate

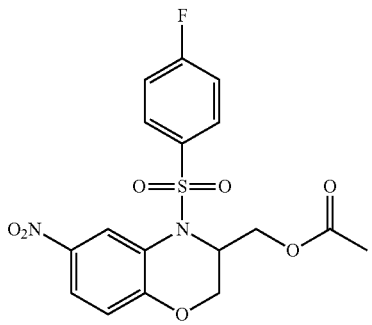 [SMILES: CC(=O)OCC1COc2ccc([N+](=O)[O-])cc2N1S(=O)(=O)c1ccc(F)cc1]

A mixture of (4-((4-fluorophenyl)sulfonyl)-6-nitro-3,4-dihydro-2H-benzo[b][1,4]oxazin-3-yl)methanol (170 mg, 0.46 mmol), triethylamine (140 mg, 1.38 mmol) and acetyl chloride (73 mg, 0.93 mmol) in dichloromethane (2 mL) was stirred at room temperature for 2 hours. The mixture was diluted with water, and extracted twice with ethyl acetate. The combined organic layers were washed with brine, dried (Na₂SO₄) and concentrated to afford the title compound as a yellow solid.

Step 5—Preparation of (6-amino-4-((4-fluorophenyl)sulfonyl)-3,4-dihydro-2H-benzo[b][1,4]oxazin-3-yl)methyl acetate

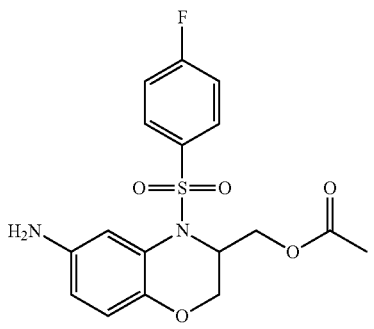

A mixture of (4-((4-fluorophenyl)sulfonyl)-6-nitro-3,4-dihydro-2H-benzo[b][1,4]oxazin-3-yl)methyl acetate (190 mg, 0.46 mmol) and 10% palladium on carbon (50 mg) in ethyl acetate (5 mL) was stirred under a hydrogen atmosphere (15 psi) overnight. The mixture was filtered through CELITE, the filter pad was washed with ethyl acetate, and the combined filtrates were concentrated to afford the title compound. LCMS (ESI): calculated for $C_{17}H_{17}FN_2O_5S$ (M+H)⁺: 381, found: 381.

Step 6—Preparation of (4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-3-yl)methyl acetate

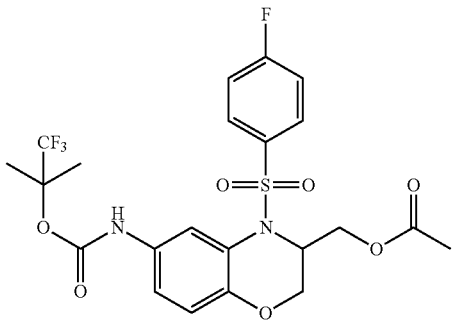 [SMILES: CC(=O)OCC1COc2ccc(NC(=O)OC(C)(C)C(F)(F)F)cc2N1S(=O)(=O)c1ccc(F)cc1]

A mixture of (6-amino-4-((4-fluorophenyl)sulfonyl)-3,4-dihydro-2H-benzo[b][1,4]oxazin-3-yl)methyl acetate (120 mg, 0.32 mmol) and 1,1,1-trifluoro-2-methylpropan-2-yl 1H-imidazole-1-carboxylate (120 mg, 0.54 mmol) in DMSO (3 mL) was stirred at 80° C. overnight. The mixture was diluted with water, extracted with twice with ethyl acetate and the combined organic layers were washed with brine, dried (Na₂SO₄) and concentrated. The residue was purified by silica gel column chromatography eluting with petroleum ether:ethyl acetate (5:1) to afford the title compound. LCMS (ESI): calculated for $C_{22}H_{22}F_4N_2O_7S$ (M+H)⁺: 535, found: 535.

Step 7—Preparation of (R and S)-1,1,1-trifluoro-2-methylpropan-2-yl (4-((4-fluorophenyl)sulfonyl)-3-(hydroxymethyl)-3,4-dihydro-2H-benzo[b][1,4]oxazin-6-yl)carbamate

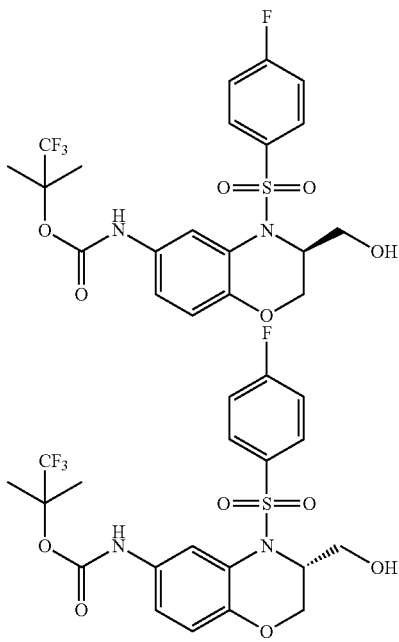

A mixture of (4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-3-yl)methyl acetate (140 mg, 0.26 mmol) and potassium carbonate (310 mg, 2.23 mmol) in MeOH (4.5 mL) and water (0.5 mL) was stirred at room temperature for four hours. The reaction mixture was diluted with water, extracted with twice with ethyl acetate and the combined organic layers were washed with brine, dried (Na$_2$SO$_4$) and concentrated. The residue was purified by silica gel column chromatography eluting with petroleum ether:ethyl acetate (5:1) to afford the title compound, which was further separated by SFC (Column: Chiralpak AD-H 250×4.6 mm I.D., 5 um Mobile phase: methanol (0.05% DEA) in CO$_2$ from 5% to 40% Flow rate: 2.35 mL/min Wavelength: 220 nm) to give two isomers. LCMS (ESI): calculated for C$_{20}$H$_{20}$F$_4$N$_2$O$_6$S (M+H)$^+$: 493, found: 493; $^1$H NMR (400 MHz, CDCl$_3$) δ 7.82 (br s, 1H), 7.68 (dd, J=4.8, 8.4 Hz, 2H), 7.23 (d, J=8.0 Hz, 1H), 7.14 (t, J=8.4 Hz, 2H), 6.81 (br s, 1H), 6.76 (d, J=8.4 Hz, 1H), 4.39 (t, J=6.4 Hz, 1H), 4.13 (d, J=11.8 Hz, 1H), 3.62-3.68 (m, 1H), 3.51-3.58 (m, 1H), 3.18 (dd, J=2.4, 11.6 Hz, 1H), 1.76 (s, 6H).

Example 24—Synthesis of [(S)-4-(3-cyano-benzenesulfonyl)-2-(2,4-dioxo-oxazolidin-3-ylmethyl)-3,4-dihydro-2H-benzo[1,4]oxazin-6-yl]-carbamic acid tert-butyl ester (24)

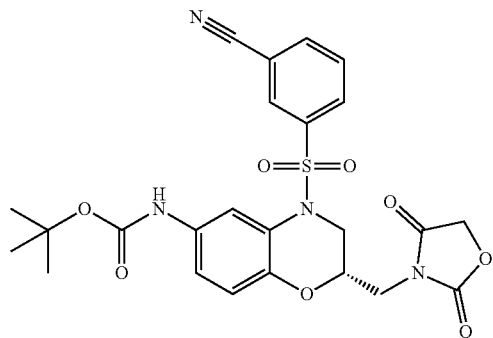 [SMILES: CC(C)(C)OC(=O)Nc1ccc2c(c1)N(S(=O)(=O)c1cccc(C#N)c1)C[C@H](CN1C(=O)COC1=O)O2]

To a solution of triphenylphosphine (1.2 g, 4.7 mmol) in tetrahydrofuran (7.5 mL) at 0° C. was added diisopropylazodicarboxylate (0.9 mL, 4.7 mmol). After fifteen minutes, [(R)-4-(3-cyano-benzenesulfonyl)-2-hydroxymethyl-3,4-dihydro-2H-benzo[1,4]oxazin-6-yl]-carbamic acid tert-butyl ester (1.4 g, 3.1 mmol) and 2,4-oxazolidinedione (0.3 g, 3.1 mmol) in tetrahydrofuran (7.5 mL) was added dropwise. After the addition was complete the mixture was allowed to warm to room temperature. The mixture was stirred an additional three hours, and partitioned between dichloromethane and 1 N HCl. The organic layer was dried (Na$_2$SO$_4$) and concentrated to afford [(S)-4-(3-cyano-benzenesulfonyl)-2-(2,4-dioxo-oxazolidin-3-ylmethyl)-3,4-dihydro-2H-benzo[1,4]oxazin-6-yl]-carbamic acid tert-butyl ester. LCMS ESI calculated for C$_{24}$H$_{25}$N$_4$O$_8$S (M+H)$^+$: 529, Found: 529.

Example 25—Preparation of Additional Carbamates of 2-((2,4-dioxooxazolidin-3-yl)methyl)-benzoxazines The compounds in Table 8 below were prepared based on the experimental procedures described in Example 24 and elsewhere in the detailed description, and can be achieved by one of skill in the art in light of the present disclosure.

TABLE 8

| Ex. No. | Structure | Name | Observed m/z |
|---|---|---|---|
| 25A | 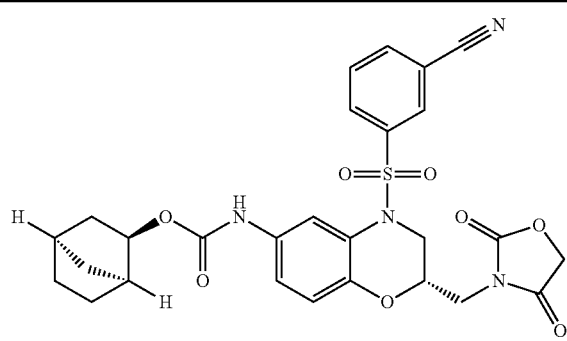 | (1S,2R,4R)-bicyclo[2.2.1]heptan-2-yl ((S)-4-((3-cyanophenyl)sulfonyl)-2-((2,4-dioxooxazolidin-3-yl)methyl)-3,4-dihydro-2H-benzo[b][1,4]oxazin-6-yl)carbamate | 584.2 (M + Na)$^+$ |
| 25B | 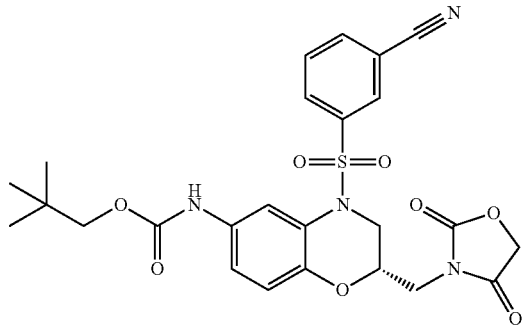 [SMILES: CC(C)(C)COC(=O)Nc1ccc2c(c1)N(S(=O)(=O)c1cccc(C#N)c1)C[C@H](CN1C(=O)COC1=O)O2] | (S)-neopentyl (4-((3-cyanophenyl)sulfonyl)-2-((2,4-dioxooxazolidin-3-yl)methyl)-3,4-dihydro-2H-benzo[b][1,4]oxazin-6-yl)carbamate | 543.1 (M + H)$^+$ |

TABLE 8-continued

| Ex. No. | Structure | Name | Observed m/z |
|---|---|---|---|
| 25C | 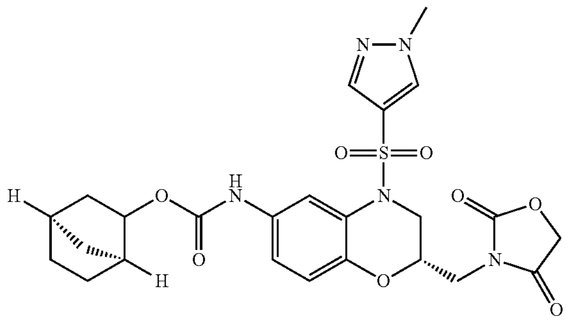 [SMILES: Cn1cc(S(=O)(=O)N2C[C@H](CN3C(=O)COC3=O)Oc3ccc(NC(=O)OC4C[C@@H]5CC[C@H]4C5)cc32)cn1] | (1S,4R)-bicyclo[2.2.1]heptan-2-yl ((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate | 563.2 (M + H$_2$O)$^+$ |
| 25D | 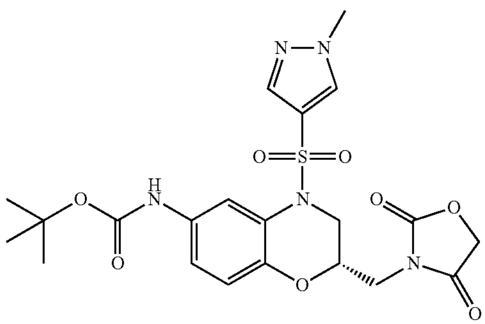 [SMILES: Cn1cc(S(=O)(=O)N2C[C@H](CN3C(=O)COC3=O)Oc3ccc(NC(=O)OC(C)(C)C)cc32)cn1] | (S)-tert-butyl (2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate | 508 (M + H)$^+$ |
| 25E | 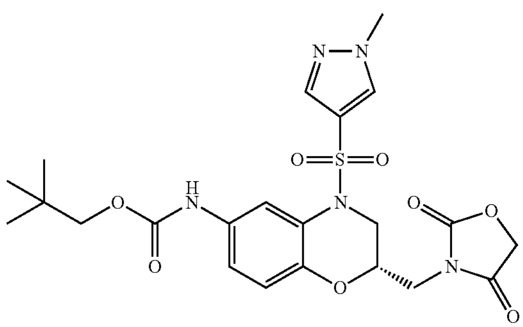 [SMILES: Cn1cc(S(=O)(=O)N2C[C@H](CN3C(=O)COC3=O)Oc3ccc(NC(=O)OCC(C)(C)C)cc32)cn1] | (S)-neopentyl (2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate | 522.1 (M + H)$^+$ |
| 25F | 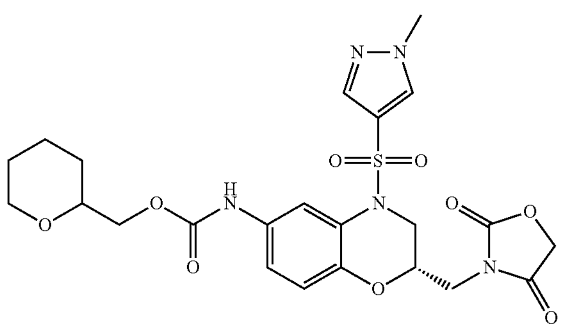 [SMILES: Cn1cc(S(=O)(=O)N2C[C@H](CN3C(=O)COC3=O)Oc3ccc(NC(=O)OCC4CCCCO4)cc32)cn1] | (tetrahydro-2H-pyran-2-yl)methyl ((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate | 550.3 (M + H)$^+$ |

TABLE 8-continued

| Ex. No. | Structure | Name | Observed m/z |
|---|---|---|---|
| 25G | 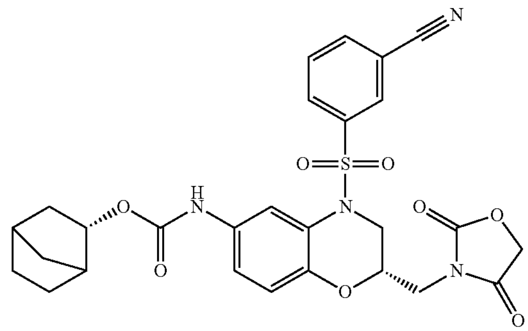 [SMILES: N#Cc1cccc(S(=O)(=O)N2C[C@H](CN3C(=O)COC3=O)Oc3ccc(NC(=O)O[C@H]4CC5CCC4C5)cc32)c1] | (2S)-bicyclo[2.2.1]heptan-2-yl ((S)-4-((3-cyanophenyl)sulfonyl)-2-((2,4-dioxooxazolidin-3-yl)methyl)-3,4-dihydro-2H-benzo[b][1,4]oxazin-6-yl)carbamate | 567.1 (M + H)+ |
| 25H | 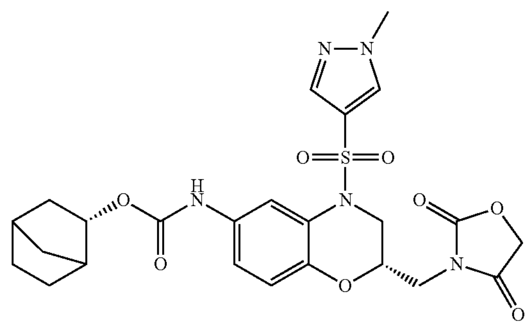 [SMILES: Cn1cc(S(=O)(=O)N2C[C@H](CN3C(=O)COC3=O)Oc3ccc(NC(=O)O[C@H]4CC5CCC4C5)cc32)cn1] | (2S)-bicyclo[2.2.1]heptan-2-yl ((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate | 546.1 (M + H)+ |

Example 26—Synthesis of [(S)-4-(3-cyano-benzenesulfonyl)-2-dimethylaminomethyl-3,4-dihydro-2H-benzo[1,4]oxazin-6-yl]-carbamic acid tert-butyl ester (26)

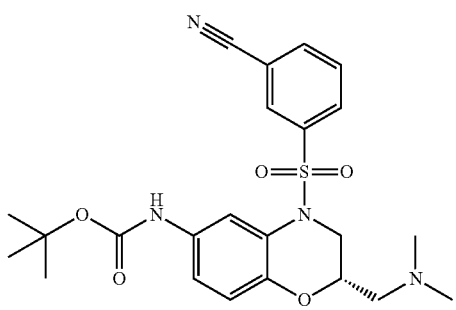 [SMILES: CN(C)C[C@H]1CN(S(=O)(=O)c2cccc(C#N)c2)c2cc(NC(=O)OC(C)(C)C)ccc2O1]

To a solution of toluene-4-sulfonic acid (R)-6-tert-butoxycarbonylamino-4-(3-cyano-benzenesulfonyl)-3,4-dihydro-2H-benzo[1,4]oxazin-2-ylmethyl ester (1.9 g, 3.2 mmol) in tetrahydrofuran (10 mL) was added dimethylamine (2 M in THF, 25 mL, 50 mmol) and the mixture was heated in a bomb at 100° C. overnight. The mixture was cooled and concentrated to afford [(S)-4-(3-cyano-benzenesulfonyl)-2-dimethylaminomethyl-3,4-dihydro-2H-benzo[1,4]oxazin-6-yl]-carbamic acid tert-butyl ester. LCMS (ESI): calculated for $C_{23}H_{29}ClN_4O_5S$ (M+H)+: 473, Found 473.

Example 27—Synthesis of [(S)-4-(3-cyano-benzenesulfonyl)-2-dimethylaminomethyl-3,4-dihydro-2H-benzo[1,4]oxazin-6-yl]-carbamic acid 2,2-dimethyl-propyl ester (27)

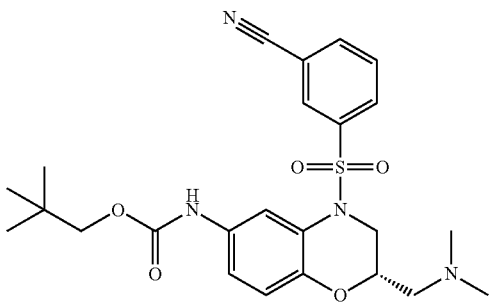 [SMILES: CN(C)C[C@H]1CN(S(=O)(=O)c2cccc(C#N)c2)c2cc(NC(=O)OCC(C)(C)C)ccc2O1]

The title compound was prepared according to the procedures described below.

Part I—Synthesis of 3-((S)-6-amino-2-dimethylaminomethyl-2,3-dihydro-benzo[1,4]oxazine-4-sulfonyl)-benzonitrile

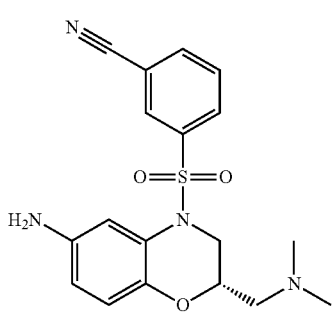 [SMILES: CN(C)C[C@H]1CN(S(=O)(=O)c2cccc(C#N)c2)c2cc(N)ccc2O1]

To a solution of [(S)-4-(3-cyano-benzenesulfonyl)-2-dimethylaminomethyl-3,4-dihydro-2H-benzo[1,4]oxazin-6-yl]-carbamic acid tert-butyl ester (3 mmol) in p-dioxane (5 mL) was added hydrochloric acid (4M in p-dioxane, 30 mL, 120 mmol). The mixture was stirred at room temperature for two hours. Additional 4M HCl in p-dioxane (10 mL) was added and the mixture allowed to stir for an additional two hours at room temperature. The mixture was quenched with saturated sodium bicarbonate, extracted into dichloromethane, then concentrated and purified by HPLC to obtain 3-((S)-6-amino-2-dimethylaminomethyl-2,3-dihydro-benzo[1,4]oxazine-4-sulfonyl)-benzonitrile. LCMS (ESI): calculated for $C_{18}H_{21}N_4O_3S$ (M+H)$^+$: 373, Found: 373.

Part II—Synthesis of [(S)-4-(3-cyano-benzenesulfonyl)-2-dimethylaminomethyl-3,4-dihydro-2H-benzo[1,4]oxazin-6-yl]-carbamic acid 2,2-dimethyl-propyl ester To a solution of 3-((S)-6-amino-2-dimethylaminomethyl-2,3-dihydro-benzo[1,4]oxazine-4-sulfonyl)-benzonitrile (15 mg, 0.04 mmol) in pyridine (0.4 mL) was added neo-pentyl chloroformate (6.3 mg, 0.05 mmol) in dichloromethane (0.5 mL). The mixture was stirred at room temperature overnight. The reaction was quenched with a small amount of water and concentrated under vacuum. The resulting residue was diluted with DMSO and purified via HPLC to obtain [(S)-4-(3-cyano-benzenesulfonyl)-2-dimethylaminomethyl-3,4-dihydro-2H-benzo[1,4]oxazin-6-yl]-carbamic acid 2,2-dimethyl-propyl ester. LCMS (ESI): calculated for $C_{25}H_{27}N_4O_8S$ (M+H)$^+$: 543, Found: 543.

Example 28—Preparation of Additional Carbamates

The compounds in Table 9 below were prepared based on the methods described in Examples 26 and 27 and elsewhere in the detailed description, and can be achieved by one of skill in the art in light of the present disclosure.

TABLE 9

| Ex. No. | Structure | Name | Observed m/z |
|---|---|---|---|
| 28A | 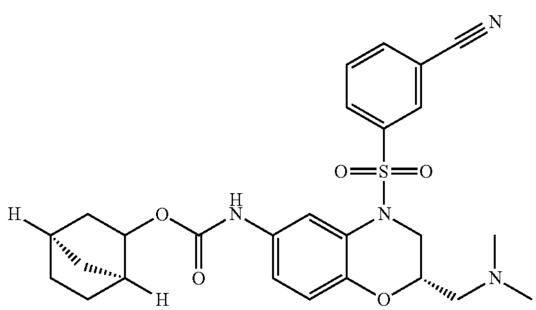 [SMILES: CN(C)C[C@H]1CN(S(=O)(=O)c2cccc(C#N)c2)c2cc(NC(=O)OC3C[C@@H]4CC[C@H]3C4)ccc2O1] | (1S,4R)-bicyclo[2.2.1]heptan-2-yl ((S)-4-((3-cyanophenyl)sulfonyl)-2-((dimethylamino)methyl)-3,4-dihydro-2H-benzo[b][1,4]oxazin-6-yl)carbamate | 511.6 (M + H)$^+$ |
| 28B | 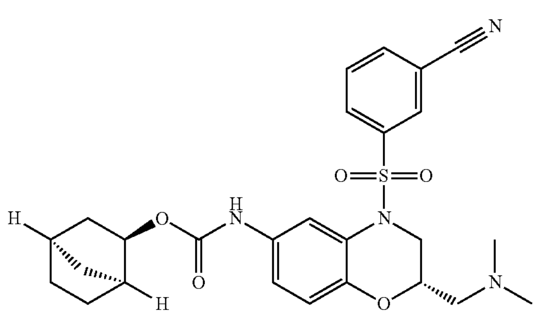 [SMILES: CN(C)C[C@H]1CN(S(=O)(=O)c2cccc(C#N)c2)c2cc(NC(=O)O[C@@H]3C[C@@H]4CC[C@H]3C4)ccc2O1] | (1S,2R,4R)-bicyclo[2.2.1]heptan-2-yl ((S)-4-((3-cyanophenyl)sulfonyl)-2-((dimethylamino)methyl)-3,4-dihydro-2H-benzo[b][1,4]oxazin-6-yl)carbamate | 511.3 (M + H)$^+$ |

TABLE 9-continued

| Ex. No. | Structure | Name | Observed m/z |
|---|---|---|---|
| 28C | 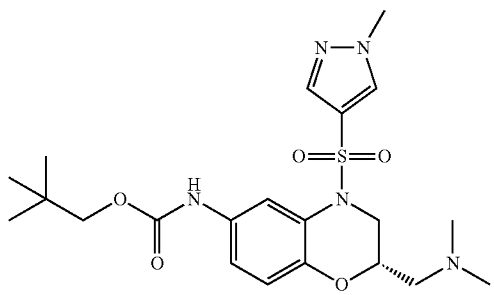 [SMILES: CN(C)C[C@H]1CN(S(=O)(=O)c2cnn(C)c2)c2cc(NC(=O)OCC(C)(C)C)ccc2O1] | (S)-neopentyl (2-((dimethylamino)methyl)-4-((1-methyl-1H-pyrazol-4-yl)sulfonyl)-3,4-dihydro-2H-benzo[b][1,4]oxazin-6-yl)carbamate | 466.3 (M + H)+ |
| 28D | 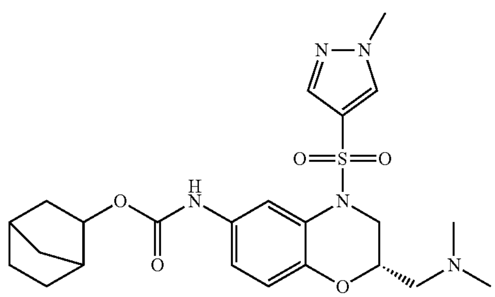 [SMILES: CN(C)C[C@H]1CN(S(=O)(=O)c2cnn(C)c2)c2cc(NC(=O)OC3CC4CCC3C4)ccc2O1] | bicyclo[2.2.1]heptan-2-yl ((S)-2-((dimethylamino)methyl)-4-((1-methyl-1H-pyrazol-4-yl)sulfonyl)-3,4-dihydro-2H-benzo[b][1,4]oxazin-6-yl)carbamate | 490.3 (M + H)+ |
| 28E | 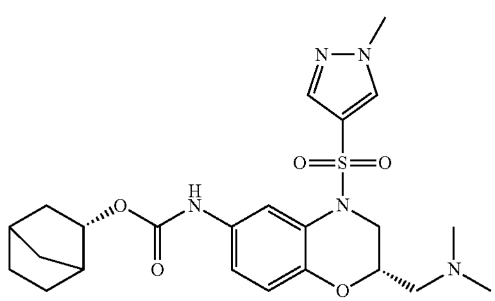 [SMILES: CN(C)C[C@H]1CN(S(=O)(=O)c2cnn(C)c2)c2cc(NC(=O)O[C@H]3CC4CCC3C4)ccc2O1] | (2S)-bicyclo[2.2.1]heptan-2-yl ((S)-2-((dimethylamino)methyl)-4-((1-methyl-1H-pyrazol-4-yl)sulfonyl)-3,4-dihydro-2H-benzo[b][1,4]oxazin-6-yl)carbamate | 490.3 (M + H)+ |
| 28F | 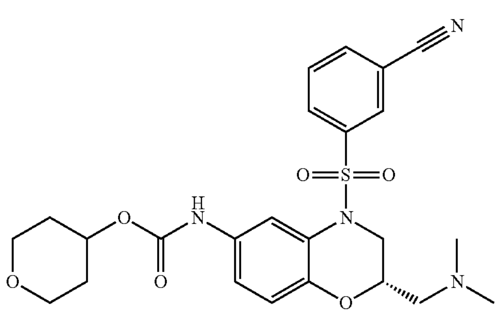 [SMILES: CN(C)C[C@H]1CN(S(=O)(=O)c2cccc(C#N)c2)c2cc(NC(=O)OC3CCOCC3)ccc2O1] | (S)-tetrahydro-2H-pyran-4-yl (4-((3-cyanophenyl)sulfonyl)-2-((dimethylamino)methyl)-3,4-dihydro-2H-benzo[b][1,4]oxazin-6-yl)carbamate | 499.3 (M + H)+ |

Example 29—Synthesis of (S)-methyl 2-(6-((tert-butoxycarbonyl)amino)-4-((3-(trifluoromethyl)phenyl)sulfonyl)-3,4-dihydro-2H-benzo[b][1,4]oxazin-2-yl)acetate (29)

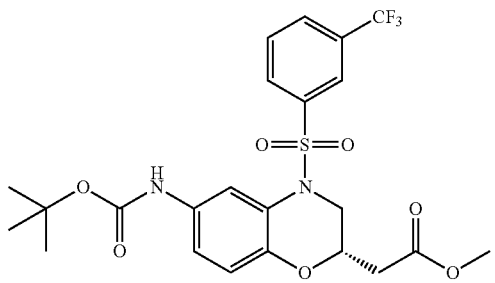 [SMILES: COC(=O)C[C@H]1CN(S(=O)(=O)c2cccc(C(F)(F)F)c2)c2cc(NC(=O)OC(C)(C)C)ccc2O1]

The title compound was prepared according to the procedures described below.

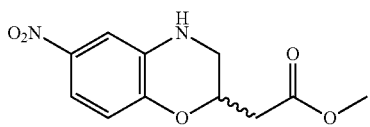 [SMILES: COC(=O)CC1CNc2cc([N+](=O)[O-])ccc2O1]

Part I—Synthesis of methyl 2-(6-nitro-3,4-dihydro-2H-benzo[b][1,4]oxazin-2-yl)acetate To a stirred mixture of 2-amino-4-nitrophenol (5 g, 32.4 mmol), sodium bicarbonate (3.27 g, 38.9 mmol), and methanol (100 mL) was added a solution of methyl 4-bromocrotonate (3.82 mL, 32.4 mmol) in methanol (50 mL) dropwise during a 30 minute period. The reaction mixture was stirred an additional 18 hours at room temperature. The reaction mixture was concentrated under reduced pressure and partitioned between ethyl acetate and water. The organic layer was dried (MgSO$_4$) and concentrated. The residual oil was dissolved in ethanol (100 mL) and potassium carbonate (1.614 g, 11.68 mmol) was added. The reaction was stirred for 2.5 hours at room temperature and concentrated. The residue was partitioned between dichloromethane and water. The organic layer was extracted with 1 N HCl. The aqueous solution was neutralized with 1N NaOH and extracted with ethyl acetate. This organic layer was dried (Na$_2$SO$_4$) and concentrated to afford the title compound. LRMS ESI calculated for C$_{11}$H$_{13}$N$_2$O$_5$ (M+H)$^+$: 253, Found: 253.

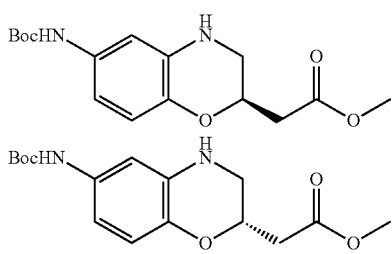

Part II—Synthesis of (R)- and (S)-methyl 2-(6-((tert-butoxycarbonyl)amino)-3,4-dihydro-2H-benzo[b][1,4]oxazin-2-yl)acetate To a stirred solution of methyl 2-(6-nitro-3,4-dihydro-2H-benzo[b][1,4]oxazin-2-yl)acetate (6.09 g, 24.15 mmol) and methanol (48 mL) purged with nitrogen was added 10% Pd/C (7.71 g, 7.24 mmol) followed by di-tert-butyl dicarbonate (6.73 mL, 29.0 mmol). The atmosphere above the reaction was purged and replaced with an atmosphere of hydrogen and was stirred at room temperature for 24 h. The crude mixture was filtered through CELITE, rinsing with methanol. The combined filtrates were concentrated. The residue was purified via MPLC eluting with a gradient of 0-100% ethyl acetate in hexanes. The racemic product was submitted for chiral SFC separation (SFC Column: Chiral Technology AZ-H 2.1×25 cm, 5 uM; MP: 30%/70% Ethanol/CO$_2$ (no other modifiers); Flow rate: 70 mL/Min, 6 min run time; WL: 220 nm; Injections of 0.30 ml were performed on the Berger Multigram II SFC). Mixture of Enantiomers LRMS ESI calculated for C$_{16}$H$_{23}$N$_2$O$_5$ (M+H)$^+$: 323, Found: 323; (R)-Enantiomer: LRMS ESI calculated for C$_{16}$H$_{23}$N$_2$O$_5$ (M+H)$^+$: 323, Found: 323; (S)-Enantiomer: LRMS ESI calculated for C$_{16}$H$_{23}$N$_2$O$_5$ (M+H)$^+$: 323, Found: 323.

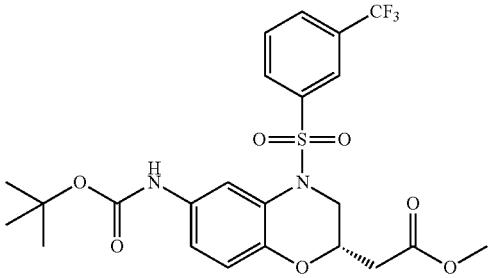 [SMILES: COC(=O)C[C@H]1CN(S(=O)(=O)c2cccc(C(F)(F)F)c2)c2cc(NC(=O)OC(C)(C)C)ccc2O1]

Part III—Synthesis of (S)-methyl 2-(6-((tert-butoxycarbonyl)amino)-4-((3-(trifluoromethyl)phenyl)sulfonyl)-3,4-dihydro-2H-benzo[b][1,4]oxazin-2-yl)acetate A stirred solution of (S)-methyl 2-(6-((tert-butoxycarbonyl)amino)-3,4-dihydro-2H-benzo[b][1,4]oxazin-2-yl)acetate (20 mg, 0.062 mmol), 3-(trifluoromethyl)benzene-1-sulfonyl chloride (12.88 µL, 0.081 mmol) in THF (310 µL) and pyridine (310 µL) was heated to 60° C. overnight. The mixture was cooled and partitioned between ethyl acetate and saturated NaHCO$_3$. The organic layer was washed with brine, dried (MgSO$_4$), and concentrated. The residue was dissolved in DMSO (1 mL), filtered, and purified by reverse phase chromatography. LRMS ESI calculated for C$_{19}$H$_{18}$F$_3$N$_2$O$_7$S (M+H-tBu)$^+$: 475, Found: 475. $^1$H NMR: (300 MHz, CDCl$_3$): δ 9.29 (1H, s), 8.08 (2H, m), 8.01 (2H, m), 7.84 (1H, t, J=6.98 Hz), 7.03 (1H, m), 6.68 (1H, d, J=9.07 Hz), 4.44 (1H, m), 3.78 (1H, m), 3.60 (3H, s), 3.37 (1H, m), 2.80 (1H, m), 2.61 (1H, m), 2.48 (9H, m).

Example 30—Preparation of Additional Carbamates of (S)-methyl (benzoxazin-2-yl)acetates The compounds in Table 10 were prepared based on the experimental procedures described in Example 29, and can be achieved by one of skill in the art in light of the present disclosure.

TABLE 10

| Ex. No. | Structure | Name | Observed m/z |
|---|---|---|---|
| 30A | 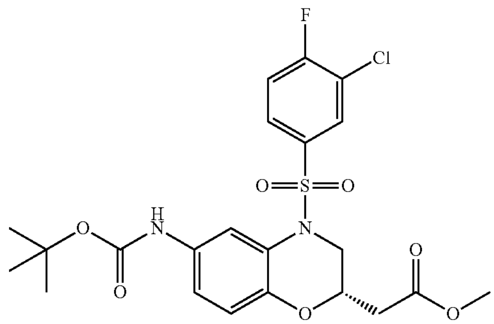 [SMILES: COC(=O)C[C@H]1CN(S(=O)(=O)c2ccc(F)c(Cl)c2)c2cc(NC(=O)OC(C)(C)C)ccc2O1] | (S)-methyl 2-(6-((tert-butoxycarbonyl)amino)-4-((3-chloro-4-fluorophenyl)sulfonyl)-3,4-dihydro-2H-benzo[b][1,4]oxazin-2-yl)acetate | 533 (M + NH$_4$)$^+$ |
| 30B | 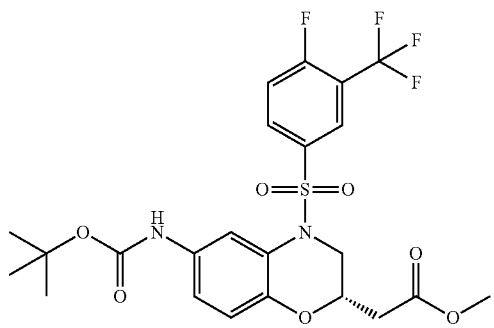 [SMILES: COC(=O)C[C@H]1CN(S(=O)(=O)c2ccc(F)c(C(F)(F)F)c2)c2cc(NC(=O)OC(C)(C)C)ccc2O1] | (S)-methyl 2-(6-((tert-butoxycarbonyl)amino)-4-((4-fluoro-3-(trifluoromethyl)phenyl)sulfonyl)-3,4-dihydro-2H-benzo[b][1,4]oxazin-2-yl)acetate | 566 (M + NH$_4$)$^+$ |
| 30C | 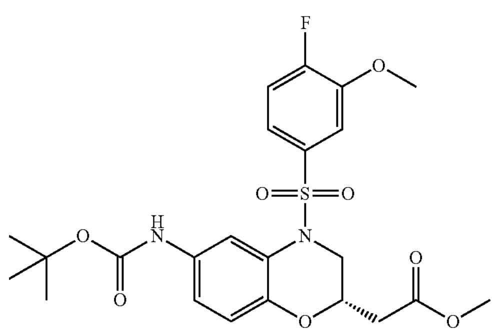 [SMILES: COC(=O)C[C@H]1CN(S(=O)(=O)c2ccc(F)c(OC)c2)c2cc(NC(=O)OC(C)(C)C)ccc2O1] | (S)-methyl 2-(6-((tert-butoxycarbonyl)amino)-4-((4-fluoro-3-methoxyphenyl)sulfonyl)-3,4-dihydro-2H-benzo[b][1,4]oxazin-2-yl)acetate | 528 (M + NH$_4$)$^+$ |
| 30D | 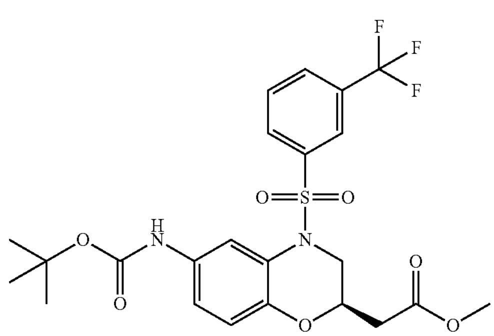 [SMILES: COC(=O)C[C@@H]1CN(S(=O)(=O)c2cccc(C(F)(F)F)c2)c2cc(NC(=O)OC(C)(C)C)ccc2O1] | (R)-methyl 2-(6-((tert-butoxycarbonyl)amino)-4-((3-(trifluoromethyl)phenyl)sulfonyl)-3,4-dihydro-2H-benzo[b][1,4]oxazin-2-yl)acetate | 475.1 (M-tBu + H)$^+$ |

TABLE 10-continued

| Ex. No. | Structure | Name | Observed m/z |
|---|---|---|---|
| 30E | [structure] | (S)-methyl 2-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)acetate | 624.7 (M + Na)+ |

Example 31—Synthesis of [(S)-6-tert-butoxycarbonylamino-4-(1-difluoromethyl-3-methyl-1H-pyrazole-4-sulfonyl)-3,4-dihydro-2H-benzo[1,4]oxazin-2-yl]-acetic acid (31)

To a stirred solution of [(S)-6-tert-butoxycarbonylamino-4-(1-difluoromethyl-3-methyl-1H-pyrazole-4-sulfonyl)-3,4-dihydro-2H-benzo[1,4]oxazin-2-yl]-acetic acid methyl ester (1.5 g, 2.9 mmol) in 1,2-dichloroethane was added trimethyltin hydroxide (2.61 g, 14.5 mmol). The mixture was heated at 90° C. for 4 hours. The reaction mixture was concentrated, and the residue was dissolved in ethyl acetate. The organic layer was washed with 0.1N HCl and brine, dried and concentrated. The residue was purified by flash column chromatography to afford the title compound. LRMS (ESI) calculated for $C_{20}H_{25}F_2N_4O_7S$ (M+H)+: 503, Found: 503.5.

Example 32—Preparation of Additional Carbamates of (S)-(benzoxazin-2-yl)acetates The compounds in Table 11 below were prepared based on the experimental procedures described in Example 31 and elsewhere in the detailed description, and can be achieved by one of skill in the art in light of the present disclosure.

TABLE 11

| Ex. No. | Structure | Name | Observed m/z |
|---|---|---|---|
| 32A | [structure] | (S)-2-(6-((tert-butoxycarbonyl)amino)-4-((4-fluoro-3-methoxyphenyl)sulfonyl)-3,4-dihydro-2H-benzo[b][1,4]oxazin-2-yl)acetic acid | 514 (M + NH4)+ |

TABLE 11-continued

| Ex. No. | Structure | Name | Observed m/z |
|---|---|---|---|
| 32B | 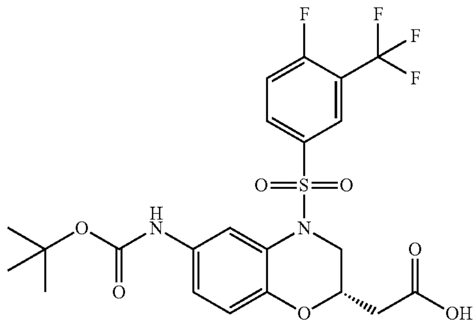 [SMILES: CC(C)(C)OC(=O)Nc1ccc2c(c1)N(S(=O)(=O)c1ccc(F)c(C(F)(F)F)c1)C[C@H](CC(=O)O)O2] | (S)-2-(6-((tert-butoxycarbonyl)amino)-4-((4-fluoro-3-(trifluoromethyl)phenyl)sulfonyl)-3,4-dihydro-2H-benzo[b][1,4]oxazin-2-yl)acetic acid | 552 $(M + NH_4)^+$ |
| 32C | 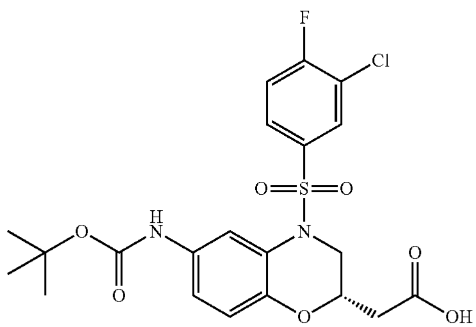 [SMILES: CC(C)(C)OC(=O)Nc1ccc2c(c1)N(S(=O)(=O)c1ccc(F)c(Cl)c1)C[C@H](CC(=O)O)O2] | (S)-2-(6-((tert-butoxycarbonyl)amino)-4-((3-chloro-4-fluorophenyl)sulfonyl)-3,4-dihydro-2H-benzo[b][1,4]oxazin-2-yl)acetic acid | 518 $(M + NH_4)^+$ |
| 32D | 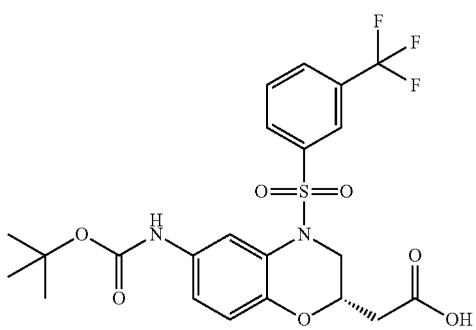 [SMILES: CC(C)(C)OC(=O)Nc1ccc2c(c1)N(S(=O)(=O)c1cccc(C(F)(F)F)c1)C[C@H](CC(=O)O)O2] | (S)-2-(6-((tert-butoxycarbonyl)amino)-4-((3-(trifluoromethyl)phenyl)sulfonyl)-3,4-dihydro-2H-benzo[b][1,4]oxazin-2-yl)acetic acid | 461.0 $(M + H-tBu)^+$ |
| 32E | 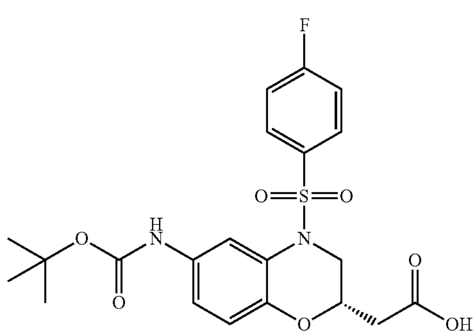 [SMILES: CC(C)(C)OC(=O)Nc1ccc2c(c1)N(S(=O)(=O)c1ccc(F)cc1)C[C@H](CC(=O)O)O2] | (S)-2-(6-((tert-butoxycarbonyl)amino)-4-((4-fluorophenyl)sulfonyl)-3,4-dihydro-2H-benzo[b][1,4]oxazin-2-yl)acetic acid | 411.1 $(M-tBu + H)^+$ |

TABLE 11-continued

| Ex. No. | Structure | Name | Observed m/z |
|---|---|---|---|
| 32F | 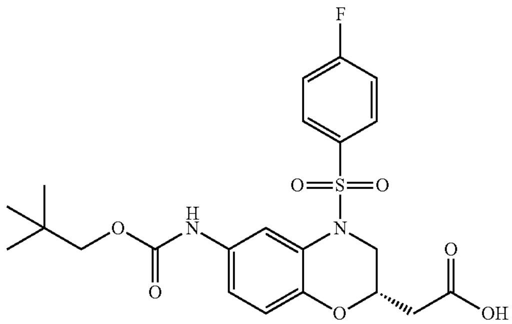 [SMILES: CC(C)(C)COC(=O)Nc1ccc2c(c1)N(S(=O)(=O)c1ccc(F)cc1)C[C@H](CC(=O)O)O2] | (S)-2-(4-((4-fluorophenyl)sulfonyl)-6-(((neopentyloxy)carbonyl)amino)-3,4-dihydro-2H-benzo[b][1,4]oxazin-2-yl)acetic acid | 481.1 (M + H)+ |
| 32G | 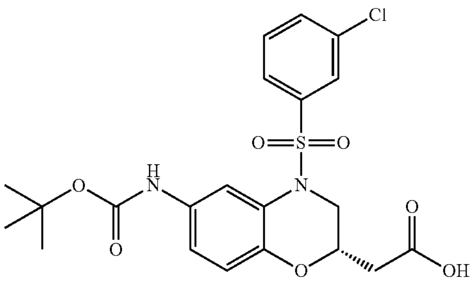 [SMILES: CC(C)(C)OC(=O)Nc1ccc2c(c1)N(S(=O)(=O)c1cccc(Cl)c1)C[C@H](CC(=O)O)O2] | (S)-2-(6-((tert-butoxycarbonyl)amino)-4-((3-chlorophenyl)sulfonyl)-3,4-dihydro-2H-benzo[b][1,4]oxazin-2-yl)acetic acid | 427.0 (M + H-tBu)+ |
| 32H | 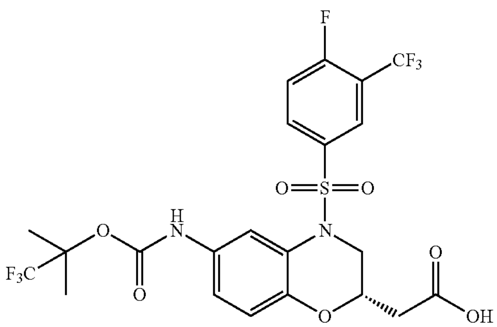 [SMILES: CC(C)(OC(=O)Nc1ccc2c(c1)N(S(=O)(=O)c1ccc(F)c(C(F)(F)F)c1)C[C@H](CC(=O)O)O2)C(F)(F)F] | (S)-2-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)acetic acid | 610.8 (M + Na)+ |

Example 33—Synthesis of (R)-6-((tert-butoxycarbonyl)amino)-4-((3-chloro-4-fluorophenyl)sulfonyl)-3,4-dihydro-2H-benzo[b][1,4]oxazine-2-carboxylic Acid (33)

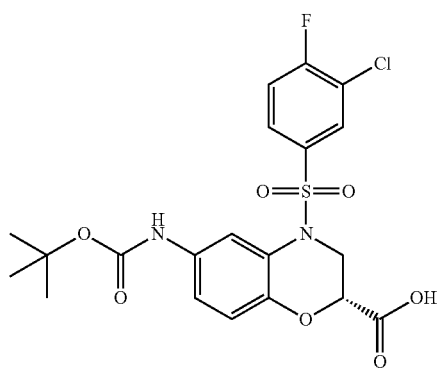 [SMILES: CC(C)(C)OC(=O)Nc1ccc2c(c1)N(S(=O)(=O)c1ccc(F)c(Cl)c1)C[C@H](C(=O)O)O2]

A mixture of (R)-tert-butyl (4-((3-chloro-4-fluorophenyl)sulfonyl)-2-(hydroxymethyl)-3,4-dihydro-2H-benzo[b][1,4]oxazin-6-yl)carbamate (500 mg, 1.057 mmol), N-methylmorpholine N-oxide (1.24 g, 10.57 mmol), tetrapropylammonium perruthenate (37.2 mg, 0.106 mmol) and acetonitrile (4.2 mL) was stirred at room temperature for fifteen minutes. The mixture was partitioned between dichloromethane and washed with pH 3 buffer. The layers were separated, and the aqueous phase was extracted with dichloromethane. The combined organic phases were dried (MgSO$_4$) and concentrated. The residue was purified by reverse phase HPLC using a solvent system of MeCN/water modified with 0.1% TFA. The product-containing fractions were diluted with ethyl acetate and washed with pH 3 buffer and saturated aqueous sodium chloride. The organic phase was dried (MgSO$_4$) and concentrated to give (R)-6-((tert-butoxycarbonyl)amino)-4-((3-chloro-4-fluorophenyl)sulfonyl)-3,4-dihydro-2H-benzo[b][1,4]oxazine-2-carboxylic acid as a white foam. MS ESI calculated for C$_{20}$H$_{24}$ClFN$_3$O$_7$S (M+NH$_4$)+: 504, Found: 504. $^1$H NMR (600 MHz, DMSO-d6) δ 9.22 (s, 1H), 8.09 (d, J=8.0 Hz, 1H), 8.03 (s, 1H), 8.02 (s, 1H), 7.99 (s, 1H), 7.79 (t, J=7.9 Hz, 1H), 6.98 (d, J=8.8 Hz, 1H), 6.64 (d, J=8.9 Hz, 1H), 4.48 (dd, J=14.0, 2.3 Hz, 1H), 3.72 (d, J=8.2 Hz, 1H), 3.25 (dd, J=14.1, 9.7 Hz, 1H), 2.39 (dd, J=15.9, 5.6 Hz, 1H), 2.32 (dd, J=16.0, 7.7 Hz, 1H), 1.44 (s, 9H).

Example 34—Preparation of Additional Carbamates of (R)-6-((tert-butoxycarbonyl)amino)-4-((substituted aryl or heteroaryl)sulfonyl)-3,4-dihydro-2H-benzo[b][1,4]oxazine-2-carboxylic Acids The compounds in Table 12 below were prepared based on the experimental procedures described in Example 33 and elsewhere in the detailed description, and can be achieved by one of skill in the art in light of the present disclosure.

TABLE 12

| Ex. No. | Structure | Name | Observed m/z |
|---|---|---|---|
| 34A | 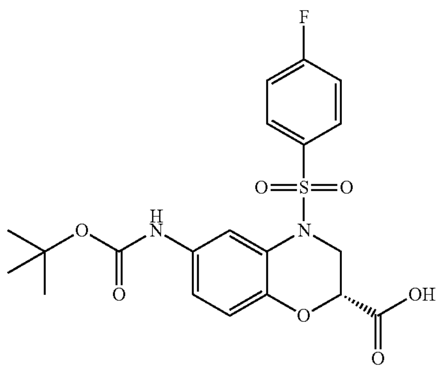 [SMILES: CC(C)(C)OC(=O)Nc1ccc2c(c1)N(S(=O)(=O)c1ccc(F)cc1)C[C@H](C(=O)O)O2] | (R)-6-((tert-butoxycarbonyl)amino)-4-((4-fluorophenyl)sulfonyl)-3,4-dihydro-2H-benzo[b][1,4]oxazine-2-carboxylic acid | 470 (M + NH$_4$)$^+$ |
| 34B | 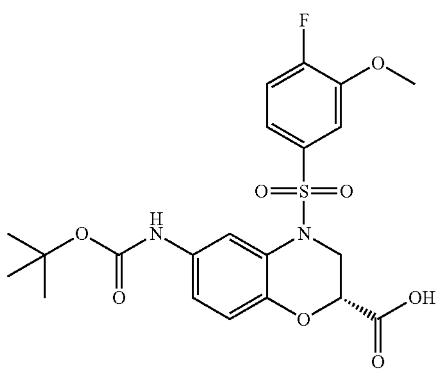 [SMILES: COc1cc(S(=O)(=O)N2C[C@H](C(=O)O)Oc3ccc(NC(=O)OC(C)(C)C)cc32)ccc1F] | (R)-6-((tert-butoxycarbonyl)amino)-4-((4-fluoro-3-methoxyphenyl)sulfonyl)-3,4-dihydro-2H-benzo[b][1,4]oxazine-2-carboxylic acid | 500.0 (M + NH$_4$)$^+$ |
| 34C | 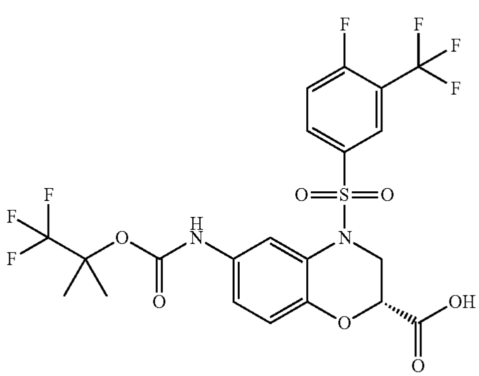 [SMILES: CC(C)(OC(=O)Nc1ccc2c(c1)N(S(=O)(=O)c1ccc(F)c(C(F)(F)F)c1)C[C@H](C(=O)O)O2)C(F)(F)F] | (R)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazine-2-carboxylic acid | 592.0 (M + NH$_4$)$^+$ |

TABLE 12-continued

| Ex. No. | Structure | Name | Observed m/z |
|---|---|---|---|
| 34D | 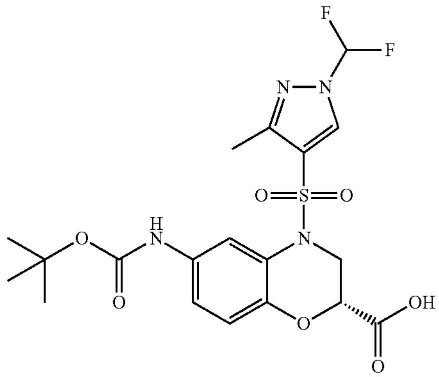 [SMILES: Cc1nn(C(F)F)cc1S(=O)(=O)N1C[C@H](C(=O)O)Oc2ccc(NC(=O)OC(C)(C)C)cc21] | (R)-6-((tert-butoxycarbonyl)amino)-4-((1-(difluoromethyl)-3-methyl-1H-pyrazol-4-yl)sulfonyl)-3,4-dihydro-2H-benzo[b][1,4]oxazine-2-carboxylic acid | 511.0 (M + Na)+ |
| 34E | 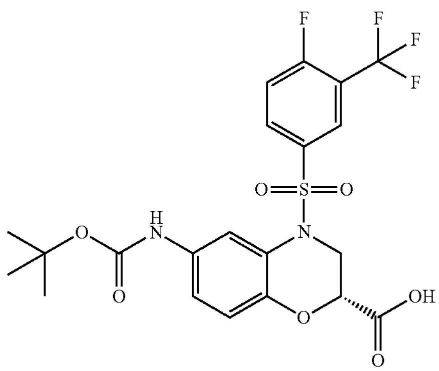 [SMILES: CC(C)(C)OC(=O)Nc1ccc2c(c1)N(S(=O)(=O)c1ccc(F)c(C(F)(F)F)c1)C[C@H](C(=O)O)O2] | (R)-6-((tert-butoxycarbonyl)amino)-4-((4-fluoro-3-(trifluoromethyl)phenyl)sulfonyl)-3,4-dihydro-2H-benzo[b][1,4]oxazine-2-carboxylic acid | 542.9 (M + Na)+ |

Example 35—Synthesis of [(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid tert-butyl ester (35)

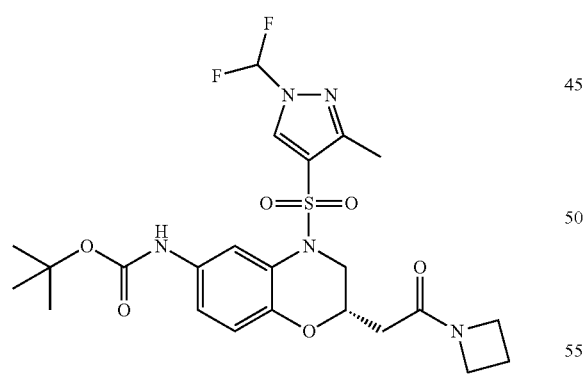

To a stirred solution of [(S)-6-tert-butoxycarbonylamino-4-(1-difluoromethyl-3-methyl-1H-pyrazole-4-sulfonyl)-3,4-dihydro-2H-benzo[1,4]oxazin-2-yl]-acetic acid (0.9 g, 1.8 mmol), azetidine hydrochloride salt (0.21 g, 2.34 mmol) and triethyl amine (1.5 mL, 10.8 mmol) in dichloromethane (92 mL) was added (benzotriazol-1-yloxy)tris(dimethylamino)phosphonium hexafluorophosphate (1.03 g, 2.34 mmol). The mixture was heated at 40° C. for an hour, then diluted with ethyl acetate and washed with 1N NaOH, brine, 0.1N HCl and water. The organic layer was then dried and concentrated. The residue was purified by silica gel chromatography to provide [(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid tert-butyl ester. LC/MC (ESI) m/z 542.5.

Example 36—Synthesis of [(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid 1,2,2-trimethyl-propyl ester (36)

The title compound was prepared according to the procedures described below.

161

Part I—Synthesis of 2-[(S)-6-amino-4-(1-difluoromethyl-3-methyl-1H-pyrazole-4-sulfonyl)-3,4-dihydro-2H-benzo[1,4]oxazin-2-yl]-1-azetidin-1-yl-ethanone, hydrochloride Salt

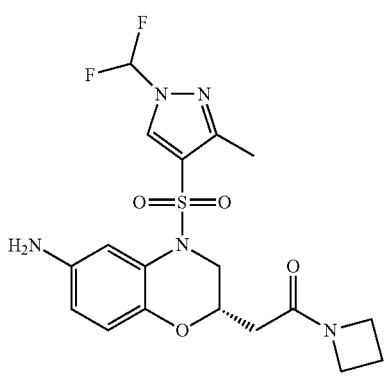 [SMILES: Cc1nn(C(F)F)cc1S(=O)(=O)N1C[C@H](CC(=O)N2CCC2)Oc2ccc(N)cc21]

[(S)-2-(2-Azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid tert-butyl ester was treated with 4N HCl-dioxane (5 mL) and the mixture was stirred at room temperature for one hour, then concentrated. The residual white solid was washed with ethyl acetate and dried to provide the title compound. LC/MC (ESI) m/z 442.4.

162

Part II—Synthesis of [(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid 1,2,2-trimethyl-propyl ester

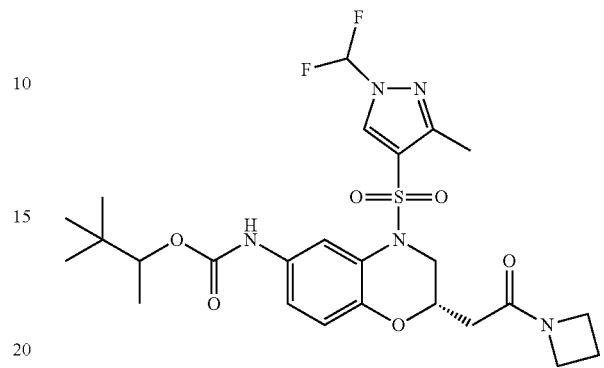

A mixture of 2-[(S)-6-amino-4-(1-difluoromethyl-3-methyl-1H-pyrazole-4-sulfonyl)-3,4-dihydro-2H-benzo[1,4]oxazin-2-yl]-1-azetidin-1-yl-ethanone, hydrochloride salt (44 mg, 0.1 mmol) and triethyl amine in anhydrous dichloromethane (0.5 mL) was added to a stirred solution of triphosgene (6 mg, 0.03 mmol) in dichloromethane (0.1 mL) at 0° C. The resulting solution was allowed to stir at room temperature for fifteen minutes and then 3,3-dimethyl-butan-2-ol (15 mg, 0.15 mmol) was added, and the resulting mixture was stirred continuously for an hour. The organic phase was concentrated and the residue was purified by HPLC to afford [(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid 1,2,2-trimethyl-propyl ester.

Example 37—Preparation of Additional Amides from (S)-(benzoxazin-2-yl)acetates

The compounds in Table 13 below were prepared based on the experimental procedures described in Examples 35 and 36 and elsewhere in the detailed description, and can be achieved by one of skill in the art in light of the present disclosure.

TABLE 13

| Ex. No. | Structure | Name | Observed m/z |
|---|---|---|---|
| 37A | 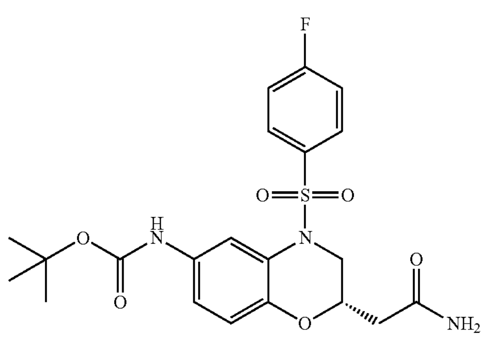 [SMILES: CC(C)(C)OC(=O)Nc1ccc2c(c1)N(S(=O)(=O)c1ccc(F)cc1)C[C@H](CC(N)=O)O2] | (S)-tert-butyl (2-(2-amino-2-oxoethyl)-4-((4-fluorophenyl)sulfonyl)-3,4-dihydro-2H-benzo[b][1,4]oxazin-6-yl)carbamate | 483 (M + H$_2$O)$^+$ |

TABLE 13-continued

| Ex. No. | Structure | Name | Observed m/z |
|---|---|---|---|
| 37B | 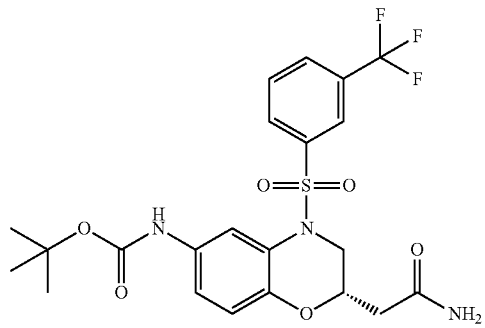 [SMILES: CC(C)(C)OC(=O)Nc1ccc2c(c1)N(S(=O)(=O)c1cccc(C(F)(F)F)c1)C[C@H](CC(N)=O)O2] | (S)-tert-butyl (2-(2-amino-2-oxoethyl)-4-((3-(trifluoromethyl)phenyl)sulfonyl)-3,4-dihydro-2H-benzo[b][1,4]oxazin-6-yl)carbamate | 460.2 (M + H-tBu)+ |
| 37C | 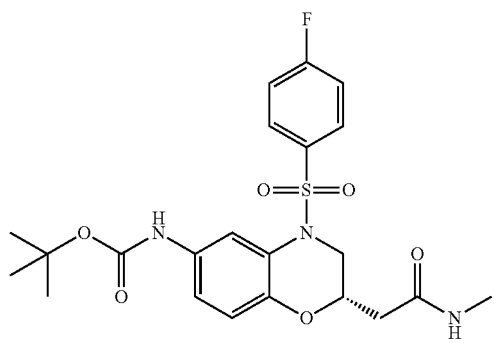 [SMILES: CNC(=O)C[C@H]1CN(S(=O)(=O)c2ccc(F)cc2)c2cc(NC(=O)OC(C)(C)C)ccc2O1] | (S)-tert-butyl (4-((4-fluorophenyl)sulfonyl)-2-(2-(methylamino)-2-oxoethyl)-3,4-dihydro-2H-benzo[b][1,4]oxazin-6-yl)carbamate | 478 (M + H)+ |
| 37D | 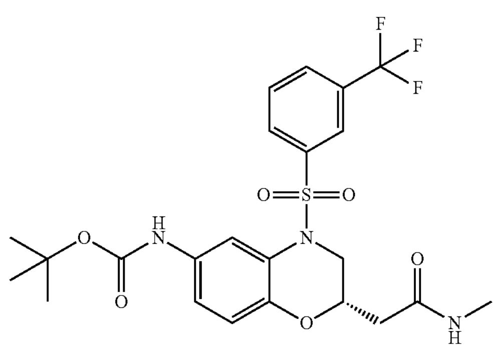 [SMILES: CNC(=O)C[C@H]1CN(S(=O)(=O)c2cccc(C(F)(F)F)c2)c2cc(NC(=O)OC(C)(C)C)ccc2O1] | (S)-tert-butyl (2-(2-(methylamino)-2-oxoethyl)-4-((3-(trifluoromethyl)phenyl)sulfonyl)-3,4-dihydro-2H-benzo[b][1,4]oxazin-6-yl)carbamate | 552 (M + Na)+ |
| 37E | 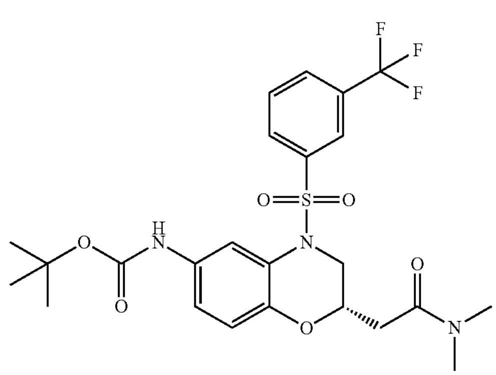 [SMILES: CN(C)C(=O)C[C@H]1CN(S(=O)(=O)c2cccc(C(F)(F)F)c2)c2cc(NC(=O)OC(C)(C)C)ccc2O1] | (S)-tert-butyl (2-(2-(dimethylamino)-2-oxoethyl)-4-((3-(trifluoromethyl)phenyl)sulfonyl)-3,4-dihydro-2H-benzo[b][1,4]oxazin-6-yl)carbamate | 544 (M + H)+ |

TABLE 13-continued

| Ex. No. | Structure | Name | Observed m/z |
|---|---|---|---|
| 37F | 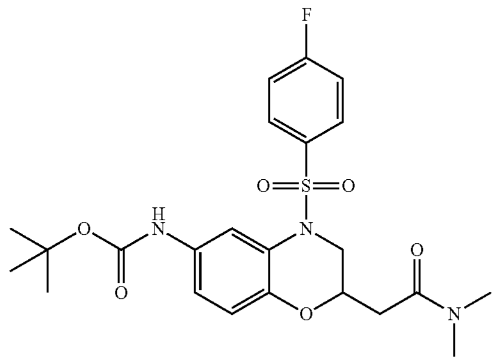 [SMILES: CN(C)C(=O)CC1CN(S(=O)(=O)c2ccc(F)cc2)c2cc(NC(=O)OC(C)(C)C)ccc2O1] | tert-butyl (2-(2-(dimethylamino)-2-oxoethyl)-4-((4-fluorophenyl)sulfonyl)-3,4-dihydro-2H-benzo[b][1,4]oxazin-6-yl)carbamate | 492 (M − H)⁻ |
| 37G | 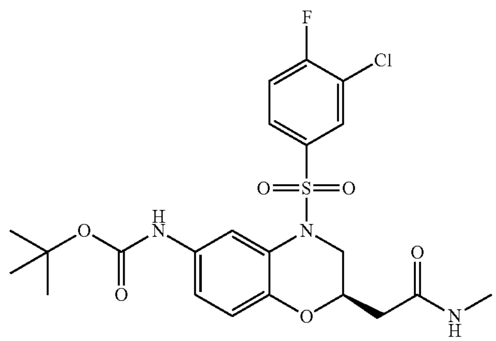 [SMILES: CNC(=O)C[C@@H]1CN(S(=O)(=O)c2ccc(F)c(Cl)c2)c2cc(NC(=O)OC(C)(C)C)ccc2O1] | (R)-tert-butyl (4-((3-chloro-4-fluorophenyl)sulfonyl)-2-(2-(methylamino)-2-oxoethyl)-3,4-dihydro-2H-benzo[b][1,4]oxazin-6-yl)carbamate | 514 (M + H)⁺ |
| 37H | 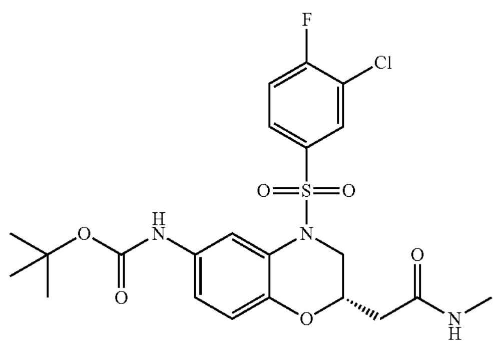 [SMILES: CNC(=O)C[C@H]1CN(S(=O)(=O)c2ccc(F)c(Cl)c2)c2cc(NC(=O)OC(C)(C)C)ccc2O1] | (S)-tert-butyl (4-((3-chloro-4-fluorophenyl)sulfonyl)-2-(2-(methylamino)-2-oxoethyl)-3,4-dihydro-2H-benzo[b][1,4]oxazin-6-yl)carbamate | 514 (M + H)⁺ |
| 37i | 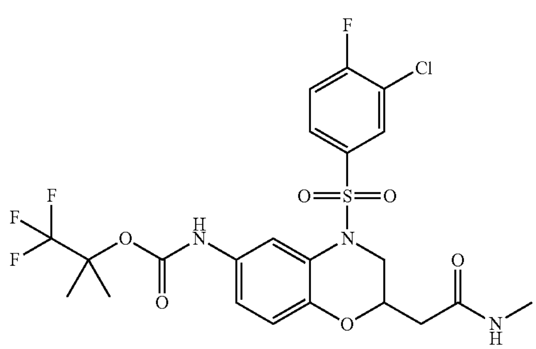 [SMILES: CNC(=O)CC1CN(S(=O)(=O)c2ccc(F)c(Cl)c2)c2cc(NC(=O)OC(C)(C)C(F)(F)F)ccc2O1] | 1,1,1-trifluoro-2-methylpropan-2-yl (4-((3-chloro-4-fluorophenyl)sulfonyl)-2-(2-(methylamino)-2-oxoethyl)-3,4-dihydro-2H-benzo[b][1,4]oxazin-6-yl)carbamate | 568 (M + H)⁺ |

TABLE 13-continued

| Ex. No. | Structure | Name | Observed m/z |
|---|---|---|---|
| 37J | 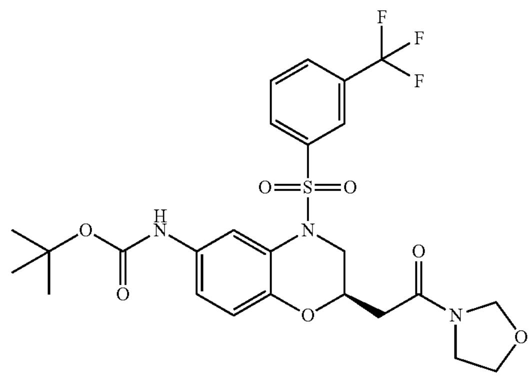 [SMILES: CC(C)(C)OC(=O)Nc1ccc2c(c1)N(S(=O)(=O)c1cccc(C(F)(F)F)c1)C[C@@H](CC(=O)N1CCOC1)O2] | (R)-tert-butyl (2-(2-(oxazolidin-3-yl)-2-oxoethyl)-4-((3-(trifluoromethyl)phenyl)sulfonyl)-3,4-dihydro-2H-benzo[b][1,4]oxazin-6-yl)carbamate | 516 (M-tBu + H)+ |
| 37K | 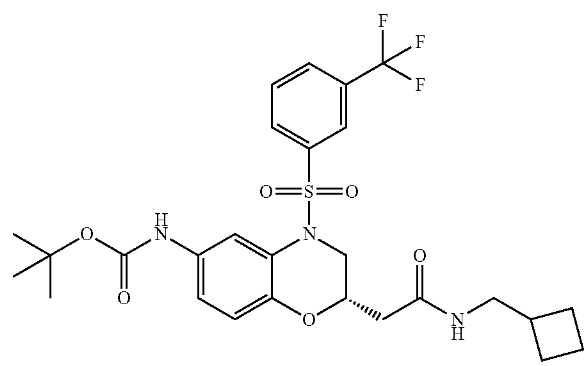 [SMILES: CC(C)(C)OC(=O)Nc1ccc2c(c1)N(S(=O)(=O)c1cccc(C(F)(F)F)c1)C[C@H](CC(=O)NCC1CCC1)O2] | (S)-tert-butyl (2-(2-((cyclobutylmethyl)amino)-2-oxoethyl)-4-((3-(trifluoromethyl)phenyl)sulfonyl)-3,4-dihydro-2H-benzo[b][1,4]oxazin-6-yl)carbamate | 528 (M-tBu + H)+ |
| 37L | 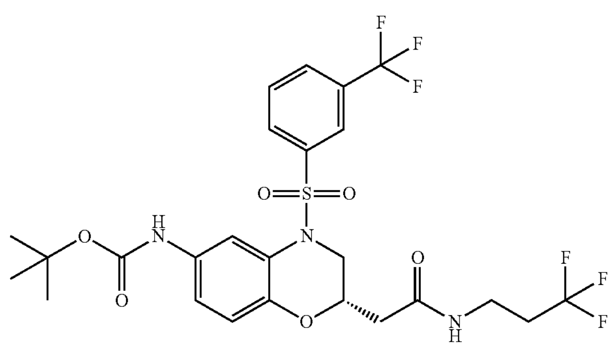 [SMILES: CC(C)(C)OC(=O)Nc1ccc2c(c1)N(S(=O)(=O)c1cccc(C(F)(F)F)c1)C[C@H](CC(=O)NCCC(F)(F)F)O2] | (S)-tert-butyl (2-(2-oxo-2-((3,3,3-trifluoropropyl)amino)ethyl)-4-((3-(trifluoromethyl)phenyl)sulfonyl)-3,4-dihydro-2H-benzo[b][1,4]oxazin-6-yl)carbamate | 556 (M-tBu + H)+ |
| 37M | 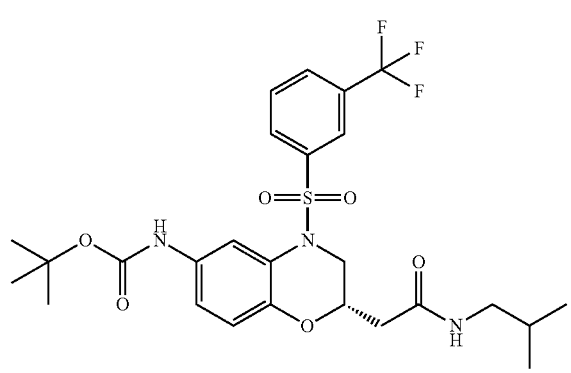 [SMILES: CC(C)CNC(=O)C[C@H]1CN(S(=O)(=O)c2cccc(C(F)(F)F)c2)c2cc(NC(=O)OC(C)(C)C)ccc2O1] | (S)-tert-butyl (2-(2-(isobutylamino)-2-oxoethyl)-4-((3-(trifluoromethyl)phenyl)sulfonyl)-3,4-dihydro-2H-benzo[b][1,4]oxazin-6-yl)carbamate | 516 (M-tBu + H)+ |

TABLE 13-continued

| Ex. No. | Structure | Name | Observed m/z |
|---|---|---|---|
| 37N | 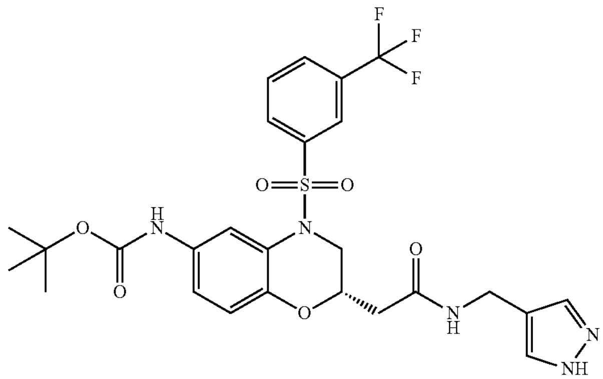 [SMILES: CC(C)(C)OC(=O)Nc1ccc2c(c1)N(S(=O)(=O)c1cccc(C(F)(F)F)c1)C[C@H](CC(=O)NCc1cn[nH]c1)O2] | (S)-tert-butyl (2-(2-(((1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate | 596 (M + H)+ |
| 37o | 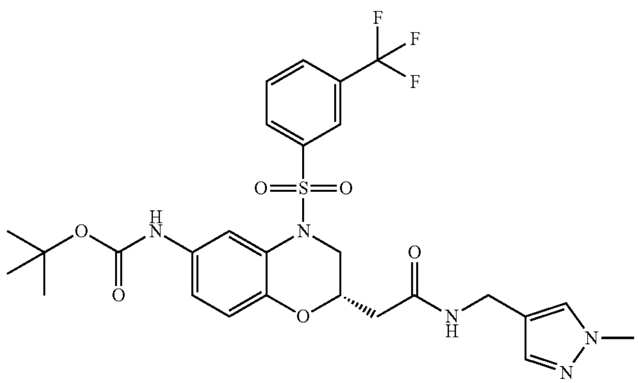 [SMILES: Cn1cc(CNC(=O)C[C@H]2CN(S(=O)(=O)c3cccc(C(F)(F)F)c3)c3cc(NC(=O)OC(C)(C)C)ccc3O2)cn1] | (S)-tert-butyl (2-(2-(((1-methyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate | 610 (M + H)+ |
| 37P | 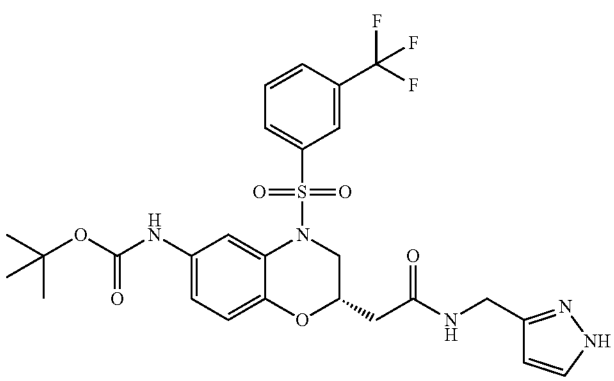 [SMILES: CC(C)(C)OC(=O)Nc1ccc2c(c1)N(S(=O)(=O)c1cccc(C(F)(F)F)c1)C[C@H](CC(=O)NCc1cc[nH]n1)O2] | (S)-tert-butyl (2-(2-(((1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate | 596 (M + H)+ |
| 37Q | 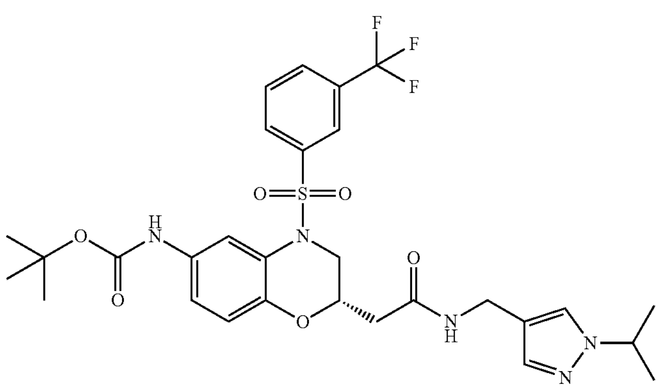 [SMILES: CC(C)n1cc(CNC(=O)C[C@H]2CN(S(=O)(=O)c3cccc(C(F)(F)F)c3)c3cc(NC(=O)OC(C)(C)C)ccc3O2)cn1] | (S)-tert-butyl (2-(2-(((1-isopropyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate | 638 (M + H)+ |

TABLE 13-continued

| Ex. No. | Structure | Name | Observed m/z |
|---|---|---|---|
| 37R | 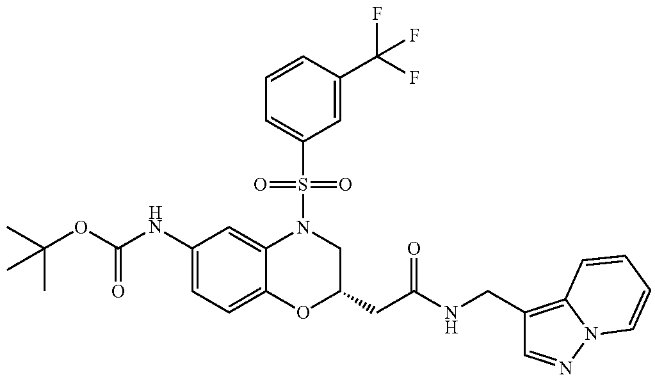 [SMILES: CC(C)(C)OC(=O)Nc1ccc2c(c1)N(S(=O)(=O)c1cccc(C(F)(F)F)c1)C[C@H](CC(=O)NCc1cnn3ccccc13)O2] | (S)-tert-butyl (2-(2-oxo-2-((pyrazolo[1,5-a]pyridin-3-ylmethyl)amino)ethyl)-4-((3-(trifluoromethyl)phenyl)sulfonyl)-3,4-dihydro-2H-benzo[b][1,4]oxazin-6-yl)carbamate | 646 (M + H)+ |
| 37S | 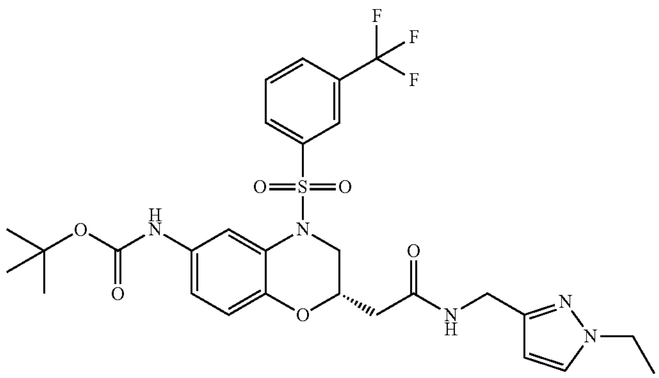 [SMILES: CCn1ccc(CNC(=O)C[C@H]2CN(S(=O)(=O)c3cccc(C(F)(F)F)c3)c3cc(NC(=O)OC(C)(C)C)ccc3O2)n1] | (S)-tert-butyl (2-(2-(((1-ethyl-1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate | 624 (M + H)+ |
| 37T | 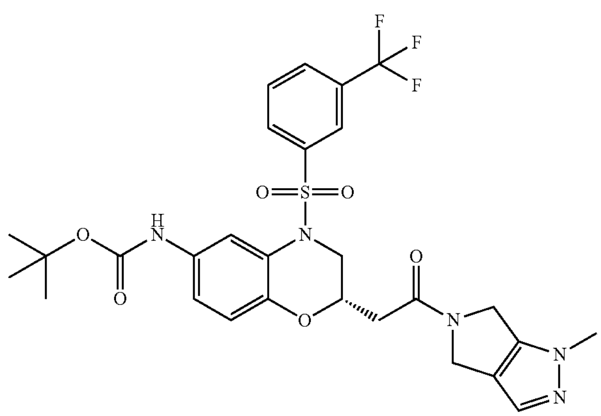 [SMILES: Cn1ncc2c1CN(C(=O)C[C@H]1CN(S(=O)(=O)c3cccc(C(F)(F)F)c3)c3cc(NC(=O)OC(C)(C)C)ccc3O1)C2] | (S)-tert-butyl (2-(2-(1-methylpyrrolo[3,4-c]pyrazol-5(1H,4H,6H)-yl)-2-oxoethyl)-4-((3-(trifluoromethyl)phenyl)sulfonyl)-3,4-dihydro-2H-benzo[b][1,4]oxazin-6-yl)carbamate | 622 (M + H)+ |
| 37U | 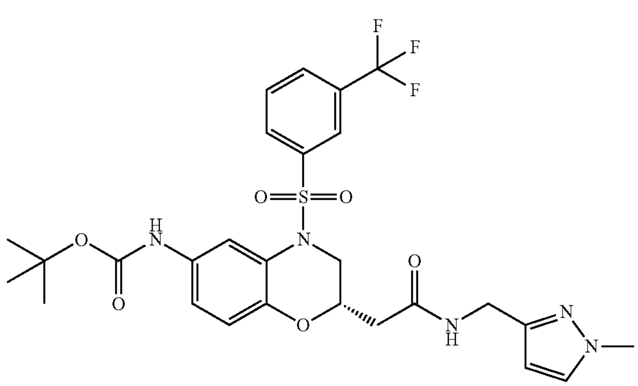 [SMILES: Cn1ccc(CNC(=O)C[C@H]2CN(S(=O)(=O)c3cccc(C(F)(F)F)c3)c3cc(NC(=O)OC(C)(C)C)ccc3O2)n1] | (S)-tert-butyl (2-(2-(((1-methyl-1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate | 610 (M + H)+ |

TABLE 13-continued

| Ex. No. | Structure | Name | Observed m/z |
|---|---|---|---|
| 37V | 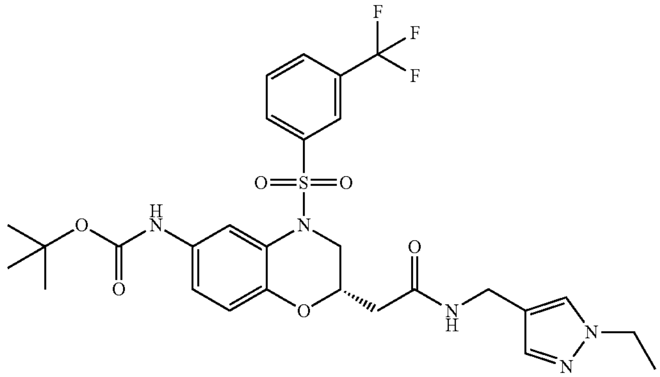 [SMILES: CCn1cc(CNC(=O)C[C@H]2CN(S(=O)(=O)c3cccc(C(F)(F)F)c3)c3cc(NC(=O)OC(C)(C)C)ccc3O2)cn1] | (S)-tert-butyl (2-(2-(((1-ethyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate | 624 (M + H)+ |
| 37W | 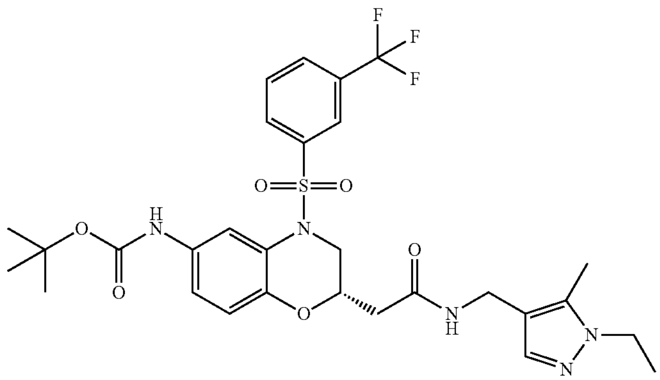 [SMILES: CCn1ncc(CNC(=O)C[C@H]2CN(S(=O)(=O)c3cccc(C(F)(F)F)c3)c3cc(NC(=O)OC(C)(C)C)ccc3O2)c1C] | (S)-tert-butyl (2-(2-(((1-ethyl-5-methyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate | 638 (M + H)+ |
| 37X | 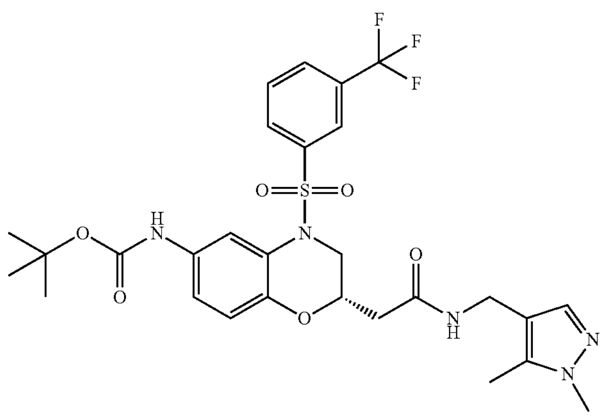 [SMILES: Cc1c(CNC(=O)C[C@H]2CN(S(=O)(=O)c3cccc(C(F)(F)F)c3)c3cc(NC(=O)OC(C)(C)C)ccc3O2)cnn1C] | (S)-tert-butyl (2-(2-(((1,5-dimethyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate | 624 (M + H)+ |
| 37Y | 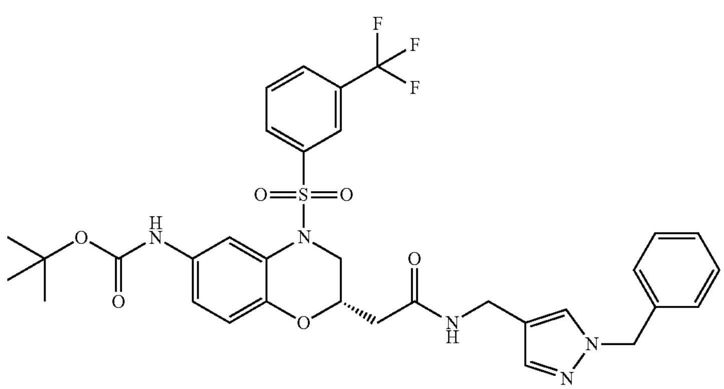 [SMILES: CC(C)(C)OC(=O)Nc1ccc2c(c1)N(S(=O)(=O)c1cccc(C(F)(F)F)c1)C[C@H](CC(=O)NCc1cnn(Cc3ccccc3)c1)O2] | (S)-tert-butyl (2-(2-(((1-benzyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate | 686 (M + H)+ |

TABLE 13-continued

| Ex. No. | Structure | Name | Observed m/z |
|---|---|---|---|
| 37Z | 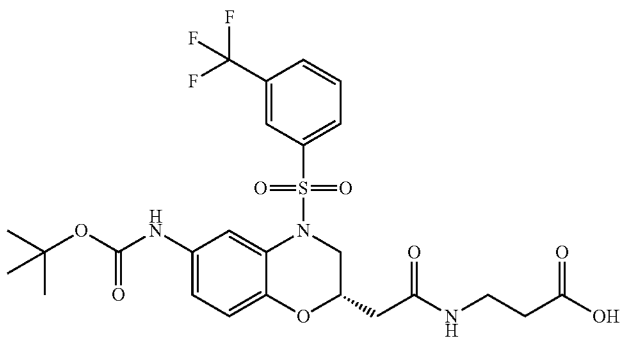 [SMILES: CC(C)(C)OC(=O)Nc1ccc2c(c1)N(S(=O)(=O)c1cccc(C(F)(F)F)c1)C[C@H](CC(=O)NCCC(=O)O)O2] | (S)-3-(2-(6-((tert-butoxycarbonyl)amino)-4-((3-(trifluoromethyl)phenyl)sulfonyl)-3,4-dihydro-2H-benzo[b][1,4]oxazin-2-yl)acetamido)propanoic acid | |
| 37AA | 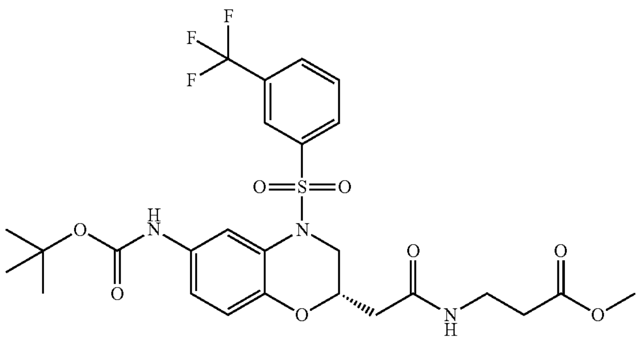 [SMILES: COC(=O)CCNC(=O)C[C@H]1CN(S(=O)(=O)c2cccc(C(F)(F)F)c2)c2cc(NC(=O)OC(C)(C)C)ccc2O1] | (S)-methyl 3-(2-(6-((tert-butoxycarbonyl)amino)-4-((3-(trifluoromethyl)phenyl)sulfonyl)-3,4-dihydro-2H-benzo[b][1,4]oxazin-2-yl)acetamido)propanoate | 546 (M-tBu + H)$^+$ |
| 37AB | 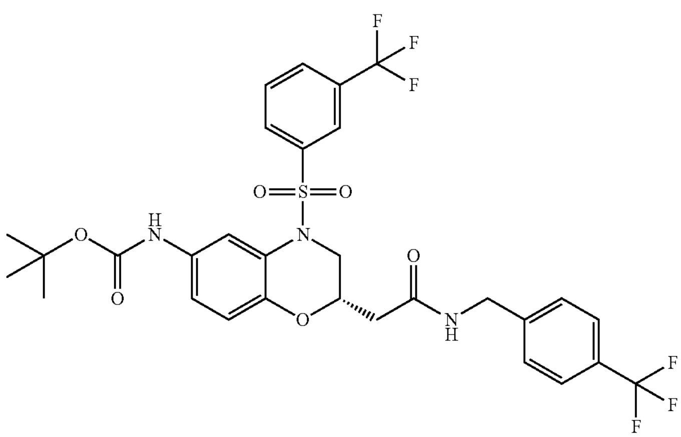 [SMILES: CC(C)(C)OC(=O)Nc1ccc2c(c1)N(S(=O)(=O)c1cccc(C(F)(F)F)c1)C[C@H](CC(=O)NCc1ccc(C(F)(F)F)cc1)O2] | (S)-tert-butyl (2-(2-oxo-2-((4-(trifluoromethyl)benzyl)amino)ethyl)-4-((3-(trifluoromethyl)phenyl)sulfonyl)-3,4-dihydro-2H-benzo[b][1,4]oxazin-6-yl)carbamate | 618 (M-tBu + H)$^+$ |
| 37AC | 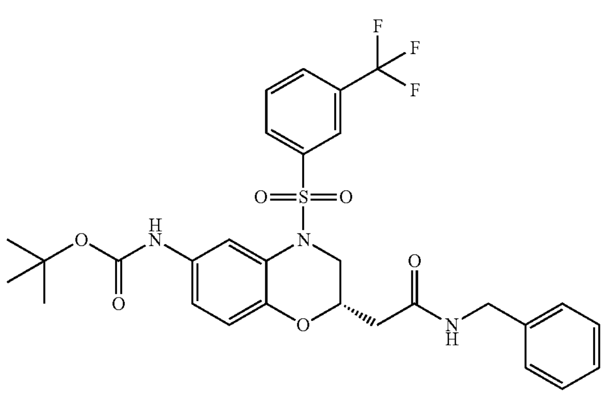 [SMILES: CC(C)(C)OC(=O)Nc1ccc2c(c1)N(S(=O)(=O)c1cccc(C(F)(F)F)c1)C[C@H](CC(=O)NCc1ccccc1)O2] | (S)-tert-butyl (2-(2-(benzylamino)-2-oxoethyl)-4-((3-(trifluoromethyl)phenyl)sulfonyl)-3,4-dihydro-2H-benzo[b][1,4]oxazin-6-yl)carbamate | 550 (M-tBu + H)$^+$ |

TABLE 13-continued

| Ex. No. | Structure | Name | Observed m/z |
|---|---|---|---|
| 37AD | 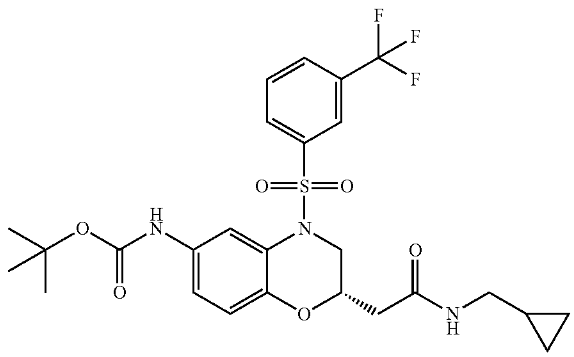 [SMILES: CC(C)(C)OC(=O)Nc1ccc2c(c1)N(S(=O)(=O)c1cccc(C(F)(F)F)c1)C[C@H](CC(=O)NCC1CC1)O2] | (S)-tert-butyl (2-(2-((cyclopropylmethyl)amino)-2-oxoethyl)-4-((3-(trifluoromethyl)phenyl)sulfonyl)-3,4-dihydro-2H-benzo[b][1,4]oxazin-6-yl)carbamate | 514 (M-tBu + H)+ |
| 37AE | 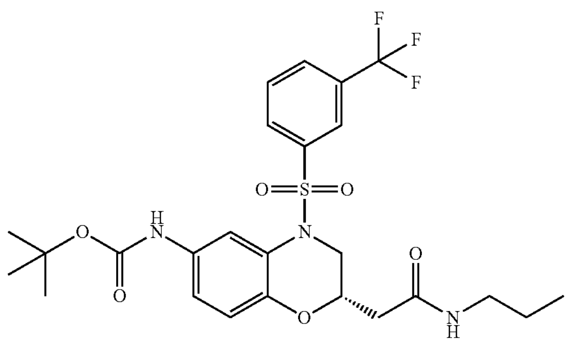 [SMILES: CCCNC(=O)C[C@H]1CN(S(=O)(=O)c2cccc(C(F)(F)F)c2)c2cc(NC(=O)OC(C)(C)C)ccc2O1] | (S)-tert-butyl (2-(2-oxo-2-(propylamino)ethyl)-4-((3-(trifluoromethyl)phenyl)sulfonyl)-3,4-dihydro-2H-benzo[b][1,4]oxazin-6-yl)carbamate | 502 (M-tBu + H)+ |
| 37AF | 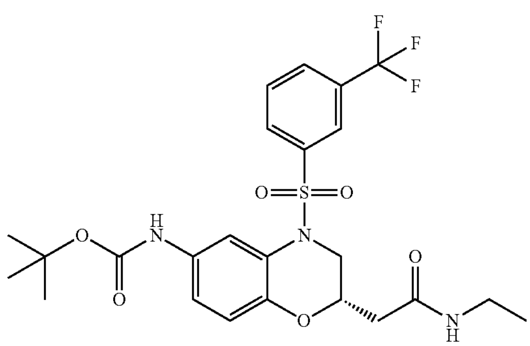 [SMILES: CCNC(=O)C[C@H]1CN(S(=O)(=O)c2cccc(C(F)(F)F)c2)c2cc(NC(=O)OC(C)(C)C)ccc2O1] | (S)-tert-butyl (2-(2-(ethylamino)-2-oxoethyl)-4-((3-(trifluoromethyl)phenyl)sulfonyl)-3,4-dihydro-2H-benzo[b][1,4]oxazin-6-yl)carbamate | 488 (M-tBu + H)+ |
| 37AG | 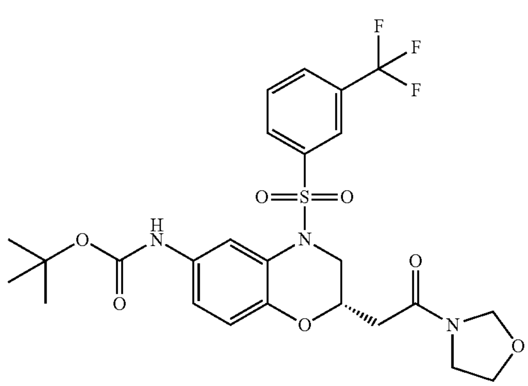 [SMILES: CC(C)(C)OC(=O)Nc1ccc2c(c1)N(S(=O)(=O)c1cccc(C(F)(F)F)c1)C[C@H](CC(=O)N1CCOC1)O2] | (S)-tert-butyl (2-(2-(oxazolidin-3-yl)-2-oxoethyl)-4-((3-(trifluoromethyl)phenyl)sulfonyl)-3,4-dihydro-2H-benzo[b][1,4]oxazin-6-yl)carbamate | 516 (M-tBu + H)+ |

TABLE 13-continued

| Ex. No. | Structure | Name | Observed m/z |
|---|---|---|---|
| 37AH | 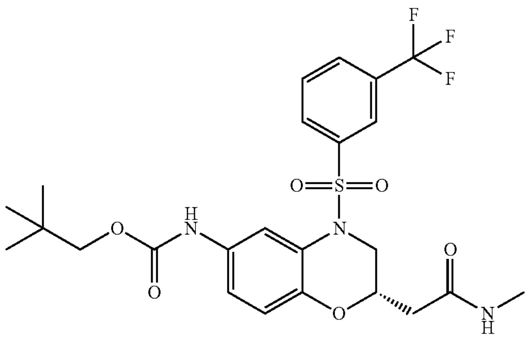 [SMILES: CNC(=O)C[C@H]1CN(S(=O)(=O)c2cccc(C(F)(F)F)c2)c2cc(NC(=O)OCC(C)(C)C)ccc2O1] | (S)-neopentyl (2-(2-(methylamino)-2-oxoethyl)-4-((3-(trifluoromethyl)phenyl)sulfonyl)-3,4-dihydro-2H-benzo[b][1,4]oxazin-6-yl)carbamate | 544 (M-tBu + H)+ |
| 37Ai | 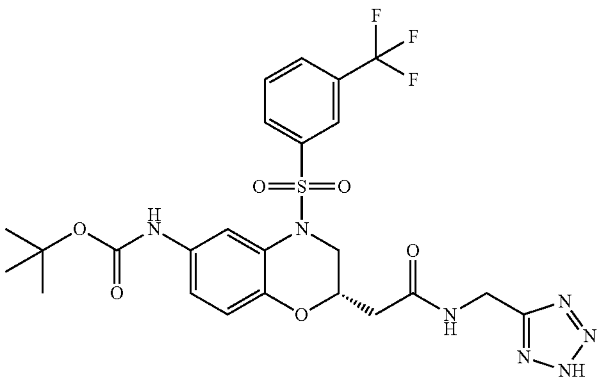 [SMILES: CC(C)(C)OC(=O)Nc1ccc2c(c1)N(S(=O)(=O)c1cccc(C(F)(F)F)c1)C[C@H](CC(=O)NCc1nn[nH]n1)O2] | (S)-tert-butyl (2-(2-(((2H-tetrazol-5-yl)methyl)amino)-2-oxoethyl)-4-((3-(trifluoromethyl)phenyl)sulfonyl)-3,4-dihydro-2H-benzo[b][1,4]oxazin-6-yl)carbamate | 542 (M-tBu + H)+ |
| 37AJ | 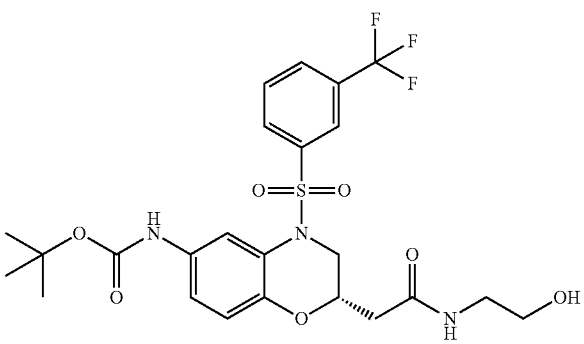 [SMILES: CC(C)(C)OC(=O)Nc1ccc2c(c1)N(S(=O)(=O)c1cccc(C(F)(F)F)c1)C[C@H](CC(=O)NCCO)O2] | (S)-tert-butyl (2-(2-((2-hydroxyethyl)amino)-2-oxoethyl)-4-((3-(trifluoromethyl)phenyl)sulfonyl)-3,4-dihydro-2H-benzo[b][1,4]oxazin-6-yl)carbamate | 560 (M + H)+ |
| 37AK | 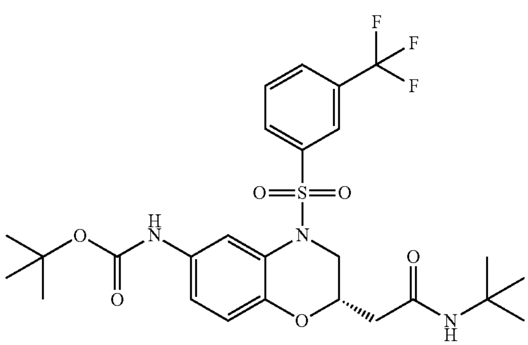 [SMILES: CC(C)(C)NC(=O)C[C@H]1CN(S(=O)(=O)c2cccc(C(F)(F)F)c2)c2cc(NC(=O)OC(C)(C)C)ccc2O1] | (S)-tert-butyl (2-(2-(tert-butylamino)-2-oxoethyl)-4-((3-(trifluoromethyl)phenyl)sulfonyl)-3,4-dihydro-2H-benzo[b][1,4]oxazin-6-yl)carbamate | 516 (M-tBu + H)+ |

TABLE 13-continued

| Ex. No. | Structure | Name | Observed m/z |
|---|---|---|---|
| 37AL | 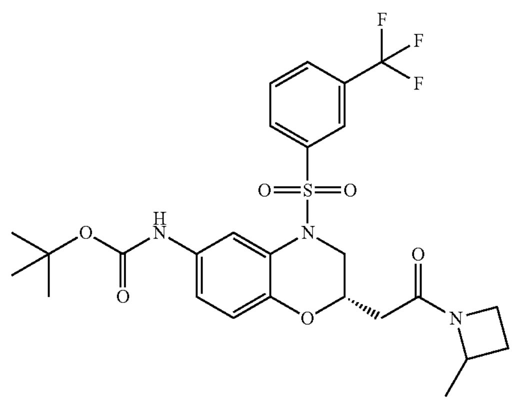 [SMILES: CC1CCN1C(=O)C[C@H]1CN(S(=O)(=O)c2cccc(C(F)(F)F)c2)c2cc(NC(=O)OC(C)(C)C)ccc2O1] | tert-butyl ((2S)-2-(2-(2-methylazetidin-1-yl)-2-oxoethyl)-4-((3-(trifluoromethyl)phenyl)sulfonyl)-3,4-dihydro-2H-benzo[b][1,4]oxazin-6-yl)carbamate | 570 (M + H)+ |
| 37AM | 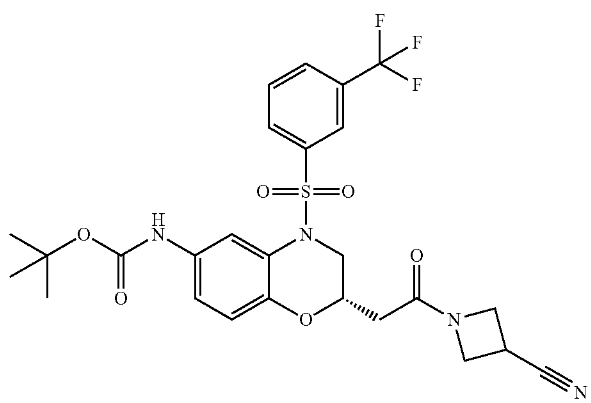 [SMILES: CC(C)(C)OC(=O)Nc1ccc2c(c1)N(S(=O)(=O)c1cccc(C(F)(F)F)c1)C[C@H](CC(=O)N1CC(C#N)C1)O2] | (S)-tert-butyl (2-(2-(3-cyanoazetidin-1-yl)-2-oxoethyl)-4-((3-(trifluoromethyl)phenyl)sulfonyl)-3,4-dihydro-2H-benzo[b][1,4]oxazin-6-yl)carbamate | 581 (M + H)+ |
| 37AN | 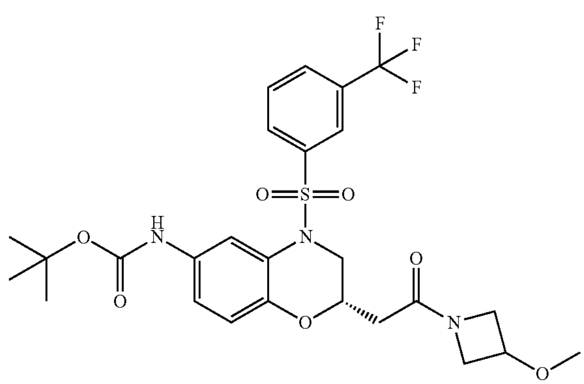 [SMILES: COC1CN(C(=O)C[C@H]2CN(S(=O)(=O)c3cccc(C(F)(F)F)c3)c3cc(NC(=O)OC(C)(C)C)ccc3O2)C1] | (S)-tert-butyl (2-(2-(3-methoxyazetidin-1-yl)-2-oxoethyl)-4-((3-(trifluoromethyl)phenyl)sulfonyl)-3,4-dihydro-2H-benzo[b][1,4]oxazin-6-yl)carbamate | 586 (M + H)+ |
| 37Ao | 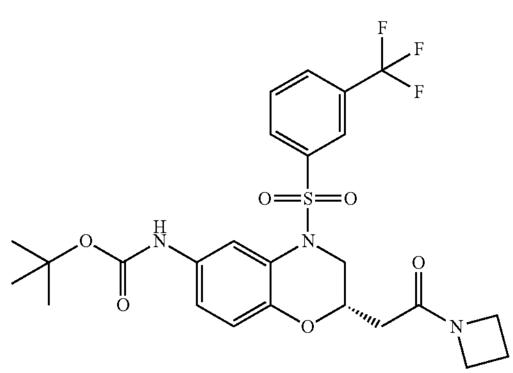 [SMILES: CC(C)(C)OC(=O)Nc1ccc2c(c1)N(S(=O)(=O)c1cccc(C(F)(F)F)c1)C[C@H](CC(=O)N1CCC1)O2] | (S)-tert-butyl (2-(2-(azetidin-1-yl)-2-oxoethyl)-4-((3-(trifluoromethyl)phenyl)sulfonyl)-3,4-dihydro-2H-benzo[b][1,4]oxazin-6-yl)carbamate | 556 (M + H)+ |

TABLE 13-continued

| Ex. No. | Structure | Name | Observed m/z |
|---|---|---|---|
| 37AP | 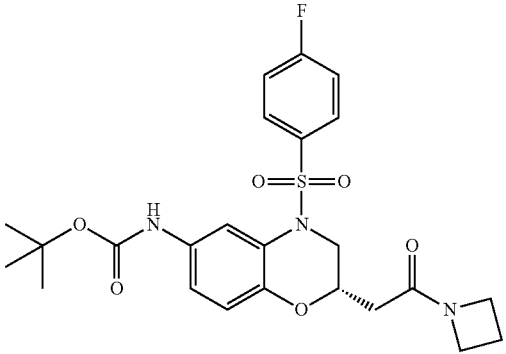 [SMILES: CC(C)(C)OC(=O)Nc1ccc2c(c1)N(S(=O)(=O)c1ccc(F)cc1)C[C@H](CC(=O)N1CCC1)O2] | (S)-tert-butyl (2-(2-(azetidin-1-yl)-2-oxoethyl)-4-((4-fluorophenyl)sulfonyl)-3,4-dihydro-2H-benzo[b][1,4]oxazin-6-yl)carbamate | 506.1 (M + H)+ |
| 39AQ | 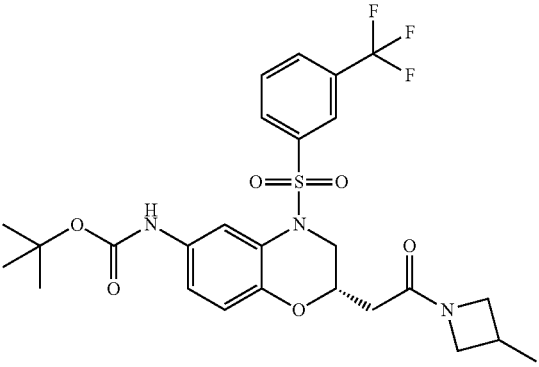 [SMILES: CC1CN(C(=O)C[C@H]2CN(S(=O)(=O)c3cccc(C(F)(F)F)c3)c3cc(NC(=O)OC(C)(C)C)ccc3O2)C1] | (S)-tert-butyl (2-(2-(3-methylazetidin-1-yl)-2-oxoethyl)-4-((3-(trifluoromethyl)phenyl)sulfonyl)-3,4-dihydro-2H-benzo[b][1,4]oxazin-6-yl)carbamate | 570 (M + H)+ |
| 37AR | 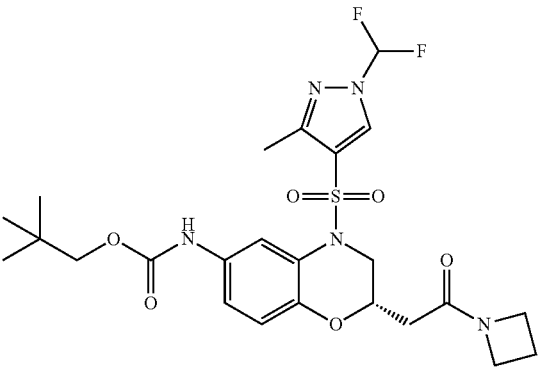 [SMILES: Cc1nn(C(F)F)cc1S(=O)(=O)N1C[C@H](CC(=O)N2CCC2)Oc2ccc(NC(=O)OCC(C)(C)C)cc21] | (S)-neopentyl (2-(2-(azetidin-1-yl)-2-oxoethyl)-4-((1-(difluoromethyl)-3-methyl-1H-pyrazol-4-yl)sulfonyl)-3,4-dihydro-2H-benzo[b][1,4]oxazin-6-yl)carbamate | 556.3 (M + H)+ |

Example 38—Preparation of amides from (R)-6-((substituted-alkoxycarbonyl)amino)-4-((substituted aryl or heteroaryl)sulfonyl)-3,4-dihydro-2H-benzo[b][1,4]oxazine-2-carboxylic Acids The compounds in Table 14 below were prepared based on the experimental procedures described in Examples 33, 34 and 36 and elsewhere in the detailed description, and can be achieved by one of skill in the art in light of the present disclosure.

TABLE 14

| Ex. No. | Structure | Name | Observed m/z |
|---|---|---|---|
| 38A | 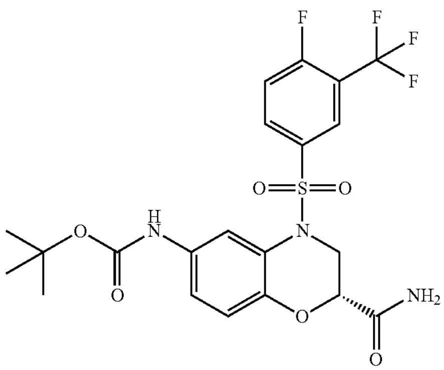 [SMILES: CC(C)(C)OC(=O)Nc1ccc2c(c1)N(S(=O)(=O)c1ccc(F)c(C(F)(F)F)c1)C[C@H](C(N)=O)O2] | (R)-tert-butyl (2-carbamoyl-4-((4-fluoro-3-(trifluoromethyl)phenyl)sulfonyl)-3,4-dihydro-2H-benzo[b][1,4]oxazin-6-yl)carbamate | 537.0 (M + NH$_4$)$^+$ |
| 38B | 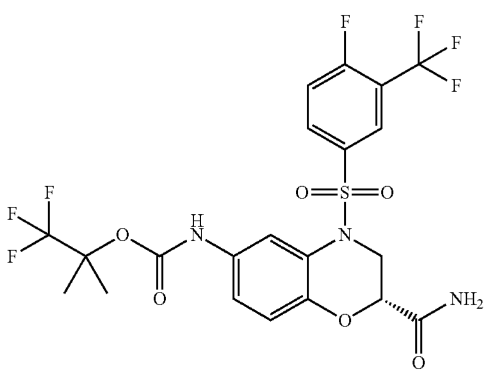 [SMILES: CC(C)(OC(=O)Nc1ccc2c(c1)N(S(=O)(=O)c1ccc(F)c(C(F)(F)F)c1)C[C@H](C(N)=O)O2)C(F)(F)F] | (R)-1,1,1-trifluoro-2-methylpropan-2-yl (2-carbamoyl-4-((4-fluoro-3-(trifluoromethyl)phenyl)sulfonyl)-3,4-dihydro-2H-benzo[b][1,4]oxazin-6-yl)carbamate | 595.9 (M + Na)$^+$ |
| 38C | 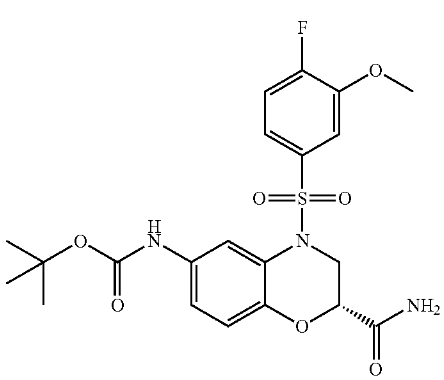 [SMILES: COc1cc(S(=O)(=O)N2C[C@H](C(N)=O)Oc3ccc(NC(=O)OC(C)(C)C)cc32)ccc1F] | (R)-tert-butyl (2-carbamoyl-4-((4-fluoro-3-methoxyphenyl)sulfonyl)-3,4-dihydro-2H-benzo[b][1,4]oxazin-6-yl)carbamate | 499.0 (M + NH$_4$)$^+$ |

TABLE 14-continued

| Ex. No. | Structure | Name | Observed m/z |
|---|---|---|---|
| 38D | 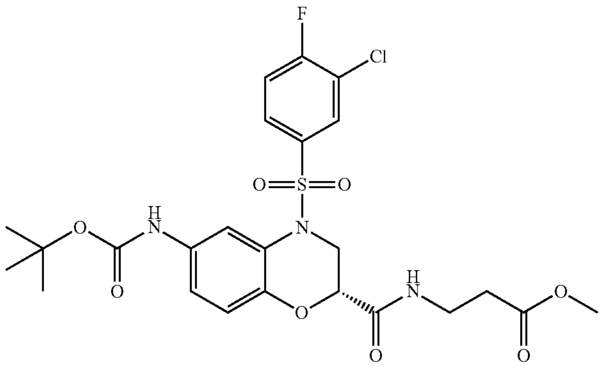 [SMILES: COC(=O)CCNC(=O)[C@H]1CN(S(=O)(=O)c2ccc(F)c(Cl)c2)c2cc(NC(=O)OC(C)(C)C)ccc2O1] | (R)-methyl 3-(6-((tert-butoxycarbonyl)amino)-4-((3-chloro-4-fluorophenyl)sulfonyl)-3,4-dihydro-2H-benzo[b][1,4]oxazine-2-carboxamido)propanoate | 573 (M + H)+ |
| 38E | 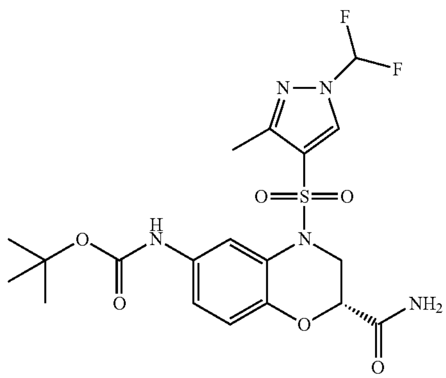 [SMILES: Cc1nn(C(F)F)cc1S(=O)(=O)N1C[C@H](C(N)=O)Oc2ccc(NC(=O)OC(C)(C)C)cc21] | (R)-tert-butyl (2-carbamoyl-4-((1-(difluoromethyl)-3-methyl-1H-pyrazol-4-yl)sulfonyl)-3,4-dihydro-2H-benzo[b][1,4]oxazin-6-yl)carbamate | 505.0 (M + Na)+ |
| 38F | 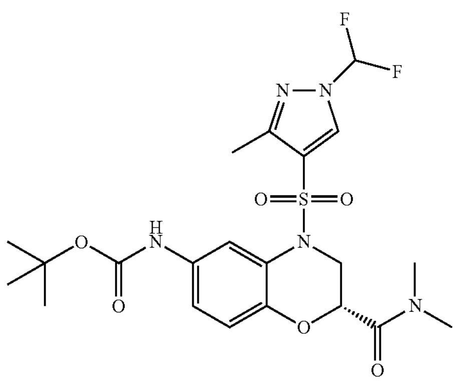 [SMILES: Cc1nn(C(F)F)cc1S(=O)(=O)N1C[C@H](C(=O)N(C)C)Oc2ccc(NC(=O)OC(C)(C)C)cc21] | (R)-tert-butyl (4-((1-(difluoromethyl)-3-methyl-1H-pyrazol-4-yl)sulfonyl)-2-(dimethylcarbamoyl)-3,4-dihydro-2H-benzo[b][1,4]oxazin-6-yl)carbamate | 538.2 (M + Na)+ |
| 38G | 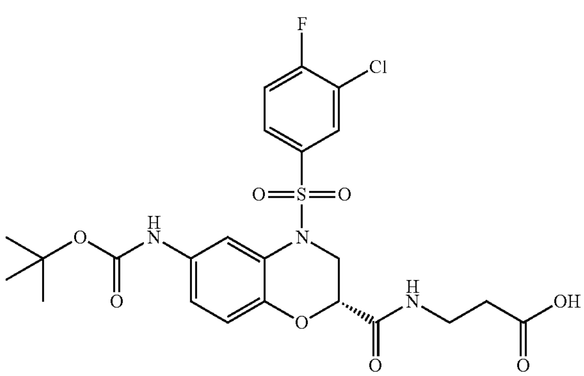 [SMILES: CC(C)(C)OC(=O)Nc1ccc2c(c1)N(S(=O)(=O)c1ccc(F)c(Cl)c1)C[C@H](C(=O)NCCC(=O)O)O2] | (R)-3-(6-((tert-butoxycarbonyl)amino)-4-((3-chloro-4-fluorophenyl)sulfonyl)-3,4-dihydro-2H-benzo[b][1,4]oxazine-2-carboxamido)propanoic acid | 575 (M + NH4)+ |

Example 39—Synthesis of tert-butyl (2-(2-cyano-propan-2-yl)-4-((4-fluorophenyl)sulfonyl)-3,4-dihydro-2H-benzo[b][1,4]oxazin-6-yl)carbamate (39)

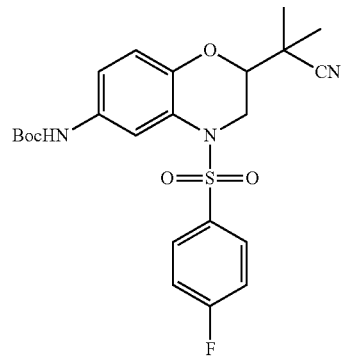 [SMILES: CC(C)(C)OC(=O)Nc1ccc2c(c1)N(S(=O)(=O)c1ccc(F)cc1)CC(C(C)(C)C#N)O2]

Step 1—Preparation of N-(3-cyano-3-methyl-2-oxobutyl)-4-fluoro-N-(2-fluoro-5-nitrophenyl)benzenesulfonamide

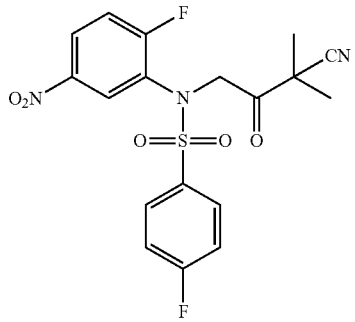 [SMILES: CC(C)(C#N)C(=O)CN(c1cc([N+](=O)[O-])ccc1F)S(=O)(=O)c1ccc(F)cc1]

To a stirred solution of 4-fluoro-N-(2-fluoro-5-nitrophenyl)benzenesulfonamide (2 g, 6.36 mmol) in DMF (25 mL) was added NaH (0.382 g, 9.55 mmol) in one portion at 0° C. After one hour, a solution of 4-bromo-2,2-dimethyl-3-oxobutanenitrile (2.419 g, 12.73 mmol) in DMF (5 mL) was added dropwise. The mixture was stirred at 0° C. for an additional two hours. The mixture was diluted with water (200 mL) and extracted with three times with ethyl acetate. The combined organic layers were washed with brine, dried (Na$_2$SO$_4$) and evaporated to dryness. The residue was cooled and triturated with petroleum ether:ethyl acetate (1:1, 20 mL). The solid was filtered, washed twice with cold EtOAc (5 mL each) and dried to afford the title compound. LCMS (ESI): calculated for C$_{18}$H$_{15}$F$_2$N$_3$O$_5$S (M+H)$^+$: 424, found: 424.

Step 2—Preparation of N-(3-cyano-2-hydroxy-3-methylbutyl)-4-fluoro-N-(2-fluoro-5-nitrophenyl)benzenesulfonamide

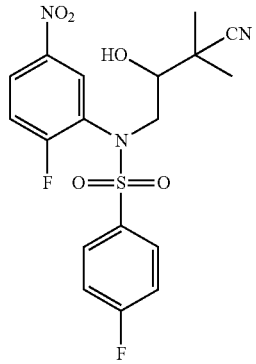 [SMILES: CC(C)(C#N)C(O)CN(c1cc([N+](=O)[O-])ccc1F)S(=O)(=O)c1ccc(F)cc1]

To a stirred solution of N-(3-cyano-3-methyl-2-oxobutyl)-4-fluoro-N-(2-fluoro-5-nitrophenyl)benzenesulfonamide (100 mg, 0.236 mmol) in EtOH (5 mL) was added sodium borohydride (89 mg, 2.362 mmol) in one portion at room temperature. The mixture was stirred at room temperature for two hours. The mixture was diluted with water (100 mL) and extracted three times with ethyl acetate. The combined organic layers were washed with brine, dried (Na$_2$SO$_4$) and concentrated. The residue was purified by prep-TLC eluting with petroleum ether:ethyl acetate (2:1) to afford the title compound as a yellow oil. LCMS (ESI): calculated for C$_{18}$H$_{17}$F$_2$N$_3$O$_5$S (M+H)$^+$: 426, found: 426.

Step 3—Preparation of 2-(4-((4-fluorophenyl)sulfonyl)-6-nitro-3,4-dihydro-2H-benzo[b][1,4]oxazin-2-yl)-2-methylpropanenitrile

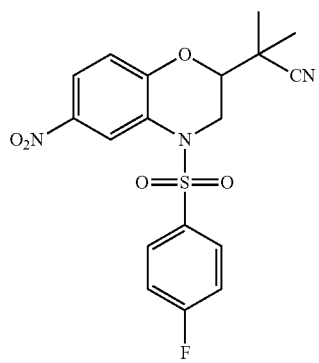 [SMILES: CC(C)(C#N)C1CN(S(=O)(=O)c2ccc(F)cc2)c2cc([N+](=O)[O-])ccc2O1]

To a stirred solution of N-(3-cyano-2-hydroxy-3-methylbutyl)-4-fluoro-N-(2-fluoro-5-nitrophenyl)benzenesulfonamide (1.88 g, 4.42 mmol) in DMF (5 mL) was added K$_2$CO$_3$ (1.83 g, 13.26 mmol) in one portion at room temperature. The mixture was heated at 80° C. for 1 h. The mixture was diluted with water (150 mL) and extracted three times with ethyl acetate. The combined organic layers were washed with brine, dried (Na$_2$SO$_4$) and concentrated. The residue was purified by prep-TLC eluting with petroleum ether:ethyl acetate (2:1) to afford the title compound as a yellow oil. LCMS (ESI): calculated for C$_{18}$H$_{16}$FN$_3$O$_5$S (M+H)$^+$: 406, found: 406.

Step 4—Preparation of tert-butyl (2-(2-cyanopropan-2-yl)-4-((4-fluorophenyl)sulfonyl)-3,4-dihydro-2H-benzo[b][1,4]oxazin-6-yl)carbamate

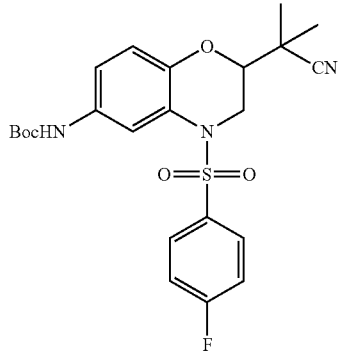 [SMILES: CC(C)(C)OC(=O)Nc1ccc2c(c1)N(S(=O)(=O)c1ccc(F)cc1)CC(C(C)(C)C#N)O2]

To a solution of 2-(4-((4-fluorophenyl)sulfonyl)-6-nitro-3,4-dihydro-2H-benzo[b][1,4]oxazin-2-yl)-2-methylpropanenitrile (100 mg, 0.247 mmol) in ethyl acetate (10 mL) was added di-tert-butyl dicarbonate (0.086 mL, 0.370 mmol) and 10% Pd/C (105 mg, 0.987 mmol) in one portion at room temperature under nitrogen. The atmosphere was purged and exchanged with one atmosphere of hydrogen, and stirred at 30° C. for four hours. The mixture was filtered through CELITE, and the filtrate was concentrated. The residue was purified by prep-HPLC and lyophilized under reduced pressure to afford the title compound as a white solid. LCMS (ESI): calculated for $C_{23}H_{26}FN_3O_5S$ (M+H)$^+$: 476, found: 476. $^1$H-NMR (400 MHz, CDCl$_3$) δ 7.60-7.77 (m, 3H), 7.24 (s, 1H), 7.16 (t, J=8.42 Hz, 2H), 6.82 (d, J=8.62 Hz, 1H), 4.44 (d, J=14.10 Hz, 1H), 3.23 (dd, J=13.90, 10.76 Hz, 1H), 3.07 (d, J=9.00 Hz, 1H), 1.52 (s, 9H), 1.38 (s, 3H), 1.35 (s, 3H).

Example 40—Synthesis of (R and S) 2-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic Acid (40)

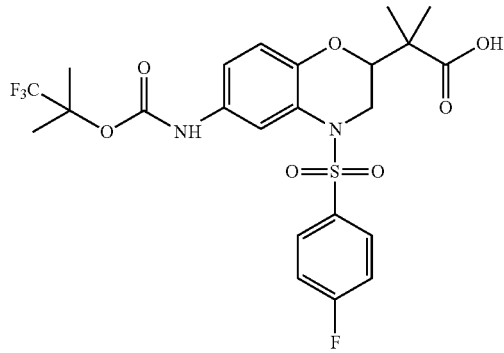 [SMILES: CC(C)(C(=O)O)C1CN(S(=O)(=O)c2ccc(F)cc2)c2cc(NC(=O)OC(C)(C)C(F)(F)F)ccc2O1]

Step 1—Preparation of tert-butyl (4-((4-fluorophenyl)sulfonyl)-2-(2-methyl-1-oxopropan-2-yl)-3,4-dihydro-2H-benzo[b][1,4]oxazin-6-yl)carbamate

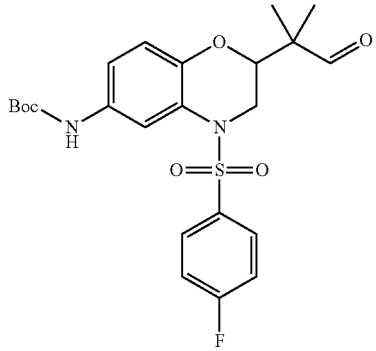 [SMILES: CC(C)(C)OC(=O)Nc1ccc2c(c1)N(S(=O)(=O)c1ccc(F)cc1)CC(C(C)(C)C=O)O2]

To a stirred solution of tert-butyl (2-(2-cyanopropan-2-yl)-4-((4-fluorophenyl)sulfonyl)-3,4-dihydro-2H-benzo[b][1,4]oxazin-6-yl)carbamate (1.4 g, 2.94 mmol) in anhydrous toluene (25 mL) at −78° C. was added dropwise diisopropylaluminum hydride (8.83 mL, 8.83 mmol). The mixture was stirred at −78° C. for an additional three hours. The mixture was quenched by MeOH at −78° C. and allowed to warm up to room temperature, and then 50 mL of water and 30 mL 1M aqueous HCl solution were added (note that on larger scales, the DIBAL reduction should be quenched by the addition of saturated aqueous Rochelle's salt). After being stirred at ambient temperature for 10 min, the resulting solution was extracted three times with ethyl acetate. The combined organic layers were washed with brine, dried (Na$_2$SO$_4$) and concentrated. The crude product of the title compound was used directly without further purification. LCMS (ESI) calculated for $C_{23}H_{27}FN_2O_6S$ (M+H)$^+$: 479, found: 479.

Step 2—Preparation of 2-(6-((tert-butoxycarbonyl)amino)-4-((4-fluorophenyl)sulfonyl)-3,4-dihydro-2H-benzo[b][1,4]oxazin-2-yl)-2-methylpropanoic Acid

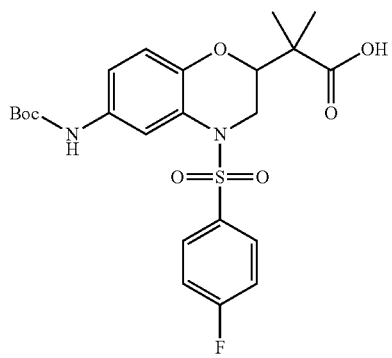 [SMILES: CC(C)(C)OC(=O)Nc1ccc2c(c1)N(S(=O)(=O)c1ccc(F)cc1)CC(C(C)(C)C(=O)O)O2]

To a solution of tert-butyl (4-((4-fluorophenyl)sulfonyl)-2-(2-methyl-1-oxopropan-2-yl)-3,4-dihydro-2H-benzo[b][1,4]oxazin-6-yl)carbamate (1.2 g, 2.508 mmol) in THF (8 mL) and water (2 mL) was added sulfamic acid (1.461 g, 15.05 mmol) and sodium chlorite (0.249 g, 2.76 mmol) in one portion at 0° C. The mixture was stirred at 0° C. for 10 min, followed by the addition of potassium dihydrogen phosphate (4.10 g, 30.1 mmol). The mixture was allowed to warm to room temperature and stirred overnight. The mixture was diluted with water (80 mL) and extracted three times with ethyl acetate. The combined organic layers were washed with brine, dried ($Na_2SO_4$) and concentrated. The title compound was used directly without purification. LCMS (ESI) calculated for $C_{23}H_{27}FN_2O_7S$ $(M+H)^+$: 495, found: 495.

Step 3—Preparation of methyl 2-(6-amino-4-((4-fluorophenyl)sulfonyl)-3,4-dihydro-2H-benzo[b][1,4]oxazin-2-yl)-2-methylpropanoate

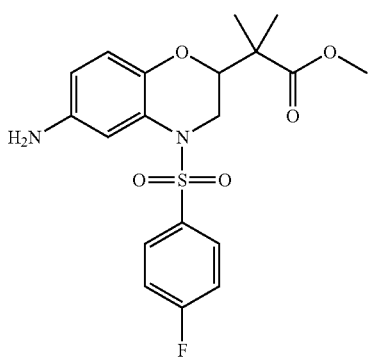 [SMILES: COC(=O)C(C)(C)C1CN(S(=O)(=O)c2ccc(F)cc2)c2cc(N)ccc2O1]

To a stirred solution of 2-((6-((tert-butoxycarbonyl) amino)-4-((4-fluorophenyl)sulfonyl)-3,4-dihydro-2H-benzo [b][1,4]oxazin-2-yl)-2-methylpropanoic acid (1 g, 2.022 mmol) in methanol (10 mL) was added a 4M solution of hydrochloric acid in methanol (30 mL, 120 mmol) at room temperature. The mixture was heated at 90° C. overnight. The mixture was concentrated, and the residue was purified by silica gel chromatography eluting with petroleum ether: ethyl acetate (3:1) to afford the title compound as a yellow oil. LCMS (ESI) calculated for $C_{19}H_{21}FN_2O_5S$ $(M+H)^+$: 409, found: 409.

Step 4—Preparation of methyl 2-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate

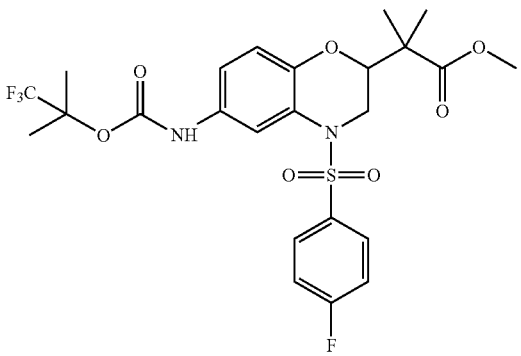 [SMILES: COC(=O)C(C)(C)C1CN(S(=O)(=O)c2ccc(F)cc2)c2cc(NC(=O)OC(C)(C)C(F)(F)F)ccc2O1]

To a solution of methyl 2-(6-amino-4-((4-fluorophenyl) sulfonyl)-3,4-dihydro-2H-benzo[b][1,4]oxazin-2-yl)-2-methylpropanoate (600 mg, 1.469 mmol) in DMSO (5 mL) was added 1,1,1-trifluoro-2-methylpropan-2-yl 1H-imidazole-1-carboxylate (424 mg, 1.91 mmol) in one portion. The mixture was heated at 80° C. overnight, diluted with water (100 mL) and extracted three times with ethyl acetate. The combined organic layers were washed with brine, dried ($Na_2SO_4$) and concentrated. The residue was purified by silica gel chromatography eluting with petroleum ether:ethyl acetate (3:1) to afford the title compound as a yellow oil. LCMS (ESI) calculated for $C_{24}H_{26}F_4N_2O_7S$ $(M+H)^+$: 563, found: 563.

Step 5—Preparation of 2-(6-amino-4-((4-fluorophenyl)sulfonyl)-3,4-dihydro-2H-benzo[b][1,4]oxazin-2-yl)-2-methylpropanoic Acid

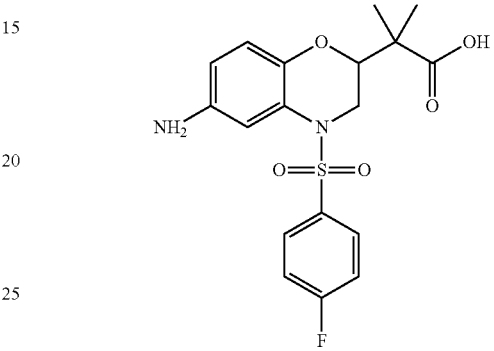

To a solution of methyl 2-(4-((4-fluorophenyl)sulfonyl)-6-((((1,1,1-trifluoro-2-methylpropan-2-yl)oxy)carbonyl) amino)-3,4-dihydro-2H-benzo[b][1,4]oxazin-2-yl)-2-methylpropanoate (110 mg, 0.196 mmol) in THF (2 mL) and water (0.5 mL) was added lithium hydroxide monohydrate (46.8 mg, 1.96 mmol) in one portion. The mixture was stirred at 25° C. overnight. The mixture was diluted with water (10 mL), and acidified with dilute HCl to pH=2. The mixture was extracted three times with ethyl acetate. The combined organic layers were washed with brine, ($Na_2SO_4$) and evaporated to dryness. The residue was purified by prep-TLC eluting with petroleum ether:ethyl acetate (1:1) to afford the title compound as a yellow oil. LCMS (ESI) calculated for $C_{18}H_{19}FN_2O_5S$ $(M+H)^+$: 395, found: 395.

Step 6—Preparation of 2-(4-((4-fluorophenyl)sulfonyl)-6-((((1,1,1-trifluoro-2-methylpropan-2-yl)oxy) carbonyl)amino)-3,4-dihydro-2H-benzo[b][1,4]oxazin-2-yl)-2-methylpropanoic Acid

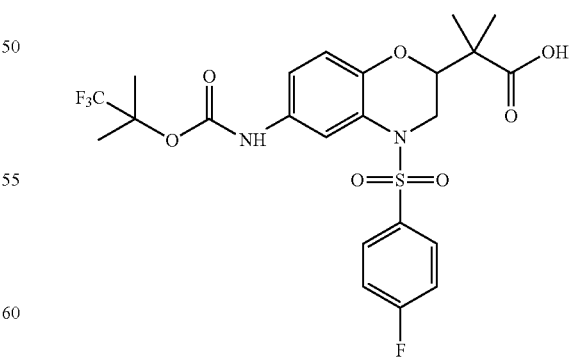

To a solution of 2-(6-amino-4-((4-fluorophenyl)sulfonyl)-3,4-dihydro-2H-benzo[b][1,4]oxazin-2-yl)-2-methylpropanoic acid (80 mg, 0.203 mmol) in DMSO (1 mL) was added 1,1,1-trifluoro-2-methylpropan-2-yl 1H-imidazole-1-carboxylate (54.1 mg, 0.243 mmol) in one portion. The mixture was stirred at 80° C. for four hours. The mixture was diluted with water (30 mL) and extracted three times with ethyl acetate. The combined organic layers were washed with brine, dried (Na$_2$SO$_4$) and concentrated. The residue was purified by prep-HPLC to afford desired compound as a white solid. LCMS (ESI) calculated for C$_{23}$H$_{24}$F$_4$N$_2$O$_7$S (M+H)$^+$: 549, found: 549. $^1$H NMR (400 MHz, CDCl3) δ 7.78 (1H, br. s.), 7.71 (2H, dd, J=8.53, 5.02 Hz), 7.24 (1H, d, J=7.53 Hz), 7.14 (2H, t, J=8.53 Hz), 6.81 (1H, d, J=9.03 Hz), 6.63-6.77 (1H, m), 4.36-4.45 (1H, m), 3.44 (1H, d, J=9.03 Hz), 3.18 (1H, dd, J=14.05, 10.54 Hz), 1.77 (6H, s), 1.25 (3H, s), 1.20 (3H, s)

Example 41—Synthesis of (R and S)-1,1,1-trifluoro-2-methylpropan-2-yl (4-((4-fluorophenyl)sulfonyl)-2-(2-(4-methyl-5-oxo-4,5-dihydro-1H-1,2,4-triazol-3-yl)propan-2-yl)-3,4-dihydro-2H-benzo[b][1,4]oxazin-6-yl)carbamate (41)

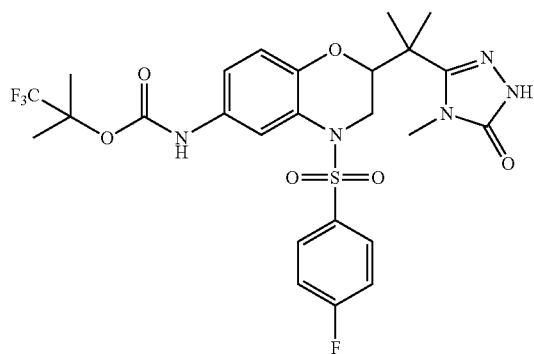 [SMILES: Cn1c(C(C)(C)C2CN(S(=O)(=O)c3ccc(F)cc3)c3cc(NC(=O)OC(C)(C)C(F)(F)F)ccc3O2)n[nH]c1=O]

Step 1—Preparation of 1,1,1-trifluoro-2-methylpropan-2-yl (4-((4-fluorophenyl)sulfonyl)-2-(1-hydrazinyl-2-methyl-1-oxopropan-2-yl)-3,4-dihydro-2H-benzo[b][1,4]oxazin-6-yl) carbamate

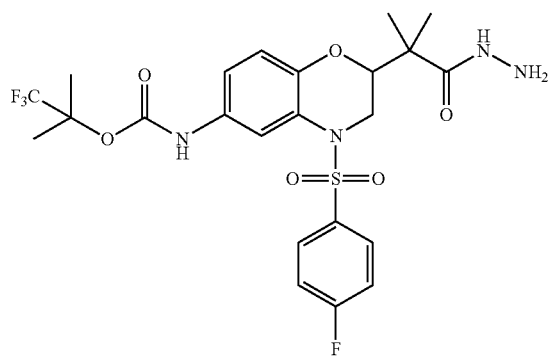 [SMILES: CC(C)(C(=O)NN)C1CN(S(=O)(=O)c2ccc(F)cc2)c2cc(NC(=O)OC(C)(C)C(F)(F)F)ccc2O1]

To a stirred solution at room temperature of 2-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid (55 mg, 0.100 mmol) in THF (2 mL) were added 1-ethyl-3-(3-dimethylaminopropyl)carbodiimide (38.4 mg, 0.201 mmol), N-hydroxybenzotriazole (23 mg, 0.15 mmol) and triethylamine (0.042 mL, 0.30 mmol) in one portion. After the mixture was stirred for an hour, hydrazine (9.44 μL, 0.301 mmol) solution in DMF (0.1 mL) was added to the mixture dropwise. The reaction mixture was stirred at room temperature for an additional hour. The mixture was diluted with water (30 mL) and extracted three times with ethyl acetate. The combined organic layers were washed with brine, dried (Na$_2$SO$_4$) and evaporated to dryness. The residue was purified by prep-TLC eluting with petroleum ether:ethyl acetate (1:1) to afford the title compound as a colorless oil. LCMS (ESI) calculated for C$_{23}$H$_{26}$F$_4$N$_4$O$_6$S (M+H)$^+$: 563, found: 563.

Step 2—Preparation of 1,1,1-trifluoro-2-methylpropan-2-yl (4-((4-fluorophenyl)sulfonyl)-2-(2-methyl-1-(2-(methylcarbamoyl)hydrazinyl)-1-oxopropan-2-yl)-3,4-dihydro-2H-benzo[b][1,4]oxazin-6-yl) carbamate

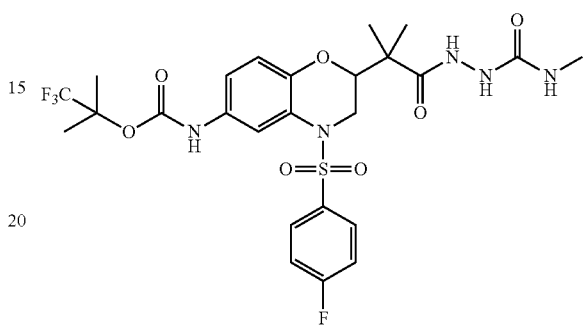

To a stirred solution at room temperature of 1,1,1-trifluoro-2-methylpropan-2-yl (4-((4-fluorophenyl)sulfonyl)-2-(1-hydrazinyl-2-methyl-1-oxopropan-2-yl)-3,4-dihydro-2H-benzo[b][1,4]oxazin-6-yl)carbamate (50 mg, 0.089 mmol) in EtOH (2 mL) was added 4-nitrophenyl methylcarbamate (52.3 mg, 0.267 mmol) in one portion. The mixture was stirred at 100° C. overnight. The mixture was concentrated and the residue was purified by prep-TLC eluting with dichloromethane:methanol (20:1) to afford the title compound as a colorless oil. LCMS (ESI) calculated for C$_{25}$H$_{29}$F$_4$N$_5$O$_7$S (M+H)$^+$: 620, found: 620.

Step 3—Preparation of 3-(2-(6-amino-4-((4-fluorophenyl)sulfonyl)-3,4-dihydro-2H-benzo[b][1,4]oxazin-2-yl)propan-2-yl)-4-methyl-1H-1,2,4-triazol-5(4H)-one

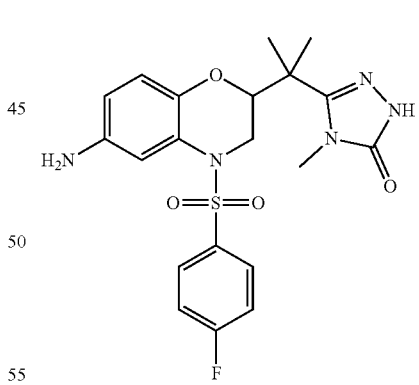

To a solution of 1,1,1-trifluoro-2-methylpropan-2-yl (4-((4-fluorophenyl)sulfonyl)-2-(1-hydrazinyl-2-methyl-1-oxopropan-2-yl)-3,4-dihydro-2H-benzo[b][1,4]oxazin-6-yl) carbamate (15 mg, 0.027 mmol) in water (2 mL) was added K$_2$CO$_3$ (18.43 mg, 0.133 mmol) in one portion at room temperature. The mixture was stirred at 110° C. for two days. The mixture was diluted with water (20 mL) and extracted three times with ethyl acetate. The combined organic layers were dried (Na$_2$SO$_4$) and concentrated. The title compound was used directly without purification. LCMS (ESI) calculated for C$_{20}$H$_{22}$FN$_5$O$_4$S (M+H)$^+$: 448, found: 448.

Step 4—Preparation of 1,1,1-trifluoro-2-methylpropan-2-yl (4-((4-fluorophenyl)sulfonyl)-2-(2-(4-methyl-5-oxo-4,5-dihydro-1H-1,2,4-triazol-3-yl)propan-2-yl)-3,4-dihydro-2H-benzo[b][1,4]oxazin-6-yl)carbamate

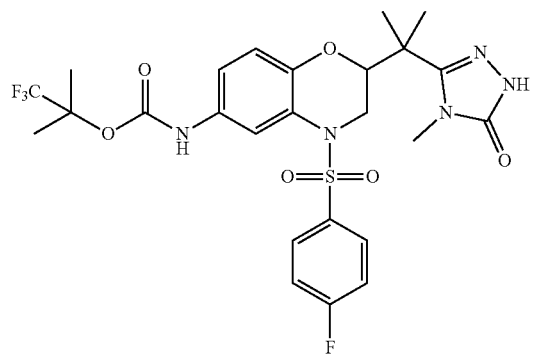 [SMILES: Cn1c(C(C)(C)C2CN(S(=O)(=O)c3ccc(F)cc3)c3cc(NC(=O)OC(C)(C)C(F)(F)F)ccc3O2)n[nH]c1=O]

To a solution of 3-(2-(6-amino-4-((4-fluorophenyl)sulfonyl)-3,4-dihydro-2H-benzo[b][1,4]oxazin-2-yl)propan-2-yl)-4-methyl-1H-1,2,4-triazol-5(4H)-one (12 mg, 0.027 mmol) in DMSO (1 mL) was added 1,1,1-trifluoro-2-methylpropan-2-yl 1H-imidazole-1-carboxylate (6.55 mg, 0.029 mmol) in one portion at room temperature. The mixture was stirred at 80° C. overnight. The mixture was diluted with water (20 mL) and extracted three times with ethyl acetate. The combined organic layers were dried (Na$_2$SO$_4$) and concentrated. The residue was purified by prep-HPLC eluting with acetonitrile with 0.75% trifluoroacetic acid in water) to afford the title compound as a white solid. LCMS (ESI) calculated for C$_{25}$H$_{27}$F$_4$N$_5$O$_6$S (M+H)$^+$: 602, found: 602. $^1$H NMR (400 MHz, CDCl$_3$) δ 9.12 (1H, br. s.), 7.69-7.79 (3H, m), 7.21-7.26 (1H, m), 7.17 (2H, t, J=8.28 Hz), 6.79 (1H, d, J=9.03 Hz), 6.69 (1H, br. s.), 4.43 (1H, d, J=13.05 Hz), 3.44 (1H, d, J=9.03 Hz), 3.32 (3H, s), 2.95 (1H, dd, J=14.56, 10.54 Hz), 1.77 (6H, s), 1.42 (3H, s), 1.40 (3H, s).

Example 42—Synthesis of (S)-tert-butyl (2-(2-oxo-2-(trifluoromethylsulfonamido)ethyl)-4-((3-(trifluoromethyl)phenyl)sulfonyl)-3,4-dihydro-2H-benzo[b][1,4]oxazin-6-yl)carbamate (42)

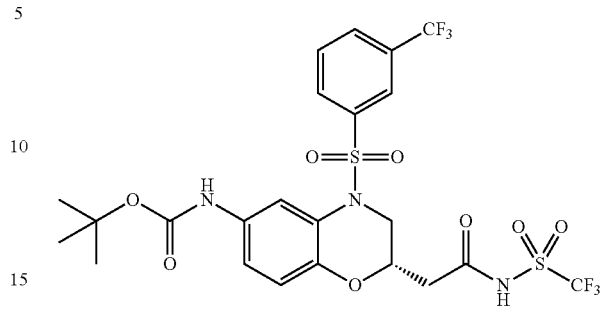

A mixture of (S)-2-(6-(((tert-butoxycarbonyl)amino)-4-((3-(trifluoromethyl)phenyl)sulfonyl)-3,4-dihydro-2H-benzo[b][1,4]oxazin-2-yl)acetic acid (500 mg, 0.968 mmol), trifluoromethanesulfonamide (173 mg, 1.162 mmol), 4-N,N-dimethylaminopyridine (142 mg, 1.16 mmol), 1-ethyl-3-(3-dimethylaminopropyl)carbodiimide (371 mg, 1.936 mmol), and dichloromethane (6450 μL) was stirred at room temperature for 16 hours. The mixture was concentrated, dissolved in DMSO, filtered, and purified directly by reverse-phase HPLC using a gradient solvent system of 10-100% MeCN/water modified with 0.1% TFA. The product-containing fractions were collected, diluted with ethyl acetate and washed with pH 3 buffer. The aqueous phase was extracted with ethyl acetate, and then the combined organic layers were washed with saturated aqueous sodium chloride, dried (MgSO4) and concentrated to yield (S)-tert-butyl (2-(2-oxo-2-(trifluoromethylsulfonamido)ethyl)-4-((3-(trifluoromethyl)phenyl)sulfonyl)-3,4-dihydro-2H-benzo[b][1,4]oxazin-6-yl)carbamate as a white foam. MS ESI calculated for C$_{19}$H$_{16}$F$_6$N$_3$O$_8$S$_2$ (M-tBu+H)$^+$: 592, Found: 592. $^1$H NMR (600 MHz, DMSO-d6) δ 9.22 (s, 1H), 8.09 (d, J=8.1 Hz, 1H), 8.03 (s, 1H), 8.02 (s, 1H), 7.99 (s, 1H), 7.79 (t, J=7.9 Hz, 1H), 6.98 (d, J=8.7 Hz, 1H), 6.64 (d, J=8.8 Hz, 1H), 4.48 (dd, J=14.0, 2.3 Hz, 1H), 3.71 (s, 1H), 3.25 (dd, J=14.1, 9.7 Hz, 1H), 2.39 (dd, J=16.0, 5.5 Hz, 1H), 2.32 (dd, J=16.0, 7.7 Hz, 1H), 1.44 (s, 9H).

Example 43—Preparation of Additional Sulfonylamides of Benzoxazines

The compounds in Table 15 below were prepared based on the experimental procedures described in Examples 42 and elsewhere in the detailed description, and can be achieved by one of skill in the art in light of the present disclosure.

TABLE 15

| Ex. No. | Structure | Name | Observed m/z |
|---|---|---|---|
| 43A | 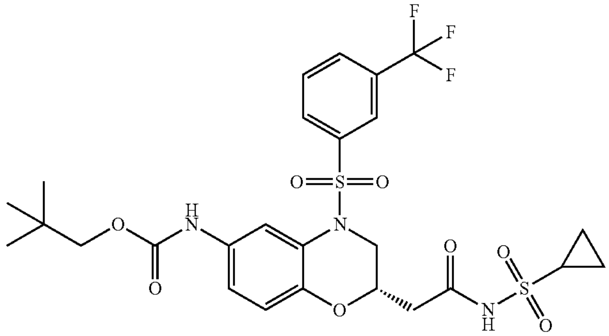 [SMILES: CC(C)(C)COC(=O)Nc1ccc2c(c1)N(S(=O)(=O)c1cccc(C(F)(F)F)c1)C[C@H](CC(=O)NS(=O)(=O)C1CC1)O2] | (S)-neopentyl (2-(2-(cyclopropanesulfonamido)-2-oxoethyl)-4-((3-(trifluoromethyl)phenyl)sulfonyl)-3,4-dihydro-2H-benzo[b][1,4]oxazin-6-yl)carbamate | 634 (M + H)$^+$ |

TABLE 15-continued

| Ex. No. | Structure | Name | Observed m/z |
|---|---|---|---|
| 43B | 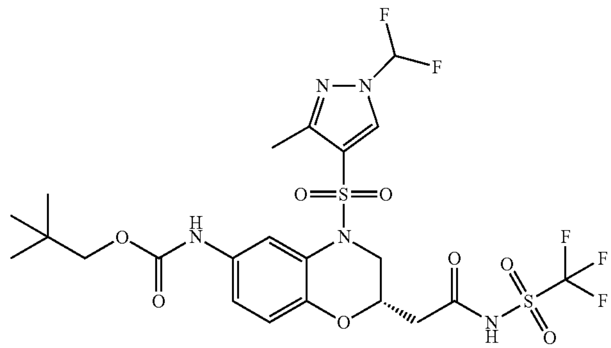 [SMILES: Cc1nn(C(F)F)cc1S(=O)(=O)N1C[C@H](CC(=O)NS(=O)(=O)C(F)(F)F)Oc2ccc(NC(=O)OCC(C)(C)C)cc21] | (S)-neopentyl (4-((1-(difluoromethyl)-3-methyl-1H-pyrazol-4-yl)sulfonyl)-2-(2-oxo-2-(trifluoromethyl-sulfonamido)ethyl)-3,4-dihydro-2H-benzo[b][1,4]oxazin-6-yl)carbamate | 670.2 (M + Na)+ |
| 43C | 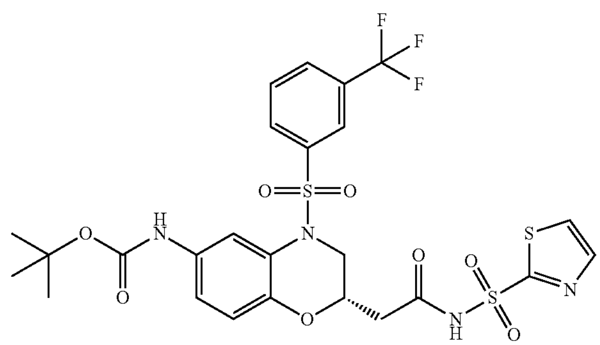 [SMILES: CC(C)(C)OC(=O)Nc1ccc2c(c1)N(S(=O)(=O)c1cccc(C(F)(F)F)c1)C[C@H](CC(=O)NS(=O)(=O)c1nccs1)O2] | (S)-tert-butyl (2-(2-oxo-2-(thiazole-2-sulfonamido)ethyl)-4-((3-(trifluoromethyl)phenyl)sulfonyl)-3,4-dihydro-2H-benzo[b][1,4]oxazin-6-yl)carbamate | 663 (M + H)+ |
| 43D | 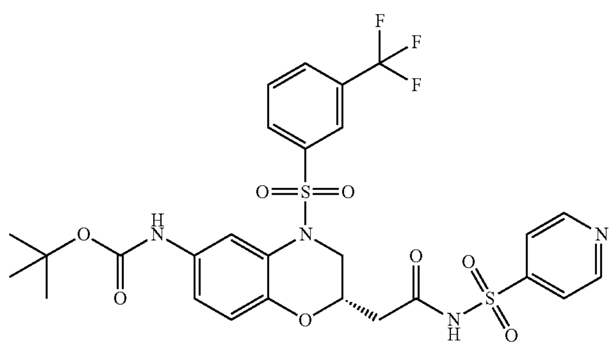 [SMILES: CC(C)(C)OC(=O)Nc1ccc2c(c1)N(S(=O)(=O)c1cccc(C(F)(F)F)c1)C[C@H](CC(=O)NS(=O)(=O)c1ccncc1)O2] | (S)-tert-butyl (2-(2-oxo-2-(pyridine-4-sulfonamido)ethyl)-4-((3-(trifluoromethyl)phenyl)sulfonyl)-3,4-dihydro-2H-benzo[b][1,4]oxazin-6-yl)carbamate | 657 (M + H)+ |
| 43E | 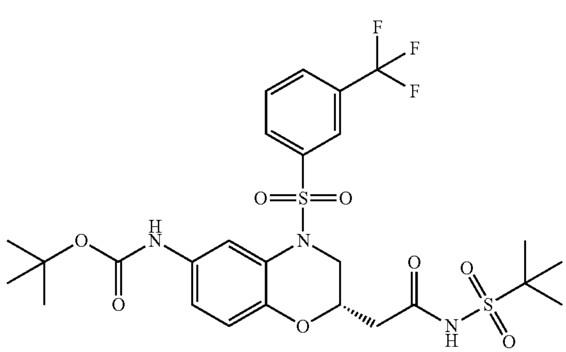 [SMILES: CC(C)(C)OC(=O)Nc1ccc2c(c1)N(S(=O)(=O)c1cccc(C(F)(F)F)c1)C[C@H](CC(=O)NS(=O)(=O)C(C)(C)C)O2] | (S)-tert-buty (2-(2-(1,1-dimethylethylsulfonamido)-2-oxoethyl)-4-((3-(trifluoromethyl)phenyl)sulfonyl)-3,4-dihydro-2H-benzo[b][1,4]oxazin-6-yl)carbamate | 580 (M − tBu + H)+ |

TABLE 15-continued

| Ex. No. | Structure | Name | Observed m/z |
|---|---|---|---|
| 43F | 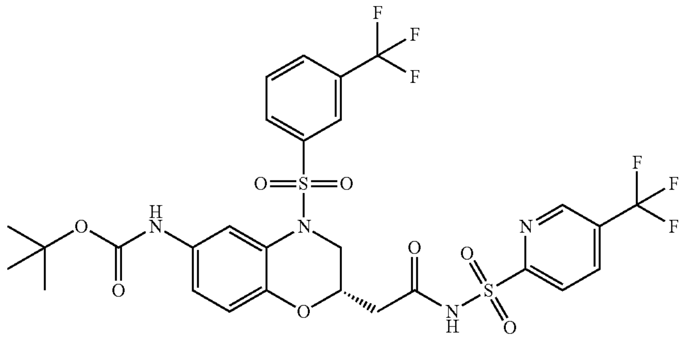 [SMILES: CC(C)(C)OC(=O)Nc1ccc2c(c1)N(S(=O)(=O)c1cccc(C(F)(F)F)c1)C[C@H](CC(=O)NS(=O)(=O)c1ccc(C(F)(F)F)cn1)O2] | (S)-tert-butyl (2-(2-oxo-2-(5-(trifluoromethyl)pyridine-2-sulfonamido)ethyl)-4-((3-(trifluoromethyl)phenyl)sulfonyl)-3,4-dihydro-2H-benzo[b][1,4]oxazin-6-yl)carbamate | 725 (M + H)+ |
| 43G | 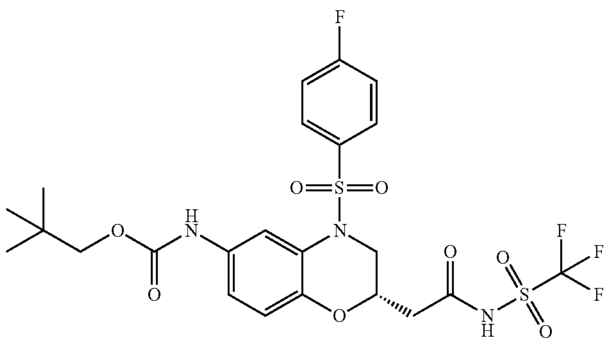 [SMILES: CC(C)(C)COC(=O)Nc1ccc2c(c1)N(S(=O)(=O)c1ccc(F)cc1)C[C@H](CC(=O)NS(=O)(=O)C(F)(F)F)O2] | (S)-neopentyl (4-((4-fluorophenyl)sulfonyl)-2-(2-oxo-2-(trifluoromethyl-sulfonamido)ethyl)-3,4-dihydro-2H-benzo[b][1,4]oxazin-6-yl)carbamate | |
| 43H | 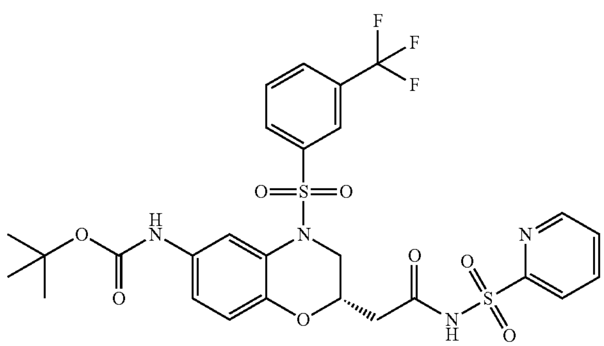 [SMILES: CC(C)(C)OC(=O)Nc1ccc2c(c1)N(S(=O)(=O)c1cccc(C(F)(F)F)c1)C[C@H](CC(=O)NS(=O)(=O)c1ccccn1)O2] | (S)-tert-butyl (2-(2-oxo-2-(pyridine-2-sulfonamido)ethyl)-4-((3-(trifluoromethyl phenyl)sulfonyl)-3,4-dihydro-2H-benzo[b][1,4]oxazin-6-yl)carbamate | 657 (M + H)+ |
| 43i | 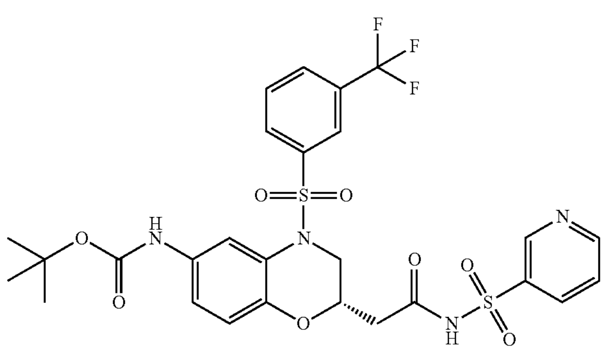 [SMILES: CC(C)(C)OC(=O)Nc1ccc2c(c1)N(S(=O)(=O)c1cccc(C(F)(F)F)c1)C[C@H](CC(=O)NS(=O)(=O)c1cccnc1)O2] | (S)-tert-butyl (2-(2-oxo-2-(pyridine-3-sulfonamido)ethyl)-4-((3-(trifluoromethyl)phenyl)sulfonyl)-3,4-dihydro-2H-benzo[b][1,4]oxazin-6-yl)carbamate | 657 (M + H)+ |

TABLE 15-continued

| Ex. No. | Structure | Name | Observed m/z |
|---|---|---|---|
| 43J | 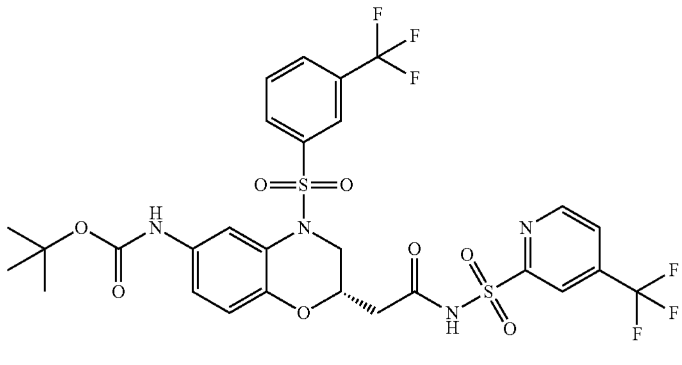 [SMILES: CC(C)(C)OC(=O)Nc1ccc2c(c1)N(S(=O)(=O)c1cccc(C(F)(F)F)c1)C[C@H](CC(=O)NS(=O)(=O)c1cc(C(F)(F)F)ccn1)O2] | (S)-tert-butyl (2-(2-oxo-2-(4-(trifluoromethyl)pyridine-2-sulfonamido)ethyl)-4-((3-(trifluoromethyl)phenyl)sulfonyl)-3,4-dihydro-2H-benzo[b][1,4]oxazin-6-yl)carbamate | 725 (M + H)+ |
| 43K | 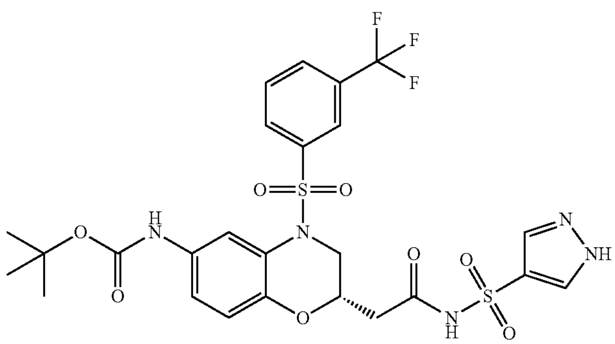 [SMILES: CC(C)(C)OC(=O)Nc1ccc2c(c1)N(S(=O)(=O)c1cccc(C(F)(F)F)c1)C[C@H](CC(=O)NS(=O)(=O)c1cn[nH]c1)O2] | (S)-tert-butyl (2-(2-oxo-2-(1H-pyrazole-4-sulfonamido)ethyl)-4-((3-(trifluoromethyl)phenyl)sulfonyl)-3,4-dihydro-2H-benzo[b][1,4]oxazin-6-yl)carbamate | 646 (M + H)+ |
| 43L | 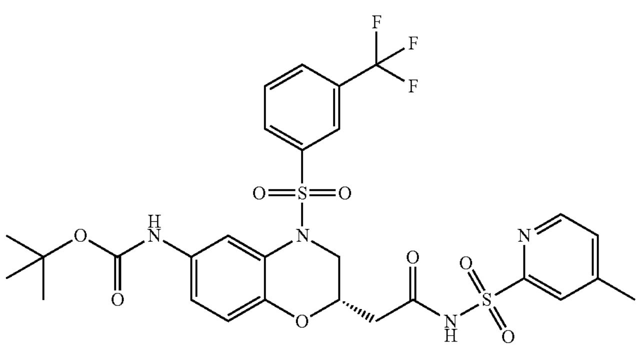 [SMILES: Cc1ccnc(S(=O)(=O)NC(=O)C[C@H]2CN(S(=O)(=O)c3cccc(C(F)(F)F)c3)c3cc(NC(=O)OC(C)(C)C)ccc3O2)c1] | (S)-tert-butyl (2-(2-(4-methylpyridine-2-sulfonamido)-2-oxoethyl)-4-((3-(trifluoromethyl)phenyl)sulfonyl)-3,4-dihydro-2H-benzo[b][1,4]oxazin-6-yl)carbamate | 671 (M + H)+ |
| 43M | 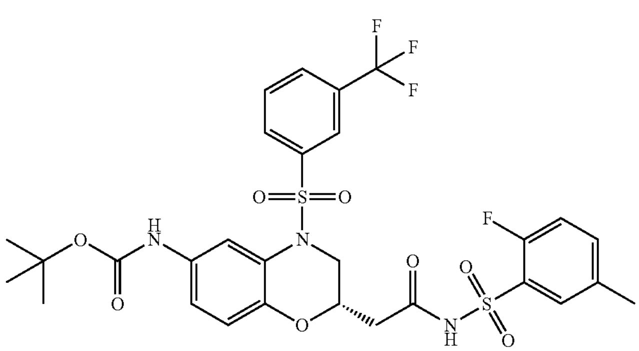 | (S)-tert-butyl (2-(2-(2-fluoro-5-methylphenyl-sulfonamido)-2-oxoethyl)-4-((3-(trifluoromethyl(phenyl)sulfonyl)-3,4-dihydro-2H-benzo[b][1,4]oxazin-6-yl)carbamate | 688 (M + H)+ |

TABLE 15-continued

| Ex. No. | Structure | Name | Observed m/z |
|---|---|---|---|
| 43N | 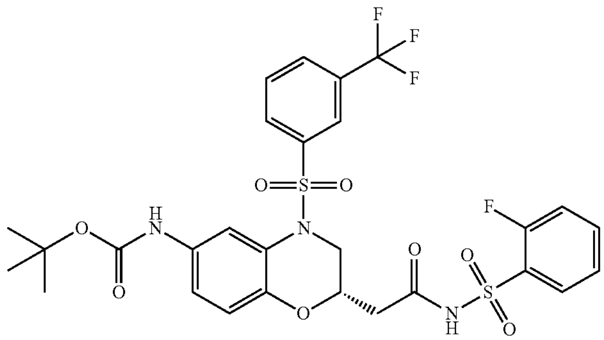 [SMILES: CC(C)(C)OC(=O)Nc1ccc2c(c1)N(S(=O)(=O)c1cccc(C(F)(F)F)c1)C[C@H](CC(=O)NS(=O)(=O)c1ccccc1F)O2] | (S)-tert-butyl (2-(2-(2-fluorophenylsulfonamido)-2-oxoethyl)-4-((3-(trifluoromethyl)phenyl)sulfonyl)-3,4-dihydro-2H-benzo[b][1,4]oxazin-6-yl)carbamate | 674 (M + H)+ |
| 43o | 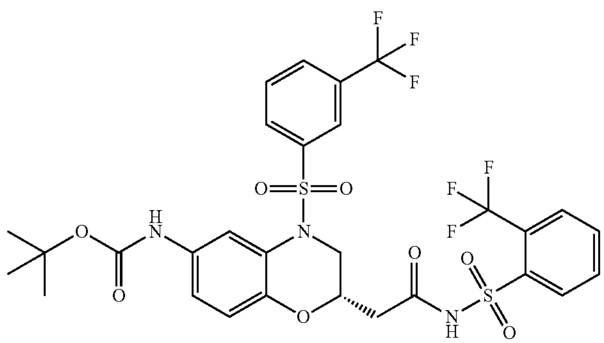 [SMILES: CC(C)(C)OC(=O)Nc1ccc2c(c1)N(S(=O)(=O)c1cccc(C(F)(F)F)c1)C[C@H](CC(=O)NS(=O)(=O)c1ccccc1C(F)(F)F)O2] | (S)-tert-butyl (2-(2-oxo-2-(2-(trifluoromethyl)phenyl-sulfonamido)ethyl)-4-((3-(trifluoromethyl)phenyl)sulfonyl)-3,4-dihydro-2H-benzo[b][1,4]oxazin-6-yl)carbamate | 724 (M + H)+ |
| 43P | 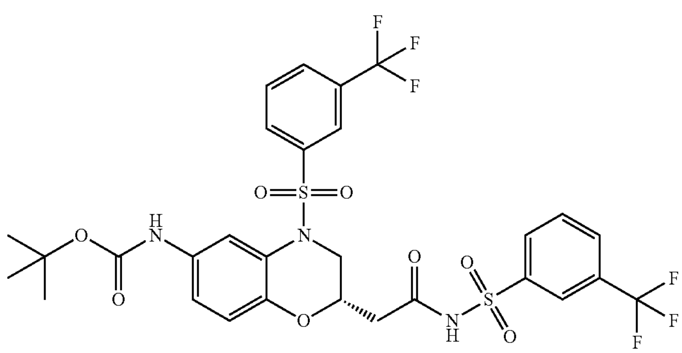 [SMILES: CC(C)(C)OC(=O)Nc1ccc2c(c1)N(S(=O)(=O)c1cccc(C(F)(F)F)c1)C[C@H](CC(=O)NS(=O)(=O)c1cccc(C(F)(F)F)c1)O2] | (S)-tert-butyl (2-(2-oxo-2-(3-(trifluoromethyl)phenyl-sulfonamido)ethyl)-4-((3-(trifluoromethyl)phenyl)sulfonyl)-3,4-dihydro-2H-benzo[b][1,4]oxazin-6-yl)carbamate | 724 (M + H)+ |
| 43Q | 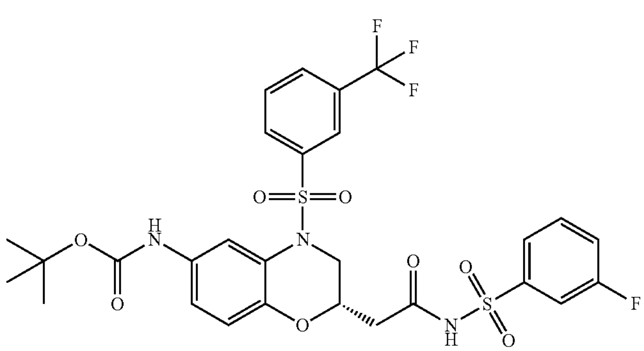 [SMILES: CC(C)(C)OC(=O)Nc1ccc2c(c1)N(S(=O)(=O)c1cccc(C(F)(F)F)c1)C[C@H](CC(=O)NS(=O)(=O)c1cccc(F)c1)O2] | (S)-tert-butyl (2-(2-(3-fluorophenyl-sulfonamido)-2-oxoethyl)-4-((3-(trifluoromethyl)phenyl)sulfonyl)-3,4-dihydro-2H-benzo[b][1,4]oxazin-6-yl)carbamate | 674 (M + H)+ |

TABLE 15-continued

| Ex. No. | Structure | Name | Observed m/z |
|---|---|---|---|
| 43R | 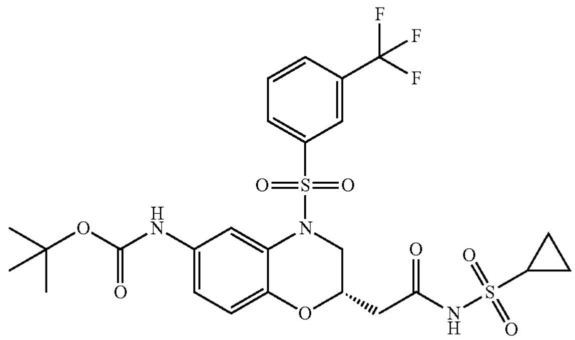 [SMILES: CC(C)(C)OC(=O)Nc1ccc2c(c1)N(S(=O)(=O)c1cccc(C(F)(F)F)c1)C[C@H](CC(=O)NS(=O)(=O)C1CC1)O2] | (S)-tert-butyl (2-(2-(cyclopropane-sulfonamido)-2-oxoethyl)-4-((3-(trifluoromethyl)phenyl)sulfonyl)-3,4-dihydro-2H-benzo[b][1,4]oxazin-6-yl)carbamate | 564 (M − tBu + H)+ |
| 43S | 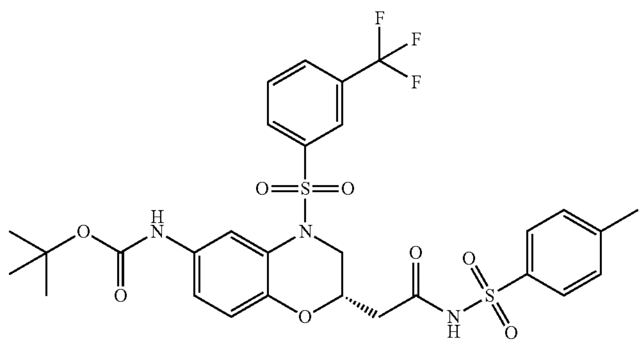 [SMILES: Cc1ccc(S(=O)(=O)NC(=O)C[C@H]2CN(S(=O)(=O)c3cccc(C(F)(F)F)c3)c3cc(NC(=O)OC(C)(C)C)ccc3O2)cc1] | (S)-tert-butyl (2-(2-(4-methylphenyl-sulfonamido)-2-oxoethyl)-4-((3-(trifluoro-methyl)phenyl)sulfonyl)-3,4-dihydro-2H-benzo[b][1,4]oxazin-6-yl)carbamate | 614 (M − tBu + H)+ |
| 43T | 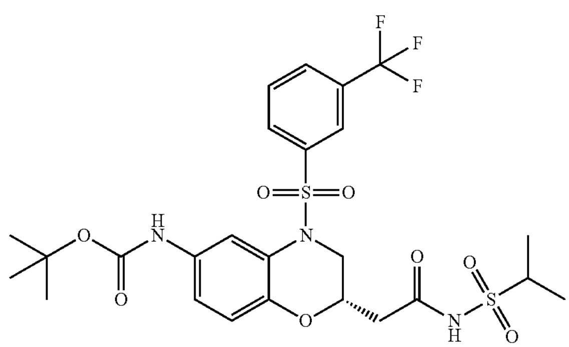 [SMILES: CC(C)S(=O)(=O)NC(=O)C[C@H]1CN(S(=O)(=O)c2cccc(C(F)(F)F)c2)c2cc(NC(=O)OC(C)(C)C)ccc2O1] | (S)-tert-butyl (2-(2-(1-methylethylsulfonamido)-2-oxoethyl)-4-((3-(trifluoromethyl)phenyl)sulfonyl)-3,4-dihydro-2H-benzo[b][1,4]oxazin-6-yl)carbamate | 639 (M + NH4)+ |
| 43U | 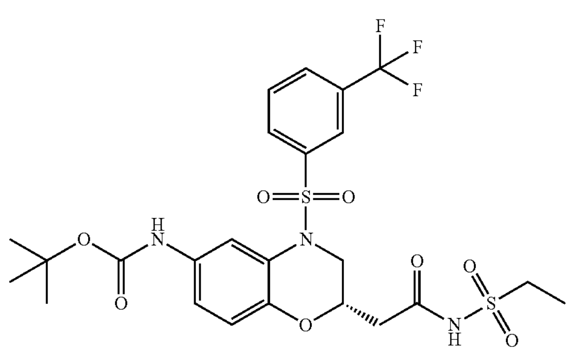 [SMILES: CCS(=O)(=O)NC(=O)C[C@H]1CN(S(=O)(=O)c2cccc(C(F)(F)F)c2)c2cc(NC(=O)OC(C)(C)C)ccc2O1] | (S)-tert-butyl (2-(2-(ethylsulfonamido)-2-oxoethyl)-4-((3-(trifluoromethyl)phenyl)sulfonyl)-3,4-dihydro-2H-benzo[b][1,4]oxazin-6-yl)carbamate | 625 (M + NH4)+ |

TABLE 15-continued

| Ex. No. | Structure | Name | Observed m/z |
|---|---|---|---|
| 43V | 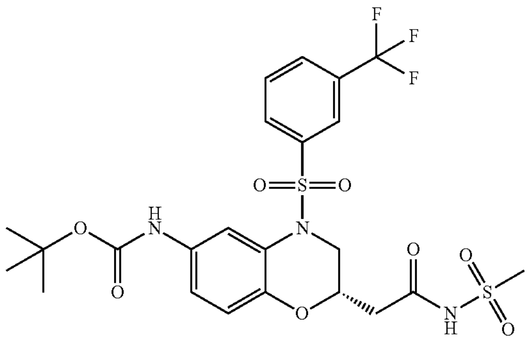 [SMILES: CC(C)(C)OC(=O)Nc1ccc2c(c1)N(S(=O)(=O)c1cccc(C(F)(F)F)c1)C[C@H](CC(=O)NS(C)(=O)=O)O2] | (S)-tert-butyl (2-(2-(methylsulfonamido)-2-oxoethyl)-4-((3-(trifluoromethyl)phenyl)sulfonyl)-3,4-dihydro-2H-benzo[b][1,4]oxazin-6-yl)carbamate | 611 (M + NH₄)⁺ |
| 43W | 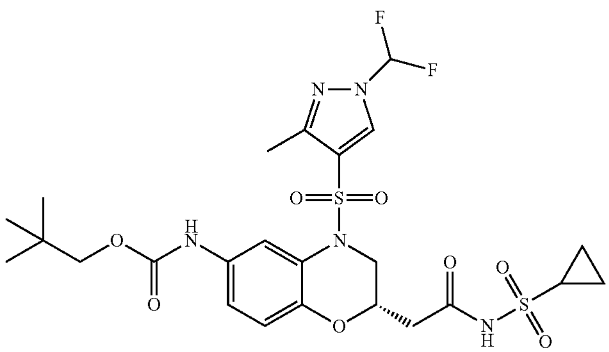 [SMILES: Cc1nn(C(F)F)cc1S(=O)(=O)N1C[C@H](CC(=O)NS(=O)(=O)C2CC2)Oc2ccc(NC(=O)OCC(C)(C)C)cc21] | (S-neopentyl (2-(2-(cyclopropane-sulfonamido)-2-oxoethyl)-4-((1-(difluoromethyl)-3-methyl-1H-pyrazol-4-yl)sulfonyl)-3,4-dihydro-2H-benzo[b][1,4]oxazin-6-yl) carbamate | 620 (M + H)⁺ |
| 43X | 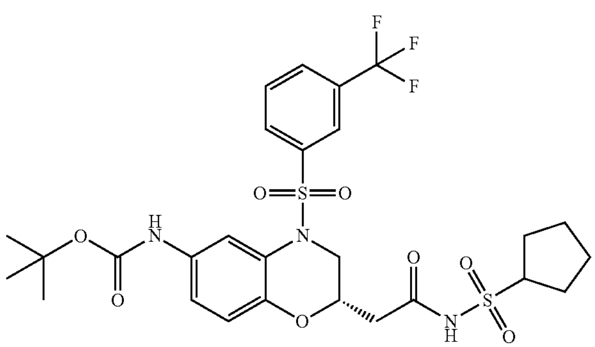 [SMILES: CC(C)(C)OC(=O)Nc1ccc2c(c1)N(S(=O)(=O)c1cccc(C(F)(F)F)c1)C[C@H](CC(=O)NS(=O)(=O)C1CCCC1)O2] | (S)-tert-butyl (2-(2-(cyclopentane-sulfonamido)-2-oxoethyl)-4-((3-(trifluoromethyl)phenyl)sulfonyl)-3,4-dihydro-2H-benzo[b][1,4]oxazin-6-yl)carbamate | 648 (M + H)⁺ |
| 43Y | 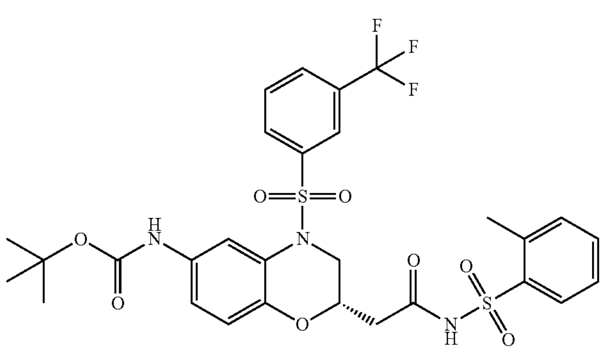 [SMILES: Cc1ccccc1S(=O)(=O)NC(=O)C[C@H]1CN(S(=O)(=O)c2cccc(C(F)(F)F)c2)c2cc(NC(=O)OC(C)(C)C)ccc2O1] | (S)-tert-butyl (2-(2-(2-methylphenyl-sulfonamido)-2-oxoethyl)-4-((3-(trifluoromethyl)phenyl)sulfonyl)-3,4-dihydro-2H-benzo[b][1,4]oxazin-6-yl)carbamate | 670 (M + H)⁺ |

TABLE 15-continued

| Ex. No. | Structure | Name | Observed m/z |
|---|---|---|---|
| 43Z | 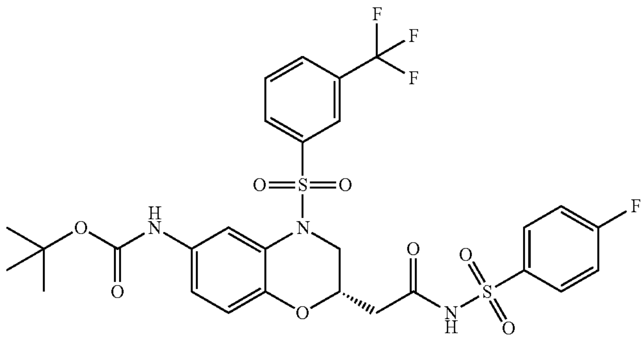 [SMILES: CC(C)(C)OC(=O)Nc1ccc2c(c1)N(S(=O)(=O)c1cccc(C(F)(F)F)c1)C[C@H](CC(=O)NS(=O)(=O)c1ccc(F)cc1)O2] | (S)-tert-butyl (2-(2-(4-fluorophenyl-sulfonamido)-2-oxoethyl)-4-((3-(trifluoromethyl)phenyl)sulfonyl)-3,4-dihydro-2H-benzo[b][1,4]oxazin-6-yl)carbamate | 674 (M + H)+ |
| 43AA | 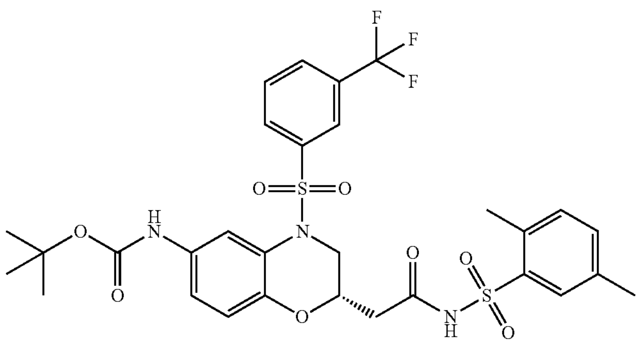 [SMILES: Cc1ccc(C)c(S(=O)(=O)NC(=O)C[C@H]2CN(S(=O)(=O)c3cccc(C(F)(F)F)c3)c3cc(NC(=O)OC(C)(C)C)ccc3O2)c1] | (S)-tert-butyl (2-(2-(2,5-dimethylphenyl-sulfonamido)-2-oxoethyl)-4-((3-(trifluoromethyl)phenyl)sulfonyl)-3,4-dihydro-2H-benzo[b][1,4]oxazin-6-yl)carbamate | 684 (M + H)+ |
| 43AB | 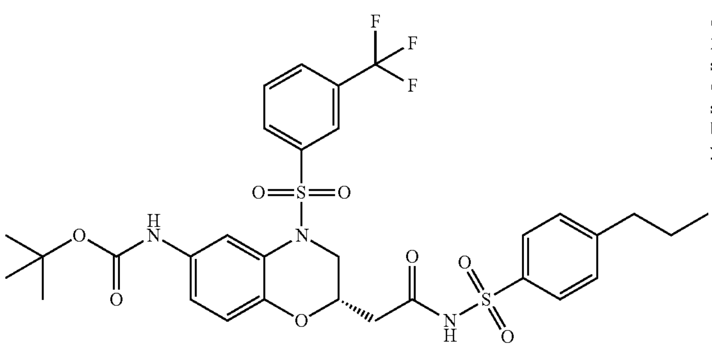 [SMILES: CCCc1ccc(S(=O)(=O)NC(=O)C[C@H]2CN(S(=O)(=O)c3cccc(C(F)(F)F)c3)c3cc(NC(=O)OC(C)(C)C)ccc3O2)cc1] | (S)-tert-butyl (2-(2-oxo-2-(4-propylphenyl-sulfonamido)ethyl)-4-((3-(trifluoromethyl)phenyl)sulfonyl)-3,4-dihydro-2H-benzo[b][1,4]oxazin-6-yl)carbamate | 698 (M + H)+ |
| 43AC | 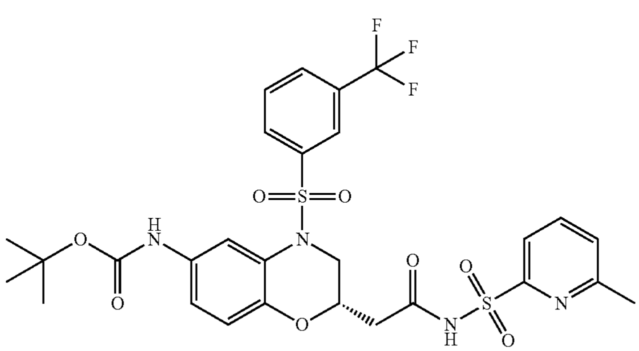 [SMILES: Cc1cccc(S(=O)(=O)NC(=O)C[C@H]2CN(S(=O)(=O)c3cccc(C(F)(F)F)c3)c3cc(NC(=O)OC(C)(C)C)ccc3O2)n1] | (S)-tert-butyl (2-(2-(6-methylpyridine-2-sulfonamido)-2-oxoethyl)-4-((3-(trifluoromethyl)phenyl)sulfonyl)-3,4-dihydro-2H-benzo[b][1,4]oxazin-6-yl)carbamate | 671 (M + H)+ |

US 9,809,561 B2

TABLE 15-continued

| Ex. No. | Structure | Name | Observed m/z |
|---|---|---|---|
| 43AD | 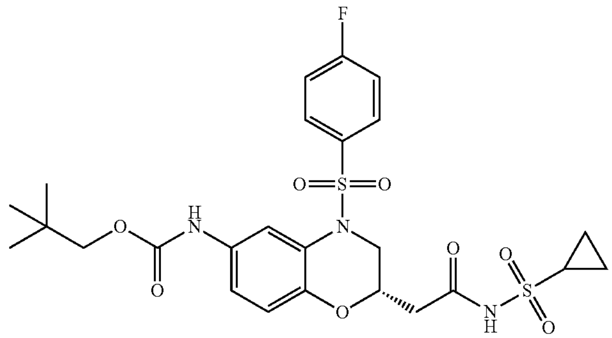 [SMILES: CC(C)(C)COC(=O)Nc1ccc2c(c1)N(S(=O)(=O)c1ccc(F)cc1)C[C@H](CC(=O)NS(=O)(=O)C1CC1)O2] | (S)-neopentyl (2-(2-(cyclopropane-sulfonamido)-2-oxoethyl)-4-((4-fluorophenyl)sulfonyl)-3,4-dihydro-2H-benzo[b][1,4]oxazin-6-yl)carbamate | 584.0 (M + H)+ |

Example 44—Synthesis of (S)-(2-(2-(methoxyamino)-2-oxoethyl)-4-((3-(trifluoromethyl)phenyl)sulfonyl)-3,4-dihydro-2H-benzo[b][1,4]oxazin-6-yl)carbamic Acid (44)

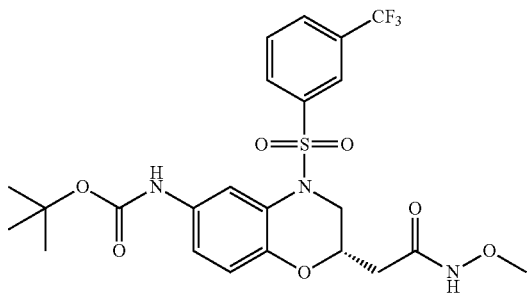 [SMILES: CONC(=O)C[C@H]1CN(S(=O)(=O)c2cccc(C(F)(F)F)c2)c2cc(NC(=O)OC(C)(C)C)ccc2O1]

A mixture of (S)-2-(6-(((tert-butoxycarbonyl)amino)-4-((3-(trifluoromethyl)phenyl)sulfonyl)-3,4-dihydro-2H-benzo[b][1,4]oxazin-2-yl)acetic acid (100 mg, 0.194 mmol), O-methylhydroxylamine hydrochloride (19.4 mg, 0.232 mmol), (O-(7-azabenzotriazol-1-yl)-N,N,N',N'-tetramethyl-uronium hexafluorophosphate) (103 mg, 0.271 mmol), DMF (1290 µL), and N,N'-diisopropylethylamine (101 µL, 0.581 mmol) was stirred at room temperature for sixteen hours. The reaction was filtered, and purified directly by mass-directed reverse phase HPLC using a mobile phase of MeCN/water modified with 0.1% TFA to afford (S)-(2-(2-(methoxyamino)-2-oxoethyl)-4-((3-(trifluoromethyl)phenyl)sulfonyl)-3,4-dihydro-2H-benzo[b][1,4]oxazin-6-yl) carbamic acid as a white solid. MS ESI calculated for $C_{19}H_{19}F_3N_3O_7S$ (M+H)+: 490, Found: 490. $^1$H NMR (600 MHz, DMSO-d6) δ 11.09 (s, 1H), 9.25 (s, 1H), 8.10-7.94 (m, 4H), 7.82 (t, J=8.0 Hz, 1H), 7.00 (d, J=8.8 Hz, 1H), 6.66 (d, J=8.9 Hz, 1H), 4.39 (dd, J=14.0, 2.2 Hz, 1H), 3.82 (s, 1H), 3.55 (s, 3H), 3.37 (dd, J=14.0, 9.4 Hz, 1H), 2.35 (dd, J=14.9, 5.6 Hz, 1H), 2.22 (dd, J=15.0, 7.2 Hz, 1H), 1.44 (s, 9H).

Example 45—Preparation of Additional Hydroxamates of Benzoxazines

The compounds in Table 16 below were prepared based on the experimental procedures described in Example 44 and elsewhere in the detailed description, and can be achieved by one of skill in the art in light of the present disclosure.

TABLE 16

| Ex. No. | Structure | Name | Observed m/z |
|---|---|---|---|
| 45A | 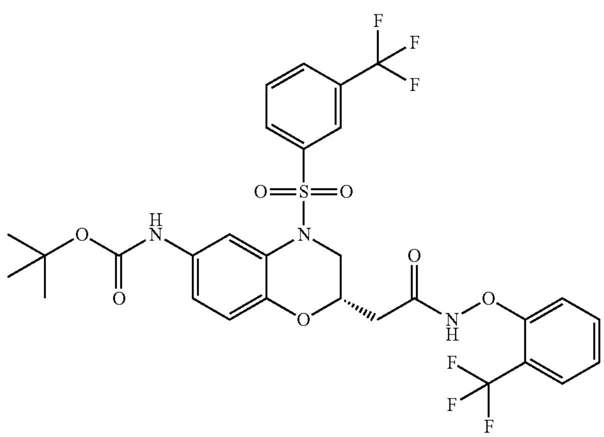 [SMILES: CC(C)(C)OC(=O)Nc1ccc2c(c1)N(S(=O)(=O)c1cccc(C(F)(F)F)c1)C[C@H](CC(=O)NOc1ccccc1C(F)(F)F)O2] | (S)-tert-butyl (2-(2-oxo-2-((2-(trifluoromethyl)phenoxy)amino)ethyl)(trifluoromethyl)phenyl)sulfonyl)-3,4-dihydro-2H-benzo[b][1,4]oxazin-6-yl)carbamate | 676 (M + H)+ |

TABLE 16-continued

| Ex. No. | Structure | Name | Observed m/z |
|---|---|---|---|
| 45B | 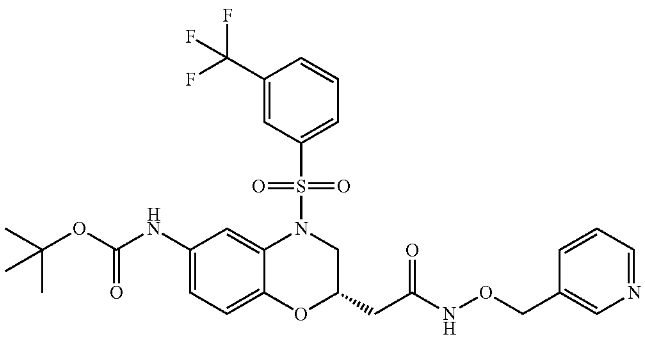 [SMILES: CC(C)(C)OC(=O)Nc1ccc2c(c1)N(S(=O)(=O)c1cccc(C(F)(F)F)c1)C[C@H](CC(=O)NOCc1cccnc1)O2] | (S)-tert-butyl (2-(2-oxo-2-((pyridin-3-ylmethoxy)amino)ethyl)-4-((3-(trifluoromethyl)phenyl)sulfonyl)-3,4-dihydro-2H-benzo[b][1,4]oxazin-6-yl)carbamate | 623 (M + H)+ |
| 45C | 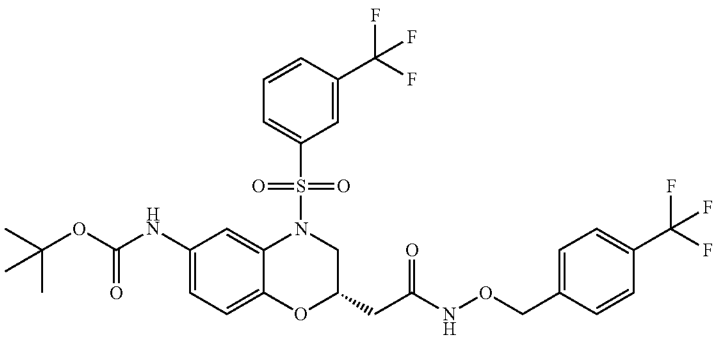 [SMILES: CC(C)(C)OC(=O)Nc1ccc2c(c1)N(S(=O)(=O)c1cccc(C(F)(F)F)c1)C[C@H](CC(=O)NOCc1ccc(C(F)(F)F)cc1)O2] | (S)-tert-butyl (2-(2-oxo-2-(((4-(trifluoromethyl)benzyl)oxy)amino)ethyl)-4-((3-(trifluoromethyl)phenyl)sulfonyl)-3,4-dihydro-2H-benzo[b][1,4]oxazin-6-yl)carbamate | 690 (M + H)+ |
| 45D | 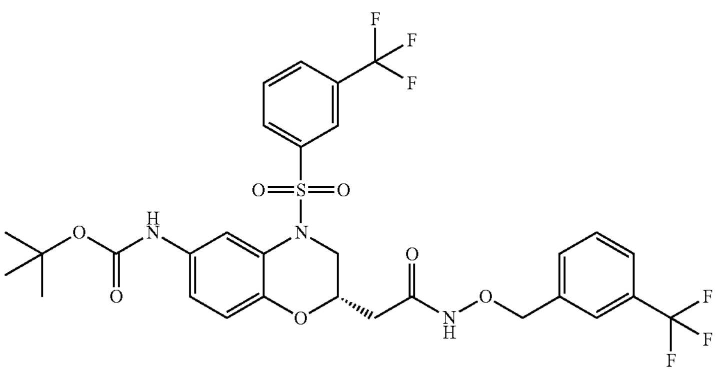 [SMILES: CC(C)(C)OC(=O)Nc1ccc2c(c1)N(S(=O)(=O)c1cccc(C(F)(F)F)c1)C[C@H](CC(=O)NOCc1cccc(C(F)(F)F)c1)O2] | (S)-tert-butyl (2-(2-oxo-2-(((3-(trifluoromethyl)benzyl)oxy)amino)ethyl)-4-((3-(trifluoromethyl)phenyl)sulfonyl)-3,4-dihydro-2H-benzo[b][1,4]oxazin-6-yl)carbamate | 690 (M + H)+ |
| 45E | 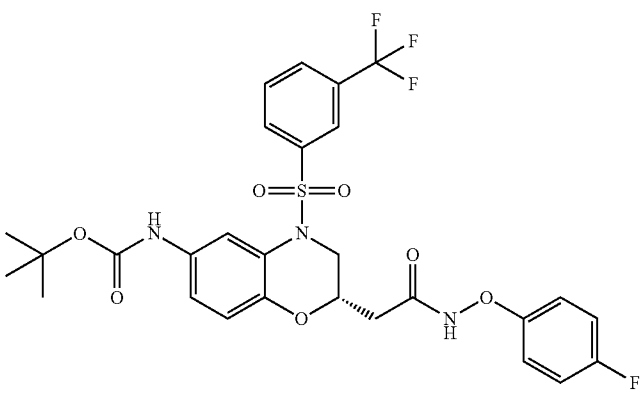 [SMILES: CC(C)(C)OC(=O)Nc1ccc2c(c1)N(S(=O)(=O)c1cccc(C(F)(F)F)c1)C[C@H](CC(=O)NOc1ccc(F)cc1)O2] | (S)-tert-butyl (2-(2-((4-fluorophenoxy)amino)-2-oxoethyl)-4-((3-(trifluoromethyl)phenyl)sulfonyl)-3,4-dihydro-2H-benzo[b][1,4]oxazin-6-yl)carbamate | 626 (M + H)+ |

TABLE 16-continued

| Ex. No. | Structure | Name | Observed m/z |
|---|---|---|---|
| 45F | 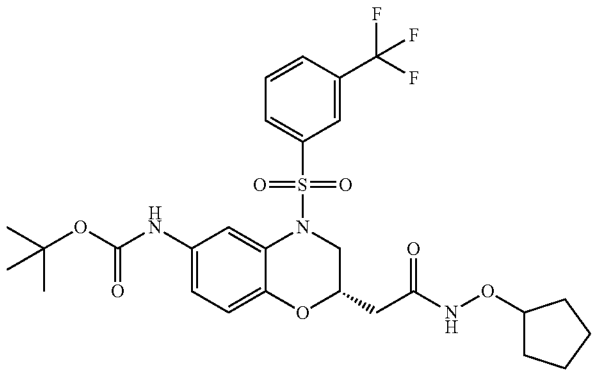 [SMILES: CC(C)(C)OC(=O)Nc1ccc2c(c1)N(S(=O)(=O)c1cccc(C(F)(F)F)c1)C[C@H](CC(=O)NOC1CCCC1)O2] | (S)-tert-butyl (2-(2-((cyclopentyloxy)amino)-2-oxoethyl)-4-((3-(trifluoromethyl)phenyl)sulfonyl)-3,4-dihydro-2H-benzo[b][1,4]oxazin-6-yl)carbamate | 600 (M + H)+ |
| 45G | 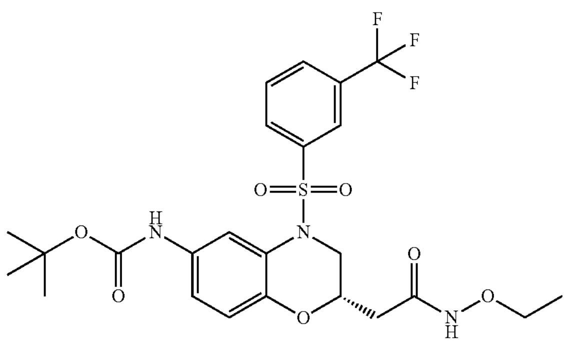 | (S)-tert-butyl (2-(2-(ethoxyamino)-2-oxoethyl)-4-((3-(trifluoromethyl)phenyl)sulfonyl)-3,4-dihydro-2H-benzo[b][1,4]oxazin-6-yl)carbamate | 560 (M + H)+ |
| 45H | 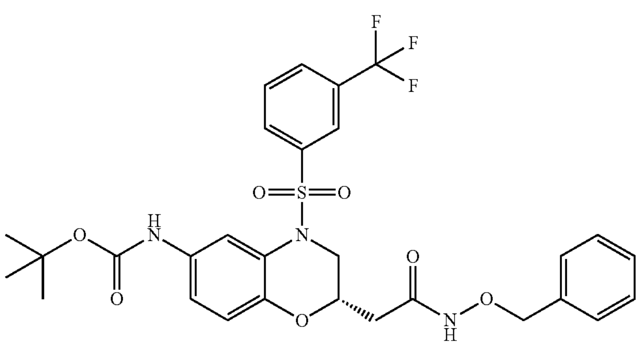 [SMILES: CC(C)(C)OC(=O)Nc1ccc2c(c1)N(S(=O)(=O)c1cccc(C(F)(F)F)c1)C[C@H](CC(=O)NOCc1ccccc1)O2] | (S)-tert-butyl (2-(2-((benzyloxy)amino)-2-oxoethyl)-4-((3-(trifluoromethyl)phenyl)sulfonyl)-3,4-dihydro-2H-benzo[b][1,4]oxazin-6-yl)carbamate | 622 (M + H)+ |
| 45i | 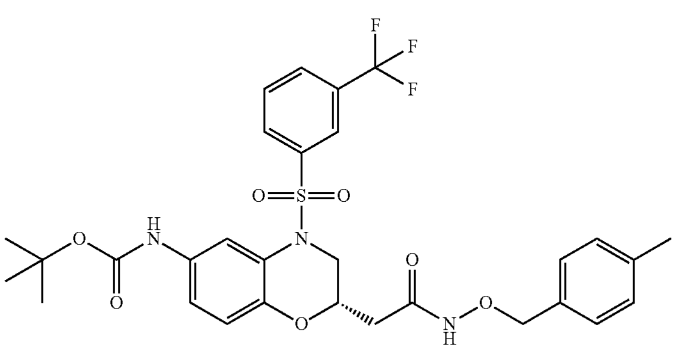 [SMILES: Cc1ccc(CONC(=O)C[C@H]2CN(S(=O)(=O)c3cccc(C(F)(F)F)c3)c3cc(NC(=O)OC(C)(C)C)ccc3O2)cc1] | (S)-tert-butyl (2-(2-(((4-methylbenzyl)oxy)amino)-2-oxoethyl)-4-((3-(trifluoromethyl)phenyl)sulfonyl)-3,4-dihydro-2H-benzo[b][1,4]oxazin-6-yl)carbamate | 636 (M + H)+ |

TABLE 16-continued

| Ex. No. | Structure | Name | Observed m/z |
|---|---|---|---|
| 45J | 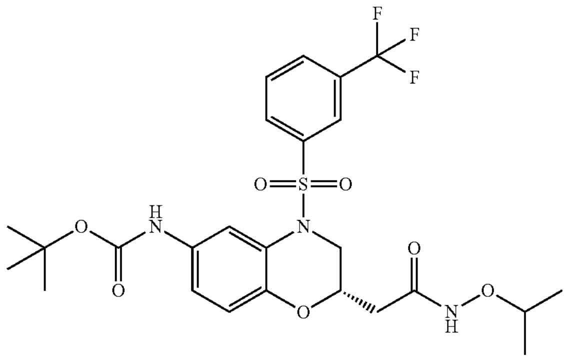 | (S)-tert-butyl (2-(2-(isopropoxyamino)-2-oxoethyl)-4-((3-(trifluoromethyl)phenyl)sulfonyl)-3,4-dihydro-2H-benzo[b][1,4]oxazin-6-yl)carbamate | 574 (M + H)+ |
| 45K | 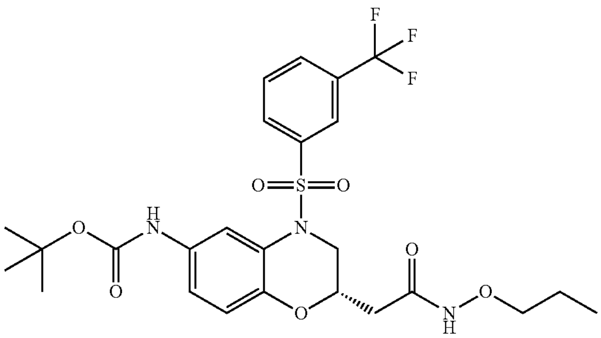 [SMILES: CCCONC(=O)C[C@H]1CN(S(=O)(=O)c2cccc(C(F)(F)F)c2)c2cc(NC(=O)OC(C)(C)C)ccc2O1] | (S)-tert-butyl (2-(2-oxo-2-(propoxyamino)ethyl)-4-((3-(trifluoromethyl)phenyl)sulfonyl)-3,4-dihydro-2H-benzo[b][1,4]oxazin-6-yl)carbamate | 574 (M + H)+ |

Example 46—Synthesis of (R)-tert-butyl (4-((4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate (46)

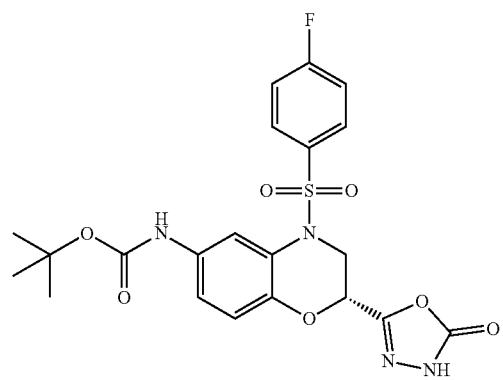 [SMILES: CC(C)(C)OC(=O)Nc1ccc2c(c1)N(S(=O)(=O)c1ccc(F)cc1)C[C@H](c1n[nH]c(=O)o1)O2]

The title compound was prepared according to the procedures described below.

Part I—Synthesis of (R)-tert-butyl (4-((4-fluorophenyl)sulfonyl)-2-(hydrazinecarbonyl)-3,4-dihydro-2H-benzo[b][1,4]oxazin-6-yl)carbamate

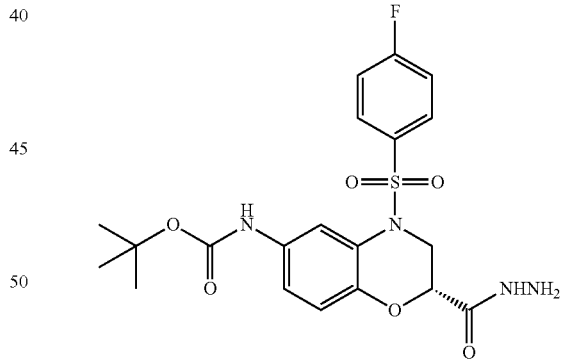

To a solution of (R)-6-((tert-butoxycarbonyl)amino)-4-((4-fluorophenyl)sulfonyl)-3,4-dihydro-2H-benzo[b][1,4]oxazine-2-carboxylic acid (500 mg, 1.105 mmol) in dichloromethane (20 mL) at room temperature was added 1-ethyl-3-(3-dimethylaminopropyl)carbodiimide (318 mg, 1.66 mmol) and N-hydroxybenzotriazole (254 mg, 1.658 mmol) followed by hydrazine hydrate (0.347 mL, 11.1 mmol) and the mixture was stirred at room temperature for five hours. The reaction mixture was diluted with ethyl acetate, washed with saturated aqueous sodium chloride, dried ($Na_2SO_4$) and concentrated. The (R)-tert-butyl (4-((4-fluorophenyl)sulfonyl)-2-(hydrazinecarbonyl)-3,4-dihydro-2H-benzo[b][1,4]oxazin-6-yl)carbamate was obtained as a brownish solid and used in the next step without further purification. MS ESI calculated for $C_{20}H_{23}N_4O_6S$ (M+H)$^+$: 467, Found: 411 (M-tBu).

Part II—Synthesis of (R)-tert-butyl (4-((4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate

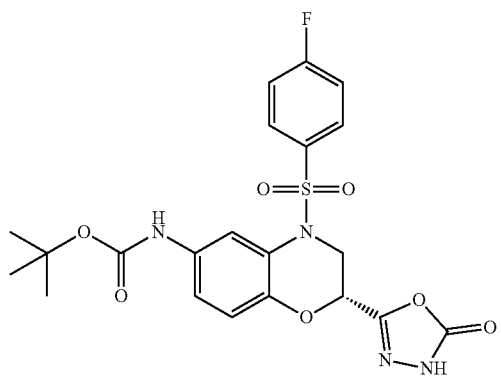 [SMILES: CC(C)(C)OC(=O)Nc1ccc2c(c1)N(S(=O)(=O)c1ccc(F)cc1)C[C@H](c1n[nH]c(=O)o1)O2]

To a solution of (R)-tert-butyl (4-((4-fluorophenyl)sulfonyl)-2-(hydrazinecarbonyl)-3,4-dihydro-2H-benzo[b][1,4]oxazin-6-yl)carbamate (100 mg, 0.214 mmol) in acetonitrile (3 mL) at room temperature was added carbonyl diimidazole (52.1 mg, 0.322 mmol) followed by triethylamine (0.045 mL, 0.322 mmol). The mixture was stirred at room temperature for 4 hours, then concentrated. The residue was dissolved in DMSO, filtered and purified by reverse phase HPLC using a mobile phase of MeCN/water modified with 0.1% TFA to yield (R)-tert-butyl (4-((4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate as a white solid. MS ESI calculated for $C_{21}H_{21}FN_4O_7S$ (M+H)$^+$: 493, Found: 493. $^1$H NMR (500 MHz, DMSO-d6) δ 12.59 (s, 1H), 9.35 (s, 1H), 7.97-7.80 (m, 3H), 7.44 (t, J=8.8 Hz, 2H), 7.15 (d, J=10.3 Hz, 1H), 6.83 (d, J=8.9 Hz, 1H), 4.80 (d, J=5.1 Hz, 1H), 4.39 (dd, J=14.3, 2.9 Hz, 1H), 3.89 (dd, J=14.3, 8.0 Hz, 1H), 1.49 (s, 9H).

Example 47—Preparation of Additional 2-(5-oxo-4,5-dihydro-1,3,4-oxadiazol-2-yl) Substituted Benzoxazines The compounds in Table 17 below were prepared based on the experimental procedures described in Example 46 and elsewhere in the detailed description, and can be achieved by one of skill in the art in light of the present disclosure.

TABLE 17

| Ex. No. | Structure | Name | Observed m/z |
|---|---|---|---|
| 47A | 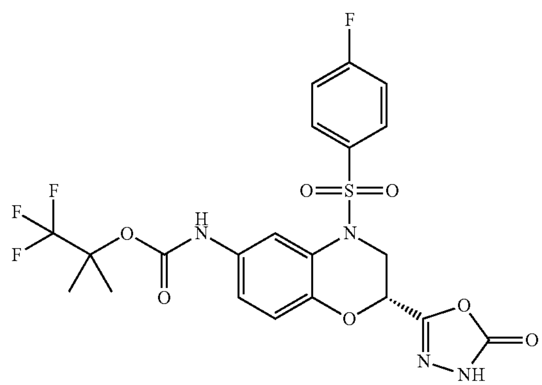 [SMILES: CC(C)(OC(=O)Nc1ccc2c(c1)N(S(=O)(=O)c1ccc(F)cc1)C[C@H](c1n[nH]c(=O)o1)O2)C(F)(F)F] | (R)-1,1,1-trifluoro-2-methylpropan-2-yl (4-((4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate | 547.0 (M + H)$^+$ |
| 47B | 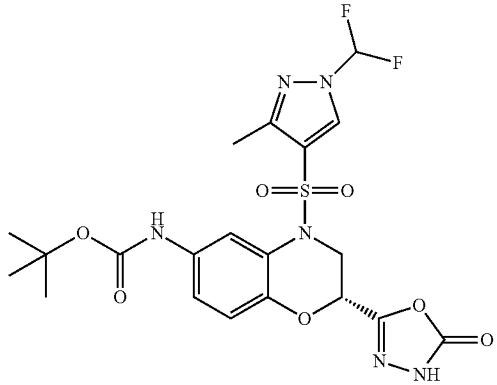 [SMILES: Cc1nn(C(F)F)cc1S(=O)(=O)N1C[C@H](c2n[nH]c(=O)o2)Oc2ccc(NC(=O)OC(C)(C)C)cc21] | (R)-tert-butyl (4-((1-(difluoromethyl)-3-methyl-1H-pyrazol-4-yl)sulfonyl)-2-(5-oxo-4,5-dihydro-1,3,4-oxadiazol-2-yl)-3,4-dihydro-2H-benzo[b][1,4]oxazin-6-yl)carbamate | 473.1 (M − tBu + H)$^+$ |

TABLE 17-continued

| Ex. No. | Structure | Name | Observed m/z |
| --- | --- | --- | --- |
| 47C | 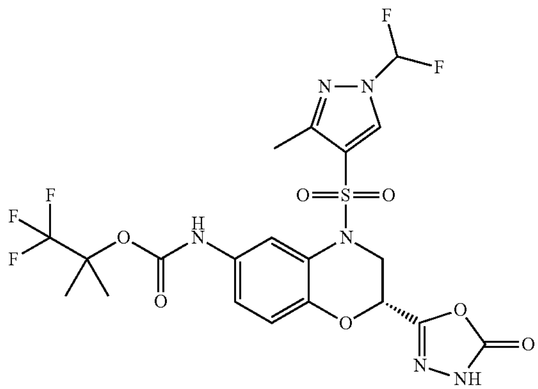 [SMILES: Cc1nn(C(F)F)cc1S(=O)(=O)N1C[C@H](c2n[nH]c(=O)o2)Oc2ccc(NC(=O)OC(C)(C)C(F)(F)F)cc21] | (R)-1,1,1-trifluoro-2-methylpropan-2-yl (4-((1-(difluoromethyl)-3-methyl-1H-pyrazol-4-yl)sulfonyl)-2-(5-oxo-4,5-dihydro-1,3,4-oxadiazol-2-yl)-3,4-dihydro-2H-benzo[b][1,4]oxazin-6-yl)carbamate | 604.9 (M + Na)+ |
| 47D | 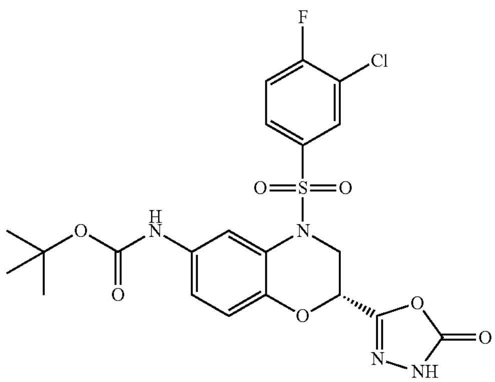 [SMILES: CC(C)(C)OC(=O)Nc1ccc2c(c1)N(S(=O)(=O)c1ccc(F)c(Cl)c1)C[C@H](c1n[nH]c(=O)o1)O2] | (R)-tert-butyl (4-((3-chloro-4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate | 544 (M + NH4)+ |
| 47E | 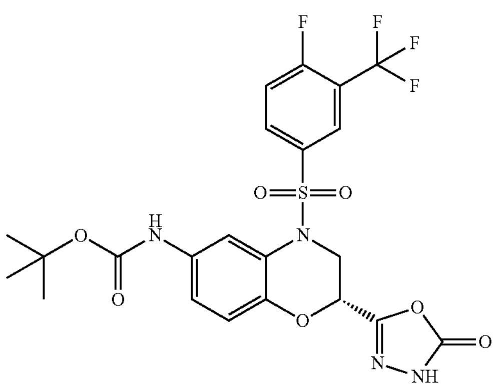 [SMILES: CC(C)(C)OC(=O)Nc1ccc2c(c1)N(S(=O)(=O)c1ccc(F)c(C(F)(F)F)c1)C[C@H](c1n[nH]c(=O)o1)O2] | (R)-tert-butyl (4-((4-fluoro-3-(trifluoromethyl)phenyl)sulfonyl)-2-(5-oxo-4,5-dihydro-1,3,4-oxadiazol-2-yl)-3,4-dihydro-2H-benzo[b][1,4]oxazin-6-yl)carbamate | 578.0 (M + NH4)+ |
| 47F | 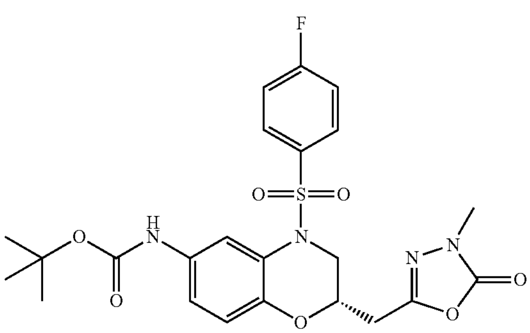 [SMILES: Cn1nc(C[C@H]2CN(S(=O)(=O)c3ccc(F)cc3)c3cc(NC(=O)OC(C)(C)C)ccc3O2)oc1=O] | (S)-tert-butyl (4-((4-fluorophenyl)sulfonyl)-2-((4-methyl-5-oxo-4,5-dihydro-1,3,4-oxadiazol-2-yl)methyl)-3,4-dihydro-2H-benzo[b][1,4]oxazin-6-yl)carbamate | 543 (M + Na)+ |

TABLE 17-continued

| Ex. No. | Structure | Name | Observed m/z |
|---|---|---|---|
| 47G | 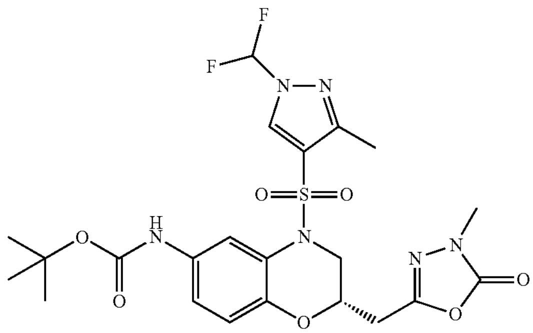 [SMILES: Cc1nn(C(F)F)cc1S(=O)(=O)N1C[C@H](Cc2nn(C)c(=O)o2)Oc2ccc(NC(=O)OC(C)(C)C)cc21] | (S)-tert-butyl (4-((1-(difluoromethyl)-3-methyl-1H-pyrazol-4-yl)sulfonyl)-2-((4-methyl-5-oxo-4,5-dihydro-1,3,4-oxadiazol-2-yl)methyl)-3,4-dihydro-2H-benzo[b][1,4]oxazin-6-yl)carbamate | 579 (M + Na)+ |
| 47H | 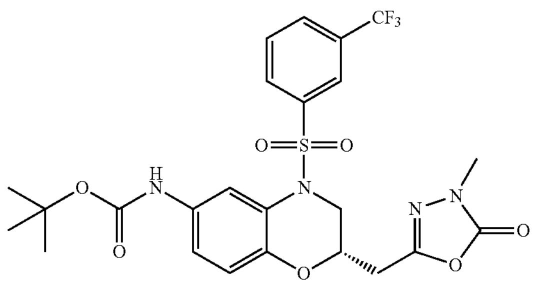 [SMILES: Cn1nc(C[C@H]2CN(S(=O)(=O)c3cccc(C(F)(F)F)c3)c3cc(NC(=O)OC(C)(C)C)ccc3O2)oc1=O] | (S)-tert-butyl (2-((4-methyl-5-oxo-4,5-dihydro-1,3,4-oxadiazol-2-yl)methyl)-4-((3-(trifluoromethyl)phenyl)sulfonyl)-3,4-dihydro-2H-benzo[b][1,4]oxazin-6-yl)carbamate | 593 (M + Na)+ |

Example 48—Synthesis of (R)-tert-butyl (4-((4-fluorophenyl)sulfonyl)-2-(4-methyl-5-oxo-4,5-dihydro-1H-1,2,4-triazol-3-yl)-3,4-dihydro-2H-benzo[b][1,4]oxazin-6-yl)carbamate (48)

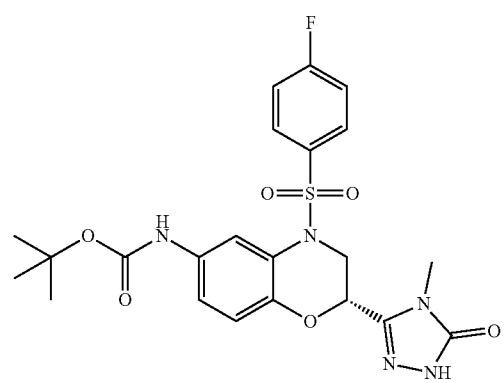 [SMILES: Cn1c([C@H]2CN(S(=O)(=O)c3ccc(F)cc3)c3cc(NC(=O)OC(C)(C)C)ccc3O2)n[nH]c1=O]

The title compound was prepared according to the procedures described below.

Part I—Synthesis of (R)-tert-butyl (4-((4-fluorophenyl)sulfonyl)-2-(hydrazinecarbonyl)-3,4-dihydro-2H-benzo[b][1,4]oxazin-6-yl)carbamate

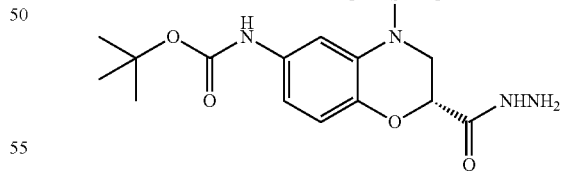

To a solution of (R)-6-((tert-butoxycarbonyl)amino)-4-((4-fluorophenyl)sulfonyl)-3,4-dihydro-2H-benzo[b][1,4]oxazine-2-carboxylic acid (400 mg, 0.884 mmol) in dichloromethane (20 mL) at room temperature was added 1-ethyl-3-(3-dimethylaminopropyl)carbodiimide (254 mg, 1.326 mmol) and N-hydroxybenzotriazole (203 mg, 1.326 mmol) followed by hydrazine hydrate (0.28 mL, 8.84 mmol). The mixture was stirred at room temperature for sixteen hours. The reaction mixture was diluted with ethyl acetate, washed with saturated aqueous sodium chloride, dried (Na$_2$SO$_4$) and concentrated. The residue was purified by silica gel chromatography eluting with a gradient of ethyl acetate/hexane (0~100%) to give (R)-tert-butyl (4-((4-fluorophenyl)sulfonyl)-2-(hydrazinecarbonyl)-3,4-dihydro-2H-benzo[b][1,4]oxazin-6-yl)carbamate as a white solid. MS ESI calculated for $C_{20}H_{23}N_4O_6S$ (M+H)$^+$: 467, Found: 411 (M-tBu).

Part II—Synthesis of (R)-tert-butyl (4-((4-fluorophenyl)sulfonyl)-2-(2-(methylcarbamoyl)hydrazinecarbonyl)-3,4-dihydro-2H-benzo[b][1,4]oxazin-6-yl)carbamate

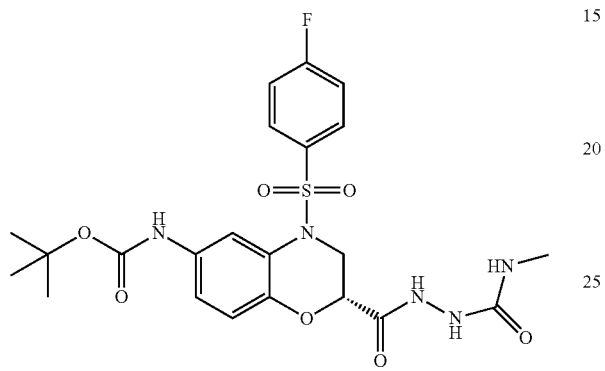

To (R)-tert-butyl (4-((4-fluorophenyl)sulfonyl)-2-(hydrazinecarbonyl)-3,4-dihydro-2H-benzo[b][1,4]oxazin-6-yl)carbamate (200 mg, 0.429 mmol) in THF (2 mL) at room temperature was added methyl isocyanate (0.032 mL, 0.51 mmol) and the mixture was stirred at room temperature for three hours. The reaction mixture was diluted with ethyl acetate, washed with saturated aqueous NaHCO$_3$, and saturated aqueous sodium chloride, dried (Na$_2$SO$_4$) and concentrated to afford (R)-tert-butyl (4-((4-fluorophenyl)sulfonyl)-2-(2-(methylcarbamoyl)hydrazinecarbonyl)-3,4-dihydro-2H-benzo[b][1,4]oxazin-6-yl)carbamate which was used in the next step without further purification.

Part III—Synthesis of (R)-tert-butyl (4-((4-fluorophenyl)sulfonyl)-2-(4-methyl-5-oxo-4,5-dihydro-1H-1,2,4-triazol-3-yl)-3,4-dihydro-2H-benzo[b][1,4]oxazin-6-yl)carbamate

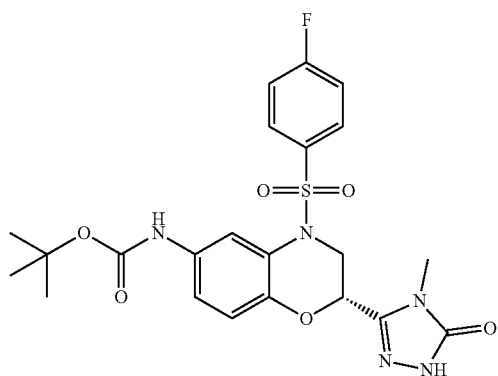 [SMILES: Cn1c([C@H]2CN(S(=O)(=O)c3ccc(F)cc3)c3cc(NC(=O)OC(C)(C)C)ccc3O2)n[nH]c1=O]

To (R)-tert-butyl (4-((4-fluorophenyl)sulfonyl)-2-(2-(methylcarbamoyl)hydrazinecarbonyl)-3,4-dihydro-2H-benzo[b][1,4]oxazin-6-yl)carbamate (200 mg, 0.382 mmol) at room temperature was added 2M NaOH (3 mL, 6.00 mmol) and the mixture was stirred at 100° C. for sixteen hours. The reaction mixture was allowed to cool to room temperature, acidified with 1N HCl (6 mL) and concentrated. The residue was redissolved in DMSO, filtered and purified by reverse phase HPLC using a solvent system of MeCN/water modified with 0.1% trifluoroacetic acid to give (R)-tert-butyl (4-((4-fluorophenyl)sulfonyl)-2-(4-methyl-5-oxo-4,5-dihydro-1H-1,2,4-triazol-3-yl)-3,4-dihydro-2H-benzo[b][1,4]oxazin-6-yl)carbamate. MS ESI calculated for $C_{22}H_{24}FN_5O_6S$ (M+H)$^+$: 506, Found: 506 and 450 (M-tBu). $^1$H NMR (500 MHz, DMSO-d6) δ 11.88 (s, 1H), 9.34 (s, 1H), 7.92-7.82 (m, 3H), 7.43-7.40 (m, 2H), 7.14 (s, 1H), 6.81 (d, J=8.8 Hz, 1H), 4.77 (d, J=6.9 Hz, 1H), 4.50 (d, J=11.7 Hz, 1H), 3.83 (dd, J=13.9, 9.2 Hz, 1H), 1.45 (s, 9H).

Example 49—Synthesis of tert-butyl (2-(cyanomethyl)-4-((3-(trifluoromethyl)phenyl)sulfonyl)-3,4-dihydro-2H-benzo[b][1,4]oxazin-6-yl)carbamate (49)

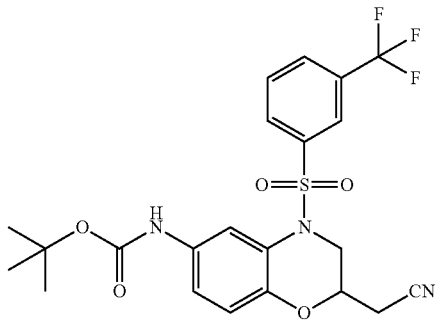 [SMILES: CC(C)(C)OC(=O)Nc1ccc2c(c1)N(S(=O)(=O)c1cccc(C(F)(F)F)c1)CC(CC#N)O2]

The title compound was prepared according to the procedures described below.

Part I—Synthesis of (R)-tert-butyl (2-(iodomethyl)-4-((3-(trifluoromethyl)phenyl)sulfonyl)-3,4-dihydro-2H-benzo[b][1,4]oxazin-6-yl)carbamate

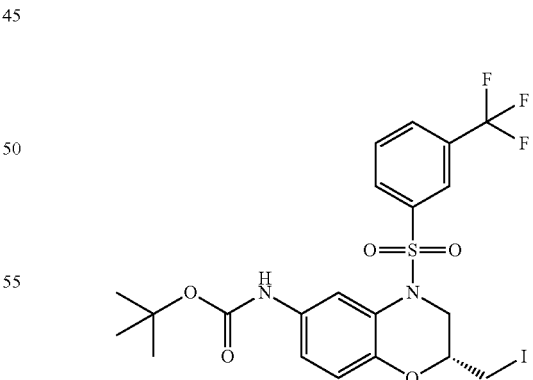

To a stirred solution of (R)-(6-((tert-butoxycarbonyl)amino)-4-((3-(trifluoromethyl)phenyl)sulfonyl)-3,4-dihydro-2H-benzo[b][1,4]oxazin-2-yl)methyl 4-methylbenzenesulfonate (7.7 g, 12 mmol) in acetone (100 mL) was added sodium iodide (7.0 g, 47 mmol). The mixture was heated at 60° C. and stirred overnight. Solvent was evaporated, brine (50 mL) was added, and the mixture was extracted three Part II—Synthesis of tert-butyl (2-(cyanomethyl)-4-((3-(trifluoromethyl)phenyl)sulfonyl)-3,4-dihydro-2H-benzo[b][1,4]oxazin-6-yl)carbamate

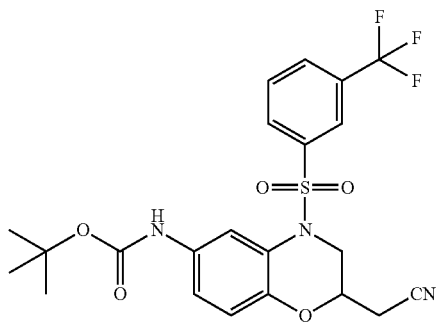 [SMILES: CC(C)(C)OC(=O)Nc1ccc2c(c1)N(S(=O)(=O)c1cccc(C(F)(F)F)c1)CC(CC#N)O2]

To a stirred solution of (R)-tert-butyl (2-(iodomethyl)-4-((3-(trifluoromethyl)phenyl)sulfonyl)-3,4-dihydro-2H-benzo[b][1,4]oxazin-6-yl)carbamate (3.0 g, 5 mmol) in DMF (30 mL) was added sodium cyanide (490 mg, 10 mmol) at room temperature. The reaction was stirred overnight. The mixture was diluted with brine (50 mL) and extracted three times with ethyl acetate (50 mL each). The organic layers were combined, dried ($Na_2SO_4$) and concentrated. The residue was purified by Prep-HPLC to give a brown solid as a racemate. LCMS (ESI) calculated for $C_{22}H_{22}F_3N_3NaO_5S$ (M+Na)$^+$: 520.1, Found: 520.0.

Example 50—Synthesis of tert-butyl (2-(2-hydroxypropyl)-4-((3-(trifluoromethyl)phenyl)sulfonyl)-3,4-dihydro-2H-benzo[b][1,4]oxazin-6-yl)carbamate (50)

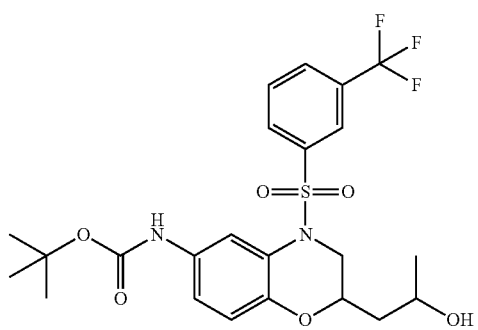

The title compound was prepared according to the procedures described below.

Part I—Synthesis of tert-butyl (2-(2-oxoethyl)-4-((3-(trifluoromethyl)phenyl)sulfonyl)-3,4-dihydro-2H-benzo[b][1,4]oxazin-6-yl)carbamate

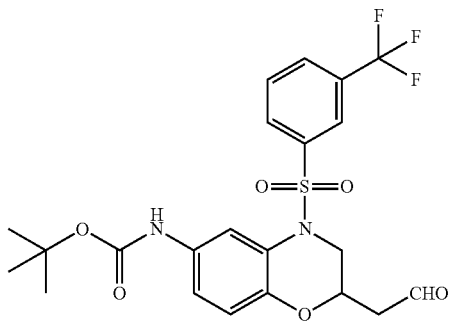 [SMILES: CC(C)(C)OC(=O)Nc1ccc2c(c1)N(S(=O)(=O)c1cccc(C(F)(F)F)c1)CC(CC=O)O2]

To a stirred solution of tert-butyl (2-(cyanomethyl)-4-((3-(trifluoromethyl)phenyl)sulfonyl)-3,4-dihydro-2H-benzo[b][1,4]oxazin-6-yl)carbamate (1.0 g, 2.0 mmol) in anhydrous toluene (30 mL) was added a 1M solution of diisobutylaluminum hydride (5 mL, 5 mmol) in toluene at −78° C. The mixture was stirred at −78° C. for one hour and then warmed to room temperature. The reaction was stirred for another hour, and quenched with brine (50 mL). The mixture was extracted three times with ethyl acetate (50 mL each). The organic phases were combined, dried ($Na_2SO_4$), filtered, and concentrated to afford tert-butyl (2-(2-oxoethyl)-4-((3-(trifluoromethyl)phenyl)sulfonyl)-3,4-dihydro-2H-benzo[b][1,4]oxazin-6-yl)carbamate as a yellow solid. LCMS (ESI) calculated for $C_{22}H_{23}F_3N_2NaO_6S$ (M+Na)$^+$: 523.1, Found: 523.0.

Part II—Synthesis of tert-butyl (2-(2-hydroxypropyl)-4-((3-(trifluoromethyl)phenyl)sulfonyl)-3,4-dihydro-2H-benzo[b][1,4]oxazin-6-yl)carbamate

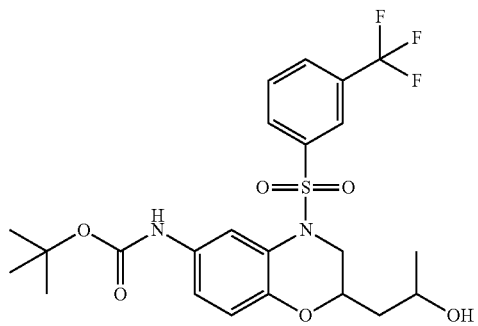

To a stirred solution of tert-butyl (2-(2-oxoethyl)-4-((3-(trifluoromethyl)phenyl)sulfonyl)-3,4-dihydro-2H-benzo[b][1,4]oxazin-6-yl)carbamate (150 mg, 0.3 mmol) in anhydrous THF (10 mL) was added a 3M solution of methyl magnesium bromide (1.0 mL, 3.0 mmol) in THF dropwise at 0° C. The mixture was stirred at 0° C. for an hour, warmed to room temperature and stirred for another hour, then quenched with saturated aqueous ammonium chloride (5 mL). Brine (10 mL) was added and extracted three times with ethyl acetate (20 mL each). The organic layers were combined, dried ($Na_2SO_4$) and concentrated. The residue was purified by Prep-HPLC to afford the title compound as a white solid. LCMS (ESI): calculated for $C_{23}H_{31}F_3N_3O_6S$ (M+NH$_4$)$^+$: 534.2, Found: 534.0.

Example 51—Synthesis of (S)-tert-butyl (2-(2-amino-2-methylpropyl)-4-((3-(trifluoromethyl)phenyl) sulfonyl)-3,4-dihydro-2H-benzo[b][1,4]oxazin-6-yl)carbamate (51)

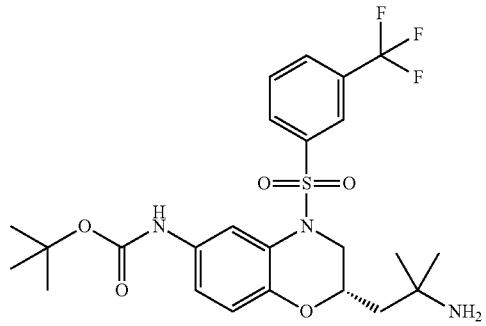 [SMILES: CC(C)(N)C[C@H]1CN(S(=O)(=O)c2cccc(C(F)(F)F)c2)c2cc(NC(=O)OC(C)(C)C)ccc2O1]

Cerium chloride (4.6 g, 18.0 mmol) was dried under vacuum at 140° C. for 2 hours before it was cooled to room temperature. Anhydrous THF (140 mL) was added and the suspension was stirred at room temperature for two hours. Then the suspension was cooled to −78° C., and 3M methyl lithium (6.0 mL, 18.0 mmol) in ether was added dropwise. The mixture was stirred at −78° C. for thirty minutes. A solution of tert-butyl (2-(cyanomethyl)-4-((3-(trifluoromethyl)phenyl)sulfonyl)-3,4-dihydro-2H-benzo[b][1,4]oxazin-6-yl)carbamate (1.5 g, 3.0 mmol) in THF (15 mL) was added dropwise and the mixture was stirred for another thirty minutes at −78° C. The resulting mixture was warmed to room temperature and stirred for 1.5 hours. Ammonium hydroxide (25-28% in water, 3 mL) was added and the resulting solution was stirred for ten minutes. Brine (40 mL) was added and extracted with ethyl acetate (30 mL×3). The organic layers were combined, dried (Na$_2$SO$_4$), concentrated and the residue purified by prep-HPLC (46-76% acetonitrile+0.75‰ trifluoroacetic acid in water) and SFC-HPLC to give two isomers. SFC separation condition: Column: Chiralpak AS-H 250×4.6 mm I.D., Sum Mobile phase: ethanol (0.05% DEA) in CO2 from 5% to 40% Flow rate: 2.35 mL/min Wavelength: 220 nm. (S)-tert-butyl (2-(2-amino-2-methylpropyl)-4-((3-(trifluoromethyl) phenyl)sulfonyl)-3,4-dihydro-2H-benzo[b][1,4]oxazin-6-yl)carbamate RT: 5.294 min. LCMS (ESI): calculated for $C_{24}H_{31}F_3N_3O_5S$ (M+H)$^+$: 530, Found: 530; and (R)-tert-butyl (2-(2-amino-2-methylpropyl)-4-((3-(trifluoromethyl) phenyl)sulfonyl)-3,4-dihydro-2H-benzo[b][1,4]oxazin-6-yl)carbamate RT: 4.789 min. LCMS (ESI): calculated for $C_{24}H_{31}F_3N_3O_5S$ (M+H)$^+$: 530, Found: 530.

Example 52—Synthesis of (S)-tert-butyl (2-(2-acetamido-2-methylpropyl)-4-((3-(trifluoromethyl)phenyl)sulfonyl)-3,4-dihydro-2H-benzo[b][1,4]oxazin-6-yl)carbamate (52)

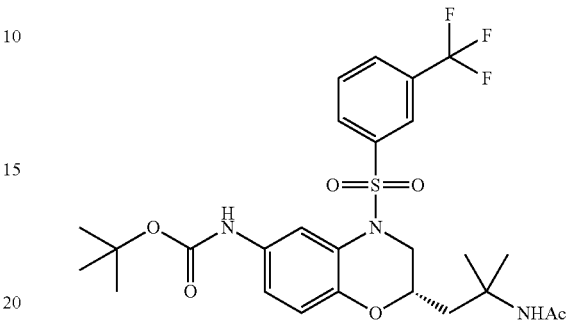

To a stirred solution of (S)-tert-butyl (2-(2-amino-2-methylpropyl)-4-((3-(trifluoromethyl)phenyl)sulfonyl)-3,4-dihydro-2H-benzo[b][1,4]oxazin-6-yl)carbamate (180 mg, 0.34 mmol) and triethyl amine (0.1 mL, 0.7 mmol) in dichloromethane (5 mL) was added acetic anhydride (71 mg, 0.7 mmol) at room temperature. The mixture was stirred at room temperature overnight. The solvent was evaporated, brine (20 mL) was added and the mixture was extracted with ethyl acetate (50 mL×3). The organic layers were combined, dried (Na$_2$SO$_4$) and concentrated. The residue was purified by prep-HPLC (45-75% acetonitrile+0.75‰ trifluoroacetic acid in water) to give (S)-tert-butyl (2-(2-acetamido-2-methylpropyl)-4-((3-(trifluoromethyl)phenyl)sulfonyl)-3,4-dihydro-2H-benzo[b][1,4]oxazin-6-yl)carbamate as a white solid. $^1$H NMR (400 MHz, CD$_3$OD) δ 8.08 (br s, 1H), 8.04~7.95 (m, 2H), 7.83~7.76 (m, 1H), 7.61 (s, 1H), 7.04 (dd, J=2.0, 8.6 Hz, 1H), 6.70 (d, J=8.6 Hz, 1H), 4.28 (dd, J=2.4, 14.4 Hz, 1H), 3.63 (br s, 1H), 3.28~3.21 (m, 1H), 2.17 (dd, J=2.8, 14.8 Hz, 1H), 1.91 (s, 3H), 1.90~1.84 (m, 1H), 1.55 (s, 9H), 1.29 (d, J=6.6 Hz, 6H). LCMS (ESI): calculated for $C_{26}H_{33}F_3N_3O_6S$ (M+H)$^+$: 572, Found: 572.

Example 53—Preparation of Additional Amides of Benzoxazines

The compounds in Table 18 below were prepared based on the experimental procedures described in Examples 49, 50, 51 and 52 and elsewhere in the detailed description, and can be achieved by one of skill in the art in light of the present disclosure.

TABLE 18

| Ex. No. | Structure | Name | Observed m/z |
|---|---|---|---|
| 53A | ![structure] | (S)-tert-butyl (2-(2-propionamidoethyl)-4-((3-(trifluoromethyl)phenyl)sulfonyl)-3,4-dihydro-2H-benzo[b][1,4]oxazin-6-yl)carbamate | 558 (M + H)$^+$ |

TABLE 18-continued

| Ex. No. | Structure | Name | Observed m/z |
|---|---|---|---|
| 53B | 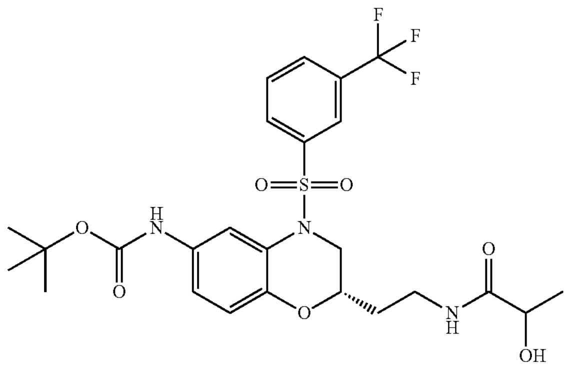 [SMILES: CC(O)C(=O)NCC[C@H]1CN(S(=O)(=O)c2cccc(C(F)(F)F)c2)c2cc(NC(=O)OC(C)(C)C)ccc2O1] | tert-butyl ((2S)-2-(2-(2-hydroxypropanamido)ethyl)-4-((3-(trifluoromethyl)phenyl)sulfonyl)-3,4-dihydro-2H-benzo[b][1,4]oxazin-6-yl)carbamate | 574 (M + H)+ |
| 53C | 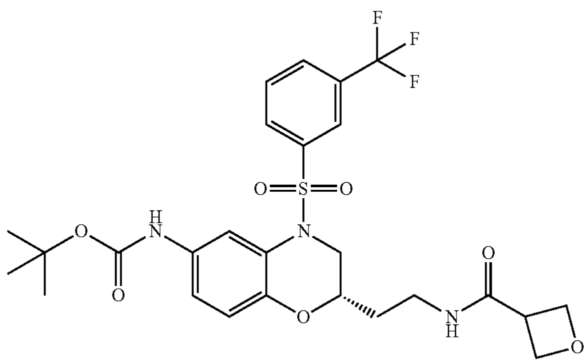 [SMILES: CC(C)(C)OC(=O)Nc1ccc2c(c1)N(S(=O)(=O)c1cccc(C(F)(F)F)c1)C[C@H](CCNC(=O)C1COC1)O2] | (S)-tert-butyl (2-(2-(oxetane-3-carboxamido)ethyl)-4-((3-(trifluoromethyl)phenyl)sulfonyl)-3,4-dihydro-2H-benzo[b][1,4]oxazin-6-yl)carbamate | 586 (M + H)+ |
| 53D | 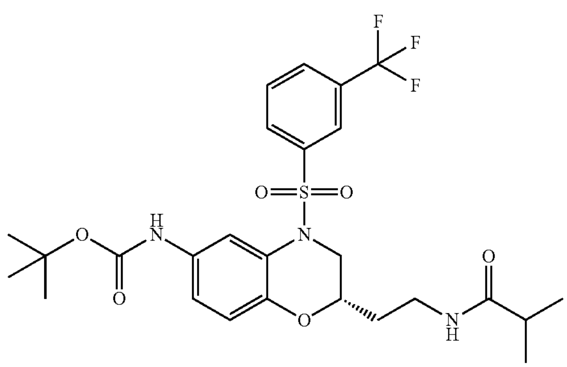 [SMILES: CC(C)C(=O)NCC[C@H]1CN(S(=O)(=O)c2cccc(C(F)(F)F)c2)c2cc(NC(=O)OC(C)(C)C)ccc2O1] | (S)-tert-butyl (2-(2-isobutyramidoethyl)-4-((3-(trifluoromethyl)phenyl)sulfonyl)-3,4-dihydro-2H-benzo[b][1,4]oxazin-6-yl)carbamate | 572 (M + H)+ |
| 53E | 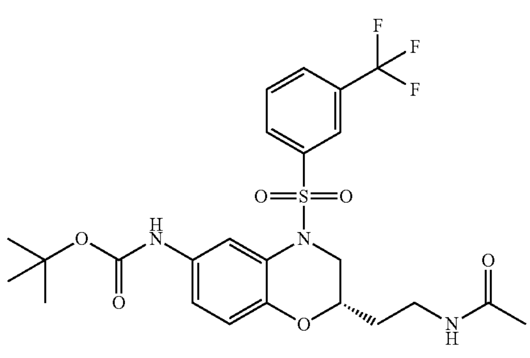 [SMILES: CC(=O)NCC[C@H]1CN(S(=O)(=O)c2cccc(C(F)(F)F)c2)c2cc(NC(=O)OC(C)(C)C)ccc2O1] | (S)-tert-butyl (2-(2-acetamidoethyl)-4-((3-(trifluoromethyl)phenyl)sulfonyl)-3,4-dihydro-2H-benzo[b][1,4]oxazin-6-yl)carbamate | 566 (M + Na)+ |

TABLE 18-continued

| Ex. No. | Structure | Name | Observed m/z |
|---|---|---|---|
| 53F | 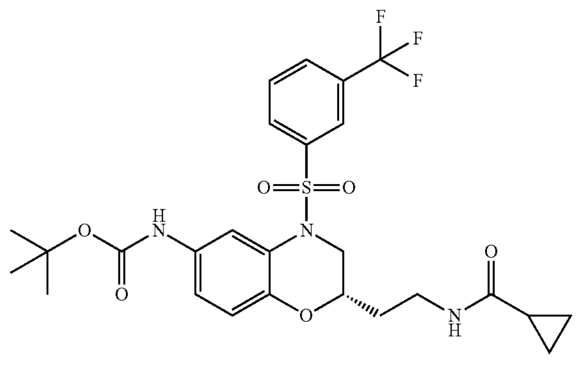 [SMILES: CC(C)(C)OC(=O)Nc1ccc2c(c1)N(S(=O)(=O)c1cccc(C(F)(F)F)c1)C[C@H](CCNC(=O)C1CC1)O2] | (S)-tert-butyl (2-(2-(cyclopropanecarboxamido)ethyl)-4-((3-(trifluoromethyl)phenyl)sulfonyl)-3,4-dihydro-2H-benzo[b][1,4]oxazin-6-yl)carbamate | 570 (M + H)+ |
| 53G | 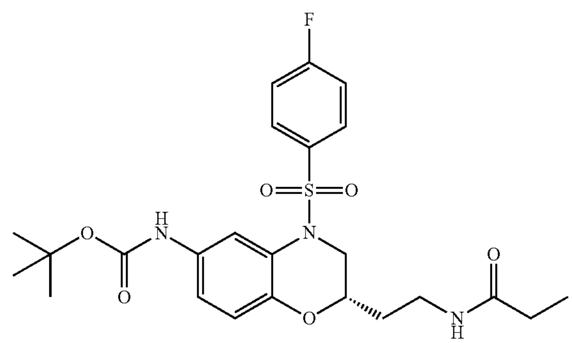 [SMILES: CCC(=O)NCC[C@H]1CN(S(=O)(=O)c2ccc(F)cc2)c2cc(NC(=O)OC(C)(C)C)ccc2O1] | (S)-tert-butyl (4-((4-fluorophenyl)sulfonyl)-2-(2-propionamidoethyl)-3,4-dihydro-2H-benzo[b][1,4]oxazin-6-yl)carbamate | 508 (M + H)+ |
| 53H | 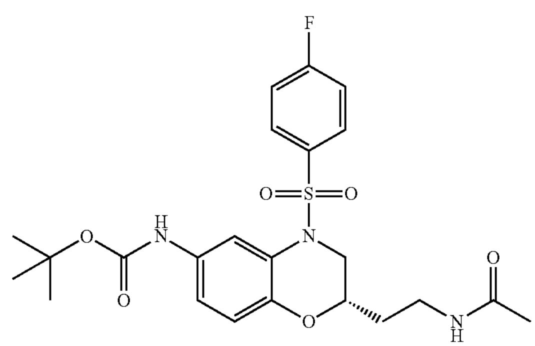 [SMILES: CC(=O)NCC[C@H]1CN(S(=O)(=O)c2ccc(F)cc2)c2cc(NC(=O)OC(C)(C)C)ccc2O1] | (S)-tert-butyl (2-(2-acetamidoethyl)-4-((4-fluorophenyl)sulfonyl)-3,4-dihydro-2H-benzo[b][1,4]oxazin-6-yl)carbamate | 494 (M + H)+ |
| 53i | 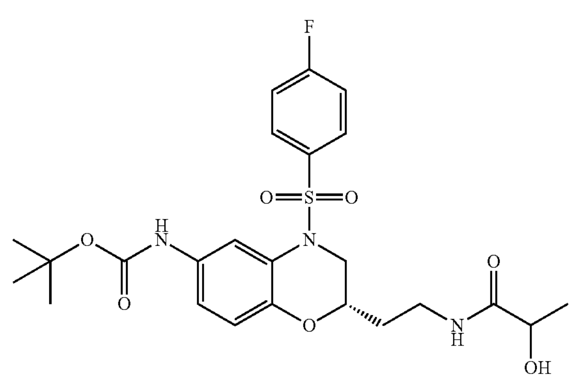 [SMILES: CC(O)C(=O)NCC[C@H]1CN(S(=O)(=O)c2ccc(F)cc2)c2cc(NC(=O)OC(C)(C)C)ccc2O1] | tert-butyl ((2S)-4-((4-fluorophenyl)sulfonyl)-2-(2-(2-hydroxypropanamido)ethyl)-3,4-dihydro-2H-benzo[b][1,4]oxazin-6-yl)carbamate | 524 (M + H)+ |

TABLE 18-continued

| Ex. No. | Structure | Name | Observed m/z |
|---|---|---|---|
| 53J | 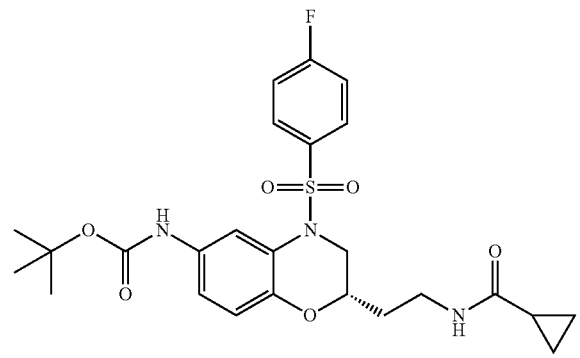 [SMILES: CC(C)(C)OC(=O)Nc1ccc2c(c1)N(S(=O)(=O)c1ccc(F)cc1)C[C@H](CCNC(=O)C1CC1)O2] | (S)-tert-butyl (2-(2-(cyclopropanecarboxamido)ethyl)-4-((4-fluorophenyl)sulfonyl)-3,4-dihydro-2H-benzo[b][1,4]oxazin-6-yl)carbamate | 520 (M + H)+ |
| 53K | 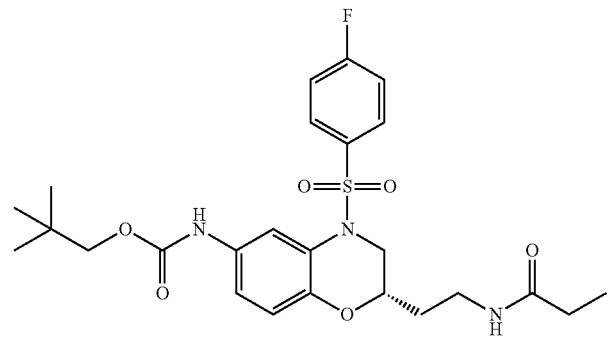 [SMILES: CCC(=O)NCC[C@H]1CN(S(=O)(=O)c2ccc(F)cc2)c2cc(NC(=O)OCC(C)(C)C)ccc2O1] | (S)-neopentyl (4-((4-fluorophenyl)sulfonyl)-2-(2-propionamidoethyl)-3,4-dihydro-2H-benzo[b][1,4]oxazin-6-yl)carbamate | 522 (M + H)+ |
| 53L | 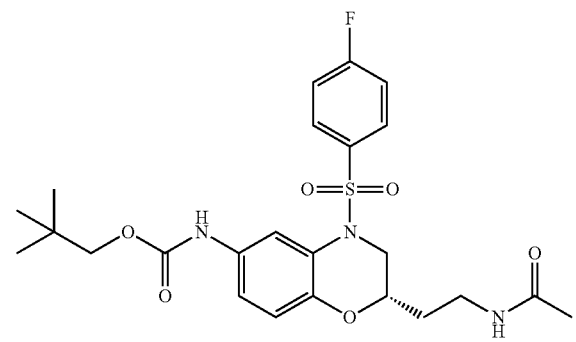 [SMILES: CC(=O)NCC[C@H]1CN(S(=O)(=O)c2ccc(F)cc2)c2cc(NC(=O)OCC(C)(C)C)ccc2O1] | (S)-neopentyl (2-(2-acetamidoethyl)-4-((4-fluorophenyl)sulfonyl)-3,4-dihydro-2H-benzo[b][1,4]oxazin-6-yl)carbamate | 508 (M + H)+ |
| 53M | 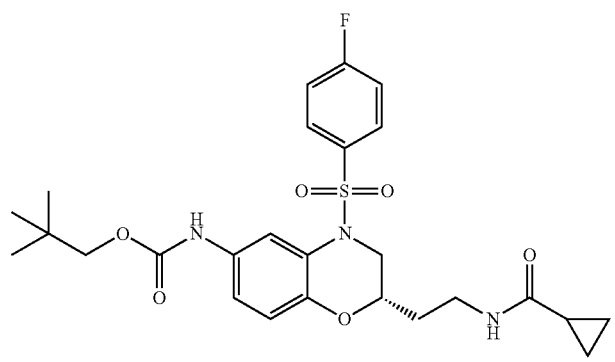 [SMILES: CC(C)(C)COC(=O)Nc1ccc2c(c1)N(S(=O)(=O)c1ccc(F)cc1)C[C@H](CCNC(=O)C1CC1)O2] | (S)-neopentyl (2-(2-(cyclopropanecarboxamido)ethyl)-4-((4-fluorophenyl)sulfonyl)-3,4-dihydro-2H-benzo[b][1,4]oxazin-6-yl)carbamate | 533 (M + H)+ |

TABLE 18-continued

| Ex. No. | Structure | Name | Observed m/z |
|---|---|---|---|
| 53N | 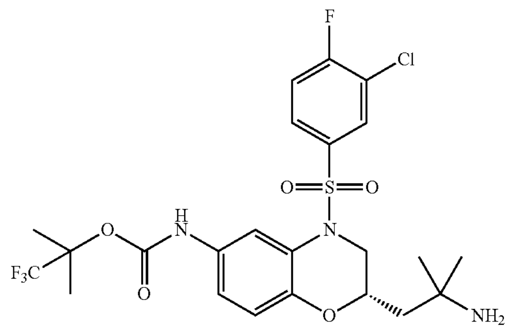 [SMILES: CC(C)(N)C[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (2-(2-amino-2-methylpropyl)-4-((3-chloro-4-fluorophenyl)sulfonyl)-3,4-dihydro-2H-benzo[b][1,4]oxazin-6-yl)carbamate | 568 (M + H)+ |
| 53o | 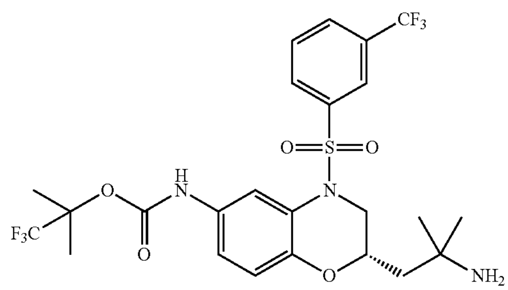 [SMILES: CC(C)(N)C[C@H]1CN(S(=O)(=O)c2cccc(C(F)(F)F)c2)c2cc(NC(=O)OC(C)(C)C(F)(F)F)ccc2O1] | (S)-1,1,1-trifluoro-2-methylpropan-2-yl (2-(2-amino-2-methylpropyl)-4-((3-(trifluoromethyl)phenyl)sulfonyl)-3,4-dihydro-2H-benzo[b][1,4]oxazin-6-yl)carbamate | 584 (M + H)+ |
| 53P | 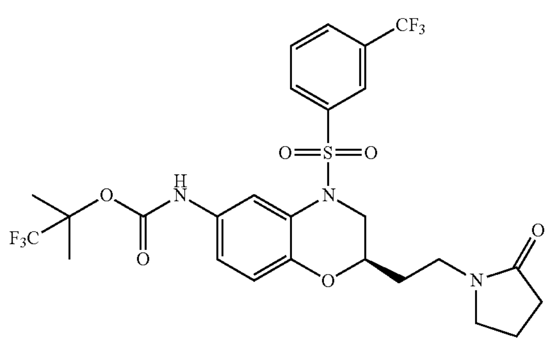 [SMILES: CC(C)(OC(=O)Nc1ccc2c(c1)N(S(=O)(=O)c1cccc(C(F)(F)F)c1)C[C@@H](CCN1CCCC1=O)O2)C(F)(F)F] | (R)-1,1,1-trifluoro-2-methylpropan-2-yl (2-(2-(2-oxopyrrolidin-1-yl)ethyl)-4-((3-(trifluoromethyl)phenyl)sulfonyl)-3,4-dihydro-2H-benzo[b][1,4]oxazin-6-yl)carbamate | 624 (M + H)+ |
| 53Q | 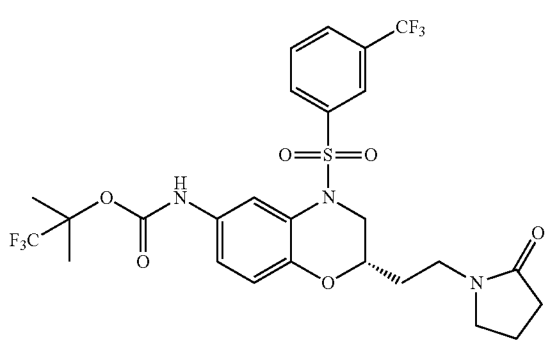 [SMILES: CC(C)(OC(=O)Nc1ccc2c(c1)N(S(=O)(=O)c1cccc(C(F)(F)F)c1)C[C@H](CCN1CCCC1=O)O2)C(F)(F)F] | (S)-1,1,1-trifluoro-2-methylpropan-2-yl (2-(2-(2-oxopyrrolidin-1-yl)ethyl)-4-((3-(trifluoromethyl)phenyl)sulfonyl)-3,4-dihydro-2H-benzo[b][1,4]oxazin-6-yl)carbamate | 624 (M + H)+ |

Example 54—Synthesis of (S)-tert-butyl (2-(2-acetamido-2-methylpropyl)-4-((3-chloro-4-fluorophenyl)sulfonyl)-3,4-dihydro-2H-benzo[b][1,4]oxazin-6-yl)carbamate (54)

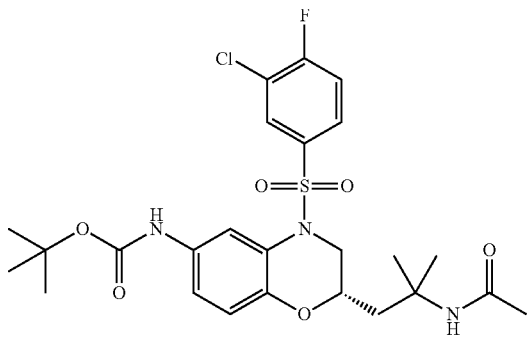

The title compound was prepared according to the procedures described below.

Part I—Synthesis of (S)-benzyl 6-((tert-butoxycarbonyl)amino)-2-(2-methoxy-2-oxoethyl)-2H-benzo[b][1,4]oxazine-4(3H)-carboxylate

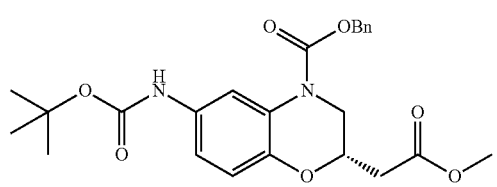 [SMILES: COC(=O)C[C@H]1CN(C(=O)OCc2ccccc2)c2cc(NC(=O)OC(C)(C)C)ccc2O1]

To a solution of (S)-methyl 2-(6-((tert-butoxycarbonyl)amino)-3,4-dihydro-2H-benzo[b][1,4]oxazin-2-yl)acetate (0.5 g, 1.6 mmol) and sodium bicarbonate (0.52 g, 6.2 mmol) in dry THF (5 mL) was added benzyl chloroformate (0.53 g, 6.2 mmol) at 0° C. The mixture was stirred at reflux for an hour, poured into ice-water (10 mL), and extracted with ethyl acetate (10 mL×3). The combined organic layers were washed with brine (5 mL), dried (Na$_2$SO$_4$) and concentrated to afford compound (S)-benzyl 6-((tert-butoxycarbonyl)amino)-2-(2-methoxy-2-oxoethyl)-2H-benzo[b][1,4]oxazine-4(3H)-carboxylate as a yellow solid. $^1$H NMR (400 MHz, CDCl$_3$) δ 7.89 (br s, 1H), 7.31~7.48 (m, 5H), 7.07 (br s, 1H), 6.80 (d, J=8.8 Hz, 1H), 6.37 (br s, 1H), 5.26 (s, 2H), 4.52~4.64 (m, 1H), 4.21 (dd, J=2.4, 13.2 Hz, 1H), 3.70 (s, 3H), 3.49 (dd, J=7.6, 13.2 Hz, 1H), 2.66~2.77 (m, 1H), 2.54~2.64 (m, 1H), 1.50 (s, 9H). LCMS (ESI): calculated for C$_{24}$H$_{29}$N$_2$O$_7$ (M+H)$^+$: 457, Found: 457.

Part II—Synthesis of (S)-benzyl 6-((tert-butoxycarbonyl)amino)-2-(2-hydroxy-2-methylpropyl)-2H-benzo[b][1,4]oxazine-4(3H)-carboxylate

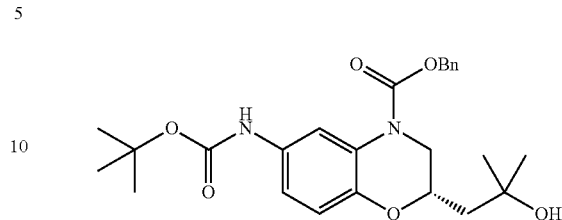

To a solution of (S)-benzyl 6-((tert-butoxycarbonyl)amino)-2-(2-methoxy-2-oxoethyl)-2H-benzo[b][1,4]oxazine-4(3H)-carboxylate (0.4 g, 0.88 mmol) in dry THF (5 mL) at 0° C. was added dropwise 3M methyl magnesium bromide (2.9 mL, 8.7 mmol) in THF. The mixture was stirred at room temperature for five hours. The resulting mixture was quenched with saturated aqueous ammonium chloride (10 mL) and extracted with ethyl acetate (10 mL×3). The combined organic layers were dried (Na$_2$SO$_4$) and concentrated to afford (S)-benzyl 6-((tert-butoxycarbonyl)amino)-2-(2-hydroxy-2-methylpropyl)-2H-benzo[b][1,4]oxazine-4(3H)-carboxylate as a white solid. $^1$H NMR (400 MHz, CDCl$_3$) δ 7.91 (br s, 1H), 7.30~7.47 (m, 5H), 7.07 (br s, 1H), 6.79 (d, J=8.8 Hz, 1H), 6.35 (br s, 1H), 5.26 (s, 2H), 4.36~4.49 (m, 1H), 4.18 (dd, J=2.0, 13.6 Hz, 1H), 3.37 (dd, J=8.0, 13.2 Hz, 1H), 2.40 (br s, 1H), 1.80~1.91 (m, 1H), 1.67 (dd, J=3.2, 14.8 Hz, 1H), 1.50 (s, 9H), 1.31 (d, J=9.6 Hz, 6H). LCMS (ESI): calculated for C$_{25}$H$_{33}$N$_2$O$_6$ (M+H)$^+$: 457, Found: 457.

Part III—Synthesis of (S)-benzyl 2-(2-acetamido-2-methylpropyl)-6-amino-2H-benzo[b][1,4]oxazine-4(3H)-carboxylate

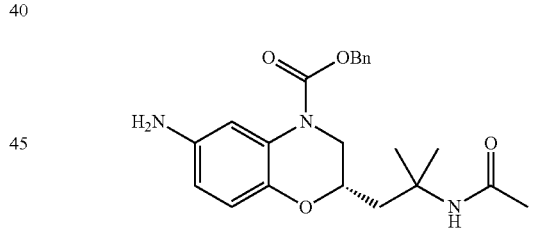

To a solution of compound (S)-benzyl 6-((tert-butoxycarbonyl)amino)-2-(2-hydroxy-2-methylpropyl)-2H-benzo[b][1,4]oxazine-4(3H)-carboxylate (0.05 g, 0.11 mmol) in acetonitrile (5 mL) was added dropwise concentrated sulfuric acid (107 mg, 1.1 mmol) at 0° C. The mixture was stirred at room temperature for 5 hours. The resulting mixture was poured into ice-water (3 mL) and extracted with ethyl acetate (10 mL×3). The combined organic layers were washed with brine (5 mL), dried (Na$_2$SO$_4$) and concentrated to afford compound (S)-benzyl 2-(2-acetamido-2-methylpropyl)-6-amino-2H-benzo[b][1,4]oxazine-4(3H)-carboxylate. $^1$H NMR (400 MHz, CDCl$_3$) δ 7.33-7.43 (m, 5H), 6.63 (d, J=8.4 Hz, 1H), 6.37 (dd, J=2.8, 8.8 Hz, 1H), 5.95 (br s, 1H), 5.24 (s, 2H), 4.21 (t, J=8.8 Hz, 1H), 4.05 (dd, J=2.0, 13.2 Hz, 1H), 3.40 (dd, J=8.4, 13.2 Hz, 1H), 1.97~2.04 (m, 2H), 1.79-1.90 (m, 3H), 1.34 (s, 6H). LCMS (ESI): calculated for C$_{22}$H$_{28}$N$_3$O$_4$ (M+H)$^+$: 398, Found: 398.

Part IV—Synthesis of (S)-benzyl 2-(2-acetamido-2-methylpropyl)-6-((tert-butoxycarbonyl)amino)-2H-benzo[b][1,4]oxazine-4(3H)-carboxylate

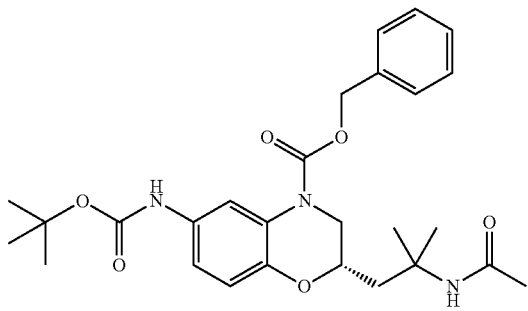 [SMILES: CC(=O)NC(C)(C)C[C@H]1CN(C(=O)OCc2ccccc2)c2cc(NC(=O)OC(C)(C)C)ccc2O1]

To a solution of (S)-benzyl 2-(2-acetamido-2-methylpropyl)-6-amino-2H-benzo[b][1,4]oxazine-4(3H)-carboxylate (1.2 g, 3 mmol) and sodium bicarbonate (0.5 g, 6 mmol) in methanol (5 mL) was added di-tert-butyl dicarbonate (0.94 g, 4.5 mmol) at 0° C. The mixture was stirred at room temperature for two hours. The resulting mixture was poured into ice-water (10 mL) and extracted with ethyl acetate (10 mL×3). The combined organic layers were washed with brine (5 mL), dried ($Na_2SO_4$) and concentrated to afford (S)-benzyl 2-(2-acetamido-2-methylpropyl)-6-((tert-butoxycarbonyl)amino)-2H-benzo[b][1,4]oxazine-4(3H)-carboxylate. $^1$H NMR (400 MHz, $CDCl_3$) δ 7.95 (br s, 1H), 7.37-7.44 (m, 5H), 7.11 (br s, 1H), 6.75 (d, J=8.8 Hz, 1H), 6.48 (br s, 1H), 6.14 (br s, 1H), 5.24~5.30 (m, 2H), 4.27 (t, J=8.4 Hz, 1H), 4.05~4.09 (d, J=13.6 Hz, 1H), 3.41~3.46 (dd, J=8.4, 13.6 Hz, 1H), 1.88~2.06 (m, 5H), 1.52 (s, 9H), 1.43 (s, 6H). LCMS (ESI): calculated for $C_{27}H_{36}N_3O_6$ (M+H)$^+$: 498, Found: 498.

Part V—Synthesis of (S)-tert-butyl (2-(2-acetamido-2-methylpropyl)-3,4-dihydro-2H-benzo[b][1,4]oxazin-6-yl)carbamate

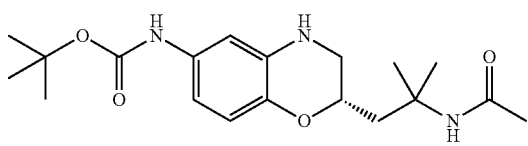 [SMILES: CC(=O)NC(C)(C)C[C@H]1CNc2cc(NC(=O)OC(C)(C)C)ccc2O1]

To a solution (S)-benzyl 2-(2-acetamido-2-methylpropyl)-6-((tert-butoxycarbonyl)amino)-2H-benzo[b][1,4]oxazine-4(3H)-carboxylate (1 g, 2 mmol) in ethyl acetate (10 mL) was added 10% Pd/C (200 mg, 10% wt) under nitrogen. The mixture was stirred at room temperature under hydrogen at 1 atmosphere for three hours. The resulting mixture was filtered through a CELITE pad and the filtrate was concentrated to afford (S)-tert-butyl (2-(2-acetamido-2-methylpropyl)-3,4-dihydro-2H-benzo[b][1,4]oxazin-6-yl) carbamate as a white solid. $^1$H NMR (400 MHz, $CDCl_3$) δ 6.89 (br s, 1H), 6.62 (d, J=8.4 Hz, 1H), 6.41 (d, J=8.0 Hz, 1H), 6.33 (br s, 1H), 6.15 (br s, 1H), 4.19~4.31 (m, 1H), 3.21~3.34 (m, 1H), 3.08~3.19 (m, 1H), 1.89~1.95 (m, 5H), 1.44 (s, 9H), 1.34 (s, 6H). LCMS (ESI): calculated for $C_{19}H_{30}N_3O_4$ (M+H)$^+$: 364, Found: 364.

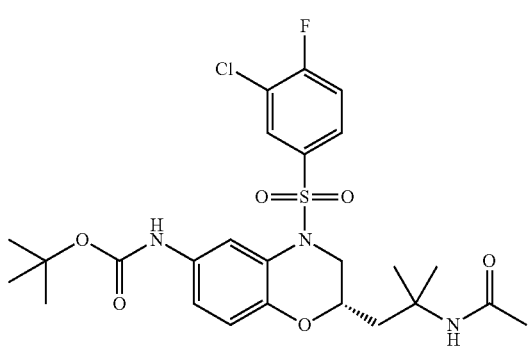 [SMILES: CC(=O)NC(C)(C)C[C@H]1CN(S(=O)(=O)c2ccc(F)c(Cl)c2)c2cc(NC(=O)OC(C)(C)C)ccc2O1]

Part VI—Synthesis of (S)-tert-butyl (2-(2-acetamido-2-methylpropyl)-4-((3-chloro-4-fluorophenyl) sulfonyl)-3,4-dihydro-2H-benzo[b][1,4]oxazin-6-yl) carbamate To a solution of (S)-tert-butyl (2-(2-acetamido-2-methylpropyl)-3,4-dihydro-2H-benzo[b][1,4]oxazin-6-yl)carbamate (0.05 g, 0.1 mmol) and pyridine (1 mL) in dry THF (2 mL) was added sulfonyl chloride (0.06 g, 1.1 mmol) at 0° C. The mixture was stirred at reflux for an hour. The resulting mixture was poured into ice-water (10 mL) and extracted with ethyl acetate (10 mL×3). The combined organic layers were washed with brine (5 mL), dried ($Na_2SO_4$) and concentrated. The residue was purified by prep-HPLC (45-75% acetonitrile+0.75%0 trifluoroacetic acid in water) to give (S)-tert-butyl (2-(2-acetamido-2-methylpropyl)-4-((3-chloro-4-fluorophenyl)sulfonyl)-3,4-dihydro-2H-benzo[b][1,4]oxazin-6-yl)carbamate as a white solid. $^1$H NMR (400 MHz, $CDCl_3$) δ 7.89 (d, J=5.2 Hz, 1H), 7.74 (br s, 1H), 7.61 (br s, 1H), 7.09~7.25 (m, 2H), 6.71 (d, J=8.8 Hz, 1H), 6.43 (br s, 1H), 5.58 (br s, 1H), 4.13 (d, J=13.6 Hz, 1H), 3.63~3.80 (m, 1H), 3.20 (dd, J=9.6, 14.0 Hz, 1H), 2.13 (d, J=14.0 Hz, 1H), 1.92 (s, 3H), 1.79 (dd, J=8.4, 14.8 Hz, 1H), 1.52 (s, 9H), 1.34 (d, J=6.8 Hz, 6H). LCMS (ESI): calculated for $C_{25}H_{32}ClFN_3O_4S$ (M+H)$^+$: 556, Found: 556.

Example 55—Preparation of Additional Amides of Benzoxazines

The compounds in Table 19 below were prepared based on the experimental procedures described in Example 54 and elsewhere in the detailed description, and can be achieved by one of skill in the art in light of the present disclosure.

TABLE 19

| Ex. No. | Structure | Name | Observed m/z |
|---|---|---|---|
| 55A | 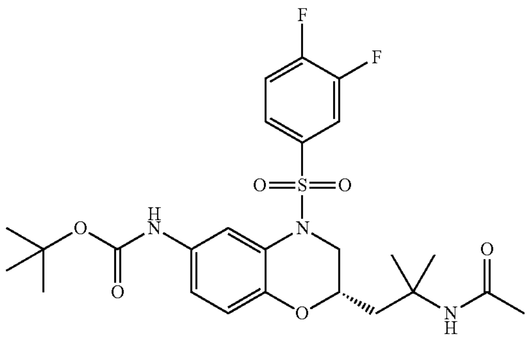 [SMILES: CC(=O)NC(C)(C)C[C@H]1CN(S(=O)(=O)c2ccc(F)c(F)c2)c2cc(NC(=O)OC(C)(C)C)ccc2O1] | (S)-tert-butyl (2-(2-acetamido-2-methylpropyl)-4-((3,4-difluorophenyl)sulfonyl)-3,4-dihydro-2H-benzo[b][1,4]oxazin-6-yl)carbamate | 540 (M + H)+ |
| 55B | 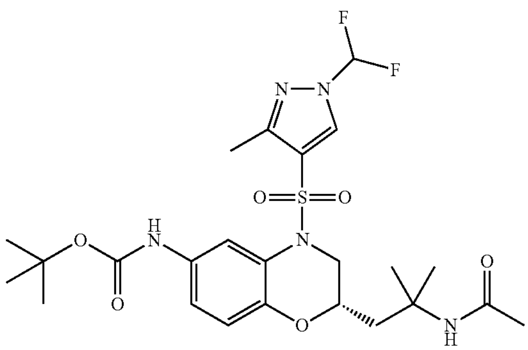 [SMILES: CC(=O)NC(C)(C)C[C@H]1CN(S(=O)(=O)c2cn(C(F)F)nc2C)c2cc(NC(=O)OC(C)(C)C)ccc2O1] | (S)-tert-butyl (2-(2-acetamido-2-methylpropyl)-4-((1-(difluoromethyl)-3-methyl-1H-pyrazol-4-yl)sulfonyl)-3,4-dihydro-2H-benzo[b][1,4]oxazin-6-yl)carbamate | 558 (M + H)+ |
| 55C | 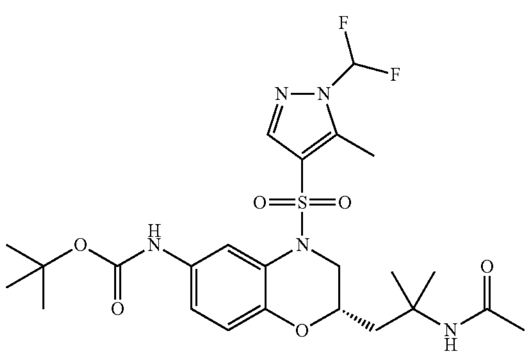 [SMILES: CC(=O)NC(C)(C)C[C@H]1CN(S(=O)(=O)c2cnn(C(F)F)c2C)c2cc(NC(=O)OC(C)(C)C)ccc2O1] | (S)-tert-butyl (2-(2-acetamido-2-methylpropyl)-4-((1-(difluoromethyl)-5-methyl-1H-pyrazol-4-yl)sulfonyl)-3,4-dihydro-2H-benzo[b][1,4]oxazin-6-yl)carbamate | 558 (M + H)+ |
| 55D | 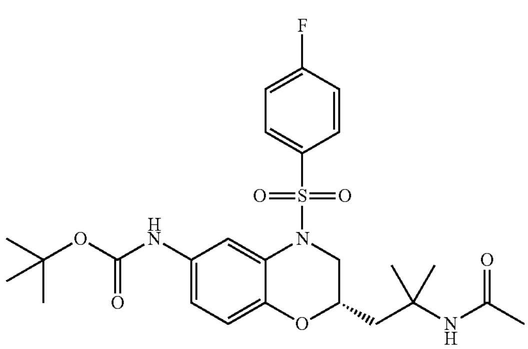 [SMILES: CC(=O)NC(C)(C)C[C@H]1CN(S(=O)(=O)c2ccc(F)cc2)c2cc(NC(=O)OC(C)(C)C)ccc2O1] | (S)-tert-butyl (2-(2-acetamido-2-methylpropyl)-4-((4-fluorophenyl)sulfonyl)-3,4-dihydro-2H-benzo[b][1,4]oxazin-6-yl)carbamate | 522 (M + H)+ |

TABLE 19-continued

| Ex. No. | Structure | Name | Observed m/z |
|---|---|---|---|
| 55E | 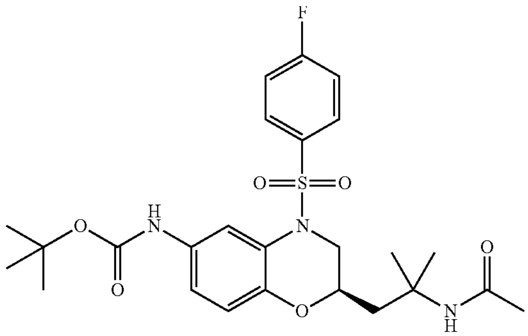 [SMILES: CC(=O)NC(C)(C)C[C@@H]1CN(S(=O)(=O)c2ccc(F)cc2)c2cc(NC(=O)OC(C)(C)C)ccc2O1] | (R)-tert-butyl (2-(2-acetamido-2-methylpropyl)-4-((4-fluorophenyl)sulfonyl)-3,4-dihydro-2H-benzo[b][1,4]oxazin-6-yl)carbamate | 522 (M + H)⁺ |

Example 56—Synthesis of (S)-1,1,1-trifluoro-2-methylpropan-2-yl (2-(2-acetamido-2-methylpropyl)-4-((3-(trifluoromethyl)phenyl)sulfonyl)-3,4-dihydro-2H-benzo[b][1,4]oxazin-6-yl)carbamate (56)

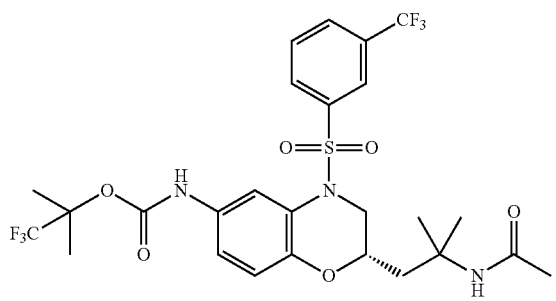 [SMILES: CC(=O)NC(C)(C)C[C@H]1CN(S(=O)(=O)c2cccc(C(F)(F)F)c2)c2cc(NC(=O)OC(C)(C)C(F)(F)F)ccc2O1]

A mixture of (S)—N-(1-(6-amino-4-((3-(trifluoromethyl)phenyl)sulfonyl)-3,4-dihydro-2H-benzo[b][1,4]oxazin-2-yl)-2-methylpropan-2-yl)acetamide (100 mg, 0.21 mmol), 4-nitrophenyl 1,1,1-trifluoro-2-methylpropan-2-yl carbonate (130 mg, 0.44 mmol) and N,N'-diisopropylethylamine (0.2 mL) were stirred at 120° C. for two hours. The mixture was diluted with water and extracted with ethyl acetate. The organic layers were washed with 1N NaOH, brine, (Na₂SO₄) and concentrated. The residue was purified by prep-TLC (petroleum ether:ethyl acetate=1:1) and prep-HPLC to give (S)-1,1,1-trifluoro-2-methylpropan-2-yl (2-(2-acetamido-2-methylpropyl)-4-((3-(trifluoromethyl) phenyl)sulfonyl)-3,4-dihydro-2H-benzo[b][1,4]oxazin-6-yl)carbamate. ¹H NMR (400 MHz, CDCl₃) δ 8.08 (br s, 1H), 7.92 (d, J=7.6 Hz, 1H), 7.85 (d, J=7.6 Hz, 2H), 7.60~7.69 (m, 1H), 7.07 (dd, J=8.8, 2.2 Hz, 1H), 6.71 (d, J=9.2 Hz, 1H), 6.65 (s, 1H), 5.92 (br s, 1H), 4.13~4.18 (m, 1H), 3.73 (br s, 1H), 3.23 (dd, J=14.0, 9.6 Hz, 1H), 1.95~2.03 (m, 4H), 1.83~1.92 (m, 1H), 1.76 (s, 6H), 1.36 (s, 3H), 1.30 (s, 3H). LCMS (ESI): calculated for $C_{26}H_{30}F_6N_3O_6S$ (M+H)⁺: 626, Found: 626.

Example 57—Preparation of Additional Amides of Benzoxazines

The compounds in Table 20 below were prepared based on the experimental procedures described in Example 56 and elsewhere in the detailed description, and can be achieved by one of skill in the art in light of the present disclosure.

TABLE 20

| Ex. No. | Structure | Name | Observed m/z |
|---|---|---|---|
| 57A | 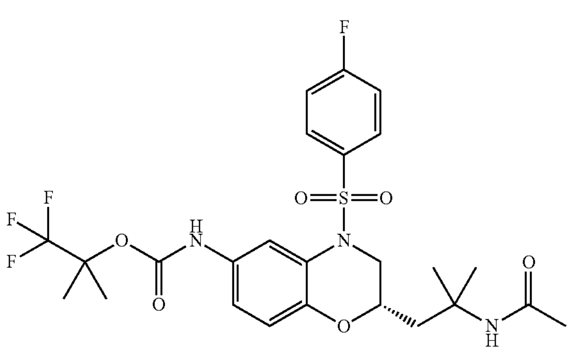 [SMILES: CC(=O)NC(C)(C)C[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-(2-acetamido-2-methylpropyl)-4-((4-fluorophenyl)sulfonyl)-3,4-dihydro-2H-benzo[b][1,4]oxazin-6-yl)carbamate | 576 (M + H)⁺ |

TABLE 20-continued

| Ex. No. | Structure | Name | Observed m/z |
|---|---|---|---|
| 57B | 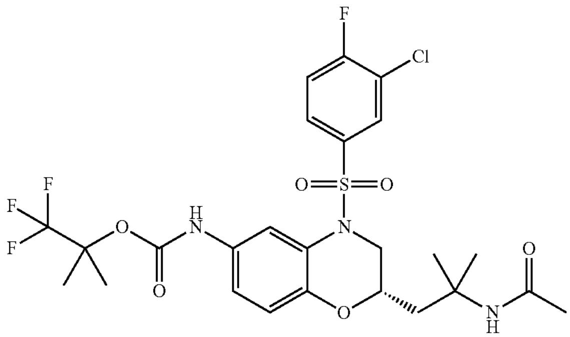 [SMILES: CC(=O)NC(C)(C)C[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (2-(2-acetamido-2-methylpropyl)-4-((3-chloro-4-fluorophenyl)sulfonyl)-3,4-dihydro-2H-benzo[b][1,4]oxazin-6-yl)carbamate | 610 (M + H)$^+$ |
| 57C | 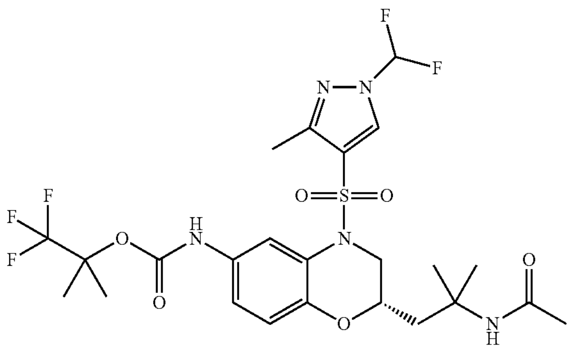 [SMILES: CC(=O)NC(C)(C)C[C@H]1CN(S(=O)(=O)c2cn(C(F)F)nc2C)c2cc(NC(=O)OC(C)(C)C(F)(F)F)ccc2O1] | (S)-1,1,1-trifluoro-2-methylpropan-2-yl (2-(2-acetamido-2-methylpropyl)-4-((1-(difluoromethyl)-3-methyl-1H-pyrazol-4-yl)sulfonyl)-3,4-dihydro-2H-benzo[b][1,4]oxazin-6-yl)carbamate | 612 (M + H)$^+$ |
| 57D | 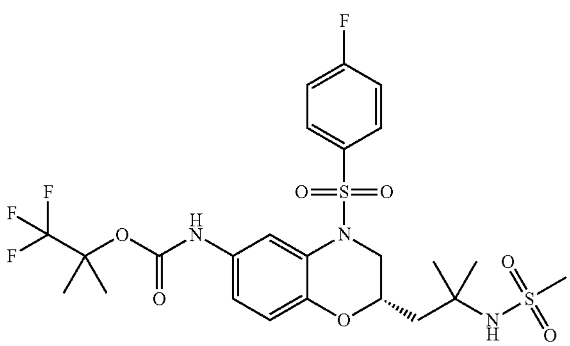 [SMILES: CC(C)(C[C@H]1CN(S(=O)(=O)c2ccc(F)cc2)c2cc(NC(=O)OC(C)(C)C(F)(F)F)ccc2O1)NS(C)(=O)=O] | (S)-1,1,1-trifluoro-2-methylpropan-2-yl (4-((4-fluorophenyl)sulfonyl)-2-(2-methyl-2-(methylsulfonamido)propyl)-3,4-dihydro-2H-benzo[b][1,4]oxazin-6-yl)carbamate | 612 (M + H)$^+$ |
| 57E | 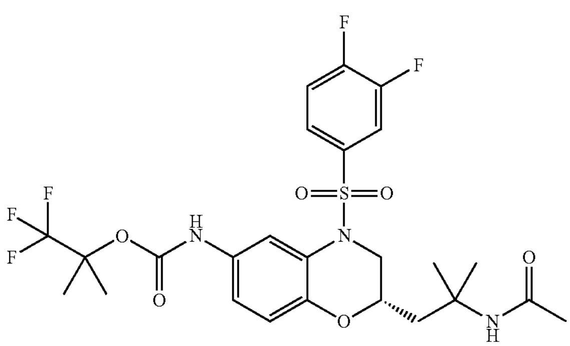 [SMILES: CC(=O)NC(C)(C)C[C@H]1CN(S(=O)(=O)c2ccc(F)c(F)c2)c2cc(NC(=O)OC(C)(C)C(F)(F)F)ccc2O1] | (S)-1,1,1-trifluoro-2-methylpropan-2-yl (2-(2-acetamido-2-methylpropyl)-4-((3,4-difluorophenyl)sulfonyl)-3,4-dihydro-2H-benzo[b][1,4]oxazin-6-yl)carbamate | 594 (M + H)$^+$ |

TABLE 20-continued

| Ex. No. | Structure | Name | Observed m/z |
|---|---|---|---|
| 57F | 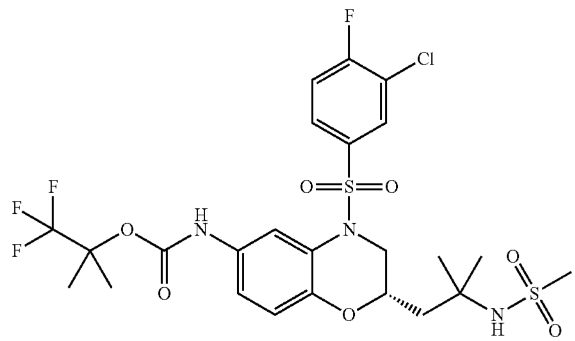 [SMILES: CC(C)(C[C@H]1CN(S(=O)(=O)c2ccc(F)c(Cl)c2)c2cc(NC(=O)OC(C)(C)C(F)(F)F)ccc2O1)NS(C)(=O)=O] | (S)-1,1,1-trifluoro-2-methylpropan-2-yl (4-((3-chloro-4-fluorophenyl)sulfonyl)-2-(2-methyl-2-(methylsulfonamido)propyl)-3,4-dihydro-2H-benzo[b][1,4]oxazin-6-yl)carbamate | 668 (M + Na)+ |
| 57G | 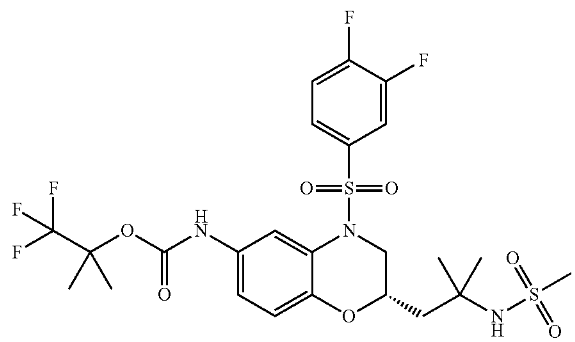 [SMILES: CC(C)(C[C@H]1CN(S(=O)(=O)c2ccc(F)c(F)c2)c2cc(NC(=O)OC(C)(C)C(F)(F)F)ccc2O1)NS(C)(=O)=O] | (S)-1,1,1-trifluoro-2-methylpropan-2-yl (4-((3,4-difluorophenyl)sulfonyl)-2-(2-methyl-2-(methylsulfonamido)propyl)-3,4-dihydro-2H-benzo[b][1,4]oxazin-6-yl)carbamate | 630 (M + H)+ |
| 57H | 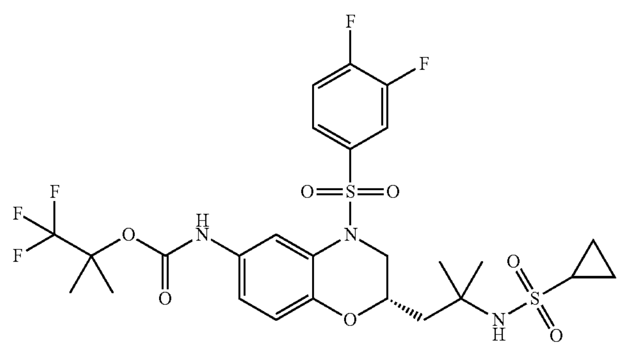 [SMILES: CC(C)(C[C@H]1CN(S(=O)(=O)c2ccc(F)c(F)c2)c2cc(NC(=O)OC(C)(C)C(F)(F)F)ccc2O1)NS(=O)(=O)C1CC1] | (S)-1,1,1-trifluoro-2-methylpropan-2-yl (2-(2-(cyclopropanesulfonamido)-2-methylpropyl)-4-((3,4-difluorophenyl)sulfonyl)-3,4-dihydro-2H-benzo[b][1,4]oxazin-6-yl)carbamate | 678 (M + Na)+ |
| 57i | 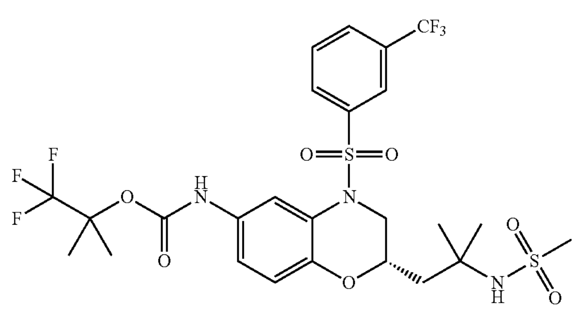 [SMILES: CC(C)(C[C@H]1CN(S(=O)(=O)c2cccc(C(F)(F)F)c2)c2cc(NC(=O)OC(C)(C)C(F)(F)F)ccc2O1)NS(C)(=O)=O] | (S)-1,1,1-trifluoro-2-methylpropan-2-yl (2-(2-methyl-2-(methylsulfonamido)propyl)-4-((3-(trifluoromethyl)phenyl)sulfonyl)-3,4-dihydro-2H-benzo[b][1,4]oxazin-6-yl)carbamate | 684 (M + Na)+ |

TABLE 20-continued

| Ex. No. | Structure | Name | Observed m/z |
|---|---|---|---|
| 57J | 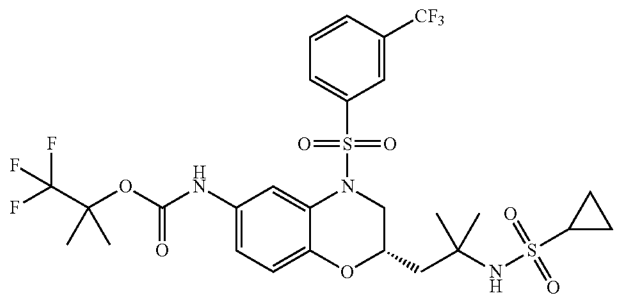 [SMILES: CC(C)(C[C@H]1CN(S(=O)(=O)c2cccc(C(F)(F)F)c2)c2cc(NC(=O)OC(C)(C)C(F)(F)F)ccc2O1)NS(=O)(=O)C1CC1] | (S)-1,1,1-trifluoro-2-methylpropan-2-yl (2-(2-(cyclopropanesulfonamido)-2-methylpropyl)-4-((3-(trifluoromethyl)phenyl)sulfonyl)-3,4-dihydro-2H-benzo[b][1,4]oxazin-6-yl)carbamate | 710 (M + Na)+ |
| 57K | 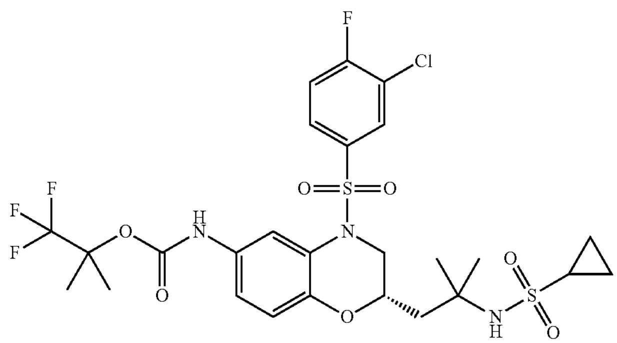 [SMILES: CC(C)(C[C@H]1CN(S(=O)(=O)c2ccc(F)c(Cl)c2)c2cc(NC(=O)OC(C)(C)C(F)(F)F)ccc2O1)NS(=O)(=O)C1CC1] | (S)-1,1,1-trifluoro-2-methylpropan-2-yl (4-((3-chloro-4-fluorophenyl)sulfonyl)-2-(2-methyl-2-(methylsulfonamido)propyl)-3,4-dihydro-2H-benzo[b][1,4]oxazin-6-yl)carbamate | 694 (M + Na)+ |
| 57L | 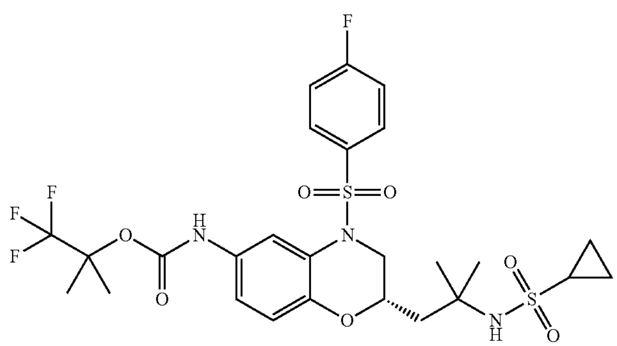 [SMILES: CC(C)(C[C@H]1CN(S(=O)(=O)c2ccc(F)cc2)c2cc(NC(=O)OC(C)(C)C(F)(F)F)ccc2O1)NS(=O)(=O)C1CC1] | (S)-1,1,1-trifluoro-2-mrthylpropan-2-yl (2-(2-(cyclopropanrsulfonamido)-2-methylpropyl)-4-((4-fluorophenyl)sulfonyl)-3,4-dihydro-2H-benzo[b][1,4]oxazin-6-yl)carbamate | 638 (M + H)+ |
| 57M | 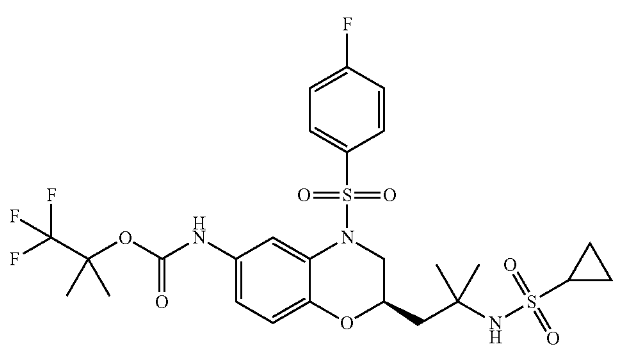 [SMILES: CC(C)(C[C@@H]1CN(S(=O)(=O)c2ccc(F)cc2)c2cc(NC(=O)OC(C)(C)C(F)(F)F)ccc2O1)NS(=O)(=O)C1CC1] | (R)-1,1,1-trifluoro-2-methylpropan-2-yl (2-(2-(cyclopropanesulfonamido)-2-methylpropyl)-4-((4-fluorophenyl)sulfonyl)-3,4-dihydro-2H-benzo[b][1,4]oxazin-6-yl)carbamate | 638 (M + H)+ |

TABLE 20-continued

| Ex. No. | Structure | Name | Observed m/z |
|---|---|---|---|
| 57N | 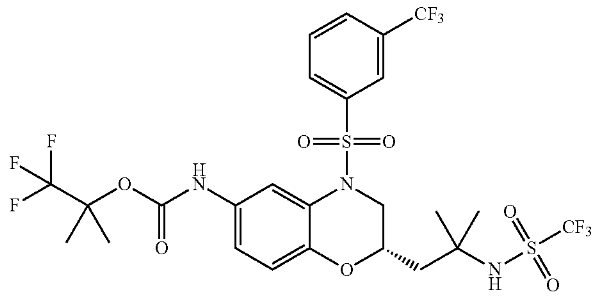 [SMILES: CC(C)(C[C@H]1CN(S(=O)(=O)c2cccc(C(F)(F)F)c2)c2cc(NC(=O)OC(C)(C)C(F)(F)F)ccc2O1)NS(=O)(=O)C(F)(F)F] | (S)-1,1,1-trifluoro-2-methylpropan-2-yl (2-(2-methyl-2-(trifluoromethylsulfonamido)propyl)-4-((3-(trifluoromethyl(phenyl(sulfonyl)-3,4-dihydro-2H-benzo[b][1,4]oxazin-6-yl)carbamate | 716 (M + H)+ |
| 57o | 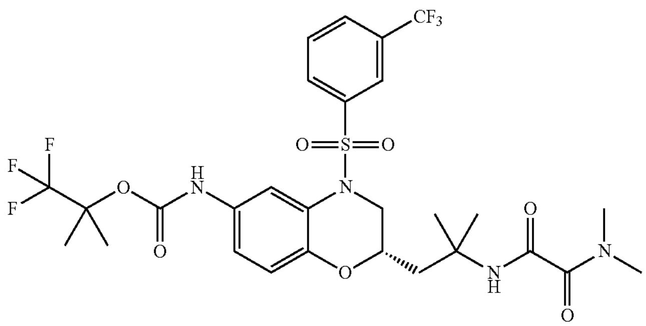 [SMILES: CN(C)C(=O)C(=O)NC(C)(C)C[C@H]1CN(S(=O)(=O)c2cccc(C(F)(F)F)c2)c2cc(NC(=O)OC(C)(C)C(F)(F)F)ccc2O1] | (S)-1,1,1-trifluoro-2-methylpropan-2-yl (2-(2-(2-(dimethylamino)-2-oxoacetamido)-2-methylpropyl)-4-((3-(trifluoromethyl)phenyl)sulfonyl)-3,4-dihydro-2H-benzo[b][1,4]oxazin-6-yl)carbamate | 683 (M + H)+ |
| 57P | 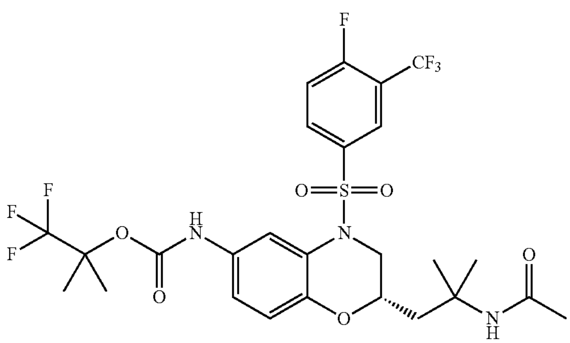 [SMILES: CC(=O)NC(C)(C)C[C@H]1CN(S(=O)(=O)c2ccc(F)c(C(F)(F)F)c2)c2cc(NC(=O)OC(C)(C)C(F)(F)F)ccc2O1] | (S)-1,1,1-trifluoro-2-methylpropan-2-yl (2-(2-acetamido-2-methylpropyl)-4-((4-fluoro-3-(trifluoromethyl)phenyl)sulfonyl)-3,4-dihydro-2H-benzo[b][1,4]oxazin-6-carbamate | 644 (M + H)+ |
| 57Q | 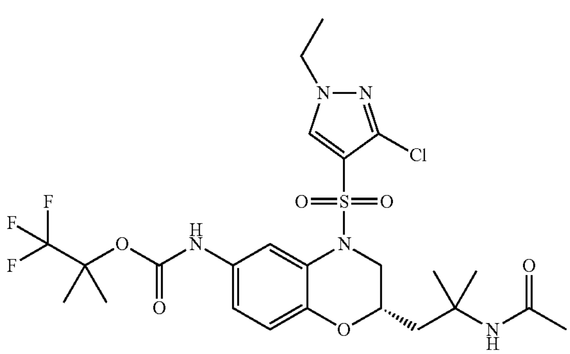 [SMILES: CCn1cc(S(=O)(=O)N2C[C@H](CC(C)(C)NC(C)=O)Oc3ccc(NC(=O)OC(C)(C)C(F)(F)F)cc32)c(Cl)n1] | (S)-1,1,1-trifluoro-2-methylpropan-2-yl (2-(2-acetamido-2-methylpropyl)-4-((3-chloro-1-ethyl-1H-pyrazol-4-yl)sulfonyl)-3,4-dihydro-2H-benzo[b][1,4]oxazin-6-yl)carbamate | 611 (M + H)+ |

TABLE 20-continued

| Ex. No. | Structure | Name | Observed m/z |
|---|---|---|---|
| 57R | 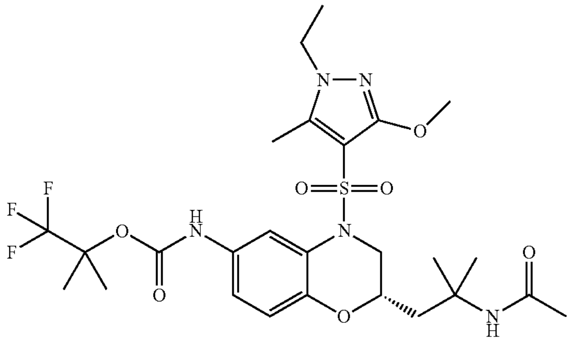 | (S)-1,1,1-trifluoro-2-methylpropan-2-yl (2-(2-acetamido-2-methylpropyl)-4-((3-methoxy-1,5-dimethyl-1H-pyrazol-4-yl)sulfonyl)-3,4-dihydro-2H-benzo[b][1,4]oxazin-6-yl)carbamate | 606 (M + H)+ |
| 57S | 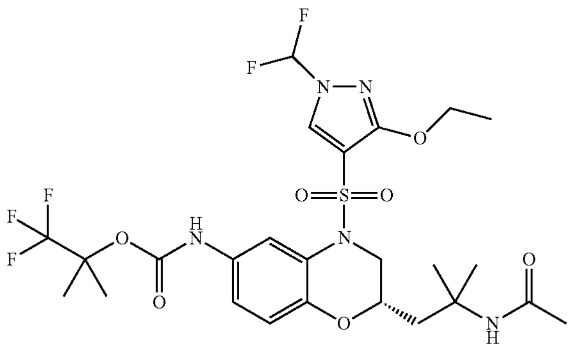 [SMILES: CCOc1nn(C(F)F)cc1S(=O)(=O)N1C[C@H](CC(C)(C)NC(C)=O)Oc2ccc(NC(=O)OC(C)(C)C(F)(F)F)cc21] | (S)-1,1,1-trifluoro-2-methylpropan-2-yl (2-(2-acetamido-2-methylpropyl)-4-((1-(difluoromethyl)-3-ethoxy-1H-pyrazol-4-yl)sulfonyl)-3,4-dihydro-2H-benzo[b][1,4]oxazin-6-yl)carbamate | 642 (M + H)+ |
| 57T | 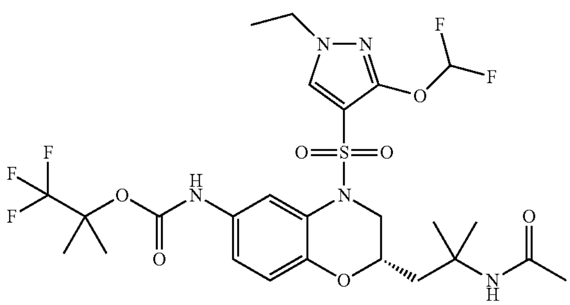 [SMILES: CCn1cc(S(=O)(=O)N2C[C@H](CC(C)(C)NC(C)=O)Oc3ccc(NC(=O)OC(C)(C)C(F)(F)F)cc32)c(OC(F)F)n1] | (S)-1,1,1-trifluoro-2-methylpropan-2-yl (2-(2-acetamido-2-methylpropyl)-4-((3-(difluoromethoxy)-1-ethyl-1H-pyrazol-4-yl)sulfonyl)-3,4-dihydro-2H-benzo[b][1,4]oxazin-6-yl)carbamate | 642 (M + H)+ |
| 57U | 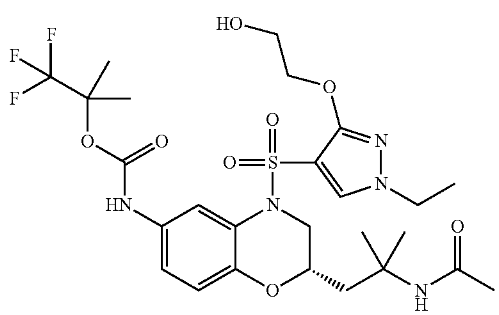 [SMILES: CCn1cc(S(=O)(=O)N2C[C@H](CC(C)(C)NC(C)=O)Oc3ccc(NC(=O)OC(C)(C)C(F)(F)F)cc32)c(OCCO)n1] | 2,2,2-trifluoro-1,1-dimethylethyl [(2S)-2-[2-(acetylamino)-2-methylpropyl]-4-{[1-ethyl-3-(2-hydroxyethoxy)-1H-pyrazol-4-yl]sulfonyl}-3,4-dihydro-2H-1,4-benzoxazin-6-yl]carbamate | 636 (M + H)+ |

Example 58—Synthesis of tert-butyl (2-(2-hydroxyethyl)-4-((3-(trifluoromethyl)phenyl)sulfonyl)-3,4-dihydro-2H-benzo[b][1,4]oxazin-6-yl)carbamate (58)

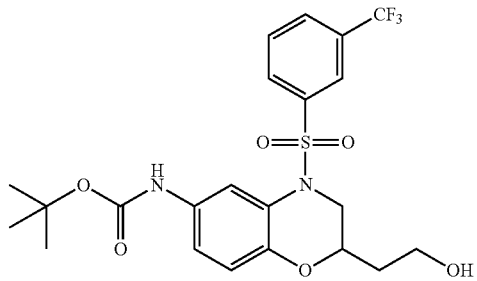 [SMILES: CC(C)(C)OC(=O)Nc1ccc2c(c1)N(S(=O)(=O)c1cccc(C(F)(F)F)c1)CC(CCO)O2]

To a solution of (6-((tert-butoxycarbonyl)amino)-4-((3-(trifluoromethyl)phenyl)sulfonyl)-3,4-dihydro-2H-benzo[b][1,4]oxazin-2-yl)acetic acid (240 mg, 0.47 mmol) in anhydrous THF (10 mL) was added 1 M solution of borane (4.5 mL, 4.65 mmol) in THF at 0° C. The mixture was stirred at room temperature overnight and quenched with methanol (5 mL). The mixture was concentrated, diluted with water (20 mL), and extracted three times with ethyl acetate (15 mL each). The organic layers were combined (Na$_2$SO$_4$) and concentrated. The residue was purified by reverse phase chromatography (water/MeOH=50/50) MPLC to give the title compound. LCMS (ESI) calculated for C$_{22}$H$_{25}$F$_3$N$_2$NaO$_6$S (M+Na)$^+$: 525.1, Found: 525.1. $^1$H NMR (400 MHz, CD$_3$OD): δ 8.08 (1H, s), 8.04 (2H, d, J=8.8 Hz), 7.96 (1H, d, J=7.6 Hz), 7.75 (1H, t, J=8.0 Hz), 7.03 (1H, dd, J=8.4, 2.0 Hz), 6.72 (1H, d, J=8.4 Hz), 4.47 (1H, dd, J=14.4, 2.0 Hz), 3.63-3.70 (3H, m), 3.24-3.30 (1H, m), 1.74-1.78 (2H, m), 1.55 (9H, s).

Example 59—Synthesis of tert-butyl (2-((1H-imidazol-2-yl)methyl)-4-((3-(trifluoromethyl)phenyl)sulfonyl)-3,4-dihydro-2H-benzo[b][1,4]oxazin-6-yl)carbamate (59)

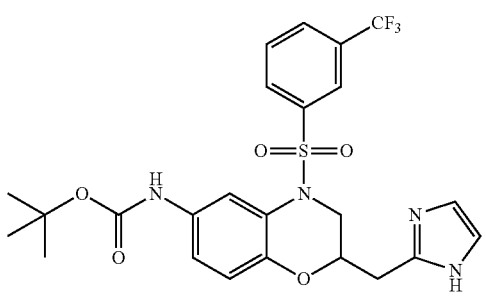 [SMILES: CC(C)(C)OC(=O)Nc1ccc2c(c1)N(S(=O)(=O)c1cccc(C(F)(F)F)c1)CC(Cc1ncc[nH]1)O2]

Aqueous ammonium hydroxide (25% w/w, 0.15 mL) was added to solution of (6-((tert-butoxycarbonyl)amino)-4-((3-(trifluoromethyl)phenyl)sulfonyl)-3,4-dihydro-2H-benzo[b][1,4]oxazin-2-yl)acetic acid (145 mg, 0.29 mmol) in methanol (2 mL). Glyoxal (40% (w/w) in water, 0.05 mL) was added dropwise to the above mixture and the reaction was stirred at room temperature for twelve hours. The solvent was removed and the residue was purified by Prep-HPLC to afford the title compound. LCMS (ESI) calculated for C$_{24}$H$_{26}$F$_3$N$_4$O$_5$S (M+H)$^+$: 539.2, Found: 539.0. $^1$H NMR (400 MHz, CD$_3$OD): δ 8.02-7.94 (4H, m), 7.74 (1H, t, J=7.6 Hz), 7.05-7.01 (3H, m), 6.76 (1H, d, J=8.8 Hz), 4.42 (1H, d, J=14.4 Hz), 3.76-3.74 (1H, m), 3.23 (1H, dd, J=14, 9.6 Hz), 3.03-2.97 (2H, m), 1.54 (9H, s).

Example 60—Synthesis of tert-butyl (2-((1-methyl-1H-imidazol-2-yl)methyl)-4-((3-(trifluoromethyl)phenyl)sulfonyl)-3,4-dihydro-2H-benzo[b][1,4]oxazin-6-yl)carbamate (60)

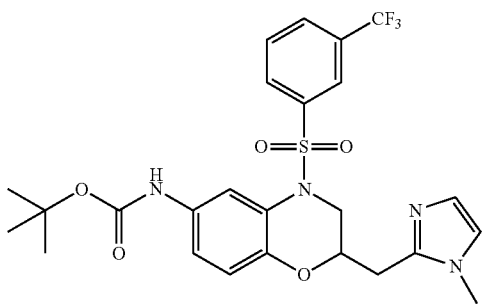 [SMILES: Cn1ccnc1CC1CN(S(=O)(=O)c2cccc(C(F)(F)F)c2)c2cc(NC(=O)OC(C)(C)C)ccc2O1]

To a solution of tert-butyl (2-((1H-imidazol-2-yl)methyl)-4-((3-(trifluoromethyl)phenyl)sulfonyl)-3,4-dihydro-2H-benzo[b][1,4]oxazin-6-yl)carbamate (30 mg, 0.056 mmol) in DMF (2 mL) was added potassium carbonate (12 mg, 0.084 mmol) and methyl iodide (8 mg, 0.056 mmol) at 0° C. The reaction was stirred at room temperature for twelve hours and then concentrated. The residue was purified by Prep-HPLC to afford the title compound. LCMS (ESI) calculated for C$_{25}$H$_{28}$F$_3$N$_4$O$_5$S (M+H)$^+$: 553.2, Found: 553.2. $^1$H NMR (400 MHz, CD$_3$OD): δ 7.93-7.89 (3H, m), 7.84 (1H, d, J=8.0 Hz), 7.63 (1H, t, J=8.0 Hz), 6.92-6.90 (2H, m), 6.80 (1H, s), 6.60 (1H, d, J=8.8 Hz), 4.34 (1H, dd, J=14.4 Hz, 2.4 Hz), 3.75-3.69 (1H, m), 3.51 (3H, s), 3.23-3.17 (1H, m), 2.93 (2H, d, J=6.0 Hz), 1.42 (9H, s).

Example 61—Synthesis of (S)-tert-butyl (4-((4-fluorophenyl)sulfonyl)-2-((2-oxopyrrolidin-1-yl)methyl)-3,4-dihydro-2H-benzo[b][1,4]oxazin-6-yl)carbamate (61)

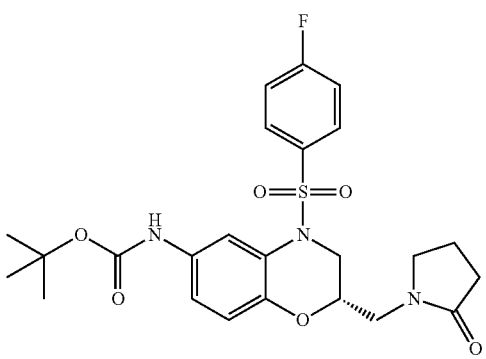 [SMILES: CC(C)(C)OC(=O)Nc1ccc2c(c1)N(S(=O)(=O)c1ccc(F)cc1)C[C@H](CN1CCCC1=O)O2]

A mixture of (S)-(6-((tert-butoxycarbonyl)amino)-4-((4-fluorophenyl)sulfonyl)-3,4-dihydro-2H-benzo[b][1,4]oxazin-2-yl)methyl 4-methylbenzenesulfonate (81.6 mg, 0.138 mmol), ethyl 4-aminobutanoate (93 mg, 0.708 mmol), and NMP (1377 μL) was stirred for three days at 100° C. The mixture was cooled, diluted with ethyl acetate and washed with saturated NaHCO₃ and brine. The combined organic layers were dried (MgSO₄) and concentrated. Purification via chromatography eluting with a gradient of 100% hexanes to 100% ethyl acetate afforded (S)-tert-butyl (4-((4-fluorophenyl)sulfonyl)-2-(2-oxopyrrolidin-1-yl)methyl)-3,4-dihydro-2H-benzo[b][1,4]oxazin-6-yl)carbamate. LRMS (ESI) calculated for C$_{20}$H$_{20}$FN$_3$O$_6$S (M-tBu+H)⁺: 450, Found: 450. ¹H NMR (500 MHz, DMSO-d6) δ 9.29 (s, 1H), 7.86 (s, 1H), 7.78 (m, 2H), 7.43 (t, 2H, J=7.95 Hz), 7.14 (d, 1H, J=8.97 Hz), 6.73 (d, 1H, J=8.96 Hz), 4.16 (d, 1H, J=14.5 Hz), 3.47 (m, 1H), 3.43 (m, 2H), 3.22 (m, 2H), 3.19 (m, 1H), 2.22 (m, 2H), 1.92 (m, 2H), 1.46 (s, 9H).

Example 62—Synthesis of (S)-tert-butyl (2-((1H-pyrazol-1-yl)methyl)-4-((3-(trifluoromethyl)phenyl)sulfonyl)-3,4-dihydro-2H-benzo[b][1,4]oxazin-6-yl)carbamate (62)

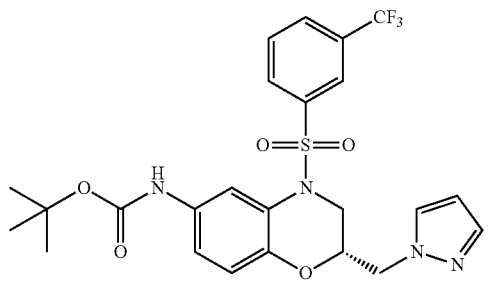 [SMILES: CC(C)(C)OC(=O)Nc1ccc2c(c1)N(S(=O)(=O)c1cccc(C(F)(F)F)c1)C[C@H](Cn1cccn1)O2]

To a suspension of sodium hydride (6.18 mg, 0.154 mmol) in DMF (1 mL) at room temperature was added a solution of 1H-pyrazole (9.01 mg, 0.132 mmol) in DMF (1 mL) and the reaction mixture was stirred for ten minutes. A solution of (R)-(6-((tert-butoxycarbonyl)amino)-4-((3-(trifluoromethyl)phenyl)sulfonyl)-3,4-dihydro-2H-benzo[b][1,4]oxazin-2-yl)methyl methanesulfonate (50 mg, 0.088 mmol) in DMF (2 mL) was added and the mixture was heated at 120° C. for fifteen minutes. The mixture was cooled, diluted with ethyl acetate, washed with water and brine, dried (Na₂SO₄), filtered and concentrated. The residue was purified by reverse phase HPLC using a solvent system of MeCN/water with 0.1% trifluoroacetic acid to yield (S)-tert-butyl (2-((1H-pyrazol-1-yl)methyl)-4-((3-(trifluoromethyl)phenyl)sulfonyl)-3,4-dihydro-2H-benzo[b][1,4]oxazin-6-yl)carbamate as white solid. MS ESI calculated for C$_{24}$H$_{25}$F$_3$N$_4$O$_2$S (M+H)⁺: 539, Found: 539. ¹H NMR (600 MHz, DMSO-d6) δ 9.27 (s, 1H), 8.10-7.88 (m, 4H), 7.79 (t, J=7.9 Hz, 1H), 7.66 (d, J=2.2 Hz, 1H), 7.45 (s, 1H), 7.02 (d, J=6.9 Hz, 1H), 6.68 (d, J=8.9 Hz, 1H), 6.23 (s, 1H), 4.42-4.27 (m, 3H), 3.80 (s, 1H), 3.47 (s, 2H), 3.28 (dd, J=14.2, 9.7 Hz, 1H), 1.43 (s, 9H).

Example 63—Preparation of Additional Heteroatom Linked Heterocycles

The compounds in Table 21 below were prepared based on the experimental procedures described in Examples 61 and 62 and elsewhere in the detailed description, and can be achieved by one of skill in the art in light of the present disclosure. In cases of where two products could be obtained, both were isolated via HPLC chromatography.

TABLE 21

| Ex. No. | Structure | Name | Observed m/z |
|---|---|---|---|
| 63A | 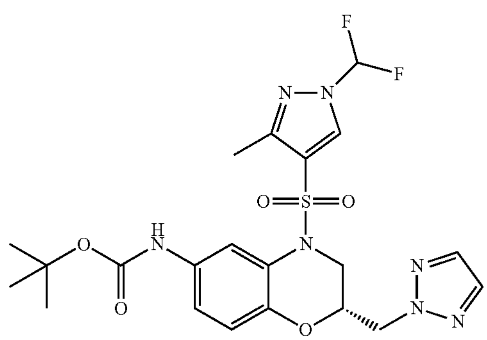 [SMILES: Cc1nn(C(F)F)cc1S(=O)(=O)N1C[C@H](Cn2nccn2)Oc2ccc(NC(=O)OC(C)(C)C)cc21] | (S)-tert-butyl (2-((2H-1,2,3-triazol-2-yl)methyl-4-((1-(difluoromethyl)-3-methyl-1H-pyrazol-4-yl)sulfonyl)-3,4-dihydro-2H-benzo[b][1,4]oxazin-6-yl)carbamate | 470.1 (M − tBu)⁺ |
| 63B | 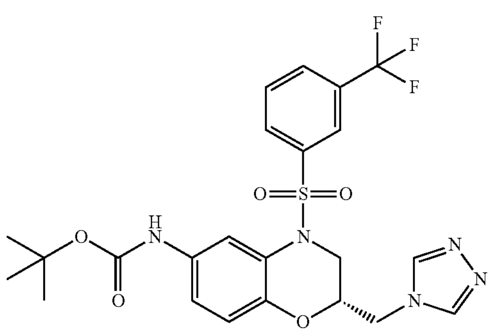 [SMILES: CC(C)(C)OC(=O)Nc1ccc2c(c1)N(S(=O)(=O)c1cccc(C(F)(F)F)c1)C[C@H](Cn1cnnc1)O2] | (S)-tert-butyl (2-((4H-1,2,4-triazol-4-yl)methyl)-4-((3-(trifluoromethyl)phenyl)sulfonyl)-3,4-dihydro-2H-benzo[b][1,4]oxazin-6-yl)carbamate | 540.2 (M + H)⁺ |

TABLE 21-continued

| Ex. No. | Structure | Name | Observed m/z |
|---|---|---|---|
| 63C | 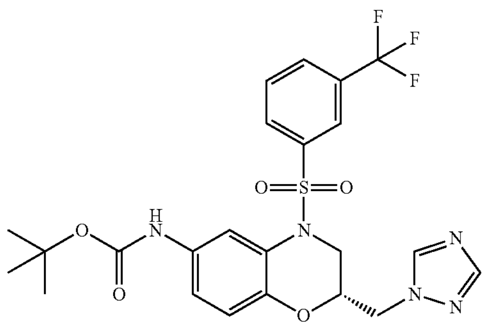 [SMILES: CC(C)(C)OC(=O)Nc1ccc2c(c1)N(S(=O)(=O)c1cccc(C(F)(F)F)c1)C[C@H](Cn1cncn1)O2] | (S)-tert-butyl (2-((1H-1,2,4-triazol-1-yl)methyl)-4-((3-(trifluoromethyl)phenyl)sulfonyl)-3,4-dihydro-2H-benzo[b][1,4]oxazin-6-yl)carbamate | 540.2 (M + H)+ |
| 63D | 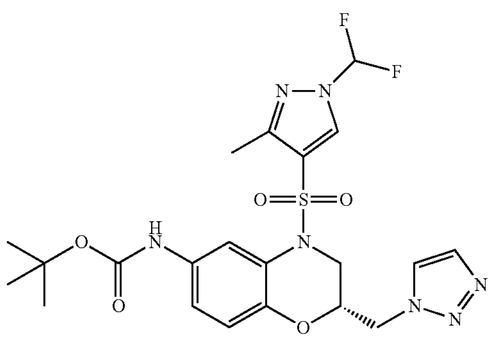 [SMILES: Cc1nn(C(F)F)cc1S(=O)(=O)N1C[C@H](Cn2ccnn2)Oc2ccc(NC(=O)OC(C)(C)C)cc21] | (S)-tert-butyl (2-((1H-1,2,3-triazol-1-yl)methyl)-4-((1-(difluoromethyl)-3-methyl-1H-pyrazol-4-yl)sulfonyl)-3,4-dihydro-2H-benzo[b][1,4]oxazin-6-yl)carbamate | 526.1 (M + H)+ |
| 63E | 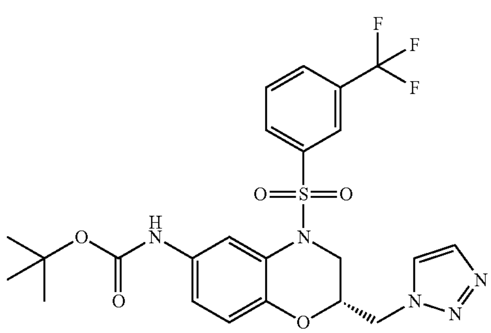 [SMILES: CC(C)(C)OC(=O)Nc1ccc2c(c1)N(S(=O)(=O)c1cccc(C(F)(F)F)c1)C[C@H](Cn1ccnn1)O2] | (S)-tert-butyl (2-((1H-1,2,3-triazol-1-yl)methyl)-4-((3-(trifluoromethyl(phenyl)sulfonyl)-3,4-dihydro-2H-benzo[b][1,4]oxazin-6-yl)carbamate | 540.1 (M + H)+ |
| 63F | 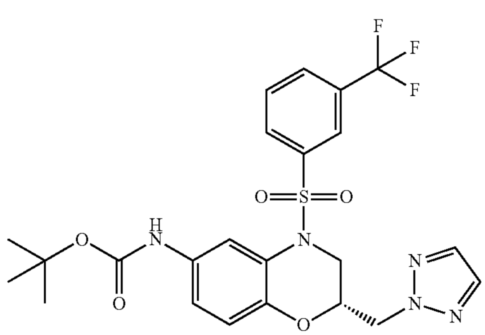 [SMILES: CC(C)(C)OC(=O)Nc1ccc2c(c1)N(S(=O)(=O)c1cccc(C(F)(F)F)c1)C[C@H](Cn1nccn1)O2] | (S)-tert-butyl (2-((2H-1,2,3-triazol-2-yl)methyl)-4-((3-(trifluoromethyl)phenyl)sulfonyl)-3,4-dihydro-2H-benzo[b][1,4]oxazin-6-yl)carbamate | 484.0 (M − tBu)+ |

TABLE 21-continued

| Ex. No. | Structure | Name | Observed m/z |
|---|---|---|---|
| 63G | 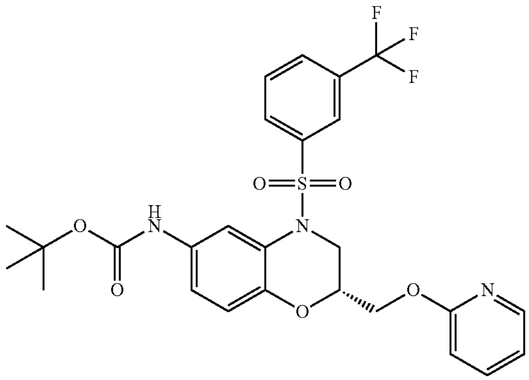 [SMILES: CC(C)(C)OC(=O)Nc1ccc2c(c1)N(S(=O)(=O)c1cccc(C(F)(F)F)c1)C[C@H](COc1ccccn1)O2] | (R)-tert-butyl (2-((pyridin-2-yloxy(methyl)-4-((3-(trifluoromethyl)phenyl)sulfonyl)-3,4-dihydro-2H-benzo[b][1,4]oxazin-6-yl)carbamate | 588.0 (M + Na)+ |
| 63H | 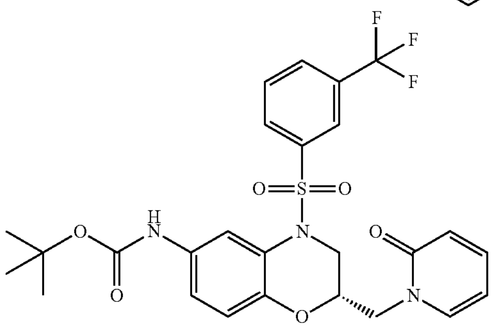 | (S)-tert-butyl (2-((2-oxopyridin-1(2H)-yl)methyl)-4-((3-(trifluoromethyl)phenyl)sulfonyl)-3,4-dihydro-2H-benzo[b][1,4]oxazin-6-yl)carbamate | 566.0 (M + H)+ |

Example 64—Synthesis of (S)-tert-butyl (2-((5-oxo-2,5-dihydro-1,2,4-oxadiazol-3-yl)methyl)-4-((3-(trifluoromethyl)phenyl)sulfonyl)-3,4-dihydro-2H-benzo[b][1,4]oxazin-6-yl)carbamate (64)

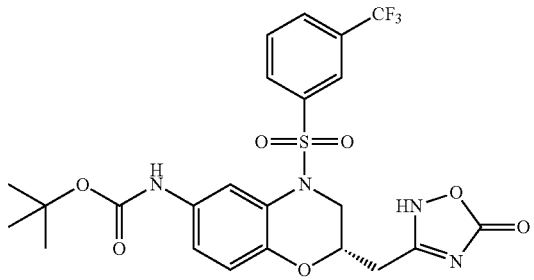 [SMILES: CC(C)(C)OC(=O)Nc1ccc2c(c1)N(S(=O)(=O)c1cccc(C(F)(F)F)c1)C[C@H](Cc1nc(=O)o[nH]1)O2]

The title compound was prepared according to the procedures described below.

Part I—Synthesis of (S)-tert-butyl (2-(cyanomethyl)-4-((3-(trifluoromethyl)phenyl)sulfonyl)-3,4-dihydro-2H-benzo[b][1,4]oxazin-6-yl)carbamate

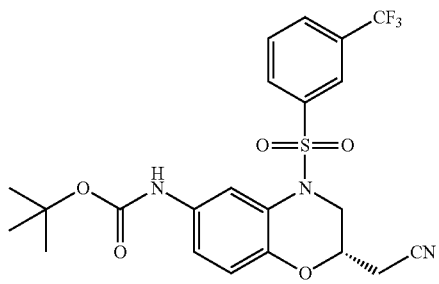

To a solution of (S)-2-(6-((tert-butoxycarbonyl)amino)-4-((3-(trifluoromethyl)phenyl)sulfonyl)-3,4-dihydro-2H-benzo[b][1,4]oxazin-2-yl)acetic acid (200 mg, 0.387 mmol), ammonium chloride (41.4 mg, 0.774 mmol) and (O-(7-azabenzotriazol-1-yl)-N,N,N',N'-tetramethyluronium hexafluorophosphate) (221 mg, 0.581 mmol) in dichloromethane (5 mL) at room temperature was added N,N'-diisopropylethylamine (0.20 mL, 1.16 mmol) and the mixture was stirred at room temperature for sixty hours. The mixture was concentrated, and then dissolved in DMF (3 mL). To DMF (1 mL) at 0° C. was added phosphoryl trichloride (0.18 mL, 1.94 mmol) dropwise and the mixture was stirred at room temperature for thirty minutes. The crude solution of the amide was added and the mixture was stirred at room temperature for an additional sixteen hours. The reaction mixture was poured into ice, and extracted with ethyl acetate. The organic phase was washed with saturated aqueous sodium chloride, dried ($Na_2SO_4$) filtered and concentrated. The residue was purified by silica gel chromatography eluting with a gradient of ethyl acetate/hexane (0~25%) to afford (S)-tert-butyl (2-(cyanomethyl)-4-((3-(trifluoromethyl)phenyl)sulfonyl)-3,4-dihydro-2H-benzo[b][1,4]oxazin-6-yl)carbamate. MS ESI calculated for $C_{22}H_{22}F_3N_3O_5S$ (M+H)+: 498, Found: 442 (M-tBu) and 520 (M+Na).

Part II—Synthesis of (S)-tert-butyl (2-(2-(hydroxyamino)-2-iminoethyl)-4-((3-(trifluoromethyl)phenyl)sulfonyl)-3,4-dihydro-2H-benzo[b][1,4]oxazin-6-yl)carbamate

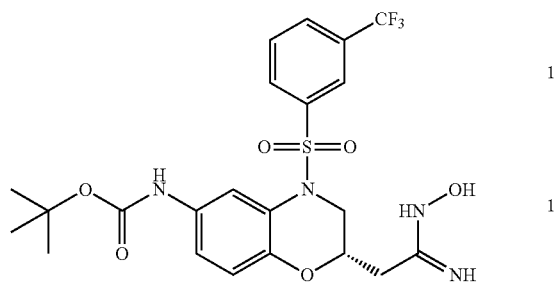

To a solution of (S)-tert-butyl (2-(cyanomethyl)-4-((3-(trifluoromethyl)phenyl)sulfonyl)-3,4-dihydro-2H-benzo[b][1,4]oxazin-6-yl)carbamate (80 mg, 0.16 mmol) in ethanol (5 mL) was added hydroxylamine hydrochloride (22.4 mg, 0.322 mmol) followed by potassium carbonate (66.7 mg, 0.482 mmol) and the mixture was heated at 70° C. for sixteen hours. Additional hydroxamine hydrochloride (20 mg) was added and the mixture was stirred at 80° C. for an additional five hours. The reaction was cooled to room temperature, filtered and washed with methanol. The filtrate was concentrated to afford (S)-tert-butyl (2-(2-(hydroxyamino)-2-iminoethyl)-4-((3-(trifluoromethyl)phenyl)sulfonyl)-3,4-dihydro-2H-benzo[b][1,4]oxazin-6-yl)carbamate, which was used without further purification.

Part III—Synthesis of (S)-tert-butyl (2-((5-oxo-2,5-dihydro-1,2,4-oxadiazol-3-yl)methyl)-4-((3-(trifluoromethyl)phenyl)sulfonyl)-3,4-dihydro-2H-benzo[b][1,4]oxazin-6-yl)carbamate

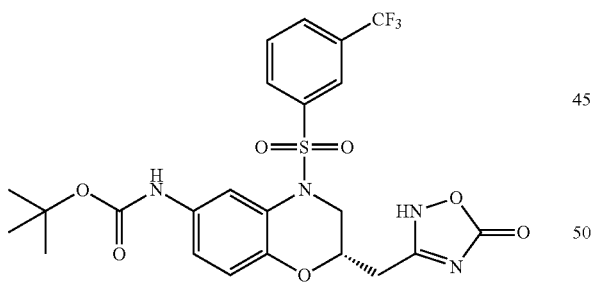

To the above prepared (S)-tert-butyl (2-(2-(hydroxyamino)-2-iminoethyl)-4-((3-(trifluoromethyl)phenyl)sulfonyl)-3,4-dihydro-2H-benzo[b][1,4]oxazin-6-yl)carbamate (0.16 mmol) in acetonitrile (5 mL) was added carbonyl diimidazole (36.7 mg, 0.226 mmol) and 1,8-diazabicyclo[5.4.0]undec-7-ene (0.091 mL, 0.60 mmol). The mixture was stirred at room temperature for three hours. The mixture was concentrated and the residue was purified by reverse phase HPLC using a solvent system of MeCN/water modified with 0.1% trifluoroacetic acid to yield (S)-tert-butyl (2-((5-oxo-2,5-dihydro-1,2,4-oxadiazol-3-yl)methyl)-4-((3-(trifluoromethyl)phenyl)sulfonyl)-3,4-dihydro-2H-benzo[b][1,4]oxazin-6-yl)carbamate as white solid. MS ESI calculated for $C_{23}H_{23}F_3N_4O_7S$ (M+H)$^+$: 557, Found: 501 (M-tBu). $^1$H NMR (600 MHz, DMSO-d6) δ 12.10 (s, 1H), 9.27 (s, 1H), 8.19-7.94 (m, 4H), 7.82 (d, J=7.7 Hz, 1H), 6.99 (s, 1H), 6.73 (d, J=9.0 Hz, 1H), 4.95 (s, 1H), 4.47 (d, J=14.0 Hz, 2H), 3.32 (m, 1H), 3.01 (d, J=11.1 Hz, 1H), 2.80 (d, J=7.8 Hz, 1H), 1.46 (s, 9H).

Example 65—Synthesis of tert-butyl (2-(2-hydroxy-2-methylpropyl)-4-((3-(trifluoromethyl)phenyl)sulfonyl)-3,4-dihydro-2H-benzo[b][1,4]oxazin-6-yl)carbamate (65)

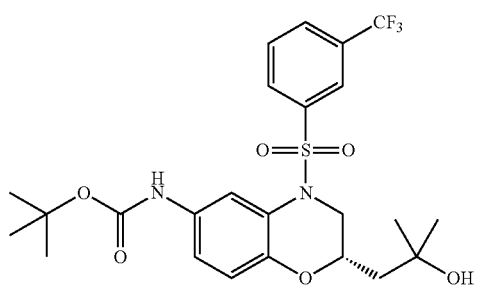 [SMILES: CC(C)(O)C[C@H]1CN(S(=O)(=O)c2cccc(C(F)(F)F)c2)c2cc(NC(=O)OC(C)(C)C)ccc2O1]

To a stirred solution of 3 M methyl magnesium bromide in THF (0.9 mL, 2.7 mmol) in anhydrous THF (5 mL) was added a solution of methyl 2-(6-((tert-butoxycarbonyl)amino)-4-((3-(trifluoromethyl)phenyl)sulfonyl)-3,4-dihydro-2H-benzo[b][1,4]oxazin-2-yl)acetate (140 mg, 0.26 mmol) in THF (2 mL) dropwise at 0° C. The mixture was stirred at 0° C. for an hour and then warmed to room temperature. The reaction was stirred for another hour and saturated aqueous ammonium chloride solution (2 mL) was added. The reaction mixture was diluted with brine (20 mL) and extracted twice with ethyl acetate. The combined organic layers were dried (Na$_2$SO$_4$) and concentrated. The residue was purified by Prep-HPLC to afford the product as a white solid. LCMS (ESI) calculated for $C_{24}H_{29}F_3N_2NaO_6S$: (M+Na)$^+$: 553.2, Found: 553.0.

Example 66—Synthesis of (S)-tert-butyl (2-((3-hydroxyazetidin-1-yl)methyl)-4-((3-(trifluoromethyl)phenyl)sulfonyl)-3,4-dihydro-2H-benzo[b][1,4]oxazin-6-yl)carbamate (66)

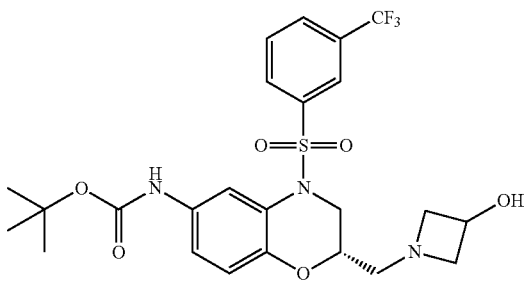 [SMILES: CC(C)(C)OC(=O)Nc1ccc2c(c1)N(S(=O)(=O)c1cccc(C(F)(F)F)c1)C[C@H](CN1CC(O)C1)O2]

To a solution of (R)-(6-((tert-butoxycarbonyl)amino)-4-((3-(trifluoromethyl)phenyl)sulfonyl)-3,4-dihydro-2H-benzo[b][1,4]oxazin-2-yl)methyl 4-methylbenzenesulfonate (300 mg, 0.467 mmol) in ethanol (7 mL) was added azetidin-3-ol hydrochloride (256 mg, 2.33 mmol) and potassium carbonate (645 mg, 4.67 mmol). The mixture was heated at 100° C. overnight. The reaction mixture was filtered and concentrated. The residue was purified by Prep-TLC (20*20 cm) (petroleum ether/ethyl acetate 1/6) to afford the title compound. LCMS (ESI) calculated for $C_{24}H_{29}F_3SN_3O_6$ (M+H)$^+$: 544.2, Found: 544.0. $^1$HNMR (500 MHz, MeOD): δ 7.97-8.07 (4H, m), 7.77 (1H, t, J=8.0 Hz), 7.06 (1H, dd, J=9.0, 2.5 Hz), 6.74 (1H, d, J=9.0 Hz), 4.33-4.39 (2H, m), 3.68-3.71 (1H, m), 3.59-3.62 (1H, m), 3.46-3.48 (1H, m), 3.28-3.31 (1H, m), 2.92-2.96 (2H, m), 2.64-2.68 (2H, m), 1.55 (9H, s).

Example 67—Preparation of Additional Amines of Benzoxazines

The compounds in Table 22 below were prepared based on the experimental procedures described in Example 66 and elsewhere in the detailed description, and can be achieved by one of skill in the art in light of the present disclosure.

TABLE 22

| Ex. No. | Structure | Name | Observed m/z |
|---|---|---|---|
| 67A | 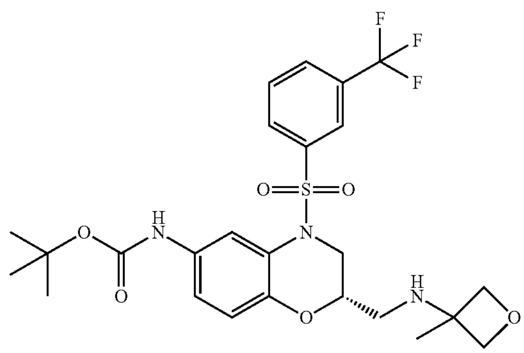 [SMILES: CC1(NC[C@H]2CN(S(=O)(=O)c3cccc(C(F)(F)F)c3)c3cc(NC(=O)OC(C)(C)C)ccc3O2)COC1] | (S)-tert-butyl (2-(((3-methyloxetan-3-yl)amino)methyl)-4-((3-(trifluoromethyl)phenyl)sulfonyl)-3,4-dihydro-2H-benzo[b][1,4]oxazin-6-yl)carbamate | 558 (M + H)$^+$ |
| 67B | 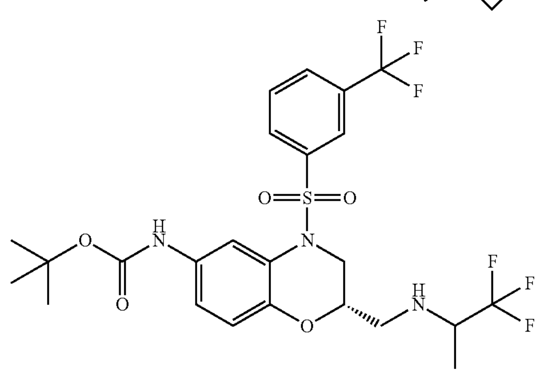 | tert-butyl ((2S)-4-((3-(trifluoromethyl)phenyl)sulfonyl)-2-(((1,1,1-trifluoropropan-2-yl)amino)methyl)-3,4-dihydro-2H-benzo[b][1,4]oxazin-6-yl)carbamate | 584 (M + NH$_4$)$^+$ |
| 67C | 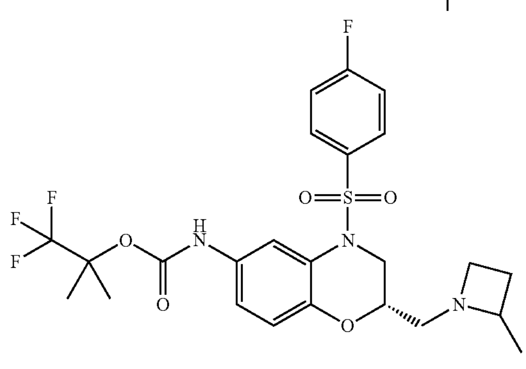 | 1,1,1-trifluoro-2-methylpropan-2-yl ((2S)-4-((4-fluorophenyl)sulfonyl)-2-((2-methylazetidin-1-yl)methyl)-3,4-dihydro-2H-benzo[b][1,4]oxazin-6-yl)carbamate | 546.1 (M + H)$^+$ |
| 67D | 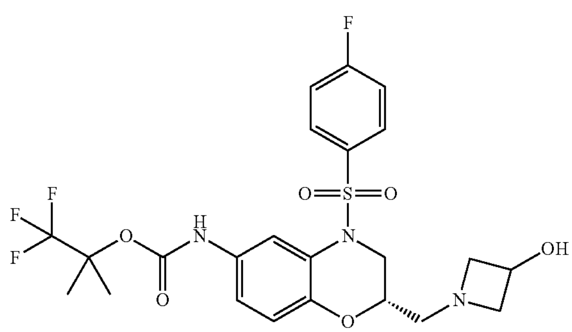 [SMILES: CC(C)(OC(=O)Nc1ccc2c(c1)N(S(=O)(=O)c1ccc(F)cc1)C[C@H](CN1CC(O)C1)O2)C(F)(F)F] | (S)-1,1,1-trifluoro-2-methylpropan-2-yl (4-((4-fluorophenyl)sulfonyl)-2-((3-hydroxyazetidin-1-yl)methyl)-3,4-dihydro-2H-benzo[b][1,4]oxazin-6-yl)carbamate | 548.1 (M + H)$^+$ |

TABLE 22-continued

| Ex. No. | Structure | Name | Observed m/z |
|---|---|---|---|
| 67E | 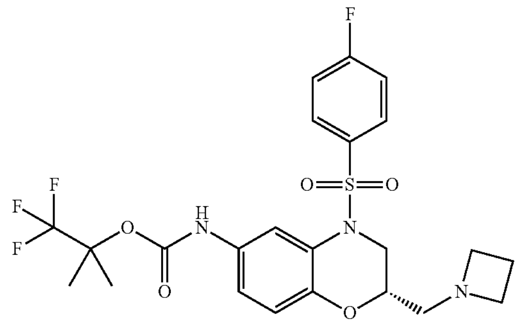 [SMILES: CC(C)(OC(=O)Nc1ccc2c(c1)N(S(=O)(=O)c1ccc(F)cc1)C[C@H](CN1CCC1)O2)C(F)(F)F] | (S)-1,1,1-trifluoro-2-methylpropan-2-yl (2-(azetidin-1-ylmethyl)-4-((4-fluorophenyl)sulfonyl)-3,4-dihydro-2H-benzo[b][1,4]oxazin-6-yl)carbamate | 532.1 (M + H)+ |

Example 68—Synthesis of (S)-tert-butyl (3-methyl-2-oxo-2,3-dihydro-1H-pyrido[2,3-b][1,4]oxazin-7-yl)carbamate (68)

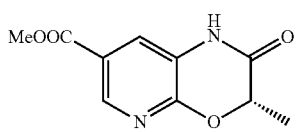

The title compound was prepared according to the procedures described below.

Part I—Synthesis of (S)-methyl 6-((1-methoxy-1-oxopropan-2-yl)oxy)-5-nitronicotinate

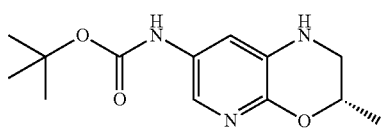 [SMILES: C[C@H]1CNc2cc(NC(=O)OC(C)(C)C)cnc2O1]

To methyl (S)-lactate (5.8 g, 55.4 mmol) and methyl 6-chloro-5-nitropyridine-3-carboxylate (10 g, 46 mmol) in anhydrous tetrahydrofuran (100 mL) under nitrogen with activated molecular sieves at 0° C. was added 1,8-diazabicyclo[5.4.0]undec-7-ene (9 mL, 60 mmol). The solution quickly turned dark, was stirred at 0° C. for thirty minutes, then was allowed to stir at ambient temperature for an hour. A solid precipitated out of solution. The solution was diluted with ethyl acetate, solids were filtered off, and then the filtrates were concentrated. The residue was purified by column chromatography eluting with a gradient of 10-50% ethyl acetate in hexanes to yield the title compound.

Part II—Synthesis of (S)-methyl 3-methyl-2-oxo-2,3-dihydro-1H-pyrido[2,3-b][1,4]oxazine-7-carboxylate

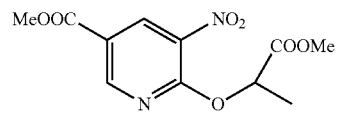 [SMILES: COC(=O)c1cnc(OC(C)C(=O)OC)c([N+](=O)[O-])c1]

In a three necked round bottomed flask equipped with an overhead stirrer was added (S)-methyl 6-((1-methoxy-1-oxopropan-2-yl)oxy)-5-nitronicotinate (9.09 g, 32 mmol) and acetic acid (100 mL). Powdered iron was carefully added (8.9 g, 160 mmol) and the suspension was heated at 70° C. for 2 hours. The reaction was cooled, filtered through CELITE and washed with 5% methanol in tetrahydrofuran (3×50 mL). The combined filtrates were concentrated to a volume of approximately 50 mL comprising mostly acetic acid and product. Upon the addition of water (100 mL), a solid crashed out, which was slurried and filtered off and washed with water to yield the title compound.

Part III—Synthesis of (S)-3-methyl-2-oxo-2,3-dihydro-1H-pyrido[2,3-b][1,4]oxazine-7-carboxylic Acid

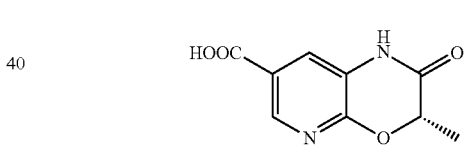

To (S)-methyl 3-methyl-2-oxo-2,3-dihydro-1H-pyrido[2,3-b][1,4]oxazine-7-carboxylate (3.9 g, 17.6 mmol) in tetrahydrofuran (30 mL) and methanol (10 mL) was added 2M sodium hydroxide and the reaction stirred at ambient temperature overnight. The volume was concentrated to 20 mL. The solution was acidified with 1 M hydrogen chloride (40 mL). The resulting solids were slurried for 20 minutes, filtered and dried to yield the title compound.

Part IV—Synthesis of (S)-tert-butyl (3-methyl-2-oxo-2,3-dihydro-1H-pyrido[2,3-b][1,4]oxazin-7-yl)carbamate

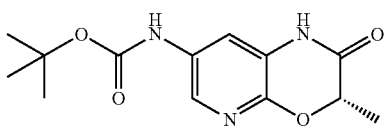 [SMILES: C[C@@H]1Oc2ncc(NC(=O)OC(C)(C)C)cc2NC1=O]

To a solution of (S)-3-methyl-2-oxo-2,3-dihydro-1H-pyrido[2,3-b][1,4]oxazine-7-carboxylic acid (2.39 g, 11.5 mmol) in anhydrous toluene (20 mL) and anhydrous tert-butanol (20 mL) with triethylamine (3.5 mL, 25 mmol) was added activated molecular sieves, and the resulting mixture was stirred for fifteen minutes before the addition of diphenylphosphoryl azide (3 mL, 13.8 mmol). The reaction was heated to reflux under nitrogen for two hours. Upon completion, the solution was cooled, filtered over filter paper, diluted with ethyl acetate, washed with water, brine, dried (Na$_2$SO$_4$) and concentrated. The residue was purified by column chromatography eluting with a gradient of 20-80% ethyl acetate in hexanes. The resulting product was repurified by column chromatography eluting with a gradient of 0-10% methanol in dichloromethane to yield the title compound.

Part V—Synthesis of (S)-tert-butyl (3-methyl-2,3-dihydro-1H-pyrido[2,3-b][1,4]oxazin-7-yl)carbamate

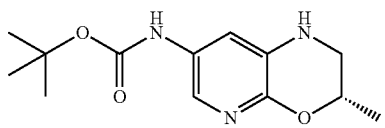

To a solution of (S)-tert-butyl (3-methyl-2-oxo-2,3-dihydro-1H-pyrido[2,3-b][1,4]oxazin-7-yl)carbamate (3.5 g, 12.5 mmol) in anhydrous tetrahydrofuran (40 mL) under nitrogen at 0° C. was added 1 M lithium aluminum hydride in tetrahydrofuran (38 mL, 38 mmol) dropwise. The reaction was stirred at 0° C. for three hours, then at ambient temperature for an hour. The suspension was recooled to 0° C. before carefully quenching it with sodium sulfate decahydrate. The suspension was slurried at ambient temperature for 1 hour before filtering solids off over CELITE. The residue was purified by column chromatography eluting with a gradient of 0.5-5% methanol in dichloromethane to yield the title compound (0.91 g, 27%).

Example 69—Synthesis of [(R)-1-((3-chloro-benzenesulfonyl)-3-hydroxymethyl-2,3-dihydro-1H-pyrido[2,3-b][1,4]oxazin-7-yl]-carbamic acid tert-butyl ester (69)

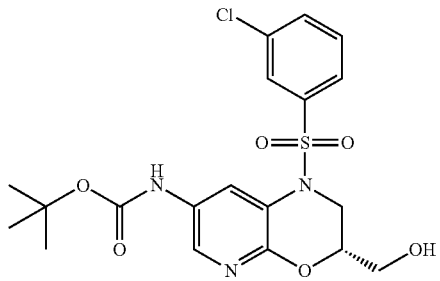

To a solution ((R)-3-hydroxymethyl-2,3-dihydro-1H-pyrido[2,3-b][1,4]oxazin-7-yl)-carbamic acid tert-butyl ester (0.56 g, 2 mmol) in pyridine (5 mL) at 0° C. was added 3-chloro phenyl sulfonyl chloride (0.42 g, 2 mmol). The reaction mixture was stirred at room temperature for two hours. The reaction mixture was diluted with ethyl acetate, washed with brine, saturated sodium bicarbonate and water. The organic layer was separated, dried (Na$_2$SO$_4$) and concentrated. The crude product was purified by column chromatography on silica gel (hexanes/AcOEt 2:1 to 1:3) to afford the title compound as a white foam. LCMS (ESI) m/z 456.

Example 70—Synthesis of [(S)-1-(3-Chloro-benzenesulfonyl)-3-(2,4-dioxo-oxazolidin-3-ylmethyl)-2,3-dihydro-1H-pyrido[2,3-b][1,4]oxazin-7-yl]-carbamic acid tert-butyl ester (70)

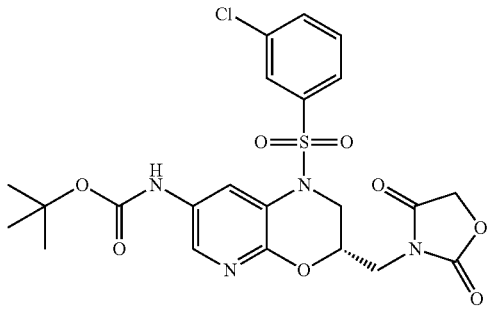 [SMILES: CC(C)(C)OC(=O)Nc1cnc2c(c1)N(S(=O)(=O)c1cccc(Cl)c1)C[C@H](CN1C(=O)COC1=O)O2]

To a solution of (91 mg, 0.2 mmol) [(R)-1-((3-chloro-benzenesulfonyl)-3-hydroxymethyl-2,3-dihydro-1H-pyrido[2,3-b][1,4]oxazin-7-yl]-carbamic acid tert-butyl ester), oxazolidine-2,4-dione (20 mg, 0.20 mmol), triphenylphosphine (78.6 mg, 0.30 mmol) in THF (2 mL) was added DIAD (60.6 mg, 0.30 mmol) and the mixture was stirred for 12 hours at room temperature. The mixture was concentrated, and the residue was purified by column chromatography to afford [(S)-1-(3-Chloro-benzenesulfonyl)-3-(2,4-dioxo-oxazolidin-3-ylmethyl)-2,3-dihydro-1H-pyrido[2,3-b][1,4]oxazin-7-yl]-carbamic acid tert-butyl ester. LCMS (ESI) m/z 539.1.

Example 71—Synthesis of 4-[(S)-6-amino-4-((3-chloro-benzenesulfonyl)-3,4-dihydro-2H-benzo[1,4]oxazin-2-ylmethyl]-1-methyl-piperazin-2-one (71)

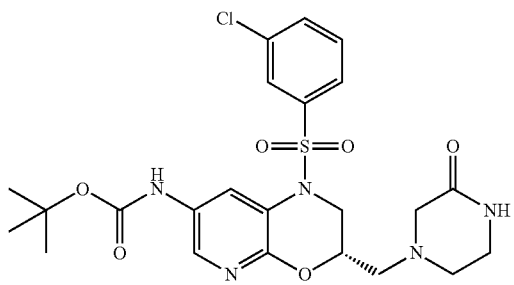 [SMILES: CC(C)(C)OC(=O)Nc1cnc2c(c1)N(S(=O)(=O)c1cccc(Cl)c1)C[C@H](CN1CCNC(=O)C1)O2]

The title compound was prepared according to the procedures described below.

Part I—Synthesis of 3-chloro-benzenesulfonic acid (R)-7-tert-butoxycarbonylamino-1-(3-chloro-benzenesulfonyl)-2,3-dihydro-1H-pyrido[2,3-b][1,4]oxazin-3-yl methyl ester

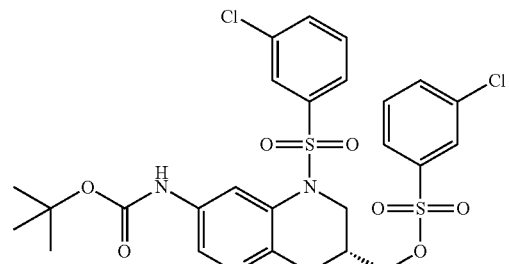

To a solution ((R)-3-hydroxymethyl-2,3-dihydro-1H-pyrido[2,3-b][1,4]oxazin-7-yl)-carbamic acid tert-butyl ester (0.56 g, 2 mmol) in pyridine (5 mL) was added 3-chlorobenzenesulphonyl chloride (0.42 g, 2 mmol). The resulting mixture was stirred for 15 minutes at 0° C., and then a second equivalent of sulfonyl chloride was added and stirring continued for an hour. The reaction mixture was diluted with ethyl acetate, washed with water, dried (Na₂SO₄) and concentrated. The residue was purified by column chromatography eluting with hexanes/ethyl acetate 2:1) to afford 3-chloro-benzenesulfonic acid (R)-6-tert-butoxycarbonylamino-4-((3-chloro-benzenesulfonyl)-3,4-dihydro-2H-benzo[1,4]oxazin-2-ylmethyl ester. LCMS (ESI) m/z 630.3.

Part II—Synthesis of 4-[(S)-6-amino-4-((3-chloro-benzenesulfonyl)-3,4-dihydro-2H-benzo[1,4]oxazin-2-ylmethyl]-1-methyl-piperazin-2-one

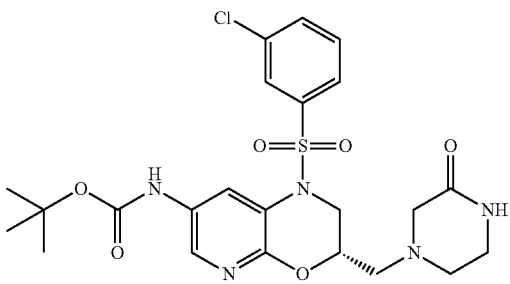 [SMILES: CC(C)(C)OC(=O)Nc1cnc2c(c1)N(S(=O)(=O)c1cccc(Cl)c1)C[C@H](CN1CCNC(=O)C1)O2]

A suspension of 3-chloro-benzenesulfonic acid (R)-6-tert-butoxycarbonylamino-4-((3-chloro-benzenesulfonyl)-3,4-dihydro-2H-benzo[1,4]oxazin-2-yl methyl ester (63 mg, 0.1 mmol), N,N'-diisopropylethylamine (2 eq), 1-methyl-piperazin-2-one hydrochloride salt (30 mg, 0.2 mmol) and potassium iodide (cat.) in THF/NMP (0.5 mL) was heated in a sealed tube for 12 h at 80° C. The mixture was partitioned between water and ethyl acetate. The organic layer was separated, washed with brine, saturated NaHCO₃ and concentrated. The residue was purified by column chromatography on silica gel to provide [(S)-4-((3-chloro-benzenesulfonyl)-2-(4-methyl-3-oxo-piperazin-1-ylmethyl)-3,4-dihydro-2H-benzo[1,4]oxazin-6-yl]-carbamic acid tert-butyl ester. LCMS (ESI) m/z 551.

Example 72—Synthesis of (S)-tert-butyl (5-((4-fluorophenyl)sulfonyl)-6-methyl-5,6,7,8-tetrahydro-1,5-naphthyridin-3-yl)carbamate (72)

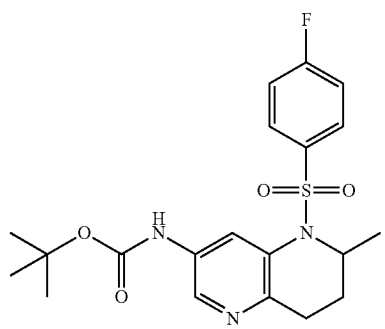 [SMILES: CC1CCc2ncc(NC(=O)OC(C)(C)C)cc2N1S(=O)(=O)c1ccc(F)cc1]

The title compound was prepared according to the procedures described below.

Part I—Synthesis of 1-benzyl-7-bromo-2-methyl-1,2,3,4-tetrahydro-1,5-naphthyridine

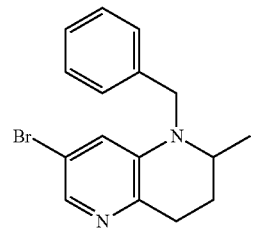 [SMILES: CC1CCc2ncc(Br)cc2N1Cc1ccccc1]

To a solution of 1-benzyl-7-bromo-3,4-dihydro-1,5-naphthyridin-2(1H)-one (1.42 g, 4.48 mmol) in anhydrous tetrahydrofuran (20 mL) under a nitrogen atmosphere at 0° C. was added 1M methylmagnesium bromide in tetrahydrofuran (17.9 mL, 17.9 mmol) slowly. The resulting red solution was stirred at ambient temperature for 2 hours, then the solution was heated for 2 hours to 50° C. To the cooled solution was slowly added acetic acid (6 mL). The resulting mixture was stirred for two minutes, then was added sodium borohydride (0.42 g, 11.2 mmol). The reaction was stirred at ambient temperature overnight. The reaction mixture was basified with 2M sodium hydroxide (12 mL), and extracted with ethyl acetate twice. The combined extracts were washed with brine, dried with sodium sulfate, filtered, and concentrated in the presence of silica. The residue was purified by column chromatography eluting with a gradient of ethyl acetate in hexanes to yield the title compound.

Part II—Synthesis of tert-butyl (5-benzyl-6-methyl-5,6,7,8-tetrahydro-1,5-naphthyridin-3-yl)carbamate

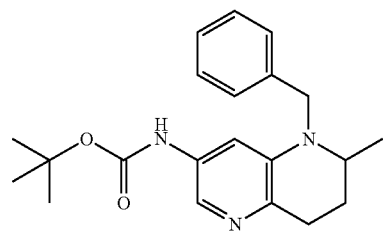 [SMILES: CC1CCc2ncc(NC(=O)OC(C)(C)C)cc2N1Cc1ccccc1]

1-Benzyl-7-bromo-2-methyl-1,2,3,4-tetrahydro-1,5-naphthyridine (0.56 g, 1.77 mmol), 2-dicyclohexylphosphino-2',4',6'-triisopropylbiphenyl (0.04 g, 0.09 mmol), tripotassium phosphate (1.1 g, 5.3 mmol), and tert-butyl carbamate (0.31 g, 2.6 mmol) were combined in toluene (5 mL) and water (1 mL). The reaction was degassed, then treated with tris(dibenzylideneacetone)dipalladium(0) (0.08 g, 0.09 mmol) and refluxed overnight. The solution was cooled, partitioned between ethyl acetate and brine, separated, dried (Na₂SO₄) and concentrated in the presence of silica. The residue was purified by column chromatography eluting with a gradient of ethyl acetate in hexane to yield the title compound.

Part III—Synthesis of tert-butyl (6-methyl-5,6,7,8-tetrahydro-1,5-naphthyridin-3-yl)carbamate

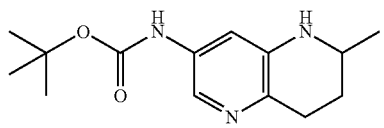 [SMILES: CC1CCc2ncc(NC(=O)OC(C)(C)C)cc2N1]

To a degassed suspension of tert-butyl (5-benzyl-6-methyl-5,6,7,8-tetrahydro-1,5-naphthyridin-3-yl)carbamate (0.26 g, 0.74 mmol) and ammonium formate (0.93 g, 14.7 mmol) under a nitrogen atmosphere in methanol (5 mL) was added 10% palladium on carbon (78 mg). The suspension was refluxed for three hours. The reaction was cooled to ambient temperature, filtered through CELITE, rinsing with methanol and concentrated. The residue was redissolved in ethyl acetate, washed with water, brine, dried with sodium sulfate, filtered and concentrated to yield the title compound.

Part IV—Synthesis of (S)-tert-butyl (5-((4-fluorophenyl)sulfonyl)-6-methyl-5,6,7,8-tetrahydro-1,5-naphthyridin-3-yl)carbamate

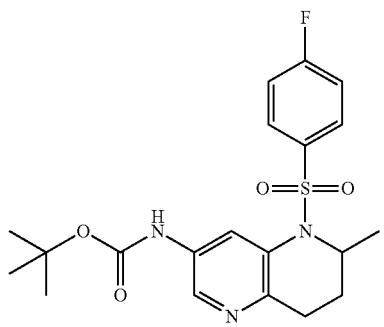 [SMILES: CC1CCc2ncc(NC(=O)OC(C)(C)C)cc2N1S(=O)(=O)c1ccc(F)cc1]

To a solution of tert-butyl (6-methyl-5,6,7,8-tetrahydro-1,5-naphthyridin-3-yl)carbamate (0.13 g, 0.49 mmol) in anhydrous pyridine (2 mL) was added 4-fluorobenzenesulfonyl chloride (0.14 g, 0.74 mmol) and the reaction was heated at 60° C. for 8 hours. The reaction was cooled, diluted with ethyl acetate, washed with 10% citric acid, water, and brine. The organics were dried with sodium sulfate, filtered and concentrated in the presence of silica. The residue was purified by column chromatography eluting with a gradient of methanol in dichloromethane. The purified racemic mixture was separated by preparatory chiral HPLC to yield the title compounds. $^1$H NMR (400 Hz, DMSO-d6) δ 9.59 (s, 1H), 8.34 (s, 1H), 8.16 (s, 1H), 7.61 (m, 2H), 7.37 (m, 2H), 4.37 (m, 1H), 2.5 (m, 1H), 2.06 (m, 1H), 1.57 (m, 1H), 1.46 (s, 9H), 1.12 (m, 3H).

Example 73—Synthesis of (S)-benzyl tert-butyl (1-((4-fluorophenyl)sulfonyl)-1,2,3,4-tetrahydro-1,5-naphthyridine-3,7-diyl)dicarbamate (73)

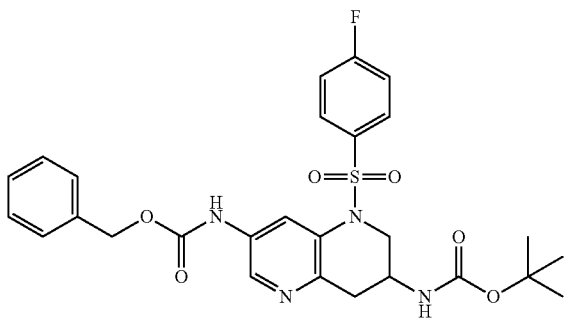 [SMILES: CC(C)(C)OC(=O)NC1Cc2ncc(NC(=O)OCc3ccccc3)cc2N(S(=O)(=O)c2ccc(F)cc2)C1]

The title compound was prepared according to the procedures described below.

Part I—Synthesis of methyl 5-amino-6-chloronicotinate

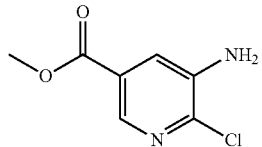

To methyl 6-chloro-5-nitro-pyridine-3-carboxylate (2.0 g, 9.2 mmol) in anhydrous methanol (30 mL) under nitrogen was added tin (II) chloride (5.3 g, 28 mmol). The resulting mixture was refluxed for eighteen hours. Then, the reaction mixture was cooled and then poured carefully into a stirred slurry of CELITE in saturated sodium bicarbonate at 0° C. The resulting suspension was stirred for twenty minutes before the mixture was filtered through CELITE to remove the solids. The solids were washed with ethyl acetate, and the filtrates were collected, washed with water, and washed with brine. The resulting organic solution was dried with sodium sulfate ($Na_2SO_4$) and concentrated to provide the title compound.

Part II—Synthesis of methyl 7-((tert-butoxycarbonyl)amino)-6-oxo-5,6,7,8-tetrahydro-1,5-naphthyridine-3-carboxylate

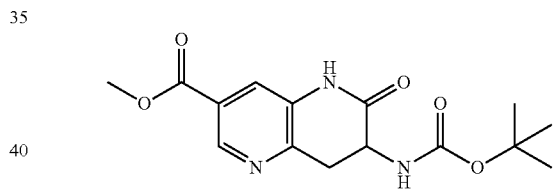

An oven-dried flask was charged with zinc powder (2.0 g, 30 mmol) and iodine (0.12 g, 0.46 mmol), and flushed with nitrogen. Next, the flask was cooled in an ice bath and a solution of methyl (2S)-2-(tert-butoxycarbonylamino)-3-iodo-propanoate (5.0 g, 15 mmol) in anhydrous N,N-dimethylformamide (20 mL) was added to the flask. The resulting reaction mixture was stirred at 0° C. for 90 minutes. Then, solid methyl 5-amino-6-chloronicotinate (3.7 g, 19.7 mmol) was added followed by addition of dichlorobistriphenyl-phosphine palladium (II) (0.53 g, 0.76 mmol). Then, the reaction mixture was heated at 40° C. for 18 hours. Next, the reaction mixture was filtered through CELITE, washing with ethyl acetate. The resulting organic solution was concentrated in vacuo to provide a residue that was redissolved in N,N-dimethylformamide (20 mL). To the resulting organic solution, potassium carbonate (2.5 g, 18 mmol) was added and the reaction mixture was heated at 80° C. for 2 hours. The resulting solution was partitioned between ethyl acetate and saturated ammonium chloride. The organic layer was separated and washed with water and brine. The resulting organic solution was dried with sodium sulfate, filtered, and concentrated in vacuo to provide a residue that was purified by column chromatography eluting with a gradient of 20-100% ethyl acetate in hexanes to provide the title compound.

Part III—Synthesis of 7-((tert-butoxycarbonyl)amino)-6-oxo-5,6,7,8-tetrahydro-1,5-naphthyridine-3-carboxylic Acid

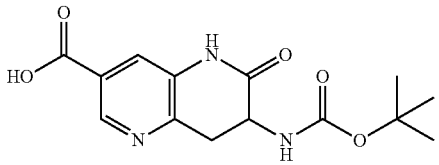 [SMILES: CC(C)(C)OC(=O)NC1Cc2ncc(C(=O)O)cc2NC1=O]

To (R)-methyl 7-((tert-butoxycarbonyl)amino)-6-oxo-5,6,7,8-tetrahydro-1,5-naphthyridine-3-carboxylate (2.63 g, 8.2 mmol) in tetrahydrofuran (20 mL) and methanol (20 mL) was added 2M sodium hydroxide (12 mL, 24 mmol). The reaction mixture was stirred at ambient temperature for two hours. Then, the volume of the reaction mixture was reduced in vacuo. The resulting solution was partitioned between ethyl acetate and 10% citric acid. The organic layer was isolated, washed with brine, dried with sodium sulfate, filtered, and concentrated in vacuo to yield the title compound.

Part IV—Synthesis of benzyl tert-butyl (2-oxo-1,2,3,4-tetrahydro-1,5-naphthyridine-3,7-diyl)dicarbamate

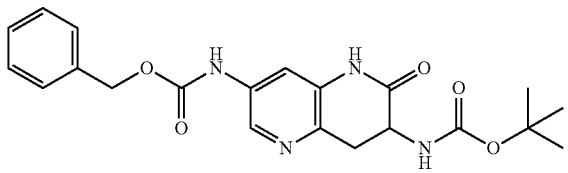 [SMILES: CC(C)(C)OC(=O)NC1Cc2ncc(NC(=O)OCc3ccccc3)cc2NC1=O]

To (R)-7-((tert-butoxycarbonyl)amino)-6-oxo-5,6,7,8-tetrahydro-1,5-naphthyridine-3-carboxylic acid (2.07 g, 6.74 mmol) in anhydrous toluene (20 mL) and benzyl alcohol (2.1 mL, 20 mmol) was added activated 4 Å molecular sieves and triethylamine (2.1 mL, 14.8 mmol). The resulting mixture was stirred at ambient temperature for 10 minutes, then diphenylphosphorylazide (1.7 mL, 8.1 mmol) was added. Next, the resulting suspension was refluxed for 2 hours. Then, the reaction mixture was filtered hot through CELITE, washing with ethyl acetate. The resulting organic solution was concentrated onto silica in vacuo to provide a residue that was purified by column chromatography eluting with a gradient of methanol in dichloromethane to provide the title compound.

Part V—Synthesis of benzyl tert-butyl (1,2,3,4-tetrahydro-1,5-naphthyridine-3,7-diyl)dicarbamate

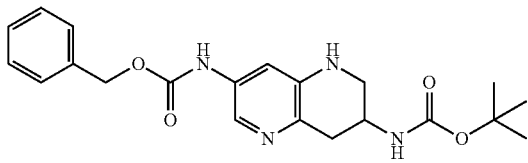 [SMILES: CC(C)(C)OC(=O)NC1CNc2cc(NC(=O)OCc3ccccc3)cnc2C1]

To a solution of benzyl tert-butyl (2-oxo-1,2,3,4-tetrahydro-1,5-naphthyridine-3,7-diyl)dicarbamate (5.35 g, 13 mmol) in anhydrous tetrahydrofuran (140 mL) under nitrogen at 0° C. was added solid lithium aluminum hydride (2.5 g, 65 mmol) in portions. After complete addition of the lithium aluminum hydride, the cooling bath was removed and the reaction was stirred at ambient temperature for 3 hours. The reaction was recooled to 0° C. before carefully quenching it with water (2.5 mL), 15% sodium hydroxide (2.5 mL), then water (7.5 mL). The solids were filtered through CELITE and washed with tetrahydrofuran, and then the filtrates were concentrated in the presence of silica. The residue was purified by column chromatography eluting with a gradient of methanol in dichloromethane to yield the title compound.

Part VI—Synthesis of (S)-benzyl tert-butyl (1-((4-fluorophenyl)sulfonyl)-1,2,3,4-tetrahydro-1,5-naphthyridine-3,7-diyl)dicarbamate

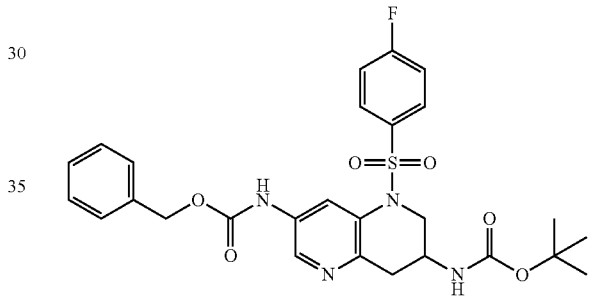

To (S)-benzyl tert-butyl (1,2,3,4-tetrahydro-1,5-naphthyridine-3,7-diyl)dicarbamate (0.28 g, 0.70 mmol) in anhydrous pyridine (4 mL) was added 4-fluorobenzenesulfonyl chloride (0.17 g, 0.88 mmol) and the mixture was heated at 60° C. for 4 hours. The mixture was cooled, diluted with ethyl acetate, washed with citric acid, water, brine, dried with sodium sulfate, filtered and concentrated in the presence of silica. The residue was purified by column chromatography eluting with a gradient of methanol in dichloromethane to yield the title compound. LRMS (ESI) calculated for $C_{27}H_{30}FN_4O_6S$ (M+H)$^+$: 557, Found: 557.

Example 74—Preparation of Additional Sulfonamides from benzyl tert-butyl (1,2,3,4-tetrahydro-1,5-naphthyridine-3,7-diyl)dicarbamate The compounds in Table 24 below were prepared based on the experimental procedures described in Example 73 and elsewhere in the detailed description, and can be achieved by one of skill in the art in light of the present disclosure.

TABLE 24

| Ex. No. | Structure | Name | Observed m/z |
|---|---|---|---|
| 74A | 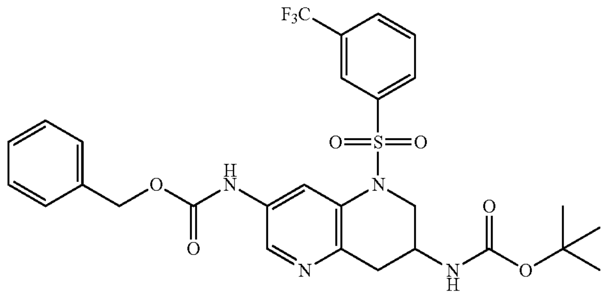 [SMILES: CC(C)(C)OC(=O)NC1Cc2ncc(NC(=O)OCc3ccccc3)cc2N(S(=O)(=O)c2cccc(C(F)(F)F)c2)C1] | benzyl tert-butyl (1-((3-(trifluoromethyl)phenyl)sulfonyl)-1,2,3,4-tetrahydro-1,5-naphthyridine-3,7-diyl)dicarbamate | 629.17 (M + Na)+ |
| 74B | 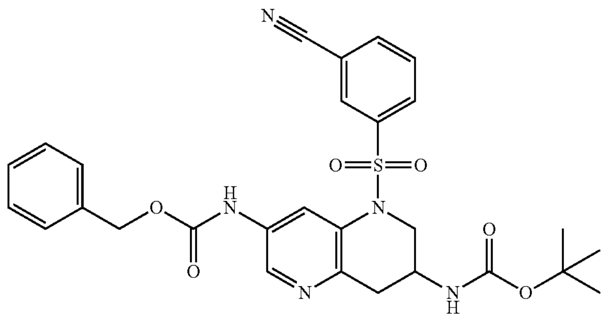 [SMILES: CC(C)(C)OC(=O)NC1Cc2ncc(NC(=O)OCc3ccccc3)cc2N(S(=O)(=O)c2cccc(C#N)c2)C1] | benzyl tert-butyl (1-((3-cyanophenyl)sulfonyl)-1,2,3,4-tetrahydro-1,5-naphthyridine-3,7-diyl)dicarbamate | 586.14 (M + Na)+ |
| 74C | 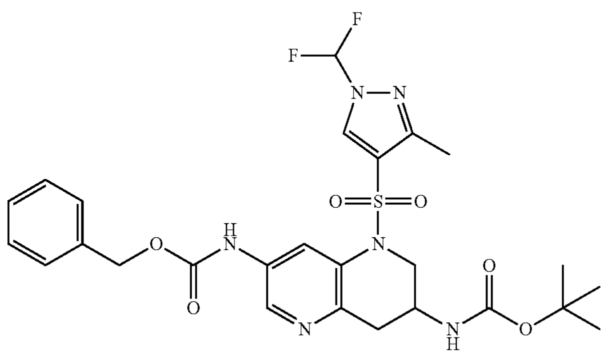 [SMILES: Cc1nn(C(F)F)cc1S(=O)(=O)N1CC(NC(=O)OC(C)(C)C)Cc2ncc(NC(=O)OCc3ccccc3)cc21] | benzyl tert-butyl (1-((1-(difluoromethyl)-3-methyl-1H-pyrazol-4-yl)sulfonyl)-1,2,3,4-tetrahydro-1,5-naphthyridine-3,7-diyl)dicarbamate | 615.19 (M + Na)+ |

Example 75—Synthesis of (S)-benzyl (5-((4-fluorophenyl)sulfonyl)-7-(2-oxopyrrolidin-1-yl)-5,6,7,8-tetrahydro-1,5-naphthyridin-3-yl)carbamate (75)

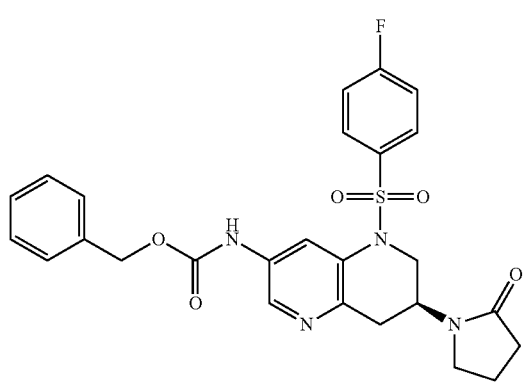 [SMILES: O=C(Nc1cnc2c(c1)N(S(=O)(=O)c1ccc(F)cc1)C[C@@H](N1CCCC1=O)C2)OCc1ccccc1]

Part 1—Synthesis of (S)-benzyl (7-amino-5-((4-fluorophenyl)sulfonyl)-5,6,7,8-tetrahydro-1,5-naphthyridin-3-yl)carbamate

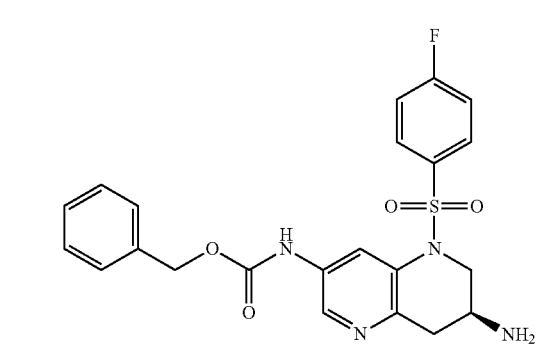 [SMILES: N[C@H]1Cc2ncc(NC(=O)OCc3ccccc3)cc2N(S(=O)(=O)c2ccc(F)cc2)C1]

The carbamate from Example 73 was separated by chiral chromatography to afford the two isomers. Products from the first to elute are isomer A, while products from the second to elute are isomer B. To a solution of (S)-benzyl tert-butyl (1-((4-fluorophenyl)sulfonyl)-1,2,3,4-tetrahydro-1,5-naphthyridine-3,7-diyl)dicarbamate (0.34 g, 0.61 mmol) in dichloromethane (3 mL) was added trifluoroacetic acid (2 mL) and the reaction was stirred at ambient temperature for 2 hours. The reaction was concentrated and dissolved in ethyl acetate, washed with saturated sodium bicarbonate, brine, dried (Na$_2$SO$_4$) and concentrated to yield the title compound. LRMS (ESI) calculated for C$_{22}$H$_{22}$FN$_4$O$_4$S (M+H)$^+$: 457, Found: 457.

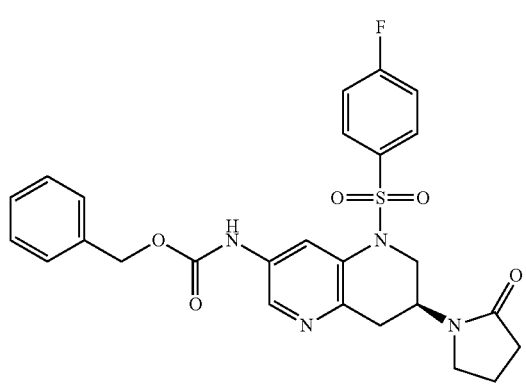 [SMILES: O=C(Nc1cnc2c(c1)N(S(=O)(=O)c1ccc(F)cc1)C[C@@H](N1CCCC1=O)C2)OCc1ccccc1]

Part 2—Synthesis of (S)-benzyl (5-((4-fluorophenyl)sulfonyl)-7-(2-oxopyrrolidin-1-yl)-5,6,7,8-tetrahydro-1,5-naphthyridin-3-yl)carbamate To a solution of (S)-benzyl (7-amino-5-((4-fluorophenyl)sulfonyl)-5,6,7,8-tetrahydro-1,5-naphthyridin-3-yl)carbamate (135 mg, 0.3 mmol) in dichloromethane (1.5 mL) and tetrahydrofuran (1.5 mL) was added tetraalkylammonium carbonate resin (0.49 g, 1.5 mmol) followed by 4-chlorobutyryl chloride (99 μL, 0.89 mmol) and the resulting solution was shaken at ambient temperature for 4 hours. The resin was filtered off and the filtrate was concentrated in the presence of silica. The crude product was purified by column chromatography eluting with a gradient of methanol in dichloromethane. The material was redissolved in anhydrous tetrahydrofuran (3 mL) under a nitrogen atmosphere, cooled to −78° C., then treated with 1M potassium tert-butoxide in tetrahydrofuran (0.59 mL, 0.59 mmol). After 20 minutes the reaction was warmed to 0° C. After 20 minutes the reaction was quenched by adding silica gel and concentrated. The residue was purified by column chromatography eluting with a gradient of methanol in dichloromethane to yield the title compound. LRMS (ESI) calculated for C$_{26}$H$_{26}$FN$_4$O$_5$S (M+H)$^+$: 525, Found: 525.

Example 76—Synthesis of (S)-neopentyl (5-((4-fluorophenyl)sulfonyl)-7-(2-oxopyrrolidin-1-yl)-5,6,7,8-tetrahydro-1,5-naphthyridin-3-yl)carbamate and (R)-neopentyl (5-((4-fluorophenyl)sulfonyl)-7-(2-oxopyrrolidin-1-yl)-5,6,7,8-tetrahydro-1,5-naphthyridin-3-yl)carbamate (Example Nos. 76A and 76B)

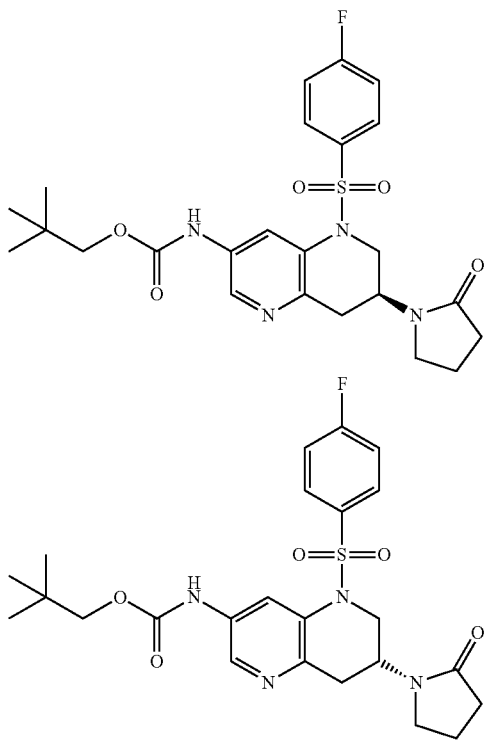

The title compounds were prepared according to the procedures described below.

Part I—Synthesis of (S)-1-(7-amino-1-((4-fluorophenyl)sulfonyl)-1,2,3,4-tetrahydro-1,5-naphthyridin-3-yl)pyrrolidin-2-one

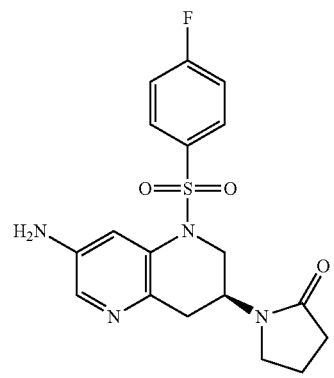 [SMILES: Nc1cnc2c(c1)N(S(=O)(=O)c1ccc(F)cc1)C[C@@H](N1CCCC1=O)C2]

To a degassed suspension of (S)-benzyl (5-((4-fluorophenyl)sulfonyl)-7-(2-oxopyrrolidin-1-yl)-5,6,7,8-tetrahydro-1,5-naphthyridin-3-yl)carbamate from Example 75 (60 mg, 0.11 mmol) and ammonium formate (72 mg, 1.1 mmol) in methanol (4 mL) under a nitrogen atmosphere was added 10% palladium on carbon (12 mg) and the reaction was refluxed for 2 hours. The reaction was cooled to ambient temperature, then filtered through a CELITE cartridge washing through with methanol. The solution was concentrated to yield the title compound, which was used without further purification.

Part II—Synthesis of (S)-neopentyl (5-((4-fluorophenyl)sulfonyl)-7-(2-oxopyrrolidin-1-yl)-5,6,7,8-tetrahydro-1,5-naphthyridin-3-yl)carbamate

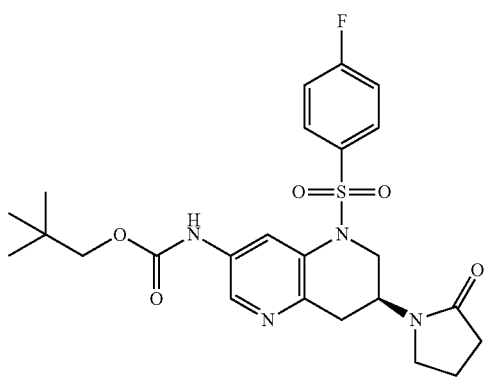 [SMILES: CC(C)(C)COC(=O)Nc1cnc2c(c1)N(S(=O)(=O)c1ccc(F)cc1)C[C@@H](N1CCCC1=O)C2]

To a solution of (S)-1-(7-amino-1-((4-fluorophenyl)sulfonyl)-1,2,3,4-tetrahydro-1,5-naphthyridin-3-yl)pyrrolidin-2-one (28 mg, 0.7 mmol) in tetrahydrofuran (1 mL) was added N,N-diisopropylethylamine (56 μL, 0.22 mmol) followed by neopentyl chloroformate (16 μL, 0.11 mmol). The reaction was shaken at ambient temperature for 1 hour, then concentrated onto silica. The residue was purified by column chromatography eluting with a gradient of methanol in dichloromethane to yield the title compound. $^1$H NMR (400 Hz, DMSO-d6) δ 9.89 (s, 1H), 8.39 (s, 1H), 8.27 (s, 1H), 7.37 (m, 2H,), 7.83 (m, 2H), 7.41 (m, 2H), 4.04-3.97 (m, 2H), 3.80 (s, 2H), 3.61 (m, 1H), 3.3-3.2 (m, 2H), 2.88 (m, 1H), 2.72 (m, 1H), 2.21 (m, 2H), 1.85 (m, 2H), 0.93 (s, 9H).

The enantiomeric compound, Example. No. 76B, was prepared in an analogous manner.

Example 77—Synthesis of tert-butyl (5-((4-fluorophenyl)sulfonyl)-7-hydroxy-5,6,7,8-tetrahydro-1,5-naphthyridin-3-yl)carbamate (77)

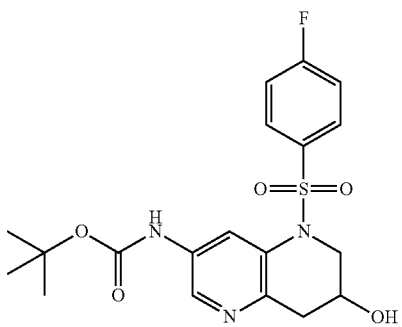 [SMILES: CC(C)(C)OC(=O)Nc1cnc2c(c1)N(S(=O)(=O)c1ccc(F)cc1)CC(O)C2]

The title compound was prepared according to the procedures described below.

Part I—Synthesis of 1-benzyl-7-bromo-3-hydroxy-3,4-dihydro-1,5-naphthyridin-2(1H)-one

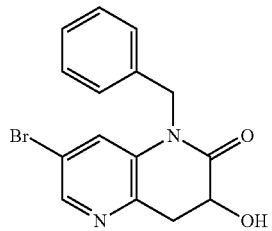 [SMILES: O=C1C(O)Cc2ncc(Br)cc2N1Cc1ccccc1]

To a solution of 1-benzyl-7-bromo-3,4-dihydro-1,5-naphthyridin-2(1H)-one (0.9 g, 2.8 mmol) in anhydrous tetrahydrofuran (3 mL) under a nitrogen atmosphere at −78° C. was added 1M lithium bis(trimethylsilyl)amide solution in tetrahydrofuran (6.2 mL, 6.2 mmol). After stirring the resulting solution for 5 minutes, (2R,8aS)-(+)-(camphorylsulfonyl)oxaziridine (0.72 g, 3.1 mmol) was added and the reaction was stirred at −78° C. for 10 minutes, before removing the cooling bath. The solution was stirred at ambient temperature for 2 hours then quenched with 10% citric acid, extracted with ethyl acetate, washed with brine, dried with sodium sulfate, filtered and concentrated. The residue was purified by column chromatography eluting with a gradient of 30-100% ethyl acetate in hexanes. The residue was triturated with ethyl acetate/hexane mixture. The filtered solids were washed with hexanes and dried to yield the title compound.

Part II—Synthesis of 1-benzyl-7-bromo-1,2,3,4-tetrahydro-1,5-naphthyridin-3-ol

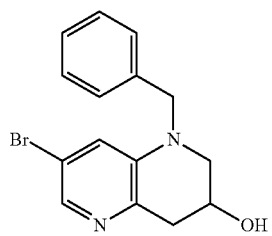 [SMILES: OC1Cc2ncc(Br)cc2N(Cc2ccccc2)C1]

To a solution of 1-benzyl-7-bromo-3-hydroxy-3,4-dihydro-1,5-naphthyridin-2(1H)-one (0.3 g, 0.9 mmol) in anhydrous tetrahydrofuran (6 mL) under nitrogen was added borane dimethylsulfide complex (0.36 mL, 3.6 mmol) and the reaction was refluxed for 1 hour. The reaction was next cooled to ambient temperature, treated with methanol (3 mL) and refluxed for 10 minutes, before being concentrated and dissolved in ethyl acetate, washed with water, brine, dried (Na$_2$SO$_4$) and concentrated to yield the title compound.

Part III—Synthesis of 1-benzyl-7-bromo-3-((tert-butyldimethylsilyl)oxy)-1,2,3,4-tetrahydro-1,5-naphthyridine

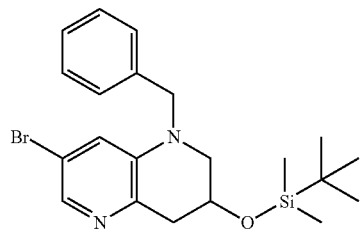 [SMILES: CC(C)(C)[Si](C)(C)OC1Cc2ncc(Br)cc2N(Cc2ccccc2)C1]

To a solution of 1-benzyl-7-bromo-1,2,3,4-tetrahydro-1,5-naphthyridin-3-ol (0.26 g, 0.81 mmol) in dichloromethane (3 mL) under nitrogen was added 2,6-lutidine (0.24 mL, 2.0 mmol) followed by tert-butyldimethylsilyl trifluoromethanesulfonate (0.21 mL, 0.9 mmol). The reaction was stirred at ambient temperature for two hours. Additional tert-butyldimethylsilyl trifluoromethanesulfonate (0.1 mL, 0.45 mmol) was added and the reaction was stirred for an additional hour, before the addition of silica. The residue was purified by column chromatography eluting with a gradient of ethyl acetate in hexanes to yield the title compound.

Part IV—Synthesis of tert-butyl (5-benzyl-7-((tert-butyldimethylsilyl)oxy)-5,6,7,8-tetrahydro-1,5-naphthyridin-3-yl)carbamate

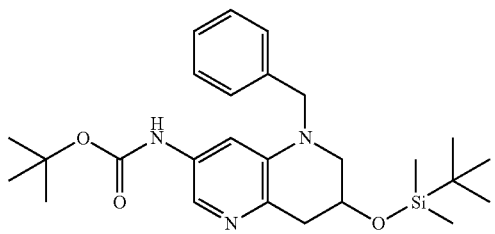 [SMILES: CC(C)(C)OC(=O)Nc1cnc2c(c1)N(Cc1ccccc1)CC(O[Si](C)(C)C(C)(C)C)C2]

1-benzyl-7-bromo-3-((tert-butyldimethylsilyl)oxy)-1,2,3,4-tetrahydro-1,5-naphthyridine (0.28 g, 0.65 mmol), 2-dicyclohexylphosphino-2',4',6'-triisopropylbiphenyl (15 mg, 0.03 mmol), tripotassium phosphate (0.41 g, 1.9 mmol), and tert-butyl carbamate (0.11 g, 0.97 mmol) were combined in toluene (5 mL) and water (1 mL). The reaction was degassed, then treated with tris(dibenzylideneacetone)dipalladium(0) (30 mg, 0.03 mmol). The solution was refluxed overnight. The solution was cooled, partitioned between ethyl acetate and brine, separated, dried, filtered and concentrated in the presence of silica. The residue was purified by column chromatography eluting with a gradient of ethyl acetate in hexane to yield the title compound.

Part V—Synthesis of tert-butyl (7-((tert-butyldimethylsilyl)oxy)-5,6,7,8-tetrahydro-1,5-naphthyridin-3-yl)carbamate

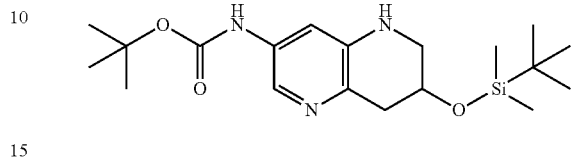

To a degassed suspension of tert-butyl (5-benzyl-7-((tert-butyldimethylsilyl)oxy)-5,6,7,8-tetrahydro-1,5-naphthyridin-3-yl)carbamate (0.11 g, 0.23 mmol) and ammonium formate (0.15 g, 2.3 mmol) under a nitrogen atmosphere in methanol (4 mL) was added 10% palladium on carbon (25 mg). The suspension was refluxed for 3 hours. The reaction was cooled to ambient temperature, filtered through CELITE, rinsing with methanol. Concentrated filtrates were dissolved in ethyl acetate, washed with water, brine, dried with sodium sulfate ($Na_2SO_4$) and concentrated to yield the title compound.

Part VI—Synthesis of tert-butyl (7-((tert-butyldimethylsilyl)oxy)-5-((4-fluorophenyl)sulfonyl)-5,6,7,8-tetrahydro-1,5-naphthyridin-3-yl)carbamate

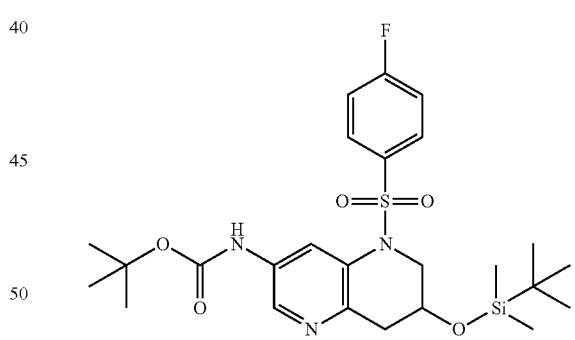

To tert-butyl (7-((tert-butyldimethylsilyl)oxy)-5,6,7,8-tetrahydro-1,5-naphthyridin-3-yl)carbamate (85 g, 0.22 mmol) in anhydrous pyridine (1 mL) was added 4-fluorobenzenesulfonyl chloride (65 mg, 0.34 mmol) and the resulting solution was heated to 70° C. for 4 hours. Upon completion, the reaction was cooled, diluted with ethyl acetate, washed with citric acid, water, brine, dried with sodium sulfate, filtered and concentrated in the presence of silica. The residue was purified by column chromatography eluting with a gradient of methanol in dichloromethane to yield the title compound.

Part VII—Synthesis of tert-butyl (5-((4-fluorophenyl)sulfonyl)-7-hydroxy-5,6,7,8-tetrahydro-1,5-naphthyridin-3-yl)carbamate

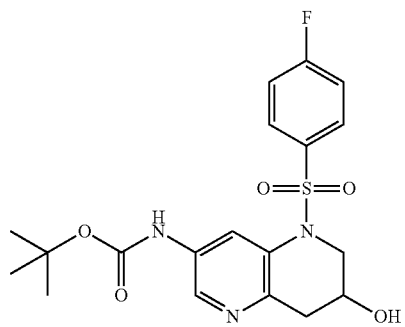 [SMILES: CC(C)(C)OC(=O)Nc1cnc2c(c1)N(S(=O)(=O)c1ccc(F)cc1)CC(O)C2]

To a solution of tert-butyl (7-((tert-butyldimethylsilyl)oxy)-5-(4-fluorophenyl)sulfonyl)-5,6,7,8-tetrahydro-1,5-naphthyridin-3-yl)carbamate (45 mg, 0.084 mmol) in anhydrous tetrahydrofuran (2 mL) under nitrogen was added 1M tetrabutylammonium fluoride in tetrahydrofuran (0.17 mL, 0.17 mmol). The reaction was stirred at ambient temperature for one hour, then partitioned between ethyl acetate and brine, dried with sodium sulfate, filtered and concentrated in the presence of silica. The residue was purified by column chromatography eluting with a gradient of methanol in dichloromethane to yield the title compound. $^1$H NMR (400 Hz, DMSO-d6) δ 9.55 (s, 1H), 8.29 (m, 1H), 8.14 (s, 1H), 7.85 (m, 2H), 7.38 (m, 2H), 5.24 (m, 1H), 3.85 (m, 2H), 3.58 (m, 1H), 2.8 (m, 1H), 2.53 (m, 1H), 1.45 (s, 9H).

Example 78—Synthesis of (R)-neopentyl (5-((1-(difluoromethyl)-3-methyl-1H-pyrazol-4-yl)sulfonyl)-7-(hydroxymethyl)-5,6,7,8-tetrahydro-1,5-naphthyridin-3-yl)carbamate and (S)-neopentyl (5-((1-(difluoromethyl)-3-methyl-1H-pyrazol-4-yl)sulfonyl)-7-(hydroxymethyl)-5,6,7,8-tetrahydro-1,5-naphthyridin-3-yl)carbamate (Example Nos. 78A and 78B)

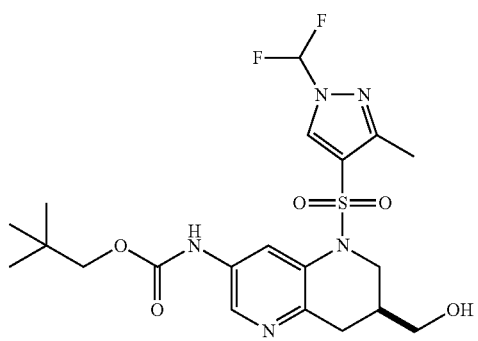

-continued

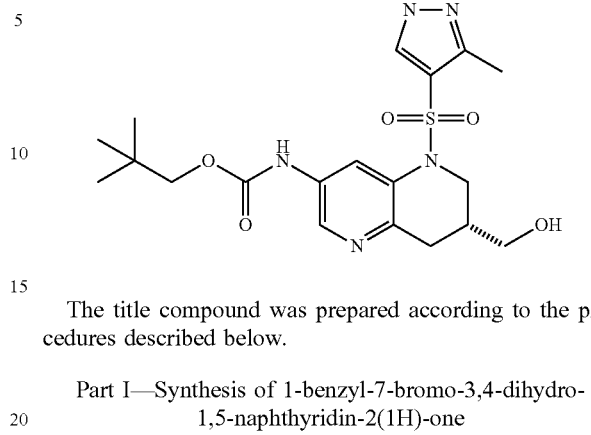

The title compound was prepared according to the procedures described below.

Part I—Synthesis of 1-benzyl-7-bromo-3,4-dihydro-1,5-naphthyridin-2(1H)-one

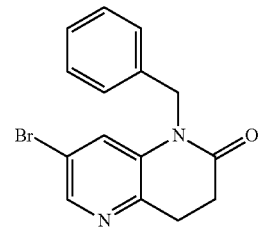 [SMILES: O=C1CCc2ncc(Br)cc2N1Cc1ccccc1]

To 7-bromo-3,4-dihydro-1,5-naphthyridin-2(1H)-one (8.1 g, 35.7 mmol) in N,N-dimethylformamide (50 mL) was added cesium carbonate (23.2 g, 71.4 mmol) followed by benzyl bromide (5.1 mL, 42.8 mmol). This mixture was stirred at 70° C. overnight. The solution was cooled, diluted with ethyl acetate, washed with water, brine, dried with sodium sulfate, filtered and concentrated. The residue was recrystallized from ethyl acetate/hexanes, and rinsed with hexanes to afford the title compound.

Part II—Synthesis of methyl 1-benzyl-7-bromo-2-oxo-1,2,3,4-tetrahydro-1,5-naphthyridine-3-carboxylate

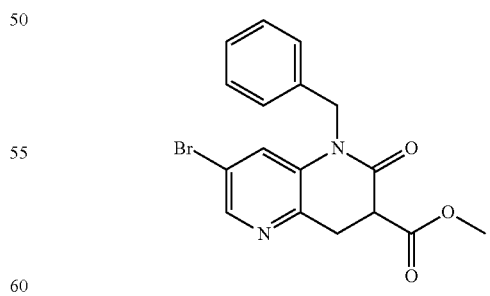

To 1-benzyl-7-bromo-3,4-dihydro-1,5-naphthyridin-2(1H)-one (4.6 g, 14.5 mmol) in anhydrous tetrahydrofuran (50 mL) under nitrogen at −78° C. was added lithium hexamethyldisilazane (1 M in tetrahydrofuran, 29 mL, 29 mmol), and the mixture was stirred for 5 minutes at −78° C. To the anion formed was added methyl chloroformate (1.2 mL, 16 mmol) and this mixture was stirred at −78° C. for an additional 30 minutes. The mixture was allowed to warm to ambient temperature, quenched with saturated aqueous ammonium chloride, extracted with ethyl acetate, washed with brine, dried with sodium sulfate, filtered and concentrated to yield the title compound.

Part III—Synthesis of (1-benzyl-7-bromo-1,2,3,4-tetrahydro-1,5-naphthyridin-3-yl)methanol

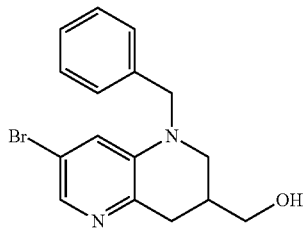 [SMILES: OCC1Cc2ncc(Br)cc2N(Cc2ccccc2)C1]

To a solution of methyl 1-benzyl-7-bromo-2-oxo-1,2,3,4-tetrahydro-1,5-naphthyridine-3-carboxylate (5.35 g, 14.3 mmol) in anhydrous tetrahydrofuran (40 mL) under nitrogen at ambient temperature was carefully added BH$_3$—SMe$_2$ (10 M in tetrahydrofuran, 5.7 mL, 57 mmol). After this addition, the reaction was refluxed for 90 minutes, then cooled to 0° C. and carefully quenched with methanol (30 mL), then refluxed for a further 10 minutes. The solution was cooled and concentrated. The residue was diluted in ethyl acetate, washed with water, brine, dried with sodium sulfate, and concentrated to yield the title compound.

Part IV—Synthesis of 1-benzyl-7-bromo-3-(((tert-butyldimethylsilyl)oxy)methyl)-1,2,3,4-tetrahydro-1,5-naphthyridine

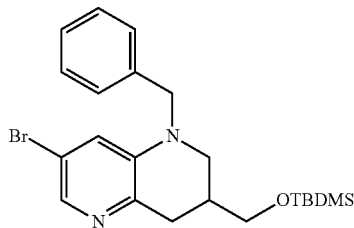 [SMILES: CC(C)(C)[Si](C)(C)OCC1Cc2ncc(Br)cc2N(Cc2ccccc2)C1]

To a solution of (1-benzyl-7-bromo-1,2,3,4-tetrahydro-1,5-naphthyridin-3-yl)methanol (4.6 g, 13.8 mmol) in dichloromethane (50 mL) was added diisopropylethylamine (5.4 mL, 20.7 mmol), tert-butyldimethylsilyl chloride (2.5 g, 16.6 mmol) and catalytic 4-dimethylaminopyridine (0.17 g, 1.4 mmol) and the resulting mixture was stirred at ambient temperature overnight. The solution was washed with saturated aqueous ammonium chloride, dried (Na$_2$SO$_4$), and concentrated in the presence of silica gel. The residue was purified by column chromatography eluting with a gradient of 0-30% ethyl acetate in hexanes to yield the title compound.

Part V—Synthesis of 5-benzyl-7-(((tert-butyldimethylsilyl)oxy)methyl)-N-(diphenylmethylene)-5,6,7,8-tetrahydro-1,5-naphthyridin-3-amine

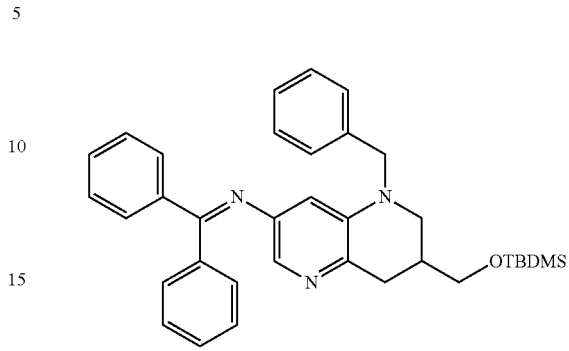

A suspension of 1-benzyl-7-bromo-3-(((tert-butyldimethylsilyl)oxy)methyl)-1,2,3,4-tetrahydro-1,5-naphthyridine (3.98 g, 8.9 mmol), benzophenone imine (1.8 mL, 10.7 mmol), cesium carbonate (4.3 g, 13.3 mmol), X-Phos (0.21 g, 0.44 mmol), and tris(dibenzylideneacetone)dipalladium (0) (0.4 g, 0.44 mmoL) in anhydrous 1,4-dioxane (50 mL) was first degassed, then heated at 110° C. under nitrogen overnight. The solution was cooled, diluted with ethyl acetate, filtered through CELITE, and concentrated in the presence of silica gel. The residue was purified by column chromatography eluting with a gradient of 5-40% ethyl acetate in hexanes to yield the title compound.

Part VI—Synthesis of 5-benzyl-7-(((tert-butyldimethylsilyl)oxy)methyl)-5,6,7,8-tetrahydro-1,5-naphthyridin-3-amine

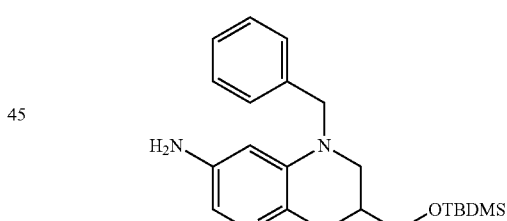

To a degassed suspension of 5-benzyl-7-(((tert-butyldimethylsilyl)oxy)methyl)-N-(diphenylmethylene)-5,6,7,8-tetrahydro-1,5-naphthyridin-3-amine (3.7 g, 6.8 mmol) and ammonium formate (8.5 g, 135 mmol) under nitrogen in methanol (75 mL) was added 10% palladium on carbon (0.7 g, 0.68 mmol). This mixture was refluxed under nitrogen for 2 hours. The reaction was cooled to ambient temperature and filtered through CELITE, rinsing with methanol. The filtrates were concentrated under reduced pressure, redissolved in ethyl acetate, washed with water, then brine, dried with sodium sulfate, filtered and concentrated in the presence of silica gel. Purification by column chromatography eluting with a gradient of ethanol in dichloromethane yielded the title compound.

Part VII—Synthesis of tert-butyl (5-benzyl-7-(((tert-butyldimethylsilyl)oxy)methyl)-5,6,7,8-tetrahydro-1,5-naphthyridin-3-yl)carbamate

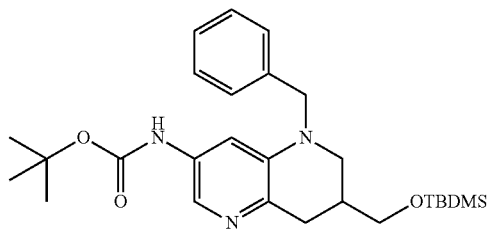 [SMILES: CC(C)(C)OC(=O)Nc1cnc2c(c1)N(Cc1ccccc1)CC(CO[Si](C)(C)C(C)(C)C)C2]

A mixture of 5-benzyl-7-(((tert-butyldimethylsilyl)oxy)methyl)-5,6,7,8-tetrahydro-1,5-naphthyridin-3-amine (3.83 g, 10 mmol), triethylamine (2.02 g, 20 mmol), and di-tert-butyl dicarbonate (2.73 g, 12.5 mmol) in dichloromethane (50 mL) was stirred at room temperature for 2 days. The reaction mixture was partitioned between dichloromethane and water. The aqueous layer was re-extracted with dichloromethane, and the combined organic layers were dried ($Na_2SO_4$) and concentrated to afford the title compound, which was used without further purification.

Part VIII—Synthesis of [7-(tert-butyl-dimethyl-silanyloxymethyl)-5,6,7,8-tetrahydro-[1,5]naphthyridin-3-yl]-carbamic acid tert-butyl ester

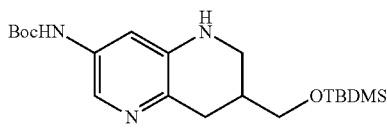 [SMILES: CC(C)(C)OC(=O)Nc1cnc2c(c1)NCC(CO[Si](C)(C)C(C)(C)C)C2]

[5-Benzyl-7-(tert-butyl-dimethyl-silanyloxymethyl)-5,6,7,8-tetrahydro-[1,5]naphthyridin-3-yl]-carbamic acid tert-butyl ester (5.9 g, 12.2 mmol) was dissolved in methanol (100 mL) and 10% Pd/C catalyst (1.0 g) was added, followed by ammonium formate (5 g). The mixture was heated at reflux for 24 hours. The cooled mixture was filtered through a pad of CELITE and the filtrate was evaporated. The residue was purified by $SiO_2$ chromatography to afford the title compound. LC/MS (ESI) m/z 394.4. This material was separated by chiral SPC chromatography into its two enantiomers. Compounds derived from the first enantiomer to elute are named with an "A" in the name. The following experimental procedures are illustrative of the chemistry employed separately for each of the two enantiomers.

Part IX—Synthesis of [7-(tert-butyl-dimethyl-silanyloxymethyl)-5-(4-fluorobenzenesulfonyl)-5,6,7,8-tetrahydro-[1,5]naphthyridin-3-yl]-carbamic acid tert-butyl ester

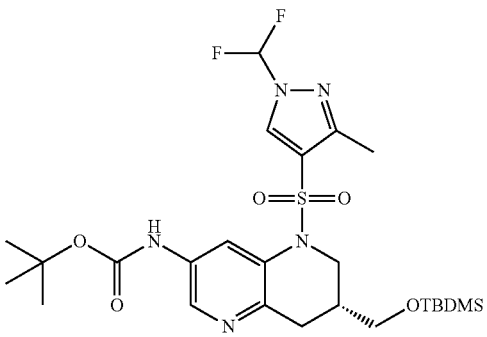 [SMILES: Cc1nn(C(F)F)cc1S(=O)(=O)N1C[C@H](CO[Si](C)(C)C(C)(C)C)Cc2ncc(NC(=O)OC(C)(C)C)cc21]

To a solution [7-(tert-butyl-dimethyl-silanyloxymethyl)-5,6,7,8-tetrahydro-[1,5]naphthyridin-3-yl]-carbamic acid tert-butyl ester (0.394 g, 1 mmol), 4-dimethylaminopyridine (0.061 g, 0.5 mmol) in pyridine (15 mL) was added 1-difluoromethyl-3-methyl-1H-pyrazole-4-sulfonyl chloride (0.277 g, 1.2 mmol). The reaction was heated at 60° C. for 4 hours. The reaction was cooled and partitioned between ethyl acetate and water. The organic layer was washed with brine, dried ($Na_2SO_4$) and concentrated. The residue was purified by chromatography on silica gel to give [7-(tert-butyl-dimethyl-silanyloxymethyl)-5-(1-difluoromethyl-3-methyl-1H-pyrazole-4-sulfonyl)-5,6,7,8-tetrahydro-[1,5]naphthyridin-3-yl]-carbamic acid tert-butyl ester. LC/MS (ESI) m/z 588.5.

The enantiomeric compound was prepared in an analogous manner.

Example 79—Preparation of Additional Sulfonamides from 7-(hydroxymethyl)-5,6,7,8-tetrahydro-1,5-naphthyridin-3-yl)carbamates The compounds in Table 25 below were prepared based on the experimental procedures described in Examples 77 and 78 and elsewhere in the detailed description, and can be achieved by one of skill in the art in light of the present disclosure.

TABLE 25

| Ex. No. | Structure | Name | Observed m/z |
|---|---|---|---|
| 79A | 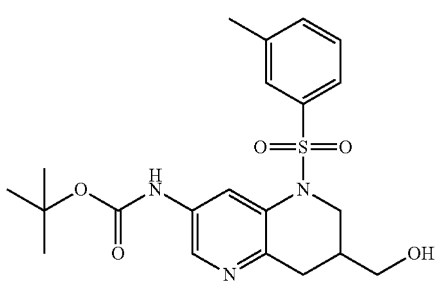 [SMILES: Cc1cccc(S(=O)(=O)N2CC(CO)Cc3ncc(NC(=O)OC(C)(C)C)cc32)c1] | tert-butyl (7-(hydroxymethyl)-5-(m-tolylsulfonyl)-5,6,7,8-tetrahydro-1,5-naphthyridin-3-yl)carbamate | 434 $(M + H)^+$ |

TABLE 25-continued

| Ex. No. | Structure | Name | Observed m/z |
|---|---|---|---|
| 79B | 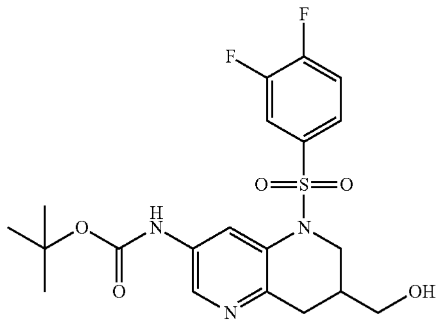 [SMILES: CC(C)(C)OC(=O)Nc1cnc2c(c1)N(S(=O)(=O)c1ccc(F)c(F)c1)CC(CO)C2] | tert-butyl (5-((3,4-difluorophenyl)sulfonyl)-7-(hydroxymethyl)-5,6,7,8-tetrahydro-1,5-naphthyridin-3-yl)carbamate | 456 (M + H)+ |
| 79C | 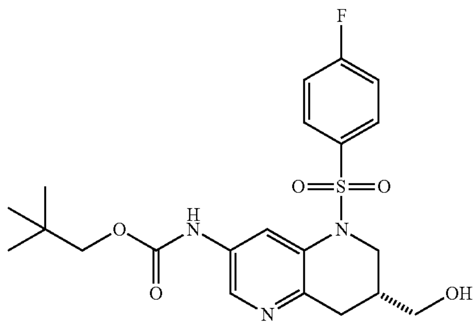 [SMILES: CC(C)(C)COC(=O)Nc1cnc2c(c1)N(S(=O)(=O)c1ccc(F)cc1)C[C@H](CO)C2] | (R or S)-neopentyl (5-((4-fluorophenyl)sulfonyl)-7-(hydroxymethyl)-5,6,7,8-tetrahydro-1,5-naphthyridin-3-yl)carbamate | 452 (M + H)+ |
| 79D | 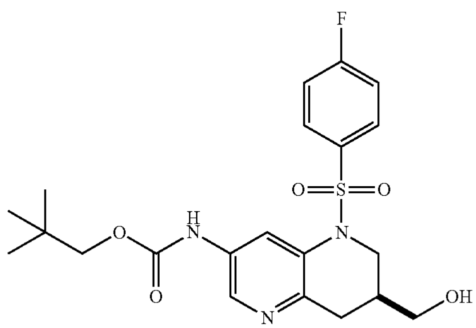 [SMILES: CC(C)(C)COC(=O)Nc1cnc2c(c1)N(S(=O)(=O)c1ccc(F)cc1)C[C@@H](CO)C2] | (S or R)-neopentyl (5-((4-fluorophenyl)sulfonyl)-7-(hydroxymethyl)-5,6,7,8-tetrahydro-1,5-naphthyridin-3-yl)carbamate | 452 (M + H)+ |

Example 80—Synthesis of neopentyl ((S)-5-((1-(difluoromethyl)-3-methyl-1H-pyrazol-4-yl)sulfonyl)-7-(((R)-3-hydroxypyrrolidin-1-yl)methyl)-5,6,7,8-tetrahydro-1,5-naphthyridin-3-yl)carbamate (Examples 80A and 80B)

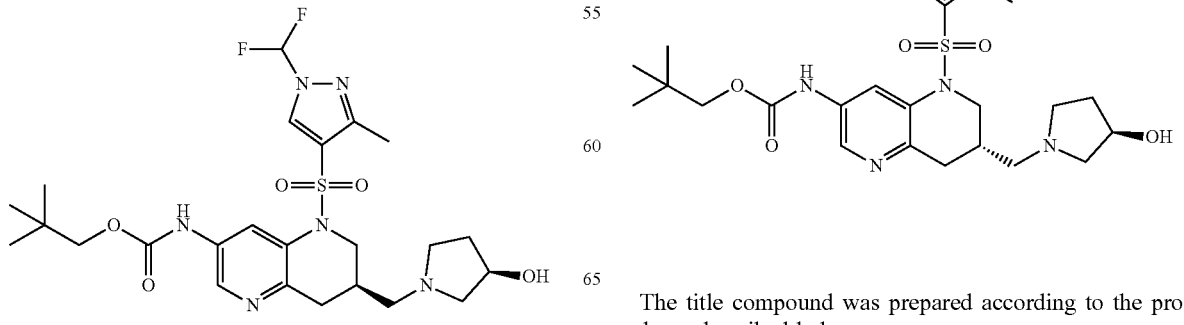

The title compound was prepared according to the procedures described below.

Part I—Synthesis of (R)-(1-((1-(difluoromethyl)-3-methyl-1H-pyrazol-4-yl)sulfonyl)-7-(((neopentyloxy)carbonyl)amino)-1,2,3,4-tetrahydro-1,5-naphthyridin-3-yl)methyl methanesulfonate

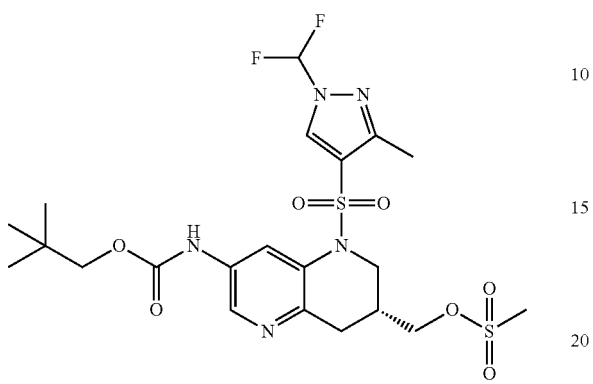

To a solution (R)-neopentyl (5-((1-(difluoromethyl)-3-methyl-1H-pyrazol-4-yl)sulfonyl)-7-(hydroxymethyl)-5,6,7,8-tetrahydro-1,5-naphthyridin-3-yl)carbamate (0.28 g, 0.59 mmol) in dichloromethane (5 mL) was added triethylamine (0.248 mL, 1.77 mmol) and methanesulfonic acid anhydride (0.153 g, 0.88 mmol). The mixture was stirred at room temperature for four hours, then concentrated, and the residue was partitioned between ethyl acetate and water. The organic layer was dried ($Na_2SO_4$) and concentrated to afford the title compound.

Part II—Synthesis of neopentyl ((S)-5-((1-(difluoromethyl)-3-methyl-1H-pyrazol-4-yl)sulfonyl)-7-(((R)-3-hydroxypyrrolidin-1-yl)methyl)-5,6,7,8-tetrahydro-1,5-naphthyridin-3-yl)carbamate

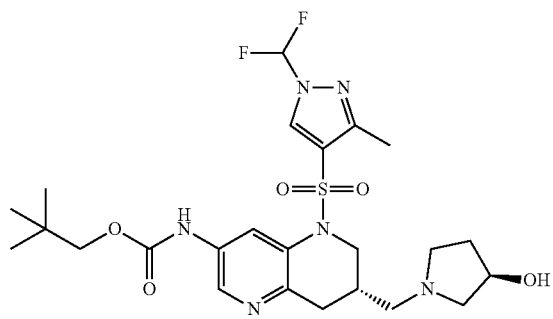 [SMILES: Cc1nn(C(F)F)cc1S(=O)(=O)N1C[C@H](CN2CC[C@@H](O)C2)Cc2ncc(NC(=O)OCC(C)(C)C)cc21]

A mixture (R)-(1-((1-(difluoromethyl)-3-methyl-1H-pyrazol-4-yl)sulfonyl)-7-(((neopentyloxy)carbonyl)amino)-1,2,3,4-tetrahydro-1,5-naphthyridin-3-yl)methyl methanesulfonate (0.10 g, 0.18 mmol) and (R)-pyrrolidine-3-ol (31.3 mg, 0.36 mmol) in THF with triethylamine (10 uL) was heated at 70° C. for 12 hours. The reaction mixture was diluted with dichloromethane and washed with water. The organic layer was dried ($Na_2SO_4$) and concentrated. The residue was purified by column chromatography eluting with dichloromethane/MeOH/triethylamine (89:10:1) to give the title compound, Example No. 80A. LRMS (ESI) calculated for $C_{24}H_{35}F_2N_6O_5S$ $(M+H)^+$: 557, Found: 557.

Ex. No. 80B was prepared in an analogous manner using the enantiomer of the starting alcohol. LRMS (ESI) calculated for $C_{24}H_{35}F_2N_6O_5S$ $(M+H)^+$: 557, Found: 557.

Example 81—Preparation of 1,1,1-trifluoro-2-methylpropan-2-yl ((R or S)-4-((3,4-difluorophenyl)sulfonyl)-2-((S or R)-2,2,2-trifluoro-1-hydroxyethyl)-3,4-dihydro-2H-benzo[b][1,4]oxazin-6-yl)carbamate (Examples 81A, 81B, and 81C)

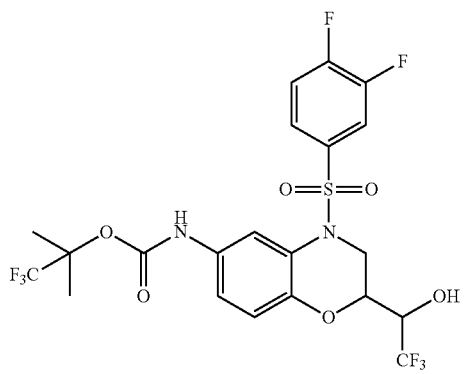 [SMILES: CC(C)(OC(=O)Nc1ccc2c(c1)N(S(=O)(=O)c1ccc(F)c(F)c1)CC(C(O)C(F)(F)F)O2)C(F)(F)F]

To a solution of (R and S)-1,1,1-trifluoro-2-methylpropan-2-yl 4-(3,4-difluorophenylsulfonyl)-2-(2,2,2-trifluoroacetyl)-3,4-dihydro-2H-benzo[b][1,4]oxazin-6-ylcarbamate (260 mg, 0.47 mmol) in 10 mL of MeOH was added $NaBH_4$ (35 mg, 0.93 mmol) and the resulting mixture was stirred at room temperature for 2 hours. Water was added and the mixture was extracted with EtOAc. The organic phase was washed with brine, dried over $Na_2SO_4$ and filtered. The filtrate was concentrated in vacuo to give the crude mixture of diastereomers as a yellow solid. LCMS (ESI): calculated for $C_{21}H_{17}F_8N_2O_6S$ $[M+H]^+$: 579, found $[M+H]^+$: 579.

The mixture of diastereomers was separated by chiral SFC to afford three eluents: First Isomer (Peak 1, Example 81A): as a white solid, $^1$H-NMR (MeOD, 400 MHz) δ 7.98 (1H, s), 7.72-7.74 (1H, m), 7.58 (1H, br s), 7.47-7.51 (1H, m), 7.08-7.11 (1H, m), 6.78 (1H, d, J=8.8 Hz), 4.40-4.43 (1H, m), 4.08-4.11 (1H, m), 3.62-3.65 (1H, m), 3.51-3.54 (1H, m), 1.77 (6H, s); Second Isomer (Peak 2, Example 81B): as a white solid, $^1$H-NMR (MeOD, 400 MHz) δ 7.97 (1H, s), 7.79-7.81 (1H, m), 7.60-7.62 (1H, m), 7.45-7.49 (1H, m), 7.09-7.12 (1H, m), 6.80-7.00 (1H, m), 4.45-4.50 (1H, m), 4.21-4.24 (1H, m), 3.68-3.70 (1H, m), 3.38-3.42 (1H, m), 1.77 (6H, s); Third Isomer (Peak 3, Example 81C): as a white solid, $^1$H-NMR (MeOD, 400 MHz) δ 7.97 (1H, s), 7.79-7.81 (1H, m), 7.60-7.62 (1H, m), 7.45-7.49 (1H, m), 7.09-7.12 (1H, m), 6.80-7.00 (1H, m), 4.45-4.50 (1H, m), 4.21-4.24 (1H, m), 3.68-3.70 (1H, m), 3.38-3.42 (1H, m), 1.77 (6H, s).

The compounds in Table 26 below were prepared based on the methods described in Example X and elsewhere in the description, and can be achieved by one of skill in the art in light of the present disclosure.

TABLE 26

| Ex. No. | Structure | Name | Observed m/z |
|---|---|---|---|
| 81D | 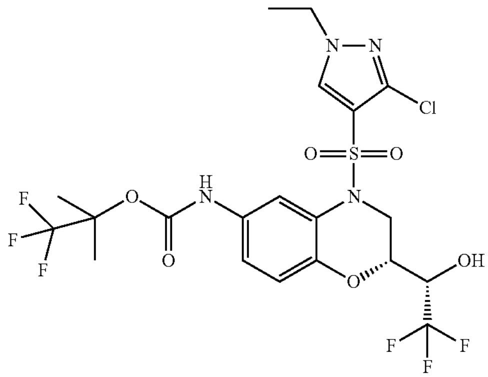 [SMILES: CCn1cc(S(=O)(=O)N2C[C@H]([C@H](O)C(F)(F)F)Oc3ccc(NC(=O)OC(C)(C)C(F)(F)F)cc32)c(Cl)n1] | 1,1,1-trifluoro-2-methylpropan-2-yl ((R or S)-4-((3-chloro-1-ethyl-1H-pyrazol-4-yl)sulfonyl)-2-((S or R)-2,2,2-trifluoro-1-hydroxyethyl)-3,4-dihydro-2H-benzo[b][1,4]oxazin-6-yl)carbamate | 612 (M + NH₄)+ |
| 81E | 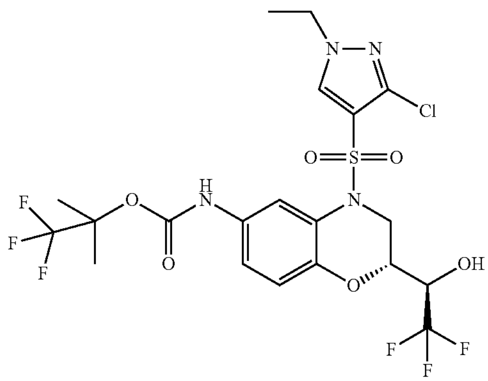 [SMILES: CCn1cc(S(=O)(=O)N2C[C@H]([C@@H](O)C(F)(F)F)Oc3ccc(NC(=O)OC(C)(C)C(F)(F)F)cc32)c(Cl)n1] | 1,1,1-trifluoro-2-methylpropan-2-yl ((R or S)-4-((3-chloro-1-ethyl-1H-pyrazol-4-yl)sulfonyl)-2-((S or R)-2,2,2-trifluoro-1-hydroxyethyl)-3,4-dihydro-2H-benzo[b][1,4]oxazin-6-yl)carbamate | 595 (M + H)+ |
| 81F | 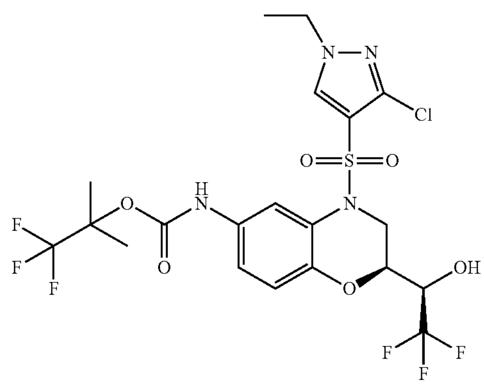 [SMILES: CCn1cc(S(=O)(=O)N2C[C@@H]([C@@H](O)C(F)(F)F)Oc3ccc(NC(=O)OC(C)(C)C(F)(F)F)cc32)c(Cl)n1] | 1,1,1-trifluoro-2-methylpropan-2-yl ((R or S)-4-((3-chloro-1-ethyl-1H-pyrazol-4-yl)sulfonyl)-2-((S or R)-2,2,2-trifluoro-1-hydroxyethyl)-3,4-dihydro-2H-benzo[b][1,4]oxazin-6-yl)carbamate | 595 (M + H)+ |
| 81G | 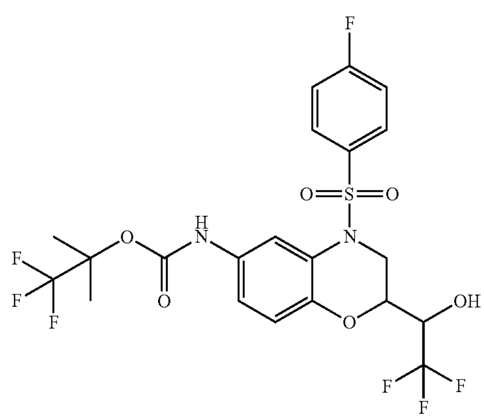 [SMILES: CC(C)(OC(=O)Nc1ccc2c(c1)N(S(=O)(=O)c1ccc(F)cc1)CC(C(O)C(F)(F)F)O2)C(F)(F)F] | 1,1,1-trifluoro-2-methylpropan-2-yl ((S and R)-4-((4-fluorophenyl)sulfonyl)-2-((S and R)-2,2,2-trifluoro-1-hydroxyethyl)-3,4-dihydro-2H-benzo[b][1,4]oxazin-6-yl)carbamate | 561 (M + H)+ |

Example 82—Preparation of 1,1,1-trifluoro-2-methylpropan-2-yl ((S)-2-((R)-1-amino-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((S)-2-((S)-1-amino-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((R)-2-((R)-1-amino-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((R)-2-((S)-1-amino-2,2,2-trifluoroethyl)-4-((4-fluorophenyl)sulfonyl)-3,4-dihydro-2H-benzo[b][1,4]oxazin-6-yl)carbamate (Examples 82A, 82B, 82C, and 82D)

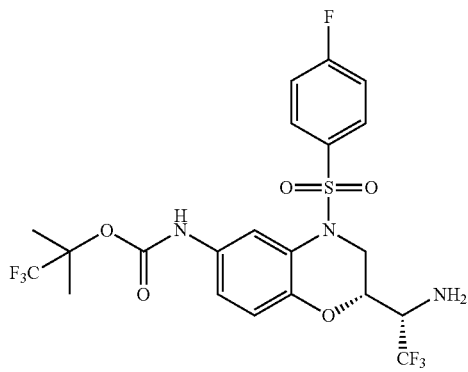 [SMILES: CC(C)(OC(=O)Nc1ccc2c(c1)N(S(=O)(=O)c1ccc(F)cc1)CC(C(OS(=O)(=O)C(F)(F)F)C(F)(F)F)O2)C(F)(F)F]

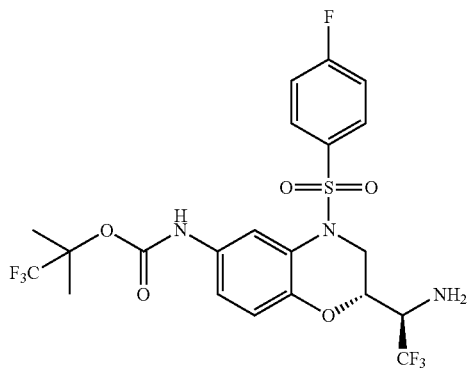

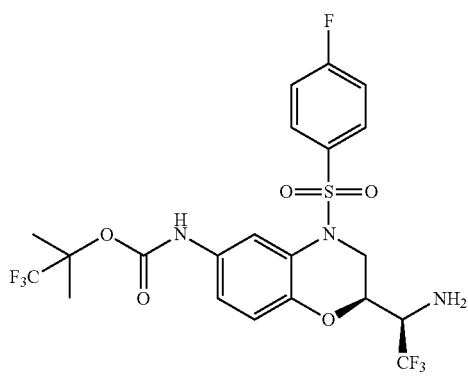

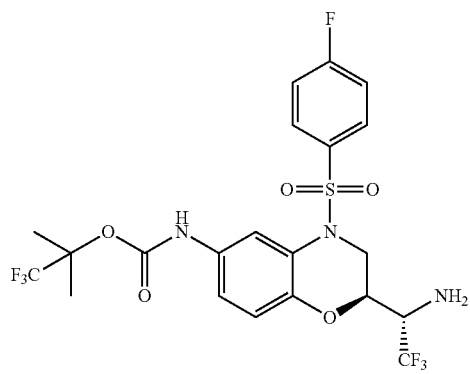

Step 1—Preparation of (S and R)-2,2,2-trifluoro-1-((R and S)-4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)ethyl trifluoromethanesulfonate

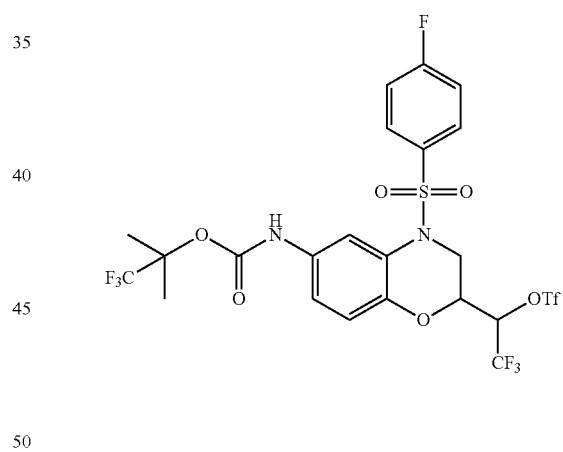

To a solution of 1,1,1-trifluoro-2-methylpropan-2-yl ((S and R)-4-((4-fluorophenyl)sulfonyl)-2-((S and R)-2,2,2-trifluoro-1-hydroxyethyl)-3,4-dihydro-2H-benzo[b][1,4]oxazin-6-yl)carbamate (600 mg, 1.07 mmol) in 25 mL/2.5 mL of DCM/pyridine was added Tf$_2$O (480 mg, 1.70 mmol) at 0° C. and the resulted mixture was stirred at 0° C. for 1 hour. 1 N HCl was then added and the mixture was extracted 3× with DCM. The combined organic layers were washed with brine, dried over Na$_2$SO$_4$ and filtered. The filtrate was concentrated in vacuo to give the crude title compound as a yellow oil, which was used in the next step without further purification. $^1$H-NMR (MeOD, 400 MHz) δ 7.95-7.97 (1H, m), 7.75-7.82 (2H, m), 7.28-7.33 (2H, m), 7.18-7.19 (1H, m), 6.82-6.84 (1H, m), 5.92-6.01 (1H, m), 4.51-4.57 (1H, m), 3.86-3.91 (1H, m), 3.36-3.44 (1H, m), 1.77 (6H, s).

Step 2—Preparation of 1,1,1-trifluoro-2-methylpropan-2-yl ((R and S)-2-((S and R)-1-azido-2,2,2-trifluoroethyl)-4-((4-fluorophenyl)sulfonyl)-3,4-dihydro-2H-benzo[b][1,4]oxazin-6-yl)carbamate

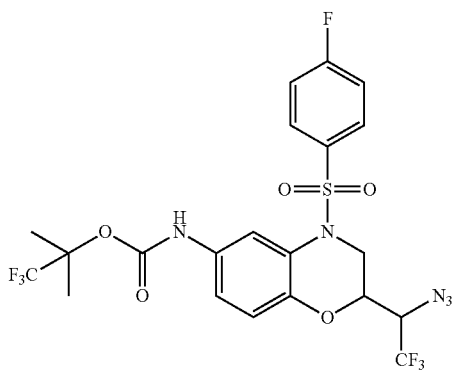 [SMILES: CC(C)(OC(=O)Nc1ccc2c(c1)N(S(=O)(=O)c1ccc(F)cc1)CC(C(N=[N+]=[N-])C(F)(F)F)O2)C(F)(F)F]

To a solution of (S and R)-2,2,2-trifluoro-1-((R and S)-4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)ethyl trifluoromethanesulfonate (600 mg, 0.87 mmol) in 20 ml, of DMSO was added NaN$_3$ (120 mg, 1.85 mmol) and then the resulted mixture was stirred at room temperature for 16 hours. Water was added and the mixture extracted 3× with EtOAc. The aqueous layer was treated with H$_2$O$_2$, followed by Na$_2$SO$_3$ before being discarded. The organic layer was washed with water, brine, dried over Na$_2$SO$_4$ and filtered. The filtrate was concentrated in vacuo to give the title compound as white solid. $^1$H-NMR (MeOD, 400 MHz) δ 7.97 (s, 1H), 7.79-7.82 (m, 2H), 7.21-7.31 (m, 2H), 7.14-7.17 (m, 1H), 6.77-6.79 (m, 1H), 4.39-4.49 (m, 1H), 4.35-4.38 (m, 1H), 3.72-3.75 (m, 1H), 3.40-3.47 (m, 1H), 1.77 (s, 6H).

Step 3—Preparation of Preparation of 1,1,1-trifluoro-2-methylpropan-2-yl ((S)-2-((R)-1-amino-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((S)-2-((S)-1-amino-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((R)-2-((R)-1-amino-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((R)-2-((S)-1-amino-2,2,2-trifluoroethyl)-4-((4-fluorophenyl)sulfonyl)-3,4-dihydro-2H-benzo[b][1,4]oxazin-6-yl)carbamate A solution of 1,1,1-trifluoro-2-methylpropan-2-yl ((R and S)-2-((S and R)-1-azido-2,2,2-trifluoroethyl)-4-((4-fluorophenyl)sulfonyl)-3,4-dihydro-2H-benzo[b][1,4]oxazin-6-yl) carbamate (300 mg, 0.51 mmol) and one drop of NH$_4$OH in 30 mL of MeOH was charged with 150 mg of Pd/C (wet) and the reaction was stirred at room temperature for 16 hours under H$_2$ balloon atmosphere. The reaction mixture was filtered through CELITE and the filtrate was concentrated to give the crude product as a yellow solid. LCMS (ESI): calculated for C$_{21}$H$_{21}$F$_7$N$_3$O$_5$S [M+H]$^+$: 560, found: 560.

The mixture was separated by chiral SFC (Chiralcel OD-3 150×4.6 mm I.D., 3 um; Mobile phase: methanol (0.05% DEA) in CO$_2$ from 5% to 40%) to afford 4 isomers. First Isomer (Peak 1, Example 82A): $^1$H-NMR (MeOD, 400 MHz) δ 7.98 (1H, s), 7.79-7.83 (1H, m), 7.25-7.30 (2H, m), 7.10-7.13 (1H, m), 6.76-6.78 (1H, m), 4.47-4.51 (1H, m), 3.56-3.59 (1H, m), 3.43-3.49 (2H, m), 1.77 (6H, s); Second Isomer (Peak 2, Example 82B): $^1$H-NMR (MeOD, 400 MHz) δ 7.98 (1H, s), 7.79-7.83 (2H, m), 7.25-7.30 (2H, m), 7.10-7.13 (1H, m), 6.76-6.78 (1H, m), 4.47-4.51 (1H, m), 3.56-3.59 (1H, m), 3.43-3.49 (2H, m), 1.77 (6H, s); Third Isomer (Peak 3, Example 82C): $^1$H-NMR (MeOD, 400 MHz) δ 7.97 (1H, s), 7.78-7.81 (2H, m), 7.25-7.29 (2H, m), 7.13-7.15 (1H, m), 6.79-6.81 (1H, m), 4.37-4.41 (1H, m), 3.43-3.58 (3H, m, 3H), 1.77 (6H, s); Fourth Isomer (Peak 4, Example 82D): $^1$H-NMR (MeOD, 400 MHz) δ 7.97 (1H, s), 7.78-7.81 (2H, m), 7.25-7.29 (2H, m), 7.13-7.15 (1H, m), 6.79-6.81 (1H, m), 4.37-4.41 (1H, m), 3.43-3.58 (3H, m), 1.77 (6H, s).

Example 83—Preparation of (S)-tert-butyl (2-(2-(ethylsulfonyl)ethyl)-4-((3-(trifluoromethyl)phenyl)sulfonyl)-3,4-dihydro-2H-benzo[b][1,4]oxazin-6-yl)carbamate (Example 83)

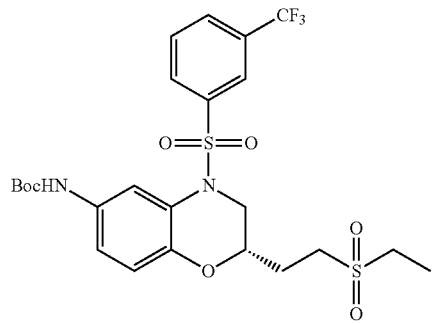 [SMILES: CCS(=O)(=O)CC[C@H]1CN(S(=O)(=O)c2cccc(C(F)(F)F)c2)c2cc(NC(=O)OC(C)(C)C)ccc2O1]

Step 1—Preparation of (S)-methyl 2-(6-((tert-butoxycarbonyl)amino)-4-((3-(trifluoromethyl)phenyl)sulfonyl)-3,4-dihydro-2H-benzo[b][1,4]oxazin-2-yl)acetate

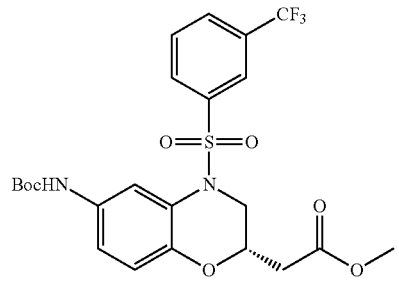 [SMILES: COC(=O)C[C@H]1CN(S(=O)(=O)c2cccc(C(F)(F)F)c2)c2cc(NC(=O)OC(C)(C)C)ccc2O1]

To a mixture of (S)-methyl 2-(6-((((1,1,1-trifluoro-2-methylpropan-2-yl)oxy)carbonyl)amino)-3,4-dihydro-2H-benzo[b][1,4]oxazin-2-yl)acetate (200 mg, 0.531 mmol) in THF (3 mL) was added 3-(trifluoromethyl)benzene-1-sulfonyl chloride (195 mg, 0.797 mmol) and pyridine (3 mL). The reaction mixture was stirred at 20° C. for 2 hours, then diluted with water (20 mL) and extracted with ethyl acetate (3×15 mL). The organic layers were separated, combined, dried over anhydrous magnesium sulfate, filtered and concentrated in vacuo and the residual oil was purified by prep-TLC (petroleum ether/ethyl acetate=3:1) to afford the title compound as a white solid. LCMS (ESI) calculated for $C_{23}H_{26}F_3N_2O_7S$ [M+H]$^+$: 531.1, found: 553.2.

Step 2—Preparation of (S)-tert-butyl (2-(2-hydroxyethyl)-4-((3-(trifluoromethyl)phenyl) sulfonyl)-3,4-dihydro-2H-benzo[b][1,4]oxazin-6-yl)carbamate

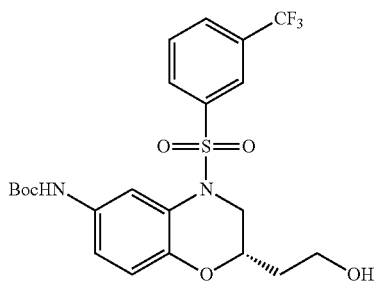 [SMILES: CC(C)(C)OC(=O)Nc1ccc2c(c1)N(S(=O)(=O)c1cccc(C(F)(F)F)c1)C[C@H](CCO)O2]

To a solution of (S)-methyl 2-(6-((tert-butoxycarbonyl)amino)-4-((3-(trifluoromethyl)phenyl) sulfonyl)-3,4-dihydro-2H-benzo[b][1,4]oxazin-2-yl)acetate (200 mg, 0.377 mmol) in dry methanol (10 mL) was added sodium borohydride (83 mg, 2.262 mmol) at 0° C. The reaction was stirred at 50° C. for 12 hours, then quenched with aqueous ammonium chloride (30 mL) and extracted with ethyl acetate (3×50 mL). The combined organic layers were dried over sodium sulfate and evaporated to dryness. The crude product was purified by column chromatography (petroleum ether/ethyl acetate=30:1 to 1:1) to give the title compound as a white solid. LCMS (ESI) calculated for $C_{22}H_{25}F_3N_2O_6SNa$ [M+Na]$^+$: 525.1, found: 525.2; $^1$H NMR (Methanol-d$_4$, 400 MHz) δ 7.98-8.04 (3H, m), 7.91 (1H, d, J=8.0 Hz), 7.68-7.73 (1H, m), 6.98 (1H, d, J=7.2 Hz), 6.67 (1H, d, J=8.4 Hz), 4.41-4.44 (1H, m), 3.61-3.66 (3H, m), 3.19-3.25 (1H, m), 1.69-1.74 (2H, m), 1.51 (9H, s).

Step 3—Preparation of (S)-2-(6-((tert-butoxycarbonyl)amino)-4-((3-(trifluoromethyl)phenyl) sulfonyl)-3,4-dihydro-2H-benzo[b][1,4]oxazin-2-yl)ethyl methanesulfonate

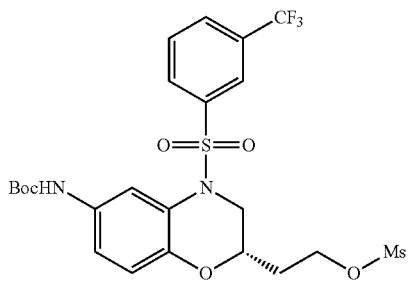 [SMILES: CC(C)(C)OC(=O)Nc1ccc2c(c1)N(S(=O)(=O)c1cccc(C(F)(F)F)c1)C[C@H](CCOS(C)(=O)=O)O2]

To a solution of (S)-tert-butyl (2-(2-hydroxyethyl)-4-((3-(trifluoromethyl)phenyl)sulfonyl)-3,4-dihydro-2H-benzo[b][1,4]oxazin-6-yl)carbamate (296 mg, 0.589 mmol), triethylamine (0.411 ml, 2.95 mmol) in dry dichloromethane (10 mL) at 0° C. was added methanesulfonyl chloride (1350 mg, 11.78 mmol). The reaction mixture was stirred at 20° C. for 4 hours, then quenched with water (20 mL). The aqueous layer was extracted with dichloromethane (3×20 mL). The organic layer was dried over sodium sulfate, evaporated, and the residue was purified by column chromatography (petroleum ether/ethyl acetate=20:1 to 4:1) to give the title compound as a colorless oil. LCMS (ESI) calculated for $C_{23}H_{27}F_3N_2O_8S_2Na$ [M+Na]$^+$: 603.1, found: 603.1.

Step 4—Preparation of (S)-tert-butyl (2-(2-(ethylthio)ethyl)-4-((3-(trifluoromethyl)phenyl)sulfonyl)-3,4-dihydro-2H-benzo[b][1,4]oxazin-6-yl)carbamate

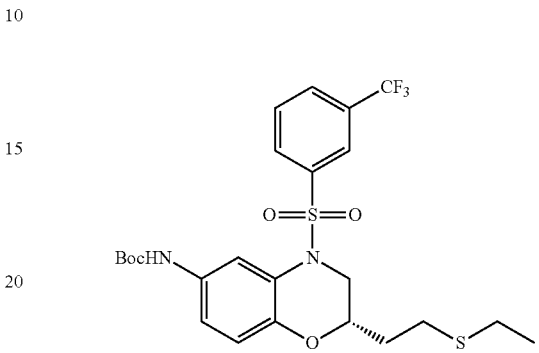

To a solution of (S)-2-(6-((tert-butoxycarbonyl)amino)-4-((3-(trifluoromethyl)phenyl)sulfonyl)-3,4-dihydro-2H-benzo[b][1,4]oxazin-2-yl)ethyl methanesulfonate (160 mg, 0.276 mmol) in EtOH (10 mL) at 0° C. was added sodium ethanethiolate (116 mg, 1.378 mmol). The reaction mixture was stirred at 80° C. for 5 hours, then poured into water and extracted with ethyl acetate (3×30 mL). The organic layer was dried over sodium sulfate, evaporated, and the residue was purified by column chromatography (petroleum ether/ethyl acetate=20:1 to 5:1) to give the titled compound as a colorless oil. LCMS (ESI) calculated for $C_{24}H_{30}F_3N_2O_5S_2$ [M+H]$^+$: 547.1, found: 547.1.

Step 5—Preparation of (S)-tert-butyl (2-(2-(ethylsulfonyl)ethyl)-4-((3-(trifluoromethyl)phenyl)sulfonyl)-3,4-dihydro-2H-benzo[b][1,4]oxazin-6-yl)carbamate

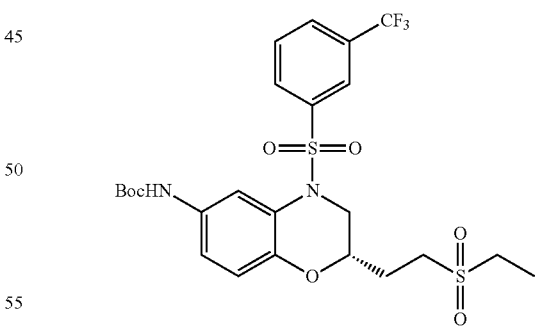

To a solution of (S)-tert-butyl (2-(2-(ethylthio)ethyl)-4-((3-(trifluoromethyl)phenyl)sulfonyl)-3,4-dihydro-2H-benzo[b][1,4]oxazin-6-yl)carbamate (140 mg, 0.256 mmol) in dichloromethane (10 mL) at 0° C. was added metachloroperbenzoic acid (133 mg, 0.768 mmol). The reaction mixture was stirred at 15° C. for 2 hours, then poured into water and extracted with dichloromethane (3×30 mL). The organic layer was dried over sodium sulfate, evaporated, and the residue was purified by column chromatography (petroleum ether/ethyl acetate=20:1 to 3:1) to give the titled compound as a colorless oil. LCMS (ESI) calculated for C$_{24}$H$_{29}$F$_3$N$_2$O$_7$S$_2$Na [M+Na]$^+$: 601.1, found: 601.0; $^1$H NMR (Methanol-d$_4$, 400 MHz) δ 8.02-8.11 (3H, m), 7.93 (1H, d, J=8.0 Hz), 7.72-7.77 (1H, m), 7.01 (1H, d, J=6.8 Hz), 6.73 (1H, d, J=8.4 Hz), 4.44 (1H, d, J=14.0 Hz), 3.71 (1H, brs), 3.08-3.34 (5H, m), 2.12-2.17 (1H, m), 1.97-2.03 (1H, m), 1.53 (9H, s), 1.33 (3H, t, J=7.6 Hz).

Example 84—Preparation of (S)-1,1,1-trifluoro-2-methylpropan-2-yl (2-(2-(ethylsulfonyl)ethyl)-4-((3-(trifluoromethyl)phenyl)sulfonyl)-3,4-dihydro-2H-benzo[b][1,4]oxazin-6-yl)carbamate (Example 84)

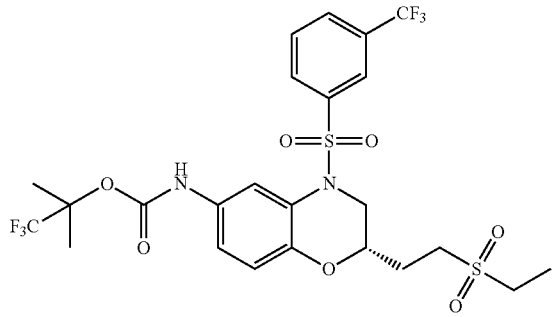 [SMILES: CCS(=O)(=O)CC[C@H]1CN(S(=O)(=O)c2cccc(C(F)(F)F)c2)c2cc(NC(=O)OC(C)(C)C(F)(F)F)ccc2O1]

Step 1—Preparation of (S)-2-(2-(ethylsulfonyl)ethyl)-4-((3-(trifluoromethyl)phenyl)sulfonyl)-3,4-dihydro-2H-benzo[b][1,4]oxazin-6-amine

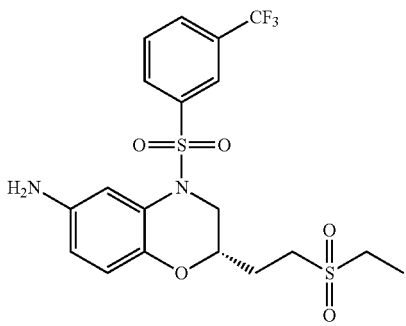 [SMILES: CCS(=O)(=O)CC[C@H]1CN(S(=O)(=O)c2cccc(C(F)(F)F)c2)c2cc(N)ccc2O1]

To a solution of (S)-tert-butyl (2-(2-(ethylsulfonyl)ethyl)-4-((3-(trifluoromethyl)phenyl)sulfonyl)-3,4-dihydro-2H-benzo[b][1,4]oxazin-6-yl)carbamate (140 mg, 0.242 mmol) in dichloromethane (5 mL) was added trifluoroacetic acid (2 mL) at 0° C. The reaction mixture was stirred at 15° C. for 2 hours, then evaporated to give the crude title compound as a colorless oil. LCMS (ESI) calculated for C$_{19}$H$_{22}$F$_3$N$_2$O$_5$S$_2$ [M+H]$^+$: 479.1, found: 479.2.

Step 2—Preparation of (S)-1,1,1-trifluoro-2-methylpropan-2-yl (2-(2-(ethylsulfonyl)ethyl)-4-((3-(trifluoromethyl)phenyl)sulfonyl)-3,4-dihydro-2H-benzo[b][1,4]oxazin-6-yl)carbamate

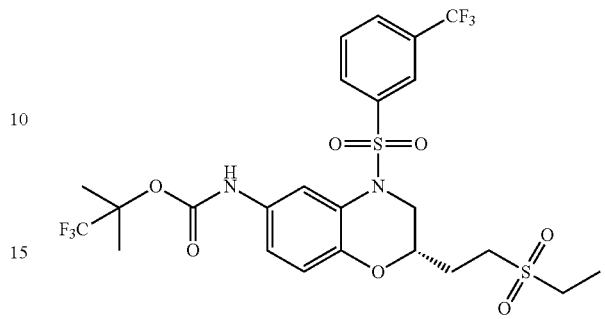

A mixture of (S)-2-(2-(ethylsulfonyl)ethyl)-4-((3-(trifluoromethyl)phenyl)sulfonyl)-3,4-dihydro-2H-benzo[b][1,4]oxazin-6-amine (50 mg, 0.104 mmol) and 3-methyl-1-(((1,1,1-trifluoro-2-methylpropan-2-yl)oxy)carbonyl)-1H-imidazol-3-ium iodide (49.6 mg, 0.209 mmol) in DMSO (3 mL) was stirred at 15° C. for 1 hour. The reaction mixture was directly purified by Prep-HPLC, eluting with Acetonitrile/Water+0.10% TFA, to give the titled compound as a white solid. LCMS (ESI) calculated for C$_{24}$H$_{27}$F$_6$N$_2$O$_7$S$_2$ [M+H]$^+$: 633.1, found: 633.0; $^1$H NMR (Methanol-d$_4$, 400 MHz) δ 8.06-8.13 (3H, m), 7.92 (1H, d, J=8.0 Hz), 7.71 (1H, t, J=8.0 Hz), 7.01 (1H, d, J=6.8 Hz), 6.73 (1H, d, J=8.8 Hz), 4.43 (1H, d, J=12.4 Hz), 3.75 (1H, brs), 3.04-3.35 (5H, m), 2.12-2.16 (1H, m), 1.97-2.02 (1H, m), 1.75 (6H, s), 1.30 (3H, t, J=7.6 Hz).

Example 85—Synthesis of 1,1,1-trifluoro-2-methylpropan-2-yl ((2S,3R)-4-((1-(difluoromethyl)-3-methyl-1H-pyrazol-4-yl)sulfonyl)-3-methyl-2-(((N-methylsulfamoyl)amino)methyl)-3,4-dihydro-2H-benzo[b][1,4]oxazin-6-yl)carbamate (Example 85)

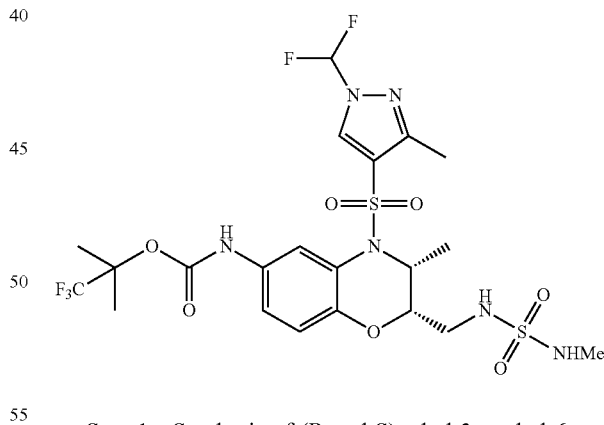

Step 1—Synthesis of (R and S)-ethyl 3-methyl-6-nitro-2H-benzo[b][1,4]oxazine-2-carboxylate

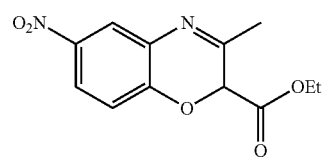 [SMILES: CCOC(=O)C1Oc2ccc([N+](=O)[O-])cc2N=C1C]

Into a 2000-mL 3-necked round-bottom flask was placed a solution of 2-amino-4-nitrophenol (80 g, 519.06 mmol, 1.00 equiv) in 1,4-dioxane (1000 mL), potassium carbonate (143 g, 1.03 mol, 2.00 equiv) and ethyl 2-chloro-3-oxobutanoate (170 g, 1.03 mol, 2.00 equiv). The resulting solution was stirred for 2 h at 100° C. in an oil bath, then cooled to 25° C., diluted with 3000 mL of H$_2$O and stirred for 1 h at room temperature. The solids were collected by filtration and the crude solid was dried and stirred in 600 mL of ether for 2 h at room temperature. The solids were collected by filtration to yield ethyl 3-methyl-6-nitro-2H-1,4-benzoxazine-2-carboxylate as a red solid.

Step 2—Synthesis of ((2S,3S,2S,3R,2R,3S and 2R,3R)-3-methyl-6-nitro-3,4-dihydro-2H-benzo[b][1,4]oxazin-2-yl)methanol

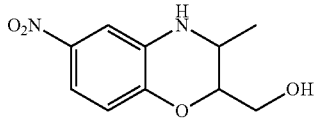 [SMILES: CC1Nc2cc([N+](=O)[O-])ccc2OC1CO]

Into a 3000-mL 3-necked round-bottom flask was placed a solution of (R and S)-ethyl 3-methyl-6-nitro-2H-benzo[b][1,4]oxazine-2-carboxylate (105 g, 397.37 mmol, 1.00 equiv) in ethanol (1500 mL), followed by the addition of NaBH$_4$ (44 g, 1.16 mol, 3.00 equiv), in portions over 30 min. The resulting solution was stirred for 3 h at 40° C., then quenched by the addition of 1500 mL of water. The resulting mixture was extracted with 3×1500 mL of ethyl acetate and the combined organic layers washed with 3×1000 mL of saturated brine, dried over anhydrous sodium sulfate and concentrated under vacuum to afford the title compound as a red syrup.

Step 3—Synthesis tert-butyl ((2R,3R)-2-(hydroxymethyl)-3-methyl-3,4-dihydro-2H-benzo[b][1,4]oxazin-6-yl)carbamate and tert-butyl ((2S,3S)-2-(hydroxymethyl)-3-methyl-3,4-dihydro-2H-benzo[b][1,4]oxazin-6-yl)carbamate

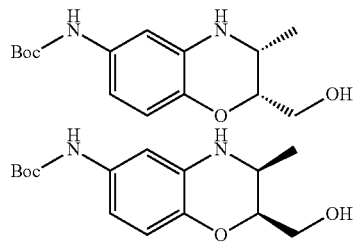

Into a 2000-mL round-bottom flask was placed a solution of (3-methyl-6-nitro-3,4-dihydro-2H-1,4-benzoxazin-2-yl)methanol (80 g, 356.80 mmol, 1.00 equiv) in ethyl acetate (1200 mL), Palladium on carbon (8 g, 0.10 equiv) and (Boc)$_2$O (116 g, 531.50 mmol, 1.50 equiv). The resulting solution was stirred for 4 h at 40° C. in an oil bath under an atmosphere of hydrogen, then filtered. The filtrate was concentrated under vacuum and the crude product was applied onto a silica gel column and eluted with ethyl acetate/petroleum ether (5:1 to 1:1). Prep-SFC separation was conducted under the following conditions: Column, ChiralPak IC, 5×25 cm, Sum; mobile phase, CO$_2$ (65%), IPA (with 0.2% DEA) (35%). Detector, UV 220 nm to afford tert-butyl N-[(2S,3S)-2-(hydroxymethyl)-3-methyl-3,4-dihydro-2H-1,4-benzoxazin-6-yl]carbamate as a white solid and of tert-butyl N-[(2R,3R)-2-(hydroxymethyl)-3-methyl-3,4-dihydro-2H-1,4-benzoxazin-6-yl]carbamate as a white solid.

tert-butyl ((2S,3S)-2-(hydroxymethyl)-3-methyl-3,4-dihydro-2H-benzo[b][1,4]oxazin-6-yl)carbamate LC-MS (ES, m/z) calculated for C$_{15}$H$_{23}$N$_2$O$_4$ [M+H]$^+$: 295, found 295 [α]$_D^{20}$=+51.3 (c=1.0 g/100 mL MeOH); $^1$H-NMR (300 MHz, CDCl$_3$, ppm): δ 6.93 (s, 1H), 6.75-6.22 (d, 1H), 6.46-6.42 (m, 1H), 6.28 (s, 1H), 4.25-4.20 (m, 1H), 3.87-3.80 (m, 1H), 3.73-3.69 (m, 1H), 3.61-3.58 (m, 1H), 1.49 (s, 9H), 1.20-1.17 (d, 3H).

tert-butyl ((2R,3R)-2-(hydroxymethyl)-3-methyl-3,4-dihydro-2H-benzo[b][1,4]oxazin-6-yl)carbamate LC-MS (ES, m/z) calculated for C$_{15}$H$_{23}$N$_2$O$_4$ [M+H]$^+$: 295, found 295 [α]$_D^{20}$=−51.1 (c=1.0 g/100 mL MeOH); $^1$H-NMR (300 MHz CDCl$_3$, ppm): δ 6.93 (s, 1H), 6.75-6.22 (d, 1H), 6.46-6.42 (m, 1H), 6.28 (s, 1H), 4.25-4.20 (m, 1H), 3.87-3.80 (m, 1H), 3.73-3.69 (m, 1H), 3.61-3.58 (m, 1H), 1.49 (s, 9H), 1.20-1.17 (d, 3H).

Step 4—Synthesis ((2R,3R)-6-((tert-butoxycarbonyl)amino)-4-((1-(difluoromethyl)-3-methyl-1H-pyrazol-4-yl)sulfonyl)-3-methyl-3,4-dihydro-2H-benzo[b][1,4]oxazin-2-yl)methyl 1-(difluoromethyl)-3-methyl-1H-pyrazole-4-sulfonate

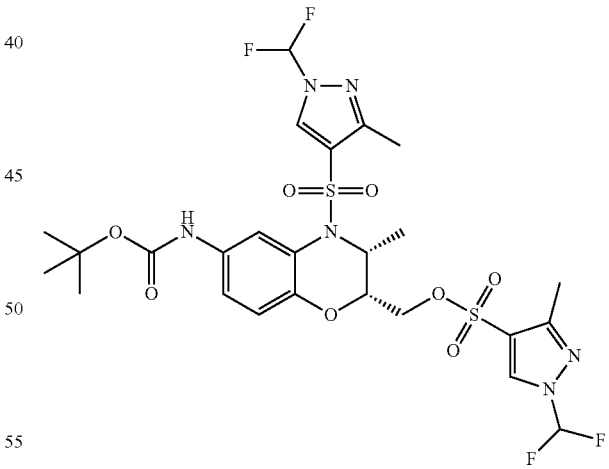

To a microwave vial equipped with a stir bar was added tert-butyl ((2R,3R)-2-(hydroxymethyl)-3-methyl-3,4-dihydro-2H-benzo[b][1,4]oxazin-6-yl)carbamate (500 mg, 1.699 mmol), 1-(difluoromethyl)-3-methyl-1H-pyrazole-4-sulfonyl chloride (1959 mg, 8.49 mmol) and pyridine (10 mL). The vial was sealed and the reaction heated to 60° C. for 1 h. Upon completion, the reaction mixture was extracted with 3×IPA/CHCl$_3$ (1:3 v/v) and NaHCO$_3$ and the combined organic layers were dried over magnesium sulfate, filtered, and concentrated under reduced pressure. The crude product was purified by flash column chromatography using 100% hexanes to 40% ethyl acetate gradient to afford the title product as a white solid. LCMS (ESI): calculated for $C_{21}H_{23}F_4N_6O_8S_2$ [M-tBu+H]$^+$: 627, found: 627.

Step 5—Synthesis tert-butyl ((2S,3R)-2-(azidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate

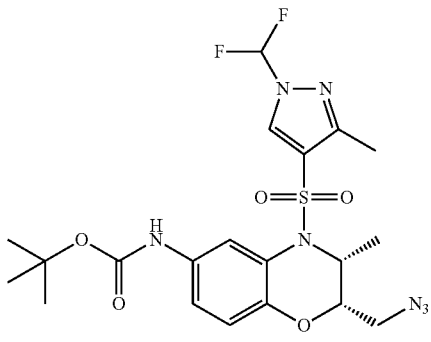 [SMILES: Cc1nn(C(F)F)cc1S(=O)(=O)N1c2cc(NC(=O)OC(C)(C)C)ccc2O[C@@H](CN=[N+]=[N-])[C@H]1C]

To a microwave vial equipped with a stir bar was added ((2R,3R)-6-((tert-butoxycarbonyl)amino)-4-((1-(difluoromethyl)-3-methyl-1H-pyrazol-4-yl)sulfonyl)-3-methyl-3,4-dihydro-2H-benzo[b][1,4]oxazin-2-yl)methyl 1-(difluoromethyl)-3-methyl-1H-pyrazole-4-sulfonate (950 mg, 1.392 mmol), DMF (16 ml) and sodium azide (452 mg, 6.96 mmol). The vial was sealed and the reaction heated to 80° C. for 1 h. Upon completion, the reaction mixture was extract 3×IPA/CHCl$_3$ (1:3, v/v) and saturated NaHCO$_3$, and the combined organic layer dried and concentrated to afford the crude title compound, which was taken forward without further purification. LCMS (ESI): calculated for $C_{16}H_{18}F_2N_7O_5S$ [M-tBu+H]$^+$: 458, found: 458.

Step 6—Synthesis of tert-butyl ((2S,3R)-2-(aminomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate

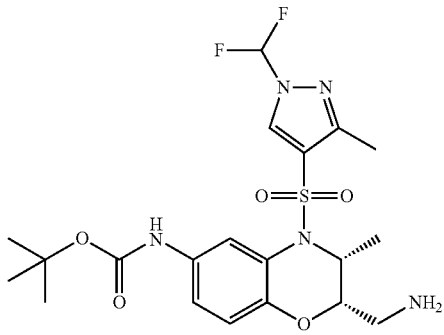 [SMILES: Cc1nn(C(F)F)cc1S(=O)(=O)N1c2cc(NC(=O)OC(C)(C)C)ccc2O[C@@H](CN)[C@H]1C]

To a flask equipped with a stir bar was added tert-butyl ((2S,3R)-2-(azidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate (715 mg, 1.392 mmol), ethyl acetate (21 ml), MeOH (7 ml) and 10% Pd/C (44.5 mg, 0.418 mmol) under a strong flow of nitrogen. The reaction flask was purged 3× with hydrogen and stirred under H$_2$ balloon atmosphere for 3 h. Upon completion, the reaction mixture was filtered through CELITE and the filtrate concentrate under vacuum. The crude product was taken forward without further purification. LCMS (ESI): calculated for $C_{16}H_{20}F_2N_5O_5S$ [M-tBu+H]$^+$: 432, found: 432.

Step 7—Synthesis tert-butyl ((2S,3R)-4-((1-(difluoromethyl)-3-methyl-1H-pyrazol-4-yl)sulfonyl)-3-methyl-2-(((N-methylsulfamoyl)amino)methyl)-3,4-dihydro-2H-benzo[b][1,4]oxazin-6-yl)carbamate

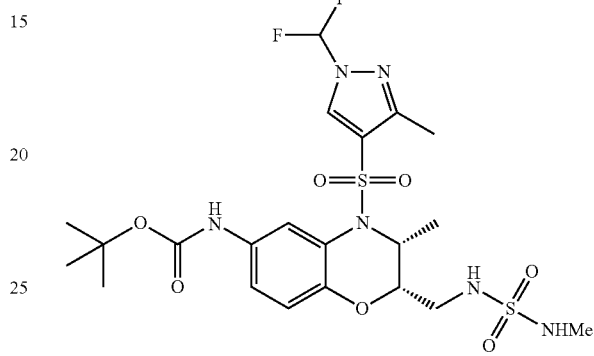

To a microwave vial equipped with a stir bar was added tert-butyl ((2S,3R)-2-(aminomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate (30 mg, 0.062 mmol), DIEA (0.043 mL, 0.246 mmol), and DCM (1 mL), followed by methylsulfamoyl chloride (15.95 mg, 0.123 mmol). The reaction was allowed to stir at room temperature for 1 h and then extracted with 3× ethyl acetate and saturated NaHCO$_3$. The combined organic layer was dried over magnesium sulfate, filtered and concentrated under reduced pressure to afford the title compound, which was taken forward without further purification. LCMS (ESI): calculated for $C_{17}H_{23}F_2N_6O_7S_2$ [M-tBu+H]$^+$: 525, found: 525.

Step 8—Synthesis of 1,1,1-trifluoro-2-methylpropan-2-yl ((2S,3R)-4-((1-(difluoromethyl)-3-methyl-1H-pyrazol-4-yl)sulfonyl)-3-methyl-2-(((N-methylsulfamoyl)amino)methyl)-3,4-dihydro-2H-benzo[b][1,4]oxazin-6-yl)carbamate

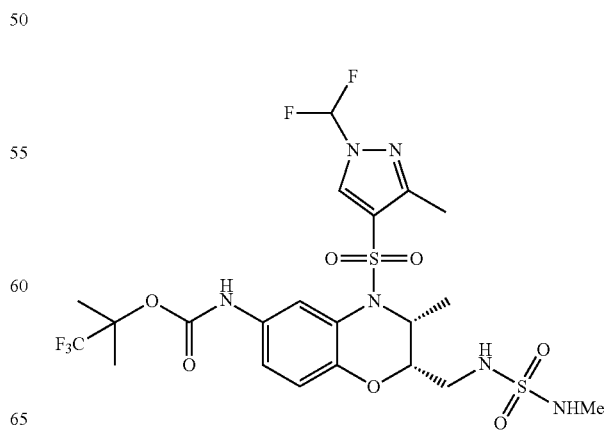

Tert-butyl ((2S,3R)-4-((1-(difluoromethyl)-3-methyl-1H-pyrazol-4-yl)sulfonyl)-3-methyl-2-(((N-methylsulfamoyl)amino)methyl)-3,4-dihydro-2H-benzo[b][1,4]oxazin-6-yl)carbamate (35.7 mg, 0.061 mmol) was stirred with 4M HCl in dioxane (0.461 ml, 1.845 mmol) for 1 h at room temperature. Upon completion, the reaction was concentrated and dried under vacuum to afford the intermediate aniline, which was next dissolved in DMF (1.0 mL) before the addition of 1,1,1-trifluoro-2-methylpropan-2-yl 1H-imidazole-1-carboxylate (27.3 mg, 0.123 mmol). The reaction mixture was heated to 80° C. for 1 h, then quenched by the addition of 3 drops of water. The resulting mixture was dissolved in 2 mL of DMSO, filtered and directly purified by reverse phase HPLC (MeCN/water using TFA buffer) to afford the desired product as a white solid. LCMS (ESI): calculated for $C_{21}H_{28}F_5N_6O_7S_2[M+H]^+$: 635, found: 635. $^1$H-NMR (CDCl$_3$, 400 MHz) δ 9.75 (s, 1H), 8.68 (s, 1H), 7.90 (m, 1H), 7.63 (t, 1H), 7.28 (m, 1H), 7.18 (m, 1H), 6.80 (m, 2H), 4.57 (m, 1H), 3.60 (m, 1H), 2.90-3.05 (m, 2H), 2.40 (m, 3H), 2.05 (s, 3H), 1.68 (s, 6H), 0.98 (m, 3H).

Example 86—Synthesis of 1,1,1-trifluoro-2-methylpropan-2-yl N-[(2S,3R)-2-[(1S)-1-[[(benzyloxy)carbonyl]amino]ethyl]-4-[(3,4-difluorobenzene)sulfonyl]-3-methyl-3,4-dihydro-2H-1,4-benzoxazin-6-yl]carbamate (Example 86)

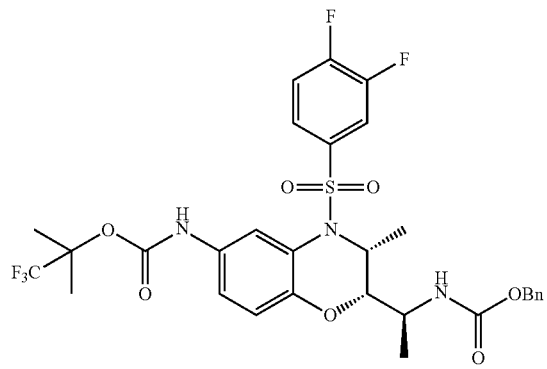 [SMILES: C[C@H](NC(=O)OCc1ccccc1)[C@@H]1Oc2ccc(NC(=O)OC(C)(C)C(F)(F)F)cc2N(S(=O)(=O)c2ccc(F)c(F)c2)[C@@H]1C]

Step 1—Synthesis of (2S,3S,4R)-4-((tert-butoxycarbonyl)amino)-3-((tert-butyldimethylsilyl)oxy)-2-methylpentanoic Acid

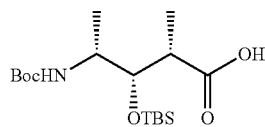

Into a 500-mL 3-necked round-bottom flask purged and maintained with an inert atmosphere of nitrogen, was placed a solution of known (*JACS*, 2003, 8218) (2S,3S,4R)-4-[[(tert-butoxy)carbonyl]amino]-3-hydroxy-2-methylpentanoic acid (9.88 g, 39.95 mmol, 1.00 equiv) in dichloromethane (200 mL), 2,6-dimethylpyridine (12.8 g, 119.46 mmol, 3.00 equiv). This was followed by the addition of TBSOTf (26.4 g, 100.00 mmol, 2.50 equiv) dropwise with stirring at −78° C. The resulting solution was stirred for 60 min at −78° C. The reaction was then quenched by the addition of water/ice. The resulting solution was extracted with 3×200 mL of ethyl acetate and the organic layers combined and concentrated under vacuum. The resulting crude intermediate was diluted with 150 mL of methanol. Then 50 mL of K$_2$CO$_3$ (0.5 M) was added and stirring was continued for an additional 60 min at room temperature. The pH value of the solution was adjusted to 2 with hydrogen chloride (1 N) and the resulting mixture was extracted with 3×300 mL of ethyl acetate. The organic layers were combined and concentrated under vacuum. The residue was applied onto a silica gel column with ethyl acetate/petroleum ether (1:1) to afford (2S,3S,4R)-4-[[(tert-butoxy)carbonyl]amino]-3-[(tert-butyldimethylsilyl)oxy]-2-methylpentanoic acid as a white solid. $^1$H-NMR (CDCl$_3$, 400 MHz) δ 4.48 (br s, 1H), 4.05 (m, 1H), 3.78 (m, 1H), 2.63 (m, 1H), 1.25-1.10 (m, 8H), 0.90 (m, 13H), 0.30 (m, 8H).

Step 2—Synthesis of benzyl tert-butyl ((2R,3S,4S)-3-((tert-butyldimethylsilyl)oxy)pentane-2,4-diyl)dicarbamate

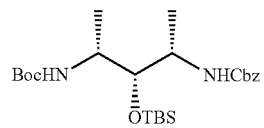 [SMILES: C[C@H](NC(=O)OCc1ccccc1)[C@H](O[Si](C)(C)C(C)(C)C)[C@@H](C)NC(=O)OC(C)(C)C]

Into a 50-mL round-bottom flask purged and maintained under an inert atmosphere of nitrogen, was placed a solution of (2S,3S,4R)-4-[[(tert-butoxy)carbonyl]amino]-3-[(tert-butyldimethylsilyl)oxy]-2-methylpentanoic acid (1.8 g, 4.98 mmol, 1.00 equiv) in toluene (20 mL), DPPA (1.38 g, 5.01 mmol, 1.00 equiv) and TEA (1.0 g, 9.88 mmol, 2.00 equiv). The resulting solution was stirred for 2 h at 60° C. Then phenylmethanol (1.62 g, 14.98 mmol, 3.00 equiv) and TEA (1.0 g, 9.88 mmol, 2.0 eq.) were added and stirring was continued for an additional 3 days at 90° C. The reaction was then quenched by the addition of water. The resulting mixture was extracted with 3×50 mL of ethyl acetate and the organic layers combined, washed with 2×30 mL of brine, dried and concentrated. The crude product was applied onto a silica gel column with ethyl acetate/petroleum ether (1:10) to afford tert-butyl N-[(2S,3S,4S)-4-[[(benzyloxy)carbonyl]amino]-3-[(tert-butyldimethylsilyl)oxy]pentan-2-yl]carbamate as a colorless oil, which was used in the next step without further purification.

Step 3—Synthesis of benzyl tert-butyl ((2R,3S,4S)-3-hydroxypentane-2,4-diyl)dicarbamate

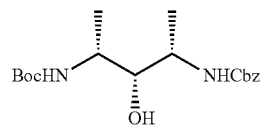

Into a 50-mL round-bottom flask, was placed a solution of tert-butyl N-[(2R,3S,4R)-4-[[(benzyloxy)carbonyl]amino]-3-[(tert-butyldimethylsilyl)oxy]pentan-2-yl]carbamate (1.3 g, 2.79 mmol, 1.00 equiv) in tetrahydrofuran (20 mL), TBAF (1.46 g, 5.58 mmol, 2.00 equiv). The resulting solution was stirred for 2 h at room temperature, then concentrated under vacuum. The crude product was applied onto a silica gel column with ethyl acetate/petroleum ether (1:2) to afford tert-butyl N-[(2S,3S,4R)-4-[[(benzyloxy)carbonyl]amino]-3-hydroxypentan-2-yl]carbamate as a colorless oil, which was used in the next step without further purification.

Step 4—Synthesis of benzyl tert-butyl ((2R,3S,4S)-3-(2-bromo-4-nitrophenoxy)pentane-2,4-diyl)dicarbamate

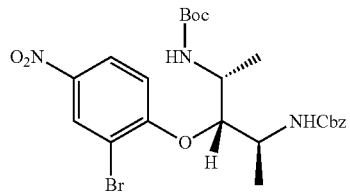 [SMILES: C[C@H](NC(=O)OCc1ccccc1)[C@H](Oc1ccc([N+](=O)[O-])cc1Br)[C@@H](C)NC(=O)OC(C)(C)C]

Into a 50-mL 3-necked round-bottom flask, was placed tert-butyl N-[(2R,3S,4S)-4-[[(benzyloxy)carbonyl]amino]-3-hydroxypentan-2-yl]carbamate (950 mg, 2.70 mmol, 1.00 equiv), followed by the addition of sodium hydride (324 mg, 8.10 mmol, 3.00 equiv) in several batches at 0° C. To this was added tetrahydrofuran (20 mL) and 2-bromo-1-fluoro-4-nitrobenzene (768 mg, 3.49 mmol, 1.30 equiv). The resulting solution was stirred for 30 min at 0° C. and at room temperature for 12 h. The reaction was then quenched by the addition of 20 mL of water/ice and the resulting mixture was extracted with 3×30 mL of ethyl acetate. The crude product was applied onto a silica gel column with ethyl acetate/petroleum ether (1:20-1:1) to afford tert-butyl N-[(2R,3S,4S)-4-[[(benzyloxy)carbonyl]amino]-3-(2-bromo-4-nitrophenoxy)pentan-2-yl]carbamate as a yellow solid.

Step 5—Synthesis of benzyl ((2S,3R,4R)-4-amino-3-(2-bromo-4-nitrophenoxy)pentan-2-yl)carbamate

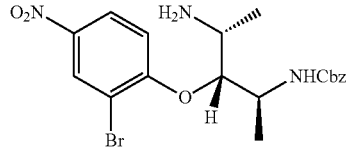 [SMILES: C[C@H](NC(=O)OCc1ccccc1)[C@H](Oc1ccc([N+](=O)[O-])cc1Br)[C@@H](C)N]

Into a 25-mL round-bottom flask was placed a solution of tert-butyl N-[(2R,3S,4S)-4-[[(benzyloxy)carbonyl]amino]-3-(2-bromo-4-nitrophenoxy)pentan-2-yl]carbamate (450 mg, 0.81 mmol, 1.00 equiv) in dichloromethane (10 mL) and CF$_3$COOH (3 mL). The resulting solution was stirred for 2 h at room temperature, then quenched with saturated NaHCO$_3$ (aq.). The resulting mixture was extracted with DCM (20 mL×3) and the combined organic layers concentrated under vacuum to afford benzyl N-[(2S,3R,4R)-4-amino-3-(2-bromo-4-nitrophenoxy)pentan-2-yl]carbamate as a yellow solid, which was carried forward without further purification.

Step 6—Synthesis of benzyl ((2S,3S,4R)-3-(2-bromo-4-nitrophenoxy)-4-(3,4-difluorophenylsulfonamido)pentan-2-yl)carbamate

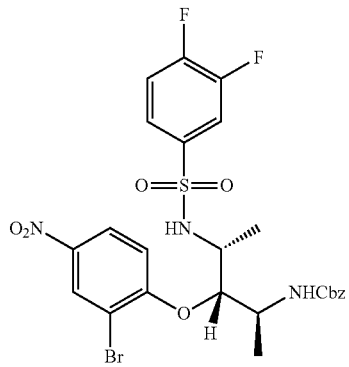 [SMILES: C[C@H](NC(=O)OCc1ccccc1)[C@H](Oc1ccc([N+](=O)[O-])cc1Br)[C@@H](C)NS(=O)(=O)c1ccc(F)c(F)c1]

Into a 25-mL round-bottom flask was placed benzyl N-[(2S,3R,4R)-4-amino-3-(2-bromo-4-nitrophenoxy)pentan-2-yl]carbamate (350 mg, 0.77 mmol, 1.00 equiv), TEA (233 mg, 2.30 mmol, 3.00 equiv), 4-dimethylaminopyridine (9.4 mg, 0.08 mmol, 0.10 equiv) and 3,4-difluorobenzene-1-sulfonyl chloride (246 mg, 1.16 mmol, 1.50 equiv). The resulting mixture was stirred overnight at room temperature, then concentrated under vacuum. The crude product was applied onto a silica gel column with ethyl acetate/petroleum ether (1:20-100:1) to afford benzyl N-[(2S,3S,4R)-3-(2-bromo-4-nitrophenoxy)-4-[(3,4-difluorobenzene)sulfonamido]pentan-2-yl]carbamate as a yellow solid.

Step 7—Synthesis of benzyl ((S)-1-((2S,3R)-4-((3,4-difluorophenyl)sulfonyl)-3-methyl-6-nitro-3,4-dihydro-2H-benzo[b][1,4]oxazin-2-yl)ethyl)carbamate

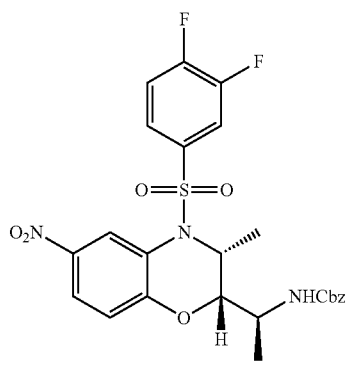

Into a 25-mL round-bottom flask was placed a solution of benzyl N-[(2S,3S,4R)-3-(2-bromo-4-nitrophenoxy)-4-[(3,4-difluorobenzene)sulfonamido]pentan-2-yl]carbamate (320 mg, 0.51 mmol, 1.00 equiv) in MeCN (10 mL), CuI (10 mg, 0.051 mmol, 0.1 equiv), potassium carbonate (140.8 mg, 1.02 mmol, 2.00 equiv) and 1-N,2-N-dimethylcyclohexane-1,2-diamine (14 mg, 0.1 mmol, 0.2 equiv). The resulting solution was stirred overnight at 70° C., then concentrated under vacuum. The crude product was applied onto a silica gel column with ethyl acetate/petroleum ether (1:20-100:1) to afford benzyl N-[(1S)-1-[(2S,3R)-4-[(3,4-difluorobenzene)sulfonyl]-3-methyl-6-nitro-3,4-dihydro-2H-1,4-benzoxazin-2-yl]ethyl]carbamate as a yellow solid, which was used in the next step without further purification.

Step 8—Synthesis of benzyl ((S)-1-((2S,3R)-6-amino-4-((3,4-difluorophenyl)sulfonyl)-3-methyl-3,4-dihydro-2H-benzo[b][1,4]oxazin-2-yl)ethyl)carbamate

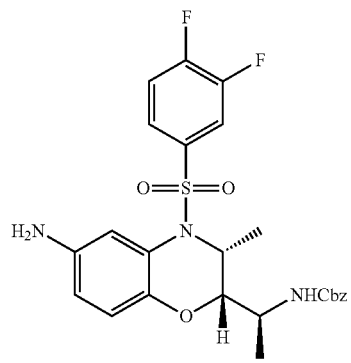 [SMILES: C[C@H](NC(=O)OCc1ccccc1)[C@@H]1Oc2ccc([N+](=O)[O-])cc2N(S(=O)(=O)c2ccc(F)c(F)c2)[C@@H]1C]

Into a 25-mL round-bottom flask was placed benzyl ((S)-1-((2S,3R)-4-((3,4-difluorophenyl)sulfonyl)-3-methyl-6-nitro-3,4-dihydro-2H-benzo[b][1,4]oxazin-2-yl)ethyl)carbamate (110 mg, 0.19 mmol, 1.00 equiv), Raney-Ni (80 mg), methanol (5 mL) and hydrazine hydrate (0.2 mL). The resulting solution was stirred at room temperature for 20 min, then the solids were filtered out and the filtrate concentrated under vacuum to afford the crude title compound as a yellow solid, which was used in the next step without further purification.

Step 9—Synthesis of 1,1,1-trifluoro-2-methylpropan-2-yl N-[(2S,3R)-2-[(1S)-1-[[(benzyloxy)carbonyl]amino]ethyl]-4-[(3,4-difluorobenzene)sulfonyl]-3-methyl-3,4-dihydro-2H-1,4-benzoxazin-6-yl]carbamate

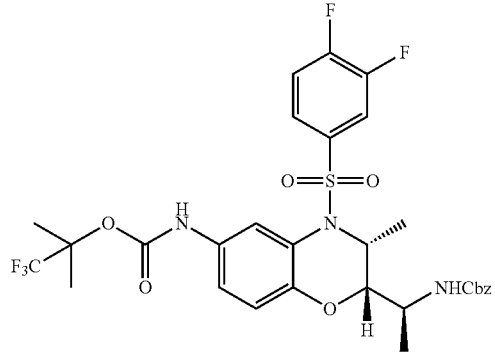 [SMILES: C[C@H](NC(=O)OCc1ccccc1)[C@@H]1Oc2ccc(NC(=O)OC(C)(C)C(F)(F)F)cc2N(S(=O)(=O)c2ccc(F)c(F)c2)[C@@H]1C]

Into a 25-mL round-bottom flask was placed benzyl N-[(1S)-1-[(2S,3R)-6-amino-4-[(3,4-difluorobenzene)sulfonyl]-3-methyl-3,4-dihydro-2H-1,4-benzoxazin-2-yl]ethyl] carbamate (130 mg, 0.25 mmol, 1.00 equiv), TEA (25 mg, 0.25 mmol, 1.00 equiv) and 1,1,1-trifluoro-2-methylpropan-2-yl (4-nitrophenyl) carbonate (60 mg, 0.25 mmol, 1.0 eq.) in THF (5 mL). The resulting solution was stirred for 6 days at 60° C., then concentrated under vacuum. The crude product was purified by prep-HPLC (MeCN/water using TFA buffer) to afford 1,1,1-trifluoro-2-methylpropan-2-yl N-[(2S,3R)-2-[(1S)-1-[[(benzyloxy)carbonyl]amino]ethyl]-4-[(3,4-difluorobenzene)sulfonyl]-3-methyl-3,4-dihydro-2H-1,4-benzoxazin-6-yl]carbamate as a white solid. $^1$H-NMR (CD$_3$OD, 400 MHz) δ 8.02 (s, 1H), 7.77 (m, 1H), 7.58 (m, 1H), 7.45-7.32 (m, 6H), 7.08 (m, 1H), 6.80 (m, 1H), 5.20 (m, 2H), 4.68 (m, 1H), 3.65 (m, 1H), 3.27 (m, 1H), 1.79 (s, 6H), 1.26 (m, 3H), 1.13 (m, 3H).

Example 87—Preparation of (R and S)-1,1,1-trifluoro-2-methylpropan-2-yl (3-(acetamidomethyl)-4-((4-fluorophenyl)sulfonyl)-3,4-dihydro-2H-benzo[b][1,4]oxazin-6-yl)carbamate (Example 87)

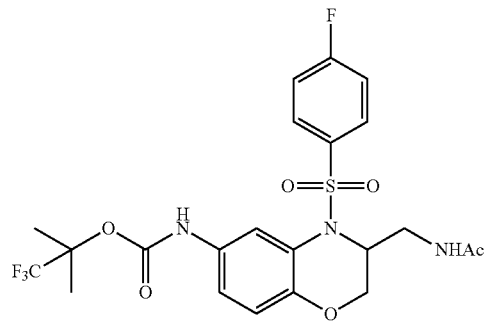 [SMILES: CC(=O)NCC1COc2ccc(NC(=O)OC(C)(C)C(F)(F)F)cc2N1S(=O)(=O)c1ccc(F)cc1]

Step 1—Preparation of (R and S)-4-((4-fluorophenyl)sulfonyl)-6-((((1,1,1-trifluoro-2-methylpropan-2-yl)oxy)carbonyl)amino)-3,4-dihydro-2H-benzo[b][1,4]oxazine-3-carboxylic Acid

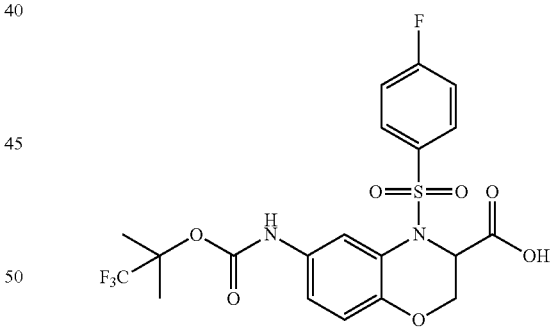

A mixture of (R and S)-1,1,1-trifluoro-2-methylpropan-2-yl (4-((4-fluorophenyl)sulfonyl)-3-(hydroxymethyl)-3,4-dihydro-2H-benzo[b][1,4]oxazin-6-yl)carbamate (310 mg, 0.63 mmol), PhI(OAc)$_2$ (507 mg, 1.57 mmol) and TEMPO (196 mg, 1.26 mmol) in CH$_3$CN/H$_2$O (5 mL/5 mL) was stirred at room temperature overnight. The reaction was diluted with water, extracted with EtOAc and the combined organic layers were washed with brine, dried over Na$_2$SO$_4$ and concentrated. The crude product was purified by silica gel column chromatography (DCM:MeOH=10:1) to afford the title product as a yellow oil. LCMS (ESI): calculated for C$_{20}$H$_{19}$F$_4$N$_2$O$_7$S [M+H]$^+$: 507, found: 507; $^1$H NMR (400 MHz, CDCl$_3$) δ 7.80-7.84 (2H, m), 7.16 (2H, t, J=8.4 Hz), 7.07 (1H, d, J=8.0 Hz), 6.77 (1H, d, J=8.4 Hz), 6.67 (1H, brs), 5.20 (1H, brs), 4.63 (1H, d, J=10.0 Hz), 3.59 (3H, dd, J=11.2, 2.5 Hz), 1.75 (6H, s).

Step 2—Preparation of (R and S)-1,1,1-trifluoro-2-methylpropan-2-yl (3-carbamoyl-4-((4-fluorophenyl)sulfonyl)-3,4-dihydro-2H-benzo[b][1,4]oxazin-6-yl)carbamate

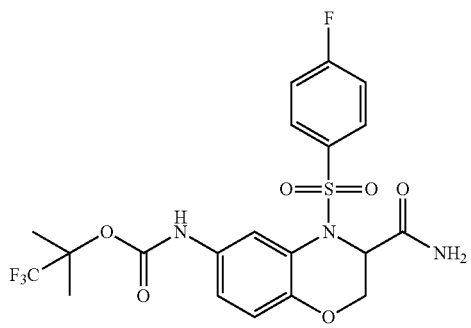 [SMILES: CC(C)(OC(=O)Nc1ccc2c(c1)N(S(=O)(=O)c1ccc(F)cc1)C(C(N)=O)CO2)C(F)(F)F]

A mixture of (R and S)-4-((4-fluorophenyl)sulfonyl)-6-(((((1,1,1-trifluoro-2-methylpropan-2-yl)oxy)carbonyl)amino)-3,4-dihydro-2H-benzo[b][1,4]oxazine-3-carboxylic acid (15 mg, 0.03 mmol), HATU (14 mg, 0.036 mmol), NH$_4$Cl (2 mg, 0.036 mmol) and DIPEA (11 mg, 0.09 mmol) in DMF (1 mL) was stirred at room temperature overnight. The reaction was diluted with water, extracted 3× with EtOAc and the combined extracts were washed with brine, dried over Na$_2$SO$_4$ and concentrated. The crude product was purified by prep-HPLC (petroleum ether:EtOAc=1.5:1) to afford the title product as a clear oil. LCMS (ESI): calculated for C$_{20}$H$_{20}$F$_4$N$_3$O$_6$S [M+H]$^+$: 506, found: 506; $^1$H NMR (400 MHz, CDCl$_3$) δ 8.03 (1H, br s), 7.68 (2H, dd, J=8.8, 5.2 Hz), 7.17 (3H, t, J=8.4 Hz), 6.80 (1H, d, J=9.2 Hz), 6.74 (1H, brs), 6.45 (1H, brs), 5.55 (1H, brs), 4.89 (1H, brs), 4.71 (1H, dd, J=11.2, 1.6 Hz), 3.10 (1H, dd, J=11.2, 3.2 Hz), 1.78 (6H, s).

Step 3—Preparation of (R and S)-1,1,1-trifluoro-2-methylpropan-2-yl (3-(aminomethyl)-4-((4-fluorophenyl)sulfonyl)-3,4-dihydro-2H-benzo[b][1,4]oxazin-6-yl)carbamate

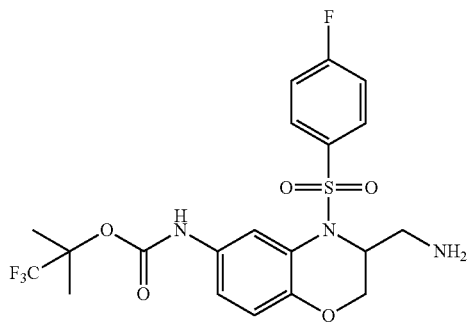 [SMILES: CC(C)(OC(=O)Nc1ccc2c(c1)N(S(=O)(=O)c1ccc(F)cc1)C(CN)CO2)C(F)(F)F]

To a solution of (R and S)-1,1,1-trifluoro-2-methylpropan-2-yl (3-carbamoyl-4-((4-fluorophenyl)sulfonyl)-3,4-dihydro-2H-benzo[b][1,4]oxazin-6-yl)carbamate (50 mg, 0.10 mmol) in THF (5 mL) was added dropwise BH$_3$.SMe$_2$(75 mg, 0.99 mmol) at 0° C. The reaction mixture was stirred at 75° C. for 48 h under N$_2$ atmosphere. Upon completion, the reaction was diluted with water, extracted 3× with EtOAc and the combined organic layers were washed with brine, dried over Na$_2$SO$_4$ and concentrated. The crude product was purified by prep-TLC (petroleum ether:EtOAc=1.5:1) to afford the title product as a clear oil. LCMS (ESI): calculated for C$_{20}$H$_{22}$F$_4$N$_3$O$_5$S [M+H]$^+$: 492, found: 492; $^1$H NMR (400 MHz, CDCl$_3$) δ 7.79 (1H, d, J=2.4 Hz), 7.60 (2H, dd, J=8.8, 4.8 Hz, 2H), 7.38 (1H, brs), 7.33 (1H, d, J=7.6 Hz), 7.10 (2H, t, J=8.4 Hz), 6.68 (1H, d, J=9.2 Hz, 1H), 4.66 (1H, d, J=8.4 Hz), 4.05 (1H, d, J=11.6 Hz), 2.92-3.16 (3H, m), 1.73 (6H, d, J=3.2 Hz).

Step 4—Preparation of (R and S)-1,1,1-trifluoro-2-methylpropan-2-yl (3-(acetamidomethyl)-4-((4-fluorophenyl)sulfonyl)-3,4-dihydro-2H-benzo[b][1,4]oxazin-6-yl)carbamate

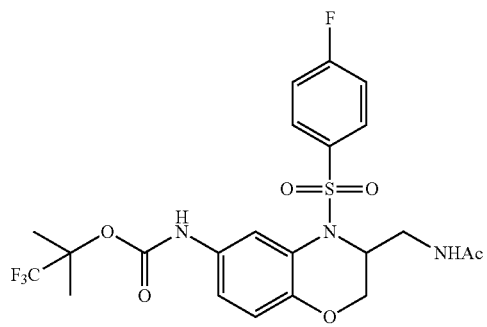 [SMILES: CC(=O)NCC1COc2ccc(NC(=O)OC(C)(C)C(F)(F)F)cc2N1S(=O)(=O)c1ccc(F)cc1]

A mixture of (R and S)-1,1,1-trifluoro-2-methylpropan-2-yl(3-(aminomethyl)-4-((4-fluorophenyl) sulfonyl)-3,4-dihydro-2H-benzo[b][1,4]oxazin-6-yl)carbamate (10 mg, 0.02 mmol), Et$_3$N (21 mg, 0.20 mmol) and AcCl (8 mg, 0.10 mmol) in DCM (3 mL) was stirred at 0° C. for 1 h. The reaction was then diluted with water and extracted 3× with EtOAc. The organic layers were washed with brine, dried over Na$_2$SO$_4$ and concentrated. The crude product was purified by prep-TLC (petroleum ether:EtOAc=1:1) to afford the title product as a yellow solid. LCMS (ESI): calculated for C$_{22}$H$_{24}$F$_4$N$_3$O$_6$S [M+H]$^+$: 534, found: 534; $^1$H NMR (400 MHz, CDCl$_3$) δ 7.94 (1H, brs), 7.66 (2H, dd, J=8.8, 5.2 Hz), 7.08-7.22 (3H, m), 6.78 (1H, d, J=9.2 Hz), 6.70 (1H, brs), 5.93 (1H, brs), 4.43 (1H, d, J=10.0 Hz), 3.99 (1H, d, J=11.2 Hz), 3.58 (1H, dd, J=14.0, 7.2 Hz), 3.12 (1H, dd, J=11.6, 3.2 Hz), 2.95 (1H, ddd, J=14.4, 10.0, 4.4 Hz), 2.05 (3H, s), 1.78 (6H, s).

Example 88—Preparation of (R)-1,1,1-trifluoro-2-methylpropan-2-yl(2-((1-carbamoylcyclopropyl)methyl)-4-((3-chloro-1-ethyl-1H-pyrazol-4-yl)sulfonyl)-3,4-dihydro-2H-benzo[b][1,4]oxazin-6-yl)carbamate and (S)-1,1,1-trifluoro-2-methylpropan-2-yl(2-((1-carbamoylcyclopropyl)methyl)-4-((3-chloro-1-ethyl-1H-pyrazol-4-yl)sulfonyl)-3,4-dihydro-2H-benzo[b][1,4]oxazin-6-yl)carbamate (Examples 88A and 88B)

Step 1—Preparation of (R)-1,1,1-trifluoro-2-methylpropan-2-yl(2-((1-carbamoylcyclopropyl)methyl)-4-tosyl-3,4-dihydro-2H-benzo[b][1,4]oxazin-6-yl)carbamate

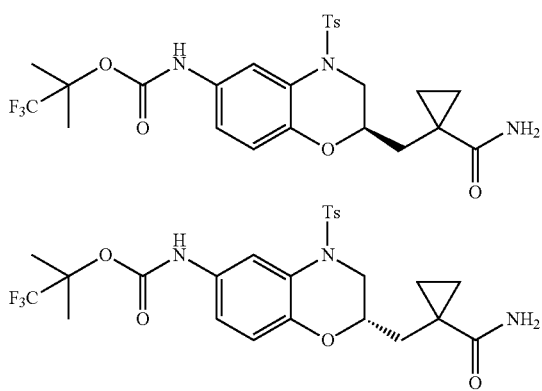

To a solution of (R or S)-1,1,1-trifluoro-2-methylpropan-2-yl (2-((1-cyanocyclopropyl)methyl)-4-tosyl-3,4-dihydro-2H-benzo[b][1,4]oxazin-6-yl)carbamate (Isomer 1 from Example 93, Step 5, 150 mg, 0.279 mmol) in DMSO (2 mL) was added $K_2CO_3$ (77 mg, 0.558 mmol) and 30% $H_2O_2$ (0.049 ml, 0.558 mmol) at 25° C. under nitrogen. The reaction mixture was stirred at 25° C. for 18 h, then diluted with ethyl acetate (40 mL) and washed with brine (15 mL×3). The combined organic layers were dried over $Na_2SO_4$ and evaporated to afford the title compound (Isomer 1 from Step 1) as yellow oil.

The other enantiomer (Isomer 2 from Step 1) was prepared using a similar procedure. Both enantiomers have the same analytical data: LCMS (ESI) calculated for $C_{25}H_{29}F_3N_3O_6S$ [M+H]$^+$: 556.1, found: 556.2.

Step 2—Preparation of (R)-1,1,1-trifluoro-2-methylpropan-2-yl(2-((1-carbamoylcyclopropyl)methyl)-3,4-dihydro-2H-benzo[b][1,4]oxazin-6-yl)carbamate and (S)-1,1,1-trifluoro-2-methylpropan-2-yl(2-((1-carbamoylcyclopropyl)methyl)-3,4-dihydro-2H-benzo[b][1,4]oxazin-6-yl)carbamate

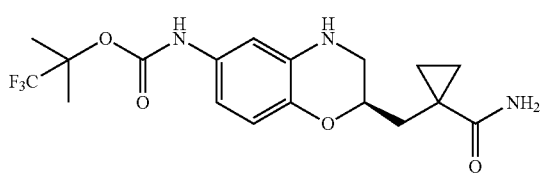

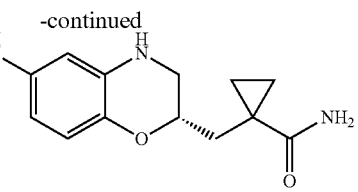

To a solution of (R or S)-1,1,1-trifluoro-2-methylpropan-2-yl(2-((1-carbamoylcyclopropyl)methyl)-4-tosyl-3,4-dihydro-2H-benzo[b][1,4]oxazin-6-yl)carbamate (Isomer 1 from Step 1, 150 mg, 0.270 mmol)) in MeOH (15 mL) was added magnesium (131 mg, 5.40 mmol) in one portion at 25° C. under nitrogen. The reaction was stirred at 25° C. for 18 hours, then quenched with saturated $NH_4Cl$ solution (60 mL) and extracted with EtOAc (3×50 mL). The organic layers were combined, dried over $Na_2SO_4$, filtered and the filtrate concentrated in vacuo. The crude product was purified by prep-TLC (petroleum ether:EtOAc=1:2) to afford the title compound (Isomer 1 from Step 2) as a colorless oil.

The other enantiomer (Isomer 2 from Step 2) was prepared using a similar procedure from Isomer 2 from Step 1. Both enantiomers have the same analytical data: LCMS (ESI) calculated for $C_{18}H_{23}F_3N_3O_4$ [M+H]$^+$: 402.1, found: 402.3.

Step 3—Preparation of (R)-1,1,1-trifluoro-2-methylpropan-2-yl(2-((1-carbamoylcyclopropyl)methyl)-4-((3-chloro-1-ethyl-1H-pyrazol-4-yl)sulfonyl)-3,4-dihydro-2H-benzo[b][1,4]oxazin-6-yl)carbamate and (S)-1,1,1-trifluoro-2-methylpropan-2-yl(2-((1-carbamoylcyclopropyl)methyl)-4-((3-chloro-1-ethyl-1H-pyrazol-4-yl)sulfonyl)-3,4-dihydro-2H-benzo[b][1,4]oxazin-6-yl)carbamate

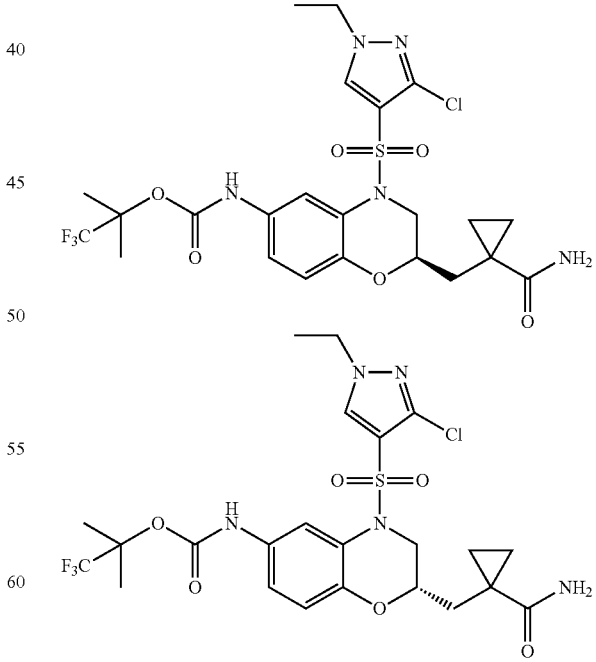

To a solution of (R or S)-1,1,1-trifluoro-2-methylpropan-2-yl(2-((1-carbamoylcyclopropyl)methyl)-3,4-dihydro-2H-benzo[b][1,4]oxazin-6-yl)carbamate (Isomer 1 from Step 2, 40 mg, 0.100 mmol) in pyridine (2 mL) and THF (2 mL) was added 3-chloro-1-ethyl-1H-pyrazole-4-sulfonyl chloride (45.7 mg, 0.199 mmol). The reaction was stirred at 25° C. for 18 h, then concentrated. The title compound (Isomer 1 from Step 3, Example 88A) was obtained by pre-HPLC (MeCN/water using TFA buffer) as a white solid.

The other enantiomer (Isomer 2 from Step 3, Example 88B) was prepared using a similar procedure from Isomer 2 from Step 2. Both enantiomers have the same analytical data: LCMS (ESI) calculated for $C_{23}H_{28}ClF_3N_5O_6S$ [M+H]$^+$: 594.1, found: 594.1; $^1$H-NMR (CDCl$_3$, 400 MHz) δ 8.10 (1H, s), 7.86 (1H, s), 6.84-6.86 (1H, m), 6.74-6.77 (2H, m), 4.36 (1H, d, J=12.0 Hz), 4.05-4.11 (3H, m,), 3.34-3.40 (1H, m), 2.07-2.13 (2H, m), 1.73 (6H, s), 1.43-1.47 (3H, m), 1.23-1.29 (2H, m), 0.77-0.82 (2H, m).

Example 89—Preparation of 1,1,1-trifluoro-2-methylpropan-2-yl ((S)-2-((R)-3-amino-2-cyclopropyl-3-oxopropyl)-4-((3-chloro-1-ethyl-1H-pyrazol-4-yl)sulfonyl)-3,4-dihydro-2H-benzo[b][1,4]oxazin-6-yl)carbamate and 1,1,1-trifluoro-2-methylpropan-2-yl ((S)-2-((S)-3-amino-2-cyclopropyl-3-oxopropyl)-4-((3-chloro-1-ethyl-1H-pyrazol-4-yl)sulfonyl)-3,4-dihydro-2H-benzo[b][1,4]oxazin-6-yl)carbamate (Examples 89A and 89B)

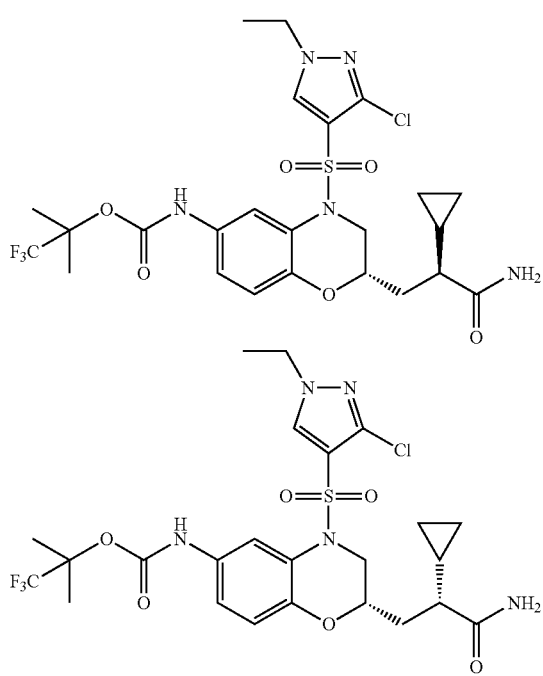

Step 1—Preparation of (S)-methyl 2-(4-benzyl-6-((tert-butoxycarbonyl)amino)-3,4-dihydro-2H-benzo[b][1,4]oxazin-2-yl)acetate

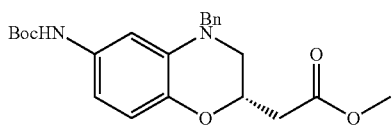 [SMILES: COC(=O)C[C@H]1CN(Cc2ccccc2)c2cc(NC(=O)OC(C)(C)C)ccc2O1]

To a solution of (S)-methyl 2-(6-((tert-butoxycarbonyl)amino)-3,4-dihydro-2H-benzo[b][1,4]oxazin-2-yl)acetate (1.3 g, 4.03 mmol) in dimethyl formamide (7 mL) was added potassium carbonate (0.836 g, 6.05 mmol) and (bromomethyl)benzene (1.035 g, 6.05 mmol). The resulting mixture was stirred at 20° C. for 18 h, then diluted with water (150 mL) and extracted with ethyl acetate (3×100 mL). The separated organic layers were washed with brine, dried with Na$_2$SO$_4$ and concentrated under reduced pressure to give the crude product which was purified by flash column chromatography (petroleum ether:ethyl acetate=10:1 to 5:1) to give the title compound as a white solid. LCMS (ESI) calculated for $C_{23}H_{29}N_2O_5$ [M+H]$^+$: 413, found: 413. $^1$H NMR (400 MHz, CDCl3) 7.28-7.38 (5H, m), 6.78 (1H, br s), 6.72 (1H, d, J=8.61 Hz), 6.59 (1H, d, J=7.43 Hz), 6.24 (1H, brs), 4.54-4.60 (1H, m), 4.37-4.49 (2H, m), 3.69 (3H, s), 3.33 (1H, dd, J=1.96, 11.74 Hz), 3.12 (1H, dd, J=6.85, 11.54 Hz), 2.76 (1H, dd, J=6.85, 15.85 Hz), 2.57 (1H, dd, J=6.26, 16.04 Hz), 1.46 (9H, s).

Step 2—Preparation of (S)-2-(4-benzyl-6-((tert-butoxycarbonyl)amino)-3,4-dihydro-2H-benzo[b][1,4]oxazin-2-yl)acetic Acid

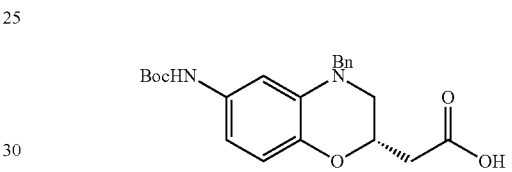

To a solution of (S)-methyl 2-(4-benzyl-6-((tert-butoxycarbonyl)amino)-3,4-dihydro-2H-benzo[b][1,4]oxazin-2-yl)acetate (2.6 g, 6.30 mmol) in dioxane (26 mL) and water (26 ml) was added lithium hydroxide (0.226 g, 9.46 mmol), and the resulting mixture was stirred at 20° C. for 18 h. The reaction was diluted with water (100 mL), extracted with ethyl acetate (50 mL×3) and the aqueous layer was acidified with hydrochloric acid (1M, 10 mL) to pH=3. The mixture was extracted with ethyl acetate (100 mL) and the combined organic layers were dried (Na$_2$SO$_4$), filtered and concentrated under reduced pressure to give the crude title compound as a yellow solid, which was used in next step without further purification. LCMS (ESI) calculated for $C_{22}H_{27}N_2O_5$ [M+H]$^+$: 399, found: 399. $^1$H NMR (400 MHz, Methanol-d4) 7.31-7.35 (5H, m), 7.23-7.26 (1H, m), 6.88 (1H, br s), 6.62-6.65 (1H, m), 6.55-6.60 (1H, m), 4.43-4.50 (3H, m), 3.35-3.39 (1H, m), 3.11 (1H, dd, J=7.28, 11.80 Hz), 2.62 (2H, t, J=6.27 Hz), 1.46 (9H, s).

Step 3—Preparation of (S)-tert-butyl (4-benzyl-2-(2-(methoxy(methyl)amino)-2-oxoethyl)-3,4-dihydro-2H-benzo[b][1,4]oxazin-6-yl)carbamate

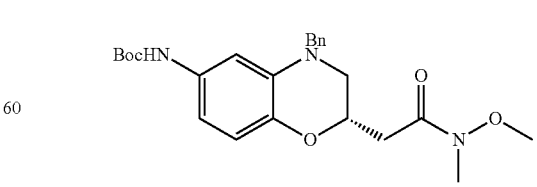

To a solution of (S)-2-(4-benzyl-6-((tert-butoxycarbonyl)amino)-3,4-dihydro-2H-benzo[b][1,4]oxazin-2-yl)acetic acid (2 g, 5.02 mmol) in dichloromethane (20 mL) were added triethylamine (3.50 ml, 25.10 mmol) and HATU (2.290 g, 6.02 mmol), and the resulting mixture was stirred at 20° C. for 30 min, followed by the addition of N,O-dimethylhydroxylamine (1.533 g, 25.10 mmol). The reaction was stirred at 20° C. for 5 minutes, then concentrated under reduced pressure to give the crude product. Flash column chromatography purification (petroleum ether:ethyl acetate=3:1 to 1:1) afforded the title compound as a yellow oil. LCMS (ESI) calculated for $C_{24}H_{32}N_3O_5$ [M+H]$^+$: 442, found: 442. $^1$H NMR (400 MHz, CDCl$_3$) 7.25-7.33 (5H, m), 6.70 (2H, d, J=8.61 Hz), 6.60 (1H, d, J=7.83 Hz), 6.24 (1H, brs), 4.64 (1H, dd, J=1.76, 6.46 Hz), 4.37-4.51 (2H, m), 3.67 (3H, s), 3.41 (1H, dd, J=1.96, 11.74 Hz), 3.21-3.24 (2H, m), 3.01 (3H, s), 2.61 (1H, dd, J=6.46, 15.85 Hz), 1.46 (9H, s), 1.36 (5H, t, J=7.24 Hz).

Step 4—Preparation of (S)-tert-butyl (4-benzyl-2-(2-cyclopropyl-2-oxoethyl)-3,4-dihydro-2H-benzo[b][1,4]oxazin-6-yl)carbamate

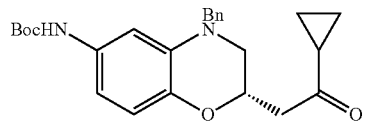 [SMILES: CC(C)(C)OC(=O)Nc1ccc2c(c1)N(Cc1ccccc1)C[C@H](CC(=O)C1CC1)O2]

To a solution of (S)-tert-butyl (4-benzyl-2-(2-(methoxy(methyl)amino)-2-oxoethyl)-3,4-dihydro-2H-benzo[b][1,4]oxazin-6-yl)carbamate (6 g, 13.59 mmol) in THF (30 mL) was added dropwise cyclopropylmagnesium bromide (272 ml, 136 mmol) at 0° C. under N$_2$. The reaction was stirred for 4 h at 0° C., then quenched with sat. NH$_4$Cl aqueous (50 mL). The biphasic mixture was extracted with EtOAc (50 mL×3), dried over Na$_2$SO$_4$ and concentrated to afford the crude title compound as a yellow solid, which was used in next step without further purification. LCMS (ESI) calculated for $C_{25}H_{31}N_2O_4$ [M+H]$^+$: 423, found: 423. $^1$HNMR (400 MHz, CDCl$_3$) δ 7.28-7.34 (5H, m), 6.76 (1H, br s), 6.71 (1H, d, J=8.8 Hz), 6.60 (1H, d, J=6.8 Hz), 6.21 (1H, br s), 4.62 (1H, d, J=0.8 Hz), 4.43 (2H, q, J=8.0 Hz), 3.33-3.36 (1H, m), 3.01-3.13 (2H, m), 2.77-2.79 (1H, m), 1.93-1.96 (1H, m), 1.47 (9H, s), 1.03-1.06 (2H, m), 0.88-0.90 (2H, m).

Step 5—Preparation of tert-butyl ((S)-4-benzyl-2-((S and R)-2-cyano-2-cyclopropylethyl)-3,4-dihydro-2H-benzo[b][1,4]oxazin-6-yl)carbamate

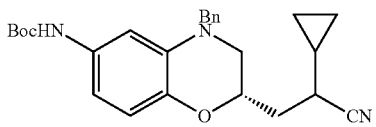 [SMILES: CC(C)(C)OC(=O)Nc1ccc2c(c1)N(Cc1ccccc1)C[C@H](CC(C#N)C1CC1)O2]

To a solution of (S)-tert-butyl (4-benzyl-2-(2-cyclopropyl-2-oxoethyl)-3,4-dihydro-2H-benzo[b][1,4]oxazin-6-yl)carbamate (4.5 g, 10.65 mmol) and 1-((isocyanomethyl)sulfonyl)-4-methylbenzene (4.16 g, 21.30 mmol) in DME (150 mL) and ethanol (5 mL) was added NaOH (1.278 g, 32.0 mmol) in portions under N$_2$ at 0° C. The reaction was stirred at 30° C. for 18 h, then diluted with DCM (100 mL), washed with water (60 mL×2) and brine and dried over Na$_2$SO$_4$. After concentration, the crude product was purified by silica gel column chromatography (petroleum ether:EtOAc=6:1) to afford the title compound as a yellow oil. LCMS (ESI) calculated for $C_{26}H_{32}N_3O_3$ [M+H]$^+$: 434, found: 434. $^1$HNMR (400 MHz, CDCl$_3$) δ 7.29-7.36 (5H, m), 6.81 (1H, d, J=7.2 Hz), 6.72 (1H, d, J=7.2 Hz), 6.60 (1H, d, J=7.2 Hz), 6.23 (1H, br s), 4.42-4.45 (2H, m), 4.33-4.38 (1H, m), 3.24-3.29 (1H, m), 3.08-3.13 (2H, m), 2.55-2.65 (1H, m), 2.41-2.47 (1H, m), 1.85-2.05 (3H, m), 1.47 (9H, s), 0.63-0.66 (2H, m), 0.41-0.45 (2H, m).

Step 6—Preparation of (R and S)-3-((S)-6-amino-4-benzyl-3,4-dihydro-2H-benzo[b][1,4]oxazin-2-yl)-2-cyclopropylpropanamide

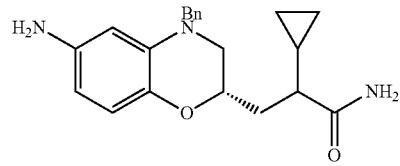 [SMILES: NC(=O)C(C[C@H]1CN(Cc2ccccc2)c2cc(N)ccc2O1)C1CC1]

To MeOH (10 mL) at 0° C. was added slowly sulfurous dichloride (3 mL, 2.076 mmol) and the mixture was stirred at 0° C. for 30 mins, followed by the addition of tert-butyl ((S)-4-benzyl-2-((S and R)-2-cyano-2-cyclopropylethyl)-3,4-dihydro-2H-benzo[b][1,4]oxazin-6-yl)carbamate (900 mg, 2.076 mmol). The reaction was stirred at 70° C. for 18 h, then quenched with 5 mL of water. The resulting mixture was adjusted to pH=7~8 with saturated solution of NaHCO$_3$, extracted with EtOAc (15 mL×3) and dried over Na$_2$SO$_4$. Purification by chromatography column (petroleum ether/EtOAc=10:1 to 1:2) afforded the title compound all as black oil. LCMS (ESI) calculated for $C_{21}H_{26}N_3O_2$ [M+H]$^+$: 352, found: 352.

Step 7—Preparation of 1,1,1-trifluoro-2-methylpropan-2-yl ((S)-2-((S and R)-3-amino-2-cyclopropyl-3-oxopropyl)-4-benzyl-3,4-dihydro-2H-benzo[b][1,4]oxazin-6-yl)carbamate

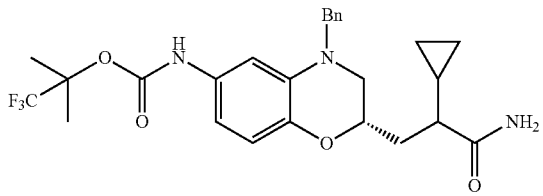 [SMILES: CC(C)(OC(=O)Nc1ccc2c(c1)N(Cc1ccccc1)C[C@H](CC(C(N)=O)C1CC1)O2)C(F)(F)F]

To a solution of (R and S)-3-((S)-6-amino-4-benzyl-3,4-dihydro-2H-benzo[b][1,4]oxazin-2-yl)-2-cyclopropylpropanamide (280 mg, 0.797 mmol) in DMSO (8 mL) was added 1-(((1,1,1-trifluoro-2-methylpropan-2-yl)oxy)carbonyl)-1H-imidazol-3-ium iodide (307 mg, 0.876 mmol), then the reaction was stirred at 20° C. for 1 h. The reaction mixture was extracted with EtOAc and water, washed with brine and dried over Na$_2$SO$_4$. The crude product was purified by prep-TLC (petroleum ether/EtOAc=1:1) to afford the title compound as a red oil. LCMS (ESI) calculated for $C_{26}H_{31}F_3N_3O_4$ [M+H]$^+$: 506.2, found: 506.2. $^1$H-NMR (CDCl$_3$, 400 MHz) δ 7.07-7.18 (5H, m), 6.48-6.52 (2H, m), 6.36 (1H, s), 5.53 (2H, d, J=10.8 Hz), 3.92-4.00 (2H, m), 3.06-3.09 (1H, m), 2.92-2.96 (1H, m), 1.62-1.73 (2H, m), 1.54 (6H, s), 0.81-0.83 (1H, m), 0.41 (2H, d, J=8.0 Hz), 0.12-0.16 (1H, m), 0.00-0.02 (1H, m).

Step 8—Preparation of 1,1,1-trifluoro-2-methylpropan-2-yl((S)-2-((S)-3-amino-2-cyclopropyl-3-oxopropyl)-3,4-dihydro-2H-benzo[b][1,4]oxazin-6-yl)carbamate and 1,1,1-trifluoro-2-methylpropan-2-yl ((S)-2-((R)-3-amino-2-cyclopropyl-3-oxopropyl)-3,4-dihydro-2H-benzo[b][1,4]oxazin-6-yl)carbamate

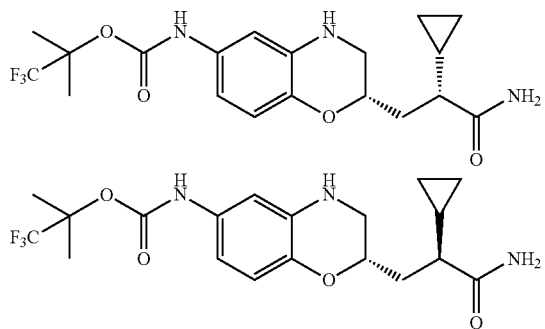

To a solution of 1,1,1-trifluoro-2-methylpropan-2-yl ((S)-2-((S and R)-3-amino-2-cyclopropyl-3-oxopropyl)-4-benzyl-3,4-dihydro-2H-benzo[b][1,4]oxazin-6-yl)carbamate (100 mg, 0.198 mmol) in EtOAc (10 mL) was added Pd/C (10 mg, 10%). The reaction was stirred under balloon of hydrogen at 20° C. for 8 hours, then filtered and concentrated. Purification by prep-TLC (petroleum ether/EtOAc=1:1) afforded the title mixture of diastereomers as a light yellow oil. LCMS (ESI) calculated for $C_{19}H_{25}F_3N_3O_4$ [M+H]$^+$: 416.1, found: 416.1.

The above mixture was resolved by SFC method (SFC-80 Column: Chiralpak AD, 10 μm, Daicel Chemical Industries, Ltd 250×30 mm I.D., Mobile phase: A: Supercritical $CO_2$, B: EtOH (25%) (contained 75% $NH_3.H_2O$) Flow rate: 60 mL/min, Wavelength: 220 nm) to yield two isomers: faster eluent (Isomer 1 from Step 8) and slower eluent (Isomer 2 from Step 8).

Step 9—Preparation of 1,1,1-trifluoro-2-methylpropan-2-yl((S)-2-((R)-3-amino-2-cyclopropyl-3-oxopropyl)-4-((3-chloro-1-ethyl-1H-pyrazol-4-yl)sulfonyl)-3,4-dihydro-2H-benzo[b][1,4]oxazin-6-yl)carbamate and 1,1,1-trifluoro-2-methylpropan-2-yl ((S)-2-((S)-3-amino-2-cyclopropyl-3-oxopropyl)-4-((3-chloro-1-ethyl-1H-pyrazol-4-yl)sulfonyl)-3,4-dihydro-2H-benzo[b][1,4]oxazin-6-yl)carbamate

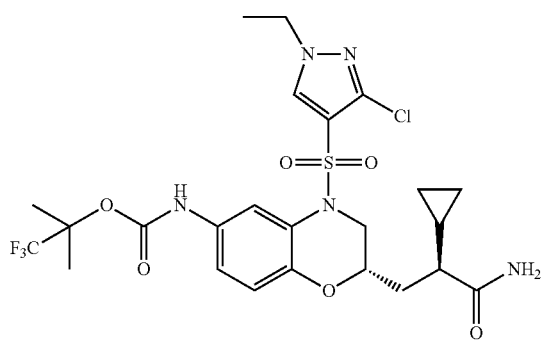

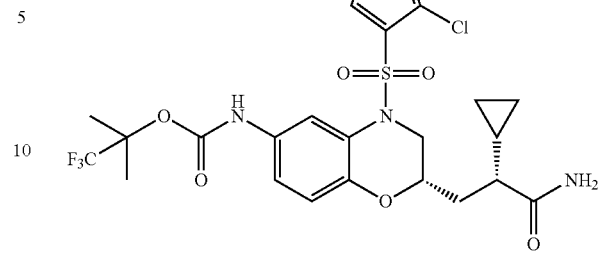

To a solution of 1,1,1-trifluoro-2-methylpropan-2-yl((S)-2-((S or R)-3-amino-2-cyclopropyl-3-oxopropyl)-3,4-dihydro-2H-benzo[b][1,4]oxazin-6-yl)carbamate (Isomer 1 from Step 8, 6 mg, 0.014 mmol) in THF (1 mL) were added pyridine (1 mL) and 3-chloro-1-ethyl-1H-pyrazole-4-sulfonyl chloride (19.85 mg, 0.087 mmol) at room temperature under $N_2$. The reaction was stirred at 20° C. for 18 h, then concentrated. Purification by prep-HPLC (MeCN/water using TFA buffer) afforded the title compound (Isomer 1, Example 89A) as a white solid. LCMS (ESI) calculated for $C_{24}H_{30}ClF_3N_5O_6S$ [M+H]$^+$: 608.1, found: 608.1; $^1$H-NMR (CDCl$_3$, 400 MHz) δ 8.10 (1H, s), 7.84 (1H, s), 6.89 (1H, d, J=7.2 Hz), 6.76 (1H, d, J=9.2 Hz), 6.01 (1H, s), 5.81 (1H, s), 4.31 (1H, d, J=14.4 Hz), 4.12 (2H, q, J=7.2 Hz), 4.02 (1H, s), 3.36 (1H, t, J=12.8 Hz), 2.05-2.15 (3H, m), 1.76 (6H, s), 1.49 (1H, t, J=7.2 Hz), 1.00 (1H, s), 0.66 (2H, d, J=7.6 Hz), 0.32-0.35 (1H, m), 0.22-0.24 (1H, m).

The other isomer (Isomer 2, Example 89B) was prepared using a similar procedure from Isomer 2 from Step 8. LCMS (ESI) calculated for $C_{24}H_{30}ClF_3N_5O_6S$ [M+H]$^+$: 608.1, found: 608.1; $^1$H-NMR (CDCl$_3$, 400 MHz) δ 8.10 (1H, s), 7.84 (1H, s), 6.89 (1H, d, J=7.2 Hz), 6.76 (1H, d, J=8.8 Hz), 6.59 (1H, s), 6.14 (1H, s), 5.84 (1H, s), 4.32 (1H, d, J=13.6 Hz), 4.12 (2H, q, J=7.2 Hz), 4.03 (1H, s), 3.37 (1H, t, J=12.0 Hz), 1.85-1.96 (2H, m), 1.76 (6H, s), 1.49 (1H, t, J=7.2 Hz), 1.00 (1H, s), 0.66 (2H, d, J=7.2 Hz), 0.33-0.37 (1H, m), 0.22-0.24 (1H, m).

Example 90—Preparation of (R)-1,1,1-trifluoro-2-methylpropan-2-yl(2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate and (S)-1,1,1-trifluoro-2-methylpropan-2-yl(2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate (Examples 90A and 90B)

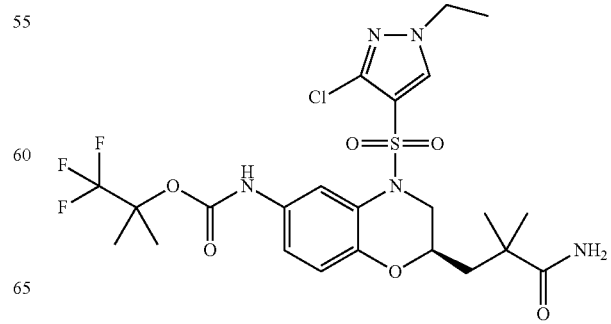

-continued

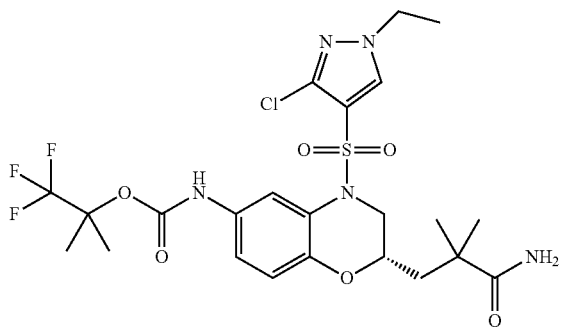

To a solution of (R or S)-1,1,1-trifluoro-2-methylpropan-2-yl(4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate (see Isomer 1 in Example 94; 40 mg, 0.069 mmol) in DMSO (0.5 ml) were added $K_2CO_3$ (28.7 mg, 0.208 mmol) and 30% $H_2O_2$ (0.141 ml, 1.384 mmol) dropwise at 0° C. under nitrogen. After 1 h, another batch of 30% $H_2O_2$ (0.141 ml, 1.384 mmol) was added. The reaction was stirred at room temperature for 6 h, then quenched with $Na_2SO_3$, filtered and concentrated. The crude product was purified by prep-HPLC (MeCN/water using TFA buffer) to afford the title product (Isomer 1, Example 90A) as a white solid.

The other enantiomer (Isomer 2, Example 90B)) was prepared using a similar procedure from Isomer 2 in Example 94. Both enantiomers have the same analytical data: LCMS (ESI) calculated for $C_{23}H_{30}ClF_3N_5O_6S$ [M+H]$^+$: 596, found: 596. $^1$H-NMR (CDCl$_3$, 400 MHz) δ 8.13 (brs, 1H), 7.86 (br s, 1H), 7.16 (br s, 1H), 6.76 (d, J=7.8 Hz, 1H), 6.65-6.72 (m, 1H), 6.60 (br s, 1H), 6.04 (br s, 1H), 4.23 (d, J=13.3 Hz, 1H), 4.08 (q, J=7.0 Hz, 3H), 3.40 (dd, J=8.6, 13.3 Hz, 1H), 2.00 (dd, J=9.3, 14.4 Hz, 1H), 1.78 (d, J=14.8 Hz, 1H), 1.73 (s, 6H), 1.45 (t, J=7.2 Hz, 3H), 1.30 (s, 6H).

Example 91—Preparation of Additional Amides from Propionic Acids

The compounds in Table 27 below were prepared based on the experimental procedures described in Examples 89 and 90 and elsewhere in the detailed description, and can be achieved by one of skill in the art in light of the present disclosure.

TABLE 27

| Ex. No. | Structure | Name | Observed m/z |
|---|---|---|---|
| 91A | 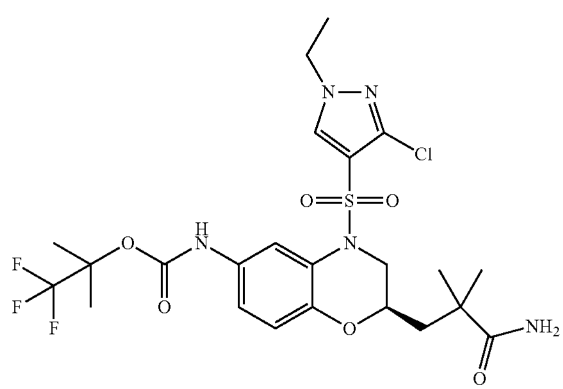 [SMILES: CCn1cc(S(=O)(=O)N2C[C@@H](CC(C)(C)C(N)=O)Oc3ccc(NC(=O)OC(C)(C)C(F)(F)F)cc32)c(Cl)n1] | (R)-1,1,1-trifluoro-2-methylpropan-2-yl (2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate | 596 (M + H)+ |
| 91B | 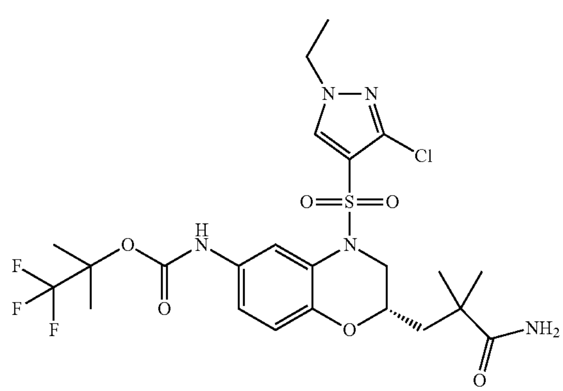 [SMILES: CCn1cc(S(=O)(=O)N2C[C@H](CC(C)(C)C(N)=O)Oc3ccc(NC(=O)OC(C)(C)C(F)(F)F)cc32)c(Cl)n1] | (S)-1,1,1-trifluoro-2-methylpropan-2-yl (2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate | 596 (M + H)+ |

TABLE 27-continued

| Ex. No. | Structure | Name | Observed m/z |
|---|---|---|---|
| 91C | 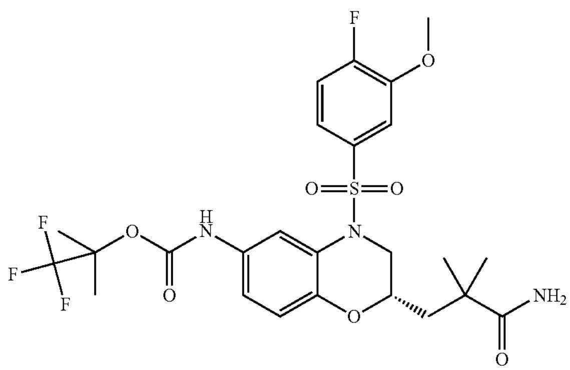 [SMILES: COc1cc(S(=O)(=O)N2C[C@H](CC(C)(C)C(N)=O)Oc3ccc(NC(=O)OC(C)(C)C(F)(F)F)cc32)ccc1F] | 2,2,2-trifluoro-1,1-dimethylethyl {(2S)-2-(3-amino-2,2-dimethyl-3-oxopropyl)-4-[(4-fluoro-3-methoxyphenyl)sulfonyl]-3,4-dihydro-2H-1,4-benzoxazin-6-yl}carbamate | 592 (M + H)+ |
| 91D | 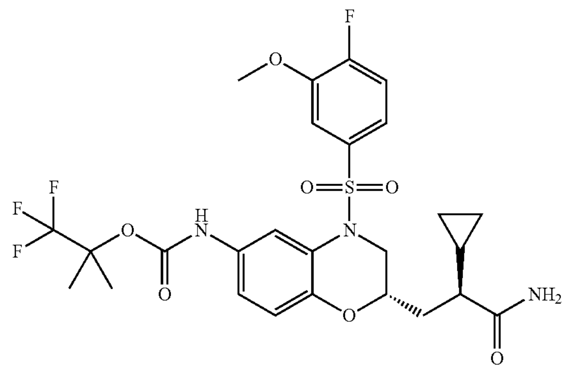 [SMILES: COc1cc(S(=O)(=O)N2C[C@H](C[C@H](C(N)=O)C3CC3)Oc3ccc(NC(=O)OC(C)(C)C(F)(F)F)cc32)ccc1F] | 1,1,1-trifluoro-2-methylpropan-2-yl ((S)-2-((S or R)-3-amino-2-cyclopropyl-3-oxopropyl)-4-((4-fluoro-3-methoxyphenyl)sulfonyl)-3,4-dihydro-2H-benzo[b][1,4]oxazin-6-yl)carbamate | 626 (M + Na)+ |
| 91E | 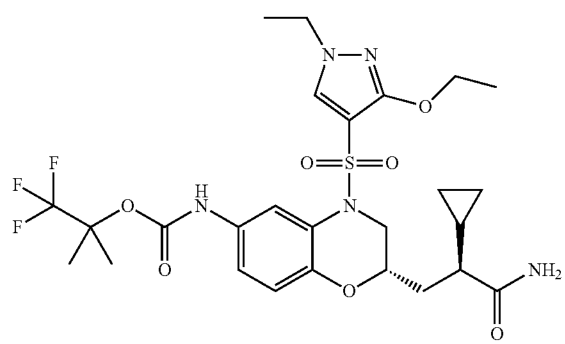 [SMILES: CCOc1nn(CC)cc1S(=O)(=O)N1C[C@H](C[C@H](C(N)=O)C2CC2)Oc2ccc(NC(=O)OC(C)(C)C(F)(F)F)cc21] | 1,1,1-trifluoro-2-methylpropan-2-yl ((S)-2-((S or R)-3-amino-2-cyclopropyl-3-oxopropyl)-4-((3-ethoxy-1-ethyl-1H-pyrazol-4-yl)sulfonyl)-3,4-dihydro-2H-benzo[b][1,4]oxazin-6-yl)carbamate | 618 (M + H)+ |
| 91F | 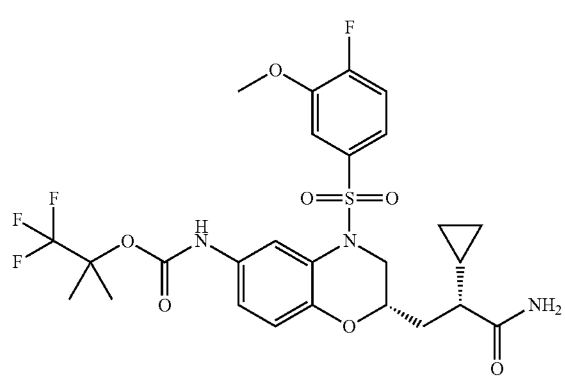 [SMILES: COc1cc(S(=O)(=O)N2C[C@H](C[C@@H](C(N)=O)C3CC3)Oc3ccc(NC(=O)OC(C)(C)C(F)(F)F)cc32)ccc1F] | 1,1,1-trifluoro-2-methylpropan-2-yl ((S)-2-((S or R)-3-amino-2-cyclopropyl-3-oxopropyl)-4-((4-fluoro-3-methoxyphenyl)sulfonyl)-3,4-dihydro-2H-benzo[b][1,4]oxazin-6-yl)carbamate | 604 (M + H)+ |

TABLE 27-continued

| Ex. No. | Structure | Name | Observed m/z |
|---|---|---|---|
| 91G | 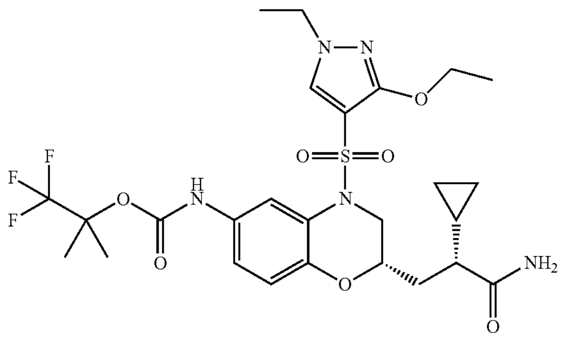 [SMILES: CCOc1nn(CC)cc1S(=O)(=O)N1C[C@H](C[C@@H](C(N)=O)C2CC2)Oc2ccc(NC(=O)OC(C)(C)C(F)(F)F)cc21] | 1,1,1-trifluoro-2-methylpropan-2-yl ((S)-2-((S or R)-3-amino-2-cyclopropyl-3-oxopropyl)-4-((3-ethoxy-1-ethyl-1H-pyrazol-4-yl)sulfonyl)-3,4-dihydro-2H-benzo[b][1,4]oxazin-6-yl)carbamate | 618 (M + H)+ |
| 91H | 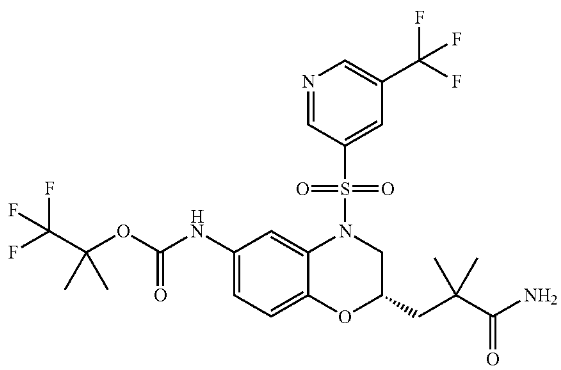 [SMILES: CC(C)(C[C@H]1CN(S(=O)(=O)c2cncc(C(F)(F)F)c2)c2cc(NC(=O)OC(C)(C)C(F)(F)F)ccc2O1)C(N)=O] | 2,2,2-trifluoro-1,1-dimethylethyl [(2S)-2-(3-amino-2,2-dimethyl-3-oxopropyl)-4-{[5-(trifluoromethyl)pyridin-3-yl]sulfonyl}-3,4-dihydro-2H-1,4-benzoxazin-6-yl]carbamate | 613 (M + H)+ |
| 91i | 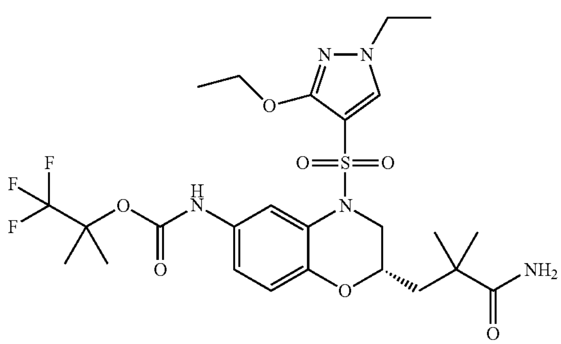 [SMILES: CCOc1nn(CC)cc1S(=O)(=O)N1C[C@H](CC(C)(C)C(N)=O)Oc2ccc(NC(=O)OC(C)(C)C(F)(F)F)cc21] | 2,2,2-trifluoro-1,1-dimethylethyl {2-(3-amino-2,2-dimethyl-3-oxopropyl)-4-[(3-ethoxy-1-ethyl-1H-pyrazol-4-yl)sulfonyl]-3,4-dihydro-2H-1,4-benzoxazin-6-yl}carbamate | 606 (M + H)+ |
| 91J | 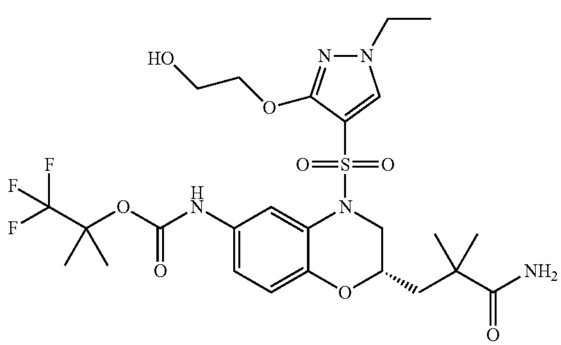 [SMILES: CCn1cc(S(=O)(=O)N2C[C@H](CC(C)(C)C(N)=O)Oc3ccc(NC(=O)OC(C)(C)C(F)(F)F)cc32)c(OCCO)n1] | 2,2,2-trifluoro-1,1-dimethylethyl [2-(3-amino-2,2-dimethyl-3-oxopropyl)-4-{[1-ethyl-3-(2-hydroxyethoxy)-1H-pyrazol-4-yl]sulfonyl}-3,4-dihydro-2H-1,4-benzoxazin-6-yl]carbamate | 622 (M + H)+ |

TABLE 27-continued

| Ex. No. | Structure | Name | Observed m/z |
|---|---|---|---|
| 91K | 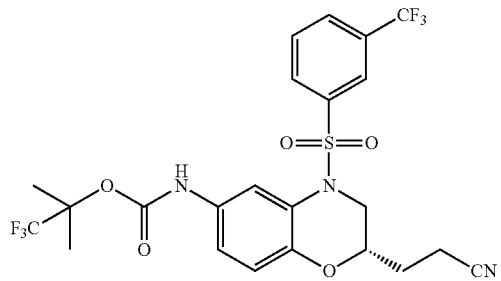 | (S)-methyl 2-((4-((2-(3-amino-2,2-dimethyl-3-oxopropyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate | 650 (M + H)+ |

Example 92—Preparation of (S)-1,1,1-trifluoro-2-methylpropan-2-yl (2-(2-cyanoethyl)-4-((3-(trifluoromethyl)phenyl)sulfonyl)-3,4-dihydro-2H-benzo[b][1,4]oxazin-6-yl)carbamate Example 92

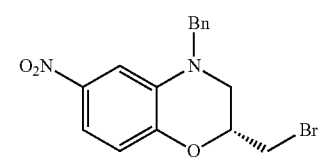 [SMILES: O=[N+]([O-])c1ccc2c(c1)N(Cc1ccccc1)C[C@H](CBr)O2]

Step 1—Preparation of (R)-4-benzyl-2-(bromomethyl)-6-nitro-3,4-dihydro-2H-benzo[b][1,4]oxazine

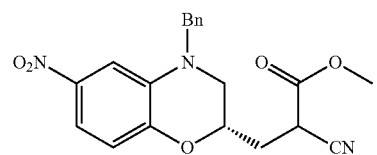 [SMILES: COC(=O)C(C#N)C[C@H]1CN(Cc2ccccc2)c2cc([N+](=O)[O-])ccc2O1]

To (R)-(4-benzyl-6-nitro-3,4-dihydro-2H-benzo[b][1,4]oxazin-2-yl)methanol (10 g, 33.3 mmol) and perbromomethane (16.56 g, 49.9 mmol) in THF (100 mL) was added triphenylphosphine (21.83 g, 83 mmol) portionwise and the reaction stirred at 30° C. for 2 h. The reaction was cooled, water (50 mL) was added and the resulting biphasic mixture was extracted with ethyl acetate (100 mL). The combined organic layers were washed with brine (30 mL), dried over Na$_2$SO$_4$, filtered and the filtrate evaporated under reduced pressure. The crude product was purified by column chromatography on silica gel, eluting with (petroleum ether: EtOAc=10:1) to give (R)-4-benzyl-2-(bromomethyl)-6-nitro-3,4-dihydro-2H-benzo[b][1,4]oxazine as a yellow solid. LCMS (ESI) calculated for C$_{16}$H$_{16}$BrN$_2$O$_3$ [M+H]$^+$: 363/365, found: 363/365. $^1$H NMR (CDCl$_3$, 400 MHz) δ 7.51-7.60 (m, 2H), 7.20-7.35 (m, 6H), 6.83 (d, J=8.6 Hz, 1H), 4.45 (d, J=4.7 Hz, 2H), 3.27-3.53 (m, 5H).

Step 2—Preparation of (R and S)-methyl 3-((S)-4-benzyl-6-nitro-3,4-dihydro-2H-benzo[b][1,4]oxazin-2-yl)-2-cyanopropanoate

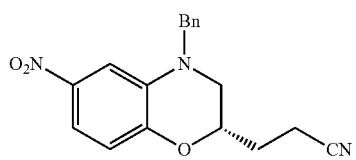 [SMILES: N#CCC[C@H]1CN(Cc2ccccc2)c2cc([N+](=O)[O-])ccc2O1]

(R)-4-benzyl-2-(bromomethyl)-6-nitro-3,4-dihydro-2H-benzo[b][1,4]oxazine (250 mg, 0.6 mmol), methyl 2-cyanoacetate (682 mg, 6.8 mmol) and K$_2$CO$_3$ (171 mg, 1.239 mmol) in DMSO (2.5 ml) were stirred at 90° C. for 0.5 h. Upon completion, the reaction solution was filtrated and the filtrate was used in the next step with no further purification. LCMS (ESI) calculated for C$_{20}$H$_{20}$N$_3$O$_5$ [M+H]$^+$: 382 found: 382.

Step 3—Preparation of methyl (S)-3-(4-benzyl-6-nitro-3,4-dihydro-2H-benzo[b][1,4]oxazin-2-yl)propanenitrile To a flask with (R and S)-methyl 3-((S)-4-benzyl-6-nitro-3,4-dihydro-2H-benzo[b][1,4]oxazin-2-yl)-2-cyanopropanoate (250 mg, 0.6 mmol) was added lithium chloride (139 mg, 3.3 mmol) in DMSO (2.5 mL) and the reaction was stirred at 160° C. for 0.5 h. The reaction solution was cooled, water (10 mL) was added and the resulting biphasic mixture was extracted with ethyl acetate (25 mL). The combined organic layers were washed with aqueous ammonium chloride (10 mL), dried (Na$_2$SO$_4$), filtered and the solvent was evaporated under reduced pressure. The crude product was purified by prep-TLC eluting with (petroleum ether:EtOAc=5:1 to 3:1) to afford the title compound as a yellow oil. LCMS (ESI) calculated for $C_{18}H_{18}N_3O_3$ [M+H]$^+$: 324, found: 324. $^1$H NMR (CDCl$_3$, 400 MHz,) δ 7.48-7.59 (m, 2H), 7.20-7.36 (m, 5H), 6.81 (d, J=8.6 Hz, 1H), 4.44 (s, 2H), 4.29 (t, J=8.0 Hz, 1H), 3.28 (dd, J=2.1, 11.9 Hz, 1H), 3.09 (dd, J=7.4, 11.7 Hz, 1H), 2.47-2.65 (m, 2H), 1.85-1.95 (m, 2H).

Step 4—Preparation of (S)-3-(6-amino-3,4-dihydro-2H-benzo[b][1,4]oxazin-2-yl)propanenitrile

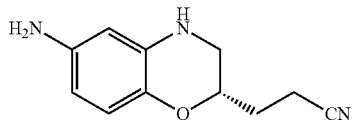 [SMILES: N#CCC[C@H]1CNc2cc(N)ccc2O1]

Methyl (S)-3-(4-benzyl-6-nitro-3,4-dihydro-2H-benzo[b][1,4]oxazin-2-yl)propanenitrile (1.6 g, 4.9 mmol) and Pd/C (1.7 g, 10%) in EtOH (30 ml) were stirred under H$_2$ at 1 atm at 25° C. for 4 h. Upon completion, the reaction mixture was filtrated and the filtrate concentrated. The crude product (S)-3-(6-amino-3,4-dihydro-2H-benzo[b][1,4]oxazin-2-yl)propanenitrile was used in next step without further purification. LCMS (ESI) calculated for $C_{11}H_{14}N_3O$ [M+H]+: 204, found: 204. $^1$H NMR (CDCl$_3$, 400 MHz) δ 6.53 (d, J=8.2 Hz, 1H), 5.87-6.04 (m, 2H), 4.07 (t, J=8.2 Hz, 1H), 3.31 (dd, J=2.1, 11.1 Hz, 1H), 3.03-3.14 (m, 1H), 2.53 (t, J=7.2 Hz, 2H), 1.82-2.00 (m, 2H).

Step 5—Preparation of (S)-1,1,1-trifluoro-2-methylpropan-2-yl(2-(2-cyanoethyl)-3,4-dihydro-2H-benzo[b][1,4]oxazin-6-yl)carbamate

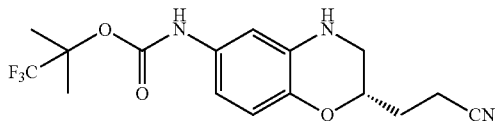 [SMILES: CC(C)(OC(=O)Nc1ccc2c(c1)NC[C@H](CCC#N)O2)C(F)(F)F]

(S)-3-(6-amino-3,4-dihydro-2H-benzo[b][1,4]oxazin-2-yl)propanenitrile (1.0 g, 4.9 mmol) and 3-methyl-1-(((1,1,1-trifluoro-2-methylpropan-2-yl)oxy)carbonyl)-1H-imidazol-3-ium iodide (1.971 g, 5.41 mmol) were stirred at 28° C. in DMSO (20 mL) for 10 h, then treated with water (150 mL) and extracted with ethyl acetate (3×100 mL). The combined organic fractions were washed with aqueous ammonium chloride (20 mL), dried (Na$_2$SO$_4$), filtered and the filtrate evaporated under reduced pressure. The crude product was purified by column chromatography on silica gel (petroleum ether:EtOAc=3:1) to give the title product as a brown oil. LCMS (ESI) calculated for $C_{16}H_{19}F_3N_3O_3$ [M+H]$^+$: 358, found: 358. $^1$H NMR (CDCl$_3$, 400 MHz) δ 6.83 (br s, 1H), 6.65 (d, J=8.6 Hz, 1H), 6.42 (d, J=6.2 Hz, 2H), 4.14 (br s, 1H), 3.36 (d, J=11.3 Hz, 1H), 3.10 (dd, J=7.2, 11.5 Hz, 1H), 2.55 (t, J=7.0 Hz, 2H), 1.82-1.97 (m, 2H), 1.67 (s, 6H).

Step 6—Preparation of (S)-1,1,1-trifluoro-2-methylpropan-2-yl (2-(2-cyanoethyl)-4-((3-(trifluoromethyl)phenyl)sulfonyl)-3,4-dihydro-2H-benzo[b][1,4]oxazin-6-yl)carbamate

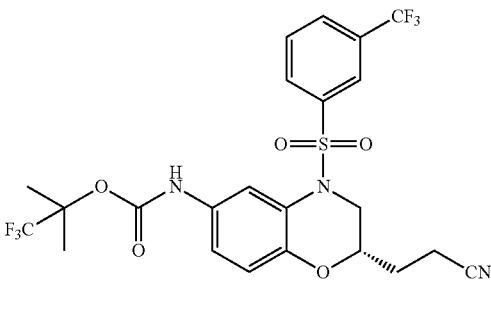 [SMILES: CC(C)(OC(=O)Nc1ccc2c(c1)N(S(=O)(=O)c1cccc(C(F)(F)F)c1)C[C@H](CCC#N)O2)C(F)(F)F]

(S)-1,1,1-trifluoro-2-methylpropan-2-yl(2-(2-cyanoethyl)-3,4-dihydro-2H-benzo[b][1,4]oxazin-6-yl)carbamate (250 mg, 0.7 mmol) and pyridine (332 mg, 4.2 mmol) in DCM (6 mL) was treated with 3-(trifluoromethyl)benzene-1-sulfonyl chloride (513 mg, 2.10 mmol) and the resulting mixture was stirred at 30° C. for 8 h. The reaction was cooled to room temperature, then treated with water (5 mL). The resulting biphasic mixture was extracted with dichloromethane (3×5 mL). The combined organic layers were washed with aqueous ammonium chloride (5 mL), dried (Na$_2$SO$_4$), filtered and the filtrate was evaporated under reduced pressure. The crude product was purified by prep-TLC (petroleum ether:EtOAc=3:1) to give the title compound as a white solid. LCMS (ESI) calculated for $C_{23}H_{22}F_6N_3O_5S$ [M+H]$^+$: 566, found: 566. $^1$H NMR (CDCl$_3$, 400 MHz) δ 7.99 (br s, 1H), 7.74-7.91 (m, 3H), 7.53-7.68 (m, 1H), 6.99 (dd, J=2.1, 8.8 Hz, 1H), 6.72 (d, J=8.6 Hz, 1H), 6.54 (brs, 1H), 4.20 (d, J=14.0 Hz, 1H), 3.57 (brs, 1H), 3.23 (dd, J=9.3, 14.0 Hz, 1H), 2.47 (t, J=6.8 Hz, 2H), 1.75-1.89 (m, 2H), 1.70 (s, 6H).

Example 93—Preparation of (S)-1,1,1-trifluoro-2-methylpropan-2-yl (4-((3-chloro-1-ethyl-1H-pyrazol-4-yl)sulfonyl)-2-((1-cyanocyclopropyl)methyl)-3,4-dihydro-2H-benzo[b][1,4]oxazin-6-yl)carbamate and (R)-1,1,1-trifluoro-2-methylpropan-2-yl (4-((3-chloro-1-ethyl-1H-pyrazol-4-yl)sulfonyl)-2-((1-cyanocyclopropyl)methyl)-3,4-dihydro-2H-benzo[b][1,4]oxazin-6-yl)carbamate (Examples 93A and 93B)

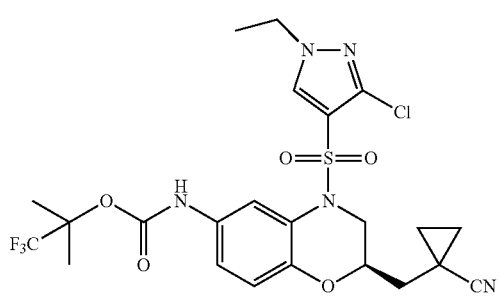

-continued

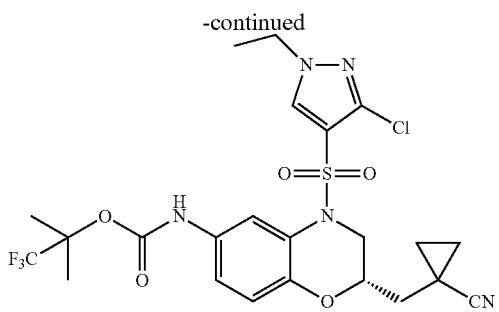

Step 1—Preparation of 1-allylcyclopropanecarbonitrile

To a solution of cyclopropanecarbonitrile (10 g, 149 mmol) in THF (10 mL) was added LDA (82 ml, 164 mmol) dropwise at 0° C. under nitrogen. After 10 min, the mixture was added dropwise to the solution of 3-bromoprop-1-ene (18.93 g, 157 mmol) in THF (20 mL) at 0° C. The reaction was stirred at 0° C. for 1 h, then quenched with saturated NH$_4$Cl solution (20 mL) and diluted with water (200 mL). The organic layer was separated and the resulting aqueous solution extracted with DCM (35 mL×3). The combined organic layers were washed with brine, dried over Na$_2$SO$_4$ and evaporated to dryness at low temperature (<30° C.). The crude product was purified by silica gel chromatography eluted with pure petroleum ether to afford the title compound as a yellow oil. $^1$H-NMR (CD$_3$OD, 400 MHz) δ 5.83 (tdd, J=6.9, 10.0, 16.8 Hz, 1H), 5.11-5.24 (m, 2H), 2.20 (brs, 2H), 1.18-1.26 (m, 2H), 0.79-0.85 (m, 2H).

Step 2—Preparation of (R and S)-1-(oxiran-2-ylmethyl)cyclopropanecarbonitrile

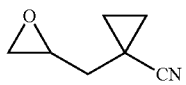

To a solution of 1-allylcyclopropanecarbonitrile (8 g, 74.7 mmol) in DCM (80 ml) was added m-CPBA (18.19 g, 90 mmol) in portions at 0° C. The reaction was stirred at 25° C. for 30 h, then diluted with DCM (100 mL). The organic layer was washed with 1M NaOH solution (60 mL×3) and brine (60 mL×2), dried over Na$_2$SO$_4$ and evaporated to afford the crude title product as a yellow oil, which was used directly in the next step without further purification. $^1$H-NMR (CD$_3$OD, 400 MHz) δ 3.11 (d, J=1.9 Hz, 1H), 2.82 (t, J=4.1 Hz, 1H), 2.56 (dd, J=2.5, 4.1 Hz, 1H), 1.89 (dd, J=5.0, 14.4 Hz, 1H), 1.42-1.54 (m, 1H), 1.20-1.31 (m, 2H), 0.90-0.99 (m, 1H), 0.82-0.88 (m, 1H).

Step 3—Preparation of (R and S)-1-((6-nitro-4-tosyl-3,4-dihydro-2H-benzo[b][1,4]oxazin-2-yl)methyl)cyclopropanecarbonitrile

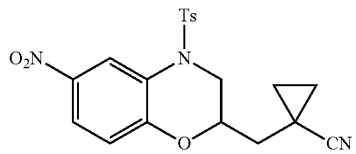

To a solution of N-(2-fluoro-5-nitrophenyl)-4-methylbenzenesulfonamide (1 g, 3.23 mmol) in DMF (10 mL) were added (R and S)-1-(oxiran-2-ylmethyl)cyclopropanecarbonitrile (1 g, 8.13 mmol), N-benzyl-N,N-diethylethanaminium chloride (0.110 g, 0.48 mmol) and potassium carbonate (1.56 g, 11.27 mmol) in one portion at room temperature under nitrogen. The reaction was stirred at 100° C. in a microwave for 2 h. Another two batches were run on the same scale as described above and all three mixtures were cooled to room temperature, combined, diluted with water (400 mL) and extracted with EtOAc (100 mL×4). The combined organic layers were washed with brine, dried over Na$_2$SO$_4$ and evaporated to dryness. The crude product was purified by silica column (petroleum ether:EtOAc=5:1 to 3:1) to afford the title product as a yellow solid. LCMS (ESI) calculated for C$_{20}$H$_{20}$N$_3$O$_5$S [M+H]$^+$: 414, found: 414. $^1$H-NMR (CDCl$_3$, 400 MHz) δ 8.75 (br s, 1H), 7.87-8.00 (m, 1H), 7.61 (d, J=8.2 Hz, 2H), 7.31 (d, J=7.8 Hz, 2H), 6.93 (d, J=9.0 Hz, 1H), 4.32 (d, J=14.4 Hz, 1H), 3.82 (br s, 1H), 3.26 (dd, J=9.3, 14.0 Hz, 1H), 2.40 (s, 3H), 1.64-1.81 (m, 2H), 1.32 (brs, 2H), 0.89-0.97 (m, 1H), 0.78-0.85 (m, 1H).

Step 4—Preparation of (R and S)-1-((6-amino-4-tosyl-3,4-dihydro-2H-benzo[b][1,4]oxazin-2-yl)methyl)cyclopropanecarbonitrile

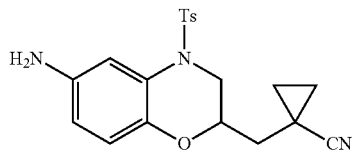 [SMILES: Cc1ccc(S(=O)(=O)N2CC(CC3(C#N)CC3)Oc3ccc([N+](=O)[O-])cc32)cc1]

To a solution of (R and S)-1-((6-nitro-4-tosyl-3,4-dihydro-2H-benzo[b][1,4]oxazin-2-yl)methyl)cyclopropanecarbonitrile (1.5 g, 3.63 mmol) in EtOAc (30 mL) was added Pd/C (0.6 g, 5.64 mmol) in one portion at room temperature. The reaction was stirred at 25° C. under a H$_2$ balloon for 8 h, then filtered and evaporated to dryness. The crude title product was used directly in the next step without further purification. LCMS (ESI) calculated for C$_{20}$H$_{22}$N$_3$O$_3$S [M+H]$^+$: 384, found: 384. $^1$H-NMR (CDCl$_3$, 400 MHz) δ 7.55 (d, J=8.2 Hz, 2H), 7.25 (d, J=7.0 Hz, 3H), 6.62 (d, J=8.6 Hz, 1H), 6.44 (dd, J=2.5, 8.4 Hz, 1H), 4.25 (dd, J=1.7, 14.2 Hz, 1H), 3.45-3.56 (m, 1H), 3.14 (dd, J=9.5, 14.2 Hz, 1H), 2.37 (s, 3H), 1.59-1.67 (m, 1H), 1.50-1.59 (m, 1H), 1.20-1.29 (m, 2H), 0.86-0.94 (m, 1H), 0.69-0.79 (m, 1H).

Step 5—Preparation of (S)-1,1,1-trifluoro-2-methyl-propan-2-yl(2-((1-cyanocyclopropyl)methyl)-4-tosyl-3,4-dihydro-2H-benzo[b][1,4]oxazin-6-yl)carbamate and (R)-1,1,1-trifluoro-2-methylpropan-2-yl (2-((1-cyanocyclopropyl)methyl)-4-tosyl-3,4-dihydro-2H-benzo[b][1,4]oxazin-6-yl)carbamate

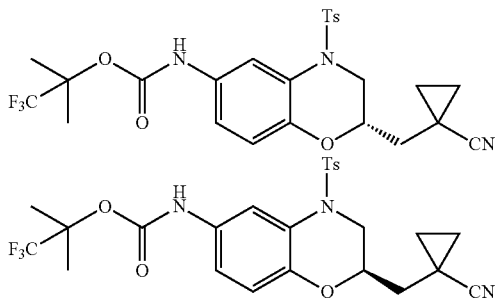

To a solution of (R and S)-1-((6-amino-4-tosyl-3,4-dihydro-2H-benzo[b][1,4]oxazin-2-yl)methyl)cyclopropanecarbonitrile (1.3 g, 3.39 mmol) in DMSO (15 ml) was added 1,1,1-trifluoro-2-methylpropan-2-yl 1H-imidazole-1-carboxylate (1.130 g, 5.09 mmol) in one portion at room temperature under N$_2$. The reaction was stirred at 90° C. for 8 h, then diluted with water (50 mL) and extracted with EtOAc (50 mL×3). The combined organic layers were washed with brine, dried over Na$_2$SO$_4$ and evaporated to dryness. The crude product was purified by silica gel column (petroleum ether:EtOAc=5:1) to afford the title compound as a white solid.

The two enantiomers were separated by chiral SFC method (Column: Chiralpak AD 250 mm*30 mm, 10 μm; Mobile phase: 35% MeOH+NH$_3$.H$_2$O; Flow rate: 80 mL/min; Wavelength: 280 nm). Both enantiomers (faster eluent Isomer 1 and slower eluent Isomer 2) have the same analytical data: LCMS (ESI) calculated for C$_{25}$H$_{27}$F$_3$N$_3$O$_5$S [M+H]$^+$: 538, found: 538. $^1$H-NMR (CDCl$_3$, 400 MHz) δ 7.69 (br s, 1H), 7.51 (d, J=8.0 Hz, 2H), 7.21 (d, J=8.0 Hz, 2H), 6.72 (d, J=9.0 Hz, 1H), 6.63 (brs, 1H), 4.19 (dd, J=1.7, 14.3 Hz, 1H), 3.51 (d, J=4.5 Hz, 1H), 3.11 (dd, J=9.5, 14.0 Hz, 1H), 2.33 (s, 3H), 1.70 (s, 6H), 1.58-1.66 (m, 1H), 1.48-1.56 (m, 1H), 1.17-1.26 (m, 2H), 0.81-0.91 (m, 1H), 0.67-0.77 (m, 1H).

Step 6—Preparation of (S)-1,1,1-trifluoro-2-methyl-propan-2-yl(2-((1-cyanocyclopropyl)methyl)-3,4-dihydro-2H-benzo[b][1,4]oxazin-6-yl)carbamate and (R)-1,1,1-trifluoro-2-methylpropan-2-yl(2-((1-cyanocyclopropyl)methyl)-3,4-dihydro-2H-benzo[b][1,4]oxazin-6-yl)carbamate

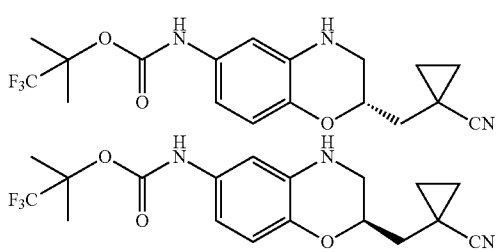

To a solution of (R or S)-1,1,1-trifluoro-2-methylpropan-2-yl (2-((1-cyanocyclopropyl)methyl)-4-tosyl-3,4-dihydro-2H-benzo[b][1,4]oxazin-6-yl)carbamate (Isomer 1 from Step 5, 200 mg, 0.372 mmol) in MeOH (10 ml) was added magnesium (181 mg, 7.44 mmol) in one portion at 25° C. under nitrogen. The reaction was stirred at 25° C. for 18 hours, then quenched with saturated NH$_4$Cl solution (80 mL) and extracted with EtOAc (3×70 mL). The organic layers were combined, dried over Na$_2$SO$_4$, filtered and the filtrate concentrated in vacuum. The crude product was purified by pre-TLC (petroleum. ether/EtOAc=3:1) to afford the title compound (Isomer 1 from Step 6) as a white solid.

The other enantiomer (Isomer 2 from Step 6) was prepared using a similar procedure starting with Isomer 2 from Step 5. Both enantiomers have the same analytical data: LCMS (ESI) calculated for C$_{18}$H$_{21}$F$_3$N$_3$O$_3$ [M+H]$^+$: 384.1, found: 384.2.

Step 7—Preparation of (R)-1,1,1-trifluoro-2-methyl-propan-2-yl(4-((3-chloro-1-ethyl-1H-pyrazol-4-yl)sulfonyl)-2-((1-cyanocyclopropyl)methyl)-3,4-dihydro-2H-benzo[b][1,4]oxazin-6-yl)carbamate and (S)-1,1,1-trifluoro-2-methylpropan-2-yl(4-((3-chloro-1-ethyl-1H-pyrazol-4-yl)sulfonyl)-2-((1-cyanocyclopropyl)methyl)-3,4-dihydro-2H-benzo[b][1,4]oxazin-6-yl)carbamate

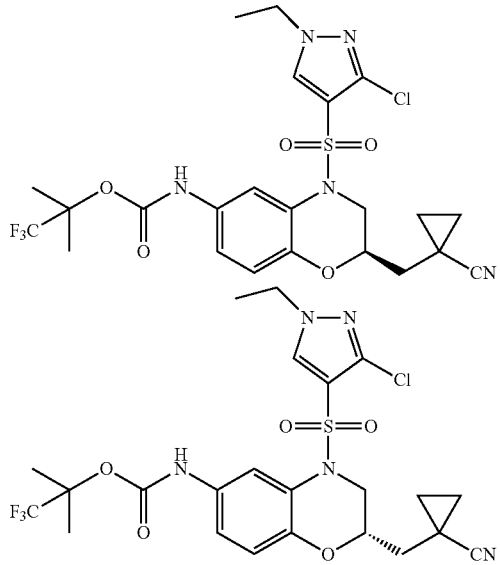

To a solution of (R or S)-1,1,1-trifluoro-2-methylpropan-2-yl(2-((1-cyanocyclopropyl)methyl)-3,4-dihydro-2H-benzo[b][1,4]oxazin-6-yl)carbamate (Isomer 1 from Step 6, 40 mg, 0.104 mmol) in pyridine (2 mL) and THF (2 mL) was added 3-chloro-1-ethyl-1H-pyrazole-4-sulfonyl chloride (47.8 mg, 0.209 mmol). The reaction was stirred at 25° C. for 18 h, then concentrated. The title compound (Isomer 1 of Step 7, Example 93A) was obtained by prep-HPLC as a white solid.

The other enantiomer, Example 93B, was prepared using a similar procedure from Isomer 2 from Step 6. Both enantiomers have the same analytical data: LCMS (ESI) calculated for C$_{23}$H$_{26}$ClF$_3$N$_5$O$_5$S [M+H]$^+$: 576.1, found: 576.1; $^1$H-NMR (CDCl$_3$, 400 MHz) δ 8.08 (1H, s), 7.81 (1H, s), 6.77-6.82 (2H, m), 6.59 (1H, s), 4.27-4.31 (1H, m,), 4.21-4.22 (1H, m), 4.01-4.07 (2H, m), 3.40-3.45 (1H, m), 2.01-2.02 (2H, m), 1.69 (6H, s), 1.39-1.43 (3H, m), 1.23-1.27 (2H, m), 0.91-0.93 (1H, m), 0.81-0.83 (2H, m).

Example 94—Preparation of (S)-1,1,1-trifluoro-2-methylpropan-2-yl (4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate and (R)-1,1,1-trifluoro-2-methylpropan-2-yl (4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate (Examples 94A and 94B)

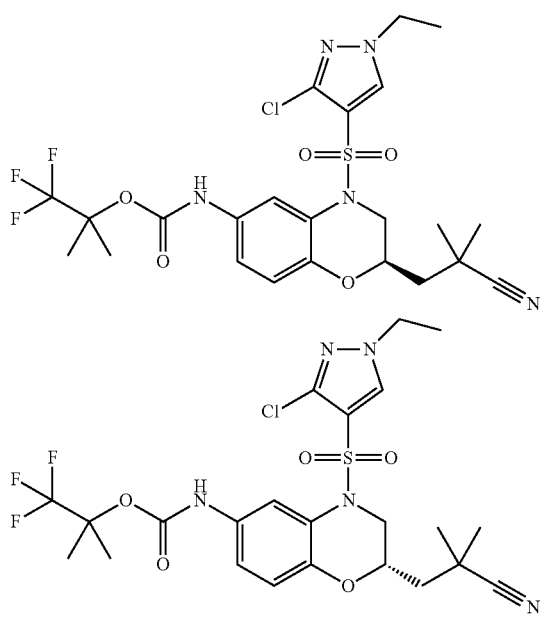

Step 1—Preparation of (R and S)-2,2-dimethyl-3-(oxiran-2-yl)propanenitrile

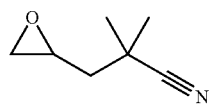

To a solution of isobutyronitrile (5 g, 72.4 mmol) in THF (10 mL) was added LDA (36.2 mL, 72.4 mmol) dropwise at −78° C. under nitrogen. After 1 h, the reaction mixture was added dropwise to a solution of 2-(bromomethyl)oxirane (9.91 g, 72.4 mmol) in THF (4 mL) at −78° C. The resulting reaction was stirred at −78° C. for 3 h, then quenched with saturated NH$_4$Cl solution (20 mL) and diluted with water (100 mL). The aqueous layer was extracted with DCM (40 mL×3) and the combined organic layers were washed with brine (40 mL×2), dried over Na$_2$SO$_4$ and evaporated to dryness. The crude product was purified by silica gel chromatography eluted with petroleum ether:EtOAc=50:1 to 40:1 to afford the title product as yellow oil. $^1$H NMR (CDCl$_3$, 400 MHz) δ 3.05-3.14 (m, 1H), 2.80 (d, J=4.3 Hz, 1H), 2.45-2.53 (m, 1H), 1.81-1.90 (m, 1H), 1.59-1.64 (m, 1H), 1.44 (s, 3H), 1.40 (s, 3H).

Step 2—Preparation of (R and S)-2,2-dimethyl-3-(6-nitro-4-tosyl-3,4-dihydro-2H-benzo[b][1,4]oxazin-2-yl)propanenitrile

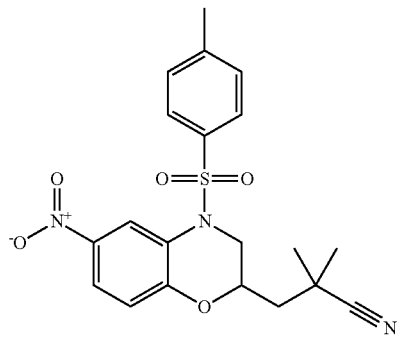

To a mixture of N-(2-fluoro-5-nitrophenyl)-4-methylbenzenesulfonamide (5 g, 16.11 mmol) and (R and S)-2,2-dimethyl-3-(oxiran-2-yl)propanenitrile (5.04 g, 40.3 mmol) in DMF (50 mL) was added K$_2$CO$_3$ (6.68 g, 48.3 mmol) in one portion at room temperature under nitrogen. The resulting mixture was stirred at 100° C. for 4 days, then diluted with water (200 mL) and extracted with EtOAc (50 mL×4). The combined organic layers were washed with brine (50 mL×2), dried over Na$_2$SO$_4$, filtered and evaporated to dryness. The crude product was purified by silica gel column (petroleum ether:EtOAc=20:1 to 3:1) to afford the title product as a yellow oil. LCMS (ESI) calculated for C$_{20}$H$_{22}$N$_3$O$_5$S [M+H]$^+$: 416, found: 416. $^1$H NMR (CDCl$_3$, 400 MHz) δ 8.72 (d, J=2.4 Hz, 1H), 7.93 (dd, J=2.4, 9.0 Hz, 1H), 7.60 (d, J=8.2 Hz, 2H), 7.29 (d, J=8.2 Hz, 2H), 6.91 (d, J=9.0 Hz, 1H), 5.27 (s, 2H), 4.24 (dd, J=2.2, 14.3 Hz, 1H), 3.78-3.87 (m, 1H), 3.26 (dd, J=9.2, 14.3 Hz, 1H), 2.38 (s, 3H), 1.78-1.86 (m, 1H), 1.68-1.75 (m, 1H), 1.38 (s, 3H), 1.35 (s, 3H).

Step 3—Preparation of (R and S)-3-(6-amino-4-tosyl-3,4-dihydro-2H-benzo[b][1,4]oxazin-2-yl)-2,2-dimethylpropanenitrile

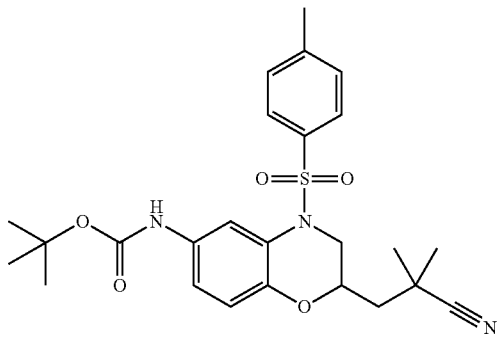 [SMILES: Cc1ccc(S(=O)(=O)N2CC(CC(C)(C)C#N)Oc3ccc(NC(=O)OC(C)(C)C)cc32)cc1]

To a solution of (R and S)-2,2-dimethyl-3-(6-nitro-4-tosyl-3,4-dihydro-2H-benzo[b][1,4]oxazin-2-yl)propanenitrile (4.6 g, 11.07 mmol) in EtOAc (50 mL) were added di-tert-butyl dicarbonate (3.62 g, 16.61 mmol) and Pd/C (0.46 g) at room temperature under nitrogen. The mixture was stirred at 25° C. overnight under H$_2$ (50 psi), then filtered over CELITE and evaporated to dryness. The crude product was purified by silica gel chromatography eluting with petroleum ether:EtOAc=5:1 to afford the title product as a yellow solid. LCMS (ESI) calculated for $C_{25}H_{32}N_3O_5S$ [M+H]$^+$: 486, found: 486. $^1$H NMR (CDCl$_3$, 400 MHz) δ 7.64 (d, J=1.9 Hz, 1H), 7.55 (d, J=8.2 Hz, 2H), 7.25 (br s, 2H), 6.73 (d, J=8.6 Hz, 1H), 6.40 (br s, 1H), 4.15 (dd, J=1.7, 14.2 Hz, 1H), 3.56 (t, J=8.8 Hz, 1H), 3.18 (dd, J=9.6, 14.2 Hz, 1H), 2.36 (s, 3H), 1.67-1.76 (m, 1H), 1.62 (dd, J=2.3, 14.8 Hz, 1H), 1.50 (s, 9H), 1.33 (s, 3H), 1.31 (s, 3H).

Step 4—Preparation of (R and S)-1,1,1-trifluoro-2-methylpropan-2-yl(2-(2-cyano-2-methyl propyl)-4-tosyl-3,4-dihydro-2H-benzo[b][1,4]oxazin-6-yl)carbamate

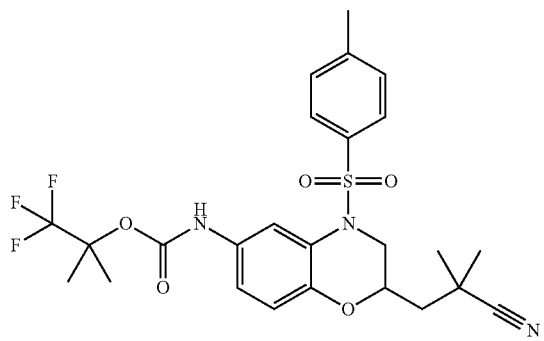 [SMILES: Cc1ccc(S(=O)(=O)N2CC(CC(C)(C)C#N)Oc3ccc(NC(=O)OC(C)(C)C(F)(F)F)cc32)cc1]

A solution of (R and S)-tert-butyl (2-(2-cyano-2-methylpropyl)-4-tosyl-3,4-dihydro-2H-benzo[b][1,4]oxazin-6-yl)carbamate (5.0 g, 10.38 mmol) in HCl in dioxane (4 M, 100 mL) was stirred at 25° C. for 1 h. The reaction solution was evaporated to dryness to give the crude (R and S)-3-(6-amino-4-tosyl-3,4-dihydro-2H-benzo[b][1,4]oxazin-2-yl)-2,2-dimethylpropanenitrile as brown oil. The crude product was used directly in the next step without further purification.

To a solution of the above product (4.0 g, 10.38 mmol) in DMSO (40 mL) was added 1,1,1-trifluoro-2-methylpropan-2-yl 1H-imidazole-1-carboxylate (2.42 g, 10.90 mmol) in one portion at room temperature under nitrogen. The mixture was stirred at 80° C. for 4 h, then diluted with water (50 mL) and extracted with EtOAc (25 mL×3). The combined organic layers were washed with brine, dried over Na$_2$SO$_4$ and evaporated to dryness. The crude product was purified by prep-TLC (petroleum ether:EtOAc=3:1) to afford the title as a yellow oil. LCMS (ESI) calculated for $C_{25}H_{29}F_3N_3O_5S$ [M+H]$^+$: 540, found: 540. $^1$H NMR (CDCl$_3$, 400 MHz) δ 7.73 (brs, 1H), 7.56 (d, J=8.2 Hz, 2H), 7.24 (s, 3H), 6.76 (d, J=8.6 Hz, 1H), 6.61 (brs, 1H), 4.15 (dd, J=2.0, 14.1 Hz, 1H), 3.58 (t, J=8.6 Hz, 1H), 3.19 (dd, J=9.4, 14.1 Hz, 1H), 2.37 (s, 3H), 1.75 (s, 6H), 1.69-1.73 (m, 1H), 1.64 (dd, J=2.4 Hz, 1H), 1.34 (s, 3H), 1.31 (s, 3H).

Step 5—Preparation of (S)-3,3-difluoro-2-methylbutan-2-yl(2-(2-cyano-2-methylpropyl)-3,4-dihydro-2H-benzo[b][1,4]oxazin-6-yl)carbamate and (R)-3,3-difluoro-2-methylbutan-2-yl (2-(2-cyano-2-methylpropyl)-3,4-dihydro-2H-benzo[b][1,4]oxazin-6-yl)carbamate To a solution of (R and S)-1,1,1-trifluoro-2-methylpropan-2-yl(2-(2-cyano-2-methylpropyl)-4-tosyl-3,4-dihydro-2H-benzo[b][1,4]oxazin-6-yl)carbamate (4.5 g, 8.34 mmol) in MeOH (60 ml) was added magnesium (2.0 g, 83 mmol) in one portion at room temperature under nitrogen. The mixture was stirred at 80° C. for 4 h, then diluted with MeOH (100 mL) and filtered. The resulting filtrate was evaporated to dryness and the crude product purified by silica gel column (petroleum ether:EtOAc=15:1 to 2:1) to afford the product of the title racemate as a yellow oil.

The two enantiomers were separated by SFC method (column: Chiralpak AD-H 250×4.6 mm I.D., Sum; Mobile phase: ethanol (0.05% DEA) in CO$_2$ from 5% to 40%; Flow rate: 2.35 mL/min wavelength: 220 nm). Isomer 1 RT=6.853 min and Isomer 2 RT=7.966 min. Both enantiomers have the same analytical data: LCMS (ESI) calculated for $C_{18}H_{23}F_3N_3O_3$ [M+H]$^+$: 386, found: 386. $^1$H NMR (CDCl$_3$, 400 MHz) δ 6.81 (brs, 1H), 6.68 (d, J=8.6 Hz, 1H), 6.51 (br s, 1H), 6.42 (d, J=8.2 Hz, 1H), 4.34 (t, J=7.0 Hz, 1H), 3.39 (d, J=11.7 Hz, 1H), 3.13 (dd, J=6.9, 11.5 Hz, 1H), 1.91 (dd, J=8.8, 14.7 Hz, 1H), 1.73-1.78 (m, 1H), 1.71 (s, 6H), 1.47 (s, 3H), 1.41 (s, 3H).

Step 6—Preparation of (S)-1,1,1-trifluoro-2-methyl-propan-2-yl (4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate and (R)-1,1,1-trifluoro-2-methylpropan-2-yl (4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate

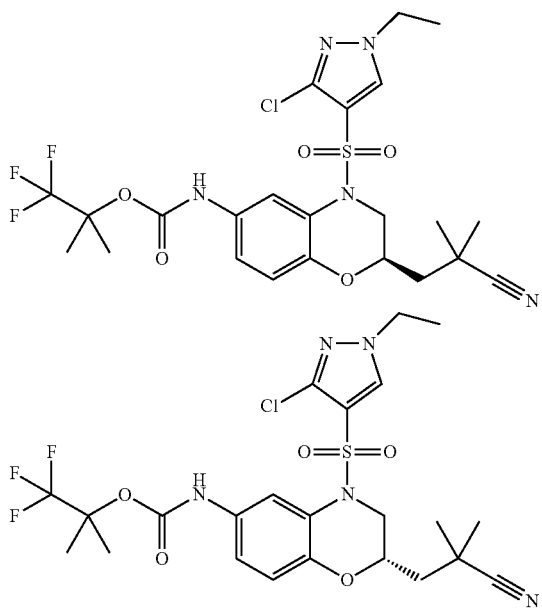

To a solution of (R or S)-1,1,1-trifluoro-2-methylpropan-2-yl(2-(2-cyano-2-methylpropyl)-3,4-dihydro-2H-benzo[b][1,4]oxazin-6-yl)carbamate (Isomer 1 from Step 5; 60 mg, 0.156 mmol, isomer 1) in THF (2 mL) were added pyridine (0.5 ml, 6.18 mmol) and 3-chloro-1-ethyl-1H-pyrazole-4-sulfonyl chloride (150 mg, 0.655 mmol) in one portion at room temperature under nitrogen. The reaction was stirred at 60° C. overnight, then evaporated to dryness. The crude product was purified by prep-TLC (petroleum ether:EtOAc=2:1) to afford the title compound (Example 94A) as a yellow oil.

The other enantiomer, (Example 94B) was prepared using a similar procedure as described above starting with Isomer 2 from Step 5. Both enantiomers have the same analytical data: LCMS (ESI) calculated for $C_{23}H_{28}ClF_3N_5O_5S$ [M+H]$^+$: 578, found: 578. $^1$H NMR (CDCl$_3$, 400 MHz) δ 8.12 (brs, 1H), 7.85 (brs, 1H), 6.78-6.87 (m, 2H), 6.75 (brs, 1H), 4.18-4.31 (m, 2H), 4.07 (q, J=7.2 Hz, 2H), 3.45 (dd, J=8.4, 12.7 Hz, 1H), 1.88 (d, J=8.6 Hz, 1H), 1.78 (brs, 1H), 1.72 (br s, 6H), 1.40-1.47 (m, 9H).

Example 95—Preparation of Additional Gem-Dimethyl Propionic Nitriles

The compounds in Table 28 below were prepared based on the experimental procedures described in Example 94 and elsewhere in the detailed description, and can be achieved by one of skill in the art in light of the present disclosure.

TABLE 28

| Ex. No. | Structure | Name | Observed m/z |
|---|---|---|---|
| 95A | 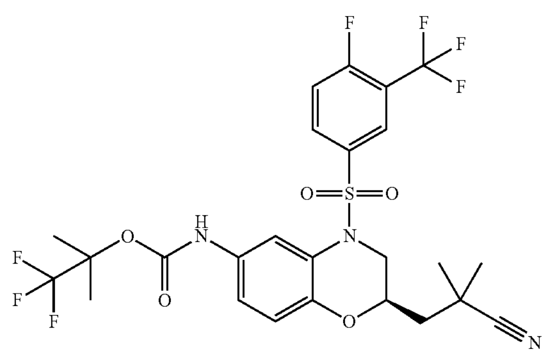 [SMILES: CC(C)(C#N)C[C@@H]1CN(S(=O)(=O)c2ccc(F)c(C(F)(F)F)c2)c2cc(NC(=O)OC(C)(C)C(F)(F)F)ccc2O1] | (R)-1,1,1-trifluoro-2-methylpropan-2-yl (2-(2-cyano-2-methylpropyl)-4-((4-fluoro-3-(trifluoromethyl)phenyl)sulfonyl)-3,4-dihydro-2H-benzo[b][1,4]oxazin-6-yl)carbamate | 612 (M + H)+ |
| 95B | 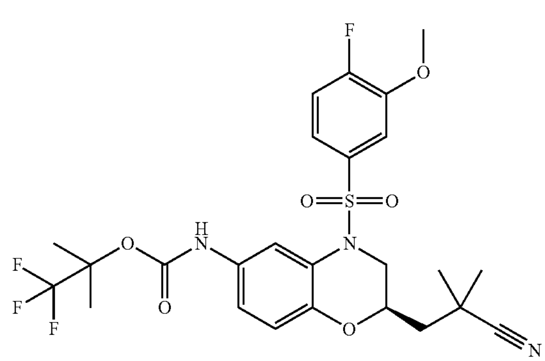 [SMILES: COc1cc(S(=O)(=O)N2C[C@@H](CC(C)(C)C#N)Oc3ccc(NC(=O)OC(C)(C)C(F)(F)F)cc32)ccc1F] | (R)-1,1,1-trifluoro-2-methylpropan-2-yl (2-(2-cyano-2-methylpropyl)-4-((4-fluoro-3-methoxyphenyl)sulfonyl)-3,4-dihydro-2H-benzo[b][1,4]oxazin-6-yl)carbamate | 596 (M + Na)+ |

TABLE 28-continued

| Ex. No. | Structure | Name | Observed m/z |
|---|---|---|---|
| 95C | 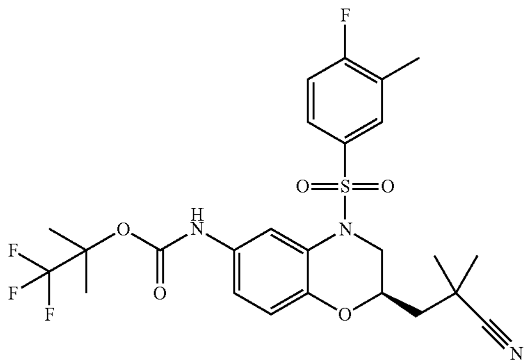 [SMILES: Cc1cc(S(=O)(=O)N2C[C@@H](CC(C)(C)C#N)Oc3ccc(NC(=O)OC(C)(C)C(F)(F)F)cc32)ccc1F] | (R)-1,1,1-trifluoro-2-methylpropan-2-yl (2-(2-cyano-2-methylpropyl)-4-((4-fluoro-3-methylphenyl)sulfonyl)-3,4-dihydro-2H-benzo[b][1,4]oxazin-6-yl)carbamate | 558 (M + H)+ |
| 95D | 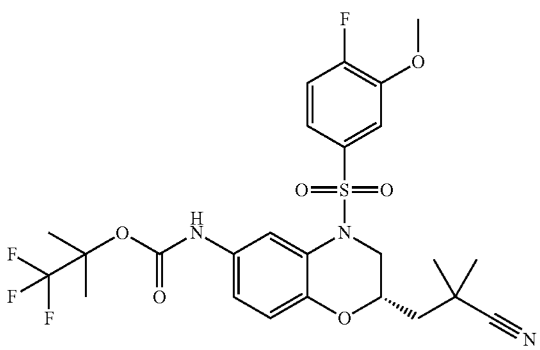 [SMILES: COc1cc(S(=O)(=O)N2C[C@H](CC(C)(C)C#N)Oc3ccc(NC(=O)OC(C)(C)C(F)(F)F)cc32)ccc1F] | (S)-1,1,1-trifluoro-2-methylpropan-2-yl (2-(2-cyano-2-methylpropyl)-4-((4-fluoro-3-methoxyphenyl)sulfonyl)-3,4-dihydro-2H-benzo[b][1,4]oxazin-6-yl)carbamate | 596 (M + Na)+ |
| 95E | 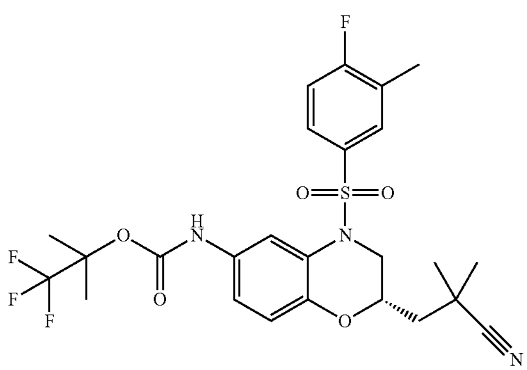 [SMILES: Cc1cc(S(=O)(=O)N2C[C@H](CC(C)(C)C#N)Oc3ccc(NC(=O)OC(C)(C)C(F)(F)F)cc32)ccc1F] | (S)-1,1,1-trifluoro-2-methylpropan-2-yl (2-(2-cyano-2-methylpropyl)-4-((4-fluoro-3-methylphenyl)sulfonyl)-3,4-dihydro-2H-benzo[b][1,4]oxazin-6-yl)carbamate | 580 (M + Na)+ |
| 95F | 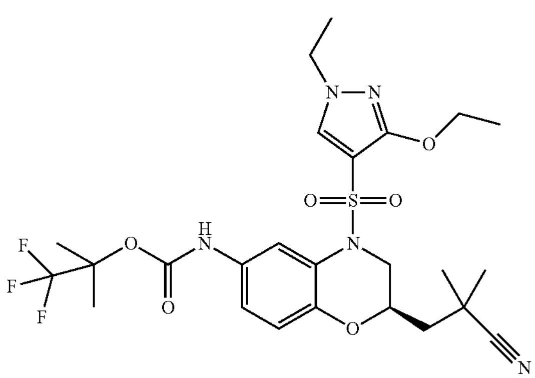 [SMILES: CCOc1nn(CC)cc1S(=O)(=O)N1C[C@@H](CC(C)(C)C#N)Oc2ccc(NC(=O)OC(C)(C)C(F)(F)F)cc21] | (R)-1,1,1-trifluoro-2-methylpropan-2-yl (2-(2-cyano-2-methylpropyl)-4-((3-ethoxy-1-ethyl-1H-pyrazol-4-yl)sulfonyl)-3,4-dihydro-2H-benzo[b][1,4]oxazin-6-yl)carbamate | 588 (M + H)+ |

TABLE 28-continued

| Ex. No. | Structure | Name | Observed m/z |
|---|---|---|---|
| 95G | 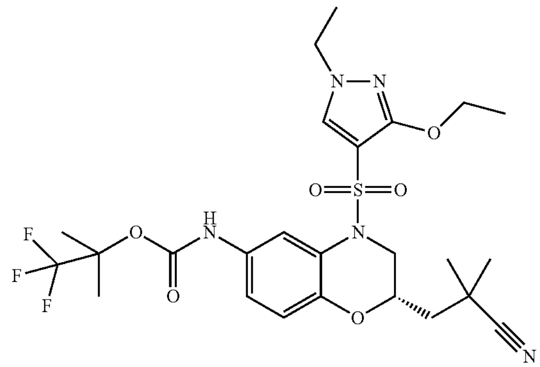 [SMILES: CCOc1nn(CC)cc1S(=O)(=O)N1C[C@H](CC(C)(C)C#N)Oc2ccc(NC(=O)OC(C)(C)C(F)(F)F)cc21] | (S)-1,1,1-trifluoro-2-methylpropan-2-yl (2-(2-cyano-2-methylpropyl)-4-((3-ethoxy-1-ethyl-1H-pyrazol-4-yl)sulfonyl)-3,4-dihydro-2H-benzo[b][1,4]oxazin-6-yl)carbamate | 588 (M + H)+ |

Example 96—Preparation of (S)-1,1,1-trifluoro-2-methylpropan-2-yl (2-(3-(cyclopropanesulfonamido)-3-oxopropyl)-4-((4-fluoro-3-(trifluoromethyl)phenyl)sulfonyl)-3,4-dihydro-2H-benzo[b][1,4]oxazin-6-yl)carbamate (Example 96)

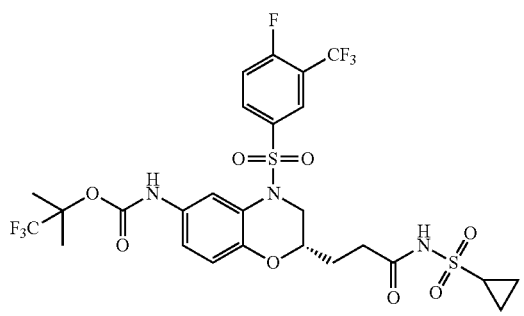 [SMILES: CC(C)(OC(=O)Nc1ccc2c(c1)N(S(=O)(=O)c1ccc(F)c(C(F)(F)F)c1)C[C@H](CCC(=O)NS(=O)(=O)C1CC1)O2)C(F)(F)F]

To a solution of (S)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid (50 mg, 0.82 mmol) in DCM (1 mL) was added EDCI (32 mg, 0.17 mmol) and DMAP (20 mg, 0.17 mmol) at 0° C. The reaction was stirred at room temperature for 1 h, then cyclopropanesulfonamide (23 mg, 0.17 mmol) and DIPEA (21 mg, 0.17 mmol) were added. After stirring for 12 h at room temperature, the reaction mixture was diluted with water and 1N HCl, then extracted 3× with EtOAc. The combined organic layers were washed with water, brine, dried over $Na_2SO_4$ and concentrated in vacuo. The crude product was purified by prep-HPLC (MeCN/water using TFA buffer) to give the title compound as a colorless oil. LCMS (ESI) calculated for $C_{26}H_{27}F_7N_3O_8S_2$ [M+H]+: 706, found: 706. $^1$H-NMR (CDCl$_3$, 400 MHz) δ 8.28 (1H, s), 8.09 (1H, d, J=4.4 Hz), 7.99 (1H, s), 7.86 (1H, s), 7.33-7.38 (1H, m), 6.97 (1H, dd, J=2.0, 8.8 Hz), 6.78 (1H, d, J=9.2 Hz), 6.65 (1H, brs), 4.29 (1H, d, J=14.0 Hz), 3.73-3.75 (1H, m), 3.24 (1H, dd, J=9.6, 13.6 Hz), 2.87-2.95 (1H, m), 2.49-2.60 (2H, m), 1.97-2.07 (1H, m), 1.80-1.87 (1H, m), 1.76 (6H, s), 1.36-1.38 (2H, m), 1.10-1.12 (2H, m).

Example 97—Preparation of 1,1,1-trifluoro-2-methylpropan-2-yl ((S)-4-((3-chloro-1-ethyl-1H-pyrazol-4-yl)sulfonyl)-2-((S)-3-(cyclopropanesulfonamido)-2-methyl-3-oxopropyl)-3,4-dihydro-2H-benzo[b][1,4]oxazin-6-yl)carbamate and 1,1,1-trifluoro-2-methylpropan-2-yl ((S)-4-((3-chloro-1-ethyl-1H-pyrazol-4-yl)sulfonyl)-2-((R)-3-(cyclopropanesulfonamido)-2-methyl-3-oxopropyl)-3,4-dihydro-2H-benzo[b][1,4]oxazin-6-yl)carbamate (Examples 97A and 97B)

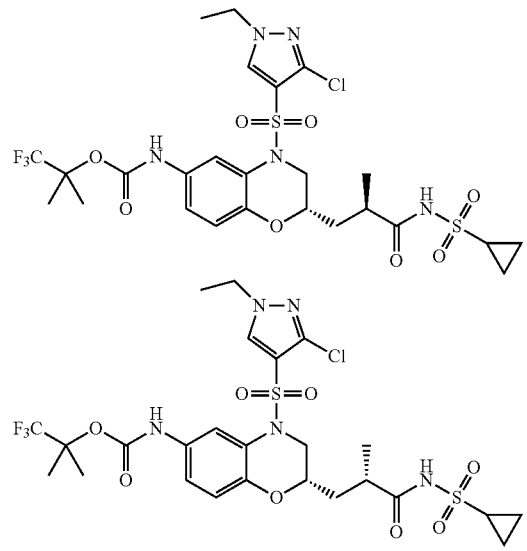

A mixture of (S or R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid (50 mg, 0.086 mmol), 2-(3H-[1,2,3]triazolo[4,5-b]pyridine-3-yl)-1,1,3,3-tetramethylisouronium hexafluorophosphate(V) (48.9 mg, 0.129 mmol) and N-ethyl-N-isopropylpropan-2-amine (33.3 mg, 0.257 mmol) in anhydrous DMF (0.5 mL) was stirred at 20° C. for 20 minutes, followed by the addition of cyclopropanesulfonamide (31.2 mg, 0.257 mmol). After stirring for 24 hours, 2 mL water was added to the reaction and the resulting mixture extracted with ethyl acetate (1.5 mL×3). The combined organic layers were dried over anhydrous sodium sulfate, filtered and the filtrate was concentrated in vacuo. The crude product was purified by prep-HPLC (MeCN/water using TFA buffer) to afford the title compound (Example 97A) as a white solid. LCMS (ESI) calculated for $C_{25}H_{32}ClF_3N_5O_8S_2$ [M+H]$^+$: 686, found: 686. $^1$H-NMR (CDCl$_3$, 400 MHz) δ 8.57 (1H, s), 8.19 (1H, s), 7.89 (1H, s), 6.86-6.92 (2H, m), 6.77 (1H, s), 4.34 (1H, dd, J=14.0, 2.0 Hz), 4.19 (2H, q, J=7.2 Hz), 4.06 (1H, br s), 3.41-3.57 (1H, m), 2.98-3.01 (1H, m), 2.78-2.80 (1H, m), 2.05-2.15 (1H, m), 1.81 (6H, s), 1.75-1.78 (1H, m), 1.55 (3H, t, J=7.6 Hz), 1.41-1.46 (1H, m), 1.27-1.37 (3H, m), 1.13-1.21 (1H, m), 1.02-1.08 (1H, m)

The other diastereomer (Example 97B) was prepared using a similar procedure as described above. LCMS (ESI) calculated for $C_{25}H_{32}ClF_3N_5O_8S_2$ [M+H]$^+$: 686, found: 686. $^1$H-NMR (CDCl$_3$, 400 MHz) δ 8.56 (1H, s), 8.12 (1H, s), 7.82 (1H, s), 6.81-6.84 (2H, m), 6.69 (1H, s), 4.37 (1H, d, J=13.6 Hz), 4.01-4.11 (4H, m), 3.26-3.30 (1H, m), 2.93-2.96 (1H, m), 2.65-2.67 (1H, m), 2.02-2.09 (1H, m), 1.73 (6H, s), 1.44 (3H, t, J=7.2 Hz), 1.32-1.40 (2H, m), 1.25 (3H, d, J=6.8 Hz), 1.11 (2H, d, J=8.0 Hz).

Example 98—Preparation of Additional Propionic Sulfonylamides of Benzoxazines

The compounds in Table 29 below were prepared based on the experimental procedures described in Examples 96 and 97 and elsewhere in the detailed description, and can be achieved by one of skill in the art in light of the present disclosure.

TABLE 29

| Ex. No. | Structure | Name | Observed m/z |
|---|---|---|---|
| 98A | 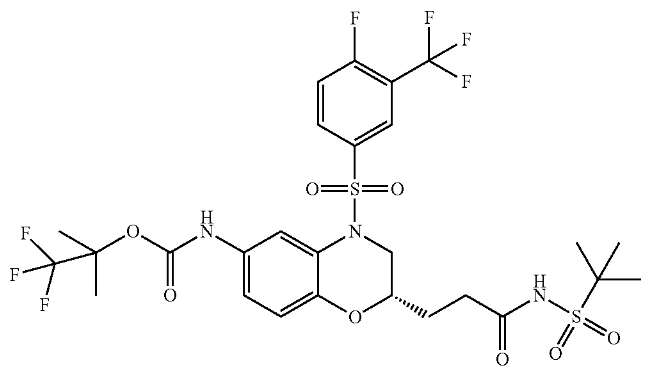 [SMILES: CC(C)(OC(=O)Nc1ccc2c(c1)N(S(=O)(=O)c1ccc(F)c(C(F)(F)F)c1)C[C@H](CCC(=O)NS(=O)(=O)C(C)(C)C)O2)C(F)(F)F] | 2,2,2-trifluoro-1,1-dimethylethyl [(2S)-2-{3-[(tert-butylsulfonyl)amino]-3-oxopropyl}-4-{[4-fluoro-3-(trifluoromethyl)phenyl]sulfonyl}-3,4-dihydro-2H-1,4-benzoxazin-6-yl]carbamate | 722 (M + H)+ |
| 98B | 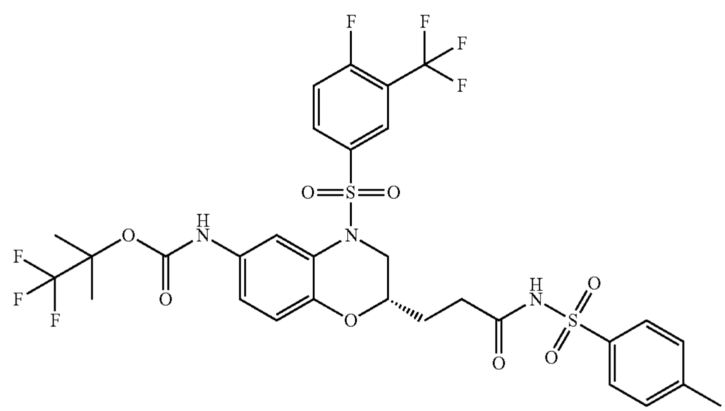 [SMILES: Cc1ccc(S(=O)(=O)NC(=O)CC[C@H]2CN(S(=O)(=O)c3ccc(F)c(C(F)(F)F)c3)c3cc(NC(=O)OC(C)(C)C(F)(F)F)ccc3O2)cc1] | 2,2,2-trifluoro-1,1-dimethylethyl [(2S)-4-{[4-fluoro-3-(trifluoromethyl)phenyl]sulfonyl}-2-(3-{[(4-methylphenyl)sulfonyl]amino}-3-oxopropyl)-3,4-dihydro-2H-1,4-benzoxazin-6-yl]carbamate | 756 (M + H)+ |
| 98C | 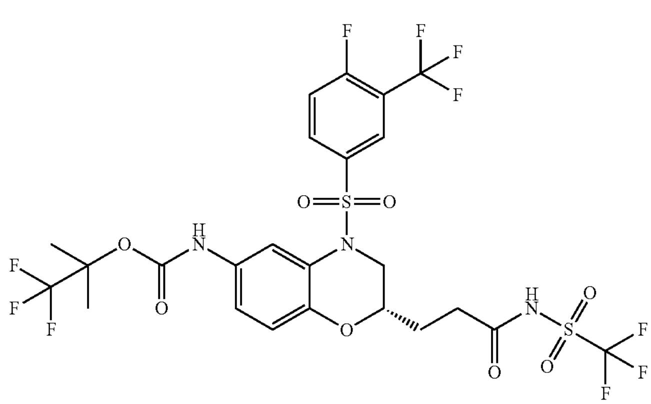 [SMILES: CC(C)(OC(=O)Nc1ccc2c(c1)N(S(=O)(=O)c1ccc(F)c(C(F)(F)F)c1)C[C@H](CCC(=O)NS(=O)(=O)C(F)(F)F)O2)C(F)(F)F] | 2,2,2-trifluoro-1,1-dimethylethyl [(2S)-4-{[4-fluoro-3-(trifluoromethyl)phenyl]sulfonyl}-2-(3-oxo-3-{[(trifluoromethyl)sulfonyl]amino}propyl)-3,4-dihydro-2H-1,4-benzoxazin-6-yl]carbamate | 734 (M + H)+ |

TABLE 29-continued

| Ex. No. | Structure | Name | Observed m/z |
|---|---|---|---|
| 98D | 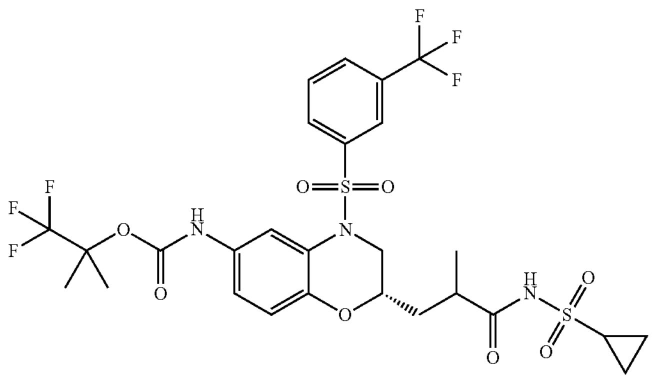 [SMILES: CC(C[C@H]1CN(S(=O)(=O)c2cccc(C(F)(F)F)c2)c2cc(NC(=O)OC(C)(C)C(F)(F)F)ccc2O1)C(=O)NS(=O)(=O)C1CC1] | 1,1,1-trifluoro-2-methylpropan-2-yl ((S)-2-((R and S)-3-(cyclopropanesulfonamido)-2-methyl-3-oxopropyl)-4-((3-(trifluoromethyl)phenyl)sulfonyl)-3,4-dihydro-2H-benzo[b][1,4]oxazin-6-yl)carbamate | 724 (M + Na)+ |
| 98E | 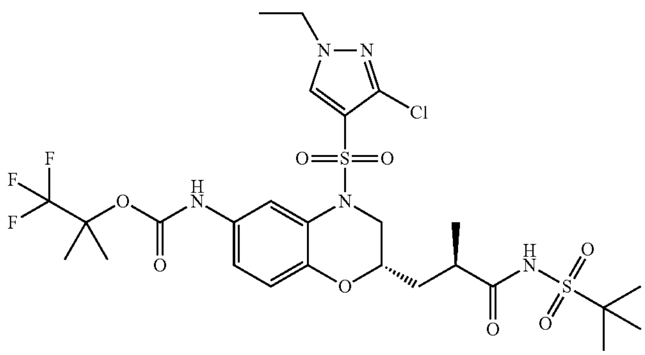 [SMILES: CCn1cc(S(=O)(=O)N2C[C@H](C[C@@H](C)C(=O)NS(=O)(=O)C(C)(C)C)Oc3ccc(NC(=O)OC(C)(C)C(F)(F)F)cc32)c(Cl)n1] | 1,1,1-trifluoro-2-methylpropan-2-yl ((S)-4-((3-chloro-1-ethyl-1H-pyrazol-4-yl)sulfonyl)-2-((R or S)-3-(1,1-dimethylethylsulfonamido)-2-methyl-3-oxopropyl)-3,4-dihydro-2H-benzo[b][1,4]oxazin-6-yl)carbamate | 702 (M + H)+ |
| 98F | 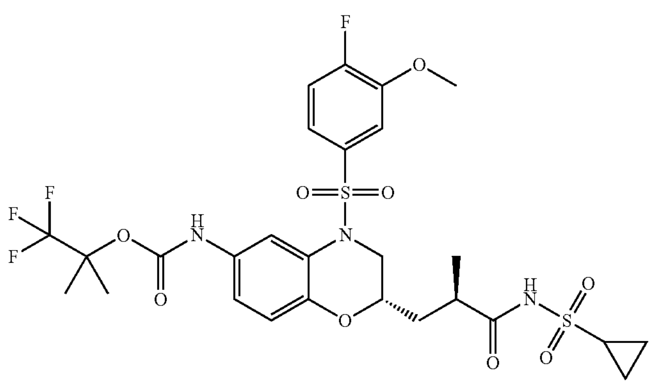 [SMILES: COc1cc(S(=O)(=O)N2C[C@H](C[C@@H](C)C(=O)NS(=O)(=O)C3CC3)Oc3ccc(NC(=O)OC(C)(C)C(F)(F)F)cc32)ccc1F] | 1,1,1-trifluoro-2-methylpropan-2-yl ((S)-2-((R or S)-3-(cyclopropanesulfonamido)-2-methyl-3-oxopropyl)-4-((4-fluoro-3-methoxyphenyl)sulfonyl)-3,4-dihydro-2H-benzo[b][1,4]oxazin-6-yl)carbamate | 704 (M + Na)+ |
| 98G | 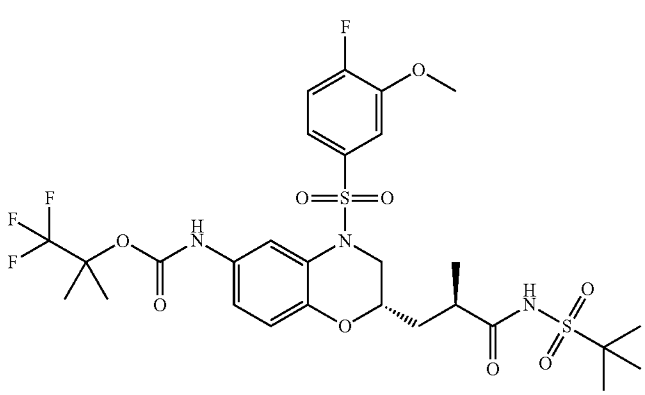 [SMILES: COc1cc(S(=O)(=O)N2C[C@H](C[C@@H](C)C(=O)NS(=O)(=O)C(C)(C)C)Oc3ccc(NC(=O)OC(C)(C)C(F)(F)F)cc32)ccc1F] | 1,1,1-trifluoro-2-methylpropan-2-yl ((S)-2-((R or S)-3-(1,1-dimethylethylsulfonamido)-2-methyl-3-oxopropyl)-4-((4-fluoro-3-methoxyphenyl)sulfonyl)-3,4-dihydro-2H-benzo[b][1,4]oxazin-6-yl)carbamate | 698 (M + H)+ |

TABLE 29-continued

| Ex. No. | Structure | Name | Observed m/z |
|---|---|---|---|
| 98H | 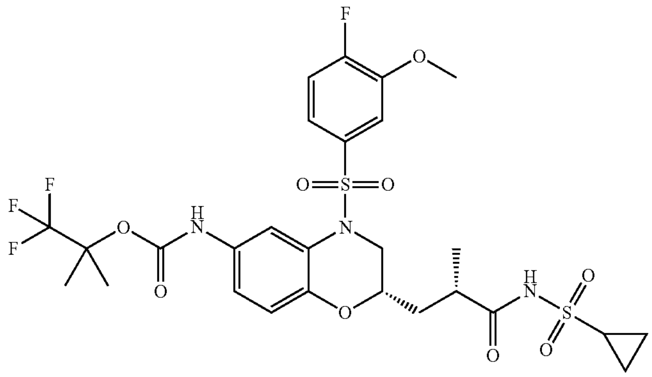 [SMILES: COc1cc(S(=O)(=O)N2C[C@H](C[C@H](C)C(=O)NS(=O)(=O)C3CC3)Oc3ccc(NC(=O)OC(C)(C)C(F)(F)F)cc32)ccc1F] | 1,1,1-trifluoro-2-methylpropan-2-yl ((S)-2-((R or S)-3-(cyclopropanesulfonamido)-2-methyl-3-oxopropyl)-4-((4-fluoro-3-methoxyphenyl)sulfonyl)-3,4-dihydro-2H-benzo[b][1,4]oxazin-6-yl)carbamate | 704 (M + Na)+ |
| 98i | 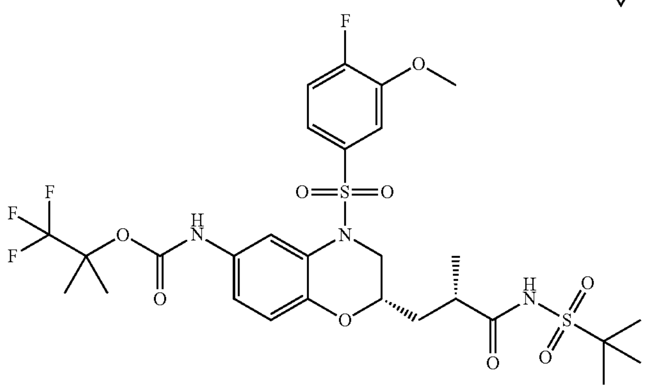 | 1,1,1-trifluoro-2-methylpropan-2-yl ((S)-2-((R or S)-3-(1,1-dimethylethylsulfonamido)-2-methyl-3-oxopropyl)-4-((4-fluoro-3-methoxyphenyl)sulfonyl)-3,4-dihydro-2H-benzo[b][1,4]oxazin-6-yl)carbamate | 696 (M − H)− |
| 98J | 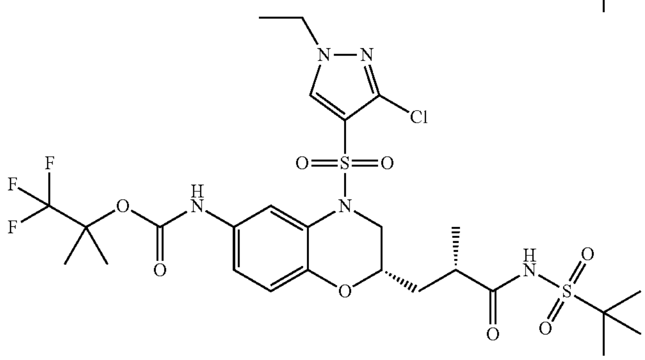 | 1,1,1-trifluoro-2-methylpropan-2-yl ((S)-4-((3-chloro-1-ethyl-1H-pyrazol-4-yl)sulfonyl)-2-((R or S)-3-(1,1-dimethylethylsulfonamido)-2-methyl-3-oxopropyl)-3,4-dihydro-2H-benzo[b][1,4]oxazin-6-yl)carbamate | 702 (M + H)+ |

Example 99—Preparation of (S)-1,1,1-trifluoro-2-methylpropan-2-yl (4-((4-fluoro-3-(trifluoromethyl)phenyl)sulfonyl)-2-(oxetan-3-ylmethyl)-3,4-dihydro-2H-benzo[b][1,4]oxazin-6-yl)carbamate (Example 99)

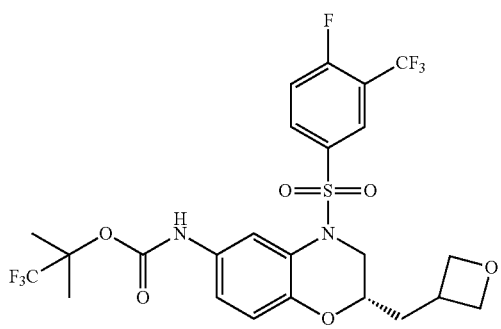 [SMILES: CC(C)(OC(=O)Nc1ccc2c(c1)N(S(=O)(=O)c1ccc(F)c(C(F)(F)F)c1)C[C@H](CC1COC1)O2)C(F)(F)F]

Step 1—Preparation of (S)-2-((4-benzyl-6-nitro-3,4-dihydro-2H-benzo[b][1,4]oxazin-2-yl)methyl)propane-1,3-diol

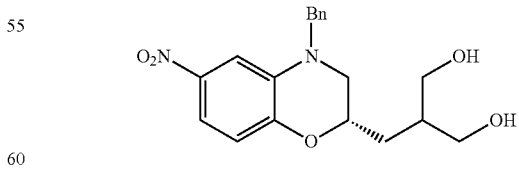

To a solution of (S)-diethyl 2-((4-benzyl-6-nitro-3,4-dihydro-2H-benzo[b][1,4]oxazin-2-yl)methyl)malonate (700 mg, 1.58 mmol) in MeOH (20 mL) was added NaBH₄ (1.00 g, 26.4 mmol) in portions and the resulting mixture was stirred at 20° C. for 6 h. The reaction was quenched with H₂O, extracted with EtOAc (3×50 mL), washed with H₂O and brine and dried over Na₂SO₄. The combined organic layers were concentrated in vacuo and purified by flash column chromatography (0-60% ethyl acetate in petroleum ether) to afford the title compound as yellow oil. LCMS (ESI) calculated for $C_{19}H_{23}N_2O_5$ [M+H]⁺: 359.2, found: 359.1, ¹H NMR (400 MHz, CDCl₃) δ 7.47-7.56 (m, 2H), 7.21-7.33 (m, 3H), 7.19 (s, 2H), 6.76 (d, J=8.2 Hz, 1H), 4.39-4.49 (m, 2H), 4.23 4.33 (m, 1H), 3.65-3.86 (m, 4H), 3.20-3.31 (m, 1H), 3.04-3.16 (m, 1H), 1.69-1.80 (m, 3H).

Step 2—Preparation of 3-((S)-4-benzyl-6-nitro-3,4-dihydro-2H-benzo[b][1,4]oxazin-2-yl)-2-(hydroxymethyl)propyl 4-methylbenzenesulfonate

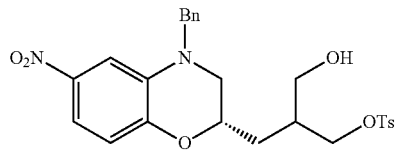 [SMILES: Cc1ccc(S(=O)(=O)OCC(CO)C[C@H]2CN(Cc3ccccc3)c3cc([N+](=O)[O-])ccc3O2)cc1]

To a solution of (S)-2-((4-benzyl-6-nitro-3,4-dihydro-2H-benzo[b][1,4]oxazin-2-yl)methyl)propane-1,3-diol (500 mg, 1.40 mmol) in 20 mL of THF was added butyllithium (1.0 mL, 1.4 mmol) at −70° C. under N₂ and the reaction was stirred at −70° C. for 1 h, then treated with 4-methylbenzene-1-sulfonyl chloride (300 mg, 1.57 mmol) in 5 mL of THF. After 1 h at −70° C., the reaction was slowly warmed to room temperature and stirred for an additional 2 h. The reaction mixture was then quenched with aq. NH₄Cl, extracted with EtOAc (3×50 mL) and the combined organic layer was concentrated in vacuo. The crude product was purified by flash column chromatography (0-70% ethyl acetate in petroleum ether) to afford the title compound as yellow oil. LCMS (ESI) calculated for $C_{26}H_{29}N_2O_7S$ [M+H]⁺: 513.2, found: 513.2, ¹H NMR (400 MHz, CDCl₃) δ 7.71 (dd, J=8.0 Hz, 2.5 Hz, 2H), 7.43-7.54 (m, 2H), 7.13-7.34 (m, 7H), 6.69 (t, J=8.8 Hz, 1H), 4.36-4.48 (m, 2H), 4.01-4.26 (m, 3H), 3.54-3.71 (m, 2H), 3.22 (d, J=12.1 Hz, 1H), 2.99 3.10 (m, 2H), 2.37 (d, J=2.7 Hz, 3H), 2.16 (d, J=5.5 Hz, 1H), 1.56-1.67 (m, 2H).

Step 3—Preparation of (S)-4-benzyl-6-nitro-2-(oxetan-3-ylmethyl)-3,4-dihydro-2H-benzo[b][1,4]oxazine

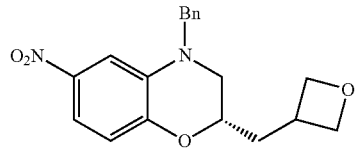 [SMILES: O=[N+]([O-])c1ccc2c(c1)N(Cc1ccccc1)C[C@H](CC1COC1)O2]

To a solution of 3-((S)-4-benzyl-6-nitro-3,4-dihydro-2H-benzo[b][1,4]oxazin-2-yl)-2-(hydroxymethyl)propyl 4-methylbenzenesulfonate (650 mg, 1.27 mmol) in 20 mL of THF was added sodium hydride (60%, 152 mg, 3.80 mmol) at 0° C. The reaction was stirred at room temperature for 20 h, then quenched with aq.NH₄Cl and extracted with EtOAc (3×20 mL). The combined organic layer was concentrated in vacuo and the crude product was purified by flash column chromatography (0-50% ethyl acetate in petroleum ether) to afford the title compound as yellow oil. LCMS (ESI) calculated for $C_{19}H_{21}N_2O_4$ [M+H]⁺: 341.1, found: 341.1, ¹H NMR (400 MHz, CDCl₃) δ 7.35-7.51 (m, 2H), 7.10-7.25 (m, 5H), 6.63 (d, J=8.6 Hz, 1H), 4.61-4.74 (m, 2H), 4.21-4.41 (m, 4H), 4.00 (brs, 1H), 3.06-3.20 (m, 2H), 2.97 (dd, J=12.1 Hz, 7.8 Hz, 1H), 1.89-2.00 (m, 1H), 1.85-1.74 (m, 1H).

Step 4—Preparation of (S)-2-(oxetan-3-ylmethyl)-3,4-dihydro-2H-benzo[b][1,4]oxazin-6-amine

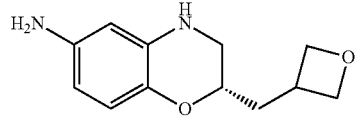

To a solution of (S)-4-benzyl-6-nitro-2-(oxetan-3-ylmethyl)-3,4-dihydro-2H-benzo[b][1,4]oxazine (400 mg, 1.18 mmol) in 20 mL of MeOH was added 10% Pd/C (300 mg, 2.82 mmol), the reaction was stirred under H₂ (50 psi) for 4 h. The reaction mixture was then filtered and concentrated in vacuo to afford the title compound as brown oil. LCMS (ESI) calculated for $C_{12}H_{17}N_2O_2$ [M+H]⁺: 221.1, found: 221.1.

Step 5—Preparation of (S)-1,1,1-trifluoro-2-methylpropan-2-yl (2-(oxetan-3-ylmethyl)-3,4-dihydro-2H-benzo[b][1,4]oxazin-6-yl)carbamate

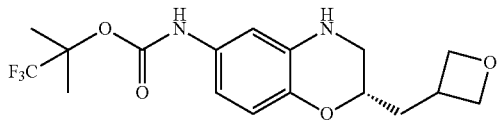 [SMILES: CC(C)(OC(=O)Nc1ccc2c(c1)NC[C@H](CC1COC1)O2)C(F)(F)F]

To a solution of (S)-2-(oxetan-3-ylmethyl)-3,4-dihydro-2H-benzo[b][1,4]oxazin-6-amine (250 mg, 1.14 mmol) in DMSO (5 mL) was added 3-methyl-1-(((1,1,1-trifluoro-2-methylpropan-2-yl)oxy)carbonyl)-1H-imidazol-3-ium iodide (413 mg, 1.14 mmol). The resulting mixture was stirred at room temperature for 0.5 h, then quenched with NH₄Cl (aq) and extracted with EtOAc (3×20 mL). The combined organic layer was concentrated in vacuo and the crude product was purified by flash column chromatography (0-40% ethyl acetate in petroleum ether) to afford the title compound as yellow oil. LCMS (ESI) calculated for $C_{17}H_{22}F_3N_2O_4$ [M+H]⁺: 375.1, found: 375.1, ¹H NMR (400 MHz, DMSO) δ 9.38 (br s, 1H), 6.81 (br s, 1H), 6.50 (s, 2H), 5.85 (br s, 1H), 4.59-4.75 (m, 2H), 4.33 (q, J=6.0 Hz, 2H), 3.89 (d, J=7.0 Hz, 1H), 3.16-3.26 (m, 2H), 2.87-2.96 (m, 1H), 1.88-2.03 (m, 2H), 1.69 (s, 6H).

361

Step 6—Preparation of (S)-1,1,1-trifluoro-2-methyl-propan-2-yl (4-((4-fluoro-3-(trifluoromethyl)phenyl)sulfonyl)-2-(oxetan-3-ylmethyl)-3,4-dihydro-2H-benzo[b][1,4]oxazin-6-yl)carbamate

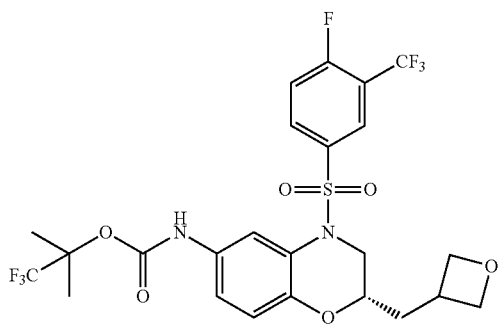 [SMILES: CC(C)(OC(=O)Nc1ccc2c(c1)N(S(=O)(=O)c1ccc(F)c(C(F)(F)F)c1)C[C@H](CC1COC1)O2)C(F)(F)F]

To a solution of (S)-1,1,1-trifluoro-2-methylpropan-2-yl (2-(oxetan-3-ylmethyl)-3,4-dihydro-2H-benzo[b][1,4]oxazin-6-yl)carbamate (30 mg, 0.080 mmol) in THF (4 mL) and pyridine (0.5 mL) was added 4-fluoro-3-(trifluoromethyl)benzene-1-sulfonyl chloride (50 mg, 0.190 mmol). The resulting mixture was stirred at 50° C. for 6 h, then quenched with 10 mL of water and extracted with EtOAc (3×10 mL). The combined organic layers were concentrated in vacuo and the crude product was purified by prep-HPLC to afford the title compound as a white solid. LCMS (ESI) calculated for $C_{24}H_{24}F_7N_2O_6S$ [M+H]$^+$: 601.1, found: 601.1, $^1$H NMR (400 MHz, MeOD) 8.18 (d, J=7.4 Hz, 2H), 8.03 (br s, 1H), 7.53-7.59 (m, 1H), 6.97 (dd, J=8.8 Hz, 2.2 Hz, 1H), 6.71 (d, J=9.0 Hz, 1H), 4.79 (d, J=5.9 Hz, 2H), 4.45 (dd, J=11.3 Hz, 5.5 Hz, 2H), 4.32-4.37 (m, 1H), 3.62 (brs, 1H), 3.35-3.39 (m, 1H), 3.23-3.29 (m, 1H), 1.95-2.05 (m, 2H), 1.77 (s, 6H).

Example 100—Preparation of (S)-1,1,1-trifluoro-2-methylpropan-2-yl (4-((3-chloro-1-ethyl-1H-pyrazol-4-yl)sulfonyl)-2-(2-(5-oxo-4,5-dihydro-1H-1,2,4-triazol-3-yl)ethyl)-3,4-dihydro-2H-benzo[b][1,4]oxazin-6-yl)carbamate (Example 100)

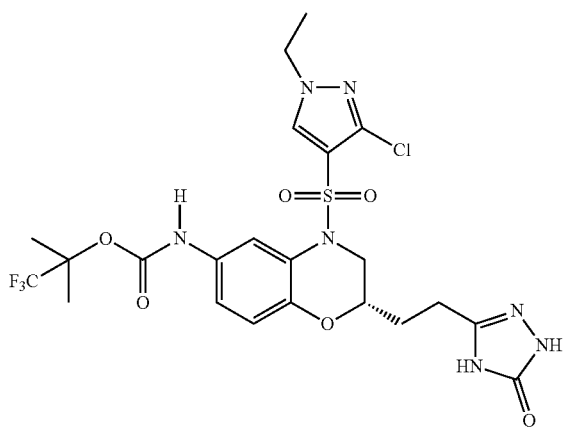 [SMILES: CCn1cc(S(=O)(=O)N2C[C@H](CCc3n[nH]c(=O)[nH]3)Oc3ccc(NC(=O)OC(C)(C)C(F)(F)F)cc32)c(Cl)n1]

362

Step 1—Preparation of (S)-ethyl 3-(4-benzyl-6-nitro-3,4-dihydro-2H-benzo[b][1,4]oxazin-2-yl)propanoate

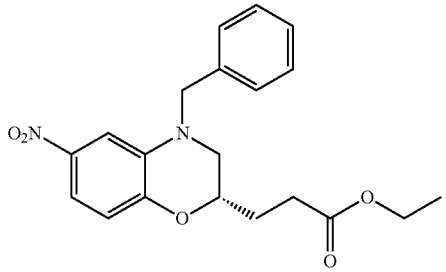 [SMILES: CCOC(=O)CC[C@H]1CN(Cc2ccccc2)c2cc([N+](=O)[O-])ccc2O1]

To a solution of (S)-diethyl 2-((4-benzyl-6-nitro-3,4-dihydro-2H-benzo[b][1,4]oxazin-2-yl)methyl)malonate (5 g, 11.30 mmol) in DMSO (50 mL) was added lithium chloride (2.395 g, 56.5 mmol). The reaction was stirred at 170° C. for 10 hours, then cooled to room temperature and diluted with ethyl acetate (200 mL) and washed with water (3×100 mL). The separated organic layers were dried with $Na_2SO_4$ and concentrated under reduced pressure to give the crude product, which was purified by flash column chromatography (petroleum ether:ethyl acetate=10:1 to 5:1 to 3:1) to give the titled compound as orange oil. LCMS (ESI) calculated for $C_{20}H_{23}N_2O_5$ [M+H]$^+$: 371.1, found: 371.0.

Step 2—Preparation of (S)-3-(4-benzyl-6-nitro-3,4-dihydro-2H-benzo[b][1,4]oxazin-2-yl)propanoic Acid

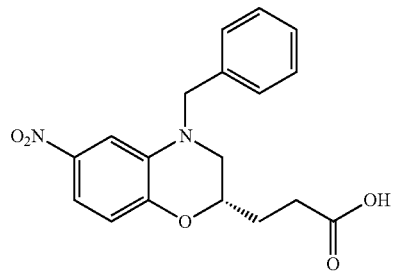 [SMILES: O=C(O)CC[C@H]1CN(Cc2ccccc2)c2cc([N+](=O)[O-])ccc2O1]

To a solution of ethyl 3-(4-benzyl-6-nitro-3,4-dihydro-2H-benzo[b][1,4]oxazin-2-yl)propanoate (500 mg, 1.350 mmol) in dioxane (5 mL) and water (3 mL) was added lithium hydroxide (48.5 mg, 2.025 mmol). The reaction was stirred at 20° C. for 4 hours, then diluted with water (10 mL) and extracted with ethyl acetate (3×5 mL). The aqueous layer was acidified with hydrochloric acid (1M, 10 mL) to pH=3 and extracted with ethyl acetate (10 mL×3). The combined organic layers were dried ($Na_2SO_4$), filtered and concentrated under reduced pressure to give the titled compound as orange oil. LCMS (ESI) calculated for $C_{18}H_{19}N_2O_5$ [M+H]$^+$: 343.1, found: 343.1; $^1$H-NMR (CDCl$_3$, 400 MHz) δ 7.52 (2H, s), 7.24-7.31 (5H, m), 6.77-6.79 (1H, m), 4.44 (2H, s), 4.22-4.24 (1H, m), 3.26-3.29 (1H, m), 3.08-3.13 (1H, m), 2.58 (2H, s), 1.91-1.93 (2H, m).

Step 3—Preparation of (S)-2-(3-(4-benzyl-6-nitro-3,4-dihydro-2H-benzo[b][1,4]oxazin-2-yl)propanoyl) hydrazinecarboxamide

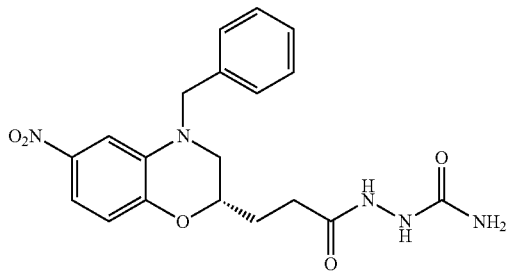 [SMILES: NC(=O)NNC(=O)CC[C@H]1CN(Cc2ccccc2)c2cc([N+](=O)[O-])ccc2O1]

To a solution of (S)-3-(4-benzyl-6-nitro-3,4-dihydro-2H-benzo[b][1,4]oxazin-2-yl)propanoic acid (500 mg, 1.461 mmol) in deimethyl formamide (0.1 mL) and toluene (5 ml) was added oxalyl dichloride (1.1 g, 8.76 mmol) dropwise. The reaction was stirred at 20° C. for 10 minutes, then heated to 80° C. and stirred at this temperature for 1 hour. After cooling to 20° C., the reaction mixture was concentrated under reduced pressure. To a solution of hydrazinecarboxamide (121 mg, 1.607 mmol) in tetrahydrofuran (10 mL) and water (2 mL) was added sodium hydroxide (117 mg, 2.92 mmol), followed by the slow addition of the crude product in tetrahydrofuran (10 mL) described above. The reaction was stirred at 0° C. for 2 hours, then concentrated to give the title compound as a red oil, which was used in the next step without further purification. LCMS (ESI) calculated for $C_{19}H_{22}N_5O_5$ [M+H]$^+$: 400.1, found: 400.1.

Step 4—Preparation of (S)-3-(2-(4-benzyl-6-nitro-3,4-dihydro-2H-benzo[b][1,4]oxazin-2-yl)ethyl)-1H-1,2,4-triazol-5(4H)-one

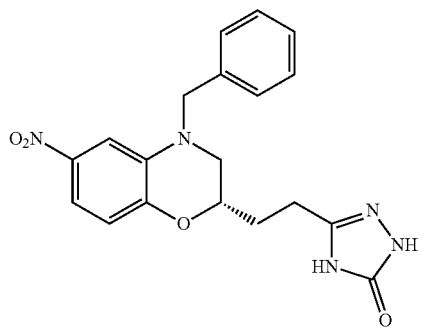 [SMILES: O=c1[nH]nc(CC[C@H]2CN(Cc3ccccc3)c3cc([N+](=O)[O-])ccc3O2)[nH]1]

A solution of (S)-2-(3-(4-benzyl-6-nitro-3,4-dihydro-2H-benzo[b][1,4]oxazin-2-yl)propanoyl)hydrazinecarboxamide (590 mg, 1.344 mmol) in 2M sodium hydroxide (20 mL), was stirred at 100° C. for 12 hours, then cooled to 20° C. and acidified with 1M hydrochloric acid to pH=2. The resulting mixture was filtered and concentrated to give the title compound as an orange solid. LCMS (ESI) calculated for $C_{19}H_{20}N_5O_4$ [M+H]$^+$: 382.1, found: 382.1. $^1$H-NMR (CDCl$_3$, 400 MHz) δ 7.51 (2H, s), 7.23-7.31 (5H, m), 6.76-6.78 (1H, m), 4.43 (2H, s), 4.23 (1H, s), 3.13-3.29 (1H, m), 3.09-3.12 (1H, m), 2.71-2.76 (1H, m), 2.54-2.56 (1H, m), 1.90-1.98 (1H, m).

Step 5—Preparation of (S)-3-(2-(6-amino-3,4-dihydro-2H-benzo[b][1,4]oxazin-2-yl)ethyl)-1H-1,2,4-triazol-5(4H)-one

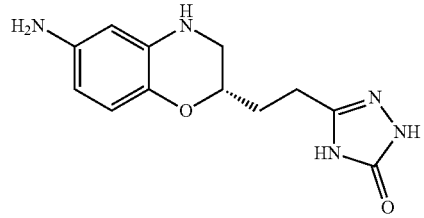 [SMILES: Nc1ccc2c(c1)NC[C@H](CCc1n[nH]c(=O)[nH]1)O2]

To a solution of (S)-3-(2-(4-benzyl-6-nitro-3,4-dihydro-2H-benzo[b][1,4]oxazin-2-yl)ethyl)-1H-1,2,4-triazol-5(4H)-one (40 mg, 0.105 mmol) in methanol (15 mL) was added Pd(OH)$_2$ under argon. The mixture was degassed under hydrogen several times, and stirred at 20° C. under H$_2$ balloon for 15 hours. The reaction was filtered and concentrated under reduced pressure to give the title compound as a dark oil. LCMS (ESI) calculated for $C_{12}H_{16}N_5O_2$ [M+H]$^+$: 262.1, found: 262.2.

Step 6—Preparation of (S)-4-(2,6-difluorobenzyl)-1-(4-fluorophenyl)-N—((R)-1-phenylethyl)piperazine-2-carboxamide

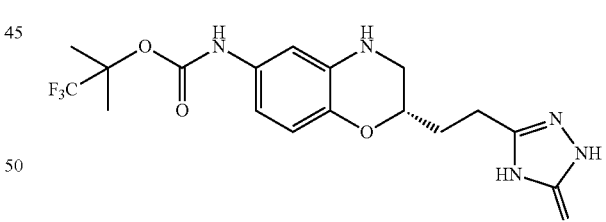

To a solution of (S)-3-(2-(6-amino-3,4-dihydro-2H-benzo[b][1,4]oxazin-2-yl)ethyl)-1H-1,2,4-triazol-5(4H)-one (20 mg, 0.077 mmol) in DMSO (3 mL) was added 3-methyl-1-(((1,1,1-trifluoro-2-methylpropan-2-yl)oxy)carbonyl)-1H-imidazol-3-ium iodide (21.79 mg, 0.092 mmol) and the reaction was stirred at 20° C. for 20 minutes. The reaction mixture was directly purified by prep-HPLC (MeCN/H$_2$O as eluent, 0.05% TFA) to give the title compound as a white solid. LCMS (ESI) calculated for $C_{17}H_{21}F_3N_5O_4$ [M+H]$^+$: 416.1, found: 416.1.

Step 7—Preparation of (S)-1,1,1-trifluoro-2-methylpropan-2-yl(4-((3-chloro-1-ethyl-1H-pyrazol-4-yl)sulfonyl)-2-(2-(5-oxo-4,5-dihydro-1H-1,2,4-triazol-3-yl)ethyl)-3,4-dihydro-2H-benzo[b][1,4]oxazin-6-yl)carbamate

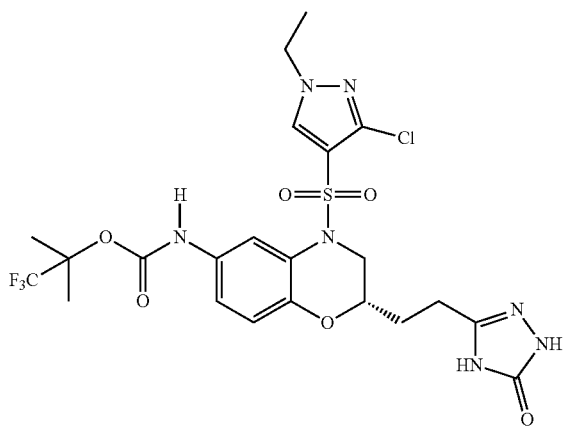 [SMILES: CCn1cc(S(=O)(=O)N2C[C@H](CCc3n[nH]c(=O)[nH]3)Oc3ccc(NC(=O)OC(C)(C)C(F)(F)F)cc32)c(Cl)n1]

To a solution of (S)-1,1,1-trifluoro-2-methylpropan-2-yl (2-(2-(5-oxo-4,5-dihydro-1H-1,2,4-triazol-3-yl)ethyl)-3,4-dihydro-2H-benzo[b][1,4]oxazin-6-yl)carbamate (10 mg, 0.024 mmol) in tetrahydrofuran (5 mL) was added pyridine (1 mL) and 3-chloro-1-ethyl-1H-pyrazole-4-sulfonyl chloride (16.5 mg, 0.072 mmol). The reaction was stirred at 15° C. for 3 hours, then directly purified by pre-HPLC (MeCN/H$_2$O as eluent, 0.05% TFA) to give the title compound as a white solid. LCMS (ESI) calculated for C$_{22}$H$_{26}$ClF$_3$N$_7$O$_6$S [M+H]$^+$: 608.1, found: 608.0; $^1$H-NMR (CDCl$_3$, 400 MHz) δ 8.27 (1H, s), 7.89 (1H, s), 6.92-6.95 (1H, m), 6.74-6.77 (1H, m), 4.34-4.37 (1H, m,), 4.07-4.11 (2H, m), 3.89 (2H, s), 3.34-3.38 (1H, m), 2.69-2.74 (2H, m), 1.92-2.01 (3H, m),1.74 (6H, s), 1.36-1.40 (3H, m).

Example 101—Preparation of (S)-1,1,1-trifluoro-2-methylpropan-2-yl(4-((3-chloro-1-ethyl-1H-pyrazol-4-yl)sulfonyl)-2-(2-(4-methyl-5-oxo-4,5-dihydro-1H-1,2,4-triazol-3-yl)ethyl)-3,4-dihydro-2H-benzo[b][1,4]oxazin-6-yl)carbamate (Example 101)

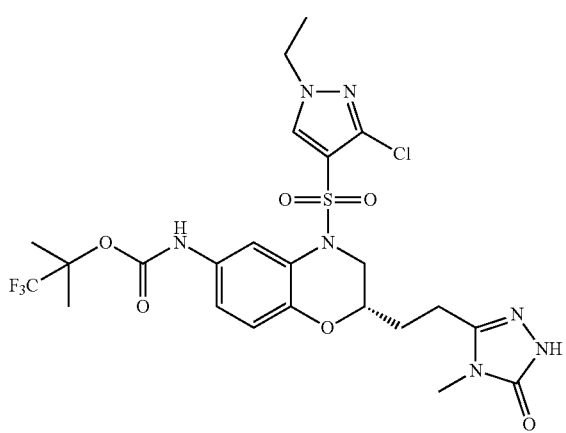 [SMILES: CCn1cc(S(=O)(=O)N2C[C@H](CCc3n[nH]c(=O)n3C)Oc3ccc(NC(=O)OC(C)(C)C(F)(F)F)cc32)c(Cl)n1]

To a solution of (S)-1,1,1-trifluoro-2-methylpropan-2-yl (4-((3-chloro-1-ethyl-1H-pyrazol-4-yl)sulfonyl)-2-(2-(5-oxo-4,5-dihydro-1H-1,2,4-triazol-3-yl)ethyl)-3,4-dihydro-2H-benzo[b][1,4]oxazin-6-yl)carbamate (30 mg, 0.049 mmol) in DMF (2 mL) was added potassium carbonate (6.82 mg, 0.049 mmol) and iodomethane (7.00 mg, 0.049 mmol) at 0° C. The reaction was stirred at 25° C. for 2 hours, then concentrated and purified by pre-HPLC (MeCN/H$_2$O as eluent, 0.05% TFA) to afford the title compound as a yellow solid. LCMS (ESI) calculated for C$_{23}$H$_{28}$ClF$_3$N$_7$O$_6$S [M+H]$^+$: 622.1, found: 622.1; $^1$H-NMR (CDCl$_3$, 400 MHz) δ 8.11 (1H, s), 7.85 (1H, s), 6.88 (2H, s), 6.77-6.79 (1H, m), 4.38 (1H, d, J=13.2 Hz), 4.08-4.10 (2H, m,), 3.64 (1H, s), 3.38-3.43 (1H, m), 3.23 (3H, s), 2.70-2.76 (2H, m), 2.00-2.04 (2H, m), 1.74 (6H, s), 1.43-1.47 (3H, m).

Example 102—Preparation of (S)-1,1,1-trifluoro-2-methylpropan-2-yl (2-(2-(5-oxo-4,5-dihydro-1,2,4-oxadiazol-3-yl)ethyl)-4-((3-(trifluoromethyl)phenyl)sulfonyl)-3,4-dihydro-2H-benzo[b][1,4]oxazin-6-yl)carbamate (Example 102)

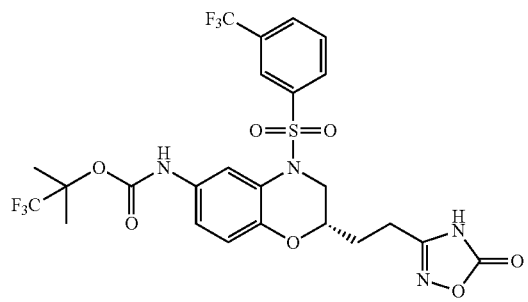 [SMILES: CC(C)(OC(=O)Nc1ccc2c(c1)N(S(=O)(=O)c1cccc(C(F)(F)F)c1)C[C@H](CCc1noc(=O)[nH]1)O2)C(F)(F)F]

Step 1—Preparation of (S)-3-(6-amino-4-((3-(trifluoromethyl)phenyl)sulfonyl)-3,4-dihydro-2H-benzo[b][1,4]oxazin-2-yl)propanenitrile

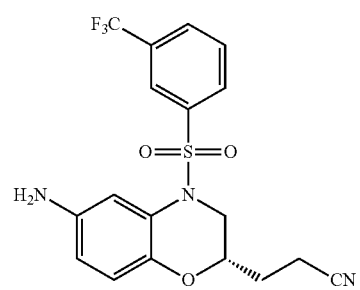 [SMILES: N#CCC[C@H]1CN(S(=O)(=O)c2cccc(C(F)(F)F)c2)c2cc(N)ccc2O1]

A mixture of (S)-1,1,1-trifluoro-2-methylpropan-2-yl(2-(2-cyanoethyl)-4-((3-(trifluoromethyl)phenyl)sulfonyl)-3,4-dihydro-2H-benzo[b][1,4]oxazin-6-yl)carbamate (see Example 92; 100 mg, 0.18 mmol), LiOH.H$_2$O (84 mg, 2 mmol), dioxane (1 mL) and H$_2$O (1 mL) were stirred at 40° C. for 6 hours. The reaction mixture was extracted with EtOAc, dried over Na$_2$SO$_4$ and concentrated in vacuo to give the crude title product as a white solid, which was used in the next step without further purification. LCMS (ESI) calculated for C$_{18}$H$_{17}$F$_3$N$_3$O$_3$S [M+H]$^+$: 412, found: 412.

Step 2—Preparation of (S)-tert-butyl (2-(2-cyanoethyl)-4-((3-(trifluoromethyl) phenyl)sulfonyl)-3,4-dihydro-2H-benzo[b][1,4]oxazin-6-yl)carbamate

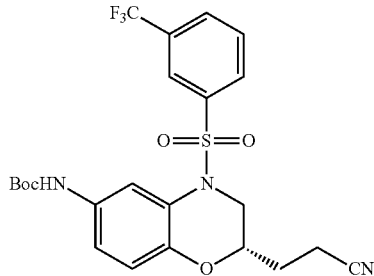 [SMILES: CC(C)(C)OC(=O)Nc1ccc2c(c1)N(S(=O)(=O)c1cccc(C(F)(F)F)c1)C[C@H](CCC#N)O2]

A mixture of (S)-3-(6-amino-4-((3-(trifluoromethyl)phenyl)sulfonyl)-3,4-dihydro-2H-benzo[b][1,4]oxazin-2-yl)propanenitrile (100 mg, 0.24 mmol), Boc$_2$O (218 mg, 1 mmol), Et$_3$N (202 mg, 2 mmol) and DCM (10 mL) were stirred at 15° C. for 16 hours. The reaction mixture was extracted with DCM and water and the organic layer washed with brine, dried over Na$_2$SO$_4$ and concentrated in vacuo. The crude product was purified by prep-TLC to give the title compound as a yellow solid. LCMS (ESI) calculated for C$_{23}$H$_{25}$F$_3$N$_3$O$_5$S [M+H]$^+$: 512, found: 512.

Step 3—Preparation of (S,Z)-tert-butyl(2-(3-amino-3-(hydroxyimino)propyl)-4-((3-(trifluoromethyl)phenyl)sulfonyl)-3,4-dihydro-2H-benzo[b][1,4]oxazin-6-yl)carbamate

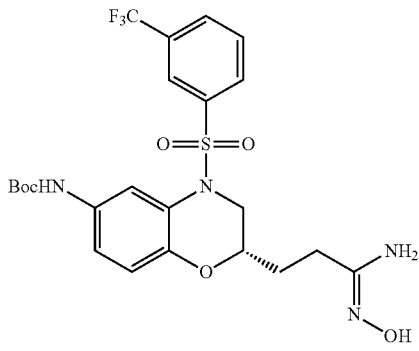 [SMILES: CC(C)(C)OC(=O)Nc1ccc2c(c1)N(S(=O)(=O)c1cccc(C(F)(F)F)c1)C[C@H](CC/C(N)=N/O)O2]

A mixture of (S)-tert-butyl (2-(2-cyanoethyl)-4-((3-(trifluoromethyl)phenyl) sulfonyl)-3,4-dihydro-2H-benzo[b][1,4]oxazin-6-yl)carbamate (20 mg, 0.04 mmol), hydroxylamine hydrochloride (138 mg, 2 mmol), K$_2$CO$_3$ (1.38 g, 10 mmol) and MeOH (10 mL) was stirred at 60° C. for 18 hours. The reaction mixture was concentrated in vacuo and extracted with water and EtOAc. The organic phase was washed with brine, dried over Na$_2$SO$_4$ and concentrated. The crude product was purified by prep-TLC to give the title compound as a white solid. LCMS (ESI) calculated for C$_{23}$H$_{28}$F$_3$N$_4$O$_6$S [M+H]$^+$: 545, found: 545. $^1$H NMR (CDCl$_3$, 400 MHz) δ 7.94 (br s, 1H), 7.85 (d, J=7.43 Hz, 1H), 7.75 (d, J=7.4 Hz, 1H), 7.69 (d, J=2.0 Hz, 1H), 7.53-7.60 (m, 1H), 7.00-7.12 (m, 1H), 6.64-6.71 (m, 1H), 6.42 (br s, 1H), 4.60 (br s, 1H), 4.20 (d, J=14.1 Hz, 1H), 3.43 (br s, 1H), 3.13 (dd, J=9.8, 13.69 Hz, 1H), 2.15-2.32 (m, 2H), 1.68-1.78 (m, 2H), 1.40-1.50 (m, 9H).

Step 4—Preparation of (S)-tert-butyl (2-(2-(5-oxo-4,5-dihydro-1,2,4-oxadiazol-3-yl)ethyl)-4-((3-(trifluoromethyl)phenyl)sulfonyl)-3,4-dihydro-2H-benzo[b][1,4]oxazin-6-yl)carbamate

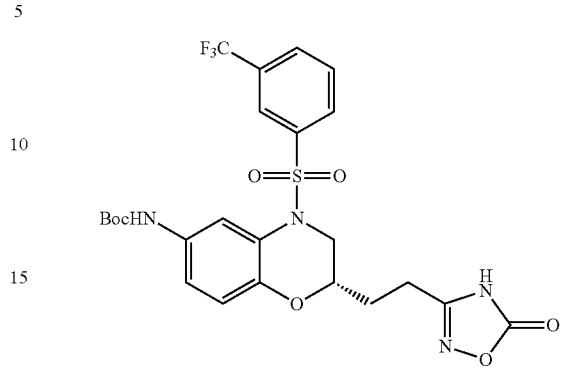

A solution of (S,Z)-tert-butyl (2-(3-amino-3-(hydroxyimino)propyl)-4-((3-(trifluoromethyl)phenyl)sulfonyl)-3,4-dihydro-2H-benzo[b][1,4]oxazin-6-yl)carbamate (20 mg, 0.04 mmol) in MeCN (5 mL) was added pyridine (0.5 mL) and triphosgene (6 mg, 0.02 mmol). After stirred for 18 hours at 15° C., the reaction mixture was concentrated in vacuo and extracted with EtOAc and water. The organic phase was washed with brine, dried over Na$_2$SO$_4$ and concentrated. The crude product was purified by prep-TLC (EtOAc) to give the title compound as yellow oil. LCMS (ESI) calculated for C$_{24}$H$_{26}$F$_3$N$_4$O$_7$S [M+H]$^+$: 571, found: 571. $^1$H NMR (CDCl$_3$, 400 MHz) δ 9.52 (br s, 1H), 7.95 (br s, 1H), 7.76-7.89 (m, 2H), 7.71 (d, J=2.0 Hz, 1H), 7.54-7.63 (m, 1H), 7.03 (d, J=7.8 Hz, 1H), 6.66 (d, J=8.6 Hz, 1H), 6.40 (br s, 1H), 4.02 (d, J=6.7 Hz, 1H), 3.50-3.60 (m, 1H), 3.22 (dd, J=9.2, 13.9 Hz, 1H), 2.60-2.74 (m, 2H), 1.82-1.93 (m, 2H), 1.18 (s, 9H).

Step 5—Preparation of (S)-1,1,1-trifluoro-2-methylpropan-2-yl (2-(2-(5-oxo-4,5-dihydro-1,2,4-oxadiazol-3-yl)ethyl)-4-((3-(trifluoromethyl)phenyl)sulfonyl)-3,4-dihydro-2H-benzo[b][1,4]oxazin-6-yl)carbamate

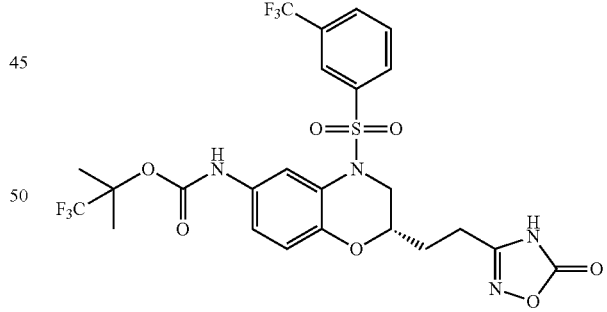

A solution of (S)-tert-butyl (2-(2-(5-oxo-4,5-dihydro-1,2,4-oxadiazol-3-yl)ethyl)-4-((3-(trifluoromethyl)phenyl)sulfonyl)-3,4-dihydro-2H-benzo[b][1,4]oxazin-6-yl)carbamate (57 mg, 0.1 mmol) in DCM (2 mL) was added TFA (1 mL). After stirred for 1 hour at 15° C., the reaction mixture was concentrated in vacuo. The aniline intermediate was next added to a solution of 3-methyl-1-(((1,1,1-trifluoro-2-methylpropan-2-yl)oxy)carbonyl)-1H-imidazol-3-ium iodide (73 mg, 0.2 mmol) in DMSO (2 mL). The reaction was stirred for 1 h and the mixture was directly purified with prep-HPLC (MeCN/water using TFA buffer) to give the title product as white solid. LCMS (ESI) calculated for C$_{24}$H$_{23}$F$_6$N$_4$O$_7$S [M+H]$^+$: 625, found: 625. $^1$H NMR (CD₃OD, 400 MHz) δ 8.02-8.24 (m, 3H), 7.97 (d, J=7.5 Hz, 1H), 7.77 (t, J=8.0 Hz, 1H), 7.03 (d, J=11.0 Hz, 1H), 6.74 (d, J=8.5 Hz, 1H), 4.41 (d, J=14.0 Hz, 1H), 3.58 (brs, 1H), 2.69-2.78 (m, 2H), 1.89-2.06 (m, 2H), 1.79 (s, 6H).

Example 103—Preparation of (R)-1,1,1-trifluoro-2-methylpropan-2-yl(4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate and (S)-1,1,1-trifluoro-2-methylpropan-2-yl(4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate (Examples 103A and 103B)

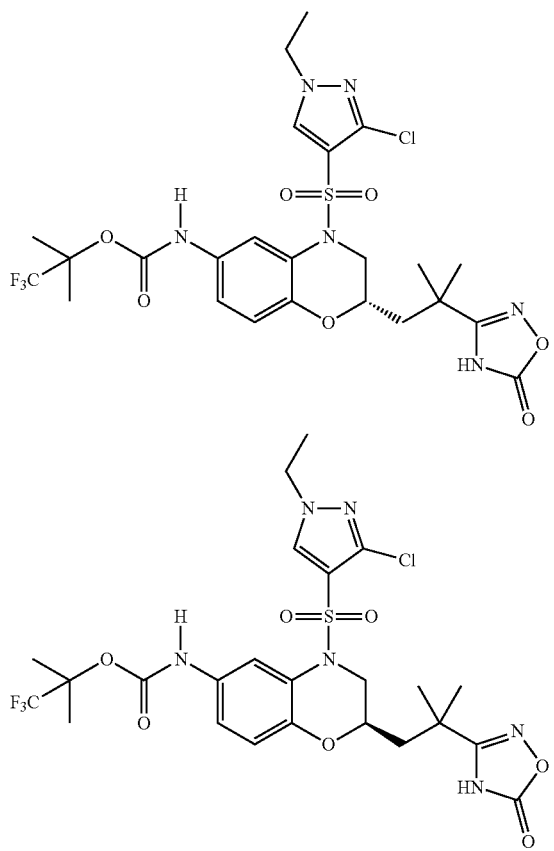

Step 1—Preparation of (R and S)—N-hydroxy-2,2-dimethyl-3-(6-nitro-4-tosyl-3,4-dihydro-2H-benzo[b][1,4]oxazin-2-yl)propanimidamide

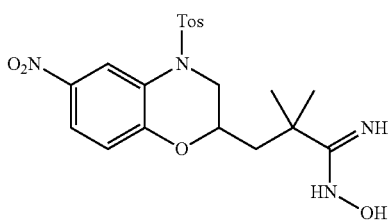

To a stirred mixture of (R and S)-2,2-dimethyl-3-(6-nitro-4-tosyl-3,4-dihydro-2H-benzo[b][1,4]oxazin-2-yl)propanenitrile (see Example 94; 3.0 g, 7.22 mmol) in EtOH (30 mL) was added NH₂OH·HCl (1.0 g, 14.39 mmol), K₂CO₃ (3.0 g, 21.71 mmol) and water (10 mL). The reaction was heated to reflux for 18 hours, then cooled to room temperature and stirred for 30 minutes. The solid was filtered off and dried under vacuum to afford N-hydroxy-2,2-dimethyl-3-(6-nitro-4-tosyl-3,4-dihydro-2H-benzo[b][1,4]oxazin-2-yl)propanimidamide as a white solid.

Step 2—Preparation of (R and S)-3-(2-methyl-1-(6-nitro-4-tosyl-3,4-dihydro-2H-benzo[b][1,4]oxazin-2-yl)propan-2-yl)-1,2,4-oxadiazol-5(2H)-one

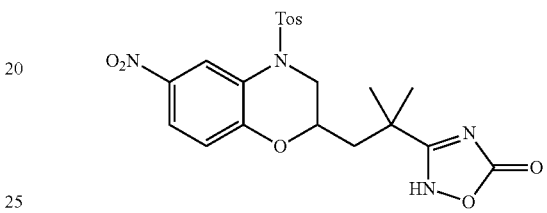

To a stirred solution of (R and S)—N-hydroxy-2,2-dimethyl-3-(6-nitro-4-tosyl-3,4-dihydro-2H-benzo[b][1,4]oxazin-2-yl)propanimidamide (900 mg, 2.007 mmol) in DMSO (10 mL) was added CDI (488 mg, 3.01 mmol) and K₂CO₃ (555 mg, 4.01 mmol). The reaction was stirred for 18 hours at 20° C., then treated with water (10 mL) and extracted with EtOAc (15 mL). The organic layers was evaporated and the crude product purified by chromatography silica gel (petroleum ether:EtOAc=2:1 to 1:2) to afford the title compound as a light-yellow solid. LCMS (ESI) calculated for $C_{21}H_{23}N_4O_7S$ [M+H]⁺: 475.1, found: 475.1; ¹H-NMR (CDCl₃, 400 MHz) δ 8.68 (1H, d, J=2.4 Hz), 7.85 (1H, dd, J=9.2, 2.4 Hz), 7.45 (2H, d, J=8.4 Hz), 7.22 (2H, d, J=8.0 Hz), 6.74 (1H, d, J=8.8 Hz), 4.17 (1H, dd, J=14.4, 2.0 Hz), 3.49 (1H, t, J=7.6 Hz), 3.07-3.13 (1H, m), 2.32 (3H, s), 1.82-1.86 (2H, m), 1.26 (6H, d, J=9.2 Hz).

Step 3—Preparation of (R and S)-3-(1-(6-amino-4-tosyl-3,4-dihydro-2H-benzo[b][1,4]oxazin-2-yl)-2-methylpropan-2-yl)-1,2,4-oxadiazol-5(2H)-one

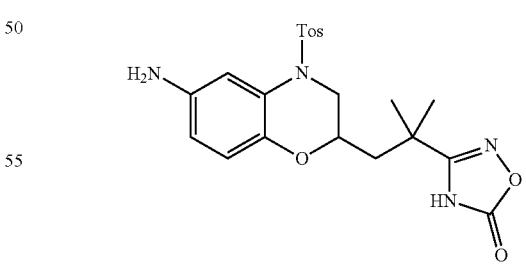

To a stirred solution of (R and S)-3-(2-methyl-1-(6-nitro-4-tosyl-3,4-dihydro-2H-benzo[b][1,4]oxazin-2-yl)propan-2-yl)-1,2,4-oxadiazol-5(2H)-one (900 mg, 1.897 mmol) in MeOH (10 mL) was added water (1 mL), Zn (124 mg, 1.897 mmol) and NH₄Cl (101 mg, 1.897 mmol). The reaction was stirred for 2 hours at 20° C., then filtered and the filtrate concentrated. The crude product was washed with EtOAc and water (20 mL each). The organic layer was concentrated to afford the title compound as a gray solid. LCMS (ESI) calculated for $C_{21}H_{25}N_4O_5S$ [M+H]$^+$: 445.1, found: 445.1.

Step 4—Preparation of (R and S)-1,1,1-trifluoro-2-methylpropan-2-yl (2-(2-methyl-2-(5-oxo-4,5-dihydro-1,2,4-oxadiazol-3-yl)propyl)-4-tosyl-3,4-dihydro-2H-benzo[b][1,4]oxazin-6-yl)carbamate

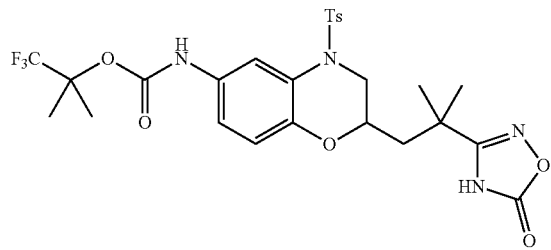 [SMILES: Cc1ccc(S(=O)(=O)N2CC(CC(C)(C)c3noc(=O)[nH]3)Oc3ccc(NC(=O)OC(C)(C)C(F)(F)F)cc32)cc1]

A mixture of 1,1,1-trifluoro-2-methylpropan-2-yl 1H-imidazole-1-carboxylate (19.99 mg, 0.090 mmol), (S and R)-3-(1-(6-amino-4-tosyl-3,4-dihydro-2H-benzo[b][1,4]oxazin-2-yl)-2-methylpropan-2-yl)-1,2,4-oxadiazol-5(4H)-one (20 mg, 0.045 mmol) and concentrated HCl (one drop) in DMSO (3 mL) was stirred at 80° C. for 4 hours. Upon completion, the reaction mixture was diluted with water (10 mL), extracted with EtOAc (3×15 ml) and the combined organic layers dried and concentrated in vacuo. The crude product was purified by prep-TLC (DCM:MeOH=15:1) to give the title compound as a brown solid. LCMS (ESI) calculated for $C_{26}H_{30}F_3N_4O_7S$ [M+H]$^+$: 599.1, found: 599.1; $^1$H-NMR (CDCl$_3$, 400 MHz) δ 7.70 (1H, s), 7.51 (2H, d, J=8.0 Hz), 7.23 (1H, s), 7.13 (1H, d, J=8.4 Hz), 6.72 (1H, s), 6.54 (1H, d, J=8.4 Hz), 4.04 (1H, d, J=12.8 Hz), 3.39-3.40 (1H, m), 3.14-3.20 (1H, m), 2.39 (3H, s), 1.81-1.83 (1H, m), 1.76 (6H, s), 1.65-1.68 (1H, m), 1.32 (3H, s), 1.23 (3H, s).

Step 5—Preparation of (R)-1,1,1-trifluoro-2-methylpropan-2-yl (2-(2-methyl-2-(5-oxo-4,5-dihydro-1,2,4-oxadiazol-3-yl)propyl)-3,4-dihydro-2H-benzo[b][1,4]oxazin-6-yl)carbamate and (S)-1,1,1-trifluoro-2-methylpropan-2-yl (2-(2-methyl-2-(5-oxo-4,5-dihydro-1,2,4-oxadiazol-3-yl)propyl)-3,4-dihydro-2H-benzo[b][1,4]oxazin-6-yl)carbamate

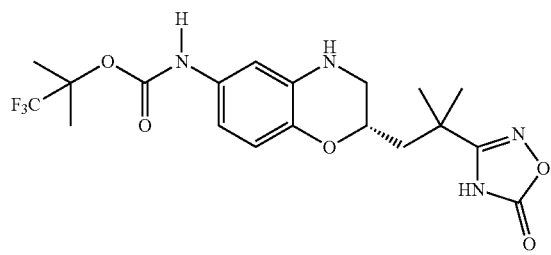

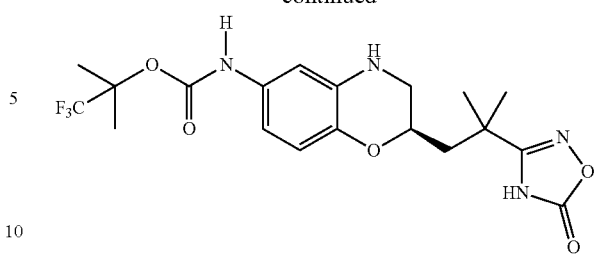

A mixture of (R and S)-1,1,1-trifluoro-2-methylpropan-2-yl(2-(2-methyl-2-(5-oxo-4,5-dihydro-1,2,4-oxadiazol-3-yl)propyl)-4-tosyl-3,4-dihydro-2H-benzo[b][1,4]oxazin-6-yl)carbamate (300 mg, 0.501 mmol) and magnesium (97 mg, 4.01 mmol) in MeOH (10 mL) was stirred at 15° C. for 36 hours. Upon completion, the reaction mixture was concentrated in vacuo, diluted with water (10 mL) and acidified with HCl (1M) to pH=2. The biphasic mixture was extracted with EtOAc (3×20 mL) and the combined organic layers dried over Na$_2$SO$_4$ and evaporated. The crude product was purified by prep-TLC to give the title racemic compound as a colorless oil.

The above racemate was resolved by SFC purification (Instrument: Thar SFC 350; Column: OD (250 mm*30 mm, 10 um); Mobile phase: 30% IPA+NH$_3$.H$_2$O; 80 mL/min; Wavelength: 220 nm) to give two enantiomers (faster eluent, Isomer 1 and slower eluent, Isomer 2), which have the same analytical data: LCMS (ESI) calculated for $C_{19}H_{24}F_3N_4O_5$ [M+H]$^+$: 445.1, found: 445.1.

Step 6—Preparation of (R)-1,1,1-trifluoro-2-methylpropan-2-yl(4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate and (S)-1,1,1-trifluoro-2-methylpropan-2-yl(4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate

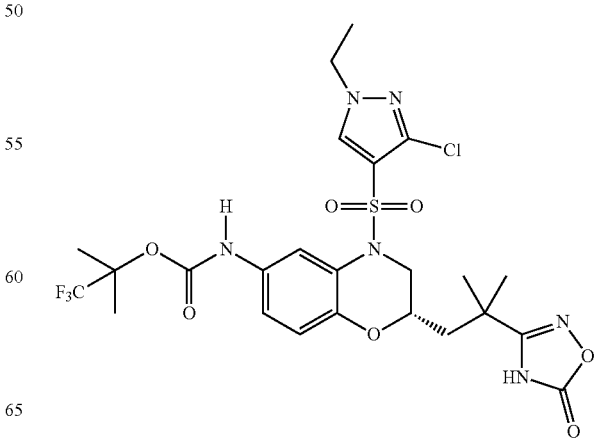

-continued

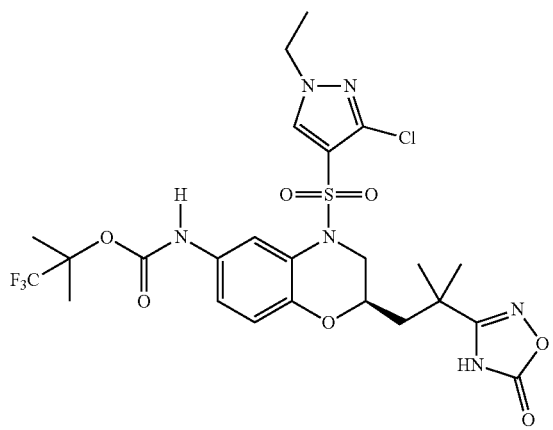

To a mixture of (R or S)-1,1,1-trifluoro-2-methylpropan-2-yl(2-(2-methyl-2-(5-oxo-4,5-dihydro-1,2,4-oxadiazol-3-yl)propyl)-3,4-dihydro-2H-benzo[b][1,4]oxazin-6-yl)carbamate (Isomer 1 from Step 5, 10 mg, 0.023 mmol) in THF (2 mL) was added 3-chloro-1-ethyl-1H-pyrazole-4-sulfonyl chloride (10.31 mg, 0.045 mmol) and pyridine (2 mL). The reaction mixture was stirred at 20° C. for 2 hours, then concentrated in vacuo. The crude product was purified by prep-HPLC (MeCN/water using TFA buffer) to afford the title compound (Isomer 1 from Step 6, Example 103A) as a white solid.

The other enantiomer (Isomer 2 from Step 6, Example 103B) was prepared using a similar procedure as described above from Isomer 2 from Step 5. Both enantiomers have the same analytical data: LCMS (ESI) calculated for $C_{24}H_{29}ClF_3N_6O_7S$ [M+H]$^+$: 637.1, found: 637.1; $^1$H-NMR (Methanol-d4, 400 MHz) δ 8.28 (1H, s), 7.90 (1H, s), 6.91 (1H, d, J=8.8 Hz), 6.54 (1H, d, J=8.4 Hz), 4.24 (1H, d, J=14.0 Hz), 4.12 (2H, q, J=7.2 Hz), 3.97 (1H, t, J=8.4 Hz), 3.35-3.41 (1H, m), 1.96-2.02 (1H, m), 1.84-1.88 (1H, m), 1.75 (6H, s), 1.41 (3H, t, J=7.2 Hz), 1.35 (6H, s).

Example 104—Preparation of Additional 1,2,4-oxadiazolones

The compounds in Table 30 below were prepared based on the experimental procedures described in Examples 102 and 103 and elsewhere in the detailed description, and can be achieved by one of skill in the art in light of the present disclosure.

TABLE 30

| Ex. No. | Structure | Name | Observed m/z |
|---|---|---|---|
| 104A | 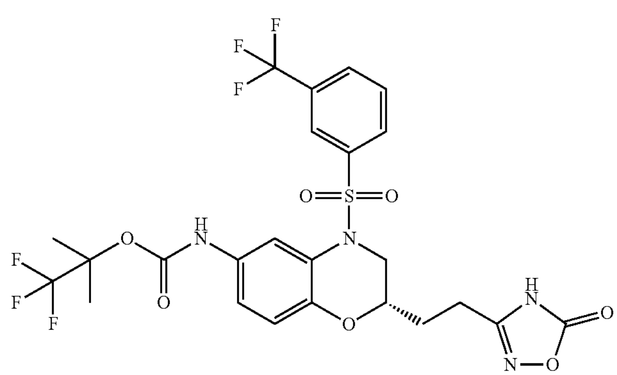 [SMILES: CC(C)(OC(=O)Nc1ccc2c(c1)N(S(=O)(=O)c1cccc(C(F)(F)F)c1)C[C@H](CCc1noc(=O)[nH]1)O2)C(F)(F)F] | 2,2,2-trifluoro-1,1-dimethylethyl [(2S)-2-[2-(5-oxo-4,5-dihydro-1,2,4-oxadiazol-3-yl)ethyl]-4-{[3-(trifluoromethyl)phenyl]sulfonyl}-3,4-dihydro-2H-1,4-benzoxazin-6-yl]carbamate | 625 (M + H)+ |
| 104B | 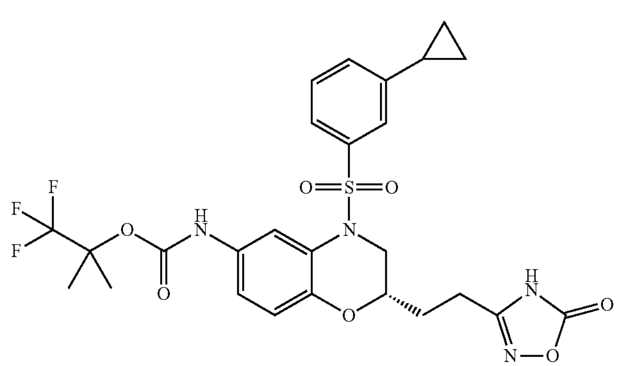 [SMILES: CC(C)(OC(=O)Nc1ccc2c(c1)N(S(=O)(=O)c1cccc(C3CC3)c1)C[C@H](CCc1noc(=O)[nH]1)O2)C(F)(F)F] | 2,2,2-trifluoro-1,1-dimethylethyl {(2S)-4-[(3-cyclopropylphenyl)sulfonyl]-2-[2-(5-oxo-4,5-dihydro-1,2,4-oxadiazol-3-yl)ethyl]-3,4-dihydro-2H-1,4-benzoxazin-6-yl}carbamate | 597 (M + H)+ |

TABLE 30-continued

| Ex. No. | Structure | Name | Observed m/z |
|---|---|---|---|
| 104C | 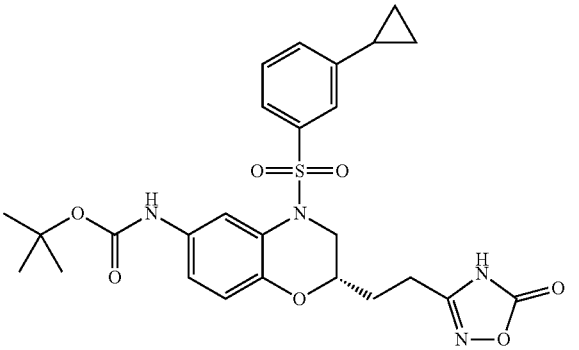 [SMILES: CC(C)(C)OC(=O)Nc1ccc2c(c1)N(S(=O)(=O)c1cccc(C3CC3)c1)C[C@H](CCc1noc(=O)[nH]1)O2] | tert-butyl {(2S)-4-[(3-cyclopropylphenyl)sulfonyl]-2-[2-(5-oxo-4,5-dihydro-1,2,4-oxadiazol-3-yl)ethyl]-3,4-dihydro-2H-1,4-benzoxazin-6-yl}carbamate | 487 (M + H—tBu)+ |
| 104D | 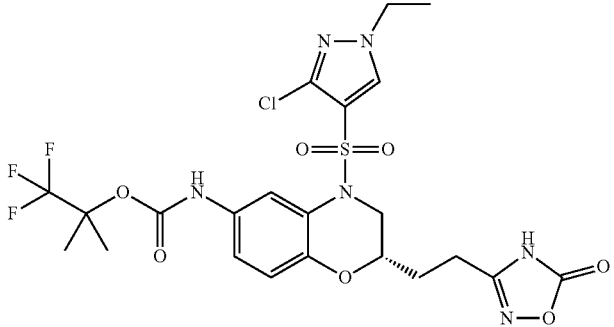 [SMILES: CCn1cc(S(=O)(=O)N2C[C@H](CCc3noc(=O)[nH]3)Oc3ccc(NC(=O)OC(C)(C)C(F)(F)F)cc32)c(Cl)n1] | (S)-1,1,1-trifluoro-2-methylpropan-2-yl (4-((3-chloro-1-ethyl-1H-pyrazol-4-yl)sulfonyl)-2-(2-(5-oxo-4,5-dihydro-1,2,4-oxadiazol-3-yl)ethyl)-3,4-dihydro-2H-benzo[b][1,4]oxazin-6-yl)carbamate | 610 (M + H)+ |
| 104E | 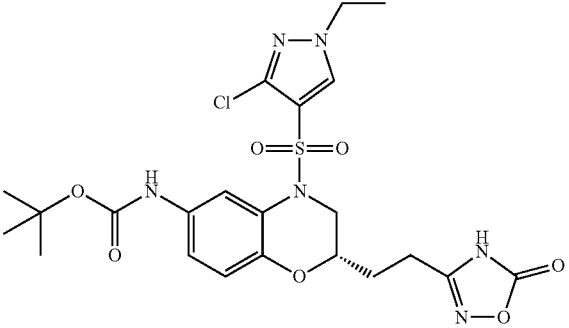 [SMILES: CCn1cc(S(=O)(=O)N2C[C@H](CCc3noc(=O)[nH]3)Oc3ccc(NC(=O)OC(C)(C)C)cc32)c(Cl)n1] | (S)-tert-butyl (4-((3-chloro-1-ethyl-1H-pyrazol-4-yl)sulfonyl)-2-(2-(5-oxo-4,5-dihydro-1,2,4-oxadiazol-3-yl)ethyl)-3,4-dihydro-2H-benzo[b][1,4]oxazin-6-yl)carbamate | 577 (M + Na)+ |
| 104F | 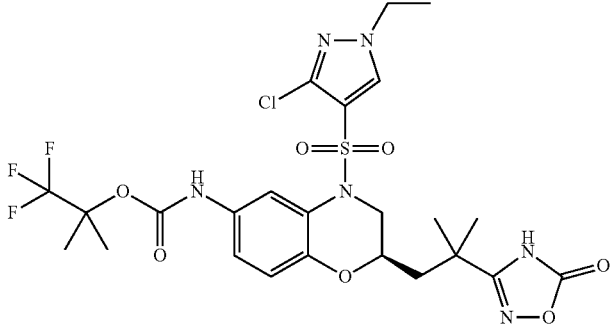 [SMILES: CCn1cc(S(=O)(=O)N2C[C@@H](CC(C)(C)c3noc(=O)[nH]3)Oc3ccc(NC(=O)OC(C)(C)C(F)(F)F)cc32)c(Cl)n1] | (R)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate | 637 (M + H)+ |

TABLE 30-continued

| Ex. No. | Structure | Name | Observed m/z |
|---|---|---|---|
| 104G | 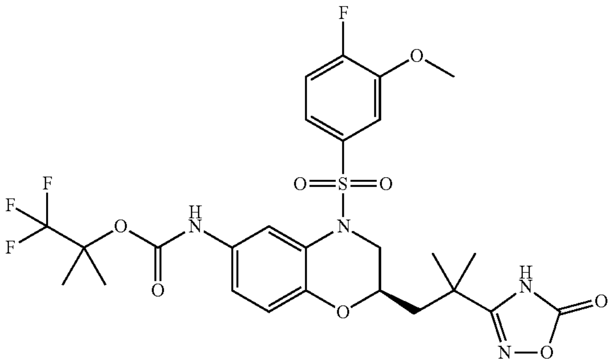 [SMILES: COc1cc(S(=O)(=O)N2C[C@@H](CC(C)(C)c3noc(=O)[nH]3)Oc3ccc(NC(=O)OC(C)(C)C(F)(F)F)cc32)ccc1F] | (R)-1,1,1-trifluoro-2-methylpropan-2-yl (4-((4-fluoro-3-methoxyphenyl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate | 633 (M + H)+ |
| 104H | 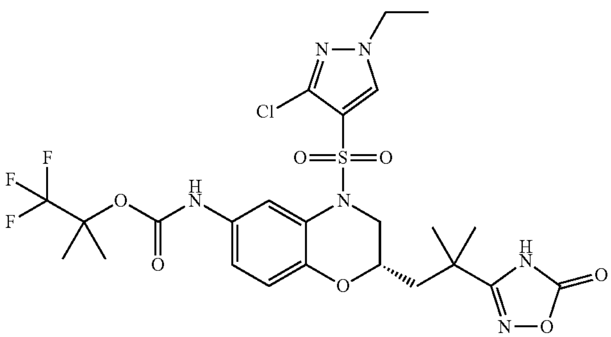 [SMILES: CCn1cc(S(=O)(=O)N2C[C@H](CC(C)(C)c3noc(=O)[nH]3)Oc3ccc(NC(=O)OC(C)(C)C(F)(F)F)cc32)c(Cl)n1] | (S)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate | 637 (M + H)+ |
| 104i | 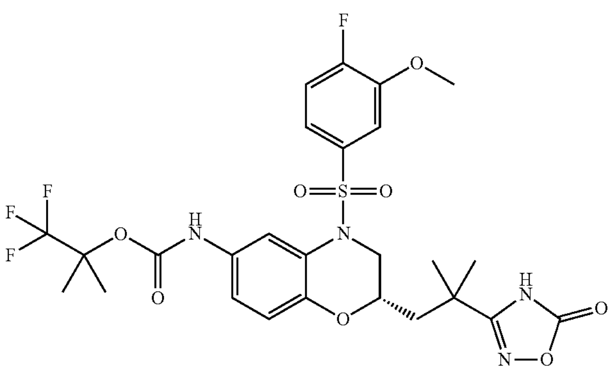 [SMILES: COc1cc(S(=O)(=O)N2C[C@H](CC(C)(C)c3noc(=O)[nH]3)Oc3ccc(NC(=O)OC(C)(C)C(F)(F)F)cc32)ccc1F] | (S)-1,1,1-trifluoro-2-methylpropan-2-yl (4-((4-fluoro-3-methoxyphenyl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate | 633 (M + H)+ |

Example 105—Preparation of (S)-1,1,1-trifluoro-2-methylpropan-2-yl(4-((3-chloro-1-ethyl-1H-pyrazol-4-yl)sulfonyl)-2-(2-(5-oxo-4,5-dihydro-1,3,4-oxadiazol-2-yl)ethyl)-3,4-dihydro-2H-benzo[b][1,4]oxazin-6-yl)carbamate (Example 105)

Step 1—Preparation of (S)-methyl 3-(4-benzyl-6-((tert-butoxycarbonyl)amino)-3,4-dihydro-2H-benzo[b][1,4]oxazin-2-yl)propanoate

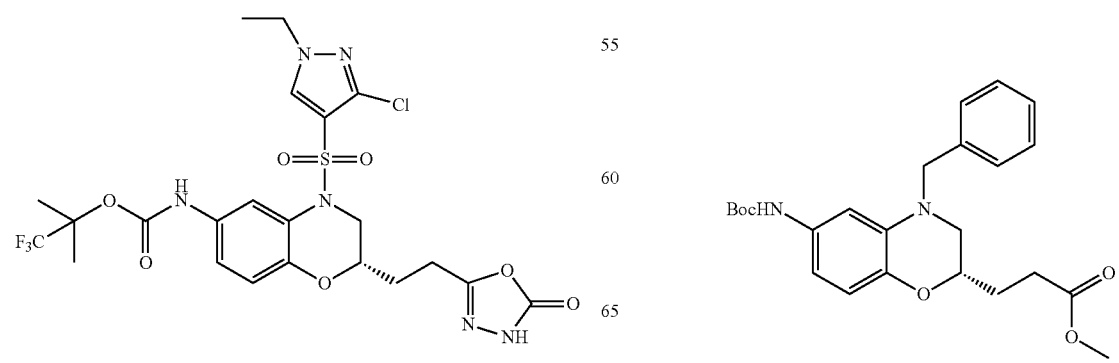

To a mixture of (S)-dimethyl 2-((4-benzyl-6-((tert-butoxycarbonyl)amino)-3,4-dihydro-2H-benzo[b][1,4]oxazin-2-yl)methyl)malonate (10.00 g, 20.64 mmol) in DMSO (100 mL) was added LiCl (5.25 g, 124 mmol). The reaction was stirred at 140° C. for 8 hours, cooled to 25° C., diluted with water (200 mL) and extracted with ethyl acetate (3×300 mL). The organic layers were combined, dried over Na$_2$SO$_4$, filtered and concentrated in vacuo. The crude product was purified by column chromatography (SiO$_2$, petroleum ether:EtOAc=20:1 to 5:1) to give the title compound as a light yellow solid. LCMS (ESI) calculated for C$_{24}$H$_{31}$N$_2$O$_5$ [M+H]$^+$: 427, found: 427.2; $^1$H NMR (CDCl$_3$, 400 MHz) δ 7.26-7.37 (5H, m), 6.73 (2H, d, J=8.6 Hz), 6.60 (1H, d, J=6.7 Hz), 6.22 (1H, br. s.), 4.44 (2H, s), 4.11 (1H, d, J=3.1 Hz), 3.68 (3H, s), 3.24 (1H, d, J=10.2 Hz), 3.10 (1H, dd, J=11.5, 7.6 Hz), 2.55 (2H, q, J=8.0 Hz), 1.89-1.98 (2H, m), 1.47 (9H, s).

Step 2—Preparation of (S)-tert-butyl (4-benzyl-2-(3-hydrazinyl-3-oxopropyl)-3,4-dihydro-2H-benzo[b][1,4]oxazin-6-yl)carbamate

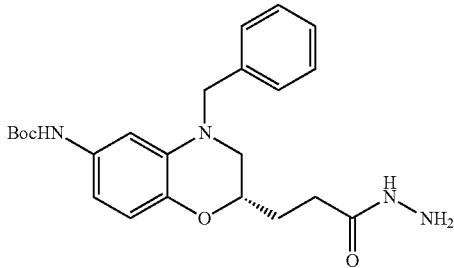 [SMILES: CC(C)(C)OC(=O)Nc1ccc2c(c1)N(Cc1ccccc1)C[C@H](CCC(=O)NN)O2]

To a mixture of (S)-methyl 3-(4-benzyl-6-((tert-butoxycarbonyl)amino)-3,4-dihydro-2H-benzo[b][1,4]oxazin-2-yl)propanoate (3.0 g, 7.03 mmol) in ethanol (40 mL) was added hydrazine hydrate (20 mL, 350 mmol) and Et$_3$N (2.94 mL, 21.10 mmol). The reaction mixture was stirred at 80° C. for 2 hours, cooled to 25° C. and concentrated in vacuo. The residual oil was diluted with H$_2$O (50 mL) and extracted with ethyl acetate (3×30 mL). The organic layers were combined, dried over Na$_2$SO$_4$, filtered and concentrated. The crude product was purified by column chromatography (SiO$_2$, petroleum ether:EtOAc=3:1 to 1:10) to give the title compound as a yellow oil. LCMS (ESI) calculated for C$_{23}$H$_{31}$N$_4$O$_4$ [M+H]$^+$: 427, found: 427.2; $^1$H NMR (CDCl$_3$, 400 MHz) δ 7.23-7.39 (5H, m), 6.69-6.78 (2H, m), 6.64 (1H, br. s.), 6.37 (1H, br. s.), 4.44 (2H, s), 4.12-4.17 (1H, m), 3.21-3.27 (1H, m), 3.10 (1H, dd, J=11.7, 7.8 Hz), 2.35-2.46 (2H, m), 1.83-1.95 (2H, m), 1.48 (9H, s).

Step 3—Preparation of (S)-tert-butyl (4-benzyl-2-(2-(5-oxo-4,5-dihydro-1,3,4-oxadiazol-2-yl)ethyl)-3,4-dihydro-2H-benzo[b][1,4]oxazin-6-yl)carbamate

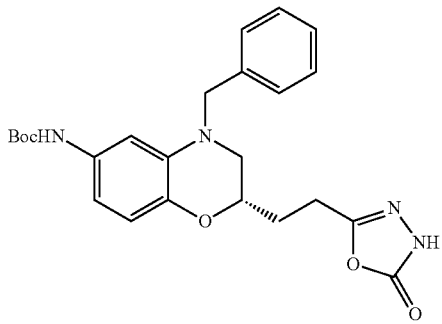 [SMILES: CC(C)(C)OC(=O)Nc1ccc2c(c1)N(Cc1ccccc1)C[C@H](CCc1n[nH]c(=O)o1)O2]

To a mixture of (S)-tert-butyl (4-benzyl-2-(3-hydrazinyl-3-oxopropyl)-3,4-dihydro-2H-benzo[b][1,4]oxazin-6-yl)carbamate (2.75 g, 6.45 mmol) in DMF (30 mL) was added Et$_3$N (2.70 mL, 19.34 mmol) and CDI (1.568 g, 9.67 mmol). The reaction was stirred at 25° C. for 3 hours, then diluted with water (100 mL) and extracted with ethyl acetate (3×50 mL). The organic layers were combined, dried over Na$_2$SO$_4$, filtered and concentrated in vacuo. The crude product was purified by column chromatography (SiO$_2$, petroleum ether:EtOAc=10:1 to 3:1) to give the title compound as a yellow solid. LCMS (ESI) calculated for C$_{24}$H$_{29}$N$_4$O$_5$ [M+H]$^+$: 453, found: 453.1; $^1$H NMR (CDCl$_3$, 400 MHz) δ 7.24-7.37 (5H, m), 6.80 (1H, br. s.), 6.72 (1H, d, J=8.6 Hz), 6.59 (1H, d, J=7.0 Hz), 6.29 (1H, br. s.), 4.43 (2H, s), 4.15-4.20 (1H, m), 3.21-3.27 (1H, m), 3.09 (1H, dd, J=11.5, 7.6 Hz), 2.73-2.84 (2H, m), 1.89-2.02 (2H, m), 1.47 (9H, s).

Step 4—Preparation of (S)-5-(2-(6-amino-4-benzyl-3,4-dihydro-2H-benzo[b][1,4]oxazin-2-yl)ethyl)-1,3,4-oxadiazol-2(3H)-one

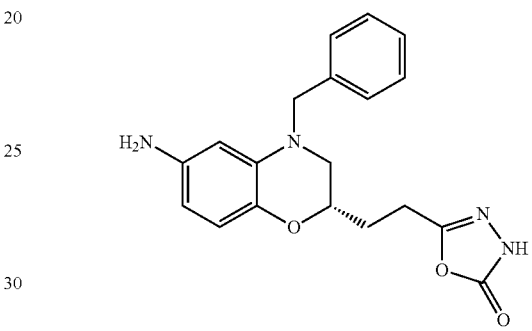

To a solution of (S)-tert-butyl (4-benzyl-2-(2-(5-oxo-4,5-dihydro-1,3,4-oxadiazol-2-yl)ethyl)-3,4-dihydro-2H-benzo[b][1,4]oxazin-6-yl)carbamate (2.86 g, 6.32 mmol) in DCM (30 mL) was added TFA (20 mL, 269 mmol), The reaction was stirred for 1 hour at 25° C., then concentrated in vacuo. The residual oil was diluted with DCM (50 mL), poured into aqueous NaHCO$_3$ and extracted with DCM (3×30 mL). The organic layers were combined, dried over Na$_2$SO$_4$, filtered and concentrated to afford the title compound as brown oil, which was used directly in the next step without further purification. LCMS (ESI) calculated for C$_{19}$H$_{21}$N$_4$O$_3$ [M+H]$^+$: 353, found: 353.1; $^1$H NMR (MeOD, 400 MHz) δ 7.17-7.34 (6H, m), 6.58 (1H, s), 6.29 (1H, s), 4.44 (2H, q, J=16.4 Hz), 3.14 (1H, dd, J=11.5, 7.6 Hz), 2.67-2.85 (2H, m), 1.93-1.99 (2H, m).

Step 5—Preparation of (S)-1,1,1-trifluoro-2-methylpropan-2-yl (4-benzyl-2-(2-(5-oxo-4,5-dihydro-1,3,4-oxadiazol-2-yl)ethyl)-3,4-dihydro-2H-benzo[b][1,4]oxazin-6-yl)carbamate

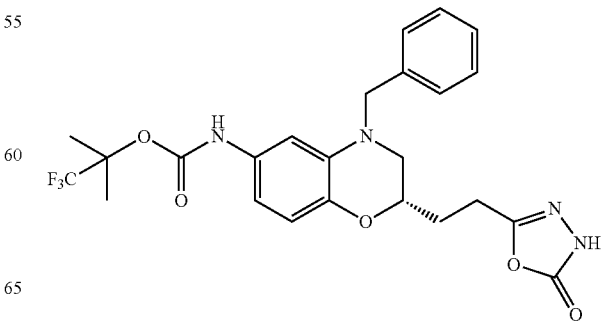

To a mixture of (S)-5-(2-(6-amino-4-benzyl-3,4-dihydro-2H-benzo[b][1,4]oxazin-2-yl)ethyl)-1,3,4-oxadiazol-2(3H)-one (2.05 g, 5.82 mmol) in DMSO (20 mL) was added 1,1,1-trifluoro-2-methylpropan-2-yl 1H-imidazole-1-carboxylate (1.551 g, 6.98 mmol) and concentrated HCl (0.25 mL, 3.04 mmol). The reaction was stirred at 80° C. for 5 hours, then diluted with water (50 mL) and extracted with ethyl acetate (3×30 mL). The organic layers were combined, dried over Na$_2$SO$_4$, filtered and concentrated in vacuo. The crude product was purified by column chromatography (SiO$_2$, petroleum ether:EtOAc=10:1 to 2:1) to give the title compound as yellow oil. LCMS (ESI) calculated for C$_{24}$H$_{26}$F$_3$N$_4$O$_5$ [M+H]$^+$: 507, found: 507.2; $^1$H NMR (CDCl$_3$, 400 MHz) δ 7.26-7.37 (5H, m), 6.71-6.80 (2H, m), 6.63 (1H, br. s.), 6.49 (1H, br. s.), 4.44 (2H, s), 4.16-4.20 (1H, m), 3.26 (1H, dd, J=11.7, 2.3 Hz), 3.12 (1H, dd, J=11.7, 7.4 Hz), 2.74-2.86 (2H, m), 1.91-2.02 (2H, m), 1.72 (6H, s).

Step 6—Preparation of (S)-1,1,1-trifluoro-2-methylpropan-2-yl(2-(2-(5-oxo-4,5-dihydro-1,3,4-oxadiazol-2-yl)ethyl)-3,4-dihydro-2H-benzo[b][1,4]oxazin-6-yl)carbamate

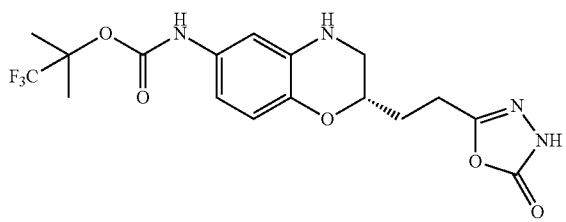 [SMILES: CC(C)(OC(=O)Nc1ccc2c(c1)NC[C@H](CCc1n[nH]c(=O)o1)O2)C(F)(F)F]

To a mixture of (S)-1,1,1-trifluoro-2-methylpropan-2-yl (4-benzyl-2-(2-(5-oxo-4,5-dihydro-1,3,4-oxadiazol-2-yl)ethyl)-3,4-dihydro-2H-benzo[b][1,4]oxazin-6-yl) carbamate (2.72 g, 5.37 mmol) in THF (100 mL) was added Pd/C (10%, 0.50 g, 0.470 mmol) under argon. The suspension was degassed under vacuum and purged with H$_2$ several times. The reaction was stirred under H$_2$ balloon (1 atm) at 25° C. for 12 hours, then filtered through a pad of CELITE and the filtrate concentrated to dryness to afford the title compound as a yellow solid, which was used directly in the next step without further purification. LCMS (ESI) calculated for C$_{17}$H$_{20}$F$_3$N$_4$O$_5$ [M+H]$^+$: 417, found: 417.2; $^1$H NMR (MeOD, 400 MHz) δ 6.77 (1H, br. s.), 6.47-6.58 (2H, m), 4.03 (1H, q, J=5.9 Hz), 3.32 (1H, d, J=2.0 Hz), 3.03 (1H, dd, J=11.9, 7.6 Hz), 2.71-2.82 (2H, m), 1.96 (2H, q, J=7.4 Hz), 1.70 (6H, s).

Step 7—Preparation of (S)-1,1,1-trifluoro-2-methylpropan-2-yl (4-((3-chloro-1-ethyl-1H-pyrazol-4-yl)sulfonyl)-2-(2-(5-oxo-4,5-dihydro-1,3,4-oxadiazol-2-yl)ethyl)-3,4-dihydro-2H-benzo[b][1,4]oxazin-6-yl)carbamate

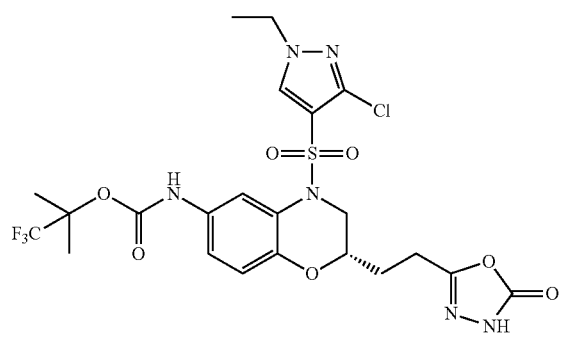 [SMILES: CCn1cc(S(=O)(=O)N2C[C@H](CCc3n[nH]c(=O)o3)Oc3ccc(NC(=O)OC(C)(C)C(F)(F)F)cc32)c(Cl)n1]

To a mixture of (S)-1,1,1-trifluoro-2-methylpropan-2-yl (2-(2-(5-oxo-4,5-dihydro-1,3,4-oxadiazol-2-yl)ethyl)-3,4-dihydro-2H-benzo[b][1,4]oxazin-6-yl)carbamate (30 mg, 0.072 mmol) in THF (1.0 mL) was added 3-chloro-1-ethyl-1H-pyrazole-4-sulfonyl chloride (33.0 mg, 0.144 mmol) and pyridine (1.0 mL). The reaction was stirred at 25° C. for 12 hours, then diluted with EtOAc (5 mL) and water (10 mL). The aqueous layer was extracted with EtOAc (3×5 mL). The combined organic phase was dried over Na$_2$SO$_4$ and concentrated in vacuo. The crude product was purified by prep-HPLC (MeCN/water using TFA buffer) to afford the title compound as a white solid. LCMS (ESI) calculated for C$_{22}$H$_{25}$ClF$_3$N$_6$O$_7$S [M+H]$^+$: 609, found: 609.1; $^1$H NMR (MeOD, 400 MHz) δ 9.39 (1H, br. s.), 8.34 (1H, t, J=7.6 Hz), 8.11 (1H, br. s.), 6.77-6.87 (2H, m), 6.73 (1H, s), 4.40 (1H, dd, J=13.7, 1.6 Hz), 4.00-4.13 (3H, m), 3.40 (1H, dd, J=13.7, 9.0 Hz), 2.78-2.87 (2H, m), 2.01-2.14 (2H, m), 1.75 (6H, s), 1.47 (3H, t, J=7.2 Hz).

Example 106—Preparation of (S)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,3,4-oxadiazol-2-yl)propyl)-3,4-dihydro-2H-benzo[b][1,4]oxazin-6-yl)carbamate (Example 106)

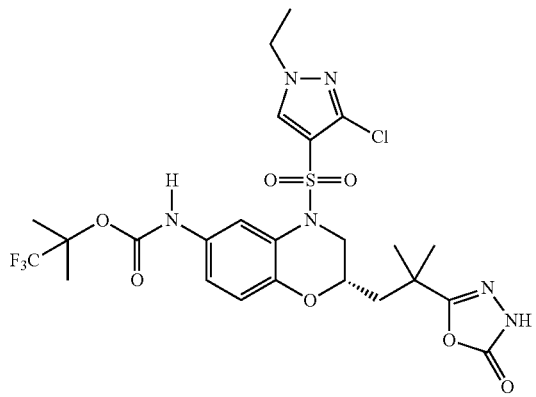 [SMILES: CCn1cc(S(=O)(=O)N2C[C@H](CC(C)(C)c3n[nH]c(=O)o3)Oc3ccc(NC(=O)OC(C)(C)C(F)(F)F)cc32)c(Cl)n1]

Step 1—Preparation of (S)-1,1,1-trifluoro-2-methylpropan-2-yl(2-(2-cyano-2-methylpropyl)-4-tosyl-3,4-dihydro-2H-benzo[b][1,4]oxazin-6-yl)carbamate

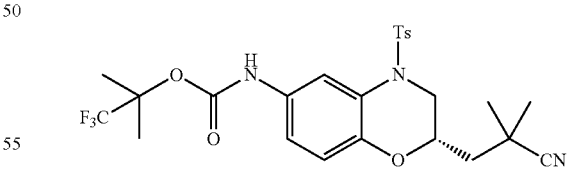

(R and S)-1,1,1-trifluoro-2-methylpropan-2-yl(2-(2-cyano-2-methylpropyl)-4-tosyl-3,4-dihydro-2H-benzo[b][1,4]oxazin-6-yl)carbamate (see Example 94; 46 g, 84.5 mmol) was resolved by SFC (Column: Chiralpak AD (250×30 mm I.D., 10 um); Mobile phase: Supercritical CO$_2$/MeOH (0.1%) NH$_3$.H$_2$O=70/30 at 80 mL/min; Column Temp: 38° C.; Nozzle Pressure: 100 Ba; Wavelength: 220 nm) to give the titled compound (faster eluent, Isomer 1) as yellow solid. LCMS (ESI) calculated for C$_{25}$H$_{29}$F$_3$N$_3$O$_5$S [M+H]$^+$: 540.2, found: 540.2.

Step 2—Preparation of (S)-1,1,1-trifluoro-2-methylpropan-2-yl(2-(2,2-dimethyl-3-oxopropyl)-4-tosyl-3,4-dihydro-2H-benzo[b][1,4]oxazin-6-yl)carbamate

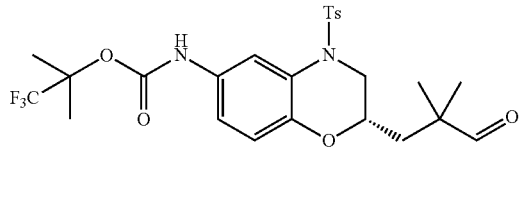 [SMILES: Cc1ccc(S(=O)(=O)N2C[C@H](CC(C)(C)C=O)Oc3ccc(NC(=O)OC(C)(C)C(F)(F)F)cc32)cc1]

To a solution of (S)-1,1,1-trifluoro-2-methylpropan-2-yl (2-(2-cyano-2-methylpropyl)-4-tosyl-3,4-dihydro-2H-benzo[b][1,4]oxazin-6-yl)carbamate (10 g, 18.53 mmol) in toluene (600 mL) was added DIBAL-H (74.1 ml, 74.1 mmol) dropwise at −78° C. under nitrogen. The reaction was stirred at −78° C. for 1 h, then quenched with MeOH (74 mL) and acidified with 1M HCl (244 mL). After stirring at 0° C. for 10 min, the resulting solution was extracted with EtOAc (500 mL×3) and the combined organic layers washed with brine, dried over $Na_2SO_4$ and evaporated to dryness. The crude product was purified by column chromatography (petroleum ether:ethyl acetate=3:1) to give the title compound as yellow solid. LCMS (ESI) calculated for $C_{25}H_{30}F_3N_2O_6S$ [M+H]$^+$: 543.2, found: 543.1.

Step 3—Preparation of (S)-2,2-dimethyl-3-(4-tosyl-6-((((1,1,1-trifluoro-2-methylpropan-2-yl)oxy)carbonyl)amino)-3,4-dihydro-2H-benzo[b][1,4]oxazin-2-yl)propanoic Acid

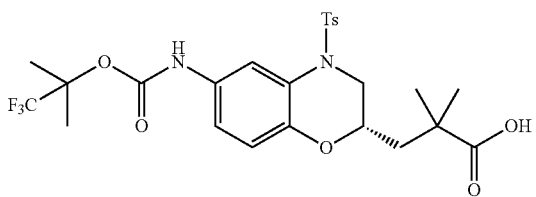 [SMILES: Cc1ccc(S(=O)(=O)N2C[C@H](CC(C)(C)C(=O)O)Oc3ccc(NC(=O)OC(C)(C)C(F)(F)F)cc32)cc1]

To a solution of (S)-1,1,1-trifluoro-2-methylpropan-2-yl (2-(2,2-dimethyl-3-oxopropyl)-4-tosyl-3,4-dihydro-2H-benzo[b][1,4]oxazin-6-yl)carbamate (10.5 g, 19.35 mmol) in THF (400 mL) and water (80 mL) were added sulfamic acid (11.27 g, 116 mmol), potassium dihydrogenphosphate (31.6 g, 232 mmol) and sodium chlorite (2.63 g, 29.0 mmol) at 0° C. The reaction was stirred at 0° C. for 1 h, then diluted with water (250 mL) and extracted with EtOAc (3×500 mL). The combined organic layers were dried over $Na_2SO_4$ and evaporated to dryness. The crude product was purified by column chromatography (petroleum ether:ethyl acetate=10:1 to 1:1) to afford the title compound as yellow solid. LCMS (ESI) calculated for $C_{25}H_{30}F_3N_2O_7S$ [M+H]$^+$: 559.2, found: 559.2.

Step 4—Preparation of (S)-tert-butyl 2-(2,2-dimethyl-3-(4-tosyl-6-((((1,1,1-trifluoro-2-methylpropan-2-yl)oxy)carbonyl)amino)-3,4-dihydro-2H-benzo[b][1,4]oxazin-2-yl)propanoyl)hydrazinecarboxylate

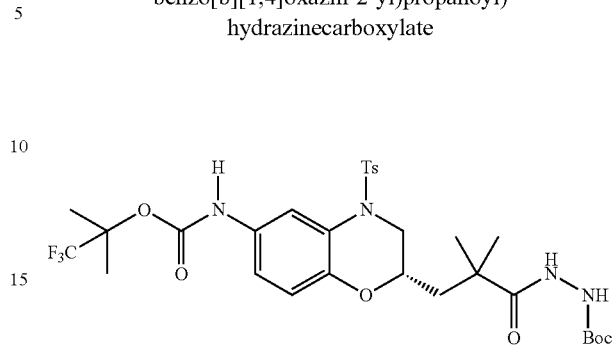

To a solution of (S)-2,2-dimethyl-3-(4-tosyl-6-((((1,1,1-trifluoro-2-methylpropan-2-yl)oxy)carbonyl)amino)-3,4-dihydro-2H-benzo[b][1,4]oxazin-2-yl)propanoic acid (650 mg, 1.164 mmol) and $Et_3N$ (0.250 mL, 1.790 mmol) in $CH_2Cl_2$ (15 mL) was added HATU (442 mg, 1.164 mmol). The mixture was stirred at 25° C. for 1 h, then treated with tert-butyl hydrazinecarboxylate (237 mg, 1.790 mmol). The mixture was stirred at 25° C. for 16 h, concentrated and the solid residue was purified by column chromatography (petroleum ether:EtOAc=2:1) to give the title compound as colorless oil. LCMS (ESI) calculated for $C_{30}H_{40}F_3N_4O_8S$ [M+H]$^+$: 673.2, found: 673.2.

Step 5—Preparation of (S)-1,1,1-trifluoro-2-methylpropan-2-yl(2-(3-hydrazinyl-2,2-dimethyl-3-oxopropyl)-4-tosyl-3,4-dihydro-2H-benzo[b][1,4]oxazin-6-yl)carbamate

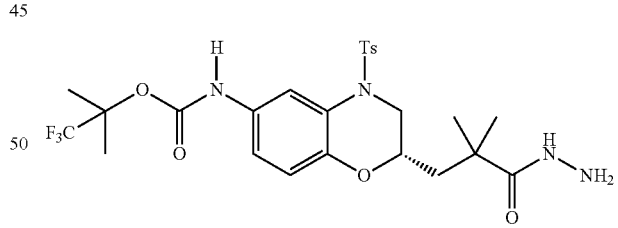

To a solution of (S)-tert-butyl 2-(2,2-dimethyl-3-(4-tosyl-6-((((1,1,1-trifluoro-2-methylpropan-2-yl)oxy)carbonyl)amino)-3,4-dihydro-2H-benzo[b][1,4]oxazin-2-yl)propanoyl)hydrazinecarboxylate (430 mg, 0.639 mmol) in ethyl acetate (3 ml) was added a solution of HCl in EtOAc (10 ml, 4 M). The reaction was stirred at 20° C. for 2 h, then concentrated to give the crude title compound as light yellow solid. LCMS (ESI) calculated for $C_{25}H_{32}F_3N_4O_6S$ [M+H]$^+$: 573.2, found: 573.1.

Step 6-Preparation of (S)-1,1,1-trifluoro-2-methyl-propan-2-yl (2-(2-methyl-2-(5-oxo-4,5-dihydro-1,3,4-oxadiazol-2-yl)propyl)-4-tosyl-3,4-dihydro-2H-benzo[b][1,4]oxazin-6-yl)carbamate

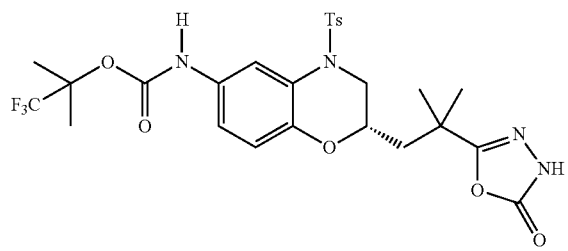 [SMILES: Cc1ccc(S(=O)(=O)N2C[C@H](CC(C)(C)c3n[nH]c(=O)o3)Oc3ccc(NC(=O)OC(C)(C)C(F)(F)F)cc32)cc1]

To a solution of (S)-1,1,1-trifluoro-2-methylpropan-2-yl (2-(3-hydrazinyl-2,2-dimethyl-3-oxopropyl)-4-tosyl-3,4-dihydro-2H-benzo[b][1,4]oxazin-6-yl)carbamate (376 mg, 0.657 mmol) and N-ethyl-N-isopropylpropan-2-amine (255 mg, 1.970 mmol) in DMF (5 mL) was added di(1H-imidazol-1-yl)methanone (160 mg, 0.985 mmol). The reaction was stirred at 25° C. for 6 h, then concentrated in vacuo. The crude product was purified by prep-TLC (petroleum ether:EtOAc=1:1) to give the title compound as yellow oil. LCMS (ESI) calculated for $C_{26}H_{30}F_3N_4O_7S$ $[M+H]^+$: 599.2, found: 599.2.

Step 7—Preparation of (S)-1,1,1-trifluoro-2-methyl-propan-2-yl(2-(2-methyl-2-(5-oxo-4,5-dihydro-1,3,4-oxadiazol-2-yl)propyl)-3,4-dihydro-2H-benzo[b][1,4]oxazin-6-yl)carbamate

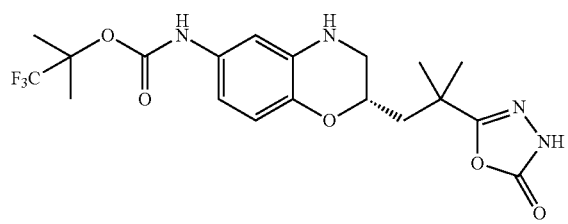 [SMILES: CC(C)(C[C@H]1CNc2cc(NC(=O)OC(C)(C)C(F)(F)F)ccc2O1)c1n[nH]c(=O)o1]

To a solution of (S)-1,1,1-trifluoro-2-methylpropan-2-yl (2-(2-methyl-2-(5-oxo-4,5-dihydro-1,3,4-oxadiazol-2-yl)propyl)-4-tosyl-3,4-dihydro-2H-benzo[b][1,4]oxazin-6-yl)carbamate (340 mg, 0.568 mmol) in MeOH (20 mL) was added Mg (276 mg, 11.36 mmol) in one portion at 25° C. under nitrogen. The reaction was stirred at 25° C. for 18 hours, then quenched with saturated $NH_4Cl$ solution and extracted with EtOAc (3×300 mL). The combined organic layers were dried over $Na_2SO_4$, filtered and the filtrate concentrated in vacuo. The crude product was purified by prep-TLC (petroleum ether:EtOAc=1:1) to afford the title compound as yellow solid. LCMS (ESI) calculated for $C_{19}H_{24}F_3N_4O_5$ $[M+H]^+$: 445.2, found: 445.2; $^1$H-NMR (400 MHz, MeOD) δ 6.85 (1H, s), 6.54 (1H, d, J=7.6 Hz), 6.39 (1H, d, J=8.8 Hz), 4.07-4.12 (1H, m), 3.24-3.25 (1H, m), 3.01-3.09 (2H, m), 1.99-2.08 (2H, m), 1.70 (6H, s), 1.25-1.41 (6H, m), 0.93-0.95 (1H, m).

Step 8—Preparation of (S)-1,1,1-trifluoro-2-methyl-propan-2-yl (4-((3-chloro-1-ethyl-1H-pyrazol-4-yl)sulfonyl)-2-(2-methyl-2-(5-oxo-4,5-dihydro-1,3,4-oxadiazol-2-yl)propyl)-3,4-dihydro-2H-benzo[b][1,4]oxazin-6-yl)carbamate

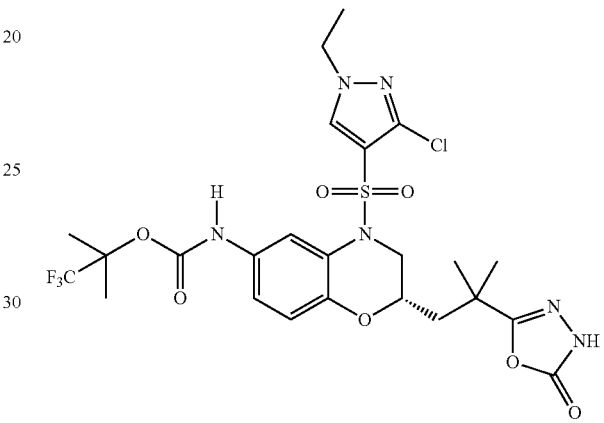

To a mixture of (S)-1,1,1-trifluoro-2-methylpropan-2-yl (2-(2-methyl-2-(5-oxo-4,5-dihydro-1,3,4-oxadiazol-2-yl)propyl)-3,4-dihydro-2H-benzo[b][1,4]oxazin-6-yl)carbamate (30 mg, 0.068 mmol) in THF (0.5 mL) was added 3-chloro-1-ethyl-1H-pyrazole-4-sulfonyl chloride (30.9 mg, 0.135 mmol) and pyridine (0.5 mL). The reaction mixture was stirred at 20° C. for 6 hours, then diluted with water (3 mL) and extracted with ethyl acetate (3×5 mL). The organic layers were combined, dried over anhydrous magnesium sulfate, filtered and concentrated in vacuo. The crude product was purified by prep-HPLC (MeCN/water using TFA buffer) to afford the title compound as white solid. LCMS (ESI) calculated for $C_{24}H_{29}ClF_3N_6O_7S$ $[M+H]^+$: 637.1, found: 637.1; $^1$H-NMR (400 MHz, MeOD) δ 8.24 (1H, s), 7.87 (1H, s), 6.90-6.93 (1H, m), 6.52 (1H, d, J=9.2 Hz), 4.23 (1H, d, J=12.4 Hz), 4.10 (2H, q, J=7.2 Hz), 3.87-3.92 (1H, m), 3.33-3.36 (1H, m), 1.96-2.02 (1H, m), 1.81-1.84 (1H, m), 1.74 (6H, s), 1.32-1.41 (9H, m).

Example 107—Preparation of Additional 1,3,4-oxadiazolone

The compounds in Table 31 below were prepared based on the experimental procedures described in Examples 105 and 106 and elsewhere in the detailed description, and can be achieved by one of skill in the art in light of the present disclosure.

TABLE 31

| Ex. No. | Structure | Name | Observed m/z |
|---|---|---|---|
| 107A | 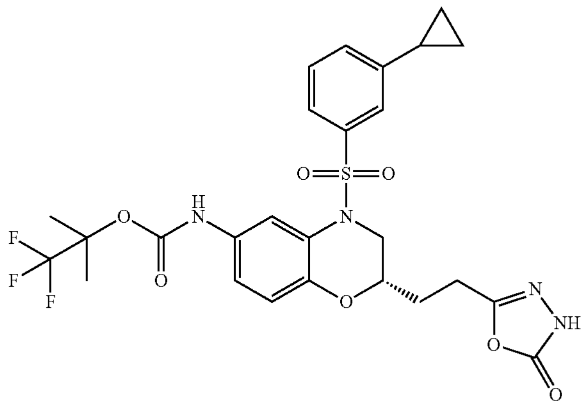 [SMILES: CC(C)(OC(=O)Nc1ccc2c(c1)N(S(=O)(=O)c1cccc(C3CC3)c1)C[C@H](CCc1n[nH]c(=O)o1)O2)C(F)(F)F] | 2,2,2-trifluoro-1,1-dimethylethyl {(2S)-4-[(3-cyclopropylphenyl)sulfonyl]-2-[2-(5-oxo-4,5-dihydro-1,3,4-oxadiazol-2-yl)ethyl]-3,4-dihydro-2H-1,4-benzoxazin-6-yl}carbamate | 597 (M + H)+ |
| 107B | 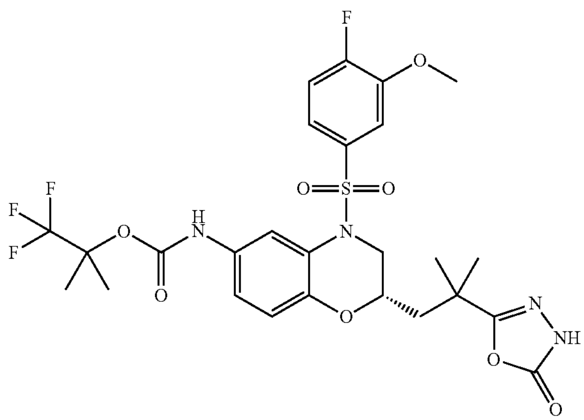 [SMILES: COc1cc(S(=O)(=O)N2C[C@H](CC(C)(C)c3n[nH]c(=O)o3)Oc3ccc(NC(=O)OC(C)(C)C(F)(F)F)cc32)ccc1F] | 2,2,2-trifluoro-1,1-dimethylethyl {(2S)-4-[(4-fluoro-3-methoxyphenyl)sulfonyl]-2-[2-methyl-2-(5-oxo-4,5-dihydro-1,3,4-oxadiazol-2-yl)propyl]-3,4-dihydro-2H-1,4-benzoxazin-6-yl}carbamate | 633 (M + H)+ |

Example 108—Preparation of (S)-1,1,1-trifluoro-2-methylpropan-2-yl(2-(2-(1H-tetrazol-5-yl)ethyl)-4-((3-(trifluoromethyl)phenyl)sulfonyl)-3,4-dihydro-2H-benzo[b][1,4]oxazin-6-yl)carbamate (Example 108)

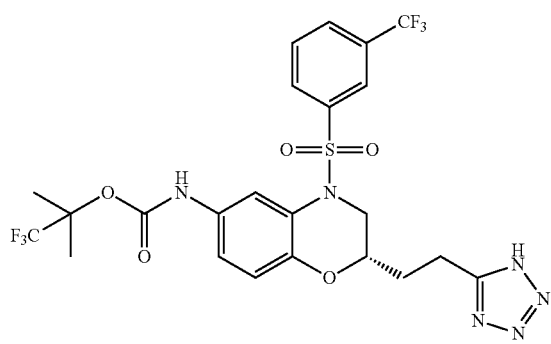 [SMILES: CC(C)(OC(=O)Nc1ccc2c(c1)N(S(=O)(=O)c1cccc(C(F)(F)F)c1)C[C@H](CCc1nnn[nH]1)O2)C(F)(F)F]

To a solution of (S)-1,1,1-trifluoro-2-methylpropan-2-yl (2-(2-cyanoethyl)-4-((3-(trifluoromethyl)phenyl)sulfonyl)- 3,4-dihydro-2H-benzo[b][1,4]oxazin-6-yl)carbamate (50 mg, 0.08 mmol) and sodium azide (28.7 mg, 0.4 mmol) in DMF (1 mL) was added NH$_4$Cl (23.6 mg, 0.4 mmol). The reaction was stirred at 110° C. for 6 h under N$_2$, then cooled and treated with water (10 mL). The biphasic mixture was extracted with ethyl acetate (10 mL) and the combined organic layers were washed with aqueous sodium hydroxide (10 mL), dried (Na$_2$SO$_4$), filtered and evaporated under reduced pressure. The crude product was purified by prep-HPLC (MeCN/water using TFA buffer) to afford the title compound as white solid. LCMS (ESI) calculated for C$_{23}$H$_{23}$F$_6$N$_6$O$_5$S [M+H]$^+$: 609, found: 609. $^1$H NMR (CDCl$_3$, 400 MHz) δ 7.95 (brs, 1H), 7.74-7.90 (m, 3H), 7.54-7.63 (m, 1H), 6.91-7.00 (m, 1H), 6.52-6.72 (m, 2H), 4.16 (d, J=12.9 Hz, 1H), 3.58 (brs, 1H), 3.23-3.35 (m, 1H), 3.07 (t, J=6.8 Hz, 2H), 1.97-2.09 (m, 2H), 1.70 (brs, 7H).

Example 109—Preparation of Additional Tetrazoles

The compounds in Table 32 below were prepared based on the experimental procedures described in Example 108 and elsewhere in the detailed description, and can be achieved by one of skill in the art in light of the present disclosure.

TABLE 32

| Ex. No. | Structure | Name | Observed m/z |
|---|---|---|---|
| 109A | 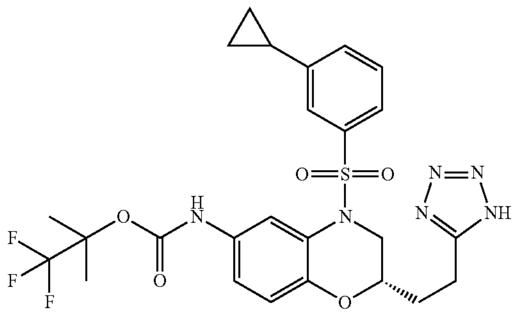 [SMILES: CC(C)(OC(=O)Nc1ccc2c(c1)N(S(=O)(=O)c1cccc(C3CC3)c1)C[C@H](CCc1nnn[nH]1)O2)C(F)(F)F] | 2,2,2-trifluoro-1,1-dimethylethyl {(2S)-4-[(3-cyclopropylphenyl)sulfonyl]-2-[2-(1H-tetrazol-5-yl)ethyl]-3,4-dihydro-2H-1,4-benzoxazin-6-yl}carbamate | 581 (M + H)+ |
| 109B | 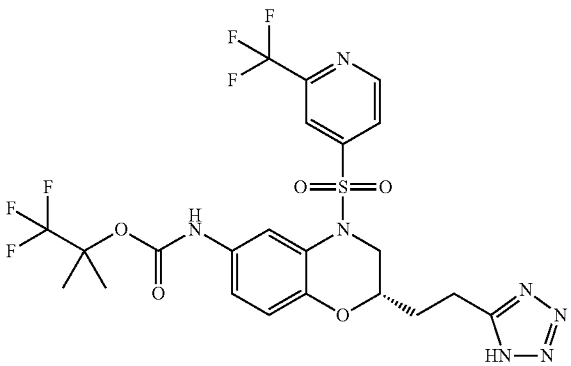 [SMILES: CC(C)(OC(=O)Nc1ccc2c(c1)N(S(=O)(=O)c1ccnc(C(F)(F)F)c1)C[C@H](CCc1nnn[nH]1)O2)C(F)(F)F] | 2,2,2-trifluoro-1,1-dimethylethyl [(2S)-2-[2-(1H-tetrazol-5-yl)ethyl]-4-{[2-(trifluoromethyl)pyridin-4-yl]sulfonyl}-3,4-dihydro-2H-1,4-benzoxazin-6-yl]carbamate | 610 (M + H)+ |
| 109C | 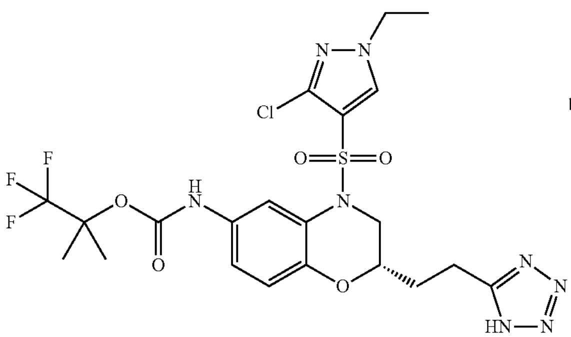 [SMILES: CCn1cc(S(=O)(=O)N2C[C@H](CCc3nnn[nH]3)Oc3ccc(NC(=O)OC(C)(C)C(F)(F)F)cc32)c(Cl)n1] | (S)-1,1,1-trifluoro-2-methylpropan-2-yl (2-(2-(1H-tetrazol-5-yl)ethyl)-4-((3-chloro-1-ethyl-1H-pyrazol-4-yl)sulfonyl)-3,4-dihydro-2H-benzo[b][1,4]oxazin-6-yl)carbamate | 593 (M + H)+ |

Example 110—Preparation of (R)-1,1,1-trifluoro-2-methylpropan-2-yl(2-(hydroxymethyl)-5-methyl-4-((3-(trifluoromethyl)phenyl)sulfonyl)-3,4-dihydro-2H-benzo[b][1,4]oxazin-6-yl)carbamate (Example 110)

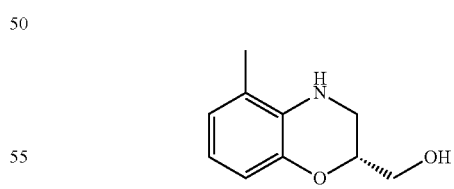

Step 1—Preparation of (R)-(5-methyl-3,4-dihydro-2H-benzo[b][1,4]oxazin-2-yl)methanol

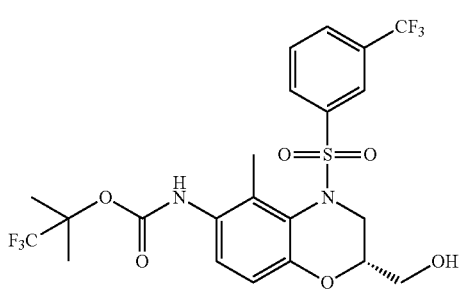 [SMILES: Cc1c(NC(=O)OC(C)(C)C(F)(F)F)ccc2c1N(S(=O)(=O)c1cccc(C(F)(F)F)c1)C[C@H](CO)O2]

(S)-2-(chloromethyl)oxirane (902 mg, 9.74 mmol) was added dropwise to a stirred mixture of 2-amino-3-methylphenol (1.00 g, 8.12 mmol) and AcOH (1.40 mL, 24.4 mmol) in ethanol (50 mL) at 100° C. under nitrogen and the resulting mixture was stirred at 100° C. for 1 h. $K_2CO_3$ (6.73 g, 48.7 mmol) was next added and the resulting solution was stirred at 100° C. for an additional 16 h. The reaction was evaporated under reduced pressure and the residue dissolved in EtOAc, washed with water and brine (50 mL), dried over $Na_2SO_4$, filtered and concentrated. The crude product was purified by silica gel column chromatography (EtOAc in petroleum ether from 0 to 33%) to afford the title compound as brown oil.

Step 2—Preparation of (R)-2-(((tert-butyldimethylsilyl)oxy)methyl)-5-methyl-3,4-dihydro-2H-benzo[b][1,4]oxazine

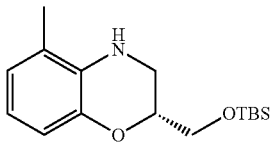 [SMILES: Cc1cccc2c1NC[C@H](CO[Si](C)(C)C(C)(C)C)O2]

A solution of (R)-(5-methyl-3,4-dihydro-2H-benzo[b][1,4]oxazin-2-yl)methanol (450 mg, 2.51 mmol), 1H-imidazole (400 mg, 5.88 mmol) and tert-butylchlorodimethylsilane (700 mg, 4.64 mmol) in DMF (2 mL) was stirred at 40-50° C. for 6 h. The reaction was then cooled and diluted with EtOAc, washed with brine, dried Na$_2$SO$_4$, filtered and concentrated. The crude product was purified by column chromatography on silica gel (EtOAc:petroleum ether=1:20-1:5) to afford the title compound as a yellow oil. LCMS (ESI) calculated for $C_{16}H_{28}NO_2Si$ [M+H]$^+$: 294.2, found: 294.1, $^1$H NMR (400 MHz, DMSO) δ 6.53 (dd, J=15.6 Hz, 7.4 Hz, 2H), 6.34-6.45 (m, 1H), 5.16 (s, 1H), 3.95 (d, J=5.3 Hz, 1H), 3.65-3.85 (m, 2H), 3.38 (d, J=2.7 Hz, 1H), 3.32 (s, 1H), 3.00-3.15 (m, 1H), 2.03 (s, 3H), 0.88 (s, 9H), 0.07 (d, J=4.7 Hz, 6H).

Step 3—Preparation of (R)-2-(((tert-butyldimethylsilyl)oxy)methyl)-5-methyl-4-((3-(trifluoromethyl)phenyl)sulfonyl)-3,4-dihydro-2H-benzo[b][1,4]oxazine

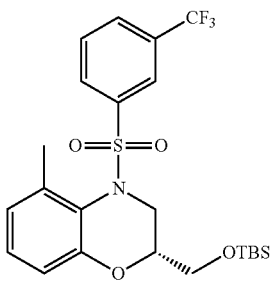 [SMILES: Cc1cccc2c1N(S(=O)(=O)c1cccc(C(F)(F)F)c1)C[C@H](CO[Si](C)(C)C(C)(C)C)O2]

A solution of (R)-2-(((tert-butyldimethylsilyl)oxy)methyl)-5-methyl-3,4-dihydro-2H-benzo[b][1,4]oxazine (100 mg, 0.341 mmol) and 3-(trifluoromethyl)benzene-1-sulfonyl chloride (100 mg, 0.409 mmol) in DCM (1 mL) and pyridine (1 mL) was stirred at room temperature for 16 h. The reaction was then acidified with 0.5 M HCl to pH=5-6 and extracted with EtOAc. The combined organic layers were washed with brine, dried with Na$_2$SO$_4$ and concentrated. The crude product was purified by column chromatography on silica gel to afford the title compound as a yellow oil. LCMS (ESI) calculated for $C_{23}H_{31}F_3NO_4SSi$ [M+H]$^+$: 502.2, found: 502.2, $^1$H NMR (400 MHz, CDCl$_3$) δ 7.77-7.90 (m, 3H), 7.55-7.66 (m, 1H), 7.05-7.13 (m, 1H), 6.89 (d, J=7.4 Hz, 1H), 6.61 (d, J=8.0 Hz, 1H), 4.24 (d, J=12.3 Hz, 1H), 3.88 (dd, J=10.4 Hz, 4.7 Hz, 1H), 3.49-3.65 (m, 2H), 3.30 (s, 1H), 2.51 (s, 3H), 0.81 (s, 10H), 0.00 (s, 3H), −0.03 (s, 3H).

Step 4—Preparation of (R)-(5-methyl-6-nitro-4-((3-(trifluoromethyl)phenyl) sulfonyl)-3,4-dihydro-2H-benzo[b][1,4]oxazin-2-yl)methanol

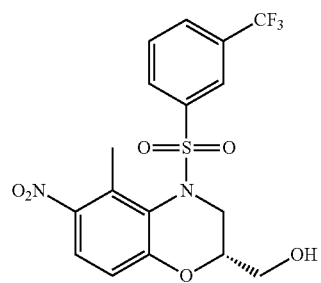 [SMILES: Cc1c([N+](=O)[O-])ccc2c1N(S(=O)(=O)c1cccc(C(F)(F)F)c1)C[C@H](CO)O2]

To a solution of (R)-2-(((tert-butyldimethylsilyl)oxy)methyl)-5-methyl-4-((3-(trifluoromethyl)phenyl)sulfonyl)-3,4-dihydro-2H-benzo[b][1,4]oxazine (300 mg, 0.598 mmol) in MeNO$_2$ (2 mL) was added nitroniumte trafluoroborate (100 mg, 0.753 mmol) in one batch, then the reaction mixture was stirred at 0° C. for 3 h. The reaction mixture was directly purified by preparative TLC to afford the title compound as a white solid. LCMS (ESI) calculated for $C_{17}H_{16}F_3N_2O_6S$ [M+H]$^+$: 433.1, found: 433.2, $^1$H NMR (400 MHz, CDCl$_3$) δ 7.88-8.00 (m, 4H), 7.62-7.73 (m, 1H), 6.82 (d, J=9.2 Hz, 1H), 4.19-4.29 (m, 1H), 3.60-3.84 (m, 3H), 3.28-3.41 (m, 1H), 2.60-2.67 (m, 3H).

Step 5—Preparation of (R)-(6-amino-5-methyl-4-((3-(trifluoromethyl) phenyl)sulfonyl)-3,4-dihydro-2H-benzo[b][1,4]oxazin-2-yl)methanol

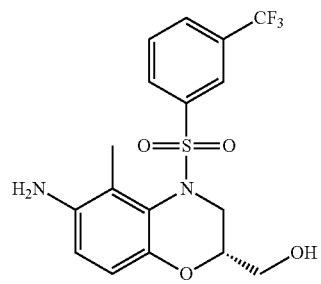

HCl (2.0 Min MeOH, 1.0 mL) was added to a solution of (R)-(5-methyl-6-nitro-4-((3-(trifluoromethyl)phenyl)sulfonyl)-3,4-dihydro-2H-benzo[b][1,4]oxazin-2-yl)methanol (120 mg, 0.278 mmol) and iron powder (150 mg, 2.69 mmol) in methanol (2 mL) and the resulting solution was stirred at room temperature for 1 h. The reaction was next filtered through CELITE and washed with methanol. The filtrate was concentrated to afford the title compound. LCMS (ESI) calculated for $C_{17}H_{18}F_3N_2O_4S$ [M+H]$^+$: 403.1, found: 403.0.

Step 6—Preparation of (R)-1,1,1-trifluoro-2-methyl-propan-2-yl (2-(hydroxymethyl)-5-methyl-4-((3-(trifluoromethyl)phenyl)sulfonyl)-3,4-dihydro-2H-benzo[b][1,4]oxazin-6-yl)carbamate

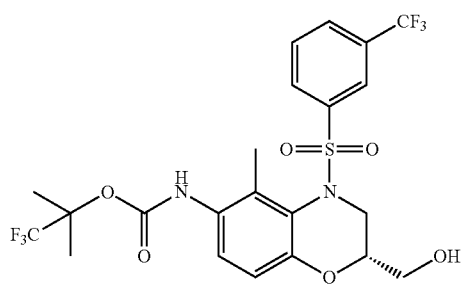 [SMILES: Cc1c(NC(=O)OC(C)(C)C(F)(F)F)ccc2c1N(S(=O)(=O)c1cccc(C(F)(F)F)c1)C[C@H](CO)O2]

To a solution of (R)-(6-amino-5-methyl-4-((3-(trifluoromethyl)phenyl)sulfonyl)-3,4-dihydro-2H-benzo[b][1,4]oxazin-2-yl)methanol (100 mg, 0.249 mmol) in DMSO (1 mL) was added (1-(((1,1,1-trifluoro-2-methylpropan-2-yl)oxy)carbonyl)-1H-imidazol-3-ium-3-yl)methanide iodide (117 mg, 0.323 mmol) and the resultant mixture was stirred at room temperature for 1 h. Water was then added and the biphasic mixture extracted with EtOAc (10 mL×2). The combined organic layers were washed with water and brine, concentrated and the crude product purified by preparative HPLC (MeCN/water using TFA buffer) to afford the title compound as a white solid. LCMS (ESI) calculated for $C_{22}H_{23}F_6N_2O_6S$ [M+H]$^+$: 557.1, found: 557.2, $^1$H NMR (400 MHz, CDCl$_3$) δ 7.40-7.97 (m, 4H), 6.68 (d, J=8.4 Hz, 1H), 6.50 (s, 1H), 4.24 (d, J=12.5 Hz, 1H), 3.87 (s, 1H), 3.65 (d, J=11.9 Hz, 1H), 3.19-3.39 (m, 1H), 2.38 (s, 3H), 1.77 (d, J=6.3 Hz, 6H).

Example 111—Preparation of (R)-1,1,1-trifluoro-2-methylpropan-2-yl (5-((3-chloro-1-ethyl-1H-pyrazol-4-yl)sulfonyl)-7-((ethylsulfonyl)methyl)-5,6,7,8-tetrahydro-1,5-naphthyridin-3-yl)carbamate and (S)-1,1,1-trifluoro-2-methylpropan-2-yl (5-((3-chloro-1-ethyl-1H-pyrazol-4-yl)sulfonyl)-7-((ethylsulfonyl)methyl)-5,6,7,8-tetrahydro-1,5-naphthyridin-3-yl)carbamate (Examples 111A and 111B)

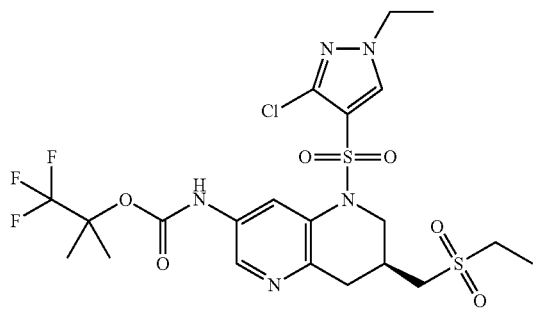

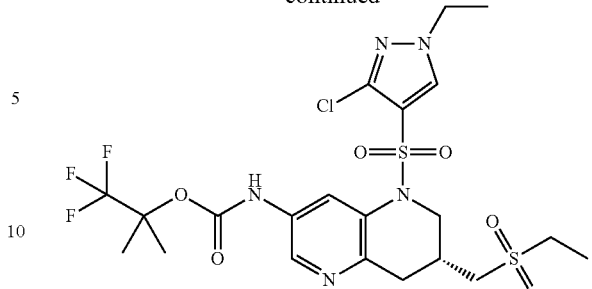

Step 1—Preparation of 1-benzyl-7-chloro-3,4-dihydro-1,5-naphthyridin-2(1H)-one

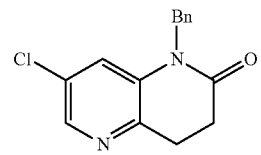 [SMILES: O=C1CCc2ncc(Cl)cc2N1Cc1ccccc1]

To a 0° C. solution of 7-chloro-3,4-dihydro-1,5-naphthyridin-2(1H)-one (2 g, 10.95 mmol) in N,N-dimethylformamide (20 mL) was added Cs$_2$CO$_3$ (5.35 g, 16.43 mmol), followed by (bromomethyl)benzene (2.061 g, 12.05 mmol). The reaction mixture was stirred at room temperature for 1 hour, then poured into water (50 mL) and extracted with EtOAc (50 mL×3). The combined organic layers were washed with brine (50 mL×3), dried over anhydrous Na$_2$SO$_4$ and concentrated under vacuum. The crude product was purified by column chromatography on silica gel (EtOAc: petroleum ether=0-30%) to afford the titled compound as a yellow solid. LCMS (ESI) calculated for $C_{15}H_{14}ClN_2O$ [M+H]$^+$: 273, found: 273. $^1$HNMR (400 MHz, CDCl$_3$) δ 8.12 (1H, s), 7.26-7.36 (3H, m), 7.19 (2H, d, J=7.2 Hz), 7.11 (1H, s), 5.11 (2H, s), 3.18 (2H, t, J=7.6 Hz), 2.90 (2H, t, J=8.0 Hz).

Step 2—Preparation of (R and S)-1-benzyl-7-chloro-2-oxo-1,2,3,4-tetrahydro-1,5-naphthyridine-3-carboxylate

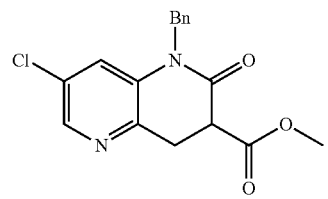 [SMILES: COC(=O)C1Cc2ncc(Cl)cc2N(Cc2ccccc2)C1=O]

To a −78° C. solution of 1-benzyl-7-chloro-3,4-dihydro-1,5-naphthyridin-2(1H)-one (2 g, 7.33 mmol) in dry tetrahydrofuran (50 mL) was added LHMDS (8.80 mL, 8.80 mmol, 1M in THF) and the mixture was stirred at −78° C. for 30 minutes. Methyl carbonochloridate (0.832 g, 8.80 mmol) was next added and the reaction was stirred at −78° C. for an additional 1 hour. The reaction was quenched with saturated aq. NH$_4$Cl (20 mL) and extracted with EtOAc (50 mL×3). The combined organic layers were washed with brine (50 mL×3), dried over anhydrous Na$_2$SO$_4$ and concentrated under vacuum. The crude product was purified by column chromatography on silica gel (EtOAc:petroleum ether=0-30%) to afford the titled compound as a yellow solid. LCMS (ESI) calculated for C$_{17}$H$_{16}$ClN$_2$O$_3$ [M+H]$^+$: 331, found: 331. $^1$HNMR (400 MHz, CDCl$_3$) δ 8.15 (1H, s), 7.25-7.35 (5H, m), 7.13 (1H, s), 5.31 (1H, d, J=16.4 Hz), 5.31 (1H, d, J=16.4 Hz), 3.91 (1H, t, J=6.8 Hz), 3.78 (3H, s), 3.58 (1H, dd, J=7.2 Hz J=16.4 Hz), 3.40 (1H, dd, J=6.4 Hz J=17.2 Hz).

Step 3—Preparation of (R and S)-1-benzyl-7-chloro-3-(methoxymethyl)-1,2,3,4-tetrahydro-1,5-naphthyridine

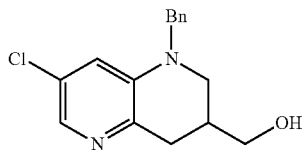 [SMILES: OCC1Cc2ncc(Cl)cc2N(Cc2ccccc2)C1]

To a 0° C. solution of methyl 1-benzyl-7-chloro-2-oxo-1,2,3,4-tetrahydro-1,5-naphthyridine-3-carboxylate (1.7 g, 5.14 mmol) in dry tetrahydrofuran (50 mL) was added BH$_3$—SMe$_2$ (2.440 mL, 25.7 mmol). The reaction mixture was stirred at 60° C. for 2 hours, then quenched with MeOH (10 mL) and concentrated under vacuum. The crude product was purified by column chromatography on silica gel (EtOAc:petroleum ether=0-30%) to afford the titled compound as a yellow solid. LCMS (ESI) calculated for C$_{16}$H$_{18}$ClN$_2$O [M+H]$^+$: 289, found: 289. $^1$HNMR (400 MHz, CDCl$_3$) δ 7.80 (1H, d, J=1.6 Hz), 7.10-7.31 (5H, m), 6.82 (1H, d, J=2.0 Hz), 4.45 (2H, q, J=16.8, 27.2 Hz), 3.77 (1H, d, J=10.8 Hz), 3.48-3.52 (3H, m), 3.28 (1H, t, J=9.2 Hz), 2.79 (1H, q, J=10.0, 18.4 Hz), 2.27-2.29 (1H, m), 1.56-1.54 (1H, m).

Step 4—Preparation of (R and S)-(1-benzyl-7-chloro-1,2,3,4-tetrahydro-1,5-naphthyridin-3-yl)methyl methanesulfonate

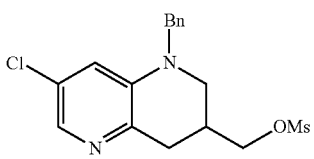 [SMILES: CS(=O)(=O)OCC1Cc2ncc(Cl)cc2N(Cc2ccccc2)C1]

To a solution of (R and S)-(1-benzyl-7-chloro-1,2,3,4-tetrahydro-1,5-naphthyridin-3-yl)methanol (2000 mg, 6.93 mmol) and Et$_3$N (1.931 mL, 13.85 mmol) in dry DCM (20 mL) at 0° C. was added methanesulfonyl chloride (2500 mg, 21.82 mmol). The reaction mixture was stirred at 20° C. for 10 hours, then quenched with water (20 mL). The biphasic mixture was extracted with DCM (3×20 mL) and the combined organic layer was dried over Na$_2$SO$_4$ and evaporated. The crude product was purified by column chromatography (SiO$_2$, petroleum ether:EtOAc=20:1 to 2:1) to give the title compound as a colorless oil. $^1$HNMR (CDCl3, 400 MHz) δ 7.80 (1H, s), 7.34-7.38 (2H, m), 7.30 (1H, d, J=7.2 Hz), 7.19-7.21 (2H, m), 6.81 (1H, s), 4.48 (2H, s), 4.28 (1H, dd, J=10.0, 5.2 Hz), 4.16-4.21 (1H, m), 3.50-3.50 (1H, m), 3.31-3.34 (1H, m), 3.11-3.12 (1H, m), 3.00 (3H, s), 2.81-2.83 (1H, m), 2.62-2.64 (1H, m).

Step 5—Preparation of (R and S)-1-benzyl-7-chloro-3-(iodomethyl)-1,2,3,4-tetrahydro-1,5-naphthyridine

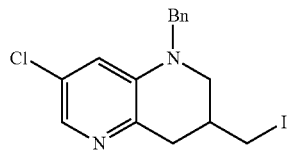 [SMILES: Clc1cnc2c(c1)N(Cc1ccccc1)CC(CI)C2]

To a solution of (R and S)-(1-benzyl-7-chloro-1,2,3,4-tetrahydro-1,5-naphthyridin-3-yl)methyl methanesulfonate (350 mg, 0.954 mmol) in acetone (10 mL) was added NaI (143 mg, 0.954 mmol). The reaction mixture was stirred at 60° C. for 10 hours, then concentrated under vacuum, diluted with water (20 mL) and extracted with EtOAc (3×20 mL). The combined organic layer was dried over Na$_2$SO$_4$, evaporated and the crude product was purified by column chromatography (petroleum ether:EtOAc=20:1 to 5:1) to give the title compound as a colorless oil. $^1$H-NMR (CDCl$_3$, 400 MHz) δ 7.79 (1H, d, J=0.4 Hz), 7.35-7.39 (2H, m), 7.31 (1H, d, J=7.2 Hz), 7.21-7.23 (2H, m), 6.77 (1H, s), 4.49 (2H, s), 3.52 (1H, d, J=1.2 Hz), 3.28-3.30 (2H, m), 3.17-3.22 (2H, m), 3.80-3.83 (1H, m), 2.34-2.37 (1H, m).

Step 6—Preparation of (R and S)-1-benzyl-7-chloro-3-((ethylsulfonyl)methyl)-1,2,3,4-tetrahydro-1,5-naphthyridine

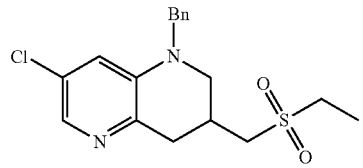 [SMILES: CCS(=O)(=O)CC1Cc2ncc(Cl)cc2N(Cc2ccccc2)C1]

To a solution of (R and S)-1-benzyl-7-chloro-3-(iodomethyl)-1,2,3,4-tetrahydro-1,5-naphthyridine (550 mg, 1.380 mmol) in DMF (10 ml) at 0° C. was added sodium ethanesulfinate (481 mg, 4.14 mmol). The reaction mixture was stirred at 110° C. for 1 h in the microwave, then cooled to room temperature, quenched with water (50 mL) and extracted with EtOAc (50 mL×3). The combined organic layer was washed with brine (30 mL×3), dried over Na$_2$SO$_4$ and concentrated under vacuum. The crude product was purified by column chromatography (SiO$_2$, petroleum ether:EtOAc=1:3) to give the title compound as a brown solid. LCMS (ESI) calculated for C$_{18}$H$_{22}$ClN$_2$O$_2$S [M+H]+: 365.1, found: 365.0. $^1$H-NMR (CDCl3, 400 MHz) δ 7.78 (1H, s), 7.32-7.36 (2H, m), 7.27-7.29 (1H, m), 7.19-7.21 (2H, m), 6.81 (1H, d, J=1.2 Hz), 4.49 (2H, s), 3.67-3.70 (1H, m), 3.45-3.48 (1H, m), 3.20-3.24 (1H, m), 2.97-3.03 (4H, m), 2.80-2.84 (1H, m), 1.39 (3H, t, J=7.6 Hz).

Step 7—Preparation of (R and S)-5-benzyl-N-(diphenylmethylene)-7-((ethylsulfonyl)methyl)-5,6,7,8-tetrahydro-1,5-naphthyridin-3-amine

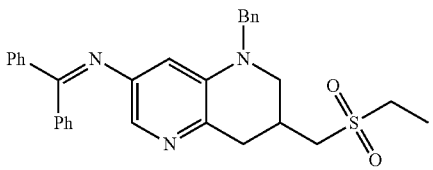 [SMILES: CCS(=O)(=O)CC1Cc2ncc(N=C(c3ccccc3)c3ccccc3)cc2N(Cc2ccccc2)C1]

A mixture of (R and S)-1-benzyl-7-chloro-3-((ethylsulfonyl)methyl)-1,2,3,4-tetrahydro-1,5-naphthyridine (350 mg, 0.959 mmol) in dioxane (10 ml) was added diphenylmethanimine (209 mg, 1.151 mmol), Cs$_2$CO$_3$ (625 mg, 1.918 mmol) and chloro(2-dicyclohexylphosphino-2',4',6'-tri-i-propyl-1,1'-biphenyl) palladium(ii) methyl-t-butyl ether adduct (159 mg, 0.192 mmol). The reaction mixture degassed under argon and stirred at 110° C. for 10 hours, then diluted with water (20 mL) and extracted with EtOAc (20 mL×3). The combined organic layer was washed with brine (10 mL×3), dried over Na$_2$SO$_4$ and concentrated under pressure. The crude product was purified by Prep-TLC (SiO$_2$, petroleum ether:EtOAc=1:2) to give the title compound as a yellow solid. LCMS (ESI) calculated for C$_{31}$H$_{32}$N$_3$O$_2$S [M+H]+: 510.2, found: 510.2. $^1$H-NMR (CDCl3, 400 MHz) δ 7.74 (1H, d, J=7.6 Hz), 7.60 (1H, d, J=7.6 Hz), 7.41-7.42 (3H, m), 7.30-7.32 (2H, m), 7.23-7.24 (3H, m), 7.17-7.18 (2H, m), 6.99-7.01 (2H, m), 6.92-6.94 (2H, m), 6.20 (1H, s), 4.26 (2H, d, J=3.6 Hz), 3.54 (1H, d, J=10.4 Hz), 3.29-3.32 (1H, m), 3.05-3.09 (1H, m), 2.89-2.94 (4H, m), 2.81-2.83 (1H, m), 2.66-2.71 (1H, m), 1.30 (3H, t, J=7.6 Hz).

Step 8—Preparation of (R and S)-7-((ethylsulfonyl)methyl)-5,6,7,8-tetrahydro-1,5-naphthyridin-3-amine

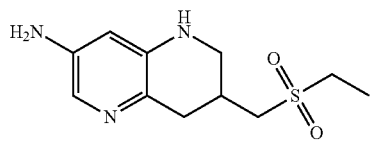 [SMILES: CCS(=O)(=O)CC1CNc2cc(N)cnc2C1]

Pd/C (146 mg, 0.137 mmol) was added to a solution of the (R and S)-5-benzyl-N-(diphenylmethylene)-7-((ethylsulfonyl)methyl)-5,6,7,8-tetrahydro-1,5-naphthyridin-3-amine (140 mg, 0.275 mmol) in MeOH (20 mL). The resulting mixture was stirred under H$_2$ atmosphere (50 psi) at 40° C. for 16 hours, then filtered. The filtrate was concentrated under vacuum to afford crude title compound as a yellow oil. LCMS (ESI) calculated for C$_{11}$H$_{18}$N$_3$O$_2$S [M+H]+: 256.1, found: 256.2.

Step 9—Preparation of (R)-1,1,1-trifluoro-2-methylpropan-2-yl (7-((ethylsulfonyl)methyl)-5,6,7,8-tetrahydro-1,5-naphthyridin-3-yl)carbamate and (S)-1,1,1-trifluoro-2-methylpropan-2-yl (7-((ethylsulfonyl)methyl)-5,6,7,8-tetrahydro-1,5-naphthyridin-3-yl)carbamate

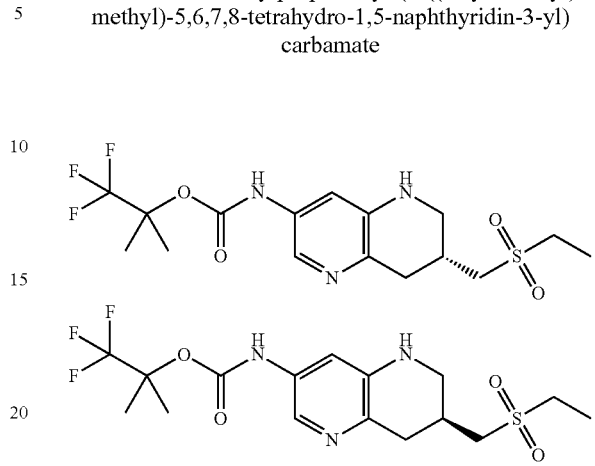

To a mixture of (R and S)-7-((ethylsulfonyl)methyl)-5,6,7,8-tetrahydro-1,5-naphthyridin-3-amine (60 mg, 0.00 mmol) and 1,1,1-trifluoro-2-methylpropan-2-yl 1H-imidazole-1-carboxylate (78 mg, 0.352 mmol) in DMSO (5 mL) was added concentrated hydrogen chloride (0.016 mL, 0.188 mmol) and the resulting reaction stirred at 80° C. for 3 hours. The reaction mixture was diluted with water (20 mL) and extracted with EtOAc (3×15 mL). The organic layer was washed with brine (3×10 mL), dried over Na$_2$SO$_4$ and concentrated under vacuum. The crude product was purified by Prep-TLC to give the titled racemate as a yellow solid.

The above racemate was separated by SFC (Instrument: Thar SFC 350; Column: AD (250 mm*30 mm, 10 um), 10 um; Mobile phase: 40% MEOH NH$_3$H$_2$O, 80 ML/MIN; Column Temp: 38° C.; Nozzle Pressure: 100 Bar Nozzle Temp: 60° C.) to give both enantiomers (faster eluent, Peak 1 from Step 9; slower eluent, Peak 2 from Step 9), which have the same analytical data: LCMS (ESI) calculated for C$_{16}$H$_{23}$F$_3$N$_3$O$_4$S [M+H]$^+$: 410.1, found: 410.1.

Step 10—Preparation of (R)-1,1,1-trifluoro-2-methylpropan-2-yl (5-((3-chloro-1-ethyl-1H-pyrazol-4-yl)sulfonyl)-7-((ethylsulfonyl)methyl)-5,6,7,8-tetrahydro-1,5-naphthyridin-3-yl)carbamate and (S)-1,1,1-trifluoro-2-methylpropan-2-yl (5-((3-chloro-1-ethyl-1H-pyrazol-4-yl)sulfonyl)-7-((ethylsulfonyl)methyl)-5,6,7,8-tetrahydro-1,5-naphthyridin-3-yl)carbamate

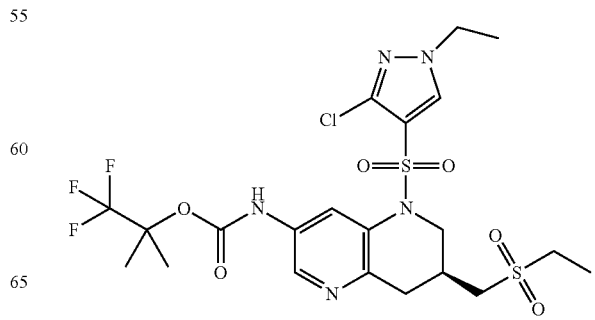

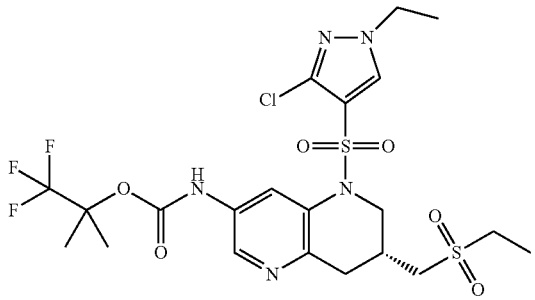

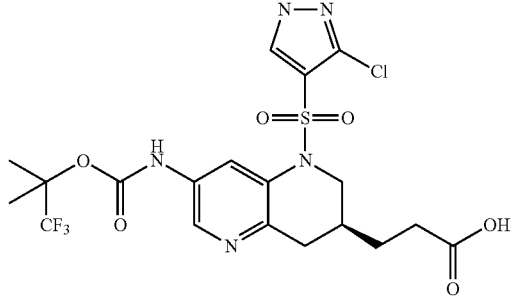

To a mixture of (R or S)-1,1,1-trifluoro-2-methylpropan-2-yl(7-((ethylsulfonyl)methyl)-5,6,7,8-tetrahydro-1,5-naphthyridin-3-yl)carbamate (Peak 1 from Step 9, 12 mg, 0.029 mmol) in tetrahydrofuran (1.5 mL) and pyridine (1.5 mL) was added 3-chloro-1-ethyl-1H-pyrazole-4-sulfonyl chloride (20.14 mg, 0.088 mmol) and DMAP (3.58 mg, 0.029 mmol). The reaction mixture was stirred at 100° C. for 1.5 hours in a microwave, then cooled to room temperature and directly purified by Prep-HPLC to afford the titled compound (Isomer 1, Example 111A) as brown solid.

The other enantiomer (Isomer 2, Example 111B) was prepared using a similar procedure from Peak 2 from Step 9. Both enantiomers have same analytical data: LCMS (ESI) calculated for $C_{21}H_{28}ClF_3N_5O_6S_2$ [M+H]+: 602.1, found: 607.1; $^1$H-NMR (Methanol-d4, 400 MHz) δ 8.83 (1H, s), 8.45 (1H, s), 8.33 (1H, s), 8.01-8.02 (1H, m), 4.16 (2H, q, J=7.2 Hz), 3.40-3.46 (2H, m), 3.10-3.19 (4H, m), 2.74-2.81 (2H, m), 2.53-2.55 (1H, m), 1.78 (6H, s), 1.46 (3H, t, J=6.8 Hz), 1.36 (3H, t, J=7.6 Hz).

Example 112: Preparation of (S)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoic acid and (R)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoic acid (Example 112A and 112B)

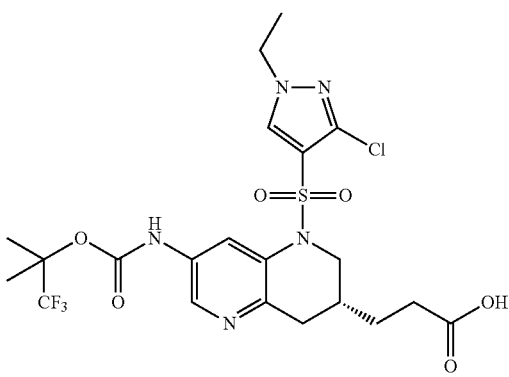

Step 1—Preparation of (E)-ethyl 3-(3-amino-5-chloropyridin-2-yl)acrylate

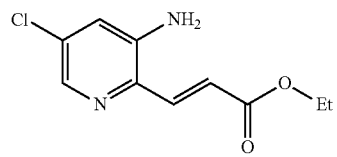 [SMILES: CCOC(=O)/C=C/c1ncc(Cl)cc1N]

To a solution of 2,5-dichloropyridin-3-amine (5 g, 30.7 mmol) in DMF (50 ml) were added ethyl acrylate (3.69 g, 36.8 mmol), DIPEA (8.04 ml, 46.0 mmol), Pd(OAc)$_2$ (0.689 g, 3.07 mmol), Bu$_4$NBr (0.989 g, 3.07 mmol) and (R)-(+)-2,2'-bis(diphenylphosphino)-1,1'-binaphthyl (1.910 g, 3.07 mmol). The reaction mixture was heated to 140° C. and stirred for 30 hours. The reaction mixture was cooled to room temperature, and then poured into water (200 mL), extracted with EtOAc (200 mL×3), the combined organic layers were washed by brine (200 mL×3), dried over anhydrous Na$_2$SO$_4$ and evaporated under vacuum. The crude product was purified by silica gel column chromatography (EtOAc:petroleum ether=0-30%) to afford (E)-ethyl 3-(3-amino-5-chloropyridin-2-yl)acrylate as a yellow solid. LCMS (ESI) calculated for $C_{10}H_{12}ClN_2O_2$[M+H]+: 227.1, found: 227.2.

Step 2—Preparation of ethyl 3-(3-amino-5-chloropyridin-2-yl)propanoate

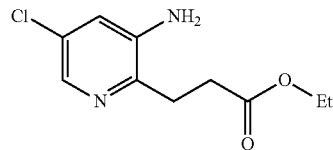 [SMILES: CCOC(=O)CCc1ncc(Cl)cc1N]

Pd/C (2.35 g, 2.21 mmol) was added to a solution of the (E)-ethyl 3-(3-amino-5-chloropyridin-2-yl)acrylate (2.5 g, 11.03 mmol) in MeOH (10 ml). The mixture was stirred under H$_2$ atmosphere (1 atm) at 0° C. for 2 h and then filtered. The filtrate was concentrated under vacuum and the crude product was purified by column chromatography on silica gel (EtOAc:petroleum ether=0-30%) to afford ethyl 3-(3-amino-5-chloropyridin-2-yl)propanoate as a yellow solid. LCMS (ESI) calculated for $C_{10}H_{14}ClN_2O_2$ [M+H]$^+$: 229.1, found: 229.1.

Step 3—Preparation of 7-chloro-3,4-dihydro-1,5-naphthyridin-2(1H)-one

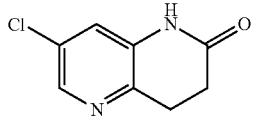

AcOH (1.502 ml, 26.2 mmol) was added to a solution of the ethyl 3-(3-amino-5-chloropyridin-2-yl)propanoate (2 g, 8.75 mmol) in tetrahydrofuran (50 ml). The mixture was heated to 60° C. and stirred for 2 hours. The reaction mixture was concentrated under vacuum and the crude product was purified by column chromatography on silica gel (EtOAc: petroleum ether=0-30%) to afford 7-chloro-3,4-dihydro-1,5-naphthyridin-2(1H)-one as a yellow solid. LCMS (ESI) calculated for $C_8H_8ClN_2O$ [M+H]$^+$: 183.0, found: 183.1.

Step 4—Preparation of 1-benzyl-7-chloro-3,4-dihydro-1,5-naphthyridin-2(1H)-one

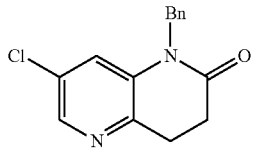 [SMILES: O=C1CCc2ncc(Cl)cc2N1Cc1ccccc1]

At 0° C., to a solution of 7-chloro-3,4-dihydro-1,5-naphthyridin-2(1H)-one (2 g, 10.95 mmol) in N,N-dimethylformamide (20 mL) was added $Cs_2CO_3$ (5.35 g, 16.43 mmol), followed by (bromomethyl)benzene (2.061 g, 12.05 mmol). The reaction mixture was stirred at room temperature for 1 hour. The reaction mixture was poured into water (50 mL), then extracted with EtOAc (50 ml×3). The combined organic layers were washed with brine (50 ml×3), dried over anhydrous $Na_2SO_4$ and concentrated under vacuum. The crude product was purified by column chromatography on silica gel (EtOAc:petroleum ether=0-30%) to afford 1-benzyl-7-chloro-3,4-dihydro-1,5-naphthyridin-2(1H)-one as a yellow solid. LCMS (ESI) calculated for $C_{15}H_{14}ClN_2O$ [M+H]$^+$: 273.1, found: 273.2.

Step 5—Preparation of (R and S)-methyl 1-benzyl-7-chloro-2-oxo-1,2,3,4-tetrahydro-1,5-naphthyridine-3-carboxylate

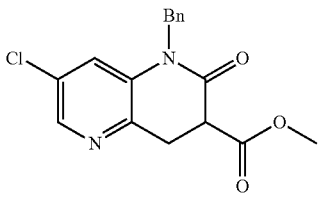 [SMILES: COC(=O)C1Cc2ncc(Cl)cc2N(Cc2ccccc2)C1=O]

At −78° C., to a solution of 1-benzyl-7-chloro-3,4-dihydro-1,5-naphthyridin-2(1H)-one (2 g, 7.33 mmol) in dry tetrahydrofuran (50 mL) was added LHMDS (8.80 mL, 8.80 mmol), the mixture was stirred at −78° C. for 30 minutes, then methyl carbonochloridate (0.832 g, 8.80 mmol) was added. The reaction mixture was stirred at −78° C. for 1 hour and quenched with saturated solution of $NH_4Cl$ (20 mL). The aqueous layer was extracted with EtOAc (50 mL×3) and the combined organic layers were washed with brine (50 mL×3), dried over anhydrous $Na_2SO_4$ and concentrated under vacuum. The crude product was purified by flash chromatography on silica gel (EtOAc:petroleum ether=0-30%) to afford (R and S)-methyl 1-benzyl-7-chloro-2-oxo-1,2,3,4-tetrahydro-1,5-naphthyridine-3-carboxylate as a yellow solid. LCMS (ESI) calculated for $C_{17}H_{16}ClN_2O_3$[M+H]$^+$: 331.1, found: 331.2.

Step 6—Preparation of (R and S)-(1-benzyl-7-chloro-1,2,3,4-tetrahydro-1,5-naphthyridin-3-yl)methanol

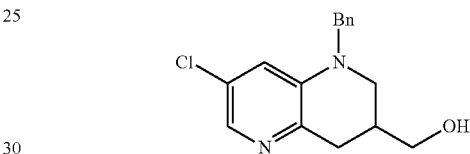

At 0° C., to a solution of (R and S)-methyl 1-benzyl-7-chloro-2-oxo-1,2,3,4-tetrahydro-1,5-naphthyridine-3-carboxylate (1.7 g, 5.14 mmol) in dry tetrahydrofuran (50 ml) was added $BH_3$—$SMe_2$ (2.440 mL, 25.7 mmol) and the reaction mixture was stirred at 60° C. for 2 hours. The reaction was quenched with MeOH (10 mL), then concentrated under vacuum. The crude product was purified by column chromatography on silica gel (EtOAc:petroleum ether=0-30%) to afford the title compound as a yellow solid. LCMS (ESI) calculated for $C_{16}H_{18}ClN_2O$ [M+H]$^+$: 289.1, found: 289.2.

Step 7—Preparation of (S and R)-1-benzyl-3-(bromomethyl)-7-chloro-1,2,3,4-tetrahydro-1,5-naphthyridine

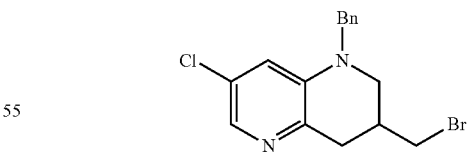

To a solution of (R and S)-(1-benzyl-7-chloro-1,2,3,4-tetrahydro-1,5-naphthyridin-3-yl)methanol (500 mg, 1.731 mmol) and $CBr_4$ (1263 mg, 3.81 mmol) in THF (20 ml) was added $Ph_3P$ (1045 mg, 3.98 mmol) portionwise. The reaction mixture was stirred at 60° C. for 16 hours, then concentrated in vacuo. The crude product was purified by column chromatography on silica gel (EtOAc:petroleum ether=0-20%) to give the title compound as a yellow solid. LCMS (ESI) calculated for $C_{16}H_{17}BrClN_2$ [M+H]$^+$: 351.0, found: 351.1.

Step 8—Preparation of (R and S)-diethyl 2-((1-benzyl-7-chloro-1,2,3,4-tetrahydro-1,5-naphthyridin-3-yl)methyl)malonate

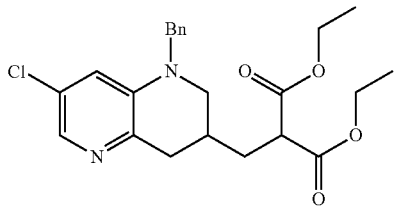 [SMILES: CCOC(=O)C(CC1Cc2ncc(Cl)cc2N(Cc2ccccc2)C1)C(=O)OCC]

To a solution of (S and R)-1-benzyl-3-(bromomethyl)-7-chloro-1,2,3,4-tetrahydro-1,5-naphthyridine (1 g, 2.84 mmol) and diethyl malonate (0.592 g, 3.70 mmol) in N,N-dimethylformamide (10 ml) was added $K_2CO_3$ (0.786 g, 5.69 mmol). The reaction mixture was stirred at 100° C. for 16 hours, then quenched with water (50 ml) and 1N HCl (5 ml). The aqueous layer was extracted with EtOAc (20 mL×3). The combined organic phase was washed with brine (20 ml×3), dried over $Na_2SO_4$, and concentrated in vacuo. The residue was purified by column chromatography (petroleum ether:EtOAc=100:1 to 10:1) to give the title compound as a yellow solid. LCMS (ESI) calculated for $C_{23}H_{28}ClN_2O_4$ $[M+H]^+$: 431.2, found: 431.2.

Step 9—Preparation of (R and S)-ethyl 3-(1-benzyl-7-chloro-1,2,3,4-tetrahydro-1,5-naphthyridin-3-yl)propanoate

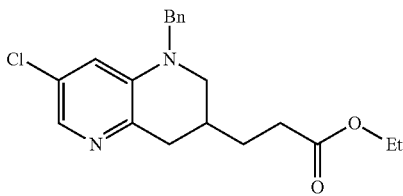 [SMILES: CCOC(=O)CCC1Cc2ncc(Cl)cc2N(Cc2ccccc2)C1]

A mixture of (R and S)-diethyl 2-((1-benzyl-7-chloro-1,2,3,4-tetrahydro-1,5-naphthyridin-3-yl)methyl)malonate (500 mg, 1.160 mmol) in DMSO (10 ml) was added LiCl (246 mg, 5.80 mmol). The reaction mixture was stirred at 170° C. for 10 h, then poured into water (100 mL) and extracted with EtOAc (50 mL×3). The organic layer was washed with brine (50 mL×3), dried over $Na_2SO_4$ and concentrated in vacuo. The crude product was purified by column chromatography (EtOAc:petroleum ether=0-20%) to give the title compound as a yellow solid. LCMS (ESI) calculated for $C_{20}H_{24}ClN_2O_2$ $[M+H]^+$: 359.1, found: 359.1.

Step 10—Preparation of (R and S)-ethyl 3-(1-benzyl-7-((diphenylmethylene)amino)-1,2,3,4-tetrahydro-1,5-naphthyridin-3-yl)propanoate

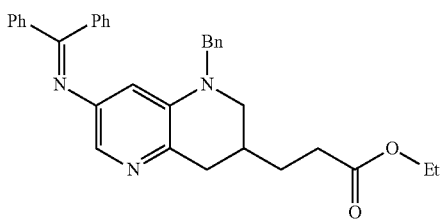 [SMILES: CCOC(=O)CCC1Cc2ncc(N=C(c3ccccc3)c3ccccc3)cc2N(Cc2ccccc2)C1]

A mixture of (R and S)-ethyl 3-(1-benzyl-7-chloro-1,2,3,4-tetrahydro-1,5-naphthyridin-3-yl)propanoate (100 mg, 0.279 mmol) in toluene (10 mL) was added diphenylmethanimine (60.6 mg, 0.334 mmol), $Pd_2(dba)_3$ (25.5 mg, 0.028 mmol) and $K_3PO_4$ (1509 mg, 7.11 mmol). The reaction mixture was stirred at 100° C. for 16 h, then quenched with water (10 mL) and extracted with EtOAc (10 mL×3). The organic layer was washed with brine (10 mL×3), dried over $Na_2SO_4$ and concentrated in vacuo. The crude product was purified by column chromatography on silica gel (EtOAc:petroleum ether=0-30%) to give the title compound as a yellow solid. LCMS (ESI) calculated for $C_{33}H_{34}N_3O_2$ $[M+H]^+$: 504.3, found: 504.3.

Step 11—Preparation of (R and S)-ethyl 3-(7-amino-1,2,3,4-tetrahydro-1,5-naphthyridin-3-yl)propanoate

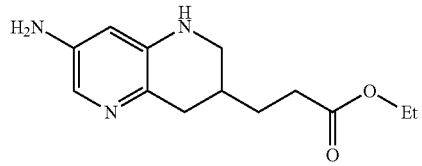 [SMILES: CCOC(=O)CCC1CNc2cc(N)cnc2C1]

Pd/C (21.13 mg, 0.020 mmol, w/w %=10%) was added to a solution of (R and S)-ethyl 3-(1-benzyl-7-((diphenylmethylene)amino)-1,2,3,4-tetrahydro-1,5-naphthyridin-3-yl)propanoate (50 mg, 0.099 mmol) in EtOH (10 mL). The mixture was stirred under $H_2$ atmosphere (50 psi) at 18° C. for 16 h, then filtered. The filtrate was concentrated under vacuum to afford the crude title compound as a yellow solid, which was used without further purification. LCMS (ESI) calculated for $C_{13}H_{20}N_3O_2$ $[M+H]^+$: 250.2, found: 250.2.

Step 12—Preparation of (S)-ethyl 3-(7-(3,3,3-trifluoro-2,2-dimethylpropanamido)-1,2,3,4-tetrahydro-1,5-naphthyridin-3-yl)propanoate and (R)-ethyl 3-(7-(3,3,3-trifluoro-2,2-dimethylpropanamido)-1,2,3,4-tetrahydro-1,5-naphthyridin-3-yl)propanoate

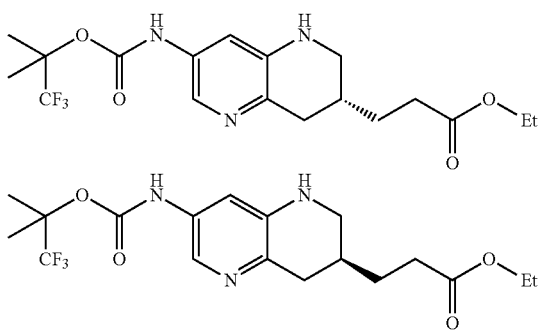

A mixture of (R and S)-ethyl 3-(7-amino-1,2,3,4-tetrahydro-1,5-naphthyridin-3-yl)propanoate (100 mg, 0.401 mmol) and 1,1,1-trifluoro-2-methylpropan-2-yl 1H-imidazole-1-carboxylate (107 mg, 0.481 mmol) in DMSO (5 ml) was treated with concentrated HCl (19.76 mg, 0.201 mmol) and stirred at 80° C. for 5 hours. The reaction mixture was diluted with water (20 ml) and extracted with EtOAc (20 ml×3). The organic layer was washed with brine (10 mL×3), dried over $Na_2SO_4$ and concentrated in vacuo. The crude product was purified by column chromatography on silica gel (EtOAc:petroleum ether=0-30%) to give an (R)- and (S)-mixture of ethyl 3-(7-((((1,1,1-trifluoro-2-methylpropan-2-yl)oxy)carbonyl)amino)-1,2,3,4-tetrahydro-1,5-naphthyridin-3-yl)propanoate as a yellow solid. LCMS (ESI) calculated for $C_{18}H_{25}F_3N_3O_4$ [M+H]$^+$: 404, found: 404.

The mixture of enantiomers (Isomer 1 and Isomer 2) was resolved by SFC (Instrument: Thar SFC 350 Column: AD 250 mm*30 mm, 10 um Mobile phase: A: Supercritical CO$_2$, B: EtOH (0.1% NH$_3$H$_2$O), A:B=80:20 at 60 ml/min; Column Temp: 38° C.; Nozzle Pressure: 100 Bar; Nozzle Temp: 60° C.; Evaporator Temp: 25° C.; Trimmer Temp: 25° C.; Wavelength: 220 nm) to afford (R)-ethyl 3-(7-((((1,1,1-trifluoro-2-methylpropan-2-yl)oxy)carbonyl)amino)-1,2,3,4-tetrahydro-1,5-naphthyridin-3-yl)propanoate and (S)-ethyl 3-(7-((((1,1,1-trifluoro-2-methylpropan-2-yl)oxy)carbonyl)amino)-1,2,3,4-tetrahydro-1,5-naphthyridin-3-yl)propanoate as a yellow solid LCMS (ESI) calculated for $C_{18}H_{25}F_3N_3O_4$ [M+H]$^+$: 404, found: 404.

Step 13—Preparation of (S)-ethyl 3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoate and (R)-ethyl 3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoate

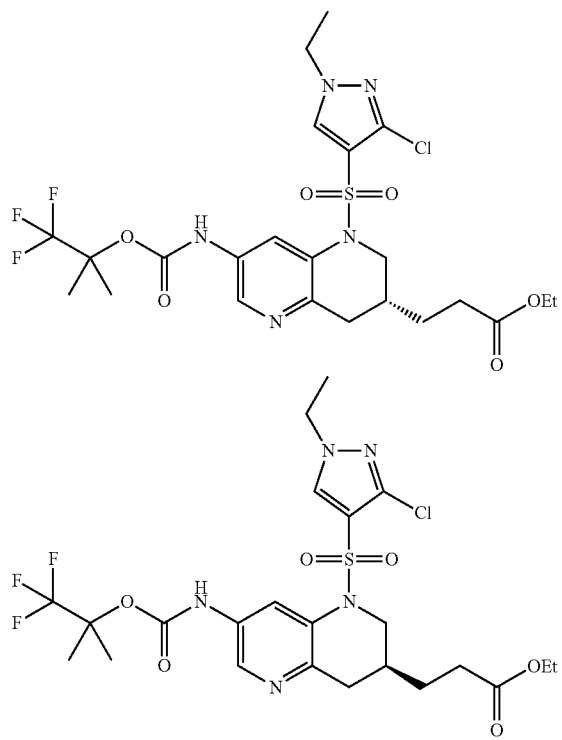

To a solution of (S or R)-ethyl 3-(7-(3,3,3-trifluoro-2,2-dimethylpropanamido)-1,2,3,4-tetrahydro-1,5-naphthyridin-3-yl)propanoate (Isomer 1 from Step 12, 50 mg, 0.124 mmol) in pyridine (2 mL) and THF (2 mL) was added 3-chloro-1-ethyl-1H-pyrazole-4-sulfonyl chloride (34.1 mg, 0.149 mmol). The reaction was stirred at 60° C. for 3 h, then treated with 1M HCl aqueous solution (pH ~4) and extracted with EtOAc (10 mL×3). The combined organic layers were dried over anhydrous Na$_2$SO$_4$, and concentrated. The title compound (Isomer 1 from Step 13) was obtained by prep-TLC (SiO$_2$, petroleum ether:EtOAc=2:1) as a yellow solid.

The other enantiomer (Isomer 2 from Step 13) was prepared using a similar procedure as described above. Both enantiomers have the same analytical data: LCMS (ESI) calculated for $C_{23}H_{30}ClF_3N_5O_6S$ [M+H]$^+$: 596, found: 596.

Step 14—Preparation of (S)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoic acid and (R)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoic Acid

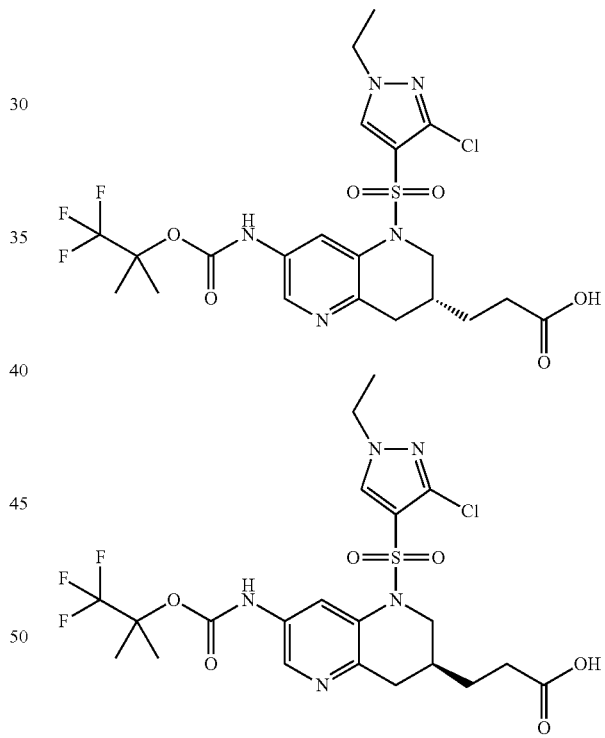

To a solution (S)-ethyl 3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydro-1,5-naphthyridin-3-yl)propanoate (Isomer 1 from Step 13, 30 mg, 0.050 mmol) in acetonitrile (2 mL) and water (2 mL) was added lithium hydroxide (1.205 mg, 0.050 mmol) and the reaction was warmed to 20° C. for 1 h. The reaction mixture was evaporated under vacuum and the residue purified by prep-HPLC (MeCN/water using TFA buffer) to afford the title compound (R or S)-3-(1-((3-chloro-1-ethyl-1H-pyrazol-4-yl)sulfonyl)-7-((((1,1,1-trifluoro-2-methylpropan-2-yl)oxy)

carbonyl)amino)-1,2,3,4-tetrahydro-1,5-naphthyridin-3-yl)propanoic acid (Isomer 1, Example 112A) as a white solid.

The other enantiomer (Isomer 2, Example 112B) was prepared using a similar procedure from Isomer 2 from Step 13. Both enantiomers have the same analytical data: LCMS (ESI) calculated for $C_{21}H_{26}ClF_3N_5O_6S$ [M+H]$^+$: 568, found: 568. $^1$HNMR (400 MHz, CDCl$_3$) δ 8.89 (1H, s), 8.79 (1H, s), 8.59 (1H, s), 8.24 (1H, s), 4.31 (1H, d, J=12.0 Hz), 4.13 (1H, q, J=7.0 Hz), 3.45-3.50 (2H, m), 3.29 (1H, d, J=15.2 Hz), 2.76 (2H, m), 2.49 (1H, br s), 2.15 (1H, br s), 1.74-1.79 (7H, m), 1.50 (1H, d, J=7.2 Hz).

Example 113—Preparation of 1,1,1-trifluoro-2-methylpropan-2-yl (14(4-fluorophenyl)sulfonyl)-1,2,3,4-tetrahydroquinolin-7-yl)carbamate (Example 113)

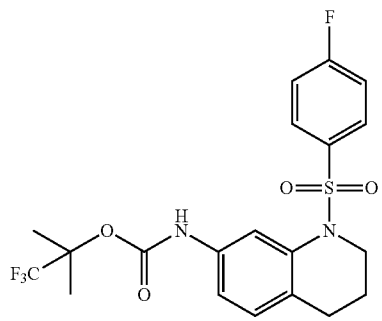 [SMILES: CC(C)(OC(=O)Nc1ccc2c(c1)N(S(=O)(=O)c1ccc(F)cc1)CCC2)C(F)(F)F]

Step 1—Preparation of 1,2,3,4-tetrahydroquinolin-7-amine

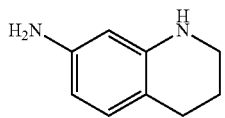

7-Nitro-1,2,3,4-tetrahydroquinoline (2 g, 11.22 mmol) and Pd/C (1.2 g) in EtOH (20 mL) were stirred under H$_2$ at 25° C. for 1 h, then filtrated. The filtrate was concentrated to obtain the product as black oil. LCMS (ESI) calculated for $C_9H_{13}N_2$ [M+H]$^+$: 149, found: 149 $^1$H NMR (CDCl$_3$ 400 MHz,) δ 6.68-6.75 (1H, m), 5.99 (1H, dd, J=2.0, 7.8 Hz), 5.78-5.86 (1H, m), 3.21-3.25 (2H, m), 2.63 (2H, t, J=6.3 Hz, 2H), 1.85-1.92 (2H, m).

Step 2—Preparation of 1,1,1-trifluoro-2-methylpropan-2-yl (1,2,3,4-tetrahydroquinolin-6-yl)carbamate

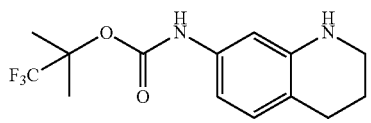 [SMILES: CC(C)(OC(=O)Nc1ccc2c(c1)NCCC2)C(F)(F)F]

A solution of 1,2,3,4-tetrahydroquinolin-6-amine (1.2 g, 8.10 mmol) and 3-methyl-1-(((1,1,1-trifluoro-2-methylpropan-2-yl)oxy)carbonyl)-1H-imidazol-3-ium iodide (1.921 g, 8.10 mmol) in 15 mL of DMSO was stirred at 25° C. for 2 h, then quenched with H$_2$O and extracted 3× with EtOAc. The combined organic layers were dried and concentrated. The crude product was purified by column chromatography (petroleum ether:EtOAc=10:1) to give 1,1,1-trifluoro-2-methylpropan-2-yl (1,2,3,4-tetrahydroquinolin-6-yl)carbamate as yellow slid. LCMS (ESI) calculated for $C_{14}H_{18}F_3N_2O_2$ [M+H]$^+$: 303, found: 303. $^1$H NMR (CDCl$_3$ 400 MHz,) δ 6.82 (1H, d, J=8.2 Hz), 6.64 (1H, br s), 6.50 (1H, brs), 6.40 (1H, d, J=7.4 Hz), 3.22-3.28 (2H, m), 2.67 (2H, t, J=6.1 Hz, 2H), 1.89 (2H, d, J=5.8 Hz, 2H), 1.72 (6H, s).

Step 3—Preparation of 1,1,1-trifluoro-2-methylpropan-2-yl (1-((4-fluorophenyl)sulfonyl)-1,2,3,4-tetrahydroquinolin-7-yl)carbamate

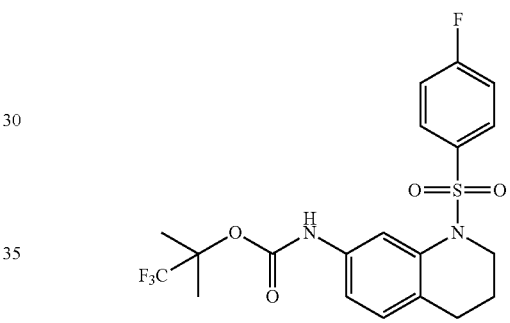

To a solution of 1,1,1-trifluoro-2-methylpropan-2-yl (1,2,3,4-tetrahydroquinolin-7-yl)carbamate (200 mg, 0.662 mmol) and pyridine (10.5 mg, 0.13 mmol) in THF (2 mL) was added 4-fluorobenzene-1-sulfonyl chloride (28 mg, 0.14 mmol) at room temperature. The reaction mixture was stirred at 80° C. overnight, then cooled and extracted with water and EtOAc. The combined organic layers were washed with brine, dried over Na$_2$SO$_4$, and concentrated in vacuo. The crude product was purified by prep-HPLC (MeCN/water using TFA buffer) to give the title compound as colorless oil. LCMS (ESI) calculated for $C_{20}H_{21}F_4N_2O_4S$ [M+H]$^+$: 461, found: 461. $^1$H NMR (CD$_3$OD, 400 MHz) δ 7.86 (brs, 1H), 7.68-7.76 (m, 2H), 7.12-7.26 (m, 3H), 6.94 (d, J=8.2 Hz, 1H), 3.77-3.85 (m, 2H), 2.41 (t, J=6.46 Hz, 2H), 1.76 (s, 6H), 1.60-1.69 (m, 2H).

Example 114—Preparation of Additional 1,2,3,4-tetrahydroquinolines

The compounds in Table 33 below were prepared based on the experimental procedures described in Example 113 and elsewhere in the detailed description, and can be achieved by one of skill in the art in light of the present disclosure.

TABLE 33

| Ex. No. | Structure | Name | Observed m/z |
|---|---|---|---|
| 114A | 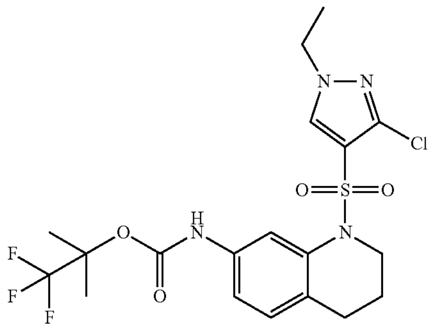 [SMILES: CCn1cc(S(=O)(=O)N2CCCc3ccc(NC(=O)OC(C)(C)C(F)(F)F)cc32)c(Cl)n1] | 2,2,2-trifluoro-1,1-dimethylethyl {1-[(3-chloro-1-ethyl-1H-pyrazol-4-yl)sulfonyl]-1,2,3,4-tetrahydroquinolin-7-yl}carbamate | 495 (M + H)+ |
| 114B | 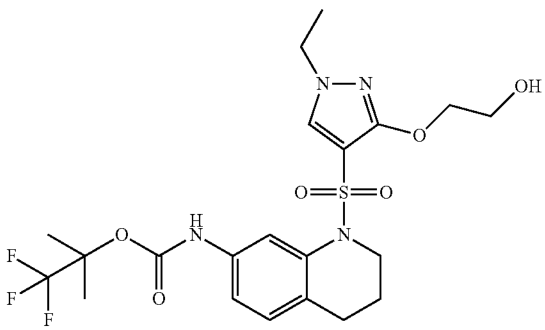 [SMILES: CCn1cc(S(=O)(=O)N2CCCc3ccc(NC(=O)OC(C)(C)C(F)(F)F)cc32)c(OCCO)n1] | 2,2,2-trifluoro-1,1-dimethylethyl (1-{[1-ethyl-3-(2-hydroxyethoxy)-1H-pyrazol-4-yl]sulfonyl}-1,2,3,4-tetrahydroquinolin-7-yl)carbamate | 521 (M + H)+ |
| 114C | 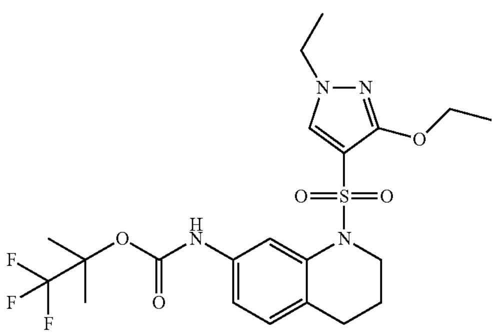 [SMILES: CCOc1nn(CC)cc1S(=O)(=O)N1CCCc2ccc(NC(=O)OC(C)(C)C(F)(F)F)cc21] | 2,2,2-trifluoro-1,1-dimethylethyl {1-[(3-ethoxy-1-ethyl-1H-pyrazol-4-yl)sulfonyl]-1,2,3,4-tetrahydroquinolin-7-yl}carbamate | 505 (M + H)+ |
| 114D | 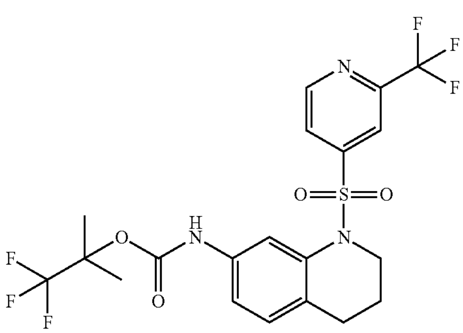 [SMILES: CC(C)(OC(=O)Nc1ccc2c(c1)N(S(=O)(=O)c1ccnc(C(F)(F)F)c1)CCC2)C(F)(F)F] | 2,2,2-trifluoro-1,1-dimethylethyl (1-{[2-(trifluoromethyl)pyridin-4-yl]sulfonyl}-1,2,3,4-tetrahydroquinolin-7-yl)carbamate | 512 (M + H)+ |

Example 115—Preparation of (R or S) and (S or R)-1,1,1-trifluoro-2-methylpropan-2-yl (3-(acetamidomethyl)-1-((4-fluoro-3-methoxyphenyl)sulfonyl)-1,2,3,4-tetrahydroquinolin-7-yl)carbamate (Examples 115A and 115B)

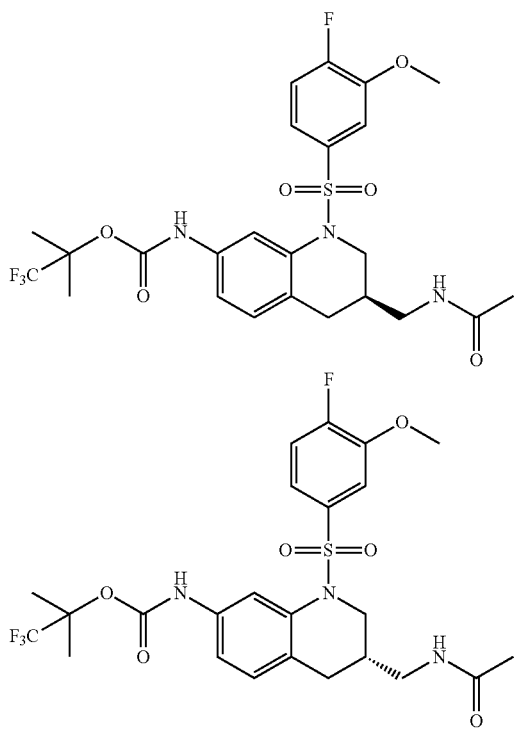

Step 1—Preparation of (2-amino-4-nitrophenyl)methanol

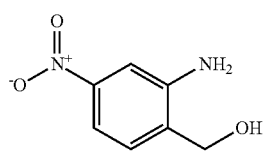

To a solution of 2-amino-4-nitrobenzoic acid (10 g, 54.9 mmol) in THF (150 mL), which was stirred in a 500 mL of sealed tube, was slowly added BH$_3$.DMS (15.64 mL, 165 mmol) dropwise at 0° C. under N$_2$. The resulting mixture was stirred at 90° C. for 4 h, then cooled to 0° C. and treated dropwise with MeOH (60 mL). The resulting suspension was concentrated to afford the crude titled compound as a yellow solid, which was directly used in the next step without further purification. LCMS (ESI) calculated for C$_7$H$_9$N$_2$O$_3$ [M+H]$^+$: 169 found: 169. $^1$HNMR (CDCl$_3$, 400 MHz) δ 7.54 (1H, s), 7.46 (1H, dd, J=8.0, 1.6 Hz), 7.31 (1H, d, J=8.4 Hz), 4.60 (2H, s).

Step 2—Preparation of 2-amino-4-nitrobenzaldehyde

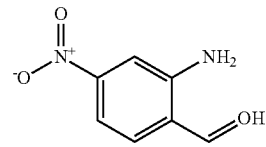

A mixture of (2-amino-4-nitrophenyl)methanol (9 g, 53.5 mmol) and manganese (IV) oxide (93 g, 1070 mmol) in DCM (150 mL) and hexane (150 mL) was stirred at 20° C. for 1 h. The suspension was filtered and washed with DCM. The filtrate was concentrated in vacuo to give the crude titled product as a yellow solid, which was directly used in next step without further purification. $^1$H-NMR (CDCl$_3$, 400 MHz) δ 9.95 (1H, s), 7.63 (1H, d, J=8.8 Hz), 7.47 (2H, d, J=6.0 Hz), 6.38 (2H, br s).

Step 3—Preparation of methyl 7-nitro-2-oxo-1,2-dihydroquinoline-3-carboxylate

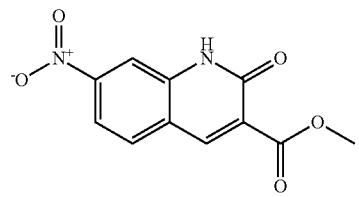

A mixture of 2-amino-4-nitrobenzaldehyde (6.6 g, 39.7 mmol), potassium acetate (0.390 g, 3.97 mmol), dimethyl malonate (6.30 g, 47.7 mmol), and diacetoxycopper (0.361 g, 1.986 mmol) in HOAc (60 mL) was stirred at 110° C. for 48 h. Most of the solvent was removed in vacuo and the resulting precipitate was collected by filtration, washed with EtOAc and dried in vacuo to give the titled compound as a yellow solid. LCMS (ESI) calculated for C$_{11}$H$_9$N$_2$O$_5$ [M+H]$^+$: 249, found: 249. $^1$H-NMR (DMSO-d6, 400 MHz) δ 12.44 (1H, s), 8.60 (1H, s), 8.07 (2H, s), 7.97 (1H, s), 3.80 (3H, s).

Step 4—Preparation of (R and S)-(7-nitro-1,2,3,4-tetrahydroquinolin-3-yl)methanol

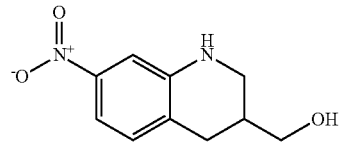

To a solution of methyl 7-nitro-2-oxo-1,2-dihydroquinoline-3-carboxylate (3 g, 12.05 mmol) in THF (200 mL) was added LiBH$_4$ (1.27 g, 60.24 mmol). The mixture was stirred at 40° C. for 18 h, then quenched by the careful addition of saturated NH$_4$Cl aqueous solution (20 mL). The biphasic mixture was stirred at 20° C. for 30 min, then extracted with EtOAc (200 mL×3). The combined organic phases were washed with brine (600 mL×2), dried over Na$_2$SO$_4$, filtered and concentrated in vacuo. Purification by silica gel column chromatography (petroleum ether/EtOAc=3:1 to 1:3) afforded the titled compound as a red solid. LCMS (ESI) calculated for $C_{10}H_{13}N_2O_3$ [M+H]$^+$: 209, found: 209; $^1$H-NMR (Methanol-d4, 400 MHz) δ 7.30 (2H, s), 7.05 (1H, d, J=7.6), 3.41-3.57 (3H, m), 3.05 (1H, t, J=10.4 Hz), 2.86 (1H, d, J=15.2 Hz), 2.54-2.58 (1H, m), 2.06 (1H, br s).

Step 5—Preparation of (R and S)-2-((7-nitro-1,2,3,4-tetrahydroquinolin-3-yl)methyl)isoindoline-1,3-dione

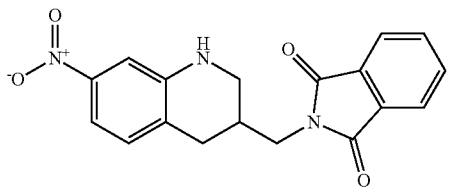

To a solution of (7-nitro-1,2,3,4-tetrahydroquinolin-3-yl)methanol (450 mg, 2.16 mmol) in THF (20 mL) was added DEAD (450 mg, 2.60 mmol), Ph$_3$P (682 mg, 2.60 mmol), and isoindoline-1,3-dione (383 mg, 2.60 mmol). The reaction was stirred at 20° C. for 16 h under N$_2$, then partitioned between EtOAc (20 mL) and H$_2$O (20 mL). The separated organic layer was washed with brine (30 mL×2) and dried over Na$_2$SO$_4$. The solvents were removed and the crude product was purified by silica gel column chromatography (petroleum ether/EtOAc=10:1 to 1:1) to afford the titled compound as a yellow solid. LCMS (ESI) calculated for $C_{18}H_{16}N_3O_4$ [M+H]$^+$: 338, found: 338; $^1$H-NMR (Methanol-d4, 400 MHz) δ 7.79-7.85 (4H, m), 7.27-7.34 (2H, m), 7.02-7.04 (1H, m), 3.70 (1H, d, J=7.2 Hz), 3.07-3.11 (2H, m), 2.83-2.91 (1H, m), 2.58-2.61 (1H, m), 2.36 (1H, br s).

Step 6—Preparation of (R)-tert-butyl (3-((1,3-dioxoisoindolin-2-yl)methyl)-1,2,3,4-tetrahydroquinolin-7-yl)carbamate and (S)-tert-butyl (3-((1,3-dioxoisoindolin-2-yl)methyl)-1,2,3,4-tetrahydroquinolin-7-yl)carbamate

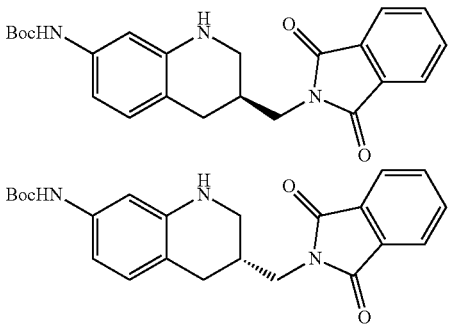

To a solution of (R and S)-2-((7-nitro-1,2,3,4-tetrahydroquinolin-3-yl)methyl)isoindoline-1,3-dione (550 mg, 1.63 mmol) in EtOAc (20 mL) was added di-tert-butyl dicarbonate (1.07 g, 4.90 mmol) and Pd/C (55 mg, 10%). The resulting mixture was stirred at 20° C. under H$_2$ balloon for 18 h, then filtered, the filtrate concentrated under the reduced pressure and purified by silica gel column chromatography (petroleum ether/EtOAc=10:1 to 1:1) to afford the title compound racemate as a light yellow solid.

The racemic mixture was resolved by chiral SFC method (Pak AS, 10 μm, Daicel Chemical Industries, Ltd 250×30 mm I.D.; Mobile phase: A: Supercritical CO$_2$, B:EtOH (contained 0.1% NH$_3$H$_2$O), A:B=50:50 at 80 mL/min) to afford the faster eluent (Peak 1 from Step 6) and the slower eluent (Peak 2 from Step 6) both as yellow oils. Both enantiomers have the same analytical data: LCMS (ESI) calculated for $C_{23}H_{26}N_3O_4$ [M+H]$^+$: 408, found: 408; $^1$H-NMR (CDCl$_3$, 400 MHz) δ 7.84-7.86 (2H, m), 7.72-7.74 (2H, m), 6.77-6.83 (2H, m), 6.38-6.40 (2H, m), 3.70 (2H, d, J=6.4 Hz), 3.30 (1H, d, J=10.8 Hz), 3.05 (1H, t, J=10.0 Hz), 2.79 (1H, dd, J=12.0, 4.0 Hz), 2.50-2.57 (1H, m), 1.49 (9H, s).

Step 7—Preparation of (R)-tert-butyl(3-((1,3-dioxoisoindolin-2-yl)methyl)-1-((4-fluoro-3-methoxyphenyl)sulfonyl)-1,2,3,4-tetrahydroquinolin-7-yl)carbamate and (S)-tert-butyl(3-((1,3-dioxoisoindolin-2-yl)methyl)-1-((4-fluoro-3-methoxyphenyl)sulfonyl)-1,2,3,4-tetrahydroquinolin-7-yl)carbamate

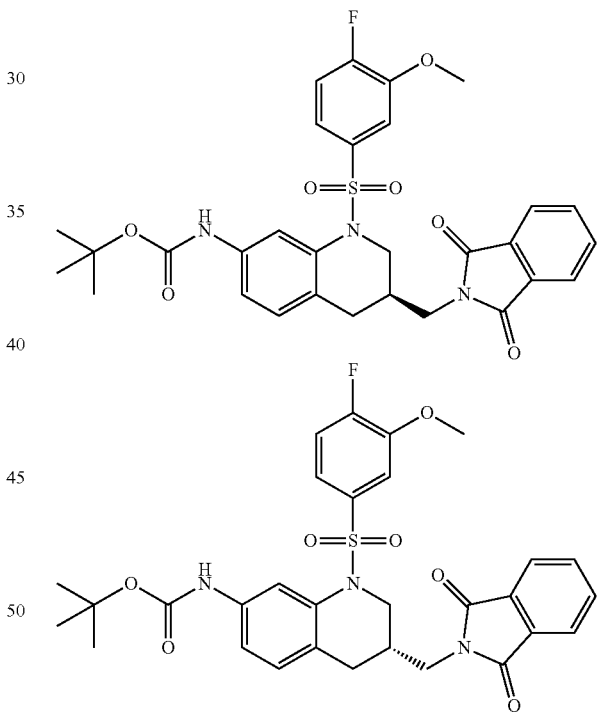

To a solution of (R or S)-tert-butyl (3-((1,3-dioxoisoindolin-2-yl)methyl)-1,2,3,4-tetrahydroquinolin-7-yl)carbamate (Peak 1 from Step 6, 120 mg, 0.290 mmol) in THF (3 mL) were added pyridine (3 mL) and 4-fluoro-3-methoxybenzene-1-sulfonyl chloride (132 mg, 0.590 mmol) at 20° C. under N$_2$. The resulting mixture was stirred at 50° C. for 18 h, then poured into water. The aqueous layer was extracted with ethyl acetate (20 mL×3) and the combined organic layers washed with brine (30 mL×2), dried over sodium sulfate and concentrated. The crude product was purified by prep-TLC (petroleum ether/EtOAc=1:1) to afford the titled compound (Peak 1 from Step 7) as a yellow oil.

The other enantiomer (Peak 2 from Step 7) was prepared using a similar procedure as described above from Peak 2 from Step 6. Both enantiomers have the same analytical data: LCMS (ESI) calculated for $C_{26}H_{23}FN_3O_7S$ [M+H-tBu]$^+$: 540, found: 540.1; $^1$H-NMR (CDCl$_3$, 400 MHz) δ 7.86-7.89 (2H, m), 7.76-7.78 (2H, m), 7.67 (1H, s), 7.57-7.60 (1H, m), 3.73 (3H, s), 3.56 (2H, d, J=6.8 Hz), 3.17 (1H, t, J=12.4 Hz), 2.55 (1H, dd, J=16.8, 5.2 Hz), 2.17-2.25 (2H, m), 2.01-2.05 (1H, m), 1.49 (9H, s).

Step 8—Preparation of (R)-tert-butyl (3-(aminomethyl)-1-((4-fluoro-3-methoxyphenyl)sulfonyl)-1,2,3,4-tetrahydroquinolin-7-yl)carbamate and (S)-tert-butyl (3-(aminomethyl)-1-((4-fluoro-3-methoxyphenyl)sulfonyl)-1,2,3,4-tetrahydroquinolin-7-yl)carbamate

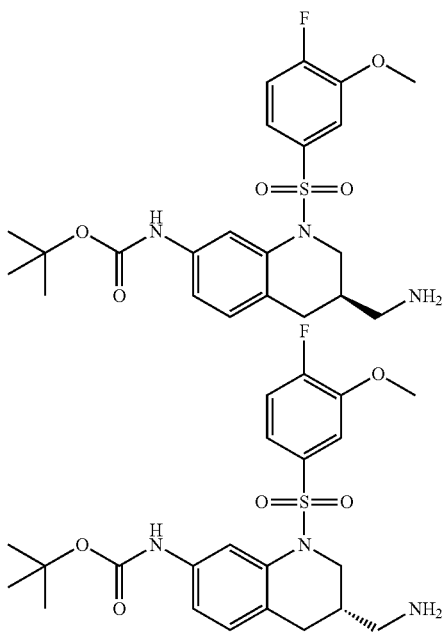

A solution of (R or S)-tert-butyl tert-butyl (3-((1,3-dioxoisoindolin-2-yl)methyl)-1-((4-fluoro-3-methoxyphenyl)sulfonyl)-1,2,3,4-tetrahydroquinolin-7-yl)carbamate (Peak 1 from Step 7, 60 mg, 0.10 mmol) in EtOH (15 mL) was treated with N$_2$H$_4$—H$_2$O (0.5 mL) for 2 h at 85° C., then cooled to room temperature and filtered. The filtrate was concentrated, purified by silica gel chromatography (EtOAc/MeOH=5:1) to afford the title compound as a light yellow solid.

The other enantiomer (Peak 2 from Step 8) was prepared using a similar procedure as described above from Peak 2 from Step 7. Both enantiomers have the same analytical data: LCMS (ESI) calculated for $C_{22}H_{29}FN_3O_5S$ [M+H]$^+$: 466, found: 466; $^1$H-NMR (CDCl$_3$, 400 MHz) δ 7.72 (1H, s), 7.47 (1H, s), 7.32 (1H, d, J=6.4 Hz), 7.11 (1H, t, J=8.8 Hz), 6.86 (1H, dd, J=25.2, 8.0 Hz), 4.32 (1H, d, J=10.8 Hz), 3.78 (3H, s), 3.48 (2H, s), 3.37 (1H, br s), 3.09 (2H, br s), 2.69 (1H, d, J=14.0 Hz), 2.46 (1H, br s), 2.27 (1H, br s), 1.49 (9H, s).

Step 9—Preparation of (R)-tert-butyl(3-(acetamidomethyl)-1-((4-fluoro-3-methoxyphenyl)sulfonyl)-1,2,3,4-tetrahydroquinolin-7-yl)carbamate and (S)-tert-butyl(3-(acetamidomethyl)-1-((4-fluoro-3-methoxyphenyl)sulfonyl)-1,2,3,4-tetrahydroquinolin-7-yl)carbamate

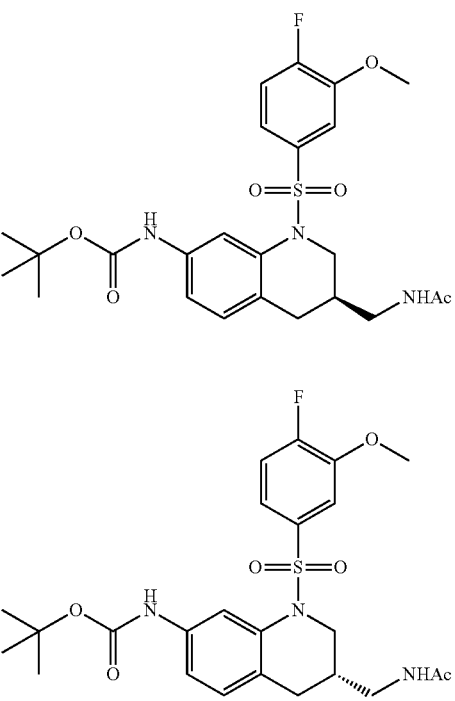

To a solution of (R or S)-tert-butyl (3-(aminomethyl)-1-((4-fluoro-3-methoxyphenyl)sulfonyl)-1,2,3,4-tetrahydroquinolin-7-yl)carbamate (Peak 1 from Step 8, 40 mg, 0.086 mmol) in 3 mL of methylene chloride is first added TEA (0.036 mL, 0.258 mmol) and then slowly treated with acetyl chloride (10.12 mg, 0.129 mmol). The reaction mixture is stirred at 20° C. for two hours, then quenched with water (0.5 mL). The separated organic layer was dried over Na$_2$SO$_4$, filtered and concentrated. The crude product was purified by prep-TLC (petroleum ether/EtOAc=1:2) to afford the title compound (Peak 1 from Step 9) as a light yellow solid.

The other enantiomer (Peak 2 from Step 9) was prepared using a similar procedure as described above from Peak 2 from Step 8. Both enantiomers have the same analytical data: LCMS (ESI) calculated for $C_{24}H_{31}FN_3O_6S$ [M+H]$^+$: 508.2, found: 508.2; $^1$H-NMR (CDCl$_3$, 400 MHz) δ 7.73 (1H, s), 7.33-7.35 (2H, m), 7.15-7.18 (1H, m), 7.06-7.08 (1H, m), 6.95 (1H, d, J=8.8 Hz), 6.61 (1H, br s), 6.06 (1H, br s), 3.91 (1H, dd, J=13.2, 2.8 Hz), 3.85 (3H, s), 3.47-3.51 (1H, m), 3.34-3.36 (1H, m), 3.05-3.09 (1H, m), 2.66 (1H, dd, J=16.4, 6.0 Hz), 2.22-2.27 (1H, m), 2.02 (3H, s), 1.51 (9H, s).

417

Step 10—Preparation of (R)—N-((7-amino-1-((4-fluoro-3-methoxyphenyl)sulfonyl)-1,2,3,4-tetrahydroquinolin-3-yl)methyl)acetamide and (S)—N-((7-amino-1-((4-fluoro-3-methoxyphenyl)sulfonyl)-1,2,3,4-tetrahydroquinolin-3-yl)methyl)acetamide

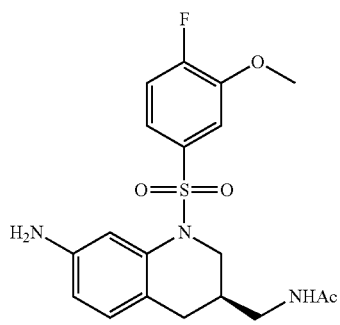

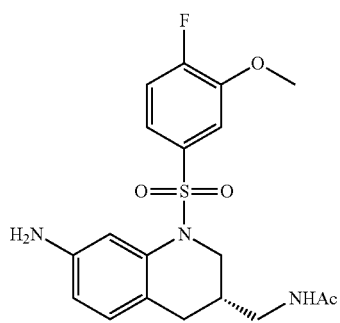

To a solution of (R or S)-tert-butyl (3-(acetamidomethyl)-1-((4-fluoro-3-methoxyphenyl)sulfonyl)-1,2,3,4-tetrahydroquinolin-7-yl)carbamate (Peak 1 from Step 9, 30 mg, 0.059 mmol) in EtOAc (1 mL) was added HCl (2 mL, 4 M in EtOAc). The reaction was stirred at 20° C. for 2 h, then concentrated and purified by prep-TLC (petroleum ether/EtOAc=1:2) to afford the titled compound (Peak 1 from Step 10) as a light yellow solid.

The other enantiomer (Peak 2 from Step 10) was prepared using a similar procedure as described above from Peak 2 from Step 9. Both enantiomers have the same analytical data: LCMS (ESI) calculated for $C_{19}H_{23}FN_3O_4S$ [M+H]$^+$: 408.1, found: 408.1; $^1$H-NMR (CDCl$_3$, 400 MHz) δ 7.26-7.28 (1H, m), 7.13-7.16 (2H, m), 7.06 (1H, d, J=2.4 Hz), 6.81 (1H, d, J=8.0 Hz), 6.46 (1H, d, J=2.0 Hz), 5.76 (1H, br s), 4.00 (1H, dd, J=13.6, 4.0 Hz), 3.78 (3H, s), 3.26-3.35 (2H, m), 3.02-3.08 (1H, m), 2.52 (1H, dd, J=16.0, 6.4 Hz), 2.66 (1H, dd, J=16.4, 6.0 Hz), 2.08-2.18 (1H, m), 2.01 (3H, s).

418

Step 11—Preparation of (R)-1,1,1-trifluoro-2-methylpropan-2-yl (3-(acetamidomethyl)-1-((4-fluoro-3-methoxyphenyl)sulfonyl)-1,2,3,4-tetrahydroquinolin-7-yl)carbamate and (S)-1,1,1-trifluoro-2-methylpropan-2-yl (3-(acetamidomethyl)-1-((4-fluoro-3-methoxyphenyl)sulfonyl)-1,2,3,4-tetrahydroquinolin-7-yl)carbamate

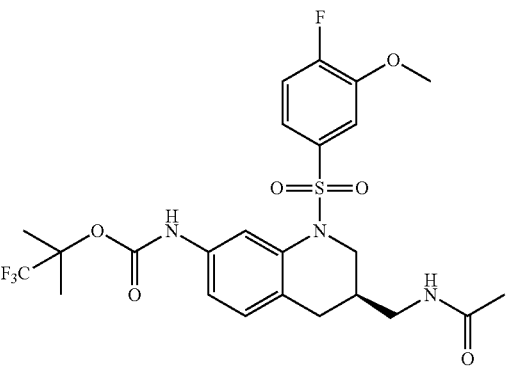

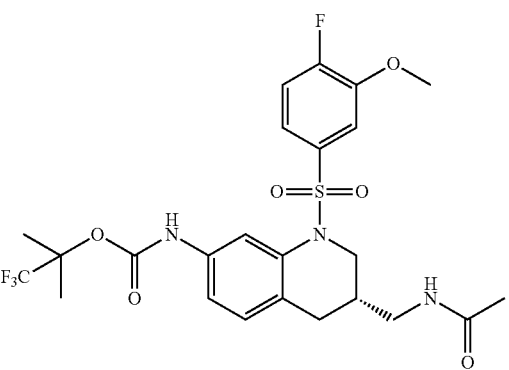

To a solution of (R or S)—N-((7-amino-1-((4-fluoro-3-methoxyphenyl)sulfonyl)-1,2,3,4-tetrahydroquinolin-3-yl)methyl)acetamide (Peak 1 from Step 10, 20 mg, 0.049 mmol) in DMSO (5 mL) was added 3-methyl-1-(((1,1,1-trifluoro-2-methylpropan-2-yl)oxy)carbonyl)-1H-imidazol-3-ium iodide (24.3 mg, 0.098 mmol). The resulting mixture was stirred at 20° C. for 1 h, then extracted with EtOAc (5 mL×3), washed with brine (5 mL×2), dried over Na$_2$SO$_4$ and purified by prep-HPLC to afford the title compound (Peak 1 from Step 11, Example 115A) as a white solid.

The other enantiomer (Peak 2 from Step 11, Example 115B) was prepared using a similar procedure as described above from Peak 2 from Step 10. Both enantiomers have the same analytical data: LCMS (ESI) calculated for $C_{24}H_{28}F_4N_3O_6S$ [M+H]$^+$: 562.1, found: 562.1; $^1$H-NMR (CDCl$_3$, 400 MHz) δ 7.75 (1H, s), 7.39 (2H, br s), 7.19 (1H, t, J=10.4 Hz), 6.68 (1H, s), 6.26 (1H, s), 3.89 (3H, s), 3.82-3.86 (1H, m), 3.64-3.67 (1H, m), 3.44-3.48 (1H, m), 3.09-3.11 (1H, m), 2.73-2.78 (2H, m), 2.33 (1H, dd, J=16.8, 6.4 Hz), 2.10 (3H, s), 1.75 (6H, d, J=4.4 Hz).

Example 116—Preparation of (R)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydroquinolin-3-yl)propanoic acid and (S)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydroquinolin-3-yl)propanoic acid (Examples 116A and 116B)

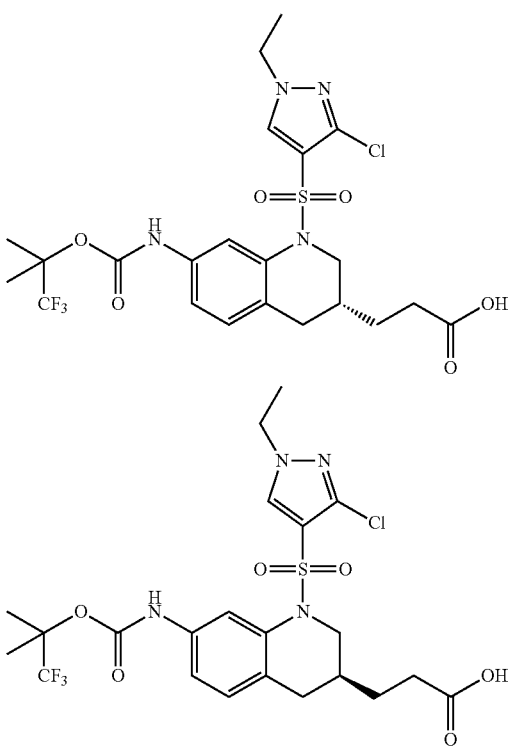

Step 1—Preparation of 7-nitroquinoline

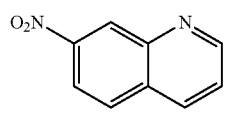 [SMILES: O=[N+]([O-])c1ccc2cccnc2c1]

To a solution of 7-nitro-1,2,3,4-tetrahydroquinoline (8 g, 44.9 mmol) in DCM (400 mL) was added 4,5-dichloro-3,6-dioxocyclohexa-1,4-diene-1,2-dicarbonitrile (21 g, 93 mmol). The mixture was stirred for 1 hour at 60° C. The reaction mixture was poured into water (500 mL), extracted with dichloromethane (200 mL×3). The combined organic phase was dried over Na$_2$SO$_4$ and concentrated in vacuo. The residue was purified by flash silica gel chromatography (SiO$_2$, PE:EtOAc=5:1 to 1:1) to give 7-nitroquinoline as a yellow solid.

Step 2—Preparation of 3-bromo-7-nitroquinoline

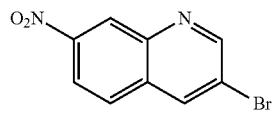

To a solution of 7-nitroquinoline (3 g, 17.23 mmol) in AcOH (50 mL) was added 1-bromopyrrolidine-2,5-dione (4.4 g, 24.72 mmol) under N$_2$. The mixture was stirred for 4 hours at 140° C. The reaction mixture was poured into water (200 mL), extracted with ethyl acetate (100 mL×3). The combined organic phase was dried over Na$_2$SO$_4$ and concentrated in vacuo. The residue was purified by flash silica gel chromatography (SiO$_2$, petroleum ether: EtOAc=100:1 to 5:1) to give 3-bromo-7-nitroquinoline as a yellow solid.

Step 3—Preparation of (E)-methyl 3-(7-nitroquinolin-3-yl)acrylate

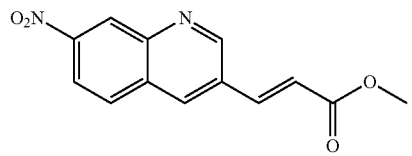 [SMILES: COC(=O)/C=C/c1cnc2cc([N+](=O)[O-])ccc2c1]

To a solution of 3-bromo-7-nitroquinoline (2 g, 7.90 mmol), potassium phosphate (3.36 g, 15.81 mmol), methyl acrylate (0.680 g, 7.90 mmol) in DMA (15 mL) and water (3 mL) was added Pd(PPh$_3$)$_4$ (0.539 g, 0.790 mmol) under N$_2$. The mixture was stirred at 90° C. for 16 hours under N$_2$. The reaction was then diluted with EtOAc (20 mL) and water (50 mL). The aqueous layer was extracted with EtOAc (3×20 mL). The combined organic phase was dried over Na$_2$SO$_4$ and concentrated in vacuo. The residue was purified by flash silica gel chromatography (SiO$_2$, petroleum ether: EtOAc=20:1 to 3:1) to give (E)-methyl 3-(7-nitroquinolin-3-yl)acrylate as a black solid. $^1$H NMR (400 MHz, CDCl$_3$) δ 3.63 (s, 3H), 6.57 (d, J=16.4 Hz, 1H), 7.63 (d, J=16.4 Hz, 1H), 7.86 (d, J=9.0 Hz, 1H), 8.12 (s, 1H), 8.21 (s, 1H), 8.74 (br. s., 1H), 8.98-9.05 (m, 1H), 9.02 (s, 1H).

Step 4—Preparation (S and R)-tert-butyl 7-((tert-butoxycarbonyl)amino)-3-(3-methoxy-3-oxopropyl)-3,4-dihydroquinoline-1(2H)-carboxylate

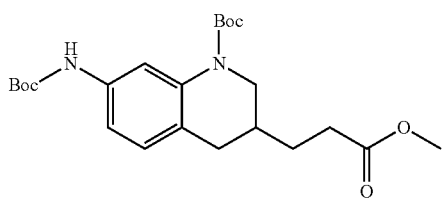 [SMILES: COC(=O)CCC1Cc2ccc(NC(=O)OC(C)(C)C)cc2N(C(=O)OC(C)(C)C)C1]

To a solution of (E)-methyl 3-(7-nitroquinolin-3-yl)acrylate (2 g, 7.75 mmol), di-tert-butyl dicarbonate (3.38 g, 15.49 mmol) in MeOH (300 mL) was added Pd/C (0.412 g, 3.87 mmol) under N$_2$. The suspension was degassed under vacuum and purged with H₂ several times. The mixture was stirred under H₂ (50 psi) at 25° C. for 16 hours. The suspension was filtered through a pad of CELITE and the filter cake was washed with MeOH (100 mL×3). The combined filtrates were concentrated to dryness. The residue was purified by flash silica gel chromatography (SiO₂, petroleum ether:EtOAc=100:1 to 5:1) to give the title compound as a brown oil.

Step 5—Preparation of (S and R)-methyl 3-(7-amino-1,2,3,4-tetrahydroquinolin-3-yl)propanoate

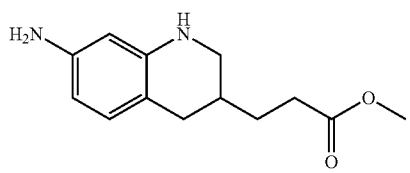 [SMILES: COC(=O)CCC1CNc2cc(N)ccc2C1]

To a mixture of (S and R)-tert-butyl 7-((tert-butoxycarbonyl)amino)-3-(3-methoxy-3-oxopropyl)-3,4-dihydroquinoline-1(2H)-carboxylate (1.2 g, 2.76 mmol) in DCM (10.0 mL) was added dropwise TFA (5.0 mL) at 0° C. The reaction mixture was stirred at 25° C. for 2 hours. Water (10 mL) was added and the mixture was adjusted to pH=9 with statured aqueous Na₂CO₃ solution, then extracted with DCM (20 mL×3). The combined organic phase was dried over Na₂SO₄ and concentrated in vacuo. The residue was purified by flash silica gel chromatography (SiO₂, petroleum ether:EtOAc=10:1 to 1:1, 0.1% Et₃N) to give the title compound as brown oil. LCMS (ESI) calculated for $C_{13}H_{19}N_2O_2$ (M+H)⁺: 235, found: 235.2.

Step 6—Preparation of (R)-methyl 3-(7-((((1,1,1-trifluoro-2-methylpropan-2-yl)oxy)carbonyl)amino)-1,2,3,4-tetrahydroquinolin-3-yl)propanoate and (S)-methyl 3-(7-((((1,1,1-trifluoro-2-methylpropan-2-yl)oxy)carbonyl)amino)-1,2,3,4-tetrahydroquinolin-3-yl)propanoate

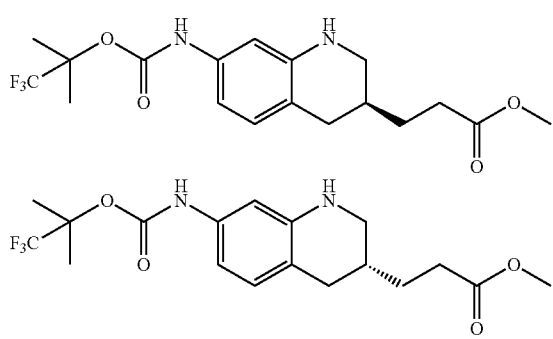

To a mixture of (S and R)-methyl 3-(7-amino-1,2,3,4-tetrahydroquinolin-3-yl)propanoate (290 mg, 1.238 mmol) in DMSO (5.0 mL) was added 3-methyl-1-(((1,1,1-trifluoro-2-methylpropan-2-yl)oxy)carbonyl)-1H-imidazol-3-ium iodide (451 mg, 1.238 mmol). The reaction mixture was stirred at 25° C. for 30 minutes. The resulting mixture was diluted with water (10 mL) and extracted with ethyl acetate (3×10 mL). The organic layers were separated, combined, dried over Na₂SO₄, filtered and concentrated in vacuo to give (S and R)-methyl 3-(7-((((1,1,1-trifluoro-2-methylpropan-2-yl)oxy)carbonyl)amino)-1,2,3,4-tetrahydroquinolin-3-yl)propanoate as a brown oil. LCMS (ESI) calculated for $C_{18}H_{24}F_3N_2O_4$ [M+H]⁺: 389, found: 389.2.

The product was resolved by SFC (Column: Chiralcel OD-3 150×4.6 mm I.D., 3 um Mobile phase: methanol (0.05% DEA) in CO₂ from 5% to 40% Flow rate: 2.5 mL/min Wavelength: 220 nm to afford Isomer 1 (210 mg, brown oil; rT=5.2 min), Isomer 2 (206 mg, brown oil; rT=7.3 min).

Step 7. Preparation of (R)-3-(7-((((1,1,1-trifluoro-2-methylpropan-2-yl) oxy)carbonyl)amino)-1,2,3,4-tetrahydroquinolin-3-yl)propanoic acid and (S)-3-(7-((((1,1,1-trifluoro-2-methylpropan-2-yl)oxy)carbonyl)amino)-1,2,3,4-tetrahydroquinolin-3-yl) propanoic Acid

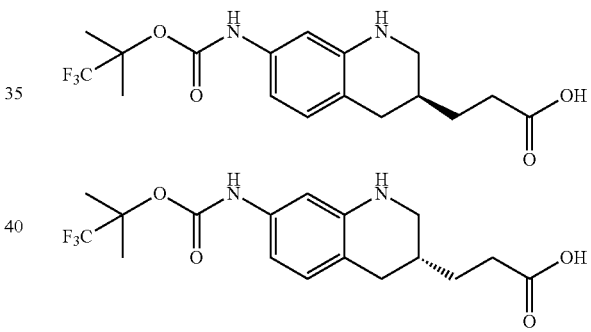

To a solution of (S or R)-methyl 3-(7-((((1,1,1-trifluoro-2-methylpropan-2-yl)oxy)carbonyl)amino)-1,2,3,4-tetrahydroquinolin-3-yl)propanoate (Isomer 1 from Step 6, 100 mg, 0.257 mmol) in 1,4-dioxane (2.0 mL) was added LiOH (37 mg, 1.545 mmol) and water (2.0 mL). The reaction mixture was stirred at 25° C. for 2 h, then quenched with hydrochloric acid (1 M, 5 mL). The resulting mixture was extracted with ethyl acetate (3×5 mL). The organic layers were combined, dried over anhydrous magnesium sulfate, filtered and concentrated in vacuo to afford the title compound (Isomer 1 from Step 7) as a yellow solid, which was used directly in the next step without further purification.

The other enantiomer (Isomer 2 from Step 7) was prepared using a similar procedure from Isomer 2 from Step 6 as described above. Both enantiomers have the same analytical data: LCMS (ESI) calculated for $C_{17}H_{22}F_3N_2O_4$ [M+H]⁺: 375, found: 375.

Step 8—Preparation of (R)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydroquinolin-3-yl)propanoic acid and (S)-3-(1-((3-chloro-1-ethyl-1H-pyrazol-4-yl)sulfonyl)-7-((((1,1,1-trifluoro-2-methylpropan-2-yl)oxy)carbonyl)amino)-1,2,3,4-tetrahydroquinolin-3-yl)propanoic Acid

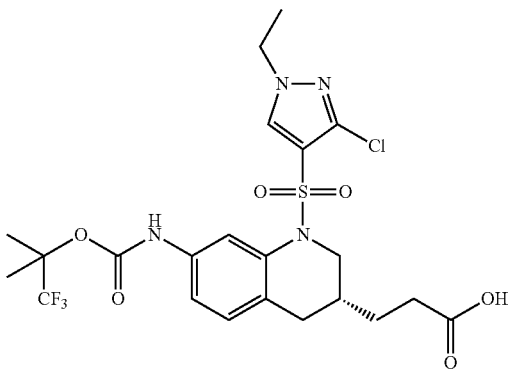

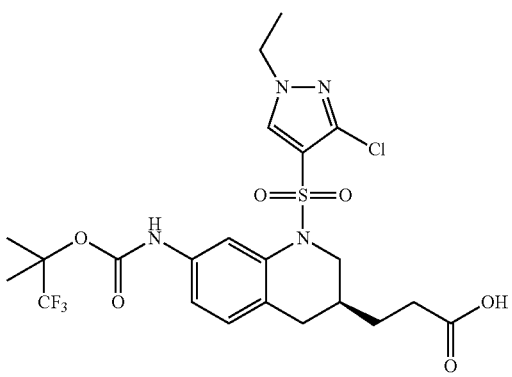

To a mixture of (R or S)-3-(7-((((1,1,1-trifluoro-2-methylpropan-2-yl)oxy)carbonyl)amino)-1,2,3,4-tetrahydroquinolin-3-yl)propanoic acid (Isomer 1 from Step 7; 30 mg, 0.080 mmol) in tetrahydrofuran (0.5 mL) was added 3-chloro-1-ethyl-1H-pyrazole-4-sulfonyl chloride (46 mg, 0.201 mmol) and pyridine (0.5 mL). The reaction mixture was stirred at 25° C. for 2 h, diluted with water (3 mL) and extracted with ethyl acetate (3 mL×3). The organic layers were combined, dried over anhydrous magnesium sulfate, filtered and concentrated in vacuo. The crude product was purified by prep-HPLC (MeCN/water using TFA buffer) to afford the title compound (Isomer 1, Example 116A) as a white solid.

The other enantiomer (Isomer 2, Example 116B) was prepared from Isomer 2 from Step 7 using a similar procedure as described above. Both enantiomers have the same analytical data: LCMS (ESI) calculated for $C_{22}H_{27}ClF_3N_4O_6S$ [M+H]$^+$: 567, found: 567. $^1$H NMR (400 MHz, CDCl$_3$) δ 8.06 (1H, s), 7.85 (1H, s), 6.99 (1H, d, J=8.2 Hz), 6.87 (1H, d, J=7.4 Hz), 6.67 (1H, br), 4.30 (1H, d, J=11.0 Hz), 3.10 (2H, q, J=7.0 Hz), 3.28-3.40 (1H, m), 2.82 (1H, dd, J=16.2, 4.6 Hz), 2.50 (2H, t, J=7.4 Hz), 2.32-2.44 (1H, m), 1.94-2.06 (2H, m), 1.78 (6H, s), 1.60-1.70 (1H, m), 1.47 (3H, t, J=7.2 Hz).

Example 117—Preparation of Additional 1,2,3,4-Tetrahydroquinolin-3-yl)propanoic Acids The compounds in Table 34 were prepared based on the experimental procedures described in Example 116, and can be achieved by one of skill in the art in light of the present disclosure.

TABLE 34

| Ex. No. | Structure | Name | Observed m/z |
|---|---|---|---|
| 117A | 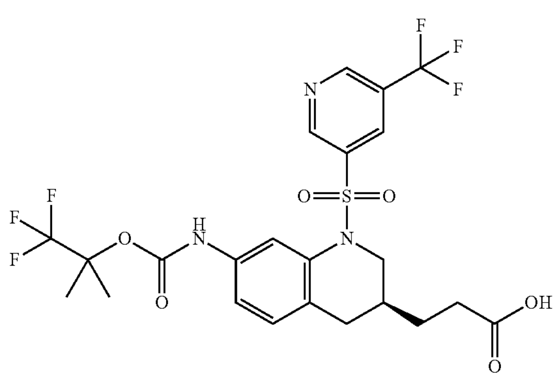 [SMILES: CC(C)(OC(=O)Nc1ccc2c(c1)N(S(=O)(=O)c1cncc(C(F)(F)F)c1)C[C@@H](CCC(=O)O)C2)C(F)(F)F] | (R or S)-3-(7-((((1,1,1-trifluoro-2-methylpropan-2-yl)oxy)carbonyl)amino)-1-((5-(trifluoromethyl)pyridin-3-yl)sulfonyl)-1,2,3,4-tetrahydroquinolin-3-yl)propanoic acid | 584 [M + H]+ |

TABLE 34-continued

| Ex. No. | Structure | Name | Observed m/z |
|---|---|---|---|
| 117B | 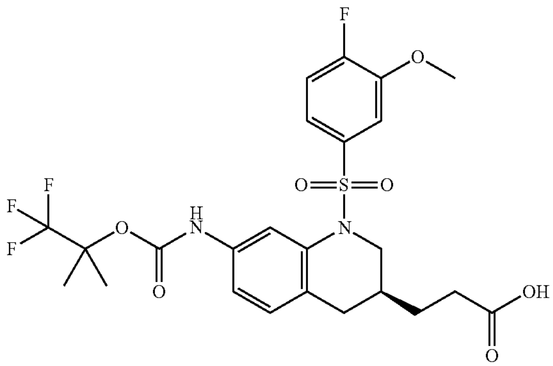 [SMILES: COc1cc(S(=O)(=O)N2C[C@@H](CCC(=O)O)Cc3ccc(NC(=O)OC(C)(C)C(F)(F)F)cc32)ccc1F] | (R or S)-3-(1-((4-fluoro-3-methoxyphenyl)sulfonyl)-7-(((((1,1,1-trifluoro-2-methylpropan-2-yl)oxy)carbonyl)amino)-1,2,3,4-tetrahydroquinolin-3-yl)propanoic acid | 563 [M + H]+ |
| 117C | 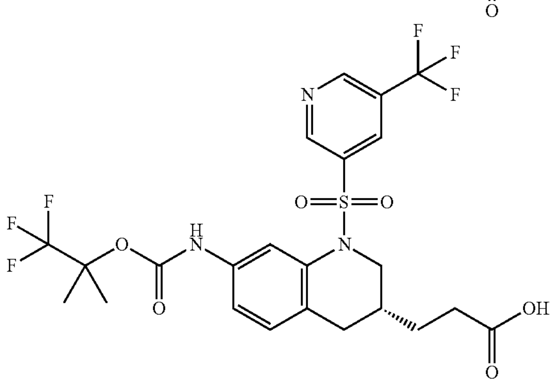 | (R or S)-3-(7-(((((1,1,1-trifluoro-2-methylpropan-2-yl)oxy)carbonyl)amino)-1-((5-(trifluoromethyl)pyridin-3-yl)sulfonyl)-1,2,3,4-tetrahydroquinolin-3-yl)propanoic acid | 584 [M + H]+ |
| 117D | 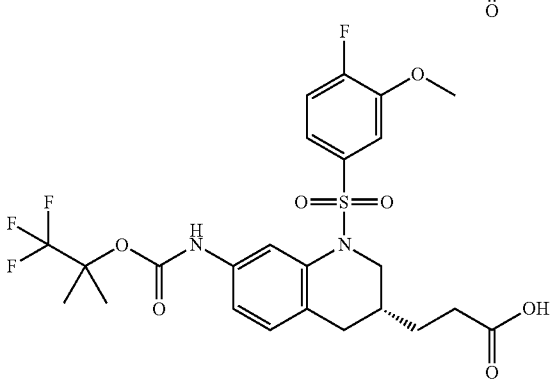 | (R or S)-3-(1-((4-fluoro-3-methoxyphenyl)sulfonyl)-7-(((((1,1,1-trifluoro-2-methylpropan-2-yl)oxy)carbonyl)amino)-1,2,3,4-tetrahydroquinolin-3-yl)propanoic acid | 563 [M + H]+ |

Example 118—Preparation of 1,1,1-trifluoro-2-methylpropan-2-yl (5-((3-chloro-1-ethyl-1-pyrazol-4-yl)sulfonyl)-8-oxo-5,6,7,8-tetrahydro-1,5-naphthyridin-3-yl)carbamate Example 118

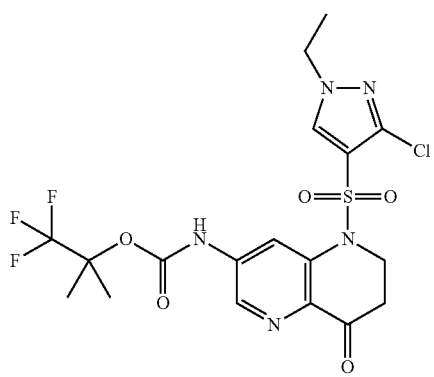 [SMILES: CCn1cc(S(=O)(=O)N2CCC(=O)c3ncc(NC(=O)OC(C)(C)C(F)(F)F)cc32)c(Cl)n1]

Step 1—Preparation of tert-butyl 7-nitro-3,4-dihydro-1,5-naphthyridine-1(2H)-carboxylate

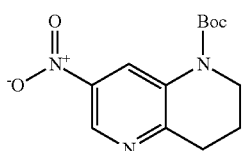

A solution of tert-butyl 3-oxopiperidine-1-carboxylate (6 g, 30.1 mmol) and 1-methyl-3,5-dinitropyridin-2(1H)-one (7.20 g, 36.1 mmol) in methanolic ammonia (1 M, 60 ml) was irradiated at 90° C. in a sealed vial for 45 min. The mixture was then concentrated and redissolved in CH$_2$Cl$_2$ (110 mL), the organics washed with saturated aqueous NaHCO$_3$ (100 ml) and water (100 mL), dried over Na$_2$SO$_4$, and evaporated. The crude product was purified by column chromatography (petroleum ether:ethyl acetate=15:1-4:1) to give the title product as a light yellow solid. LCMS (ESI) calculated for $C_{13}H_{18}N_3O_4$ [M+H]$^+$: 280.1, found: 280.2; $^1$H-NMR (CDCl$_3$, 400 MHz) δ 8.97 (2H, s), 3.79-3.76 (2H, m), 3.06-3.02 (2H, m), 2.06-2.00 (2H, m), 1.54 (9H, s).

Step 2—Preparation of 5-(tert-butoxycarbonyl)-3-nitro-5,6,7,8-tetrahydro-1,5-naphthyridine 1-oxide

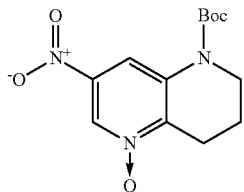

A mixture of tert-butyl 7-nitro-3,4-dihydro-1,5-naphthyridine-1(2H)-carboxylate (500 mg, 1.790 mmol) and m-CPBA (618 mg, 3.58 mmol) in CH$_2$Cl$_2$ (15 mL) was stirred at 20° C. for 18 hours. Additional CH$_2$Cl$_2$ (10 mL) was added to dissolve the solids and the organics washed with saturated sodium bicarbonate, water, brine and dried over sodium sulfate. The solvent was removed to give the crude title compound as a dark yellow solid, which was used directly in the next step. LCMS (ESI) calculated for $C_{13}H_{18}N_3O_5$ [M+H]$^+$: 296.1, found: 296.1.

Step 3—Preparation of tert-butyl 4-acetoxy-7-nitro-3,4-dihydro-1,5-naphthyridine-1(2H)-carboxylate

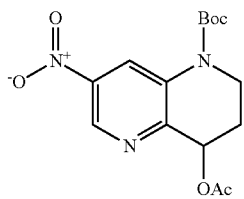

A mixture of 5-(tert-butoxycarbonyl)-3-nitro-5,6,7,8-tetrahydro-1,5-naphthyridine 1-oxide (503 mg, 1.703 mmol), Ac$_2$O (6 ml, 63.6 mmol) and toluene (6 mL) was heated to reflux for 5 hours under nitrogen. The reaction was concentrated under vacuum and azeotroped three times with toluene to give the crude title compound as black oil. LCMS (ESI) calculated for $C_{15}H_{20}N_3O_6$ [M+H]$^+$: 338.1, found: 338.1; $^1$H-NMR (CDCl$_3$, 400 MHz) δ 9.19 (1H, s), 9.07 (1H, d, J=2.0 Hz), 6.04-6.01 (1H, m), 4.17-4.12 (2H, m), 3.69-3.63 (2H, m), 2.15 (3H, s), 1.58 (9H, s).

Step 4—Preparation of tert-butyl 4-hydroxy-7-nitro-3,4-dihydro-1,5-naphthyridine-1(2H)-carboxylate

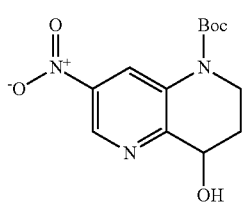

A mixture of tert-butyl 4-acetoxy-7-nitro-3,4-dihydro-1,5-naphthyridine-1(2H)-carboxylate (592 mg, 1.755 mmol) and 2N potassium carbonate (2.63 ml, 5.26 mmol) in MeOH (8 ml) and THF (8 mL) was stirred at 20° C. for 15 h. The organic solvents were removed under vacuum and the aqueous residue extracted with ethyl acetate (3×12 mL). The organic layer was washed with brine (8 mL) and dried over sodium sulfate. The solvent was removed and the crude product was purified by column chromatography (petroleum ether:ethyl acetate=3:1) to give the titled compound as a yellow oil. $^1$H-NMR (CDCl$_3$, 400 MHz) δ 9.11 (1H, s), 8.96 (1H, d, J=1.6 Hz), 4.71-4.67 (1H, m), 4.11 (1H, s), 3.90-3.85 (1H, m), 3.74-3.68 (1H, m), 2.41-2.36 (1H, m), 1.86-1.80 (1H, m), 1.51 (9H, s).

Step 5—Preparation of tert-butyl 7-nitro-4-oxo-3,4-dihydro-1,5-naphthyridine-1(2H)-carboxylate

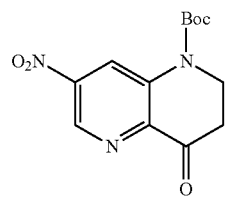 [SMILES: CC(C)(C)OC(=O)N1CCC(=O)c2ncc([N+](=O)[O-])cc21]

A mixture of tert-butyl 4-hydroxy-7-nitro-3,4-dihydro-1,5-naphthyridine-1(2H)-carboxylate (291 mg, 0.985 mmol) and manganese (IV) oxide (857 mg, 9.85 mmol) in CH$_2$Cl$_2$ (10 mL) was stirred at 25° C. for 18 hours. Additional CH$_2$Cl$_2$ (15 mL) was added, the solution filtered and the filtrate concentrated under vacuum. The residue was purified by column chromatography (petroleum ether:ethyl acetate=3:1) to give the title compound as a yellow solid. $^1$H-NMR (CDCl$_3$, 400 MHz) δ 9.23 (2H, s), 4.29 (2H, t, J=6.4 Hz), 3.02-2.98 (2H, m), 1.61 (9H, s).

Step 6—Preparation of tert-butyl 4,4-difluoro-7-nitro-3,4-dihydro-1,5-naphthyridine-1(2H)-carboxylate

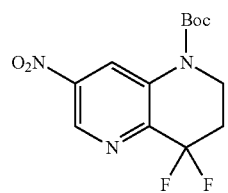 [SMILES: CC(C)(C)OC(=O)N1CCC(F)(F)c2ncc([N+](=O)[O-])cc21]

To a solution of tert-butyl 7-nitro-4-oxo-3,4-dihydro-1,5-naphthyridine-1(2H)-carboxylate (184 mg, 0.627 mmol) in CH$_2$Cl$_2$ (8 mL) was added DAST (2 mL, 15.14 mmol) at −20° C. under nitrogen. The reaction was allowed to warm up to 20° C. slowly and stirred at 20° C. for 18 h. The resulting mixture was diluted with CH$_2$Cl$_2$ (15 mL), poured into cooled sat. NaHCO$_3$ (10 mL) and extracted with CH$_2$Cl$_2$ (3×15 mL). The combined organic layers were washed with brine (8 mL), dried over anhydrous Na$_2$SO$_4$, filtered and concentrated. The crude product was purified by column chromatography (petroleum ether:ethyl acetate=9:1) to afford the title compound as yellow solid. $^1$H-NMR (CDCl₃, 400 MHz) δ 9.27 (1H, s), 9.17 (1H, d, J=2.0 Hz), 4.10-4.05 (2H, m), 2.60-2.51 (2H, m), 1.58 (9H, s).

Step 7—Preparation of tert-butyl 7-amino-4,4-difluoro-3,4-dihydro-1,5-naphthyridine-1(2H)-carboxylate

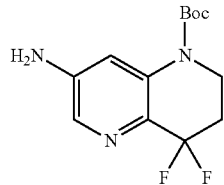

To a solution of tert-butyl 4,4-difluoro-7-nitro-3,4-dihydro-1,5-naphthyridine-1(2H)-carboxylate (120 mg, 0.381 mmol) in EtOAc (8 mL) was added nickel (11.17 mg, 0.190 mmol) in one portion at 25° C. under nitrogen. The reaction was stirred at 25° C. under H₂ (15 psi) for 4 hours, then filtered and evaporated to afford crude tert-butyl 7-amino-4,4-difluoro-3,4-dihydro-1,5-naphthyridine-1(2H)-carboxylate as a yellow oil. LCMS (ESI) calculated for C₁₃H₁₈F₂N₃O₂ [M+H]⁺: 286.1, found: 286.3.

Step 8—Preparation of tert-butyl 4,4-difluoro-7-((((1,1,1-trifluoro-2-methylpropan-2-yl)oxy)carbonyl)amino)-3,4-dihydro-1,5-naphthyridine-1(2H)-carboxylate

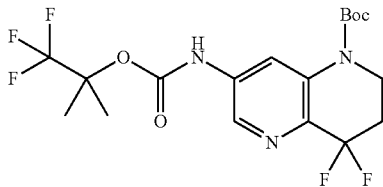 [SMILES: CC(C)(C)OC(=O)N1CCC(F)(F)c2ncc(NC(=O)OC(C)(C)C(F)(F)F)cc21]

To a solution of tert-butyl 7-amino-4,4-difluoro-3,4-dihydro-1,5-naphthyridine-1(2H)-carboxylate (65 mg, 0.228 mmol) and 3-methyl-1-(((1,1,1-trifluoro-2-methylpropan-2-yl)oxy)carbonyl)-1H-imidazol-3-ium iodide (83 mg, 0.228 mmol) in DMSO (2 mL) was stirred at 20° C. under nitrogen for 24 hours. The reaction was diluted with EtOAc (10 mL) and washed with brine (3×6 mL). The organic layer was dried over Na₂SO₄, filtered, and the filtrate was concentrated in vacuum to give crude title compound as yellow solid. LCMS (ESI) calculated for C₁₈H₂₃F₅N₃O₄ [M+H]⁺: 440.2, found: 440.1.

Step 9—Preparation of 1,1,1-trifluoro-2-methylpropan-2-yl (8-oxo-5,6,7,8-tetrahydro-1,5-naphthyridin-3-yl)carbamate

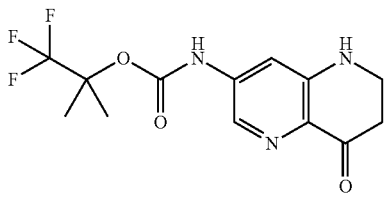 [SMILES: CC(C)(OC(=O)Nc1cnc2c(c1)NCCC2=O)C(F)(F)F]

To a solution of tert-butyl 4,4-difluoro-7-((((1,1,1-trifluoro-2-methylpropan-2-yl)oxy)carbonyl)amino)-3,4-dihydro-1,5-naphthyridine-1(2H)-carboxylate (43 mg, 0.098 mmol) in EtOAc (1 mL) was added a solution of HCl in EtOAc (3 ml, 4 N). The reaction was stirred at 20° C. for 2 h, then concentrated to give the crude title compound as yellow oil. LCMS (ESI) calculated for C₁₃H₁₅F₃N₃O₃ [M+H]⁺: 318.1, found: 318.0.

Step 10—Preparation of 1,1,1-trifluoro-2-methylpropan-2-yl (5-((3-chloro-1-ethyl-1H-pyrazol-4-yl)sulfonyl)-8-oxo-5,6,7,8-tetrahydro-1,5-naphthyridin-3-yl)carbamate

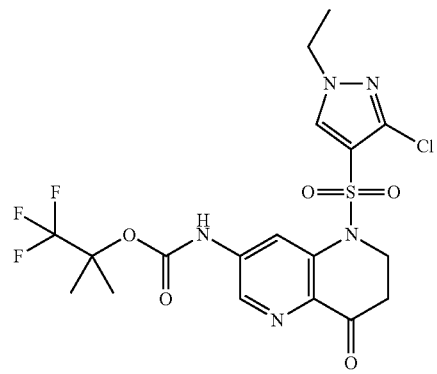 [SMILES: CCn1cc(S(=O)(=O)N2CCC(=O)c3ncc(NC(=O)OC(C)(C)C(F)(F)F)cc32)c(Cl)n1]

To a mixture of 1,1,1-trifluoro-2-methylpropan-2-yl (8-oxo-5,6,7,8-tetrahydro-1,5-naphthyridin-3-yl)carbamate (10 mg, 0.032 mmol) in THF (1 mL) was added 3-chloro-1-ethyl-1H-pyrazole-4-sulfonyl chloride (14.4 mg, 0.063 mmol) and pyridine (1 mL). The reaction was stirred at 25° C. for 16 hours, then diluted with water (3 mL) and extracted with ethyl acetate (3×6 mL). The organic layers were combined, dried over anhydrous magnesium sulfate, filtered and concentrated in vacuum. The crude product was purified by prep-HPLC (MeCN/water using TFA buffer) to afford the title compound as white solid. LCMS (ESI) calculated for C₁₈H₂₀ClF₃N₅O₅S [M+H]⁺: 510.1, found: 510.0; ¹H-NMR (CDCl₃, 400 MHz) δ 8.57 (1H, s), 8.14 (1H, s), 7.46 (1H, s), 4.34 (s, 2H), 4.08 (2H, d, J=7.2 Hz), 2.90 (2H, s), 1.71 (6H, s), 1.46 (3H, s).

Example 119—Preparation of 1,1,1-trifluoro-2-methylpropan-2-yl (1-((4-fluoro-3-(trifluoromethyl)phenyl)sulfonyl)-4-oxo-1,2,3,4-tetrahydroquinolin-7-yl)carbamate (Example 119)

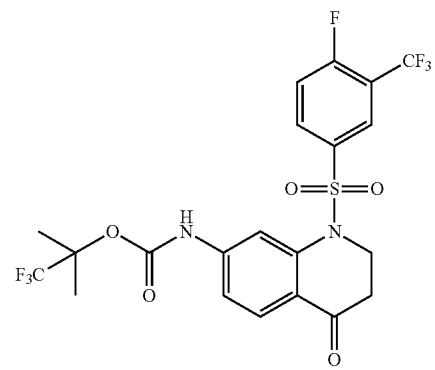 [SMILES: CC(C)(OC(=O)Nc1ccc2c(c1)N(S(=O)(=O)c1ccc(F)c(C(F)(F)F)c1)CCC2=O)C(F)(F)F]

Step 1—Preparation of 1,2,3,4-tetrahydroquinolin-7-amine

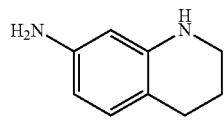

7-nitro-1,2,3,4-tetrahydroquinoline (2 g, 11.22 mmol) and Pd/C (1.2 g) in EtOH (20 mL) were stirred under $H_2$ at 25° C. for 1 h, then filtered. The filtrate was concentrated to obtain the crude product as black oil, which was used in the next step without further purification. LCMS (ESI) calculated for $C_9H_{13}N_2$ [M+H]$^+$: 149, found: 149 $^1$H NMR (CDCl$_3$ 400 MHz,) δ 6.68-6.75 (1H, m), 5.99 (1H, dd, J=2.0, 7.8 Hz), 5.78-5.86 (1H, m), 3.21-3.25 (2H, m), 2.63 (2H, t, J=6.3 Hz, 2H), 1.85-1.92 (2H, m).

Step 2—Preparation of 1,1,1-trifluoro-2-methylpropan-2-yl (1,2,3,4-tetrahydroquinolin-6-yl)carbamate

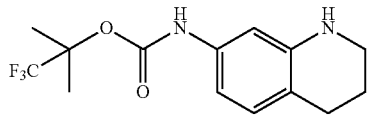 [SMILES: CC(C)(OC(=O)Nc1ccc2c(c1)NCCC2)C(F)(F)F]

To a solution of 1,2,3,4-tetrahydroquinolin-6-amine (1.2 g, 8.10 mmol) and 3-methyl-1-(((1,1,1-trifluoro-2-methylpropan-2-yl)oxy)carbonyl)-1H-imidazol-3-ium iodide (1.921 g, 8.10 mmol) in 15 mL of DMSO was stirred at 25° C. for 2 h. The reaction was quenched with $H_2O$ and extracted with EtOAc. The organic layer was dried, concentrated and the crude product was purified by column chromatography (petroleum ether:EtOAc=10:1) to give 1,1,1-trifluoro-2-methylpropan-2-yl (1,2,3,4-tetrahydroquinolin-6-yl)carbamate as yellow solid. LCMS (ESI) calculated for $C_{14}H_{17}F_3N_2O_2$ [M+H]$^+$: 303, found: 303 $^1$H NMR (CDCl$_3$ 400 MHz) δ 6.82 (1H, d, J=8.2 Hz), 6.64 (1H, br s), 6.50 (1H, br s), 6.40 (1H, d, J=7.4 Hz), 3.22-3.28 (2H, m), 2.67 (2H, t, J=6.1 Hz, 2H), 1.89 (2H, d, J=5.8 Hz, 2H), 1.72 (6H, s).

Step 3-Preparation of 1,1,1-trifluoro-2-methylpropan-2-yl(1-((4-fluoro-3-(trifluoromethyl)phenyl)sulfonyl)-1,2,3,4-tetrahydroquinolin-7-yl)carbamate

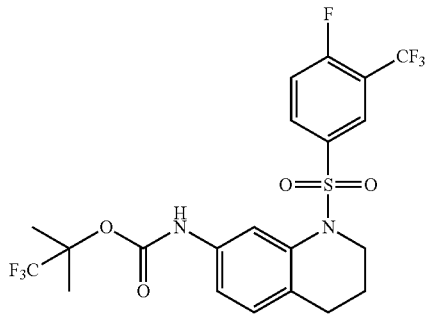 [SMILES: CC(C)(OC(=O)Nc1ccc2c(c1)N(S(=O)(=O)c1ccc(F)c(C(F)(F)F)c1)CCC2)C(F)(F)F]

To a solution of 1,1,1-trifluoro-2-methylpropan-2-yl (1,2,3,4-tetrahydroquinolin-7-yl)carbamate (200 mg, 0.662 mmol) and pyridine (105 mg, 1.32 mmol) in THF (2 mL) was added 4-fluoro-3-(trifluoromethyl)benzene-1-sulfonyl chloride (347 mg, 1.323 mmol) and the reaction mixture was stirred at 80° C. overnight, then extracted with EtOAc and water. The combined organic phase was washed with brine, dried over sodium sulfate, and concentrated in vacuo. The crude product was purified by prep-TLC (petroleum ether:EtOAc=10:1) to give crude title product as colorless oil, which was taken forward without further purification. $^1$H NMR (CDCl$_3$, 400 MHz) δ 7.94 (1H, d, J=5.1 Hz), 7.80-7.66 (2H, m), 7.16 (1H, s), 7.12-7.04 (1H, m), 6.91 (1H, d, J=8.2 Hz), 6.60 (1H, brs), 3.81-3.72 (2H, m), 2.42 (2H, t, J=6.5 Hz), 1.70 (6H, s), 1.67-1.61 (2H, m).

Step 4-Preparation of 1,1,1-trifluoro-2-methylpropan-2-yl(1-((4-fluoro-3-(trifluoromethyl)phenyl)sulfonyl)-4-oxo-1,2,3,4-tetrahydroquinolin-7-yl)carbamate

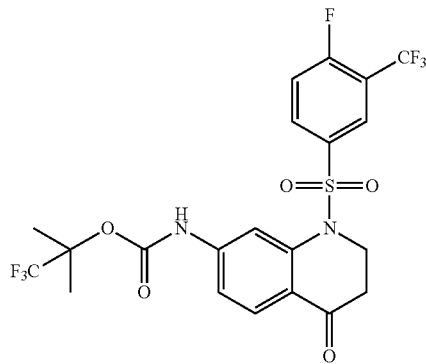 [SMILES: CC(C)(OC(=O)Nc1ccc2c(c1)N(S(=O)(=O)c1ccc(F)c(C(F)(F)F)c1)CCC2=O)C(F)(F)F]

To a solution of 1,1,1-trifluoro-2-methylpropan-2-yl(1-((4-fluoro-3-(trifluromethyl)phenyl)sulfonyl)-1,2,3,4-tetrahydroquinolin-7-yl)carbamate (200 mg, 0.378 mmol) in n-butanol (5 mL) was added solution of $KMnO_4$ (269 mg, 1.703 mmol) and $KH_2PO_4$ (232 mg, 1.703 mmol) solution (dissolved in 1 mL $H_2O$) in portions at 0° C. The reaction was stirred at 15° C. overnight, then quenched with $H_2O$ and extracted with EtOAc. The organic layer was dried and concentrated to give 1,1,1-trifluoro-2-methylpropan-2-yl (1-((4-fluoro-3-(trifluoromethyl)phenyl)sulfonyl)-4-oxo-1,2,3,4-tetrahydroquinolin-7-yl)carbamate as colorless oil. LCMS (ESI) calculated for $C_{21}H_{18}F_7N_2O_5S$ [M+H]$^+$: 543.1, found: 543.0.

Example 120—Preparation of (R or S)-1,1,1-trifluoro-2-methylpropan-2-yl (6-methyl-8-oxo-5-((3-(trifluoromethyl)phenyl)sulfonyl)-5,6,7,8-tetrahydro-1,5-naphthyridin-3-yl)carbamate (Example 120)

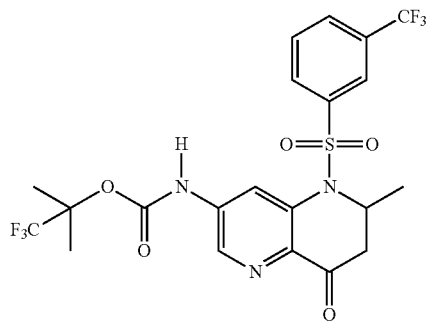 [SMILES: CC1CC(=O)c2ncc(NC(=O)OC(C)(C)C(F)(F)F)cc2N1S(=O)(=O)c1cccc(C(F)(F)F)c1]

Step 1—Preparation of 2,5-dibromopyridin-3-amine

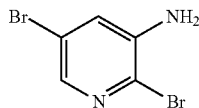

To a solution of 2,5-dibromo-3-nitropyridine (13.00 g, 46.1 mmol) in acetone (150 mL) was added ammonium chloride (24.67 g, 461 mmol) and zinc dust (15.08 g, 231 mmol) and the resulting mixture was stirred at room temperature for 5 h under $N_2$. Water (100 mL) was next added and the aqueous layer was extracted with EtOAc (3×200 mL). The combined organic layers were concentrated in vacuo and the crude product was purified by flash chromatography (0-30% EtOAc in petroleum ether) to afford the title compound as a white solid. $^1$H NMR (400 MHz, MeOD) δ 7.67 (d, J=2.0 Hz, 1H), 7.29 (d, J=2.0 Hz, 1H).

Step 2. Preparation of N-(2,5-dibromopyridin-3-yl)-3-(trifluoromethyl)-N-((3-(trifluoromethyl)phenyl)sulfonyl)benzenesulfonamide

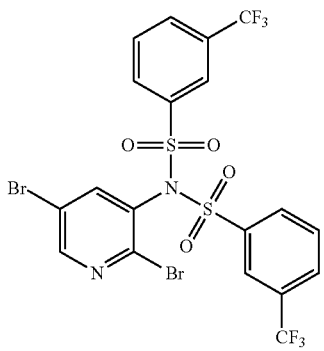 [SMILES: O=S(=O)(c1cccc(C(F)(F)F)c1)N(c1cc(Br)cnc1Br)S(=O)(=O)c1cccc(C(F)(F)F)c1]

To a solution of 2,5-dibromopyridin-3-amine (1.00 g, 3.97 mmol) in THF (15 mL) and pyridine (15 mL) was added 3-(trifluoromethyl)benzene-1-sulfonyl chloride (1.16 g, 4.74 mmol) and the resulting mixture was stirred at room temperature for 18 h under $N_2$. The reaction was quenched with aqueous $NH_4Cl$ (20 mL) and the aqueous layer was extracted with EtOAc (3×50 mL). The combined organic layers were concentrated in vacuo to afford the title compound as yellow solid. LCMS (ESI) calculated for $C_{19}H_{11}Br_2F_6N_2O_4S_2$ [M+H]$^+$: 666.8, found: 668.7.

Step 3—Preparation of N-(2,5-dibromopyridin-3-yl)-3-(trifluoromethyl)benzenesulfonamide

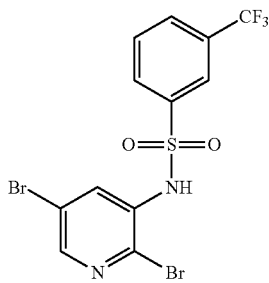 [SMILES: O=S(=O)(Nc1cc(Br)cnc1Br)c1cccc(C(F)(F)F)c1]

To a solution of N-(2,5-dibromopyridin-3-yl)-3-(trifluoromethyl)-N-((3-(trifluoromethyl)phenyl)sulfonyl)benzenesulfonamide (10.0 g, 14.97 mmol) in MeOH (30 mL) was added KOH (4.20 g, 74.8 mmol) in water (10 mL). The resulting mixture was stirred at 60° C. for 2 h under $N_2$. The solution was adjusted to pH=4 with 1 M HCl and the aqueous layer was extracted with EtOAc (3×100 mL). The combined organic layers were concentrated in vacuo and the crude product was purified by flash chromatography (0-50% EtOAc in petroleum ether) to afford the title compound as yellow oil. $^1$H NMR (400 MHz, MeOD) 8.29 (d, J=1.6 Hz, 1H), 8.00-8.11 (m, 2H), 7.95 (d, J=7.4 Hz, 2H), 7.66-7.78 (m, 1H).

Step 4-Preparation of N-(2,5-dibromopyridin-3-yl)-N-(pent-4-en-2-yl)-3-(trifluoromethyl) benzenesulfonamide

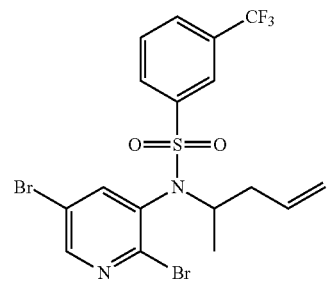 [SMILES: C=CCC(C)N(c1cc(Br)cnc1Br)S(=O)(=O)c1cccc(C(F)(F)F)c1]

To a solution of N-(2,5-dibromopyridin-3-yl)-3-(trifluoromethyl)benzenesulfonamide (5.00 g, 10.87 mmol) in THF (50 mL) was added triphenylphosphine (3.42 g, 13.04 mmol), pent-4-en-2-ol (1.12 g, 13.00 mmol) and (E)-diethyl diazene-1,2-dicarboxylate (2.27 g, 13.03 mmol) at room temperature. The resulting mixture was heated to 60° C. for 36 h, then treated with 100 mL of water. The aqueous layer was extracted with EtOAc (3×100 mL) and the combined organic layers were concentrated in vacuo. The crude product was purified by flash chromatography (0-20% EtOAc in petroleum ether) to afford the title compound as a white solid. LCMS (ESI) calculated for $C_{17}H_{16}Br_2F_3N_2O_2S$ [M+H]$^+$: 526.9, found: 529.0.

Step 5—Preparation of 7-bromo-2-methyl-4-methylene-1-((3-(trifluoromethyl)phenyl) sulfonyl)-1,2,3,4-tetrahydro-1,5-naphthyridine

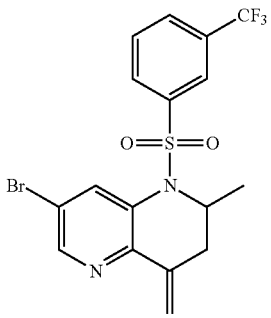 [SMILES: C=C1CC(C)N(S(=O)(=O)c2cccc(C(F)(F)F)c2)c2cc(Br)cnc21]

To a solution of N-(2,5-dibromopyridin-3-yl)-N-(pent-4-en-2-yl)-3-(trifluoromethyl)benzenesulfonamide (500 mg, 0.95 mmol) in 1,4-dioxane (20 mL) was added $Cs_2CO_3$ (617 mg, 1.89 mmol), followed by Pd₂(dba)₃ (43 mg, 0.047 mmol). The resulting mixture was stirred at 80° C. for 18 h under N₂, then concentrated in vacuo. The crude product was purified by flash chromatography (0-20% EtOAc in petroleum ether) to afford the title compound as a white solid. LCMS (ESI) calculated for $C_{17}H_{15}BrF_3N_2O_2S$ [M+H]⁺: 447.0, found: 449.0, ¹H NMR (400 MHz, MeOD) 8.51 (br s, 1H), 7.94-8.09 (m, 3H), 7.72-7.85 (m, 2H), 5.52-5.75 (m, 1H), 4.93-5.09 (m, 2H), 4.15-4.34 (m, 1H), 2.71-2.82 (m, 1H), 2.24-2.34 (m, 1H), 2.03-2.16 (m, 1H), 1.22 (d, J=6.6 Hz, 2H), 1.15 (d, J=6.6 Hz, 1H).

Step 6—Preparation of 7-bromo-2-methyl-1-((3-(trifluoromethyl)phenyl)sulfonyl)-2,3-dihydro-1,5-naphthyridin-4(1H)-one

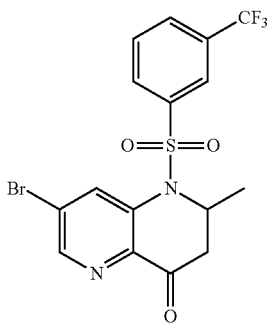 [SMILES: CC1CC(=O)c2ncc(Br)cc2N1S(=O)(=O)c1cccc(C(F)(F)F)c1]

To a solution of 7-bromo-2-methyl-4-methylene-1-((3-(trifluoromethyl)phenyl)sulfonyl)-1,2,3,4-tetrahydro-1,5-naphthyridine (400 mg, 0.89 mmol) in MeOH (20 mL) was added sodium periodate (574 mg, 2.68 mmol), followed by aqueous osmium tetroxide (0.056 mL, 0.18 mmol) and water (10 mL). The resulting mixture was stirred at room temperature for 3 h under N₂, then concentrated in vacuo. The crude product was purified by flash chromatography (0-20% EtOAc in petroleum ether) to afford the title compound as a white solid. LCMS (ESI) calculated for $C_{16}H_{13}BrF_3N_2O_3S$ [M+H]⁺: 449.0, found: 449.1.

Step 7—Preparation of (R)-tert-butyl (6-methyl-8-oxo-5-((3-(trifluoromethyl)phenyl)sulfonyl)-5,6,7,8-tetrahydro-1,5-naphthyridin-3-yl)carbamate and (S)-tert-butyl (6-methyl-8-oxo-5-((3-(trifluoromethyl)phenyl)sulfonyl)-5,6,7,8-tetrahydro-1,5-naphthyridin-3-yl)carbamate

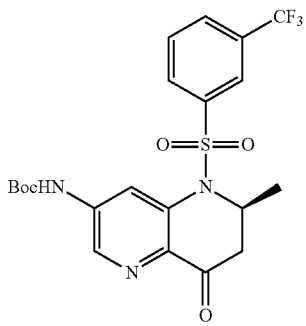

-continued

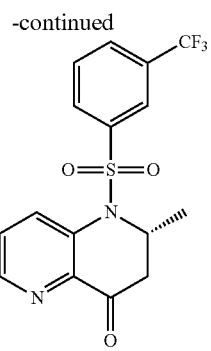

To a solution of 7-bromo-2-methyl-1-((3-(trifluoromethyl)phenyl)sulfonyl)-2,3-dihydro-1,5-naphthyridin-4 (1H)-one (120 mg, 0.27 mmol) in 1,4-Dioxane (2 mL) was added Cs₂CO₃ (174 mg, 0.53 mmol), followed by tert-butyl carbamate (62 mg, 0.53 mmol) and (RuPhos) palladium(II) phenethylamine chloride (10 mg, 0.014 mmol). The resulting mixture was stirred at 90° C. for 18 h under N₂, then filtered and washed with EtOAc (20 mL). The combined organics were removed in vacuo and the crude product was purified by prep-HPLC (MeCN/water using TFA buffer) to afford the title racemate as a white solid.

The above racemic mixture was separated by chiral SFC (Column: IC 250×4.6 mm I.D., 5 um; Mobile phase: isopropanol (0.05% DEA) in CO₂ from 5% to 40%; Flow rate: 2.5 mL/min; Wavelength: 220 nm) to afford two enantiomers (faster eluent, Isomer 1 from Step 7 and slower eluent, Isomer 2 from Step 7), which have the same analytical data: LCMS (ESI) calculated for $C_{21}H_{23}F_3N_3O_5S$ [M+H]⁺: 486.1, found: 486.3, ¹H NMR (400 MHz, MeOD) 8.53 (d, J=11.7 Hz, 2H), 7.92-8.03 (m, 3H), 7.78 (t, J=7.8 Hz, 1H), 4.64 (br s, 1H), 2.96 (br s, 1H), 1.82-1.89 (m, 1H), 1.55 (s, 9H), 0.97 (d, J=6.6 Hz, 3H).

Step 8—Preparation of (R)-7-amino-2-methyl-1-((3-(trifluoromethyl)phenyl)sulfonyl)-2,3-dihydro-1,5-naphthyridin-4(1H)-one and (S)-7-amino-2-methyl-1-((3-(trifluoromethyl)phenyl)sulfonyl)-2,3-dihydro-1,5-naphthyridin-4(1H)-one

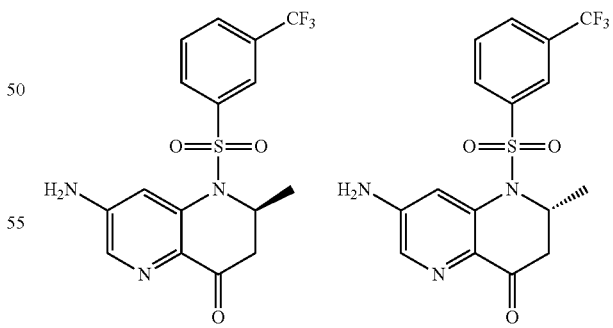

To a solution of (R or S)-tert-butyl (6-methyl-8-oxo-5-((3-(trifluoromethyl)phenyl)sulfonyl)-5,6,7,8-tetrahydro-1,5-naphthyridin-3-yl)carbamate (Isomer 1 from Step 7, 10 mg, 0.021 mmol) in DCM (1 mL) was added TFA (2 mL, 26.0 mmol). The reaction mixture was stirred at room temperature for 3 h, then concentrated in vacuo to afford the title compound as colorless oil.

The other enantiomer (Isomer 2 from Step 8) was prepared using a similar procedure as described above from Isomer 2 from Step 7. Both enantiomers have same analysis data: LCMS (ESI) calculated for $C_{16}H_{15}F_3N_3O_3S$ [M+H]$^+$: 386.1, found: 386.1.

Step 9. Preparation of (R or S)-1,1,1-trifluoro-2-methylpropan-2-yl (6-methyl-8-oxo-5-((3-(trifluoromethyl)phenyl)sulfonyl)-5,6,7,8-tetrahydro-1,5-naphthyridin-3-yl)carbamate

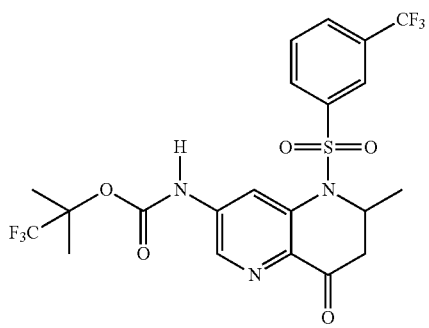 [SMILES: CC1CC(=O)c2ncc(NC(=O)OC(C)(C)C(F)(F)F)cc2N1S(=O)(=O)c1cccc(C(F)(F)F)c1]

To a solution of (R or S)-7-amino-2-methyl-1-((3-(trifluoromethyl)phenyl)sulfonyl)-2,3-dihydro-1,5-naphthyridin-4(1H)-one (Isomer 1 from Step 8, 7 mg, 0.018 mmol) in DMSO (1 mL) was added 3-methyl-1-(((1,1,1-trifluoro-2-methylpropan-2-yl)oxy)carbonyl)-1H-imidazol-3-ium iodide (10 mg, 0.027 mmol). The reaction mixture was stirred at room temperature for 16 h and then purified by prep-HPLC (MeCN/water using TFA buffer) to afford the title compound as a white solid.

LCMS (ESI) calculated for $C_{21}H_{20}F_6N_3O_5S$ [M+H]$^+$: 540.1, found: 540.1, $^1$H NMR (400 MHz, MeOD) 8.46 (d, J=14.1 Hz, 2H), 7.94 (d, J=16.8 Hz, 3H), 7.76 (t, J=7.8 Hz, 1H), 4.63 (brs, 1H), 2.90 (d, J=10.2 Hz, 1H), 1.85 (brs, 1H), 1.77 (s, 3H), 1.18 (d, J=6.7 Hz, 3H), 0.94 (d, J=6.7 Hz, 3H).

Example 121: Preparation of 1,1,1-trifluoro-2-methylpropan-2-yl ((R and S)-2-((R and S)-5-oxopyrrolidin-2-yl)-4-tosyl-3,4-dihydro-2H-benzo[b][1,4]oxazin-6-yl)carbamate (Example 121)

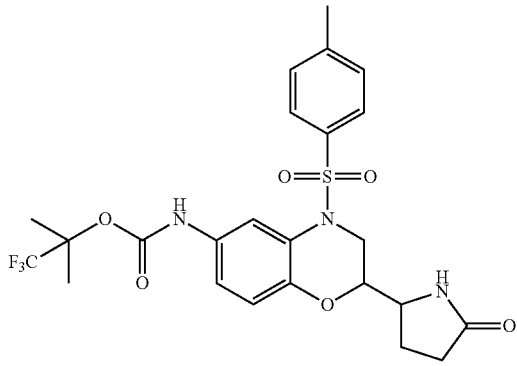 [SMILES: Cc1ccc(S(=O)(=O)N2CC(C3CCC(=O)N3)Oc3ccc(NC(=O)OC(C)(C)C(F)(F)F)cc32)cc1]

Step 1—Preparation of (R and S)-tert-butyl 2-((R and S)-6-nitro-4-tosyl-3,4-dihydro-2H-benzo[b][1,4]oxazin-2-yl)-5-oxopyrrolidine-1-carboxylate

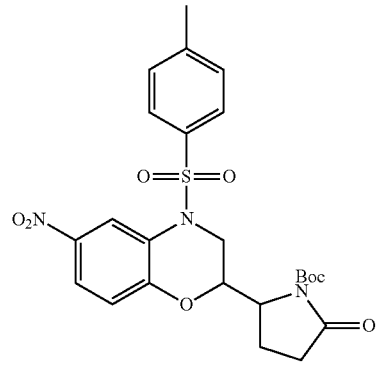 [SMILES: Cc1ccc(S(=O)(=O)N2CC(C3CCC(=O)N3C(=O)OC(C)(C)C)Oc3ccc([N+](=O)[O-])cc32)cc1]

A mixture of benzyltriethylammonium chloride (40 mg, 0.176 mmol), $K_2CO_3$ (122 mg, 0.88 mmol), 2-(benzylamino)-4-nitrophenol (322 mg, 1.32 mmol) and tert-butyl 2-(oxiran-2-yl)-5-oxopyrrolidine-1-carboxylate (200 mg, 0.880 mmol) in DMF (5 mL) was stirred at 100° C. for 16 h. The reaction mixture was diluted with ethyl acetate, washed with brine, dried and concentrated, then purified by prep-TLC (petroleum ether/ethyl acetate=1:1) to afford the title compound as a white solid. LCMS (ESI) calculated for $C_{24}H_{28}N_3O_8S$ [M+H]$^+$: 518 found 518.

Step 2—Preparation of (R and S)-5-((R and S)-6-nitro-4-tosyl-3,4-dihydro-2H-benzo[b][1,4]oxazin-2-yl)pyrrolidin-2-one

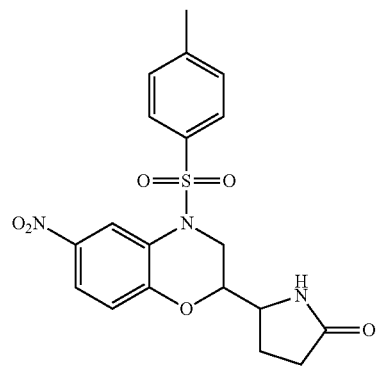 [SMILES: Cc1ccc(S(=O)(=O)N2CC(C3CCC(=O)N3)Oc3ccc([N+](=O)[O-])cc32)cc1]

To a solution of (R and S)-tert-butyl 2-((R and S)-6-nitro-4-tosyl-3,4-dihydro-2H-benzo[b][1,4]oxazin-2-yl)-5-oxopyrrolidine-1-carboxylate (400 mg, 0.773 mmol) in DCM (5 mL) was added TFA (441 mg, 3.86 mmol). The reaction mixture was stirred at 30° C. for 6 h, then washed with aq. NaHCO$_3$ and brine, dried over sodium sulfate, filtered and concentrated to afford the title compounds as yellow oil. LCMS (ESI) calculated for $C_{19}H_{20}N_3O_6S$ [M+H]$^+$: 418, found 418, $^1$H NMR (400 MHz, CDCl$_3$) δ 8.19-8.27 (1H, m), 8.08-8.17 (1H, m), 7.82-7.95 (1H, m), 7.67 (2H, brs), 7.32-7.43 (2H, m), 4.20-4.33 (1H, m), 3.67-3.92 (2H, m), 3.44-3.64 (1H, m), 2.46 (3H, s), 2.21-2.43 (4H, m).

Step 3—Preparation of (R and S)-5-((R and S)-6-amino-4-tosyl-3,4-dihydro-2H-benzo[b][1,4]oxazin-2-yl)pyrrolidin-2-one

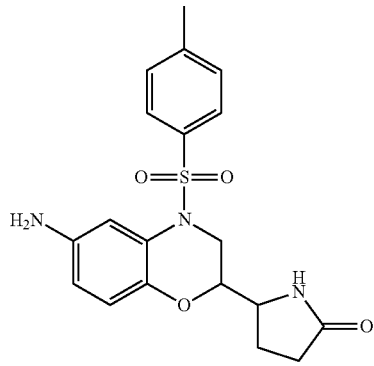

10% Pd/C (122 mg, 0.115 mmol) was added to a solution of (R and S)-5-((R and S)-6-nitro-4-tosyl-3,4-dihydro-2H-benzo[b][1,4]oxazin-2-yl)pyrrolidin-2-one (160 mg, 0.383 mmol) in methanol (10 mL). The reaction mixture was stirred at room temperature for 16 h under a $H_2$ balloon, then filtered through CELITE and concentrated to afford the titled compound as colorless oil. LCMS (ESI) calculated for $C_{19}H_{22}N_3O_4S$ [M+H]$^+$: 388, found 388.

Step 4—Preparation of 1,1,1-trifluoro-2-methylpropan-2-yl ((R and S)-2-((R and S)-5-oxopyrrolidin-2-yl)-4-tosyl-3,4-dihydro-2H-benzo[b][1,4]oxazin-6-yl)carbamate

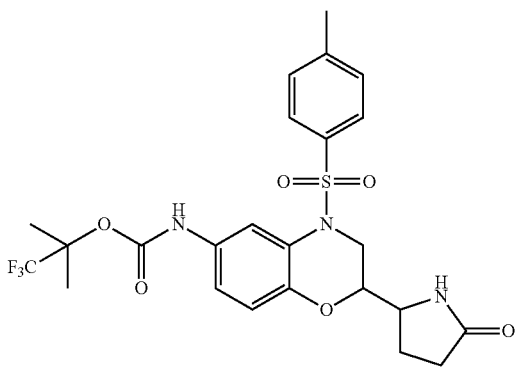 [SMILES: Cc1ccc(S(=O)(=O)N2CC(C3CCC(=O)N3)Oc3ccc(NC(=O)OC(C)(C)C(F)(F)F)cc32)cc1]

To a solution of (R and S)-5-((R and S)-6-amino-4-tosyl-3,4-dihydro-2H-benzo[b][1,4]oxazin-2-yl)pyrrolidin-2-one (9 mg, 0.023 mmol) in DMSO (3 mL) was added 1-iodo-1-methyl-3-(((1,1,1-trifluoro-2-methylpropan-2-yl)oxy)carbonyl)-2,3-dihydro-1H-imidazol-1-ium-2-ide (9 mg, 0.025 mmol) and the resulting mixture was stirred at 20° C. for 1 h. Then water was added and the mixture extracted with ethyl acetate (10 mL×2). The combined organic layers were washed with water and brine, concentrated and the crude product was purified by preparative HPLC (MeCN/water using TFA buffer) to afford the title compound as white solid. LCMS (ESI) calculated for $C_{24}H_{27}F_3N_3O_6S$ [M+H]$^+$: 542 found 542. $^1$H NMR (400 MHz, CDCl$_3$) δ 7.70 (1H, br s), 7.60 (2H, d, J=8.2 Hz), 7.30 (2H, d, J=7.8 Hz), 7.19-7.25 (1H, m), 6.78-6.85 (1H, m), 6.47-6.69 (2H, m), 4.05-4.26 (1H, m), 3.77-3.87 (1H, m), 3.63-3.87 (1H, m), 3.31 (2H, d, J=8.2 Hz), 2.43 (3H, s), 2.34-2.41 (3H, m), 1.97-2.11 (1H, m), 1.78 (6H, s).

Biological Assays

The compounds of the invention inhibit RORgammaT activity. Activation of RORgammaT activity can be measured using, e.g., a biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (SEQ ID NO:1) (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was recombinantly expressed in *Escherichia coli*. The RORγ-LBD protein was purified by Ni$^{2+}$-affinity resin. Purified protein was then diluted in assay buffer (50 mM Tris pH 7.0, 50 mM KCl, 1 mM EDTA, 0.1 mM DTT, 100 µg/mL bovine serum albumin, delipidated) to obtain a RORγ-LBD final concentration of 3 nM. Europium tagged anti-HIS antibody was also added to this solution (1.25 nM). Separately, SF9 cells not expressing any recombinant protein were lysed (32,000 cells per µl in 25 mM Tris, 50 mM NaCl) and the previously frozen lysate was added to the diluted RORγ-LBD solution at a ratio of 0.75 µl SF9 lysate per 15 µl of diluted RORγ-LBD.

Compounds to be tested were injected to the 384-well assay plate using Acoustic Droplet Ejection technology by Echo 550 liquid handler (Labcyte, CA).

A stock of biotinylated-LXXLL peptide from coactivator SRC1 (Biotin-SPSSHSSLTERHKILHRLLQEGSP) (SEQ ID NO:2) and APC-conjugated streptavidin (final concentrations 100 nM and 8 nM respectively) were also added to each well.

The final assay mixture was incubated overnight at 4° C., warmed to room temperature and the fluorescence signal was measured on an Envision plate reader: (Excitation filter=340 nm; APC emission=665 nm; Europium emission=615 nm; dichroic mirror=D400/D630; delay time=100 µs, integration time=200 µs). IC$_{50}$ values for test compounds were calculated from the quotient of the fluorescence signal at 665 nm divided by the fluorescence signal at 615 nm.

The IC$_{50}$ values for representative compounds of the invention are set forth below.

| Ex. No. | IC$_{50}$ (nM) |
| --- | --- |
| 1 | 3.011 |
| 2A | 8.586 |
| 2B | 8.547 |
| 2C | 4.571 |
| 2D | 7.99 |
| 2E | 237.6 |
| 2F | 9.743 |
| 2G | 15.18 |
| 2H | 11.27 |
| 3 | 325.2 |

-continued

| Ex. No. | IC$_{50}$ (nM) |
|---|---|
| 4A | 28.44 |
| 4B | 6.772 |
| 5 | 25.79 |
| 6 | 11.84 |
| 7 | 83.41 |
| 8 | 31.65 |
| 9 | 4.229 |
| 10A | 41.73 |
| 10B | 158.9 |
| 10C | 22.78 |
| 10D | 10.45 |
| 10E | 18.36 |
| 10F | 47.27 |
| 10G | 29.41 |
| 10H | 18.97 |
| 10i | 72.52 |
| 10J | 10.77 |
| 10K | 195 |
| 11 | 5.79 |
| 12 | 2.723 |
| 13A | 7.25 |
| 13B | 12.72 |
| 13C | 7.315 |
| 13D | 11.64 |
| 13E | 6.611 |
| 13F | 14.53 |
| 13G | 56.79 |
| 13H | 36.86 |
| 13i | 15.7 |
| 13J | 5.74 |
| 13K | 27.75 |
| 13L | 9.327 |
| 13M | 5.42 |
| 13N | 20.02 |
| 13o | 27.51 |
| 13P | 15.72 |
| 13Q | 15.41 |
| 13R | 24.43 |
| 13S | 14.6 |
| 13T | 9.188 |
| 13U | 8.801 |
| 13V | 5.297 |
| 13W | 5.999 |
| 13X | 10.1 |
| 13Y | 3.045 |
| 13Z | 5.817 |
| 13AA | 5.903 |
| 13AB | 3.916 |
| 13AC | 8.073 |
| 13AD | 5.112 |
| 13AE | 4.81 |
| 13AF | 3.928 |
| 14 | 4.129 |
| 15A | 7.388 |
| 15B | 9.537 |
| 15C | 7.751 |
| 15D | 10.27 |
| 15E | 5.877 |
| 15F | 5.184 |
| 16 | 4.16 |
| 17A | 5.552 |
| 17B | 11.25 |
| 17C | 4.808 |
| 17D | 5.135 |
| 17E | 7.841 |
| 17F | 3.861 |
| 18 | 3.276 |
| 19A | 6.322 |
| 19B | 13.1 |
| 19C | 6.113 |
| 19D | 5.331 |
| 19E | 5.08 |
| 20 | 10.08 |
| 21 | 692.6 |
| 22A | 920.1 |
| 22B | 10.04 |
| 23A | 4674 |

-continued

| Ex. No. | IC$_{50}$ (nM) |
|---|---|
| 23B | 27.72 |
| 24 | 11.56 |
| 25A | 12.33 |
| 25B | 11.49 |
| 25C | 623.3 |
| 25D | 203.1 |
| 25E | 167.9 |
| 25F | 9593 |
| 25G | 51.31 |
| 25H | 107.6 |
| 26 | 30.68 |
| 27 | 29.17 |
| 28A | 189.8 |
| 28B | 20.67 |
| 28C | 450.5 |
| 28D | 847.7 |
| 28E | 189.9 |
| 28F | 1765 |
| 29 | 3.758 |
| 30A | 2.241 |
| 30B | 3.126 |
| 30C | 2.154 |
| 30D | 15.83 |
| 30E | 4.943 |
| 31 | 54.68 |
| 32A | 16.34 |
| 32B | 9.557 |
| 32C | 51.75 |
| 32D | 19.93 |
| 32E | 563.2 |
| 32F | 241.6 |
| 32G | 81.56 |
| 32H | 26.59 |
| 33 | 43.31 |
| 34A | 155.5 |
| 34B | 60.79 |
| 34C | 54.12 |
| 34D | 182.2 |
| 34E | 58.3 |
| 35 | 17.25 |
| 36 | 10.01 |
| 37A | 3.889 |
| 37B | 3.656 |
| 37C | 7.091 |
| 37D | 4.805 |
| 37E | 6.015 |
| 37F | 11.03 |
| 37G | 19.84 |
| 37H | 2.805 |
| 37i | 4.835 |
| 37J | 1.961 |
| 37K | 6.884 |
| 37L | 7.555 |
| 37M | 7.898 |
| 37N | 7.056 |
| 37o | 5.743 |
| 37P | 7.645 |
| 37Q | 10.77 |
| 37R | 3.79 |
| 37S | 4.47 |
| 37T | 19.13 |
| 37U | 5.462 |
| 37V | 6.858 |
| 37W | 9.682 |
| 37X | 8.031 |
| 37Y | 10.78 |
| 37Z | 6.021 |
| 37AA | 2.526 |
| 37AB | 45.75 |
| 37AC | 11.97 |
| 37AD | 4.711 |
| 37AE | 4.379 |
| 37AF | 4.164 |
| 37AG | 2.557 |
| 37AH | 2.113 |
| 37Ai | 13.4 |
| 37AJ | 5.726 |

| Ex. No. | IC$_{50}$ (nM) |
|---|---|
| 37AK | 12.82 |
| 37AL | 8.413 |
| 37AM | 6.153 |
| 37AN | 9.446 |
| 37Ao | 5.409 |
| 37AP | 9.273 |
| 37AQ | 10.16 |
| 37AR | 17.51 |
| 38A | 4.691 |
| 38B | 6.584 |
| 38C | 6.948 |
| 38D | 4.871 |
| 38E | 50.09 |
| 38F | 42.52 |
| 38G | 12.5 |
| 39 | 140.4 |
| 40 | 1136 |
| 41 | 36.68 |
| 42 | 19.25 |
| 43A | 128.5 |
| 43B | 58.86 |
| 43C | 41.18 |
| 43D | 35.53 |
| 43E | 73.44 |
| 43F | 50.44 |
| 43G | 46.62 |
| 43H | 24.9 |
| 43i | 26.98 |
| 43J | 97.22 |
| 43K | 41.3 |
| 43L | 91.23 |
| 43M | 55.32 |
| 43N | 63.3 |
| 43o | 110.2 |
| 43P | 62.94 |
| 43Q | 36.63 |
| 43R | 36.23 |
| 43S | 31.14 |
| 43T | 60.69 |
| 43U | 47.48 |
| 43V | 33.19 |
| 43W | 534.5 |
| 43X | 212.8 |
| 43Y | 72.99 |
| 43Z | 57.26 |
| 43AA | 99.03 |
| 43AB | 85.9 |
| 43AC | 72.84 |
| 43AD | 296.8 |
| 44 | 4.073 |
| 45A | 126.9 |
| 45B | 12.63 |
| 45C | 43.79 |
| 45D | 63.16 |
| 45E | 25.19 |
| 45F | 11.25 |
| 45G | 5.587 |
| 45H | 14.64 |
| 45i | 17.1 |
| 45J | 6.848 |
| 45K | 6.301 |
| 46 | 12.09 |
| 47A | 12.26 |
| 47B | 8.827 |
| 47C | 5.714 |
| 47D | 5.982 |
| 47E | 5.951 |
| 47F | 27.74 |
| 47G | 26.58 |
| 47H | 5.975 |
| 48 | 5.72 |
| 49 | 2.464 |
| 50 | 4.828 |
| 51 | 42.66 |
| 52 | 6.14 |
| 53A | 4.073 |
| 53B | 6.26 |
| 53C | 4.878 |
| 53D | 5.515 |
| 53E | 4.379 |
| 53F | 6.138 |
| 53G | 7.733 |
| 53H | 6.766 |
| 53i | 4.975 |
| 53J | 6.373 |
| 53K | 10.55 |
| 53L | 5.987 |
| 53M | 15.2 |
| 53N | 68.44 |
| 53o | 53.11 |
| 53P | 3.423 |
| 53Q | 10.17 |
| 54 | 3.489 |
| 55A | 3.133 |
| 55B | 7.848 |
| 55C | 8.624 |
| 55D | 136.2 |
| 55E | 4.09 |
| 56 | 4.919 |
| 57A | 5.667 |
| 57B | 3.987 |
| 57C | 6.441 |
| 57D | 4.524 |
| 57E | 4.173 |
| 57F | 7.503 |
| 57G | 5.759 |
| 57H | 10.64 |
| 57i | 8.268 |
| 57J | 12.49 |
| 57K | 10.96 |
| 57L | 12.5 |
| 57M | 393.6 |
| 57N | 30.88 |
| 57o | 12.83 |
| 57P | 11.69 |
| 57Q | 7.383 |
| 57R | 13.8 |
| 57S | 14.85 |
| 57T | 12.7 |
| 58 | 3.564 |
| 59 | 4.77 |
| 60 | 5.973 |
| 61 | 14.9 |
| 62 | 8.874 |
| 63A | 21.18 |
| 63B | 9.753 |
| 63C | 3.037 |
| 63D | 37.89 |
| 63E | 2.798 |
| 63F | 2.782 |
| 63G | 5.595 |
| 63H | 8.436 |
| 64 | 16.59 |
| 65 | 4.573 |
| 66 | 6.846 |
| 67A | 4.899 |
| 67B | 5.793 |
| 67C | 23.19 |
| 67D | 21.57 |
| 67E | 38.19 |
| 72 | 314.5 |
| 73 | 903.5 |
| 74A | 194.8 |
| 74B | 902.5 |
| 74C | 4955 |
| 75 | 1923 |
| 76A | 3309 |
| 76B | 270.2 |
| 77 | 192.2 |
| 78A | 830 |
| 78B | 312.6 |
| 79A | 63.48 |
| 79B | 130.1 |
| 79C | 603 |

| Ex. No. | IC$_{50}$ (nM) |
|---|---|
| 79D | 189.8 |
| 80 | 330.4 |
| 6B | 40.02 |
| 13AG | 5.84 |
| 57U | 19.43 |
| 81A | 99.79 |
| 81B | 28.43 |
| 81C | 5.137 |
| 81D | 16.03 |
| 81E | 9.026 |
| 81F | 3.325 |
| 81G | 27.02 |
| 82A | 231.4 |
| 82B | 8.849 |
| 82C | 157.8 |
| 82D | 7.904 |
| 83 | 4.808 |
| 84 | 7.487 |
| 85 | 13.84 |
| 86 | 64.76 |
| 87 | 232.8 |
| 88A | 7.651 |
| 88B | 5.954 |
| 89A | 22.56 |
| 89B | 12.94 |
| 90A | 26.14 |
| 90B | 6.971 |
| 91A | 26.14 |
| 91B | 6.971 |
| 91C | 6.966 |
| 91D | 15.85 |
| 91E | 13.89 |
| 91F | 18.09 |
| 91G | 147.7 |
| 91H | 9.3 |
| 91i | 24.42 |
| 91J | 70.36 |
| 91K | 42.73 |
| 92 | 3.109 |
| 93A | 5.389 |
| 93B | 32.15 |
| 94A | 74.69 |
| 94B | 4.792 |
| 95A | 32.31 |
| 95B | 137.6 |
| 95C | 78.9 |
| 95D | 5.727 |
| 95E | 4.518 |
| 95F | 524.4 |
| 95G | 10.12 |
| 96 | 26.17 |
| 97A | 12.55 |
| 97B | 29.01 |
| 98A | 40.06 |
| 98B | 46.07 |
| 98C | 1436 |
| 98D | 29.74 |
| 98E | 44.81 |
| 98F | 10.82 |
| 98G | 38.66 |
| 98H | 6.325 |
| 98i | 41.49 |
| 98J | 28.06 |
| 99 | 8.291 |
| 100 | 10.36 |
| 101 | 11.67 |
| 102 | 11.2 |
| 103A | 119.7 |
| 103B | 28.22 |
| 104A | 11.2 |
| 104B | 12.65 |
| 104C | 8.77 |
| 104D | 11.87 |
| 104E | 9.238 |
| 104F | 50.7 |
| 104G | 119.7 |
| 104H | 15.24 |
| 104i | 28.22 |
| 105 | 6.303 |
| 106 | 5.708 |
| 107A | 6.081 |
| 107B | 7.533 |
| 108 | 6.621 |
| 109A | 12.62 |
| 109B | 39.56 |
| 109C | 8.263 |
| 110 | 62.3 |
| 111A | 2724 |
| 111B | 78.26 |
| 112A | 72.09 |
| 112B | 288.9 |
| 113 | 12.35 |
| 114A | 3.869 |
| 114B | 4.194 |
| 114C | 6.863 |
| 114D | 3.456 |
| 115A | 2.026 |
| 115B | 4.961 |
| 116A | 9.578 |
| 116B | 8.798 |
| 117A | 10.47 |
| 117B | 6.515 |
| 117C | 7.75 |
| 117D | 5.748 |
| 118 | 720.5 |
| 119 | 4.49 |

While the present invention has been described in conjunction with the specific embodiments set forth above, many alternatives, modifications, and other variations thereof will be apparent to those of ordinary skill in the art in light of the present disclosure. All such alternatives, modifications, and variations are intended to fall within the spirit and scope of the present invention.

What is claimed is:

1. A compound of the Formula (I)

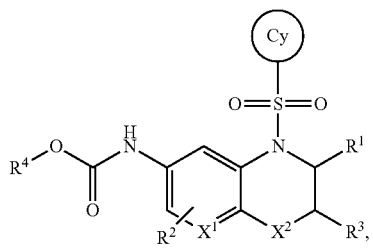

or a pharmaceutically acceptable salt thereof,
wherein:
$X^1$ is $C(R^2)$;
$X^2$ is O;
$R^1$ is H, $C_1$-$C_3$ alkyl, or $C_1$-$C_3$ alkyl substituted by hydroxy;
$R^2$ is H, halo, or $C_1$-$C_3$ alkyl;
$R^3$ is selected from the group consisting of:
- (a.) H;
- (b.) $C_1$-$C_6$ alkyl;
- (c.) —$(C(R^a)_2)_{n1}$OH;
- (d.) —$(C(R^a)_2)_{n1}$N$(R^b)_2$;
- (e.) —$(C(R^a)_2)_{n1}$N(H)C(O)N$(R^b)_2$;
- (f.) —$(C(R^a)_2)_{n1}$N(H)C(O)$R^d$;
- (g.) —$(C(R^a)_2)_{n1}$N(H)S(O)$_2$N$(R^b)_2$;
- (h.) —$(C(R^a)_2)_{n1}$N(H)S(O)$_2$$R^d$;
- (i.) —$(C(R^a)_2)_{n2}$CO$_2$$R^c$;
- (j.) —$(C(R^a)_2)_{n2}$C(O)N$(R^b)_2$;
- (k.) —$(C(R^a)_2)_{n1}$S(O)$_2$N$(R^b)_2$;
- (l.) —$(C(R^a)_2)_{n2}$N(H)C(O)O$R^d$;
- (m.) —$(C(R^a)_2)_{n2}$C(O)N(H)S(O)$_2$$R^d$;
- (n.) —$(C(R^a)_2)_{n1}$N(H)S(O)$_2$O$R^d$;
- (o.) —$(C(R^a)_2)_{n1}$S(O)$_{n3}$$R^d$;
- (p.) —$(C(R^a)_2)_{n2}$C(O)N(H)O$R^d$;
- (q.) —$(C(R^a)_2)_{n1}$CN;
- (r.) —$C^H$ or —$(C(R^a)_2)_{n1}$—$C^H$;
- (s.) —$C(R^a)_2$O—$C^C$; and
- (t.) —C(O)CF$_3$;

each $R^a$ is independently H, $C_1$-$C_3$ alkyl, $C_1$-$C_3$ fluoroalkyl, or $C_3$-$C_6$ cycloalkyl, or alternatively two $R^a$ when bonded to a common carbon atom may together with the common carbon atom form a cyclopropyl ring;

each $R^b$ is independently:
- (i.) H;
- (ii.) $C_1$-$C_6$ alkyl, wherein said $C_1$-$C_6$ alkyl is unsubstituted or independently substituted by 1 to 3 fluoro, or hydroxyl;
- (iii.) —$(CH_2)_{n3}$CO$_2$$R^e$; or
- (iv.) —$C^C$ or —$CH_2$—$C^C$; or
alternatively, two $R^b$ together with the N atom to which they are attached form a 5- to 9-membered heterocyclyl, wherein said heterocyclyl is a saturated, partially saturated, or aromatic ring system containing 0, 1, or 2 additional heteroatoms independently selected from the group consisting of N, O, S, and S(O)$_2$; wherein said heterocyclyl is unsubstituted or substituted by 1 to 4 moieties independently selected from the group consisting of $C_1$-$C_6$ alkyl, $C_1$-$C_3$ alkoxy, fluoro, hydroxyl, oxo, cyano, amino, $C_1$-$C_3$ alkylamino, and $C_1$-$C_3$ dialkylamino;

$R^c$ is
- (i.) H;
- (ii.) $C_1$-$C_6$ alkyl, wherein said $C_1$-$C_6$ alkyl is unsubstituted or independently substituted by 1 to 3 fluoro or hydroxy; or
- (iii.) —$C^C$ or $CH_2$—$C^C$;

$R^d$ is
- (i.) $C_1$-$C_6$ alkyl, wherein said $C_1$-$C_6$ alkyl is unsubstituted or independently substituted by 1 to 3 fluoro or hydroxy;
- (ii). —C(O)N$(R^f)_2$; or
- (iii.) —$C^C$ or $CH_2$—$C^C$;

$R^e$ is H or $C_1$-$C_3$ alkyl;
$R^f$ is H or $C_1$-$C_3$ alkyl;
ring $C^H$ is
- (i.) $C_3$-$C_6$ cycloalkyl;
- (ii.) phenyl; or
- (iii.) a 4- to 9-membered mono- or bicyclic heterocyclyl, wherein said heterocyclyl is a saturated, partially saturated, or aromatic ring system containing 1 to 4 heteroatoms independently selected from the group consisting of N, O, S, and S(O)$_2$;

wherein ring $C^H$ is unsubstituted or independently substituted by 1 to 4 $C_1$-$C_6$ alkyl, $C_1$-$C_3$ alkoxy, halo, hydroxyl, oxo, cyano, amino, $C_1$-$C_3$ alkylamino, or $C_1$-$C_3$ dialkylamino;

ring $C^C$ is
(i.) $C_3$-$C_6$ cycloalkyl;
(ii.) phenyl; or
(iii.) a heterocyclyl of the formula

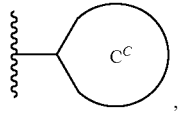

wherein said heterocyclyl is a 5- to 9-membered heterocyclyl, wherein said heterocyclyl is a saturated, partially saturated, or aromatic ring system that contains 1, 2, or 3 heteroatoms independently selected from the group consisting of N, O, S, and $S(O)_2$;
wherein ring $C^C$ is unsubstituted or independently substituted by 1 to 4 $C_1$-$C_6$ alkyl, $C_1$-$C_3$ alkoxy, halo, hydroxyl, oxo, cyano, amino, $C_1$-$C_3$ alkylamino, or $C_1$-$C_3$ dialkylamino;
the subscript n1 is 1, 2, or 3;
the subscript n2 is 0, 1, 2, or 3;
the subscript n3 is 1 or 2;

$R^4$ is
(a.) $C_1$-$C_8$ alkyl, wherein said $C_1$-$C_8$ alkyl of $R^4$ is unsubstituted or independently substituted by 1 to 6 halo, $C_1$-$C_3$ alkoxy, hydroxy, cyano, trimethylsilyl, or methylsulfonyl;
(b.) $C_2$-$C_8$ alkenyl, wherein said $C_2$-$C_8$ alkenyl of $R^4$ is unsubstituted or independently substituted by 1 to 6 fluoro or cyano; or
(c.) a group of the formula -M-$R^{CH}$;
M is
(i.) a bond; or
(ii.) $C_1$-$C_6$ alkylene, wherein said $C_1$-$C_6$ alkylene of M is unsubstituted or substituted by 1 to 6 fluoro;
$R^{CH}$ is a ring selected from the group consisting of
(i.) $C_3$-$C_9$ mono- or bicycloalkyl;
(ii.) phenyl; and
(iii.) a 3- to 6-membered heterocyclyl, wherein said heterocyclyl of $R^{CH}$ is a saturated, partially saturated or aromatic ring system containing 1 to 2 heteroatoms independently selected from the group consisting of N, O, and S;
wherein $R^{CH}$ is unsubstituted or independently substituted by 1 to 4 halo, $C_1$-$C_3$ alkyl, $C_1$-$C_3$ trifluoroalkyl, cyano, $C_1$-$C_4$ alkylcarbonylamino, or oxo;
Cy is
(a.) phenyl;
(b.) $C_3$-$C_6$ cycloalkyl; or
(c.) a 5- to 9-membered mono- or bicyclic heterocyclyl, wherein said heterocyclyl of Cy is a saturated, partially saturated, or aromatic ring system containing 1 to 3 heteroatoms independently selected from the group consisting of N, O, S and $S(O)_2$;
wherein Cy is unsubstituted or independently substituted by 1 to 4 $R^k$ moieties selected from the group consisting of:
(i.) $C_1$-$C_6$ alkyl, wherein said $C_1$-$C_6$ alkyl is unsubstituted or independently substituted by 1 to 3 hydroxy or fluoro;

(ii.) $C_1$-$C_6$ alkoxy, wherein said $C_1$-$C_6$ alkoxy is unsubstituted or independently substituted by 1 to 3 fluoro, hydroxy, amino, ($C_1$-$C_3$ alkyl)amino, di($C_1$-$C_3$ alkyl)amino, methoxy, or phenyl;
(iii.) —N($R^{e1}$)$_2$;
(iv.) —O(CH$_2$)$_{n4}$C(O)N($R^{e1}$)$_2$;
(v.) —O(CH$_2$)$_{n5}$CO$_2R^{e1}$;
(vi.) hydroxyl;
(vii.) oxo;
(viii.) halo;
(ix.) $C_1$-$C_3$ alkylsulfonyl;
(x.) cyano;
(xi.) oxetanyl; and
(xii.) cyclopropyl;
or alternatively, two $R^k$ moieties, when substituted on adjacent ring atoms of Cy, form a second ring, wherein said second ring is a 5- to 7-membered saturated, partially saturated, or aromatic ring system that contains 0, 1, or 2 heteroatoms independently selected from the group consisting of N, O, and S; wherein said second ring is unsubstituted or substituted by 1 to 3 $R^k$ moieties independently selected from (i)-(xi);
each $R^{e1}$ is independently H or $C_1$-$C_3$ alkyl;
the subscript n4 is 1, 2, or 3; and
the subscript n5 is 1, 2, or 3.

2. The compound of claim 1 or a pharmaceutically acceptable salt thereof, wherein $R^4$ is a group of the formula

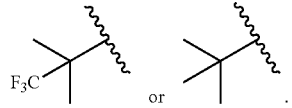

3. The compound of claim 1 or a pharmaceutically acceptable salt thereof, wherein $R^1$ is H or methyl.

4. The compound of claim 1 or a pharmaceutically acceptable salt thereof, wherein Cy is a group of the formula,

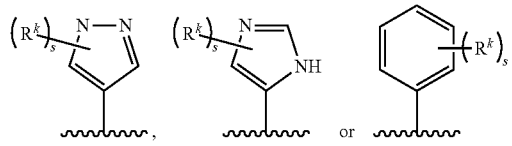

wherein the subscript s is 0, 1, 2, or 3.

5. The compound of claim 1 or a pharmaceutically acceptable salt thereof, wherein $R^3$ is a group of the formula —(C($R^a$)$_2$)$_{n1}$N(H)S(O)$_2$N($R^b$)$_2$.

6. The compound of claim 5 or a pharmaceutically acceptable salt thereof, wherein the subscript n1 is 1.

7. The compound of claim 6 or a pharmaceutically acceptable salt thereof, wherein each $R^b$ is independently:
(i.) H;
(ii.) $C_1$-$C_4$ alkyl, wherein said $C_1$-$C_4$ alkyl is unsubstituted or substituted by 1 to 3 fluoro; or
(iii.) —$C^C$; or
alternatively, two $R^b$ together with the N atom to which they are attached form a 5- to 6-membered heterocyclyl, wherein said heterocyclyl is selected from the group consisting of pyrrolidinyl, piperidinyl, and morpholinyl; wherein said heterocyclyl is unsubstituted or substituted by 1 to 2 moieties independently selected from the group consisting of $C_1$-$C_6$ alkyl, $C_1$-$C_3$ alkoxy, fluoro, hydroxyl, oxo, cyano, amino, $C_1$-$C_3$ alkylamino, and $C_1$-$C_3$ dialkylamino; and ring $C^C$ is $C_3$-$C_6$ cycloalkyl;

wherein ring $C^C$ is unsubstituted or independently substituted by 1 to 2 $C_1$-$C_6$ alkyl, $C_1$-$C_3$ alkoxy, halo, hydroxyl, oxo, cyano, amino, $C_1$-$C_3$ alkylamino, or $C_1$-$C_3$ dialkylamino.

8. The compound of claim 1 or a pharmaceutically acceptable salt thereof, wherein
$R^1$ is H or methyl;
$R^2$ is H;
$R^3$ is —$(C(R^a)_2)_{n1}N(H)S(O)_2N(R^b)_2$;
$R^4$ is a group of the formula

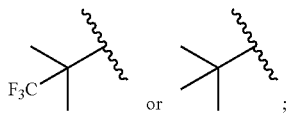

and
Cy is a group of the formula

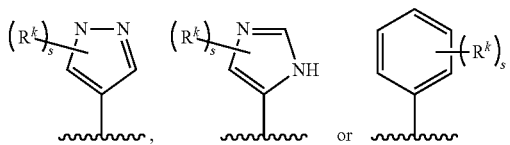

wherein the subscript s is 0, 1, 2, or 3.

9. The compound of claim 8 or a pharmaceutically acceptable salt thereof, wherein each $R^b$ is independently:
(i.) H;
(ii.) $C_1$-$C_4$ alkyl, wherein said $C_1$-$C_4$ alkyl is unsubstituted or substituted by 1 to 3 fluoro; or
(iii.) —$C^C$; or
alternatively, two $R^b$ together with the N atom to which they are attached form a 5- to 6-membered heterocyclyl, wherein said heterocyclyl is selected from the group consisting of pyrrolidinyl, piperidinyl, and morpholinyl; wherein said heterocyclyl is unsubstituted or substituted by 1 to 2 moieties independently selected from the group consisting of $C_1$-$C_6$ alkyl, $C_1$-$C_3$ alkoxy, fluoro, hydroxyl, oxo, cyano, amino, $C_1$-$C_3$ alkylamino, and $C_1$-$C_3$ dialkylamino; and
ring $C^C$ is $C_3$-$C_6$ cycloalkyl;
wherein ring $C^C$ is unsubstituted or independently substituted by 1 to 2 $C_1$-$C_6$ alkyl, $C_1$-$C_3$ alkoxy, halo, hydroxyl, oxo, cyano, amino, $C_1$-$C_3$ alkylamino, or $C_1$-$C_3$ dialkylamino.

10. A pharmaceutical composition comprising a therapeutically effective amount of a compound of claim 1 or a pharmaceutically acceptable salt thereof and a pharmaceutically acceptable carrier.

11. A method of treating a disease or condition mediated by RORgammaT comprising administering a therapeutically effective amount of a compound of claim 1 or a pharmaceutically acceptable salt thereof to a patient in need of such treatment, wherein the disease or condition is multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis, or mucosal leishmaniasis.

12. The method of claim 11, further comprising administering an additional therapeutic agent to the patient.

13. The method of claim 11, wherein the disease or condition is multiple sclerosis, inflammatory bowel disease, Crohn's disease, ankylosing spondylitis, psoriasis, rheumatoid arthritis, or asthma.

14. The method of claim 11, wherein the disease or condition is ankylosing spondylitis or psoriasis.

15. The method of claim 14, wherein the compound is a compound of claim 8.

16. A compound selected from the following, or a pharmaceutically acceptable salt thereof:

(R)-tert-butyl (2-(hydroxymethyl)-4-((3-(trifluoromethyl)phenyl)sulfonyl)-3,4-dihydro-2H-benzo[b][1,4]oxazin-6-yl)carbamate;

(R)-tert-butyl (4-((5-bromo-2-chloropyridin-3-yl)sulfonyl)-2-(hydroxymethyl)-3,4-dihydro-2H-benzo[b][1,4]oxazin-6-yl)carbamate;

(R)-4-((6-((tert-butoxycarbonyl)amino)-2-(hydroxymethyl)-2H-benzo[b][1,4]oxazin-4(3H)-yl)sulfonyl)-1-(difluoromethyl)-3-methyl-1H-pyrazol-2-e;

[(R)-4-(3-chloro-benzenesulfonyl)-2-hydroxymethyl-3,4-dihydro-2H-benzo[1,4]oxazin-6-yl]-carbamic acid tert-butyl ester;

(R)-tert-butyl (4-((5-bromopyridin-3-yl)sulfonyl)-2-(hydroxymethyl)-3,4-dihydro-2H-benzo[b][1,4]oxazin-6-yl)carbamate;

(R)-tert-butyl (2-(hydroxymethyl)-4-((1-methyl-1H-pyrazol-4-yl)sulfonyl)-3,4-dihydro-2H-benzo[b][1,4]oxazin-6-yl)carbamate;

(R)-tert-butyl (2-(hydroxymethyl)-4-((3-(methylsulfonyl)phenyl)sulfonyl)-3,4-dihydro-2H-benzo[b][1,4]oxazin-6-yl)carbamate;

(R)-tert-butyl (4-((2-chloro-5-methylpyridin-3-yl)sulfonyl)-2-(hydroxymethyl)-3,4-dihydro-2H-benzo[b][1,4]oxazin-6-yl)carbamate;

(R)-tert-butyl (4-((3-cyanophenyl)sulfonyl)-2-(hydroxymethyl)-3,4-dihydro-2H-benzo[b][1,4]oxazin-6-yl)carbamate;

(R)-tert-butyl (2-(hydroxymethyl)-4-((5-methyl-2-oxo-1,2-dihydropyridin-3-yl)sulfonyl)-3,4-dihydro-2H-benzo[b][1,4]oxazin-6-yl)carbamate;

(R)-tert-butyl (4-((4-fluorophenyl)sulfonyl)-2-(2-hydroxypropan-2-yl)-3,4-dihydro-2H-benzo[b][1,4]oxazin-6-yl)carbamate;

(S)-tert-butyl (4-((4-fluorophenyl)sulfonyl)-2-(2-hydroxypropan-2-yl)-3,4-dihydro-2H-benzo[b][1,4]oxazin-6-yl)carbamate;

(R and S)-1,1,1-trifluoro-2-methylpropan-2-yl 4-(3,4-difluorophenylsulfonyl)-2-(2,2,2-trifluoroacetyl)-3,4-dihydro-2H-benzo[b][1,4]oxazin-6-ylcarbamate;

(R and S)-1,1,1-trifluoro-2-methylpropan-2-yl (4-((3-chloro-1-ethyl-1H-pyrazol-4-yl)sulfonyl)-2-(2,2,2-trifluoroacetyl)-3,4-dihydro-2H-benzo[b][1,4]oxazin-6-yl)carbamate;

(S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(((benzyloxy)carbonyl)aminomethyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-(tetrahydro-2H-pyran-4-yl)ureido)methyl)-3,4-dihydro-2H-benzo[b][1,4]oxazin-6-yl)carbamate;

(S)-tert-butyl (2-(((benzyloxy)carbonyl)aminomethyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (2-(((benzyloxy)carbonyl)aminomethyl)-4-((4-fluorophenyl)sulfonyl)-3,4-dihydro-2H-benzo[b][1,4]oxazin-6-yl)carbamate;

(S)-tert-butyl (2-(((methoxy)carbonyl)aminomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-cyclopropylureido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-cyclobutylureido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(3-(tert-butyl)ureido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-isopropylureido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-(thiophen-3-yl)ureido)methyl)-3,4-dihydro-2H-benzo[b][1,4]oxazin-6-yl)carbamate;

(S)-1,1,1-trifluoro-2-methylpropan-2-yl (2-((3-ethylureido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-cyclohexylureido)methyl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (4-((3-chloro-4-fluorophenyl)sulfonyl)-2-((5-methyl-1,1-dioxido-1,2,5-thiadiazolidin-2-yl)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((morpholine-4-sulfonamido)methyl)-3,4-dihydro-2H-benzo[b][1,4]oxazin-6-yl)carbamate;

(S)-1,1,1-trifluoro-2-methylpropan-2-yl (2-(((N,N-diethylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(((N,N-dimethylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((piperidine-1-sulfonamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((pyrrolidine-1-sulfonamido)methyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((2-methylpiperidine-1-sulfonamido)methyl)-3,4-dihydro-2H-benzo[b][1,4]oxazin-6-yl)carbamate;

1,1,1-trifluoro-2-methylpropan-2-yl ((2S)-2-((2,6-dimethylmorpholine-4-sulfonamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((4-methylpiperidine-1-sulfonamido)methyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((2-methylmorpholine-4-sulfonamido)methyl)-3,4-dihydro-2H-benzo[b][1,4]oxazin-6-yl)carbamate;

(S)-1,1,1-trifluoro-2-methylpropan-2-yl (2-(((N-cyclopropyl-N-methylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(((N-cyclopentyl-N-methylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(((N-methyl-N-(2,2,2-trifluoroethyl)sulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((piperidine-1-sulfonamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methylpiperidine-1-sulfonamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methylmorpholine-4-sulfonamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-methyl-N-(2,2,2-trifluoroethyl) sulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-isobutyl-N-methylsulfamoyl)amino)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((3-methylpyrrolidine-1-sulfonamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-ethylsulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(((N-isopropylsulfamoyl)amino)methyl)-3,4-dihydro-2H-benzo[b][1,4]oxazin-6-yl)carbamate;

(S)-1,1,1-trifluoro-2-methylpropan-2-yl (2-(((N-ethylsulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(((N-isopropylsulfamoyl)amino)methyl)-3,4-dihydro-2H-benzo[b][1,4]oxazin-6-yl)carbamate;

(S)-1,1,1-trifluoro-2-methylpropan-2-yl (2-(((N-(tert-butyl)sulfamoyl)amino)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((3,4-difluorophenyl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((3-ethoxy-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((1-ethyl-3-methyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((3-(2,2-difluoroethoxy)-1-ethyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((1-(2,2-difluoroethyl)-3-ethoxy-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((1-(difluoromethyl)-3-methyl-1H-pyrazol-4-yl)sulfonyl)-2-(((N-methylsulfamoyl)amino)methyl)-3,4-dihydro-2H-benzo[b][1,4]oxazin-6-yl)carbamate;

(S)-1,1,1-trifluoro-2-methylpropan-2-yl (4-((2-methoxy-5,6-dihydro-4H-pyrrolo[1,2-b]pyrazol-3-yl)sulfonyl)-2-(((N-methylsulfamoyl)amino)methyl)-3,4-dihydro-2H-benzo[b][1,4]oxazin-6-yl)carbamate;

(R)-tert-butyl (2-((pyridin-2-ylthio)methyl)-4-((3-(trifluoromethyl)phenyl)sulfonyl)-3,4-dihydro-2H-benzo[b][1,4]oxazin-6-yl)carbamate;

(R)-tert-butyl (2-((cyclopentylthio)methyl)-4-((3-(trifluoromethyl)phenyl)sulfonyl)-3,4-dihydro-2H-benzo[b][1,4]oxazin-6-yl)carbamate;

(R)-tert-butyl (2-((benzylthio)methyl)-4-((3-(trifluoromethyl)phenyl)sulfonyl)-3,4-dihydro-2H-benzo[b][1,4]oxazin-6-yl)carbamate;

(R)-tert-butyl (2-((tert-butylthio)methyl)-4-((3-(trifluoromethyl)phenyl)sulfonyl)-3,4-dihydro-2H-benzo[b][1,4]oxazin-6-yl)carbamate;

(R)-tert-butyl (2-(((4,5-dimethyl-1H-imidazol-2-yl)thio)methyl)-4-((3-(trifluoromethyl)phenyl)sulfonyl)-3,4-dihydro-2H-benzo[b][1,4]oxazin-6-yl)carbamate;

(R)-tert-butyl (2-((phenyl thio)methyl)-4-((3-(trifluoromethyl)phenyl)sulfonyl)-3,4-dihydro-2H-benzo[b][1,4]oxazin-6-yl)carbamate;

(R)-tert-butyl (2-((methylthio)methyl)-4-((3-(trifluoromethyl)phenyl)sulfonyl)-3,4-dihydro-2H-benzo[b][1,4]oxazin-6-yl)carbamate;

(R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((tert-butylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-(((4,5-dimethyl-1H-imidazol-2-yl)sulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((phenylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((cyclopentylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((benzylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((methylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((pyridin-2-ylsulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((N-cyclopropylsulfamoyl)methyl)-4-((3-(trifluoromethyl)phenyl)sulfonyl)-3,4-dihydro-2H-benzo[b][1,4]oxazin-6-yl)carbamate;

(R)-tert-butyl (2-((N-(2,2,2-trifluoroethyl)sulfamoyl)methyl)-4-((3-(trifluoromethyl)phenyl)sulfonyl)-3,4-dihydro-2H-benzo[b][1,4]oxazin-6-yl)carbamate;

(R)-tert-butyl (2-((morpholinosulfonyl)methyl)-4-((3-(trifluoromethyl)phenyl)sulfonyl)-3,4-dihydro-2H-benzo[b][1,4]oxazin-6-yl)carbamate;

(R)-tert-butyl (2-((N-ethylsulfamoyl)methyl)-4-((3-(trifluoromethyl)phenyl)sulfonyl)-3,4-dihydro-2H-benzo[b][1,4]oxazin-6-yl)carbamate;

(R)-tert-butyl (2-((N,N-dimethylsulfamoyl)methyl)-4-((3-(trifluoromethyl)phenyl)sulfonyl)-3,4-dihydro-2H-benzo[b][1,4]oxazin-6-yl)carbamate;

1,1,1-trifluoro-2-methylpropan-2-yl (S)-(4-((3-ethoxy-1-ethyl-1H-pyrazol-4-yl)sulfonyl)-2-methyl-3,4-dihydro-2H-benzo[b][1,4]oxazin-6-yl)carbamate;

[(2S,3S and 2R,3R)-4-(3-cyano-benzenesulfonyl)-2-hydroxymethyl-3-methyl-3,4-dihydro-2H-benzo[1,4]oxazin-6-yl]-carbamic acid 2,2-dimethyl-propyl ester;

(S)-1,1,1-trifluoro-2-methylpropan-2-yl (4-((4-fluorophenyl)sulfonyl)-3-methyl-3,4-dihydro-2H-benzo[b][1,4]oxazin-6-yl)carbamate;

(R)-1,1,1-trifluoro-2-methylpropan-2-yl (4-((4-fluorophenyl)sulfonyl)-3-methyl-3,4-dihydro-2H-benzo[b][1,4]oxazin-6-yl)carbamate;

(R)-1,1,1-trifluoro-2-methylpropan-2-yl (4-((4-fluorophenyl)sulfonyl)-3-(hydroxymethyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-3-(hydroxymethyl)-3,4-dihydro-2H-benzo[b][1,4]oxazin-6-yl)carbamate;

[(S)-4-(3-cyano-benzenesulfonyl)-2-(2,4-dioxo-oxazolidin-3-ylmethyl)-3,4-dihydro-2H-benzo[1,4]oxazin-6-yl]-carbamic acid tert-butyl ester;

(1S,2R,4R)-bicyclo[2.2.1]heptan-2-yl ((S)-4-((3-cyanophenyl)sulfonyl)-2-((2,4-dioxooxazolidin-3-yl)methyl)-3,4-dihydro-2H-benzo[b][1,4]oxazin-6-yl)carbamate;

(S)-neopentyl (4-((3-cyanophenyl)sulfonyl)-2-((2,4-dioxooxazolidin-3-yl)methyl)-3,4-dihydro-2H-benzo[b][1,4]oxazin-6-yl)carbamate;

(1S,4R)-bicyclo[2.2.1]heptan-2-yl ((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

(S)-tert-butyl (2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

(S)-neopentyl (2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

(tetrahydro-2H-pyran-2-yl)methyl ((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

(2S)-bicyclo[2.2.1]heptan-2-yl ((S)-4-((3-cyanophenyl)sulfonyl)-2-((2,4-dioxooxazolidin-3-yl)methyl)-3,4-dihydro-2H-benzo[b][1,4]oxazin-6-yl)carbamate;

(2S)-bicyclo[2.2.1]heptan-2-yl ((S)-2-((2,4-dioxooxazolidin-3-yl)methyl)-4-((1-methyl-1H-pyrazol-4-yl)sulfonyl)-3,4-dihydro-2H-benzo[b][1,4]oxazin-6-yl)carbamate;

[(S)-4-(3-cyano-benzenesulfonyl)-2-dimethylaminomethyl-3,4-dihydro-2H-benzo[1,4]oxazin-6-yl]-carbamic acid tert-butyl ester;

[(S)-4-(3-cyano-benzenesulfonyl)-2-dimethylaminomethyl-3,4-dihydro-2H-benzo[1,4]oxazin-6-yl]-carbamic acid 2,2-dimethyl-propyl ester;

(1S,4R)-bicyclo[2.2.1]heptan-2-yl ((S)-4-((3-cyanophenyl)sulfonyl)-2-((dimethylamino)methyl)-3,4-dihydro-2H-benzo[b][1,4]oxazin-6-yl)carbamate;

(1S,2R,4R)-bicyclo[2.2.1]heptan-2-yl ((S)-4-((3-cyanophenyl)sulfonyl)-2-((dimethylamino)methyl)-3,4-dihydro-2H-benzo[b][1,4]oxazin-6-yl)carbamate;

(S)-neopentyl (2-((dimethylamino)methyl)-4-((1-methyl-1H-pyrazol-4-yl)sulfonyl)-3,4-dihydro-2H-benzo[b][1,4]oxazin-6-yl)carbamate;

bicyclo[2.2.1]heptan-2-yl ((S)-2-((dimethylamino)methyl)-4-((1-methyl-1H-pyrazol-4-yl)sulfonyl)-3,4-dihydro-2H-benzo[b][1,4]oxazin-6-yl)carbamate;

(2S)-bicyclo[2.2.1]heptan-2-yl ((S)-2-((dimethylamino)methyl)-4-((1-methyl-1H-pyrazol-4-yl)sulfonyl)-3,4-dihydro-2H-benzo[b][1,4]oxazin-6-yl)carbamate;

(S)-tetrahydro-2H-pyran-4-yl (4-((3-cyanophenyl)sulfonyl)-2-((dimethylamino)methyl)-3,4-dihydro-2H-benzo[b][1,4]oxazin-6-yl)carbamate;

(S)-methyl 2-(6-((tert-butoxycarbonyl)amino)-4-((3-(trifluoromethyl)phenyl)sulfonyl)-3,4-dihydro-2H-benzo[b][1,4]oxazin-2-yl)acetate;

(S)-methyl 2-(6-((tert-butoxycarbonyl)amino)-4-((3-chloro-4-fluorophenyl)sulfonyl)-3,4-dihydro-2H-benzo[b][1,4]oxazin-2-yl)acetate;

(S)-methyl 2-(6-((tert-butoxycarbonyl)amino)-4-((4-fluoro-3-(trifluoromethyl)phenyl)sulfonyl)-3,4-dihydro-2H-benzo[b][1,4]oxazin-2-yl)acetate;

(S)-methyl 2-(6-((tert-butoxycarbonyl)amino)-4-((4-fluoro-3-methoxyphenyl)sulfonyl)-3,4-dihydro-2H-benzo[b][1,4]oxazin-2-yl)acetate;

(R)-methyl 2-(6-((tert-butoxycarbonyl)amino)-4-((3-(trifluoromethyl)phenyl)sulfonyl)-3,4-dihydro-2H-benzo[b][1,4]oxazin-2-yl)acetate;

(S)-methyl 2-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)acetate;

[(S)-6-tert-butoxycarbonylamino-4-(1-difluoromethyl-3-methyl-1H-pyrazole-4-sulfonyl)-3,4-dihydro-2H-benzo[1,4]oxazin-2-yl]-acetic acid;

(S)-2-(6-((tert-butoxycarbonyl)amino)-4-((4-fluoro-3-methoxyphenyl)sulfonyl)-3,4-dihydro-2H-benzo[b][1,4]oxazin-2-yl)acetic acid;

(S)-2-(6-((tert-butoxycarbonyl)amino)-4-((4-fluoro-3-(trifluoromethyl)phenyl)sulfonyl)-3,4-dihydro-2H-benzo[b][1,4]oxazin-2-yl)acetic acid;

(S)-2-(6-((tert-butoxycarbonyl)amino)-4-((3-chloro-4-fluorophenyl)sulfonyl)-3,4-dihydro-2H-benzo[b][1,4]oxazin-2-yl)acetic acid;

(S)-2-(6-((tert-butoxycarbonyl)amino)-4-((3-(trifluoromethyl)phenyl)sulfonyl)-3,4-dihydro-2H-benzo[b][1,4]oxazin-2-yl)acetic acid;

(S)-2-(6-((tert-butoxycarbonyl)amino)-4-((4-fluorophenyl)sulfonyl)-3,4-dihydro-2H-benzo[b][1,4]oxazin-2-yl)acetic acid;

(S)-2-(4-((4-fluorophenyl)sulfonyl)-6-(((neopentyloxy)carbonyl)amino)-3,4-dihydro-2H-benzo[b][1,4]oxazin-2-yl)acetic acid;

(S)-2-(6-((tert-butoxycarbonyl)amino)-4-((3-chlorophenyl)sulfonyl)-3,4-dihydro-2H-benzo[b][1,4]oxazin-2-yl)acetic acid;

(S)-2-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)acetic acid;

(R)-6-((tert-butoxycarbonyl)amino)-4-((3-chloro-4-fluorophenyl)sulfonyl)-3,4-dihydro-2H-benzo[b][1,4]oxazine-2-carboxylic acid;

(R)-6-((tert-butoxycarbonyl)amino)-4-((4-fluorophenyl)sulfonyl)-3,4-dihydro-2H-benzo[b][1,4]oxazine-2-carboxylic acid;

(R)-6-((tert-butoxycarbonyl)amino)-4-((4-fluoro-3-methoxyphenyl)sulfonyl)-3,4-dihydro-2H-benzo[b][1,4]oxazine-2-carboxylic acid;

(R)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazine-2-carboxylic acid;

(R)-6-((tert-butoxycarbonyl)amino)-4-((1-(difluoromethyl)-3-methyl-1H-pyrazol-4-yl)sulfonyl)-3,4-dihydro-2H-benzo[b][1,4]oxazine-2-carboxylic acid;

(R)-6-((tert-butoxycarbonyl)amino)-4-((4-fluoro-3-(trifluoromethyl)phenyl)sulfonyl)-3,4-dihydro-2H-benzo[b][1,4]oxazine-2-carboxylic acid;

[(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid tert-butyl ester;

[(S)-2-(2-azetidin-1-yl-2-oxo-ethyl)-4-(1-difluoromethyl-3-methyl-1H-pyrazole-4-sulfonyl)-3,4-dihydro-2H-benzo[1,4]oxazin-6-yl]-carbamic acid 1,2,2-trimethyl-propyl ester;

(S)-tert-butyl (2-(2-amino-2-oxoethyl)-4-((4-fluorophenyl)sulfonyl)-3,4-dihydro-2H-benzo[b][1,4]oxazin-6-yl)carbamate;

(S)-tert-butyl (2-(2-amino-2-oxoethyl)-4-((3-(trifluoromethyl)phenyl)sulfonyl)-3,4-dihydro-2H-benzo[b][1,4]oxazin-6-yl)carbamate;

(S)-tert-butyl (4-((4-fluorophenyl)sulfonyl)-2-(2-(methylamino)-2-oxoethyl)-3,4-dihydro-2H-benzo[b][1,4]oxazin-6-yl)carbamate;

(S)-tert-butyl (2-(2-(methylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(dimethylamino)-2-oxoethyl)-4-((3-(trifluoromethyl)phenyl)sulfonyl)-3,4-dihydro-2H-benzo[b][1,4]oxazin-6-yl)carbamate;

tert-butyl (2-(2-(dimethylamino)-2-oxoethyl)-4-((4-fluorophenyl)sulfonyl)-3,4-dihydro-2H-benzo[b][1,4]oxazin-6-yl)carbamate;

(R)-tert-butyl (4-((3-chloro-4-fluorophenyl)sulfonyl)-2-(2-(methylamino)-2-oxoethyl)-3,4-dihydro-2H-benzo[b][1,4]oxazin-6-yl)carbamate;

(S)-tert-butyl (4-((3-chloro-4-fluorophenyl)sulfonyl)-2-(2-(methylamino)-2-oxoethyl)-3,4-dihydro-2H-benzo[b][1,4]oxazin-6-yl)carbamate;

1,1,1-trifluoro-2-methylpropan-2-yl (4-((3-chloro-4-fluorophenyl)sulfonyl)-2-(2-(methylamino)-2-oxoethyl)-3,4-dihydro-2H-benzo[b][1,4]oxazin-6-yl)carbamate;

(R)-tert-butyl (2-(2-(oxazolidin-3-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-((cyclobutylmethyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-((3,3,3-trifluoropropyl)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(isobutylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-methyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-isopropyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-((pyrazolo[1,5-a]pyridin-3-ylmethyl)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-ethyl-1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(1-methylpyrrolo[3,4-c]pyrazol-5(1H,4H,6H)-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-methyl-1H-pyrazol-3-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-ethyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1-ethyl-5-methyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((1,5-dimethyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate (S)-tert-butyl (2-(2-(((1-benzyl-1H-pyrazol-4-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-3-(2-(6-((tert-butoxycarbonyl)amino)-4-((3-(trifluoromethyl)phenyl)sulfonyl)-3,4-dihydro-2H-benzo[b][1,4]oxazin-2-yl)acetamido)propanoic acid (S)-methyl 3-(2-(6-((tert-butoxycarbonyl)amino)-4-((3-(trifluoromethyl)phenyl)sulfonyl)-3,4-dihydro-2H-benzo[b][1,4]oxazin-2-yl)acetamido)propanoate;

(S)-tert-butyl (2-(2-oxo-2-((4-(trifluoromethyl)benzyl)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(benzylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-((cyclopropylmethyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(propylamino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(ethylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(oxazolidin-3-yl)-2-oxoethyl)-4-((3-(trifluoromethyl)phenyl)sulfonyl)-3,4-dihydro-2H-benzo[b][1,4]oxazin-6-yl)carbamate;

(S)-neopentyl (2-(2-(methylamino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(((2H-tetrazol-5-yl)methyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-((2-hydroxyethyl)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(tert-butylamino)-2-oxoethyl)-4-((3-(trifluoromethyl)phenyl)sulfonyl)-3,4-dihydro-2H-benzo[b][1,4]oxazin-6-yl)carbamate;

tert-butyl ((2S)-2-(2-(2-methylazetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(3-cyanoazetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(3-methoxyazetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(azetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(azetidin-1-yl)-2-oxoethyl)-4-((4-fluorophenyl)sulfonyl)-3,4-dihydro-2H-benzo[b][1,4]oxazin-6-yl)carbamate;

(S)-tert-butyl (2-(2-(3-methylazetidin-1-yl)-2-oxoethyl)-4-((3-(trifluoromethyl)phenyl)sulfonyl)-3,4-dihydro-2H-benzo[b][1,4]oxazin-6-yl)carbamate;

(S)-neopentyl (2-(2-(azetidin-1-yl)-2-oxoethyl)-4-((1-(difluoromethyl)-3-methyl-1H-pyrazol-4-yl)sulfonyl)-3,4-dihydro-2H-benzo[b][1,4]oxazin-6-yl)carbamate;

(R)-tert-butyl (2-carbamoyl-4-((4-fluoro-3-(trifluoromethyl)phenyl)sulfonyl)-3,4-dihydro-2H-benzo[b][1,4]oxazin-6-yl)carbamate;

(R)-1,1,1-trifluoro-2-methylpropan-2-yl (2-carbamoyl-4-((4-fluoro-3-(trifluoromethyl)phenyl)sulfonyl)-3,4-dihydro-2H-benzo[b][1,4]oxazin-6-yl)carbamate;

(R)-tert-butyl (2-carbamoyl-4-((4-fluoro-3-methoxyphenyl)sulfonyl)-3,4-dihydro-2H-benzo[b][1,4]oxazin-6-yl)carbamate;

(R)-methyl 3-(6-((tert-butoxycarbonyl)amino)-4-((3-chloro-4-fluorophenyl)sulfonyl)-3,4-dihydro-2H-benzo[b][1,4]oxazine-2-carboxamido)propanoate;

(R)-tert-butyl (2-carbamoyl-4-((1-(difluoromethyl)-3-methyl-1H-pyrazol-4-yl)sulfonyl)-3,4-dihydro-2H-benzo[b][1,4]oxazin-6-yl)carbamate;

(R)-tert-butyl (4-((1-(difluoromethyl)-3-methyl-1H-pyrazol-4-yl)sulfonyl)-2-(dimethylcarbamoyl)-3,4-dihydro-2H-benzo[b][1,4]oxazin-6-yl)carbamate;

(R)-3-(6-((tert-butoxycarbonyl)amino)-4-((3-chloro-4-fluorophenyl)sulfonyl)-3,4-dihydro-2H-benzo[b][1,4]oxazine-2-carboxamido)propanoic acid;

tert-butyl (2-(2-cyanopropan-2-yl)-4-((4-fluorophenyl)sulfonyl)-3,4-dihydro-2H-benzo[b][1,4]oxazin-6-yl)carbamate;

(R and S) 2-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R and S)-1,1,1-trifluoro-2-methylpropan-2-yl (4-((4-fluorophenyl)sulfonyl)-2-(2-(4-methyl-5-oxo-4,5-dihydro-1H-1,2,4-triazol-3-yl)propan-2-yl)-3,4-dihydro-2H-benzo[b][1,4]oxazin-6-yl)carbamate;

(S)-tert-butyl (2-(2-oxo-2-(trifluoromethylsulfonamido)ethyl)-4-((3-(trifluoromethyl)phenyl)sulfonyl)-3,4-dihydro-2H-benzo[b][1,4]oxazin-6-yl)carbamate;

(S)-neopentyl (2-(2-(cyclopropanesulfonamido)-2-oxoethyl)-4-((3-(trifluoromethyl)phenyl)sulfonyl)-3,4-dihydro-2H-benzo[b][1,4]oxazin-6-yl)carbamate;

(S)-neopentyl (4-(((1-(difluoromethyl)-3-methyl-1H-pyrazol-4-yl)sulfonyl)-2-(2-oxo-2-(trifluoromethylsulfonamido)ethyl)-3,4-dihydro-2H-benzo[b][1,4]oxazin-6-yl)carbamate;

(S)-tert-butyl (2-(2-oxo-2-(thiazole-2-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(pyridine-4-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(1,1-dimethylethylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(5-(trifluoromethyl)pyridine-2-sulfonamido)ethyl)-4-((3-(trifluoromethyl)phenyl)sulfonyl)-3,4-dihydro-2H-benzo[b][1,4]oxazin-6-yl)carbamate;

(S)-neopentyl (4-((4-fluorophenyl)sulfonyl)-2-(2-oxo-2-(trifluoromethylsulfonamido)ethyl)-3,4-dihydro-2H-benzo[b][1,4]oxazin-6-yl)carbamate;

(S)-tert-butyl (2-(2-oxo-2-(pyridine-2-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(pyridine-3-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(4-(trifluoromethyl)pyridine-2-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(1H-pyrazole-4-sulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(4-methylpyridine-2-sulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(2-fluoro-5-methylphenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(2-fluorophenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(2-(trifluoromethyl)phenylsulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(3-(trifluoromethyl)phenylsulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(3-fluorophenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(cyclopropanesulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(4-methylphenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(1-methylethylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(ethylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(methylsulfonamido)-2-oxoethyl)-4-((3-(trifluoromethyl)phenyl)sulfonyl)-3,4-dihydro-2H-benzo[b][1,4]oxazin-6-yl)carbamate;

(S)-neopentyl (2-(2-(cyclopropanesulfonamido)-2-oxoethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-(2-(cyclopentanesulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(2-methylphenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(4-fluorophenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-(2,5-dimethylphenylsulfonamido)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(4-propylphenylsulfonamido)ethyl)-4-((3-(trifluoromethyl)phenyl)sulfonyl)-3,4-dihydro-2H-benzo[b][1,4]oxazin-6-yl)carbamate;

(S)-tert-butyl (2-(2-(6-methylpyridine-2-sulfonamido)-2-oxoethyl)-4-((3-(trifluoromethyl)phenyl)sulfonyl)-3,4-dihydro-2H-benzo[b][1,4]oxazin-6-yl)carbamate;

(S)-neopentyl (2-(2-(cyclopropanesulfonamido)-2-oxoethyl)-4-((4-fluorophenyl)sulfonyl)-3,4-dihydro-2H-benzo[b][1,4]oxazin-6-yl)carbamate;

(S)-(2-(2-(methoxyamino)-2-oxoethyl)-4-((3-(trifluoromethyl)phenyl)sulfonyl)-3,4-dihydro-2H-benzo[b][1,4]oxazin-6-yl)carbamic acid;

(S)-tert-butyl (2-(2-oxo-2-((2-(trifluoromethyl)phenoxy)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-((pyridin-3-ylmethoxy)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(((4-(trifluoromethyl)benzyl)oxy)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-oxo-2-(((3-(trifluoromethyl)benzyl)oxy)amino)ethyl)-4-((3-(trifluoromethyl)phenyl)sulfonyl)-3,4-dihydro-2H-benzo[b][1,4]oxazin-6-yl)carbamate;

(S)-tert-butyl (2-(2-((4-fluorophenoxy)amino)-2-oxoethyl)-4-((3-(trifluoromethyl)phenyl)sulfonyl)-3,4-dihydro-2H-benzo[b][1,4]oxazin-6-yl)carbamate;

(S)-tert-butyl (2-(2-((cyclopentyloxy)amino)-2-oxo-ethyl)-4-((3-(trifluoromethyl)phenyl)sulfonyl)-3,4-dihydro-2H-benzo[b][1,4]oxazin-6-yl)carbamate;
(S)-tert-butyl (2-(2-(ethoxyamino)-2-oxoethyl)-4-((3-(trifluoromethyl)phenyl)sulfonyl)-3,4-dihydro-2H-benzo[b][1,4]oxazin-6-yl)carbamate;
(S)-tert-butyl (2-(2-((benzyloxy)amino)-2-oxoethyl)-4-((3-(trifluoromethyl)phenyl)sulfonyl)-3,4-dihydro-2H-benzo[b][1,4]oxazin-6-yl)carbamate;
(S)-tert-butyl (2-(2-(((4-methylbenzyl)oxy)amino)-2-oxoethyl)-4-((3-(trifluoromethyl)phenyl)sulfonyl)-3,4-dihydro-2H-benzo[b][1,4]oxazin-6-yl)carbamate;
(S)-tert-butyl (2-(2-(isopropoxyamino)-2-oxoethyl)-4-((3-(trifluoromethyl)phenyl)sulfonyl)-3,4-dihydro-2H-benzo[b][1,4]oxazin-6-yl)carbamate;
(S)-tert-butyl (2-(2-oxo-2-(propoxyamino)ethyl)-4-((3-(trifluoromethyl)phenyl)sulfonyl)-3,4-dihydro-2H-benzo[b][1,4]oxazin-6-yl)carbamate;
(R)-tert-butyl (4-((4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate;
(R)-1,1,1-trifluoro-2-methylpropan-2-yl (4-((4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate;
(R)-tert-butyl (4-((1-(difluoromethyl)-3-methyl-1H-pyrazol-4-yl)sulfonyl)-2-(5-oxo-4,5-dihydro-1,3,4-oxadiazol-2-yl)-3,4-dihydro-2H-benzo[b][1,4]oxazin-6-yl)carbamate;
(R)-1,1,1-trifluoro-2-methylpropan-2-yl (4-((1-(difluoromethyl)-3-methyl-1H-pyrazol-4-yl)sulfonyl)-2-(5-oxo-4,5-dihydro-1,3,4-oxadiazol-2-yl)-3,4-dihydro-2H-benzo[b][1,4]oxazin-6-yl)carbamate;
(R)-tert-butyl (4-((3-chloro-4-fluorophenyl)sulfonyl)-2-(5-oxo-4,5-dihydro-1,3,4-oxadiazol-2-yl)-3,4-dihydro-2H-benzo[b][1,4]oxazin-6-yl)carbamate;
(R)-tert-butyl (4-((4-fluoro-3-(trifluoromethyl)phenyl)sulfonyl)-2-(5-oxo-4,5-dihydro-1,3,4-oxadiazol-2-yl)-3,4-dihydro-2H-benzo[b][1,4]oxazin-6-yl)carbamate;
(S)-tert-butyl (4-((4-fluorophenyl)sulfonyl)-2-((4-methyl-5-oxo-4,5-dihydro-1,3,4-oxadiazol-2-yl)methyl)-3,4-dihydro-2H-benzo[b][1,4]oxazin-6-yl)carbamate;
(S)-tert-butyl (4-((1-(difluoromethyl)-3-methyl-1H-pyrazol-4-yl)sulfonyl)-2-((4-methyl-5-oxo-4,5-dihydro-1,3,4-oxadiazol-2-yl)methyl)-3,4-dihydro-2H-benzo[b][1,4]oxazin-6-yl)carbamate;
(S)-tert-butyl (2-((4-methyl-5-oxo-4,5-dihydro-1,3,4-oxadiazol-2-yl)methyl)-4-((3-(trifluoromethyl)phenyl)sulfonyl)-3,4-dihydro-2H-benzo[b][1,4]oxazin-6-yl)carbamate;
(R)-tert-butyl (4-((4-fluorophenyl)sulfonyl)-2-(4-methyl-5-oxo-4,5-dihydro-1H-1,2,4-triazol-3-yl)-3,4-dihydro-2H-benzo[b][1,4]oxazin-6-yl)carbamate;
tert-butyl (2-(cyanomethyl)-4-((3-(trifluoromethyl)phenyl)sulfonyl)-3,4-dihydro-2H-benzo[b][1,4]oxazin-6-yl)carbamate;
tert-butyl (2-(2-hydroxypropyl)-4-((3-(trifluoromethyl)phenyl)sulfonyl)-3,4-dihydro-2H-benzo[b][1,4]oxazin-6-yl)carbamate;
(S)-tert-butyl (2-(2-amino-2-methylpropyl)-4-((3-(trifluoromethyl)phenyl) sulfonyl)-3,4-dihydro-2H-benzo[b][1,4]oxazin-6-yl)carbamate;
(S)-tert-butyl (2-(2-acetamido-2-methylpropyl)-4-((3-(trifluoromethyl)phenyl)sulfonyl)-3,4-dihydro-2H-benzo[b][1,4]oxazin-6-yl)carbamate;

(S)-tert-butyl (2-(2-propionamidoethyl)-4-((3-(trifluoromethyl)phenyl)sulfonyl)-3,4-dihydro-2H-benzo[b][1,4]oxazin-6-yl)carbamate;
tert-butyl ((2S)-2-(2-(2-hydroxypropanamido)ethyl)-4-((3-(trifluoromethyl)phenyl)sulfonyl)-3,4-dihydro-2H-benzo[b][1,4]oxazin-6-yl)carbamate;
(S)-tert-butyl (2-(2-(oxetane-3-carboxamido)ethyl)-4-((3-(trifluoromethyl)phenyl)sulfonyl)-3,4-dihydro-2H-benzo[b][1,4]oxazin-6-yl)carbamate;
(S)-tert-butyl (2-(2-isobutyramidoethyl)-4-((3-(trifluoromethyl)phenyl)sulfonyl)-3,4-dihydro-2H-benzo[b][1,4]oxazin-6-yl)carbamate;
(S)-tert-butyl (2-(2-acetamidoethyl)-4-((3-(trifluoromethyl)phenyl)sulfonyl)-3,4-dihydro-2H-benzo[b][1,4]oxazin-6-yl)carbamate;
(S)-tert-butyl (2-(2-(cyclopropanecarboxamido)ethyl)-4-((3-(trifluoromethyl)phenyl)sulfonyl)-3,4-dihydro-2H-benzo[b][1,4]oxazin-6-yl)carbamate;
(S)-tert-butyl (4-((4-fluorophenyl)sulfonyl)-2-(2-propionamidoethyl)-3,4-dihydro-2H-benzo[b][1,4]oxazin-6-yl)carbamate;
(S)-tert-butyl (2-(2-acetamidoethyl)-4-((4-fluorophenyl)sulfonyl)-3,4-dihydro-2H-benzo[b][1,4]oxazin-6-yl)carbamate;
tert-butyl ((2S)-4-((4-fluorophenyl)sulfonyl)-2-(2-(2-hydroxypropanamido)ethyl)-3,4-dihydro-2H-benzo[b][1,4]oxazin-6-yl)carbamate;
(S)-tert-butyl (2-(2-(cyclopropanecarboxamido)ethyl)-4-((4-fluorophenyl)sulfonyl)-3,4-dihydro-2H-benzo[b][1,4]oxazin-6-yl)carbamate;
(S)-neopentyl (4-((4-fluorophenyl)sulfonyl)-2-(2-propionamidoethyl)-3,4-dihydro-2H-benzo[b][1,4]oxazin-6-yl)carbamate;
(S)-neopentyl (2-(2-acetamidoethyl)-4-((4-fluorophenyl)sulfonyl)-3,4-dihydro-2H-benzo[b][1,4]oxazin-6-yl)carbamate;
(S)-neopentyl (2-(2-(cyclopropanecarboxamido)ethyl)-4-((4-fluorophenyl)sulfonyl)-3,4-dihydro-2H-benzo[b][1,4]oxazin-6-yl)carbamate;
(S)-1,1,1-trifluoro-2-methylpropan-2-yl (2-(2-amino-2-methylpropyl)-4-((3-chloro-4-fluorophenyl)sulfonyl)-3,4-dihydro-2H-benzo[b][1,4]oxazin-6-yl)carbamate;
(S)-1,1,1-trifluoro-2-methylpropan-2-yl (2-(2-amino-2-methylpropyl)-4-((3-(trifluoromethyl)phenyl)sulfonyl)-3,4-dihydro-2H-benzo[b][1,4]oxazin-6-yl)carbamate;
(R)-1,1,1-trifluoro-2-methylpropan-2-yl (2-(2-(2-oxopyrrolidin-1-yl)ethyl)-4-((3-(trifluoromethyl)phenyl)sulfonyl)-3,4-dihydro-2H-benzo[b][1,4]oxazin-6-yl)carbamate;
(S)-1,1,1-trifluoro-2-methylpropan-2-yl (2-(2-(2-oxopyrrolidin-1-yl)ethyl)-4-((3-(trifluoromethyl)phenyl)sulfonyl)-3,4-dihydro-2H-benzo[b][1,4]oxazin-6-yl)carbamate;
(S)-tert-butyl (2-(2-acetamido-2-methylpropyl)-4-((3-chloro-4-fluorophenyl)sulfonyl)-3,4-dihydro-2H-benzo[b][1,4]oxazin-6-yl)carbamate;
(S)-tert-butyl (2-(2-acetamido-2-methylpropyl)-4-((3,4-difluorophenyl)sulfonyl)-3,4-dihydro-2H-benzo[b][1,4]oxazin-6-yl)carbamate;
(S)-tert-butyl (2-(2-acetamido-2-methylpropyl)-4-((1-(difluoromethyl)-3-methyl-1H-pyrazol-4-yl)sulfonyl)-3,4-dihydro-2H-benzo[b][1,4]oxazin-6-yl)carbamate;
(S)-tert-butyl (2-(2-acetamido-2-methylpropyl)-4-((1-(difluoromethyl)-5-methyl-1H-pyrazol-4-yl)sulfonyl)-3,4-dihydro-2H-benzo[b][1,4]oxazin-6-yl)carbamate;

(S)-tert-butyl (2-(2-acetamido-2-methylpropyl)-4-((4-fluorophenyl)sulfonyl)-3,4-dihydro-2H-benzo[b][1,4]oxazin-6-yl)carbamate;

(R)-tert-butyl (2-(2-acetamido-2-methylpropyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((1-(difluoromethyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(2-methyl-2-(methylsulfonamido)propyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3,4-difluorophenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(2-methyl-2-(methylsulfonamido)propyl)-3,4-dihydro-2H-benzo[b][1,4]oxazin-6-yl)carbamate;

(S)-1,1,1-trifluoro-2-methylpropan-2-yl (4-((3,4-difluorophenyl)sulfonyl)-2-(2-methyl-2-(methylsulfonamido)propyl)-3,4-dihydro-2H-benzo[b][1,4]oxazin-6-yl)carbamate;

(S)-1,1,1-trifluoro-2-methylpropan-2-yl (2-(2-(cyclopropanesulfonamido)-2-methylpropyl)-4-((3,4-difluorophenyl)sulfonyl)-3,4-dihydro-2H-benzo[b][1,4]oxazin-6-yl)carbamate;

(S)-1,1,1-trifluoro-2-methylpropan-2-yl (2-(2-methyl-2-(methylsulfonamido)propyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-(cyclopropanesulfonamido)-2-methylpropyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(2-methyl-2-(methylsulfonamido)propyl)-3,4-dihydro-2H-benzo[b][1,4]oxazin-6-yl)carbamate;

(S)-1,1,1-trifluoro-2-methylpropan-2-yl (2-(2-(cyclopropanesulfonamido)-2-methylpropyl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (2-(2-(cyclopropanesulfonamido)-2-methylpropyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-methyl-2-(trifluoromethylsulfonamido)propyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-(2-(dimethylamino)-2-oxoacetamido)-2-methylpropyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((4-fluoro-3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-methoxy-1,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((1-(difluoromethyl)-3-ethoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(2-acetamido-2-methylpropyl)-4-((3-(difluoromethoxy)-1-ethyl-1H-pyrazol-4-yl)sulfonyl)-3,4-dihydro-2H-benzo[b][1,4]oxazin-6-yl)carbamate;

tert-butyl (2-(2-hydroxyethyl)-4-((3-(trifluoromethyl)phenyl)sulfonyl)-3,4-dihydro-2H-benzo[b][1,4]oxazin-6-yl)carbamate;

tert-butyl (2-((1H-imidazol-2-yl)methyl)-4-((3-(trifluoromethyl)phenyl)sulfonyl)-3,4-dihydro-2H-benzo[b][1,4]oxazin-6-yl)carbamate;

tert-butyl (2-((1-methyl-1H-imidazol-2-yl)methyl)-4-((3-(trifluoromethyl)phenyl)sulfonyl)-3,4-dihydro-2H-benzo[b][1,4]oxazin-6-yl)carbamate;

(S)-tert-butyl (4-((4-fluorophenyl)sulfonyl)-2-((2-oxopyrrolidin-1-yl)methyl)-3,4-dihydro-2H-benzo[b][1,4]oxazin-6-yl)carbamate;

(S)-tert-butyl (2-((1H-pyrazol-1-yl)methyl)-4-((3-(trifluoromethyl)phenyl)sulfonyl)-3,4-dihydro-2H-benzo[b][1,4]oxazin-6-yl)carbamate;

(S)-tert-butyl (2-((2H-1,2,3-triazol-2-yl)methyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-((4H-1,2,4-triazol-4-yl)methyl)-4-((3-(trifluoromethyl)phenyl)sulfonyl)-3,4-dihydro-2H-benzo[b][1,4]oxazin-6-yl)carbamate;

(S)-tert-butyl (2-((1H-1,2,4-triazol-1-yl)methyl)-4-((3-(trifluoromethyl)phenyl)sulfonyl)-3,4-dihydro-2H-benzo[b][1,4]oxazin-6-yl)carbamate;

(S)-tert-butyl (2-((1H-1,2,3-triazol-1-yl)methyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-((1H-1,2,3-triazol-1-yl)methyl)-4-((3-(trifluoromethyl)phenyl)sulfonyl)-3,4-dihydro-2H-benzo[b][1,4]oxazin-6-yl)carbamate;

(S)-tert-butyl (2-((2H-1,2,3-triazol-2-yl)methyl)-4-((3-(trifluoromethyl)phenyl)sulfonyl)-3,4-dihydro-2H-benzo[b][1,4]oxazin-6-yl)carbamate;

(R)-tert-butyl (2-((pyridin-2-yloxy)methyl)-4-((3-(trifluoromethyl)phenyl)sulfonyl)-3,4-dihydro-2H-benzo[b][1,4]oxazin-6-yl)carbamate;

(S)-tert-butyl (2-((2-oxopyridin-1(2H)-yl)methyl)-4-((3-(trifluoromethyl)phenyl)sulfonyl)-3,4-dihydro-2H-benzo[b][1,4]oxazin-6-yl)carbamate;

(S)-tert-butyl (2-((5-oxo-2,5-dihydro-1,2,4-oxadiazol-3-yl)methyl)-4-((3-(trifluoromethyl)phenyl)sulfonyl)-3,4-dihydro-2H-benzo[b][1,4]oxazin-6-yl)carbamate;

tert-butyl (2-(2-hydroxy-2-methylpropyl)-4-((3-(trifluoromethyl)phenyl)sulfonyl)-3,4-dihydro-2H-benzo[b][1,4]oxazin-6-yl)carbamate;

(S)-tert-butyl (2-((3-hydroxyazetidin-1-yl)methyl)-4-((3-(trifluoromethyl)phenyl)sulfonyl)-3,4-dihydro-2H-benzo[b][1,4]oxazin-6-yl)carbamate;

(S)-tert-butyl (2-(((3-methyloxetan-3-yl)amino)methyl)-4-((3-(trifluoromethyl)phenyl)sulfonyl)-3,4-dihydro-2H-benzo[b][1,4]oxazin-6-yl)carbamate;

tert-butyl ((2S)-4-((3-(trifluoromethyl)phenyl)sulfonyl)-2-(((1,1,1-trifluoropropan-2-yl)amino)methyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((2-methylazetidin-1-yl)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-hydroxyazetidin-1-yl)methyl)-3,4-dihydro-2H-benzo[b][1,4]oxazin-6-yl)carbamate;

(S)-1,1,1-trifluoro-2-methylpropan-2-yl (2-(azetidin-1-ylmethyl)-4-((4-fluorophenyl)sulfonyl)-3,4-dihydro-2H-benzo[b][1,4]oxazin-6-yl)carbamate;

1,1,1-trifluoro-2-methylpropan-2-yl (4-((4-fluorophenyl)sulfonyl)-2-(2,2,2-trifluoroacetyl)-3,4-dihydro-2H-benzo[b][1,4]oxazin-6-yl)carbamate;

2,2,2-trifluoro-1,1-dimethylethyl [(2S)-4-{[1-(difluoromethyl)-3-(2-hydroxyethoxy)-1H-pyrazol-4-yl]sulfonyl}-2-{[(methylsulfamoyl)amino]methyl}-3,4-dihydro-2H-1,4-benzoxazin-6-yl]carbamate;

2,2,2-trifluoro-1,1-dimethylethyl [(2S)-2-[2-(acetylamino)-2-methylpropyl]-4-{[1-ethyl-3-(2-hydroxyethoxy)-1H-pyrazol-4-yl]sulfonyl}-3,4-dihydro-2H-1,4-benzoxazin-6-yl]carbamate;

1,1,1-trifluoro-2-methylpropan-2-yl ((R)-4-((3,4-difluorophenyl)sulfonyl)-2-((S)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((S)-4-((3,4-difluorophenyl)sulfonyl)-2-((R)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((R)-4-((3,4-difluorophenyl)sulfonyl)-2-((R)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((S)-4-((3,4-difluorophenyl)sulfonyl)-2-((S)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((R)-4-((3-chloro-1-ethyl-1H-pyrazol-4-yl)sulfonyl)-2-((S)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((R)-4-((3-chloro-1-ethyl-1H-pyrazol-4-yl)sulfonyl)-2-((R)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((S)-2,2,2-trifluoro-1-hydroxyethyl)-3,4-dihydro-2H-benzo[b][1,4]oxazin-6-yl)carbamate;

1,1,1-trifluoro-2-methylpropan-2-yl ((R)-4-((3-chloro-1-ethyl-1H-pyrazol-4-yl)sulfonyl)-2-((R)-2,2,2-trifluoro-1-hydroxyethyl)-3,4-dihydro-2H-benzo[b][1,4]oxazin-6-yl)carbamate;

1,1,1-trifluoro-2-methylpropan-2-yl (4-((4-fluorophenyl)sulfonyl)-2-(2,2,2-trifluoro-1-hydroxyethyl)-3,4-dihydro-2H-benzo[b][1,4]oxazin-6-yl)carbamate;

1,1,1-trifluoro-2-methylpropan-2-yl ((S)-2-((R)-1-amino-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S)-2-((S)-1-amino-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((R)-1-amino-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((S)-1-amino-2,2,2-trifluoroethyl)-4-((4-fluorophenyl)sulfonyl)-3,4-dihydro-2H-benzo[b][1,4]oxazin-6-yl)carbamate;

(S)-tert-butyl (2-(2-(ethylsulfonyl)ethyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(2-(ethylsulfonyl)ethyl)-4-((3-(trifluoromethyl)phenyl)sulfonyl)-3,4-dihydro-2H-benzo[b][1,4]oxazin-6-yl)carbamate;

1,1,1-trifluoro-2-methylpropan-2-yl ((2S,3R)-4-((1-(difluoromethyl)-3-methyl-1H-pyrazol-4-yl)sulfonyl)-3-methyl-2-(((N-methylsulfamoyl)amino)methyl)-3,4-dihydro-2H-benzo[b][1,4]oxazin-6-yl)carbamate;

1,1,1-trifluoro-2-methylpropan-2-yl N-[(2S,3R)-2-[(1S)-1-S[[(benzyloxy)carbonyl]amino]ethyl]-4-[(3,4-difluorobenzene)sulfonyl]-3-methyl-3,4-dihydro-2H-1,4-benzoxazin-6-yl]carbamate;

1,1,1-trifluoro-2-methylpropan-2-yl (3-(acetamidomethyl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl(2-((1-carbamoylcyclopropyl)methyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl(2-((1-carbamoylcyclopropyl)methyl)-4-((3-chloro-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-2-((R)-3-amino-2-cyclopropyl-3-oxopropyl)-4-((3-chloro-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-2-((S)-3-amino-2-cyclopropyl-3-oxopropyl)-4-((3-chloro-1-ethyl-1H-pyrazol-4-yl)sulfonyl)-3,4-dihydro-2H-benzo[b][1,4]oxazin-6-yl)carbamate;

(R)-1,1,1-trifluoro-2-methylpropan-2-yl(2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl(2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate;

(R)-1,1,1-trifluoro-2-methylpropan-2-yl (2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(3-amino-2,2-dimethyl-3-oxopropyl)-4-((3-chloro-1-ethyl-1H-pyrazol-4-yl)sulfonyl)-3,4-dihydro-2H-benzo[b][1,4]oxazin-6-yl)carbamate;

2,2,2-trifluoro-1,1-dimethylethyl {(2S)-2-(3-amino-2,2-dimethyl-3-oxopropyl)-4-[(4-fluoro-3-methoxyphenyl)sulfonyl]-3,4-dihydro-2H-1,4-benzoxazin-6-yl}carbamate;

1,1,1-trifluoro-2-methylpropan-2-yl ((S)-2-((S)-3-amino-2-cyclopropyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-2-((S)-3-amino-2-cyclopropyl-3-oxopropyl)-4-((3-ethoxy-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-2-((R)-3-amino-2-cyclopropyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-2-((R)-3-amino-2-cyclopropyl-3-oxopropyl)-4-((3-ethoxy-1-ethyl-1H-pyrazol-4-yl)sulfonyl)-3,4-dihydro-2H-benzo[b][1,4]oxazin-6-yl)carbamate;

2,2,2-trifluoro-1,1-dimethylethyl [(2S)-2-(3-amino-2,2-dimethyl-3-oxopropyl)-4-{[5-(trifluoromethyl)pyridin-3-yl]sulfonyl}-3,4-dihydro-2H-1,4-benzoxazin-6-yl]carbamate;

2,2,2-trifluoro-1,1-dimethylethyl {2-(3-amino-2,2-dimethyl-3-oxopropyl)-4-[(3-ethoxy-1-ethyl-1H-pyrazol-4-yl)sulfonyl]-3,4-dihydro-2H-1,4-benzoxazin-6-yl}carbamate;

2,2,2-trifluoro-1,1-dimethylethyl [2-(3-amino-2,2-dimethyl-3-oxopropyl)-4-{1-ethyl-3-(2-hydroxyethoxy)-1H-pyrazol-4-yl]sulfonyl}-3,4-dihydro-2H-1,4-benzoxazin-6-yl]carbamate;

(S)-methyl 2-(4-((2-(3-amino-2,2-dimethyl-3-oxopropyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

(S)-1,1,1-trifluoro-2-methylpropan-2-yl (2-(2-cyanoethyl)-4-((3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-((1-cyanocyclopropyl)methyl)-3,4-dihydro-2H-benzo[b][1,4]oxazin-6-yl)carbamate;

(R)-1,1,1-trifluoro-2-methylpropan-2-yl (4-((3-chloro-1-ethyl-1H-pyrazol-4-yl)sulfonyl)-2-((1-cyanocyclopropyl)methyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate;

(R)-1,1,1-trifluoro-2-methylpropan-2-yl (4-((3-chloro-1-ethyl-1H-pyrazol-4-yl)sulfonyl)-2-(2-cyano-2-methylpropyl)-3,4-dihydro-2H-benzo[b][1,4]oxazin-6-yl)carbamate;

(R)-1,1,1-trifluoro-2-methylpropan-2-yl (2-(2-cyano-2-methylpropyl)-4-((4-fluoro-3-(trifluoromethyl)phenyl)sulfonyl)-3,4-dihydro-2H-benzo[b][1,4]oxazin-6-yl)carbamate;

(R)-1,1,1-trifluoro-2-methylpropan-2-yl (2-(2-cyano-2-methylpropyl)-4-((4-fluoro-3-methoxyphenyl)sulfonyl)-3,4-dihydro-2H-benzo[b][1,4]oxazin-6-yl)carbamate;

(R)-1,1,1-trifluoro-2-methylpropan-2-yl (2-(2-cyano-2-methylpropyl)-4-((4-fluoro-3-methylphenyl)sulfonyl)-3,4-dihydro-2H-benzo[b][1,4]oxazin-6-yl)carbamate;

(S)-1,1,1-trifluoro-2-methylpropan-2-yl (2-(2-cyano-2-methylpropyl)-4-((4-fluoro-3-methoxyphenyl)sulfonyl)-3,4-dihydro-2H-benzo[b][1,4]oxazin-6-yl)carbamate;

(S)-1,1,1-trifluoro-2-methylpropan-2-yl (2-(2-cyano-2-methylpropyl)-4-((4-fluoro-3-methylphenyl)sulfonyl)-3,4-dihydro-2H-benzo[b][1,4]oxazin-6-yl)carbamate;

(R)-1,1,1-trifluoro-2-methylpropan-2-yl (2-(2-cyano-2-methylpropyl)-4-((3-ethoxy-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(2-cyano-2-methylpropyl)-4-((3-ethoxy-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(3-(cyclopropanesulfonamido)-3-oxopropyl)-4-((4-fluoro-3-(trifluoromethyl)phenyl)sulfonyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((S)-3-(cyclopropanesulfonamido)-2-methyl-3-oxopropyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((R)-3-(cyclopropanesulfonamido)-2-methyl-3-oxopropyl)-3,4-dihydro-2H-benzo[b][1,4]oxazin-6-yl)carbamate;

2,2,2-trifluoro-1,1-dimethylethyl [(2S)-2-{3-[(tert-butylsulfonyl)amino]-3-oxopropyl}-4-{[4-fluoro-3-(trifluoromethyl)phenyl]sulfonyl}-3,4-dihydro-2H-1,4-benzoxazin-6-yl]carbamate;

2,2,2-trifluoro-1,1-dimethylethyl [(2S)-4-{[4-fluoro-3-(trifluoromethyl)phenyl]sulfonyl}-2-(3-{[(4-methylphenyl) sulfonyl]amino}-3-oxopropyl)-3,4-dihydro-2H-1,4-benzoxazin-6-yl]carbamate;

2,2,2-trifluoro-1,1-dimethylethyl [(2S)-4-{[4-fluoro-3-(trifluoromethyl)phenyl]sulfonyl}-2-(3-oxo-3-{[(trifluoromethyl) sulfonyl]amino}propyl)-3,4-dihydro-2H-1,4-benzoxazin-6-yl]carbamate;

1,1,1-trifluoro-2-methylpropan-2-yl ((S)-2-((R and S)-3-(cyclopropanesulfonamido)-2-methyl-3-oxopropyl)-4-((3-(trifluoromethyl)phenyl)sulfonyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((R)-3-(1,1-dimethylethylsulfonamido)-2-methyl-3-oxopropyl)-3,4-dihydro-2H-benzo[b][1,4]oxazin-6-yl)carbamate;

1,1,1-trifluoro-2-methylpropan-2-yl ((S)-2-((R)-3-(cyclopropanesulfonamido)-2-methyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-2-((R)-3-(1,1-dimethylethylsulfonamido)-2-methyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-2-((S)-3-(cyclopropanesulfonamido)-2-methyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-2-((S)-3-(1,1-dimethylethylsulfonamido)-2-methyl-3-oxopropyl)-4-((4-fluoro-3-methoxyphenyl)sulfonyl)-3,4-dihydro-2H-benzo[b][1,4]oxazin-6-yl)carbamate;

1,1,1-trifluoro-2-methylpropan-2-yl ((S)-4-((3-chloro-1-ethyl-1H-pyrazol-4-yl)sulfonyl)-2-((S)-3-(1,1-dimethylethylsulfonamido)-2-methyl-3-oxopropyl)-3,4-dihydro-2H-benzo[b][1,4]oxazin-6-yl)carbamate;

(S)-1,1,1-trifluoro-2-methylpropan-2-yl (4-((4-fluoro-3-(trifluoromethyl)phenyl)sulfonyl)-2-(oxetan-3-ylmethyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(2-(5-oxo-4,5-dihydro-1H-1,2,4-triazol-3-yl)ethyl)-3,4-dihydro-2H-benzo[b][1,4]oxazin-6-yl)carbamate;

(S)-1,1,1-trifluoro-2-methylpropan-2-yl(4-((3-chloro-1-ethyl-1H-pyrazol-4-yl)sulfonyl)-2-(2-(4-methyl-5-oxo-4,5-dihydro-1H-1,2,4-triazol-3-yl)ethyl)-3,4-dihydro-2H-benzo[b][1,4]oxazin-6-yl)carbamate;

(S)-1,1,1-trifluoro-2-methylpropan-2-yl (2-(2-(5-oxo-4,5-dihydro-1,2,4-oxadiazol-3-yl)ethyl)-4-((3-(trifluoromethyl)phenyl)sulfonyl)-3,4-dihydro-2H-benzo[b][1,4]oxazin-6-yl)carbamate;

(R)-1,1,1-trifluoro-2-methylpropan-2-yl(4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(S)-1,1,1-trifluoro-2-methylpropan-2-yl(4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

2,2,2-trifluoro-1,1-dimethylethyl [(2S)-2-[2-(5-oxo-4,5-dihydro-1,2,4-oxadiazol-3-yl)ethyl]-4-{3-(trifluoromethyl)phenyl]sulfonyl}-3,4-dihydro-2H-1,4-benzoxazin-6-yl]carbamate;

2,2,2-trifluoro-1,1-dimethylethyl {(2S)-4-[(3-cyclopropylphenyl)sulfonyl]-2-[2-(5-oxo-4,5-dihydro-1,2,4-oxadiazol-3-yl)ethyl]-3,4-dihydro-2H-1,4-benzoxazin-6-yl}carbamate;

tert-butyl {(2S)-4-[(3-cyclopropylphenyl)sulfonyl]-2-[2-(5-oxo-4,5-dihydro-1,2,4-oxadiazol-3-yl)ethyl]-3,4-dihydro-2H-1,4-benzoxazin-6-yl}carbamate;

(S)-1,1,1-trifluoro-2-methylpropan-2-yl (4-((3-chloro-1-ethyl-1H-pyrazol-4-yl)sulfonyl)-2-(2-(5-oxo-4,5-dihydro-1,2,4-oxadiazol-3-yl)ethyl)-3,4-dihydro-2H-benzo[b][1,4]oxazin-6-yl)carbamate;

(S)-tert-butyl (4-((3-chloro-1-ethyl-1H-pyrazol-4-yl)sulfonyl)-2-(2-(5-oxo-4,5-dihydro-1,2,4-oxadiazol-3-yl)ethyl)-3,4-dihydro-2H-benzo[b][1,4]oxazin-6-yl)carbamate;

(R)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(R)-1,1,1-trifluoro-2-methylpropan-2-yl (4-((4-fluoro-3-methoxyphenyl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(S)-1,1,1-trifluoro-2-methylpropan-2-yl (4-((4-fluoro-3-methoxyphenyl)sulfonyl)-2-(2-methyl-2-(5-oxo-4,5-dihydro-1,2,4-oxadiazol-3-yl)propyl)-3,4-dihydro-2H-benzo[b][1,4]oxazin-6-yl)carbamate;

(S)-1,1,1-trifluoro-2-methylpropan-2-yl(4-((3-chloro-1-ethyl-1H-pyrazol-4-yl)sulfonyl)-2-(2-(5-oxo-4,5-dihydro-1,3,4-oxadiazol-2-yl)ethyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-(2-methyl-2-(5-oxo-4,5-dihydro-1,3,4-oxadiazol-2-yl)propyl)-3,4-dihydro-2H-benzo[b][1,4]oxazin-6-yl)carbamate;

2,2,2-trifluoro-1,1-dimethylethyl {(2S)-4-[(3-cyclopropylphenyl) sulfonyl]-2-[2-(5-oxo-4,5-dihydro-1,3,4-oxadiazol-2-yl)ethyl]-3,4-dihydro-2H-1,4-benzoxazin-6-yl}carbamate;

2,2,2-trifluoro-1,1-dimethylethyl {(2S)-4-[(4-fluoro-3-methoxyphenyl)sulfonyl]-2-[2-methyl-2-(5-oxo-4,5-dihydro-1,3,4-oxadiazol-2-yl)propyl]-3,4-dihydro-2H-1,4-benzoxazin-6-yl}carbamate;

(S)-1,1,1-trifluoro-2-methylpropan-2-yl(2-(2-(1H-tetrazol-5-yl)ethyl)-4-((3-(trifluoromethyl)phenyl)sulfonyl)-3,4-dihydro-2H-benzo[b][1,4]oxazin-6-yl)carbamate;

2,2,2-trifluoro-1,1-dimethylethyl {(2S)-4-[(3-cyclopropylphenyl) sulfonyl]-2-[2-(1H-tetrazol-5-yl)ethyl]-3,4-dihydro-2H-1,4-benzoxazin-6-yl}carbamate;

2,2,2-trifluoro-1,1-dimethylethyl [(2S)-2-[2-(1H-tetrazol-5-yl)ethyl]-4-{[2-(trifluoromethyl)pyridin-4-yl]sulfonyl}-3,4-dihydro-2H-1,4-benzoxazin-6-yl]carbamate;

(S)-1,1,1-trifluoro-2-methylpropan-2-yl (2-(2-(1H-tetrazol-5-yl)ethyl)-4-((3-chloro-1-ethyl-1H-pyrazol-4-yl)sulfonyl)-3,4-dihydro-2H-benzo[b][1,4]oxazin-6-yl)carbamate;

(R)-1,1,1-trifluoro-2-methylpropan-2-yl(2-(hydroxymethyl)-5-methyl-4-((3-(trifluoromethyl)phenyl)sulfonyl)-3,4-dihydro-2H-benzo[b][1,4]oxazin-6-yl)carbamate; and (S)-tert-butyl (4-((4-fluorophenyl)sulfonyl)-2-((3-methylureido)methyl)-3,4-dihydro-2H-benzo[b][1,4]oxazin-6-yl)carbamate.

* * * * *